United States Patent [19]

Los

[11] Patent Number: 4,638,068

[45] Date of Patent: Jan. 20, 1987

[54] 2-(2-IMIDAZOLIN-2-YL)-PYRIDINES AND QUINOLINES, PROCESS AND INTERMEDIATES FOR THE PREPARATION THEREOF, AND USE OF SAID COMPOUNDS AS HERBICIDAL AGENTS

[75] Inventor: Marinus Los, Pennington, N.J.

[73] Assignee: American Cyanamid Company, Stamford, Conn.

[21] Appl. No.: 382,041

[22] Filed: May 25, 1982

Related U.S. Application Data

[63] Continuation-in-part of Ser. No. 252,704, Apr. 9, 1981, abandoned, which is a continuation-in-part of Ser. No. 155,909, Jun. 2, 1980, abandoned, Ser. No. 155,910, Jun. 2, 1980, abandoned, Ser. No. 155,867, Jun. 2, 1980, abandoned, Ser. No. 155,908, Jun. 2, 1980, abandoned, and Ser. No. 155,865, Jun. 2, 1980, abandoned.

[51] Int. Cl.[4] .................. C07D 213/56; C07D 215/14; C07D 221/04

[52] U.S. Cl. .................................... 546/169; 546/304; 71/86; 546/307; 546/310; 71/87; 546/316; 546/318; 71/92; 548/546; 71/94; 544/131; 546/5; 546/14; 546/15; 546/63; 546/64; 546/65; 546/82; 546/84; 546/86; 546/90; 546/112; 546/113; 546/153; 546/156; 546/167; 546/168; 546/170; 546/278; 546/283; 546/286; 546/287; 546/288; 546/289; 546/290; 546/296; 546/297; 546/299

[58] Field of Search ................... 546/278, 5, 112, 169, 546/318, 283, 288, 291, 309, 156, 286, 289, 290; 424/263, 258

[56] References Cited

U.S. PATENT DOCUMENTS

| | | | |
|---|---|---|---|
| 3,336,326 | 8/1967 | Godefroi et al. | 546/278 |
| 4,188,487 | 2/1980 | Los | 548/301 |
| 4,404,012 | 9/1983 | Orwick et al. | 546/278 X |
| 4,459,409 | 7/1984 | Ladner | 546/168 X |

*Primary Examiner*—Joseph Paul Brust

*Attorney, Agent, or Firm*—H. G. Jackson

[57] ABSTRACT

There are provided novel 2-(2-imidazolin-2-yl)pyridine and quinoline compounds, a process and intermediate compounds for the preparation thereof, and a method for controlling a wide variety of annual and perennial plant species therewith.

8 Claims, No Drawings

2-(2-IMIDAZOLIN-2-YL)-PYRIDINES AND QUINOLINES, PROCESS AND INTERMEDIATES FOR THE PREPARATION THEREOF, AND USE OF SAID COMPOUNDS AS HERBICIDAL AGENTS

This is a continuation-in-part of copending U.S. application Ser. No. 252,704, filed Apr. 9, 1981and now abandoned, which is a continuation-in-part of U.S. Ser. Nos. 155,909; 155,910; 155,867; 155,908; 155,865 which were all filed June 2, 1980, and are now abandoned.

SUMMARY OF THE INVENTION

The invention is novel intermediates of the structure

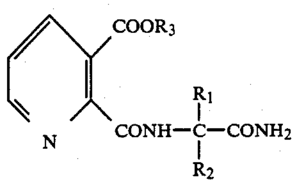

useful in the synthesis of herbicidal 2-(2-imidazolin-2-yl)-pyridines and quinolines.

More particularly, this invention relates to 2-(2-imidazolin-2-yl)pyridine and quinoline compounds having the structure:

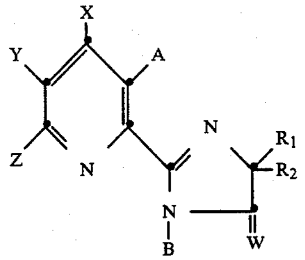

(I)

wherein $R_1$ is $C_1$–$C_4$ alkyl;

$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;

A is $COOR_3$, $CONHR_6$, CHO, $CH_2OH$, $COCH_3$, $COC_6H_5$, CN, $CH_3$, CH=NOH, $CH_2COOH$, CONHOH, $CHR_8OH$, $CH_2CH_2COOH$,

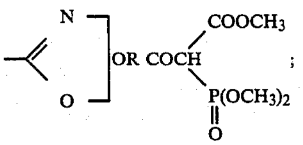

;

$R_3$ is hydrogen, diloweralkylimino;

$C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;

$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;

$C_3$–$C_6$ cycloalkyl optionally substituted with one or two $C_1$–$C_3$ alkyl groups;

$C_3$–$C_{10}$ alkynyl optionally substituted with one or two $C_1$–$C_3$ alkyl groups; or, A cation selected from the group consisting of alkali metals, alkaline earth metals, manganese, copper, iron, zinc, cobalt, lead, silver, nickel, ammonium and organic ammonium;

$R_6$ is hydrogen, hydroxyl, $C_3$-alkenyl, $C_3$-alkynyl or $C_1$–$C_4$ alkyl optionally substituted with one hydroxyl or one chlorine group;

B is H, $COR_4$ or $SO_2R_5$; provided that when B is $COR_4$ or $SO_2$—$R_5$; A is $COOR_3$ in which $R_3$ is other than H, or a salt-forming cation, $CH_3$ or CN; W is O; and Y and Z are not alkylamino, hydroxyl; or hydroxyloweralkyl;

$R_4$ is $C_1$–$C_{11}$ alkyl, chloromethyl or phenyl optionally substituted with one chloro, one nitro or one methoxy group;

$R_5$ is $C_1$–$C_4$ alkyl or phenyl optionally substituted with one methyl group;

W is O or S;

$R_8$ is $C_1$–$C_4$-alkyl or phenyl;

X is hydrogen, halogen, hydroxyl or methyl, with the proviso that when Y and Z are taken together to form a ring and YZ is represented by the structure: $—(CH_2)_n—$, where n is 3 or 4, X is hydrogen;

Y and Z each represent members selected from the group consisting of hydrogen, halogen, $C_1$–$C_6$ alkyl, $C_1$–$C_4$ hydroxyloweralkyl, $C_1$–$C_6$ alkoxy, $C_1$–$C_4$ alkylthio, phenoxy, $C_1$–$C_4$-haloalkyl, nitro, cyano, $C_1$–$C_4$ alkylamino, diloweralkylamino $C_1$–$C_4$ alkylsulfonyl group, or phenyl optionally substituted with one $C_1$–$C_4$ alkyl, $C_1$–$C_4$ alkoxy or halogen; and, when taken together, Y and Z may form a ring in which YZ are represented by the structure: $—(CH_2)_n—$, where n is an integer selected from 3 and 4, provided that X is hydrogen; or

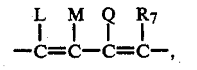

where L, M, Q and $R_7$ each represent members selected from the group consisting of hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, $NO_2$, CN, phenyl, phenoxy, amino, $C_1$–$C_4$ alkylamino, diloweralkylamino, chlorophenyl, methylphenyl, or phenoxy substituted with one Cl, $CF_3$, $NO_2$ or $CH_3$ group, with the proviso that only one of L, M, Q or $R_7$, may represent a substituent other than hydrogen, halogen, $C_1$–$C_4$ alkyl or $C_1$–$C_4$-alkoxy;

and when W is O and A is CN, $CH_3$ or $COOR_3$, provided that $R_3$ cannot be unsaturated alkyl and Y and Z cannot be alkylamino, dialkylamino or alkylthio, and the N-oxides thereof, and when $R_1$ and $R_2$ are not the same, the optical isomers thereof, and, except when $R_3$ is a salt-forming cation, the acid addition salts thereof.

A preferred group of 2-(2-imidazolin-2-yl)pyridine compounds have the formula shown as I above, wherein $R_1$ is methyl; $R_2$ is methyl, ethyl, isopropyl or cyclopropyl; W is oxygen; B is hydrogen, CO-alkyl $C_1$–$C_6$ or CO-phenyl optionally substituted with chloro, nitro or methoxy; A is $COOR_3$, $CH_2OH$ or CHO where $R_3$ is as described in formula I above, X is hydrogen, Y and Z are each selected from the group consisting of hydrogen, $C_1$–$C_6$ alkyl, $C_1$–$C_6$ alkoxy, halo, phenyl, nitro, cyano, trifluoromethyl or methylsulfonyl; and when Y and Z are taken together, YZ is $-(CH_2)_4$.

A more preferred group of these 2-(2-imidazolin-2-yl)pyridines may be illustrated by the formula (Ia):

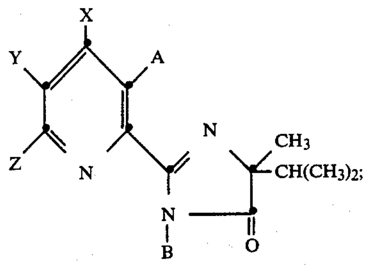

(Ia)

wherein B is hydrogen, CO-alkyl $C_1$–$C_6$ or CO-phenyl; A is $COOR_3$ where $R_3$ is as described in formula (I) above; X is hydrogen and Y and Z each represent hydrogen, $C_1$–$C_6$ alkyl, $C_1$–$C_4$-alkoxy, halo, $C_1$–$C_4$-haloalkyl, or phenyl and, when taken together, YZ represent $-(CH_2)_4-$.

The most preferred formula (Ia), 2-(2-imidazolin-2-yl)pyridine compounds are those wherein B, X, Y and Z are each hydrogen; A is $COOR_3$ and $R_3$ is as described in formula (I) above.

The 2-(2-imidazolin-2-yl)quinoline compounds are illustrated by formula (II) below:

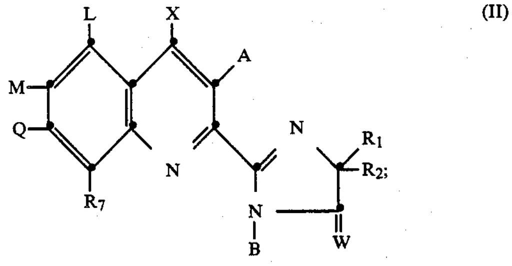

(II)

wherein $R_1$, $R_2$, W, B, A, X, L, M, Q and $R_7$ are as defined in reference to formula (I) above.

Formula (II) 2-(2-imidazolin-2-yl)quinoline compounds which are preferred herbicidal agents are those wherein $R_1$ is methyl; $R_2$ is methyl, ethyl, isopropyl or cyclopropyl; W is oxygen; B is hydrogen, CO-alkyl $C_1$–$C_6$, CO-phenyl optionally substituted with one chloro, nitro or methoxy group; A is $COOR_3$, $CH_2OH$ or CHO; $R_3$ is as defined in formula (I); X is hydrogen and L, M, Q and $R_7$ are each selected from the group consisting of hydrogen, halogen, methoxy, nitro, alkyl $C_1$–$C_4$, $CF_3$, CN, $N(CH_3)_2$, $NH_2$, $SCH_3$, or $SO_2CH_3$, provided that only one of L, M, Q or $R_7$ may be nitro, $CF_3$, CN, $N(CH_3)_2$, $NH_2$, $SCH_3$ or $SO_2CH_3$.

A more preferred group of formula (II) 2-(2-imidazolin-2-yl)quinoline compounds are those wherein X, L and $R_7$ are each hydrogen; $R_1$ is methyl; $R_2$ is methyl, ethyl, isopropyl or cyclopropyl; B is hydrogen or $COCH_3$; A is $COOR_3$, $CH_2OH$ or CHO and $R_3$ is as defined in formula (I); W is oxygen and M and Q each represent a member selected from hydrogen, halogen, methyl, methoxy, nitro, $CF_3$, CN, $N(CH_3)_2$, $NH_2$, $SCH_3$ or $SO_2CH_3$, provided that only one of M or Q may be a substituent other than hydrogen, halogen, methyl or methoxy.

A still more preferred group of formula (II) 2-(2-imidazolin-2-yl)quinolines are those in which $R_1$ is methyl; $R_2$ is isopropyl; W is oxygen; B, X, L, M, Q and $R_7$ are hydrogen; A is $COOR_3$ where $R_3$ is $C_1$–$C_8$ alkyl, hydrogen, $C_3$–$C_8$ alkenyl, $C_3$–$C_8$ alkynyl, $C_3$–$C_6$ cycloalkyl or a cation selected from alkali metals, alkaline earth metals, manganese, copper, iron, zinc, cobalt, lead, silver, nickel, ammonium and aliphatic ammonium.

In formulas (I), (Ia) and (II) above, alkali metals include: sodium, potassium and lithium, but sodium is generally preferred. Further, the term "organic ammonium," is defined as a group consisting of a positively charged nitrogen atom joined to from one to four aliphatic groups, each containing from one to 20 carbon atoms. Among the organic ammonium groups which are illustrative for the preparation of the aliphatic ammonium salts of the formula (I) imidazolinyl nicotinic acids herein are: monoalkylammonium dialkylammonium, trialkylammonium tetraalkylammonium, monoalkenylammonium, dialkenylammonium trialkenylammonium, monoalkynylammonium, dialkynylammonium, trialkynylammonium, monoalkanolammonium, dialkanolammonium, trialkanolammonium, $C_5$–$C_6$-cycloalkylammonium, piperidinium, morpholinium, pyrrolidinium, benzylammonium and equivalents thereof. Exemplary of halogen hereinabove are chlorine, fluorine, bromine, and iodine, but chlorine and bromine are preferred.

As indicated above, the present invention relates to 2-(2-imidazolin-2-yl)pyridine and 2-(2-imidazolin-2-yl)quinoline compounds and their use as herbicidal agents. These novel pyridine and quinoline compounds are represented by formula (I) which is generic to both compound groups. Formula (II) is more specific and is directed to the 2-(2-imidazolin-2-yl)quinolines.

While many process steps, hereinafter described, are common to the preparation of both the pyridine and quinoline derivatives of this invention, for convenience, process steps limited to the preparation of quinoline derivatives will be discussed separately following the discussion relating to the preparation of the pyridine derivatives.

In accordance with the process of the present invention, formula (I), 2-(2-imidazolin-2-yl)pyridine esters, wherein A is $COOR_3$ and $R_3$ represents a substituent other than hydrogen or a salt-forming cation, and $R_1$, $R_2$, X, Y and Z are as described above, can be prepared by reacting an imidazopyrrolopyridinedione, represented by formula (III), hereinbelow, with an appropriate alcohol and corresponding alkali metal alkoxide at a temperature ranging between about 20° C. and about 50° C.

In these reactions, the alcohol can function both as reactant and solvent. As such, a secondary solvent is not required. However, when an expensive alcohol is employed in the reaction, a less expensive secondary solvent, such as dioxane, tetrahydrofuran or other non-protic solvent, may be added to the reaction mixture. The amount of non-protic solvent added to the reaction mixture may be widely varied.

The overall reaction can be graphically illustrated as follows:

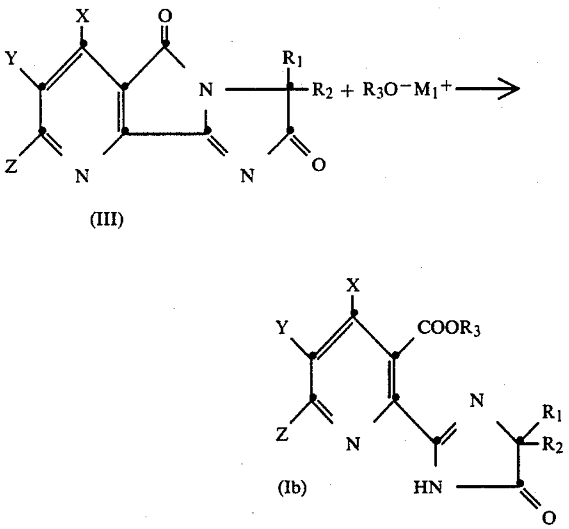

(III)

(Ib)

where $M_1$ is an alkali metal, and X, Y, X, $R_1$, $R_2$ and $R_3$ are as above defined.

Advantageously, the formula (Ib) 2-(2-imidazolin-2-yl)pyridine esters can also be prepared from a formula (IV) dioxopyrrolopyridine acetamide, wherein $R_1$, $R_2$, X, Y and Z are as described above, by cyclization thereof with a strong base, such as 1,5-diazabicyclo[5.4.-0]undec-5-ene (DBU), in the presence of an inert organic solvent such as xylene or toluene to give the crude imidazopyrrolopyridine of formula (III). The reaction mixture is heated to a temperature between 100° C. and 150° C., and water is removed from the reaction mixture during the reaction using any convenient means, e.g., a Dean-Stark water separator. At least one equivalent of alcohol, represented by the formula (V) $R_3OH$, wherein $R_3$ represents a member other than hydrogen or a salt-forming cation, and $R_1$, $R_2$, X, Y and Z are as hereinabove described, is then added to the reaction mixture and the thus prepared mixture heated to reflux at a temperature between 100° C. and 150° C. to yield the formula (Ib) 2-(2-imidazolin-2-yl)pyridine ester. The overall reaction can be graphically illustrated as follows:

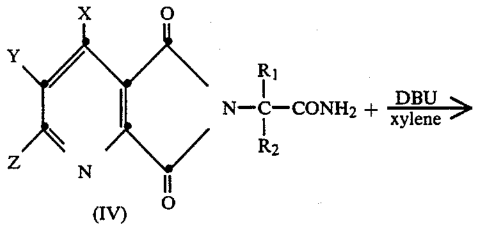

(IV)

-continued

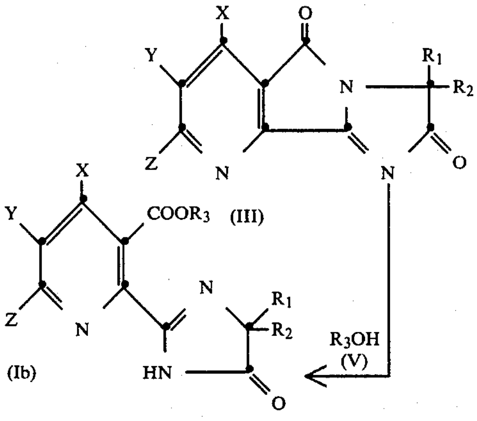

(III)

(Ib)

wherein X, Y, Z, $R_1$, $R_2$ and $R_3$ are as described above.

In still another embodiment relating to the preparation of the formula (Ib) 2-(2-imidazolin-2-yl)pyridine esters, the cyclization of a carbamoyl nicotinic acid ester, represented by formula (VI), with phosphorus pentachloride at an elevated temperature, generally between about 60° C. and 100° C. occurs. The reaction is preferably conducted in the presence of an inert inorganic solvent, such as toluene or benzene. Good yields of the hydrochloride salt of the desired formula (Ib) ester are attained. The hydrochloride salt is then readily converted to the formula (Ib) ester by dissolution of the acid addition salt in water and neutralization of the thus-prepared solution with base, such as sodium or potassium carbonate. The overall reactions can be illustrated as follows:

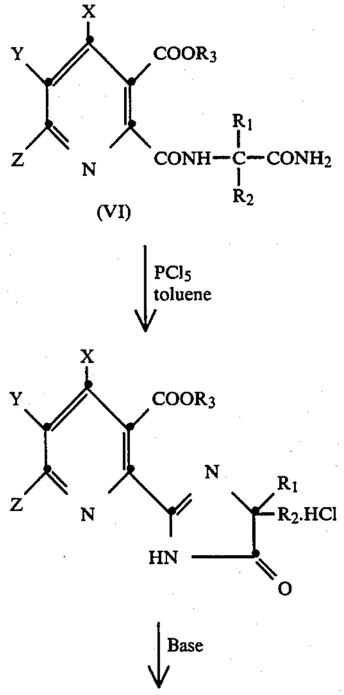

(VI)

-continued

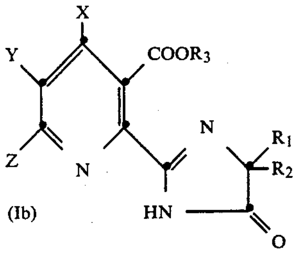

(Ib)

wherein A is $COOR_3$ and $R_3$ is a substituent other than hydrogen or a salt-forming cation, and $R_1$, $R_2$, X, Y and Z are as hereinabove described.

In still another embodiment for the preparation of the formula (Ib) 2-(2-imidazolin-2-yl)pyridines esters of the present invention, the cyclization of a carbamoyl nicotinic acid ester represented by formula (VI) using a mixture of phosphorus pentachloride and phosphorus oxychloride is accomplished. The reaction mixture is stirred at room temperature from about four to eight hours and then the $POCl_3$ removed in vacuo. The remaining residue is dispersed in an organic solvent such as toluene. The solvent is removed and the residue dispersed in water and heated to between 80° C. and 100° C. After cooling, the pH of the aqueous mixture is adjusted to 5–6 with sodium bicarbonate, and the product extracted into methylene chloride to give the desired formula (Ib) 2-(2-imidazolin-2-yl)pyridine ester. The reaction can be graphically illustrated as follows:

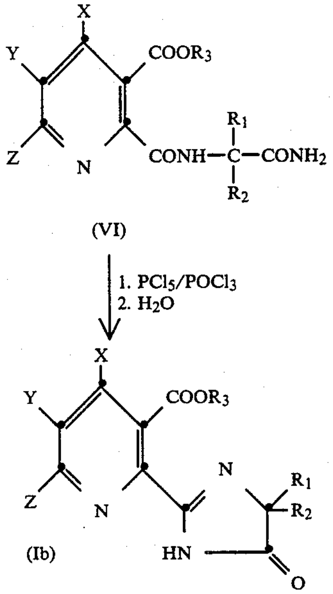

(VI)

(Ib)

where A is $COOR_3$ and $R_3$ is a substituent other than hydrogen or a salt-forming cation, and $R_1$, $R_2$, X, Y and Z are as described above.

The formula (Ib) 2-(2-imidazolin-2-yl)pyridine ester in which A is $COOR_3$ and $R_3$ is alkyl $C_1$–$C_{12}$, alkenyl $C_3$–$C_{12}$, alkynyl $C_3$–$C_{10}$, cycloalkyl $C_3$–$C_6$ or the substituted derivatives of these groups and X, Y, Z, $R_1$ and $R_2$ are as described above, may be converted to the corresponding amide where A is $CONH_2$ by reaction with ammonia under superatmospheric pressure at a temperature between about 25° C. and 125° C. This reaction can be conducted in a protic solvent such as a lower alkanol or an aprotic solvent such as tetrahydrofuran, dioxane or the like. Likewise, using similar conditions but substituting hydroxylamine for ammonia in the above reaction yields the hydroxamic acid. These reactions may be graphically illustrated as follows:

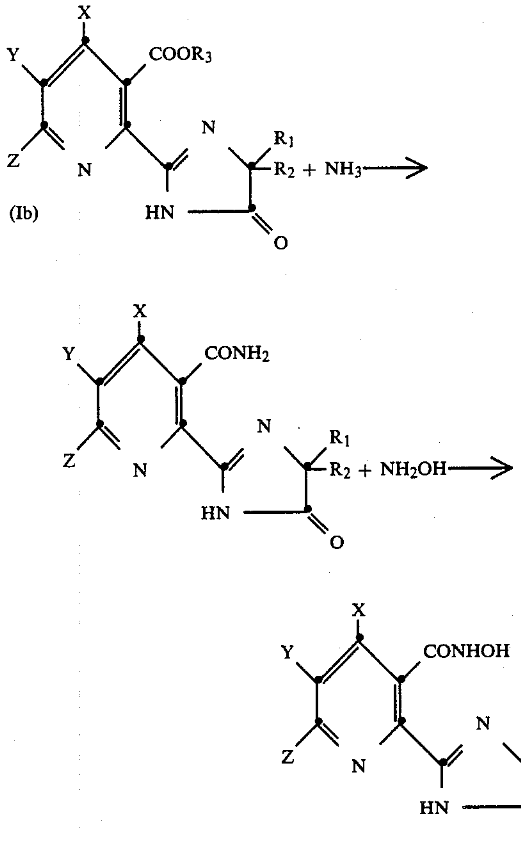

(Ib)

Treatment of the thus prepared primary amide described above with titanium tetrachloride and triethylamine, preferably in the presence of an inert aprotic solvent, such as tetrahydrofuran yields the corresponding nitrile. The reaction is generally conducted under a blanket of inert gas, such as nitrogen, at a temperature between about 0° C. and 10° C. The reaction may be illustrated as follows:

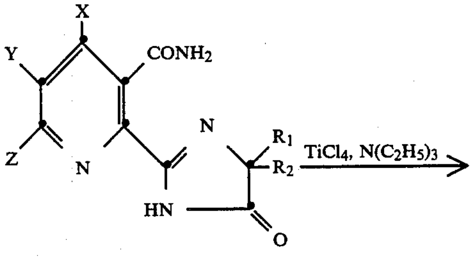

-continued

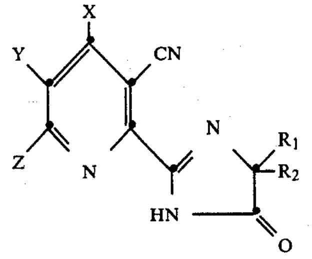

where X, Y, Z, $R_1$ and $R_2$ are as described above.

Preparation of the formula (VIII) N-substituted imidazolinone derivatives, wherein B is $COR_4$ or $SO_2R_5$; and A is $CH_3$, CN or $COOR_3$; and W is O; and $R_1$, $R_2$, $R_3$, X, Y and Z are as described above, excepting that $R_3$ cannot be H or a salt-forming cation and Y and Z cannot be alkylamino, hydroxy or hydroxyloweralkyl; can be achieved by reaction of the appropriately substituted formula (I) 2-(2-imidazolin-2-yl)pyridine with an excess of acyl halide, acyl anhydride, or sulfonyl halide, alone or in a solvent such as pyridine or toluene at an elevated temperature between about 50° C. and 125° C. The reaction can be graphically illustrated as follows:

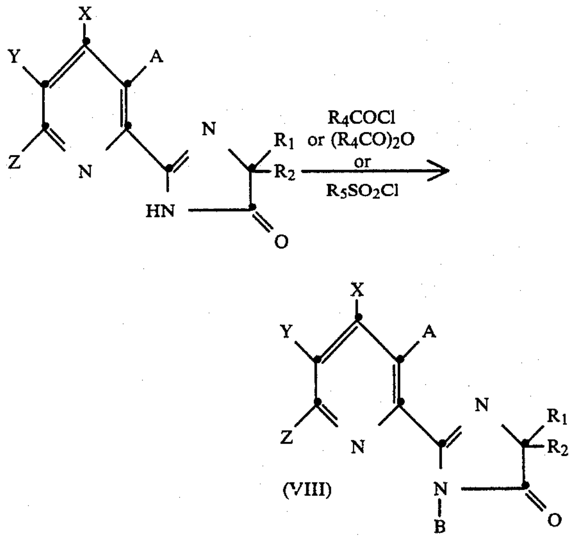

(VIII)

where A is $CH_3$, CN or $COOR_3$; $R_1$, $R_2$, $R_3$, $R_4$, $R_5$, X, Y and Z are as described above excepting that Y and/or Z cannot be alkylamino, hydroxyl, hydroxyloweralkyl.

Reaction of either the formula (I) 2-(2-imidazolin-2-yl)pyridine or the formula (VIII) N-substituted imidazolinone derivatives, described and illustrated immediately above, wherein A is $CH_3$, CN or $COOR_3$ provided that $R_3$ is as described above, excepting that it cannot be an unsaturated alkyl group, B is $R_4CO$ or $R_5SO_2$ and Y or Z cannot be alkylamino, alkylthio or dialkylamino; with an excess of m-chloroperbenzoic acid in the presence of an inert solvent such as methylene chloride, at refluxing temperature, yields the N-oxide corresponding to the pyridine derivative utilized as starting material. The reaction may be illustrated as follows:

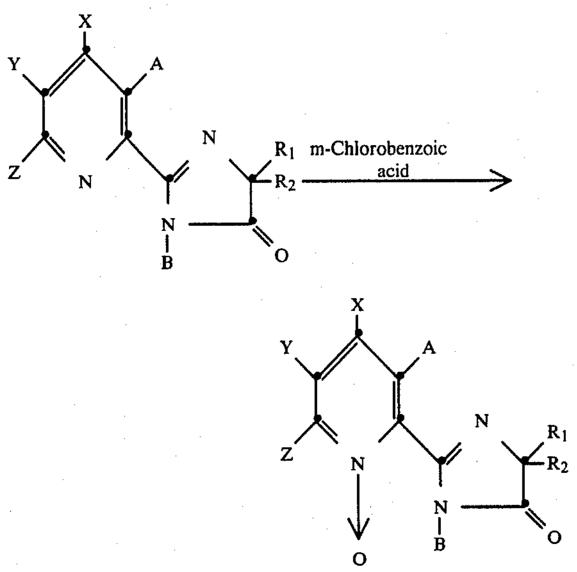

wherein A is $CH_3$, CN or $COOR_3$ is as described above excepting that $R_3$ cannot be an unsaturated alkyl group; B is $COR_4$ or $SO_2R_5$, $R_1$, $R_2$, $R_4$, $R_5$, X, Y and Z are as described above excepting that Y and Z cannot be alkylamino, alkylthio or dialkylamino.

Hydrolysis of the thus prepared N-oxide using a strong base such as sodium hydroxide in a lower alcohol yields the corresponding N-oxide in which B is H.

Advantageously, formula (I) esters in which B is hydrogen; W is oxygen and A is $COOR_3$ wherein $R_3$ is a saturated $C_1$-$C_{12}$ alkyl, $C_3$-$C_6$ cycloalkyl or benzyl substituent, and $R_1$, $R_2$, X, Y and Z are as defined above; can be prepared by reaction of the corresponding acid, i.e., where A is COOH, with an appropriate alcohol in the presence of a catalytic amount of a strong mineral acid such as hydrochloric acid, sulfuric acid or the like; at a temperature between about 50° C. and 100° C. The reaction may be illustrated as follows:

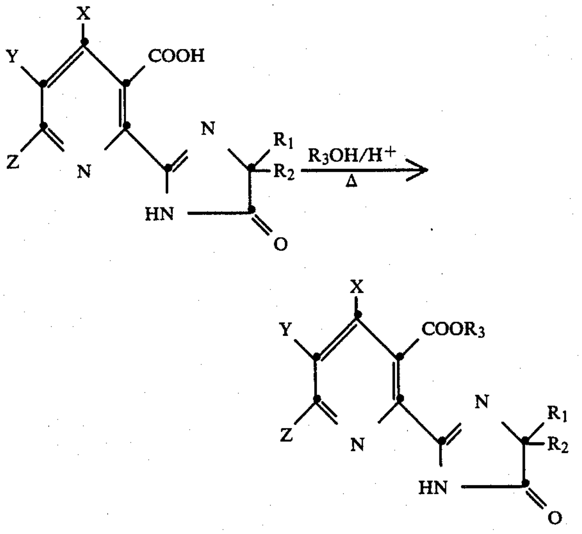

wherein $R_3$ is $C_1$–$C_{12}$ alkyl, $C_3$-$C_6$ cycloalkyl or benzyl; and $R_1$, $R_2$, X, Y and Z are as defined above.

The formula (I) acid as shown immediately above where A is COOH; B is hydrogen; W is oxygen and $R_1$, $R_2$, X, Y and Z are as defined above, is also readily converted to the corresponding methyl ester by reaction with diazomethane at a temperature between about 0° C. and 25° C. The thus prepared methyl ester may then be reacted with an alkali metal alkoxide such as a sodium or potassium alkoxide, for convenience shown as $R_3ONa$, and an appropriate alcohol represented by the structure $R_3OH$, wherein $R_3$ is $C_1$–$C_{12}$ alkyl optionally substituted with one $C_1$–$C_3$ alkoxy, $C_3$–$C_6$ cycloalkyl, benzyloxy, furyl, phenyl, halophenyl, loweralkylphenyl, loweralkoxyphenyl, nitrophenyl or cyano; $C_3$–$C_{12}$ alkenyl optionally substituted with one or two $C_1$–$C_3$ alkoxy, phenyl or halogen groups; $C_3$–$C_6$ cycloalkyl optionally substituted with one or two $C_1$–$C_3$ alkyl groups or with $C_3$–$C_{10}$ alkynyl optionally substituted with one or two $C_1$–$C_3$ alkyl groups. The above reactions may be illustrated as follows:

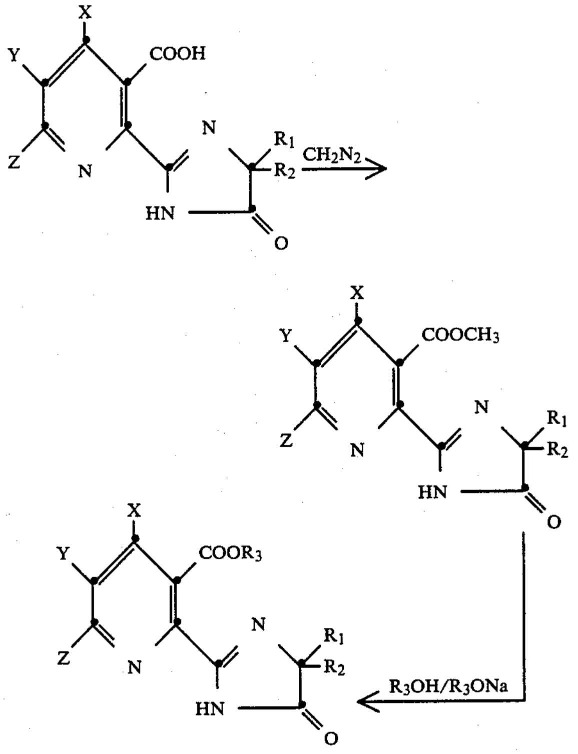

wherein $R_1$, $R_2$, $R_3$, X, Y and Z are as defined above.

Conversion of the above-identified formula (I) esters to their corresponding acid addition salts is readily achieved by treatment of said esters with strong acids, particularly strong mineral acids such as hydrochloric acid, sulfuric acid or hydrobromic acid.

Where the hydrohalide acid addition salts are desired, the formula (I) ester, wherein A is $COOR_3$ and $R_3$ is other than hydrogen or a salt-forming cation, and $R_1$, $R_2$, X, Y and Z are as described above, is dissolved in an organic solvent such as methylene chloride, chloroform, ether or the like. Addition of at least one equivalent of acid to the thus-prepared solution then yields the desired acid addition salt. The reaction may be illustrated as follows:

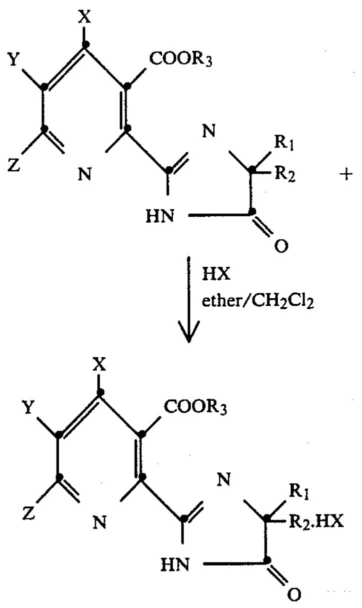

When the sulfuric acid salt of the ester is desired, the formula (I) ester is generally dissolved in a lower aliphatic alcohol such as methanol, ethanol, isopropanol or the like or mixtures of the above with water. Treatment of the mixture with at least one equivalent of sulfuric acid yields the sulfuric acid addition salt of the formula (I) ester.

In a further embodiment of the invention, the formula (I) compounds, wherein A is $COOR_3$ and $R_3$ is hydrogen and $R_1$, $R_2$, X, Y and Z, are as defined above, except that X, Y and Z cannot be $NO_2$ or halogen, can be prepared by hydrogenolysis of the benzyl ester of the imidazolinyl pyridine shown in formula (XV), wherein $R_1$, $R_2$, X, Y and Z, are as above-defined employing a palladium or platinum catalyst. In this reaction, the formula (XV) benzyl ester is dissolved or dispersed in an organic solvent, such as lower alcohol, an ether such as dioxane, tetrahydrofuran or the like, toluene or xylene. The catalyst, preferably palladium on a carbon carrier, is added to the mixture and the mixture heated to between 20° C. and 50° C. The heated mixture is then treated with hydrogen gas to yield the desired acid. The reaction may be graphically illustrated as follows:

(XV)

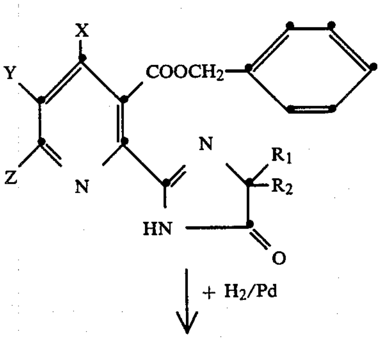

-continued

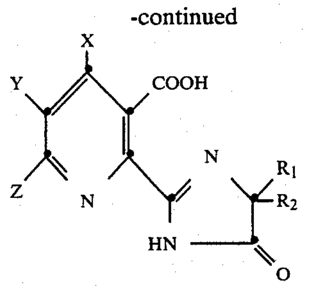

(I)

Alternatively, the formula (I) acids where A is COOH may be prepared by treatment of an aqueous solution of the formula (I) ester with a strong base. In practice the formula (I) ester is generally treated with one equivalent of base in aqueous solution, and the mixture heated to between 20° C. and 50° C. The mixture is then cooled and adjusted to pH 6.5 to 7.5 and preferably pH 7, with a strong mineral acid. Such treatment yields the desired acid. The reaction can be illustrated as follows:

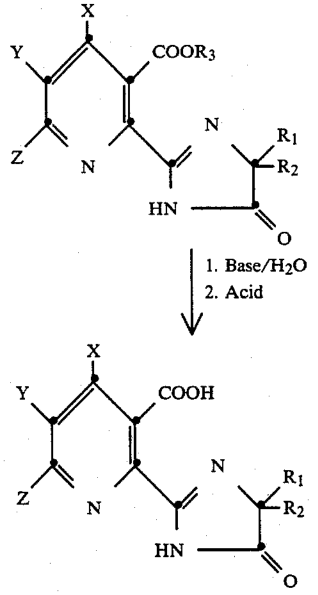

where $R_3$ is other than hydrogen or a salt-forming cation, and $R_1$, $R_2$, X, Y and Z are as described with reference to formula (I).

The formula (I) acids wherein A is COOH; B is hydrogen; W is oxygen and X, Y, Z, $R_1$ and $R_2$ are as described, can be prepared by reaction of the appropriately substituted formula (XVIII) imidazolinone with alkyl lithium, preferably in the presence of an inert solvent such as tetrahydrofuran under a blanket of nitrogen at a temperature between about −70° C. and −80° C. The thus-formed mixture is then treated with hexamethylphosphoramide and carbon dioxide preferably in an inert solvent such as tetrahydrofuran, to yield the desired product. Where it is desirable to obtain the formula (I) pyridine derivatives in which A is $CH_3$ and X, Y, Z, $R_1$ and $R_2$ are as stated above, the formula (XVIII) imidazolinone is treated in the same manner as described for the preparation of the acid, excepting that methyl iodide is substituted for the carbon dioxide. If dimethylformamide is substituted for the methyl iodide, the corresponding formyl derivatives are obtained. These reactions may be illustrated as follows:

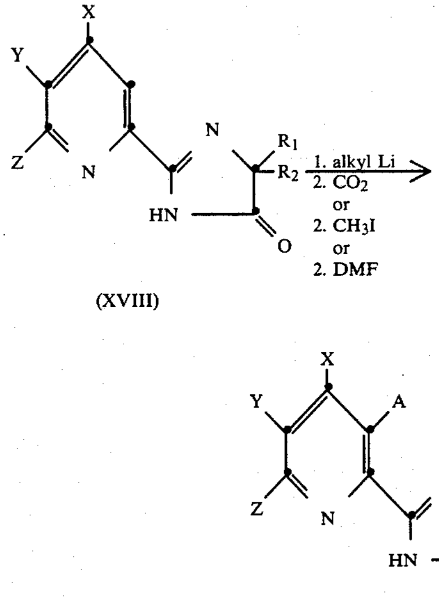

(XVIII)

A = COOH
A = $CH_3$
A = CHO

Advantageously, the formula (I) imidazolinones can be prepared by a rather unique procedure involving heating, from about 1 to 20 equivalents and preferably at least 1.5 equivalents of a 5-substituted formula (LXX) 2-picoline with at least 1 equivalent of an appropriate formula (XIII) aminocarboxamide in the presence of at least 3 equivalents of sulfur. In this reaction, at least a 3 to 1 ratio of sulfur to aminocarboxamide is essential for good product yields. Also, at least 1 and preferably 1.5 equivalents of the picoline is required for good product yields. However, with regard to the picoline, it is found that said compound, while being a reactant, may also be used as a solvent for the reaction mixture and used in large excess. The reaction mixture is boiled, and the vapors therefrom passed through a column packed with molecular sieves to remove any water formed during reaction. The dried condensate is then returned to the reaction vessel, and heating of the mixture is continued for several hours. Thereafter, the mixture is cooled, dissolved in an organic solvent such as ethyl acetate, diethyl ether or the like and filtered. The filtrate is extracted with aqueous mineral acid such as sulfuric acid or hydrochloric acid, and the aqueous phase treated with aqueous base to liberate the formula (I) imidazolinone. If the product precipitates as a solid, it is recovered by filtration; if as an oil, it is extracted into a solvent such as dichloromethane, ether, and the like, and the product purified by conventional methods. The reaction may be graphically illustrated as follows:

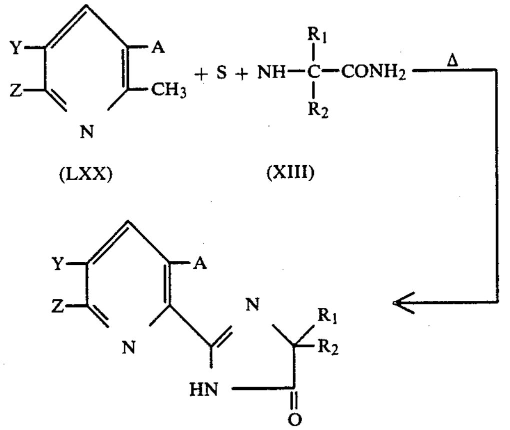

(LXX) (XIII)

(I)

wherein Z is hydrogen; Y is hydrogen, $C_1$-$C_6$ alkyl, $C_1$-$C_6$ alkoxy, phenyl or substituted phenyl; A is hydrogen, $CH_3$ or $COOR_3$ where $R_3$ is $C_1$-$C_{12}$ alkyl and $R_1$ and $R_2$ are $C_1$-$C_4$ alkyl; and when taken together, they may represent $C_3$-$C_6$ cycloalkyl optionally substituted with methyl and when $R_1$ and $R_2$ are not the same, the optical isomers thereof; and when taken together, Y and Z may form a ring in which YZ is —CH═CH—CH═CH— and A, $R_1$, $R_2$ and $R_3$ are as described above. This process is described in U.S. Pat. No. 4,474,962 (1984) incorporated herein by reference thereto. Said processs is thus highly effective for preparing variously substituted formula (XVIII) imidazolinones from 2-picolines and substituted quinaldines.

Preparation of the 5-alkoxy-2-picoline employed in the above reaction for the preparation of 2-(5-alkoxy-2-pyridyl)-5,5-di(lower)alkyl-2-imidazolin-4-one compounds is achieved by reacting 5-hydroxy-2-methylpyridine with an equivalent amount of a $C_1$-$C_4$ alkyl iodide in the presence of sodium hydride and a solvent such as dry dimethylformamide at a temperature of from 0° to 5° C. under a blanket of inert gas such as nitrogen.

Advantageously, the formula (I) acids may be converted to the formula (VII) 5-H-imidazo[1',2':1,2]pyrrolo[3,4-b]pyridine-3(2H),5-diones by reaction with dicyclohexylcarbodiimide (DCC). The reaction is preferably conducted using approximately an equimolar amount of the carbodiimide in the presence of a chlorinated hydrocarbon solvent at a temperature between about 20° C. to 32° C. The reaction may be graphically illustrated as follows:

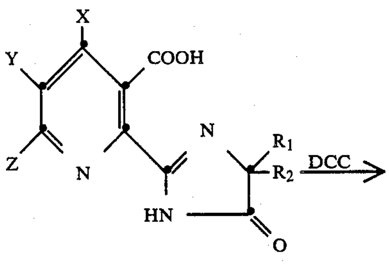

(I)

-continued

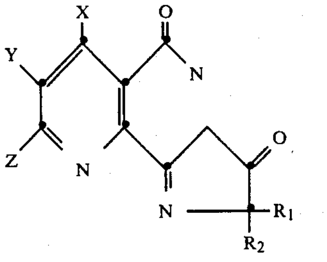

(VII)

The formula (VII) 5H-imidazo[1',2':1,2]pyrrolo[3,4-b]pyridine-3(2H),5-diones are isomers of the formula (III) imidazopyrrolopyridinediones referred to above, and are especially useful in the preparation of a variety of the formula (I) 2-(2-imidazolin-2-yl)pyridine derivatives of the present invention, as will become apparent from the following discussion.

In practice, it is found that the formula (VII) 3(2H),5-diones can be reacted with at least one equivalent of an appropriate formula (V) $R_3OH$ alcohol in the presence of triethylamine as catalyst to yield the formula (I) pyridine ester corresponding to the alcohol used. The reaction is preferably conducted at a temperature between about 20° C. and 50° C. in the presence of an inert aprotic solvent, such as tetrahydrofuran, dioxane or the like. The reaction may be illustrated as follows:

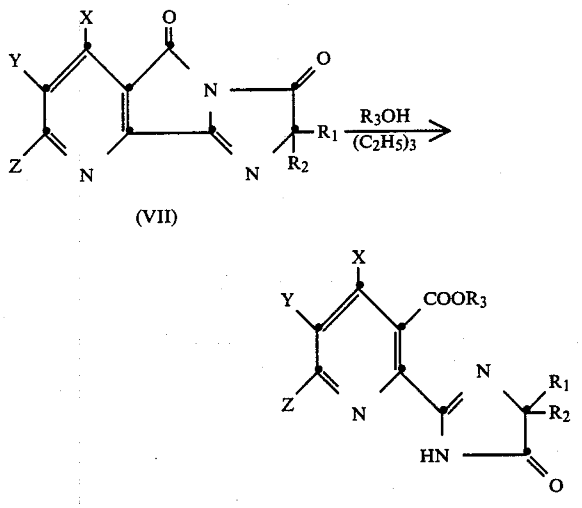

(VII)

(Ib)

wherein $R_3$ represents a substituent as described above, excepting that hydrogen and salt-forming cations are excluded, and $R_1$, $R_2$, X, Y and Z, are as described above.

The formula (VII) 3(2H),5-diones are also readily converted to the formula (Ib) 2-(2-imidazolin-2-yl)pyridine derivatives wherein $R_1$, $R_2$, X, Y and Z, are as described above; W is oxygen; B is hydrogen, and A is acetyl, benzoyl, trimethylphosphonoacetate or hydroxymethyl; by reaction thereof with methyl magnesium bromide, phenyl lithium, sodium trimethyl phosphonoacetate or sodium borohydride; respectively. The methyl magnesium bromide, phenyl lithium and sodium trimethylphosphonoacetate reactions are preferably carried out at a temperature between about −50° C. and −80° C., in the presence of an inert solvent such as tetrahydrofuran or dioxane under a blanket of inert gas, such as nitrogen. Reaction of the above-said formula (VII) diones with sodium borohydride is relatively mild. The reaction does not require a blanket of inert gas and can be conducted at temperatures between about −10° C. and +15° C.

Reaction of the formula (VII) diones with at least one equivalent of acetone oxime yields the acetone oxime ester of the formula (I) 2-(2-imidazolin-2-yl)pyridine where A is $COON{=}C(CH_3)_2$, B is hydrogen and $R_1$, $R_2$, X, Y and Z, are as described for formula (I) pyridine derivatives. The above reaction is generally conducted in the presence of an inert organic solvent such as toluene, benzene, xylene or the like at a temperature between about 40° C. and 80° C.

The above reactions are graphically illustrated below:

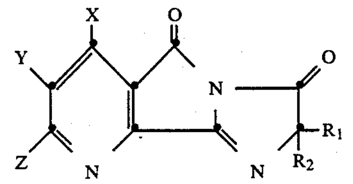

Reactants

1. $CH_3MgBr$
2. Phenyl lithium
3. Sodium trimethyl phosphonoacetate
4. $NaBH_4$
5. $HON{=}C(CH_3)$

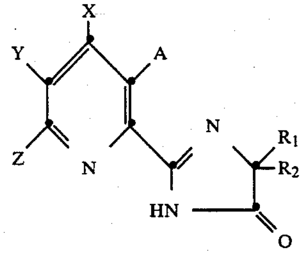

A in Formula I

1. $COCH_3$
2. $COC_6H_5$
3. $COCH—COOCH_3$
   $|$
   $P(OCH_3)_2$
   $||$
   O
4. $CH_2OH$
5. $COON{=}C(CH_3)_2$ wherein $R_1$, $R_2$, X, Y and Z are as described above.

Formula (I) compounds, wherein A is $COOR_3$ and $R_3$ represents a salt-forming cation such as an alkali metal, alkaline earth metal, ammonium or aliphatic ammonium and $R_1$, $R_2$, X, Y and Z are as described above, can be prepared by dissolving the formula (I) 2-(2-imidazolin-2-yl)pyridine acid in an appropriate solvent and, thereafter, treating the solution of the acid with one equivalent of salt-forming cation. For compounds in which the salt-forming cation is an inorganic salt such as sodium, potassium, calcium, barium or the like, the formula (I) acid may be dissolved or dispersed in water or a lower alcohol or mixtures thereof. One equivalent of the salt-forming cation generally in the form of the hydroxide, carbonate, bicarbonate or the like, but preferably as the hydroxide, is admixed with the solution of the formula (I) acid. After several minutes, the formula (I) compound, wherein $R_3$ is the inorganic salt-forming cation, generally precipitates and can be recovered from the mixture by either filtration or through azeotropic distillation with an organic solvent such as dioxane.

To prepare the formula (I) compound in which A is $COOR_3$ and $R_3$ is ammonium or organic ammonium, the formula (I) acid is dissolved or dispersed in an organic solvent such as dioxane, tetrahydrofuran or the like, and the mixture treated with one equivalent of ammonia or the amine or the tetralkylammonium hydroxide. Among the amines which may be used in the above-said reaction are: methylamine, ethylamine, n-propylamine, iso-propylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, tallowamine, cyclopentylamine, cyclohexylamine, dicyclohexylamine, piperidine, morpholine, and pyrrolidine. Among tetralkylammonium hydroxides contemplated methyl, tetraethyl, trimethylbenzylammonium hydroxides. In practice, after several minutes, the ammonium or organic ammonium salt precipitates and can be separated from the solution by any convenient means, as by filtration or centrifugation. Additionally, the reaction mixture may be concentrated, and the remaining solvent removed with hexane, and the residue then dried to recover the ammonium or organic ammonium formula (I) salt. The above reactions may be graphically illustrated as follows:

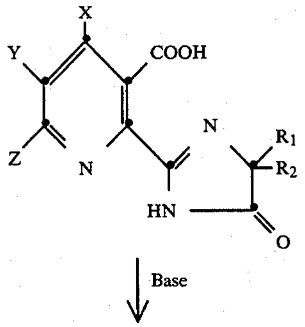

-continued

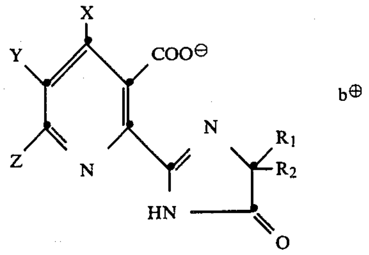

wherein $R_1$, $R_2$, X, Y and Z are as described above, and b is the salt forming cation.

When $R_1$ and $R_2$ represent different substituents, the carbon to which $R_1$ and $R_2$ are attached is an asymmetric center, and the products (as well as their intermediates) exist in d- and l-forms as well as dl-forms.

It should also be understood that the 2-(2-imidazolin-2-yl)pyridines and quinolines represented by formula (I) in which B=H may be tautomeric, while for convenience, they are depicted by a single structure identified as formula (I), they may exist in either of the isomeric forms illustrated as follows:

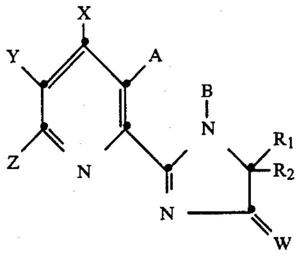

(I)

OR

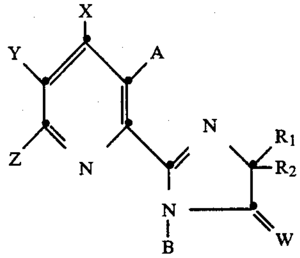

(I)

wherein A, W, X, Y, Z, $R_1$ and $R_2$ are as hereinabove defined and B is H. As such, both isomeric forms of the 2-(imidazolin-2-yl)pyridines and 2-(2-imidazolin-2-yl)quinolines are meant to be included under the formula (I) definitions.

One general method for the preparation of the formula (I) compounds involves the reaction of a quinolinic anhydride of formula (XVI) hereinbelow, with an appropriately substituted α-aminocarbonitrile of formula (XVII), hereinbelow, to yield a mixture of the monoamides of quinolinic acid of formula (IX) and formula (X).

This reaction is carried out at a temperature between about 20° C. and 70° C. and preferably between about 35° C. and 40° C. in an inert solvent, such as tetrahydrofuran, methylene chloride, ether, chloroform, toluene or the like. The thus-formed acids are then cyclized to the corresponding pyrrolopyridine acetonitrile, depicted by formula (XI), by heating the reaction mixture with an excess of acetic anhydride in the presence of a catalytic amount of sodium acetate or potassium acetate.

In general, the above reaction is carried out by treating the reaction mixture with acetic anhydride, acetyl chloride, thionyl chloride or the like and heating said mixture to a temperature between about 20° C. and 100° C. Hydration of the thus-formed pyrrolopyridine acetonitrile formula (XI) is carried out by treating said acetonitrile with a strong acid such as sulfuric acid. This reaction yields the formula (XII) pyrrolopyridine acetamide. Although the addition of a non-miscible solvent such as methylene chloride, chloroform or the like is not essential to the conduct of the above described reaction, addition of such a solvent to the reaction mixture is generally preferred. Said reaction is usually carried out at a temperature between about 10° C. to 70° C.

The cyclization of the formula (XII), hereinbelow, pyrrolopyridine acetamide yields the tricyclic formula (III) imidazopyrrolopyridinediones which are intermediates for the imidazolinyl nicotinic acids and esters of the present invention referred to above and represented by formula (Ib).

The product of this reaction is predominantly the desired imidazopyrrolopyridinedione (85%) together with the isomer of formula (IIIa). Mixtures of this ratio of the two isomers generally give substantially isomerically pure nicotinate product.

The cyclization reaction is preferably conducted at a temperature of from 80° C. to 150° C. in the presence of a base such as sodium or potassium hydride or an acid such as an aromatic sulfonic acid and a solvent which will form an azeotropic mixture with water, permitting virtually immediate removal thereof from the reaction mixture as it is formed. Among the solvents which may be employed are toluene, benzene, xylenes and cyclohexane. Bases which may be used include alkali metal hydroxides, alkali metal hydrides, alkali metal oxides, tertiary amines such as diisopropyl ethylamine, 1,5-diazabicyclo[3.4]nonene-5,1,5-diazobicyclo[5.4.0]undecene-5,1,4-diazabicyclo[2.2.2]octane, tetramethylguanidine, potassium fluoride and quaternary ammonium hydroxide, such as trimethylbenzyl ammonium hydroxide and strongly basic ion exchange resins.

Finally, acidic reagents which can be employed herein include aromatic sulfonic acids, such as p-toluenesulfonic acid, β-naphthalenesulfonic acid, naphthalenedisulfonic acid, and the like.

The mixture of compounds of formula (III) and formula (IIIa) is then converted to formula (Ib), as discussed above, with an alkali metal alkoxide and alcohol.

The above reactions are graphically illustrated on Flow Diagram I below, when X, Y, Z, $R_1$, $R_2$ and $R_3$ are as defined above.

FLOW DIAGRAM I

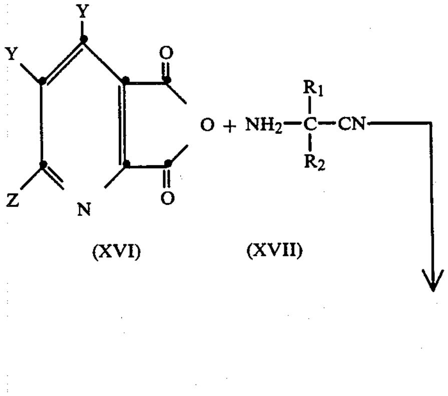

(XVI) (XVII)

-continued

FLOW DIAGRAM I

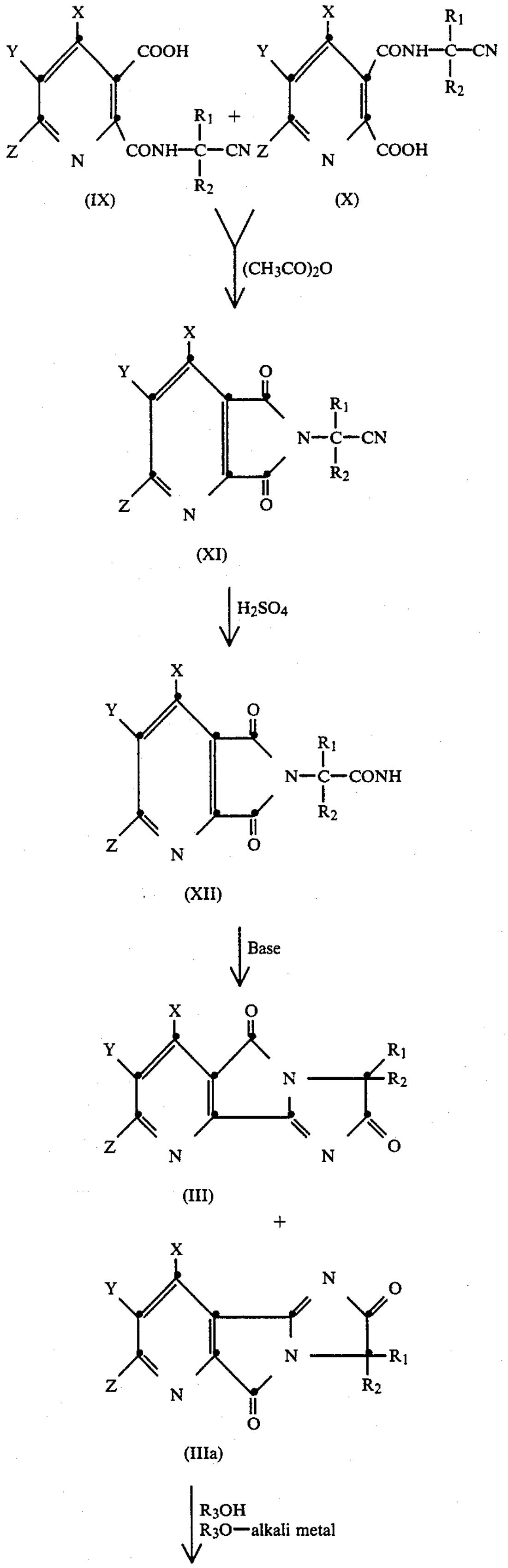

-continued

FLOW DIAGRAM I

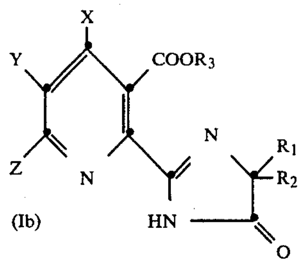

(Ib)

Another general method for the preparation of the formula (I) pyridine derivatives involves the reaction of a quinolinic anhydride of formula (XVI), with an appropriately substituted α-aminocarboxylic acid such as α-methylvaline represented by formula (XIX), preferably in a ketonic solvent such as acetone under a blanket of nitrogen to yield an isomeric mixture of the formula (XX) and formula (XXI) acids. The mixture is then treated with acetic anhydride and a catalytic amount of sodium acetate at an elevated temperature to give the dihydrodioxopyrrolopyridine acid formula (XXII). Reaction of the thus-formed acid with a thionyl halide, such as thionyl chloride or thionyl bromide, in the presence of an organic solvent such as toluene, xylene, benzene or the like, at an elevated temperature, i.e., 80° C. to 150° C., gives the formula (XXIII) acid halide corresponding to the formula (XXII) acid. Treatment of this acid halide with excess ammonia then yields the formula (IV) dihydrodioxopyrrolopyridine acetamide. The reaction is preferably carried out in the presence of an aprotic solvent.

Reaction of the formula (IV) acetamide with 1,8-diazabicyclo[5,4,0]undec-7-ene in an inert organic solvent such as toluene or xylene at an elevated temperature between about 80° C. and 125° C. gives the formula (III) imidazopyrrolopyridinedione which may be heated with morpholine or an appropriate $NH_2R_6$ amine to yield the 2-(2-imidazolin-2-yl)nicotinamides. These reactions are illustrated as Flow Diagram II.

FLOW DIAGRAM II

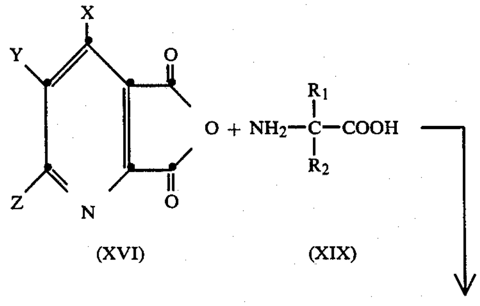

(XVI) (XIX)

-continued

FLOW DIAGRAM II

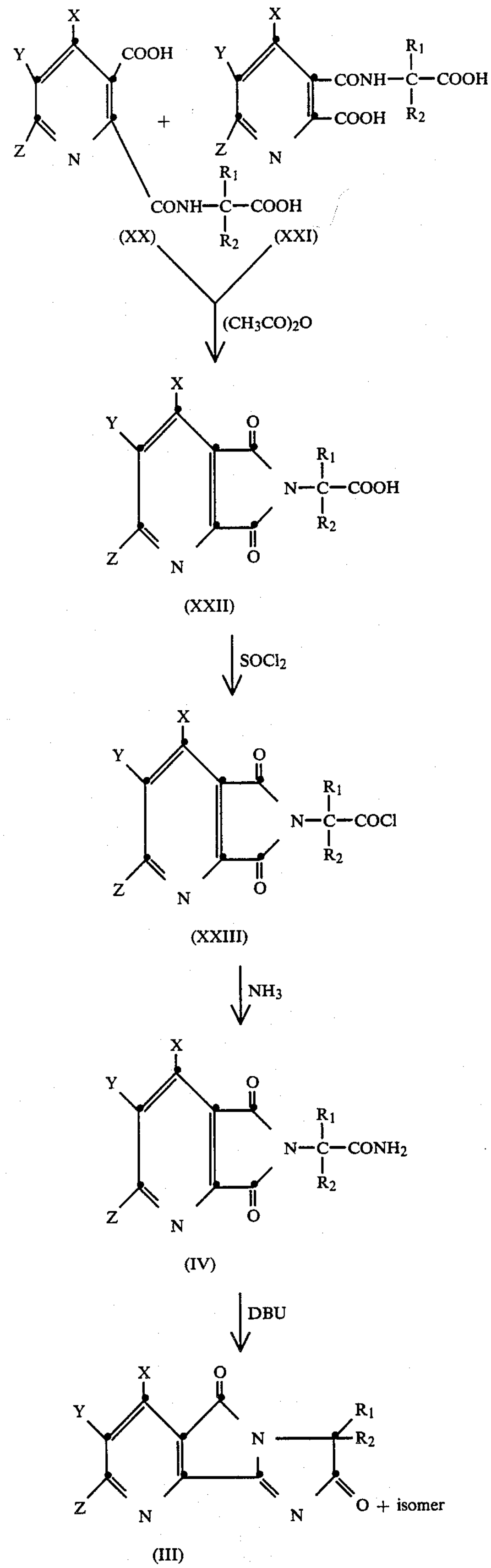

-continued

FLOW DIAGRAM II

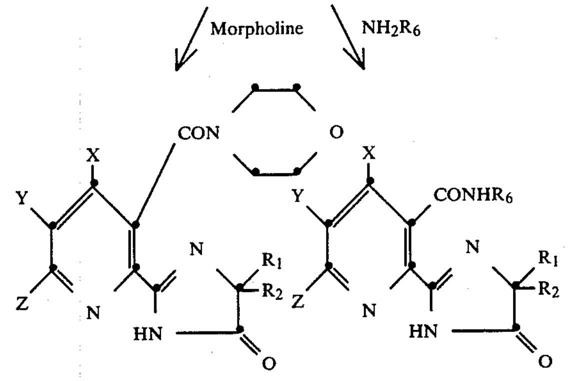

As described and graphically illustrated in Flow Diagrams I and II above, quinolinic anhydrides of formula (XVI) are used in the preparation of the herbicidally-effective formula (I) 2-(2-imidazolin-2-yl)pyridine and quinoline compounds. While said quinolinic anhydrides can be prepared by any of the several synthetic routes described in the chemical literature, a particularly effective method of synthesis of these compounds involves reaction of an appropriate formula (LXXI) acetylenic ketone having the structure: Z—CO—C≡CH, wherein Z is hydrogen, $C_1$-$C_6$ alkyl or phenyl optionally substituted with $C_1$-$C_4$ alkyl, halogen, $C_1$-$C_4$ alkoxy, nitro, or $C_1$-$C_4$ alkylthio; with an appropriate formula (LXXII) aminomaleate having the structure:

$$\begin{array}{l} H_2NC—CO—Q' \\ \;\;\;\;\;\| \\ \;\;\;HC—CO—Q' \end{array}$$

wherein Q' is $C_1$-$C_4$ alkoxy; or an appropriate formula (LXXIII) aminofumarate having the structure:

$$\begin{array}{l} Q'—CO—C—NH_2 \\ \;\;\;\;\;\;\;\;\;\;\;\;\;\;\| \\ \;\;\;\;\;\;\;\;\;\;\;\;HC—CO—Q' \end{array}$$

wherein Q' is $C_1$-$C_4$ alkoxy. The ratio of acetylenic ketone to aminomaleate or aminofumarate is preferably about 1:1 and the reaction is generally carried out in a polar solvent such as dimethylformamide (DMF), acetonitrile or a $C_1$-$C_4$ alcohol, preferably ethanol, at a temperature between about 50° and 100° C. This reaction yields the 6-substituted-2,3-pyridinedicarboxylic acid diester of formula (LXXIV).

This process is described in U.S. Pat. No. 4,460,776 (1984) incorporated herein by reference thereto. The formula (LXXIV) diester may then be hydrolyzed to the corresponding 6-substituted-2,3-pyridinedicarboxylic acid by reaction thereof with a strong base such as potassium hydroxide or sodium hydroxide at a temperature between about 30° and 100° C., preferably in the presence of a water miscible solvent such as methanol or ethanol. The reaction mixture is then cooled and treated with a strong mineral acid, such as sulfuric acid. The reaction mixture is then treated with a ketonic solvent such as acetone and solid sodium sulfate, filtered and the filtrate concentrated. The remaining residue is triturated with ether, and the formula (LXXV) recovered. Treatment of the formula (LXXV) 6-substituted- 2,3-pyridinedicarboxylic acid with, for example, acetic anhydride in the presence of dimethoxyethane and pyridine yields the desired 6-substituted-2,3-pyridinedicarboxylic acid anhydride of formula (XVI). This reaction is graphically illustrated in Flow Diagram II-A below.

FLOW DIAGRAM II-A

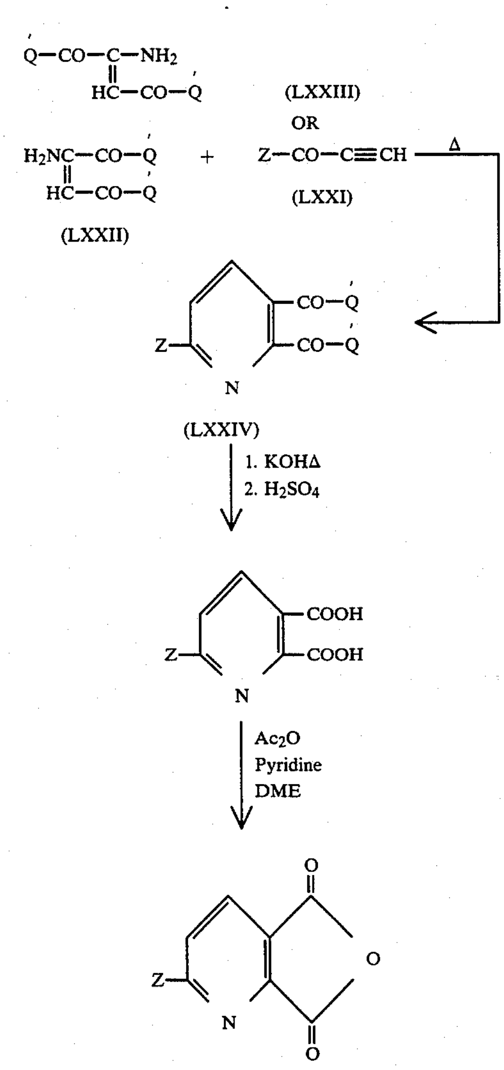

It has also been found that heating the formula (LXXIII) aminofumarate with an equivalent amount of 2-formylcyclohexanone at a temperature between about 100° and 200° C. will yield the dialkyl 5,6,7,8-tetrahydroquinoline-2,3-dicarboxylate of formula (LXXVI). This reaction may be illustrated as follows:

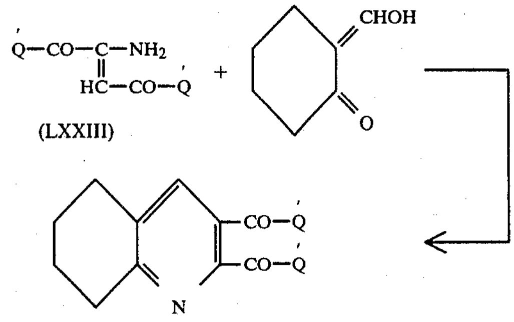

(LXXVI)

herein Q is $C_1$–$C_4$ alkoxy. The thus-formed diester can then be converted to the corresponding diacid by heating with strong base and thereafter acidifying the reaction mixture with a strong mineral acid, such as sulfuric acid. The thus-formed diacid can then be reacted with acetic anhydride, dimethoxyethane and pyridine to obtain the pyridine-2,3-dicarboxylic acid anhydride.

Reaction of the formula (LXXIII) aminofumarate with 4-dimethylamino-3-methyl-3-buten-2-one in the presence of acetic acid, at a temperature between about 50° and 100° C., yields the 5,6-dimethylpyridine-2,3-dicarboxylic acid dimethyl ester which can be hydrolyzed to the corresponding acid by the procedure described in Flow Diagram II-A above. The diacid is then readily converted to corresponding 5,6-dimethyl quinolinic anhydride of formula (XVI) using, for example, acetic anhydride pyridine and dimethoxyethane as described above.

A preferred method for preparing the 2-(5,5-disubstituted-4-oxo(or thioxo)-2-imidazolin-2-yl)nicotinic acids and 3-quinolinecarboxylic acids involves: the reaction of an appropriately substituted formula (XVI) quinolinic anhydride with an aminocarboxamide or aminothiocarboxamide depicted by formula (XIIIa) to yield an isomeric mixture of the formula (XVa) carbamoylnicotinic or 3-quinolinecarboxylic acid and formula (XVb) carbamoylpicolinic or quinaldic acid. This reaction is carried out, preferably using equivalent amounts of the anhydride and carboxamide or thiocarboxamide, in the presence of an inert organic solvent such as a low-boiling ether (diethyl ether, tetrahydrofuran, dimethoxyethane), acetonitrile, ethyl acetate or a halogenated hydrocarbon; at a temperature between about 20° and 60° C. and preferably 25° to 30° C., under a blanket of inert gas such as nitrogen. When the reaction is essentially complete, the product is isolated by any convenient means, e.g., filtration, distillation of the solvent or by extraction into aqueous base if the solvent is water-immiscible; giving the isomeric pyridine monoacid/monoamide products or the isomeric quinoline monoacid/monoamide products shown as formula (XVa) and formula (XVb) in Flow Diagram II-B.

The thus-formed mixture is then heated to a temperature of from 25° to about 110° C. (i.e., reflux temperature) with about 2 to 10 molar equivalents of aqueous or aqueous alcoholic sodium or potassium hydroxide, preferably under a blanket of inert gas such as nitrogen. The mixture is cooled to about 25° C. and acidified to pH 2 to 4 with a strong mineral acid such as hydrochloric acid or sulfuric acid to give the herbicidal product. If the product is insoluble in water, it will precipitate from the aqueous phase and can be recovered by filtration or extraction. If the product is soluble in water, the mixture can be extracted with an organic solvent such as ether or methylene chloride, and the extract concentrated to provide the herbicidally effective 2-(5,5-disubstituted-4-oxo-(or thiono)-2-imidazolin-2-yl)nicotinic or 3-quinolinecarboxylic acids, encompassed by formula (I).

This process is described in U.S. Pat. No. 4,518,780 (1985) incorporated herein by reference thereto.

FLOW DIAGRAM II-B

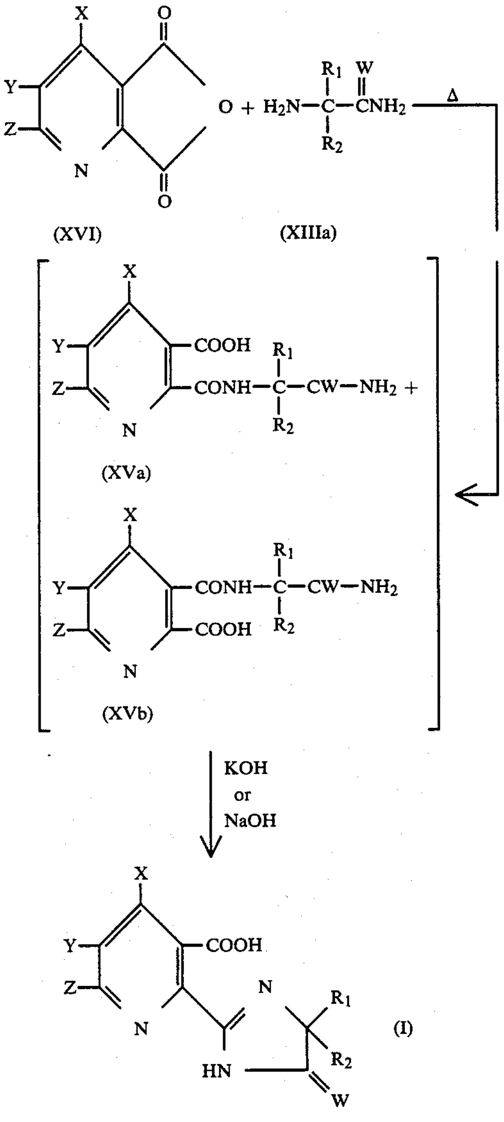

(XVI) (XIIIa) (XVa) (XVb) (I)

In another general procedure, the 2-(2-imidazolin-2-yl)pyridine acids and esters of formula (I), can be prepared by reacting the 2-carboalkoxynicotinoyl chloride of formula (XIV), hereinbelow, preferably as the methyl ester and preferably in the form of the hydrochloride salt, with the appropriate aminocarboxamide depicted by formula (XIII). The reaction yields the carbamoyl picolinate, formula (XV), and is preferably carried out in an inert blanket of gas such as nitrogen. The reaction mixture is generally maintained at a temperature below 30° C. during the reaction period.

The thus-formed carbamoyl picolinate, formula (XV), hereinbelow, can then be dispersed in an inert non-protic solvent such as xylene or toluene and heated to about 50° C. to 130° C. with 1,5-diazabicyclo-[5.4.0]undec-5-ene. The reaction yields a mixture of the formula (III) and formula (IIIa), imidazopyrrolopyridinedione isomers which can be used without separation in the following reaction, wherein the reaction mixture is treated with an alkali metal alkoxide, in the presence of an alcohol to yield a mixture of the imidazolinyl nicotinate and the imidazolinyl picolinate. The desired formula (Ib) nicotinate can be readily separated from the picolinate by neutralizing the reaction mixture, preferably with glacial acetic acid, concentrating the neutralized solution and chromatographing the resulting residue on silica gel in ether.

Conversion of the imidazolinyl nicotinate esters to the corresponding acids or acid addition salts can be readily achieved by the methods previously described. Similarly, the imidazolinyl nicotinic acids can be converted to the corresponding alkali metal, ammonium, or organic ammonium salts by the methods previously described.

Preparation of the formula (I) acids and esters, by the route described above, is graphically illustrated in Flow Diagram III below.

FLOW DIAGRAM III

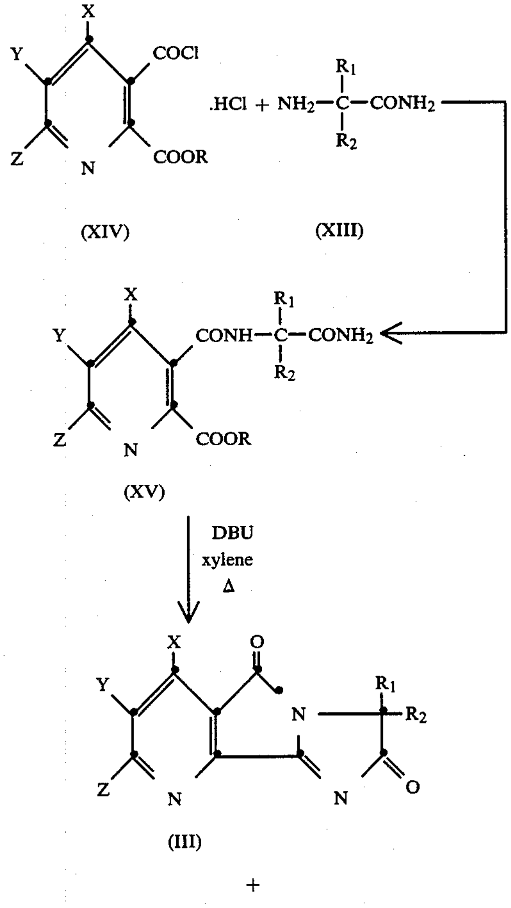

(XIV) (XIII) (XV) (III)

+

-continued

FLOW DIAGRAM III

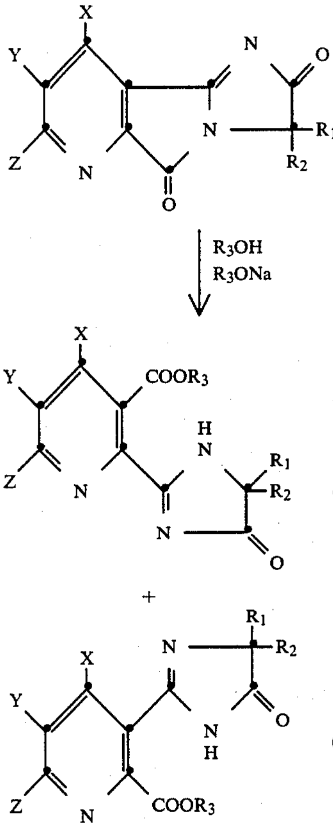

(IIIa)

(Nicotinate)
(Ib)

(Picolinate)

Advantageously, many of the formula (II) 2-(2-imidazolin-2-yl)quinoline derivatives of the present invention can be prepared by the procedure described above for the preparation of the formula (I) 2-(2-imidazolin-2-yl)pyridine compounds. For example, the formula (XXXVI) 2-(2-imidazolin-2-yl)quinolinecarboxylate esters, wherein $R_3$ represents a substituent other than hydrogen or a salt-forming cation, and $R_1$, $R_2$, X, L, M, Q and $R_7$ are as described above, can be prepared by reacting the formula (XXXVII) dione, with an appropriate alcohol and alkali metal alkoxide at a temperature between about 20° C. and 50° C. In these reactions, as with similar reactions in which the formula (I) pyridines are prepared, the alcohol can function both as a reactant and a solvent. As such, a secondary solvent is not required, but can be employed if so desired. When a secondary solvent is used, it is preferable to employ a non-protic solvent such as tetrahydrofuran or dioxane. The reaction may be illustrated as follows:

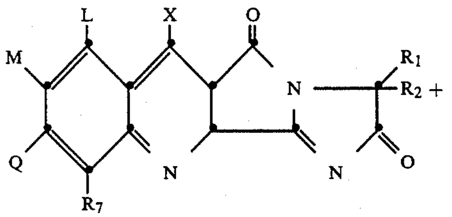

(XXXVII)

-continued

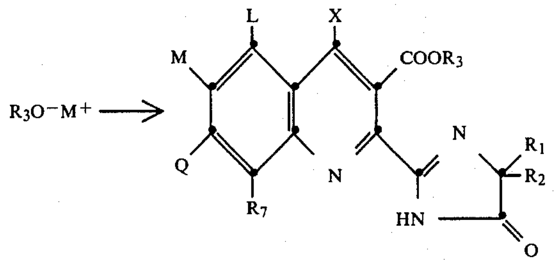

(XXXVI)

where M is an alkali metal; X is hydrogen, halogen, hydroxyl or methyl, with the proviso that when one of L, M, Q or $R_7$ is a substitutent other than hydrogen, halogen, $C_1$–$C_6$ alkyl, or $C_1$–$C_4$ alkoxy, X is hydrogen; L, M, Q and $R_7$ each represent members selected from the group consisting of hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, $NO_2$, CN, phenyl, phenoxy, amino, $C_1$–$C_4$ alkylamino, diloweralkylamino, chlorophenyl, methylphenyl or phenoxy substituted with one Cl, $CF_3$, $NO_2$ or $CH_3$ group, with the proviso that only one of L, M, Q, or $R_7$ may represent a substituent other than hydrogen, halogen, $C_1$–$C_4$ alkyl or $C_1$–$C_4$ alkoxy, and $R_1$, $R_2$ and $R_3$ are as described above.

The formula (XXXVI) 2-(2-imidazolin-2-yl)quinolinecarboxylate esters can also be prepared from a formula (XXXVIII) dioxopyrroloquinoline acetamide, wherein $R_1$, $R_2$, X, L, M, Q and $R_7$ are as described above, by cyclization thereof with a strong base, such as 1,5-diazabicyclo[5.4.0]undec-5-ene (DBU) in the presence of an inert organic solvent such as xylene or toluene to give the crude imidazopyrroloquinolinedione of formula (XXXVII). The reaction mixture is heated to a temperature between 100° C. and 150° C., and water removed from the reaction mixture using a Dean-Stark water separator. At least one equivalent of alcohol $R_3OH$ represented by formula (V); wherein $R_3$ is a substituent as described above, but excluding hydrogen and salt-forming cations, is then added to the reaction mixture, and the thus prepared mixture heated to reflux at a temperature between 100° C. and 150° C. to yield the formula (XXXVI) ester. The reaction may be graphically illustrated as follows:

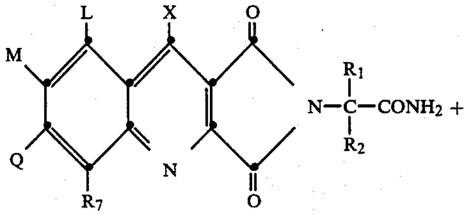

(XXXVIII)

-continued

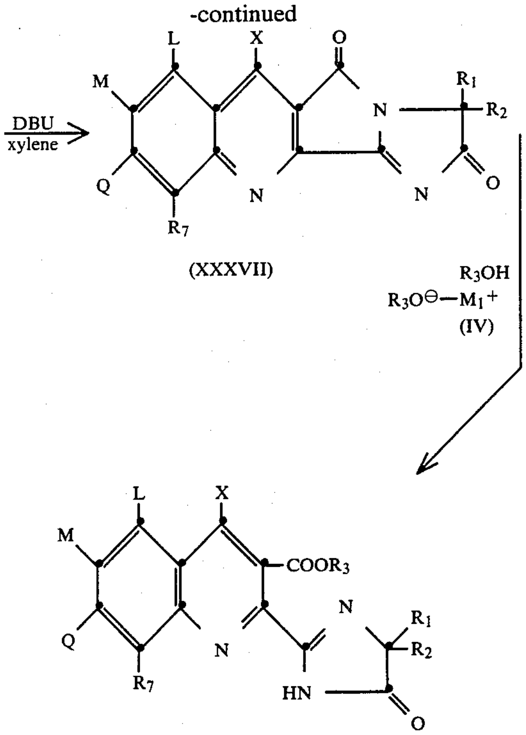

(XXXVII)

(XXXVI)

wherein $R_1$, $R_2$, $R_3$, X, L, M, Q and $R_7$ are as described above.

The formula (XXXVI) 2-(2-imidazolin-2-yl)quinolinecarboxylate esters can also be prepared by cyclization of a carbamoyl quinolinecarboxylate ester, represented by formula (XXXIX), with phosphorus pentachloride at an elevated temperature between about 60° C. and 100° C. The reaction is generally conducted in the presence of an inert organic solvent, such as toluene or benzene, and yields the hydrochloride salt of the formula (XXXVI) 2-(2-imidazolin-2-yl)quinolinecarboxylate ester. Treatment of the thus formed hydrohalide salt with base, such as sodium or potassium carbonate, then yields the formula (XXXVI) 2-(2-imidazolin-2-yl)quinolinecarboxylate ester. The carbamoyl quinolinecarboxylate ester, formula (XXXIX), used in the above reaction may be shown as follows:

(XXXIX)

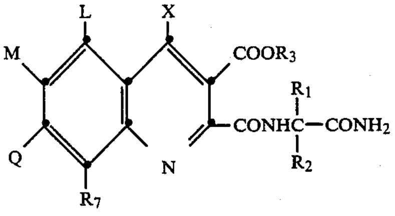

wherein $R_3$ is a substituent as described above, but excluding hydrogen or a salt-forming cation and $R_1$, $R_2$, X, L, M, Q and $R_7$ are as described above.

The 2-(2-imidazolin-2-yl)quinolinecarboxylate esters of formula (XXXVI) are also formed by cylization of the carbamoyl quinolinecarboxylate esters represented by formula (XXXIX), and having the structure:

(XXXIX)

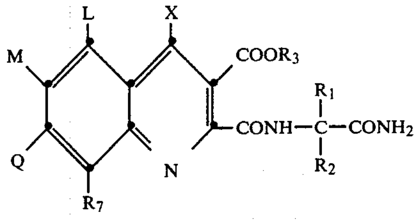

wherein $R_3$ is as described above excepting that hydrogen and salt-forming cations are excluded and $R_1$, $R_2$, X, L, M, Q and $R_7$ are as described above. Cyclization of the carbamoyl quinolinecarboxylate ester is achieved by reaction thereof with a mixture of phosphorus pentachloride and phosphorus oxychloride. The reaction mixture is stirred for several hours at a temperature between about 15° C. and 35° C., and the $POCl_3$ then removed in vacuo. The residue from this treatment is dispersed in an organic solvent such as toluene. The solvent is then separated from the resulting mixture, and the remaining residue dispersed in water heated to between 80° C. and 100° C. After cooling, the pH of the aqueous mixture is adjusted to 5–6 with sodium or potassium bicarbonate, and the product extracted into methylene chloride to give the 2-(2-imidazolin-2-yl)quinolinecarboxylate ester, formula (XXXVI).

The formula (XXXVI) quinoline ester in which $R_3$ is as described above, but excluding hydrogen or salt-forming cations, and $R_1$, $R_2$, X, L, M, Q and $R_7$ are as described above, is readily converted to its corresponding acid addition salt by reaction of said ester with at least one equivalent of a strong acid. Strong mineral acids such as hydrochloric acid, sulfuric acid, and hydrobromic acid are employed although organic acids may also be used. In practice, it is also found that the reaction proceeds most satisfactorily when conducted in the presence of an inert organic solvent such as ether, chloroform, methylene, chloride, or mixtures thereof. Sulfuric acid salts are generally prepared by this procedure, but substituting a lower aliphatic alcohol for the above-mentioned solvents.

Preparation of the formula (II) 2-(2imidazolin-2-yl)quinoline derivatives wherein A is COOH: B is hydrogen; W is oxygen and $R_1$, $R_2$, X, L, M, Q and $R_7$ are as defined, with the proviso that X, L, M, Q and $R_7$ are not halogen or nitro, can be achieved by hydrogenolysis of the benzyl ester of the formula (XXXVI) 2-(2-imidazolin-2-yl)quinolinecarboxylate. The reaction involves dispersion of the benzyl ester in an organic solvent, such as described above for the hydrogenolysis of the formula (XV) benzyl ester in the 2-(2-imidazolin-2-yl)pyridine series, and treatment of the thus-prepared reaction mixture with hydrogen gas in the presence of a catalyst such as palladium or platinum on a carbon carrier. The hydrogenolysis is generally carried out at a temperature between about 20° C. and 50° C.

The acids of the formula (II) 2-(2-imidazolin-2-yl)quinoline derivatives in which A is COOH; B is hydrogen; W is oxygen and $R_1$, $R_2$, X, L, M, Q and $R_7$ are as described above, are also prepared by reaction of a formula (XXXVI) ester, in which $R_3$ is a substituent as described above, but excluding hydrogen and salt-forming cations and $R_1$, $R_2$, X, L, M, Q and $R_7$ are as described, with at least one equivalent of strong aqueous base, such as an aqueous solution of an alkali metal hydroxide, at a temperature between 20° C. and 50° C.

The mixture is cooled and then adjusted to pH 6.5 to 7.5 with a strong mineral acid. Such treatment yields the desired acid.

Preparation of the formula (II) 2-(2-imidazolin-2-yl)quinoline derivatives in which A is $COOR_3$; $R_3$ is a salt-forming cation; B is hydrogen; W is oxygen and $R_1$, $R_2$, L, M, Q and $R_7$ are as described above, can be prepared by dissolving an acid, represented by formula (II) wherein A is COOH; B is hydrogen; W is oxygen and $R_1$, $R_2$, L, M, Q and $R_7$ are as described above, in an appropriate solvent and treating the thus prepared mixture with at least one equivalent of a salt-forming cation. The reaction is essentially the same as described for the preparation of the formula (I) pyridines in which A is $COOR_3$ and $R_3$ is a salt-forming cation.

It should also be understood that the imidazolinyl quinolinearcarboxylic acids and esters depicted by formula (II) in which B is H may be tautomeric.

It should also be understood that when $R_1$ and $R_2$ represent different substituents on the formula (II) 2-(2-imidazolin-2-yl)quinoline derivatives and the formula (XXXVII) imidazopyrroloquinolinediones, the carbon to which $R_1$ and $R_2$ are attached is an asymmetric center, and the products (as well as their intermediates) exist in d- and l- forms as well as dl forms.

Cyclization of the formula (XXXVIII) imidazopyrroloquinoline acetamide yields the tetracyclic formula (XXXVII) and formula (XXXVIIa) imidazopyrroloquinolinediones which are intermediates for the formula (II) 2-(2-imidazolin-2-yl)quinolinecarboxylate acids and esters.

The product of this reaction is predominately the desired imidazopyrroloquinolinedione together with a small amount of the formula (XXXVIIa) isomer. Treatment of the isomeric mixture with an alkali metal alkoxide gives substantially isomerically pure quinolinecarboxylate product.

The cyclization reaction is preferably conducted at a temperature of from 80° C. to 150° C. in the presence of a base such as sodium or potassium hydride or an acid such as an aromatic sulfonic acid and a solvent which will form an azeotropic mixture with water, permitting virtually immediate removal thereof from the reaction mixture as it is formed. Among the solvents which may be employed are toluene, benzene, xylenes and cyclohexane. Bases which may be used include alkali metal hydroxides, alkali metal hydrides, alkali metal oxides, tertiary amines such as diisopropyl ethylamine, 1,5-diazabicyclo[3.4]nonene-5,1,5-diazobicyclo[5.4.0]undecene-5,1,4-diazabicyclo[2.2.2]octane, tetramethylguanidine, potassium fluoride and quaternary ammonium hydroxide, such as trimethylbenzyl ammonium hydroxide and strongly basic ion exchange resins.

Finally, acidic reagents which can be employed herein include aromatic sulfonic acids, such as p-toluenesulfonic acid, $\beta$-naphthalenesulfonic acid, naphthalenedisulfonic acid, and the like.

The reactions are graphically illustrated in Flow Diagram IV.

FLOW DIAGRAM IV

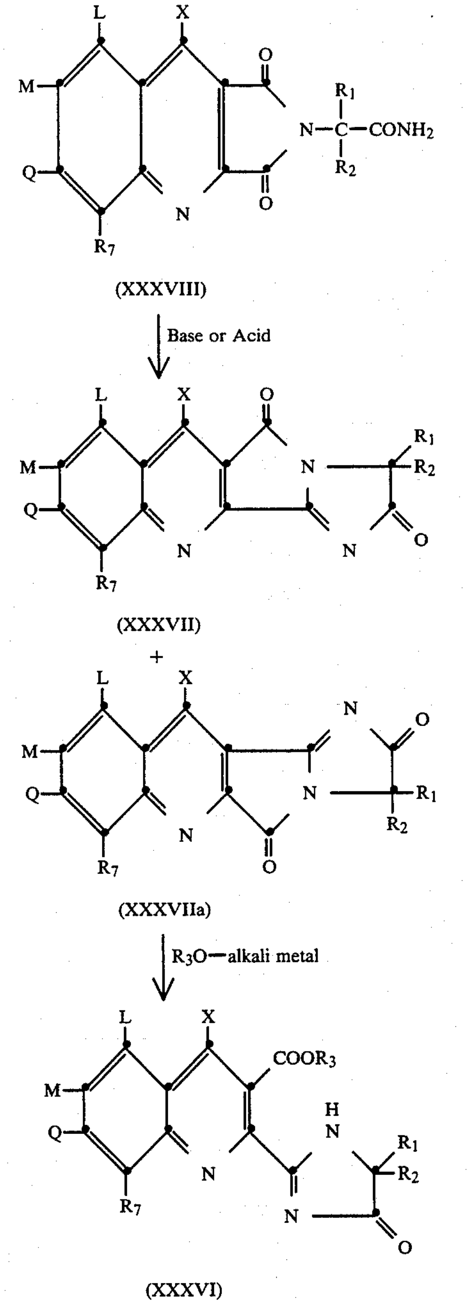

(XXXVIII)

(XXXVII)

(XXXVIIa)

(XXXVI)

Several routes are employed to prepare pyrroloquinoline acetamides represented by formula (XXXVIII). Preferably hydration of the pyrroloquinoline acetonitrile of formula (XXXX) is accomplished by treatment with a strong acid such as sulfuric acid. This reaction yields the formula (XXXVIII) pyrroloquinoline acetamide. Although the addition of a non-miscible solvent such as methylene chloride, chloroform or the like is not essential to the conduct of the above described reaction, addition of such a solvent to the reaction mixture may be preferred. Said reaction is usually carried out at a temperature between 10° C. to 70° C.

Alternatively, the pyrroloquinoline acetamide of formula (XXXVIII) may be obtained by the Diels-Alder cycloaddition reaction between substituted anthranils of formula (XXXXI) and the dioxopyrroline acetamide of formula (XXXXII). These reactions are carried out in a wide temperature range: below 130° C. significant amounts of the intermediate aldehyde of formula (XXXXIII) are obtained, but at 130° C.–200° C. the pyrroloquinoline acetamide of formula (XXXVIII) is formed. Alternatively, the intermediate aldehyde of formula (XXXXIII) may be isolated and cyclized in refluxing xylene in the presence of an acid catalst, such as p-toluene sulfonic acid. This reaction yields the desired formula (XXXVIII) pyrroloquinoline acetamide. These reactions may be graphically illustrated as shown below on Flow Diagram V.

FLOW DIAGRAM V

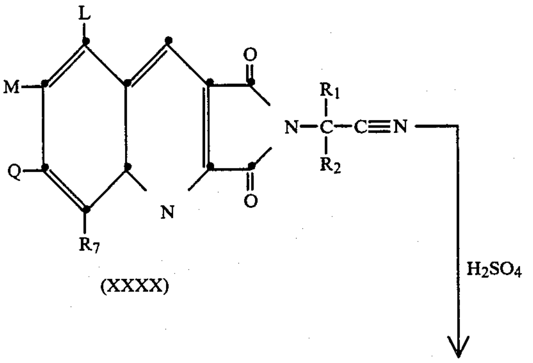

(XXXX)

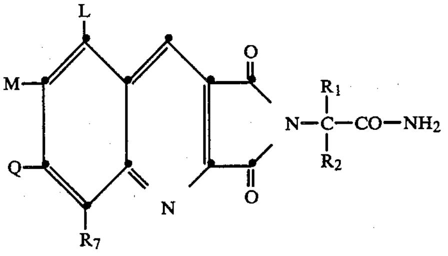

(XXXVIII)

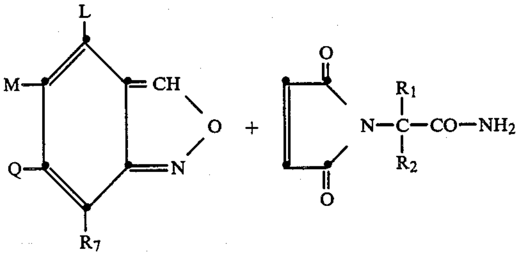

(XXXXI) (XXXXII)

-continued

FLOW DIAGRAM V

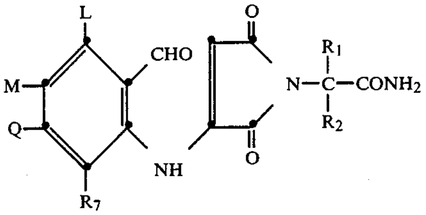

(XXXXIII)

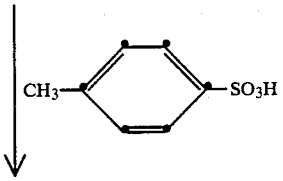

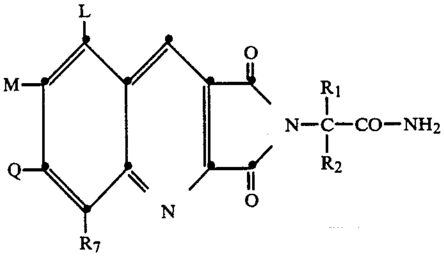

(XXXVIII)

A variety of routes may also be employed to obtain the formula (XXXX) pyrroloquinoline acetonitriles depending on the nature of the L, M, Q and $R_7$ substituents.

The formula (XXXX) pyrroloquinoline acetonitriles may be prepared by reacting the appropriately substituted anhydride (XXXXIV) with an appropriately substituted α-aminocarbonitrile of formula (XVII), to yield a mixture of the monoamides of the formula (XXXXVa) and formula (XXXXVb) acids.

This reaction is carried out at a temperature between 20° C. and 70° C. and preferably between about 35° C. and 40° C. in an inert solvent, such as tetrahydrofuran, methylene chloride, ether, chloroform, toluene or the like. The thus-formed acids are then cyclized to the corresponding pyrroloquinoline acetonitrile, depicted by formula (XXXX). This is accomplished by heating the reaction mixture to a temperature between about 75° C. and 150° C. with an excess of acetic anhydride in the presence of a catalytic amount of sodium acetate or potassium acetate.

In general, the above reaction is carried out by treating the reaction mixture with acetic anhydride, acetyl chloride, thionyl chloride or the like, and heating said mixture to a temperature between about 20° C. and 100° C. The above reactions are illustrated graphically on Flow Diagram VI below, wherein $R_1$, $R_2$, X, L, M, Q and $R_7$, are as defined above.

FLOW DIAGRAM VI

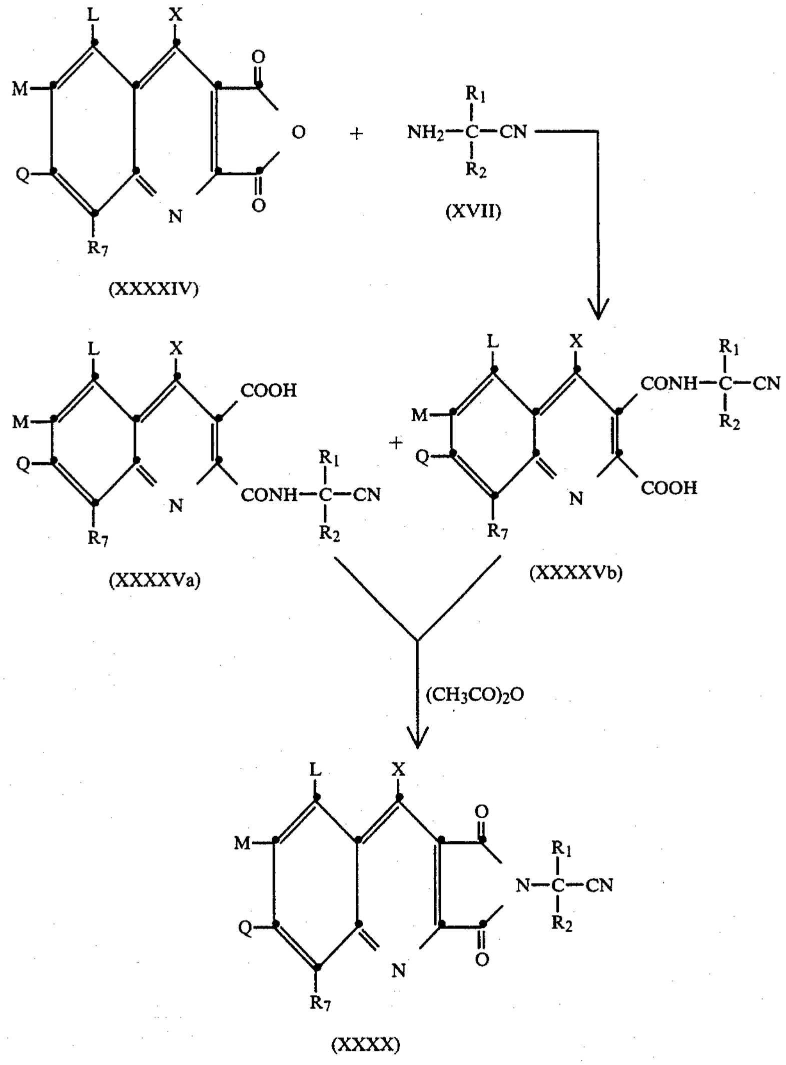

(XXXXIV) (XVII) (XXXXVa) (XXXXVb) (XXXX)

A preferred route to pyrroloquinoline acetonitrile of formula (XXXX) is the Diels-Alder thermal cycloaddition reaction of an appropriately substituted maleimide of formula (XXXXVI) with an appropriately substituted anthranil. In this route X must be hydrogen.

The outcome of this reaction is dependent upon the reaction temperature. Intermediate of formula (XXXXVII) is obtained at ~55° C. As the reaction mixture is heated further, to temperatures between 55° C. and 130° C., the intermediate of formula (XXXXIII) aldehyde is obtained. If the reaction is conducted in the presence of an aprotic solvent such as o-dichlorobenzene, and the reaction mixture heated to between 140° C. and 200° C., the reaction yields the pyrroloquinoline acetonitrile of formula (XXXX). The reaction is illustrated on Flow Diagram VII below.

FLOW DIAGRAM VII

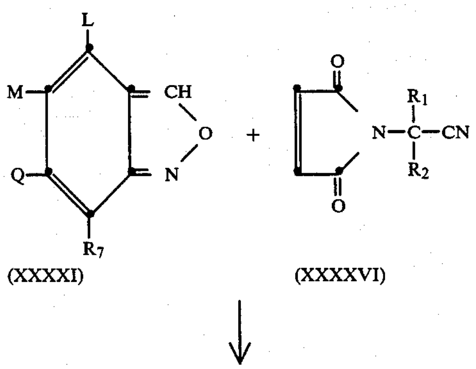

(XXXXXI) (XXXXVI)

-continued

FLOW DIAGRAM VII

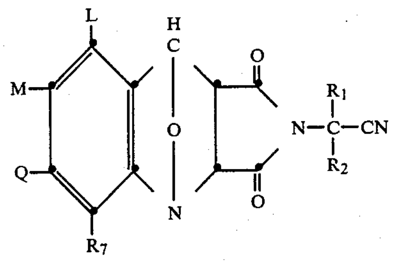

(XXXXVII)

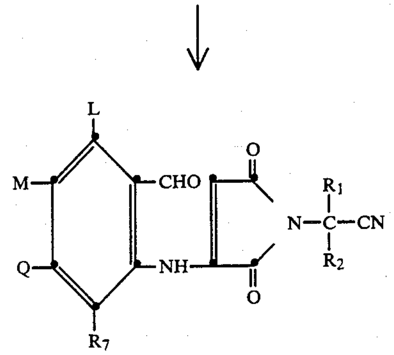

(XXXXIII)

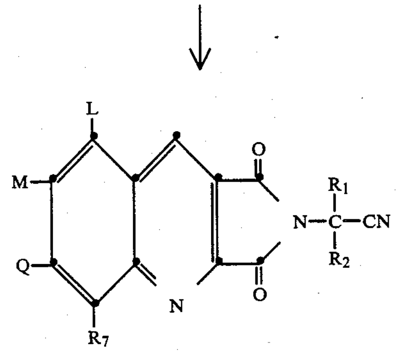

(XXXX)

The above route is particularly effective when L, M, Q and $R_7$ groups are electronegative, e.g., halogens, nitro, $CF_3$, $SO_2CH_3$, CN.

A variation of this procedure involves the reaction of an o-aminoacetal of formula (XXXXVIII) with an appropriately substituted formula (XXXXX) maleimide or dioxopyrroline acetamide, in the presence of an aprotic solvent such as xylene or toluene at a temperature between about 50° C. and 130° C. These reactions are graphically illustrated below.

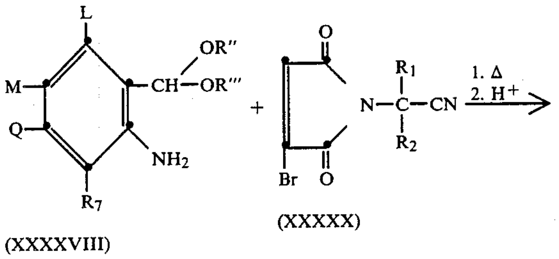

(XXXXVIII) (XXXXX)

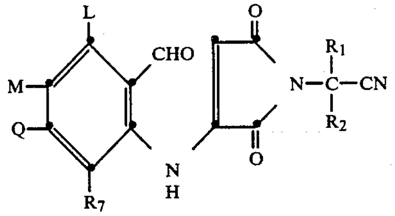

(XXXXXI)

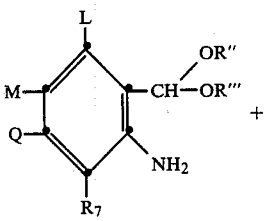

(XXXXVIII)

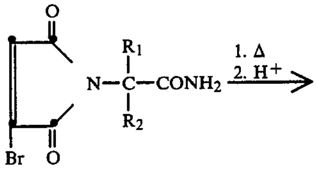

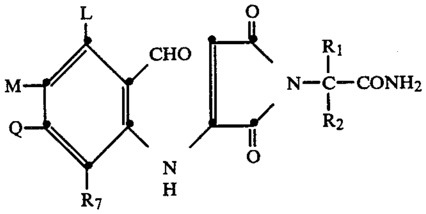

(XXXXIII)

Yet a further variation, useful for synthesis from anilines bearing electron donor substitution in the L, M, Q and $R_7$, positions or one halogen or $CF_3$ function, is the interaction of o-alkyl or arylthiomethylanilines formula (XXXXIX) with a bromomaleimide of formula (XXXXX) to give the maleimide of formula (XXXXXI) which is oxidized to the maleimide of formula (XXXXXII). The maleimide of formula (XXXXXII) is then cyclized in an acid catalyzed reaction to yield the pyrroloquinoline acetonitrile of formula (XXXX). The reactions are graphically illustrated below. $R_1$, $R_2$, L, M, Q and $R_7$ are as defined above.

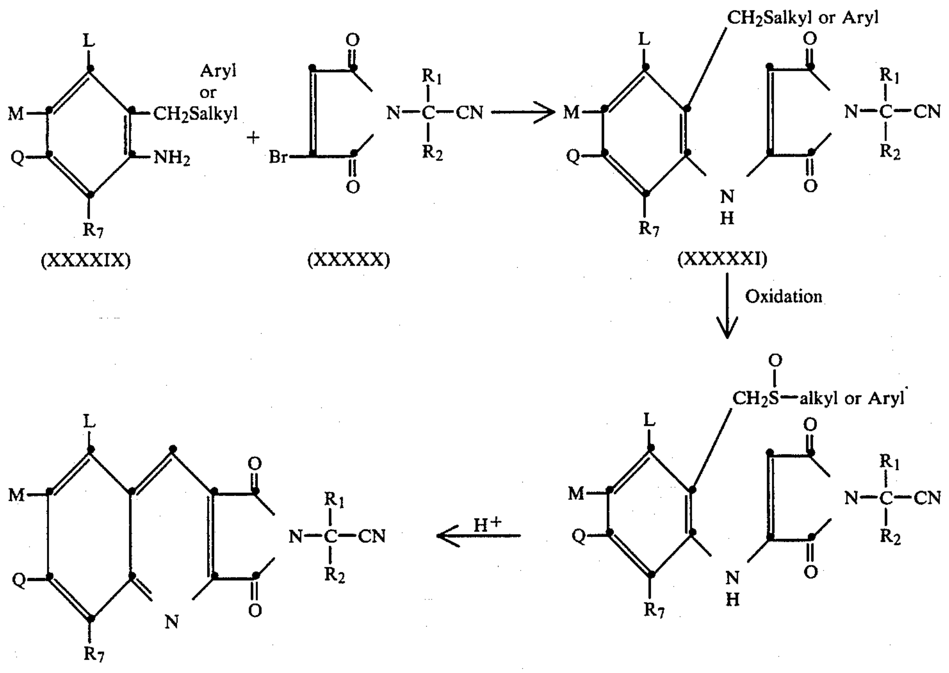

(XXXXIX) (XXXXX) (XXXXXI)

(XXXX) (XXXXXII)

Compounds of formula (XXXX) bearing electron donor substitution on the L, M, Q and $R_7$ positions, such as alkyl, alkoxy, alkylthio, dialkylamino, hydroxy and a single halogen may be prepared by reaction of an appropriately substituted o-aminobenzyl alcohol of formula (XXXXXIII) or anthranilic acid of formula (XXXXIV) with a bromo(or chloro)maleimide of formula (XXXXX).

This reaction is conducted in the presence of a protic solvent, such as isopropyl or t-butylalcohol at 0° C. to 30° C. to yield respectively, the hydroxymethylanilinomaleimide of formula (XXXXXV) or dioxopyrrolinyl anthranilic acid of formula (XXXXXVI). A variety of base acceptors can be employed in the above reactions, e.g., alkaline earth metal hydroxides, such as $Ba(OH)_2$, BaO or sodium acetate. However, the reactions in many instances proceed satisfactorily without the aid of the base acceptor.

Oxidation of the formula (XXXXXV) alcohol to the formula (XXXXIII) aldehyde may be accomplished using a wide variety of oxidizing agents exemplified by pyridiniumchlorochromate in methylene chloride or activated manganese dioxide in t-butanol. Cyclization of the aldehyde of formula (XXXXIII) to the pyrroloquinoline acetonitrile of formula (XXXX) is achieved by one of the methods described above, such as heating said aldehyde to between 140° C. and 200° C. in the presence of an aprotic solvent.

Cyclization of the o-anilinocarboxylic acid of formula (XXXXXVI) to the acetoxyquinoline of formula (XXXXXVII) is accomplished with acetic anhydride, triethylamine and 4-dimethylaminopyridine at ambient temperatures. Mild reductive elimination gives the pyrroloquinoline acetonitrile of formula (XXXX). Hydrolysis in warm aqueous acetic acid gives formula (XXXX) where X=OH, further reaction with phosphorus oxychloride and pyridine, affords compounds where X is chlorine. These reactions are illustrated in Flow Diagram VIII below.

FLOW DIAGRAM VIII

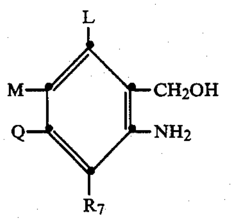

(XXXXXIII)

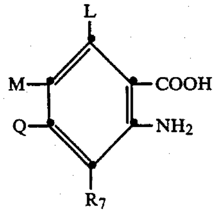

(XXXXXIV)

-continued

FLOW DIAGRAM VIII

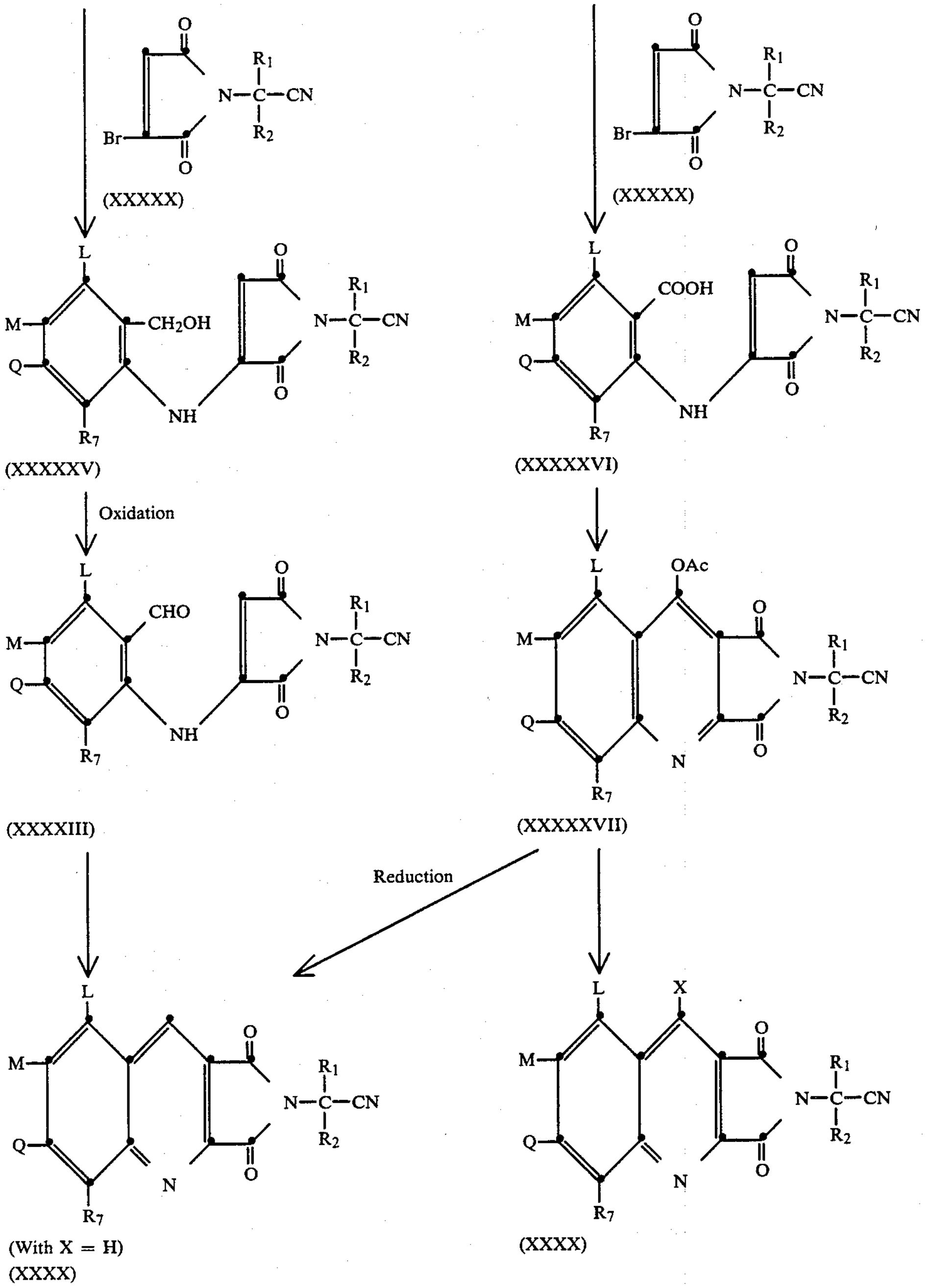

Another route to the 2-(2-imidazolin-2-yl)quinoline compounds of formula (II), particularly useful in synthesizing analogs in which the A group is varied, employs the 2-(2-imidazolin-2-yl)quinoline of formula (XXXXXIX). This intermediate is prepared from quinolinecarboxylic acid of formula (XXXXXVIII) which is converted to the acid chloride or anhydride and then reacted with either an appropriately substituted α-aminocarbonitrile of formula (XVII) to give the formula (XXXXXX) nitrile, or with the aminoamide of formula (XXXXXXI) to give the carboxamidoamide of formula (XXXXXXII). Cyclization of said carboxamidoamide is accomplished by the previously discussed procedures, although cyclization with sodium hydride in the presence of xylene is preferred. Introduction of a variety of groups, A, is made possible by treatment of the 2-(2-imidazolin-2-yl)quinoline of formula (XXXXXIX) with metallating reagents. Most organo metallic agents have some effect when two moles are used with the formation of a dianion, but the yield and reaction composition is dependent upon the nature of the organometallic reagent, reaction solvent, reaction temperature and the electrophile used to quench the reaction. In practice organometallic reagents such as alkyl lithiums are preferred and anion formation is obtained with methyl, n-butyl, sec-butyl and tert-butyl lithium. Phenyl lithium and lithium diisopropylamide may also be employed. Solvents must be aprotic and diethylether is preferred. Reaction temperatures employed to form the dianion range from −78° C. to 0° C. with −30° C. to −10° C. preferred. Quenching with an electrophile is usually accomplished at −78° C. to +20° C. If necessary, this is followed by acid treatment. All reactions are run under an inert atmosphere. Examples of reactive electrophiles include: $CO_2$, $ClCO_2CH_3$, $(CH_3)_2NCHO$, $CH_3HCO$, $C_6H_5CHO$, $CH_3I$. The corresponding values for A in formula (IIa) are COOH, COOCH$_3$, CHO, CH(OH)CH$_3$, CH(OH)C$_6$H$_5$, CH$_3$. Furthermore, following the quenching of the electrophile, the products may be modified. Thus the aldehyde (A=CHO) prepared from a DMF quench, reacts with hydroxylamine to afford an oxime. The above route is also useful for the synthesis of A=COOH compounds by treatment of the dianion with carbon dioxide.

Not all X, L, M, Q and R$_7$, substituents are compatible with this organometallic process. Thus, if the above mentioned substituents are Br, I or sometimes fluorine, competitive loss of these groups occurs as well as replacement of the 3-proton of quinoline. Chlorine, however, is compatible with this process. When L, M, Q or R$_7$, is methoxy, competitive anion formation can occur ortho to the methoxy group.

The above-described reactions are graphically illustrated on Flow Diagram IX below.

FLOW DIAGRAM IX

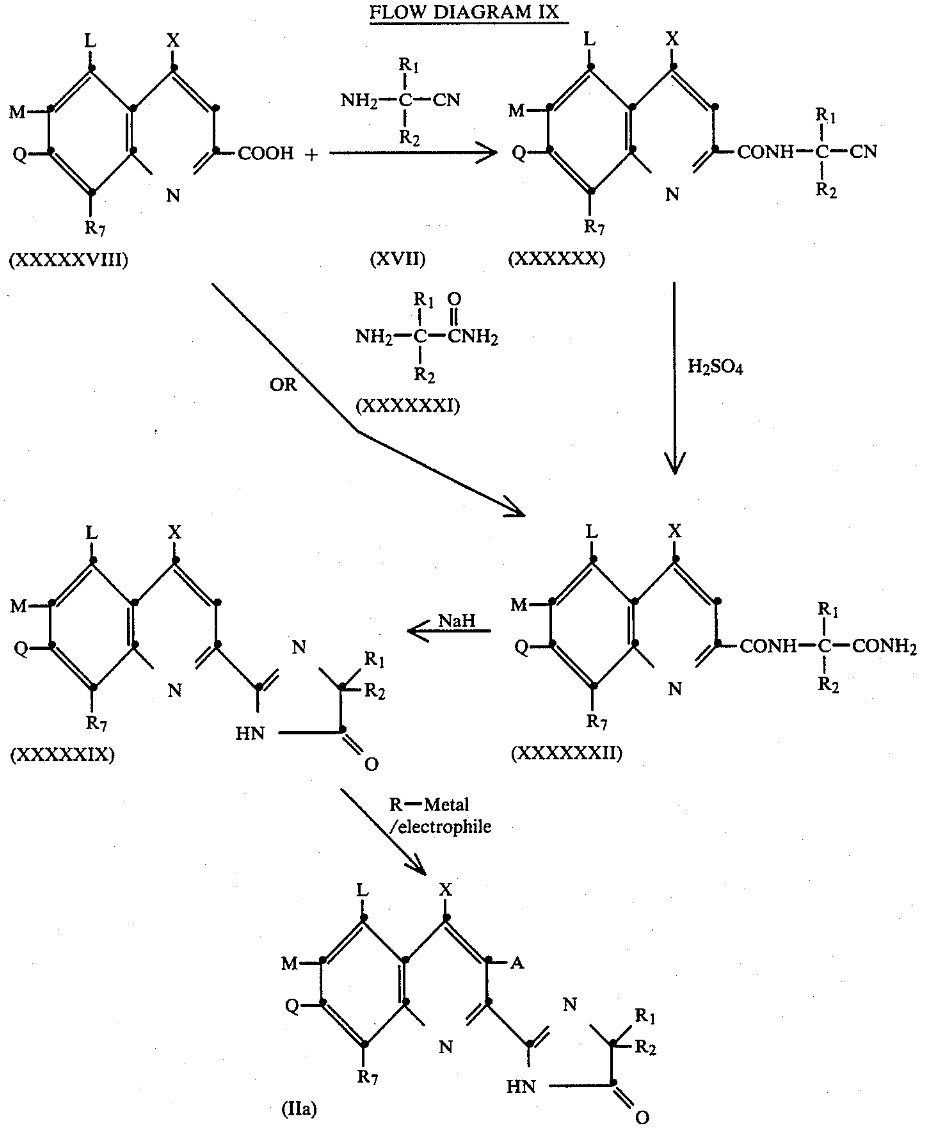

Several functional groups, A, are prepared by an alternative approach. Thus reaction of the imidazopyrroloquinolinedione of formula (XXXVII) with R$_3$OM$^+$ affords the 2-(2-imidazolin-2-yl)quinoline esters of formula (XXXVI). In the case of formula (II) compounds in which A is the CONHCH$_2$CH$_2$OH group, this may be cyclized to the oxazoline group via reaction of the above-identified compound with triethylphosphite in refluxing xylene. Formula (II) derivatives, in which A is —CONH$_2$, may be converted to the corresponding cyano derivative, i.e., A=CN, by dehydration of the —CONH$_2$ function.

The majority of compounds containing L, M, Q, and R$_7$ substituents may be prepared by the procedures previously outlined; however, amino, alkylamino, and dialkylamino compounds are conveniently formed by reductive alkylation of the appropriate nitro substituent in the L, M, Q, or R$_7$ position. Alkylsulfonyl compounds are most readily formed by mild oxidation of the alkylthio group in the L, M, Q, or $R_7$ position at 0° C.–20° C. using m-chloroperbenzoic acid. Under these conditions, N-oxidation of the quinoline nitrogen is minimized.

Oxidation of the quinoline to the N-oxide can be accomplished by prior N-protection of the imidazolone ring with, e.g., a $COCH_3$ group; N-oxidation can now be accomplished by peracetic acid or trifluoroperacetic acid, at elevated temperatures, if necessary.

Preparation of 2-(2-imidazolin-2-yl)-3-quinolinecarboxylic acids, i.e., formula (II) compounds where A is COOH, can also be prepared by a rather unique procedure involving the reaction of an appropriately substituted formula (LXXVII) aniline wherein L, M, Q, and $R_7$ are as described above, with a keto-ester depicted as formula (LXXVIII) wherein R′ is $CH_3$ or $CO_2R''$ and R″ is $C_1$–$C_4$ alkyl. This reaction is optionally conducted in the presence of an organic acid such as p-toluenesulfonic acid hydrate in the presence of an organic solvent such as toluene, xylene, benzene, or the like, at a temperature of from about 20° to 110° C., preferably 100° C. to 110° C. The reaction yields the β-anilino-α,β-unsaturated ester of formula (LXXIX). The thus-formed β-anilino-α,β-unsaturated ester of formula (LXXIX) is then reacted with an immonium salt depicted by formula $$Cl-CH=\overset{\oplus}{N}-(R''')_2\overset{\ominus}{Cl} \qquad (LXXX)$$

wherein R‴ is $C_1$–$C_6$ alkyl or

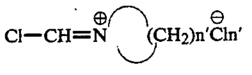

is 4 or 5, in the presence of a low boiling chlorinated hydrocarbon solvent such as methylene chloride or dichloroethane at a temperature between about 40° and 90° C., for a period of time sufficient to essentially complete the reaction and yield the formula (LXXXI) alkyl ester of 2-methyl-3-quinolinecarboxylic acid when R′ is methyl or the dialkyl ester of quinoline-2,3-dicarboxylic acid when R′ is COOR″.

Alternatively, the formula (LXXVII) substituted aniline, wherein L, M, Q, and $R_7$ are as described above, can be reacted with an acetylene dicarboxylate of the structure shown as formula (LXXXII) wherein R″ is $C_1$–$C_4$ alkyl. This reaction is generally carried out in the presence of solvent such as dichloroethane or a $C_1$–$C_4$ alcohol such as methanol, at a temperature between 0° and 100° C., to yield a β-anilino-α,β-unsaturated ester shown as formula (LXXXIII). The β-anilino-α,β-unsaturated ester of formula (LXXXIII) is then reacted with an immonium salt depicted by formula (LXXX). This reaction is generally carried out in the presence of a low-boiling solvent such as methylene chloride or dichloroethane at a temperature between 40° and 90° C. for a period of time sufficient to complete the reaction and yield the quinoline-2,3-dicarboxylate shown as formula (LXXXIV) wherein L, M, Q, $R_7$, and R″ are as described above.

This process is graphically illustrated in Flow Diagram X below and described in the copending application for United States Letters Patent of Robert Doehner, Ser. No. 381,815, filed concurrently herewith and now abandoned in view of Ser. No. 698,192 filed Feb. 4, 1985 and incorporated herein by reference thereto.

The immonium salt formula (LXXX) utilized in the above cyclization reactions may thereinafter, be referred to as the Vilsmeier reagent. This reagent may be generated from a formamide (alkyl or phenyl) reaction with $POCl_3$, $COCl_2$, ClCO—COCl, or $SOCl_2$ in a chlorinated hydrocarbon solvent.

While the anion in formula (LXXX) is shown as $Cl^{\ominus}$, it should be recognized that when $POCl_3$ is used to prepare the Vilsmeier reagent, the anion is $PO_2Cl^{\ominus}_2$.

Conversion of the formula (LXXXI) alkyl ester of 2-methyl-3-quinolinecarboxylic acid, to the 2,3-quinolinedicarboxylic acid of formula (LXXXV) is achieved by a very distinctive process involving the simultaneous oxidation of the R′ methyl function and the hydrolysis of the ester function R″ of the alkyl ester of 2-methyl-3-quinolinecarboxylic acid. This is accomplished by admixing the formula (LXXXI) alkyl ester of 2-methyl-3-quinolinecarboxylic acid with a sufficient amount of water to give a 0.02 to 1.0M solution of said compound and adding thereto about 5–15% by weight of aqueous alkali metal hydroxide such as sodium or potassium hydroxide. The mixture is stirred to provide an essentially homogenous mixture. The practice, it has been found beneficial, although not essential, for the formula (LXXXI) starting material to have some solubility in the reaction medium, either initially or after saponification of the functional group R′. The reaction mixture is then treated with from 3.0 to 4.0 molar equivalents (preferably up to 1 molar equivalent excess) of nickel peroxide. Addition of the nickel peroxide to the mixture can be made in small increments or all at once. However, the temperature of the reaction mixture should be maintained at from 0° to 30° C., and the mixture should be stirred until the oxidation and hydrolysis are essentially complete. At the end of the reaction time, no starting material is detectable, and the insoluble inorganic materials are removed by decantation, filtration, or the like. The filtrate is then acidified to pH 2 with hydrochloric acid to give the formula (LXXXV) quinoline-2,3-dicarboxylic acid wherein L, M, Q, $R_7$, are as described above, excepting that they may not represent $C_1$–$C_4$ alkylthio, amino, $C_1$–$C_4$ alkylamino or diloweralkylamino.

This process is graphically illustrated in Flow Diagram X and described in U.S. Pat. No. 4,459,409 (1984) incorporated herein by reference thereto.

Following isolation, the formula (LXXXV) quinoline-2,3-dicarboxylic acid is heated to about 70° to 95° C. with an excess of acetic anhydride to yield the formula (LXXXVI) 2,3-quinolinedicarboxylic acid anhydride. A co-solvent such as pyridine or pyridinedimethoxyethane may also be used in this reaction, but is not essential to obtain the desired product.

Reaction of the formula (LXXXVI) 2,3-quinolinedicarboxylic acid anhydride with an aminocarboxamide or aminothiocarboxamide depicted by formula (LXXXVII) is preferably carried out using equivalent amounts of the anhydride and carboxamide or thiocarboxamide in the presence of an inert organic solvent such as tetrahydrofuran, diethyl ether, or the like at a temperature between about 0° and 30° C. When the reaction is essentially complete, the solvent is evaporated, and the residue triturated with a solvent such as ethyl acetate to afford an isomeric mixture of the 3-quinolinecarboxylic acid and the quinaldic acid shown, respectively, as formula (LXXXVIIIa) and formula (LXXXVIIIb).

The thus-formed mixture is then heated to a temperature of from 25° to about 110° C. with about 2 to 10 molar equivalents of aqueous or aqueous alcoholic sodium or potassium hydroxide, preferably under a blanket of inert gas such as nitrogen. The mixture is cooled to about 25° C. and acidified to pH 2 to 4 with a strong mineral acid such as hydrochloric acid or sulfuric acid to give the herbicidally effective 2-(5,5-disubstituted-4-oxo-(or thiono)-2-imidazolin-2-yl)-3-quinolinecarboxylic acids, encompassed by formula (LXXXIX); wherein $R_1$ is $C_1$-$C_4$ alkyl; $R_2$ is $C_1$-$C_4$ alkyl or $C_3$-$C_6$ cycloalkyl; and when $R_1$ and $R_2$ are taken together, they may represent $C_3$-$C_6$ cycloalkyl optionally substituted with methyl, and when $R_1$ and $R_2$ are not the same, the optical isomers thereof; W is O or S; and L, M, Q, and $R_7$ each represent members selected from the group consisting of hydrogen, halogen, $C_1$-$C_4$ haloalkyl, difluoromethoxy, diloweralkylamino, $C_1$-$C_4$ alkylthio nitro, phenyl, phenoxy or monosubstituted phenyl or phenoxy where the substituent is $C_1$-$C_4$ alkoxy or halogen; with the proviso that only one of L, M, Q, or $R_7$ may represent a substituent other than hydrogen, halogen, $C_1$-$C_4$ alkyl or $C_1$-$C_4$ alkoxy.

FLOW DIAGRAM X

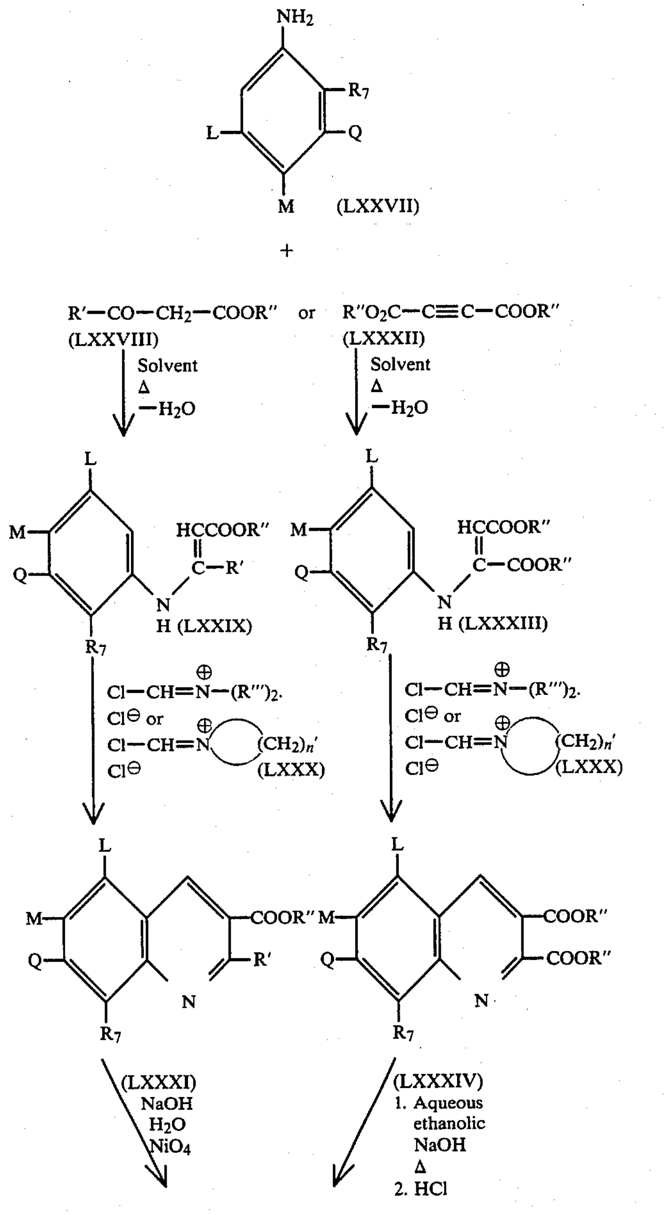

-continued

FLOW DIAGRAM X

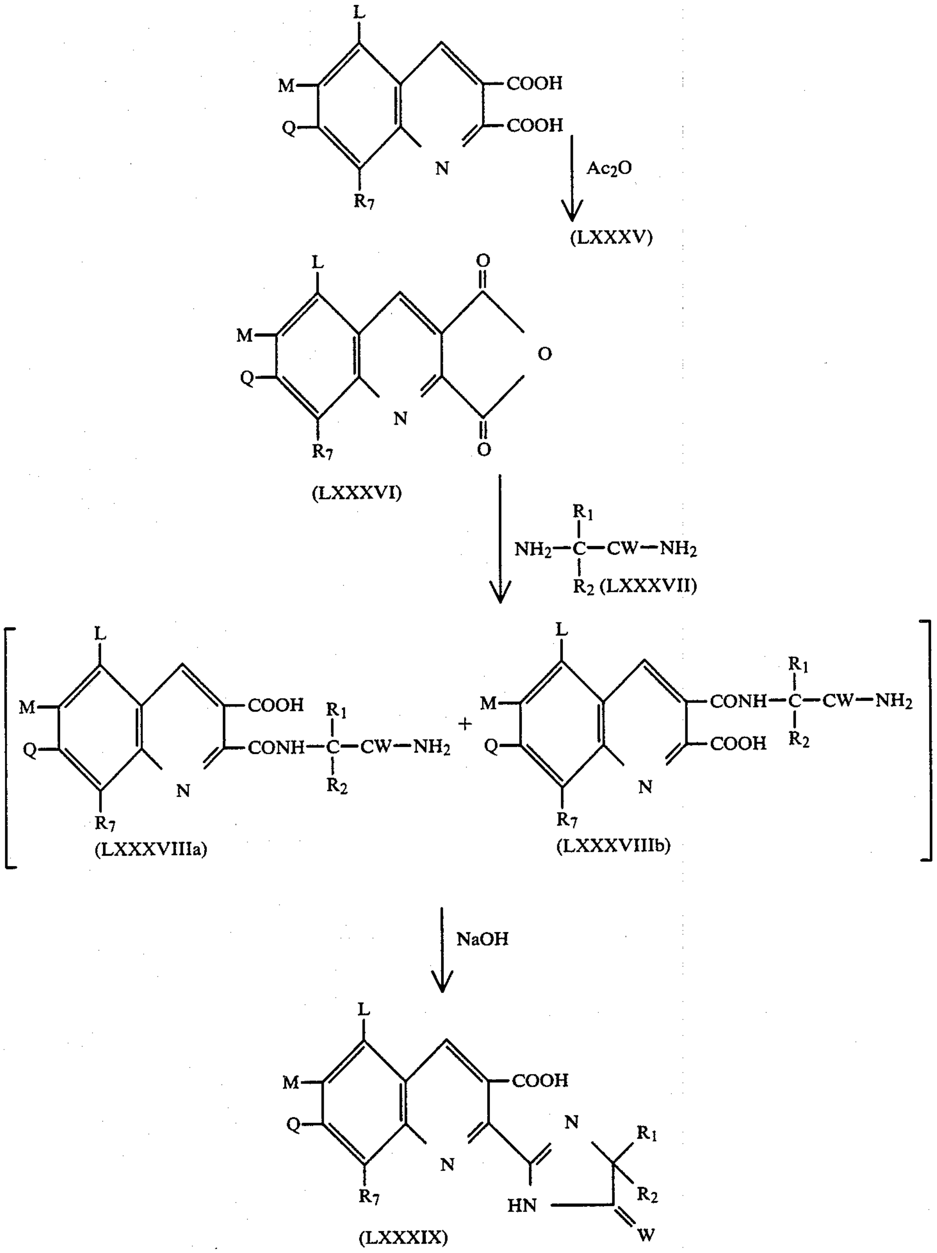

(LXXXV) (LXXXVI) (LXXXVII) (LXXXVIIIa) (LXXXVIIIb) (LXXXIX)

The formula (I) and formula (II) 2-(2-imidazolin-2-yl)pyridines and 2-(2-imidazolin-2-yl)quinolines and the formula (III) and formula (XXXVII) imidazopyrrolopyridinediones and imidazopyrroloquinolinediones of the present invention are exceedingly effective herbicidal agents useful for the control of an exceptionally wide variety of herbaceous and woody annula and perennial monocotyledonous and dicotyledonous plants. Moreover, these compounds are herbicidally effective for controlling weeds indigenous to both dry land and wet land areas. They are also useful as aquatic herbicides and are unique in their effectiveness in controlling the above-said plants when applied to the foliage thereof or to soil or water containing seeds or other propagating organs of said plants such as tubers, rhizomes or stolons, at rates of from about 0.016 to 4.0 kg/ha, and preferably at rates from about 0.032 to 2.0 kg/ha.

It is, of course, obvious that rates of application above the 4.0 kg/ha level can also be used to effectively kill undesirable plant species; however, rates of application of toxicant above the level necessary to kill the undesirable plants should be avoided since application of excessive amounts of toxicant is costly and serves no useful function in the environment.

Among the plants which may be controlled with the compounds of this invention are: *Elatine triandra, Sagittaria pygmaea, Scirpus hotarui, Cyperus serotinus, Eclipta alba, Cyperus difformis, Rotala indica, Lindernia pyridoria, Echinochloa crus-galli, Digitaria sanguinalis, Setaria viridis, Cyperus rotundus, Convolvulus arvensis, Agropyron repens, Datura stramonium, Alopecurus myosuroides,* Ipomoea spp. *Sida sponosa, Ambrosia ar-*

*temisiifolia, Eichhornia crassipes, Xanthium pensylvanicum, Sesbania exaltata, Avena fatua, Abutilon theophrasti, Bromus tectorum, Sorghum halepense,* Lolium spp., *Panicum dichotomiflorum,* Matricaria spp., *Amaranthus retroflexus, Cirsium arvense,* and *Rumex japonicus.*

Surprisingly, it has now been found that some of the formula (I) and formula (II) compounds of the invention are selective herbicides when applied to the foliage of plants or to soil containing seeds of said plants at relatively low rates of application, i.e., at from 0.016 to about 2.0 kg per hectare, depending on the compound used and crop treated.

In practice, it has been found that generally the formula (I) 2-(2-imidazolin-2-yl)pyridines are best suited for use as broad spectrum herbicides, whether employed preemergence or post-emergence to the locus in which weed control is desired. This is not to say, however, that all of the formula (I) pyridines are non-selective. Actually, some of the 2-(2-imidazolin-2-yl)pyridines, particularly the five-substituted formula (I) and formula (Ia), pyridines are selective in leguminous crops, particularly crops such as soybeans. Similarly, it has been found that the formula (I) and (II) 2-(2-imidazolin-2-yl)quinolines are generally selective herbicides, particularly effective for controlling undesirable weeds in the presence of leguminous crops such as soybeans. However, certain of the formula (I) and formula (II) compounds are less selective than others in this series.

It has also been found that several of the formula (I) and formula (II) 2-(2-imidazolin-2-yl)pyridines and 2-(2-imidazolin-2-yl)quinolines are effective as defoliants for cotton when applied at rates of application between about 0.016 to 4.0 kg hectare. At rates of application not exceeding about 0.01 kg per hectare, it has also been found that certain of the formula (I) and formula (II) pyridines and quinolines are effective for increasing branching of leguminous crops and affecting early maturation of grains.

The formula (XI) pyrrolopyridine acetonitriles, formula (IV) pyrrolopyridine acetamides formula (XXXX) pyrroloquinoline acetonitriles and formula (XXXVIII) pyrroloquinoline acetamides are useful as intermediates for the preparation of the above-mentioned herbicidal formula (I) and formula (II) 2-(2-imidazolin-2-yl)pyridines and quinolines and the herbicidal formula (III) and formula (XXXVII) imidazopyrrolopyridinediones and imidazopyrroloquinolinediones.

Since the formula (I) and formula (II) imidazolinylpyridine and quinoline derivatives, wherein $R_3$ is a salt-forming cation, are water soluble, these compounds can simply be dispersed in water and applied as a dilute aqueous spray to the foliage of plants or to soil containing propagating organs thereof. These salts also lend themselves to formulation as flowable concentrates.

The formula (I) and formula (II) 2-(2-imidazolin-2-yl)pyridines and quinolines and the formula (III) and formula (XXXVII) imidazopyrrolopyridinediones and imidazopyrroloquinolinediones, can also be formulated as wettable powders, flow concentrates, emulsifiable concentrates, granular formulations and the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not be be deemed limited thereby except as defined in the claims. Unless otherwise noted, all parts are by weight.

EXAMPLE 1

Preparation of 5,7-Dihydro-α-isopropyl-α-methyl-5,7-dioxo-6H-pyrrolo[3,4-b]pyridine-6-acetonitrile To a stirred solution containing 212 g quinolinic anhydride in 950 ml methylene chloride is added at a moderate rate 167 g of 2-amino-2,3-dimethylbutyronitrile. The mixture had reached the boiling point of the solution after about one quarter of the aminonitrile had been added and the rate of addition is adjusted to maintain this temperature. After the addition the solution is heated under reflux for a further 4 hours. The solution is cooled, filtered and concentrated to a thick oil. This oil is dissolved in 950 ml acetic anhydride, 6 g anhydrous sodium acetate added and the mixture distilled until the vapor temperature reached 118° C. when the heating was continued under reflux for 3 hours. The mixture is concentrated in vacuo the residue dissolved in 500 ml toluene and again concentrated. This is repeated. The residue is slurried with a mixture of ether and hexane and the crude product which crystallizes collected (349 g). This is dissolved in 700 ml methylene chloride and filtered through a column containing 700 g silica gel and the product eluted with methylene chloride. Concentration of the eluant gave 258 g of the desired product. An analytically pure sample with mp 95°-96° C. can be obtained by the recrystallization of the product from ether-methylene chloride.

Using the appropriate amino nitrile and quinolinic anhydride in the above procedure, the following pyrrolopyridines are prepared:

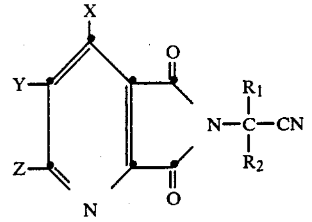

| $R_1$ | $R_2$ | X | Y | Z | mp °C. |
|---|---|---|---|---|---|
| $CH_3$ | $CH_3$ | H | H | H | 119-123 |
| $CH_3$ | $C_2H_5$ | H | H | H | 95-97 |
| $CH_3$ | 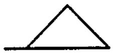 | H | H | H | 69-73 |
| $CH_3$ | $CH_2CH(CH_3)_2$ | H | H | H | oil |
| | $-(CH_2)_5-$ | H | H | H | 85-87 |
| $C_2H_5$ | $C_2H_5$ | H | H | H | 71-72.5 |
| $CH_3$ | $CH(CH_3)_2$ | $CH_3$ | H | H | 129.5-131.3 |
| $CH_3$ | $CH(CH_3)_2$ | H | H | $OCH_3$ | 108-110 |
| $CH_3$ | $CH(CH_3)_2$ | H | H | Cl | 94-96 |
| $CH_3$ | $CH(CH_3)_2$ | H | $-(CH_2)_4-$ | | 165-167 |

EXAMPLE 2

Preparation of 5,7-Dihydro-α-isopropyl-α-methyl-5,7-dioxo-6H-pyrrolo[3,4-b]pyridine-6-acetamide To 330 ml concentrated sulfuric acid is added portion wise with thorough stirring 298 g finely divided nitrile so that the temperature did not go about 72° C. After the addition the temperature is adjusted to 60°-65° C. and maintained there for 1½ hours. The mixture is cooled, quenched with ice and finally diluted to approximately 4 liters. After adding 454 g sodium acetate and cooling at 0° C. for 2 hours the mixture is filtered, the solids collected and washed twice with 500 ml water containing sodium acetate followed by water to remove all the sulfuric acid. The solid is dried to give 289 g of product, mp 176°-178° C. Material made in a similar way and analytically pure had mp 188°-190° C.

Employing the appropriate pyrrolopyridineacetonitrile in the above procedure, the following pyrrolopyridineacetamides are prepared.

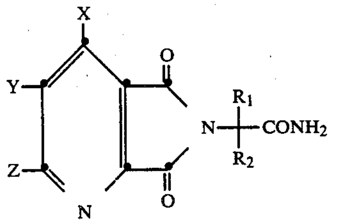

| $R_1$ | $R_2$ | X | Y | Z | mp °C. |
|---|---|---|---|---|---|
| $CH_3$ | $CH_3$ | H | H | H | 203-5 |
| $CH_3$ | $C_2H_5$ | H | H | H | 158-161 |
| $CH_3$ | 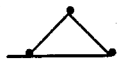 | H | H | H | 195-198 |

EXAMPLE 3

Preparation of 3-Isopropyl-3-methyl-5H-imidazo[1',2',:1,2]pyrrolo[3,4,6]pyridine-2-(3H),5-dione A mixture of 50 g amide and 450 ml toluene is heated under a Dean-Stark water separator to remove traces of water. To the cooled mixture is added 10.1 g of a 50% suspension of sodium hydride in mineral oil and the mixture heated under reflux for 23 hours. The hot solution is filtered, concentrated in vacuo where upon the residue is crystallized. The mineral oil is removed by decantation and the solid washed with hexanes and dried in vacuo to give 45.5 g product which, by nmr analysis, is approximately 90% the desired isomer II and 10% the undesired isomer IIa.

A pure sample of isomer II can be obtained by recrystallizing the crude product from hexanemethylene chloride mp 107°-115° C.

The cyclisation can be achieved by either the basic reagent sodium and potassium hydroxide, or the acidic reagent p-toluenesulfonic acid in a toluene solvent. It should be understood that a mixture of products corresponding to Structures II and IIa above is obtained and in general these are not purified but used directly for the preparation of the derived nicotinic acid esters.

Employing the appropriate pyrrolopyridine carboxamide, the following imidazopyrrolopyridines are prepared.

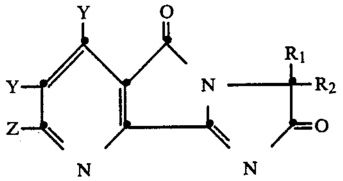

| $R_1$ | $R_2$ | X | Y | Z | mp °C. |
|---|---|---|---|---|---|
| $CH_3$ | $CH_3$ | H | H | H | |
| $CH_3$ | $C_2H_5$ | H | H | H | |
| $CH_3$ | 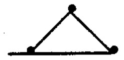 | H | H | H | |
| $-\underset{CH_3}{CH}-CH_2CH_2CH_2CH_2-$ | | H | H | H | 125-130 |
| $CH_3$ | $CH(CH_3)_2$ | H | H | $OCH_3$ | 147-147.5 |

EXAMPLE 4

Preparation of 3-Isopropyl-5-H-imidazo[2',2':1,2]pyrrolo[3,4-6]pyridine-2(3H)-dione A mixture containing 52 g of 3-(1-Carbamoyl-1,2-dimethylpropyl)picolinate, 1.77 ml 1,5-diazabicyclo[5.4.0]-undec-5-ene(DBU) in 400 ml xylene is heated under reflux under a Dean-Stark water separator for 2 hours. The mixture is concentrated in vacuo and the residue is chromatographed on 400 g basic alumina. The mixture of desired products is eluted with methylene chloride and used without further purification.

EXAMPLE 5

Preparation of Methyl 2-(isopropyl-5-methyl-4-oxo-2-imidazolin-2-yl)nicotinate

To 20 ml dry methanol in which 10 mg sodium hydride had reacted is added 2.0 g of a mixture of the imidazopyrrolopyridines. After stirring for 16 hours, 0.03 g glacial acetic acid is added (to neutralize the base), the solution concentrated in vacuo and the residue chromatographed on silica gel in ether. The faster moving material, the desired ester, is obtained in several fractions, combined, concentrated and crystallized from acetonitrile to give the imidazolinyl nicotinate, mp 121°-123.5° C. An analytically pure sample crystallized from methylene chloride hexane exhibits a melting point of from 121°-122° C.

EXAMPLE 6

Preparation of Methyl 2-(5-isopropyl-5-methyl-4-oxo-2-imidazolin-yl)nicotinate

This method involves the formation of the tricyclic compounds of Example 3 and 4, without isolation, directly forming the nicontinic acid esters:

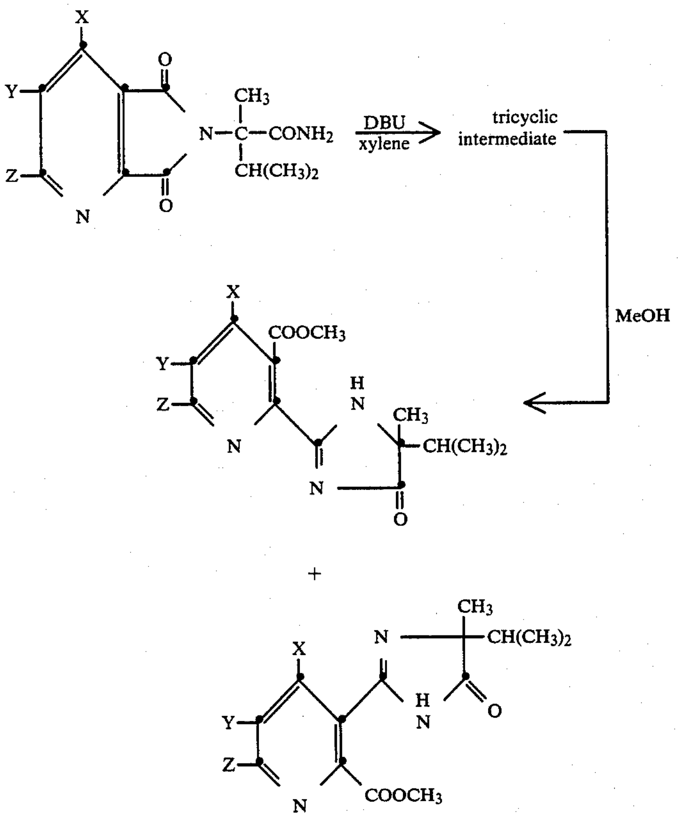

A mixture of 25 g amide and 1 ml 1,5-diaza-bicyclo-[5.4.0]undec-5-ene(DBU) in 500 ml xylene is heated under reflux for 1 hour under a Dean-Stark water separator. The mixture is cooled somewhat, the water separator removed, 100 ml anhydrous methanol added and the mixture heated under reflux for 1 hour. The solvents are then removed in vacuo and the product isolated by chromatography as described in Example 5 above to give 13.65 g product mp 120°-122° C. identical to that described in Example 5 above.

EXAMPLE 7

Preparation of Methyl 2-(5-isopropyl 5-methyl-4-oxo-2-imidazolin-2-yl)nicotinate Method A (Flow Diagram)

A mixture of 13.65 g of the nicotinate and 9.69 g phosphorus pentachloride in 110 ml dry toluene is heated with stirring to 80° C. After 1½ hours, the thick mixture is cooled, filtered and the solid washed with ether and dried. This is the hydrochloride salt of the desired product.

This salt is dissolved in 60 ml water; neutralized with sodium bicarbonate, the resulting precipitate removed by filtration, washed with water and air-dried to give the product identical to that prepared by the procedure of Example 5.

Method B

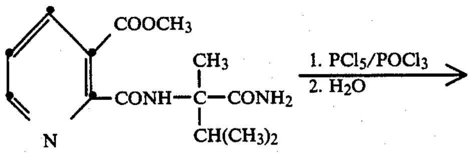

-continued

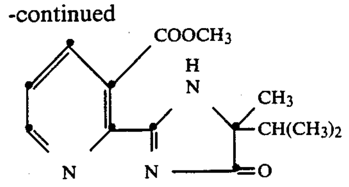

A mixture of 5.0 g nicotinate and 7.1 g phosphorus pentachloride in 40 ml phosphorus oxychloride is stirred at room temperature overnight. The phosphorous oxychloride is removed in vacuo, the residue suspended in 40 ml toluene and again concentrated. This is repeated. Water (40 ml) is added to the residue and the mixture heated to reflux and held there for 1 hour. After cooling, the mixture is extracted with methylene chloride, the extract dried and concentrated to give 1.05 g of the desired product. The pH of the aqueous phase from the methylene chloride extraction is adjusted to 5–6 with sodium bicarbonate solution and the mixture extracted again with methylene chloride. The dried extract was concentrated and the residue crystallized to give a further 2.65 g of the desired product identical to that described in Example 5.

The following nicotinic acid esters are prepared by one or more of the methods described above:

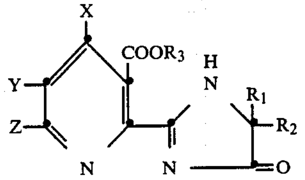

| $R_3$ | $R_1$ | $R_2$ | X | Y | Z | mp °C. |
|---|---|---|---|---|---|---|
| $CH_3$ | $CH_3$ | $C_2H_5$ | H | H | H | 126.5–128.5 |
| $CH_2{\equiv}CH$ | $CH_3$ | $CH(CH_3)_2$ | H | H | H | 104–106 |
| $CH_3$ | $-\underset{\overset{\vert}{CH_3}}{CH}-(CH_2)_4-$ | | H | H | H | 151–155.3 |
| $CH_2C{\equiv}CH$ | $-\underset{\overset{\vert}{CH_3}}{CH}-(CH_2)_4-$ | | H | H | H | 117–120 |
| $CH_2C_6H_5$ | $-\underset{\overset{\vert}{CH_3}}{CH}-(CH_2)_4-$ | | H | H | H | 148.5–151.3 |
| $CH_2C{\equiv}CH$ | $CH_3$ | $CH_3$ | H | H | H | 171–173 |
| $CH_3$ | $CH_3$ | $CH_3$ | H | H | H | 148–150 |
| $CH_2C_6H_5$ | $CH_3$ | $CH_3$ | H | H | H | 142–144 |
| $CH_2C_6H_5$ | $CH_3$ | $C_2H_5$ | H | H | H | 118–120 |
| $CH_2C{\equiv}CH$ | $CH_3$ | $C_2H_5$ | H | H | H | 138–140 |
| $-C_{12}H_{25}-n$ | $CH_3$ | $CH(CH_3)_2$ | H | H | H | 55–57 |
| $-C_2H_5$ | $CH_3$ | $CH(CH_3)_2$ | H | H | H | 72–75 |
| $CH_2CH_2OCH_2C_6H_5$ | $CH_3$ | $CH(CH_3)_2$ | H | H | H | 90–92.5 |
| 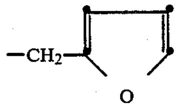 | $CH_3$ | $CH(CH_3)_2$ | H | H | H | 120.5–122 |
| $-CH(CH_3)_2$ | $CH_3$ | $CH(CH_3)_2$ | H | H | H | 94–97.5 |
| $-CH_2C_6H_5$ | $CH_3$ | $CH(CH_3)_2$ | H | H | H | 122–125 |
| $-CH_2-C{\equiv}C-C_7H_{15}-n$ | $CH_3$ | $CH(CH_3)_2$ | H | H | H | oil |
| $CH_2CH_2OCH_3$ | $CH_3$ | $CH(CH_3)_2$ | H | H | H | 60–63 |
| $CH_2CH{=}CH_2$ | $CH_3$ | $CH(CH_3)_2$ | H | H | H | 81–84 |
| $-\underset{\overset{\vert}{CH_3}}{CH}-CH{=}CH_2$ | $CH_3$ | $CH(CH_3)_2$ | H | H | H | oil |
| $CH_2-\underset{\overset{\vert}{CH_3}}{C}{=}CH_2$ | $CH_3$ | $CH(CH_3)_2$ | H | H | H | 98–100 |
| $\underset{\overset{\vert}{CH_3}}{CH}-C{\equiv}CH$ | $CH_3$ | $CH(CH_3)_2$ | H | H | H | oil |
| $CH_2-CH{=}CHCH_3$ | $CH_3$ | $CH(CH_3)_2$ | H | H | H | 87–89 |
| $-C(CH_3)_3$ | $CH_3$ | $CH(CH_3)_2$ | H | H | H | 124–126 |

-continued

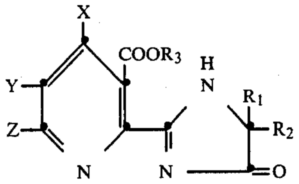

| R3 | R1 | R2 | X | Y | Z | mp °C. |
|---|---|---|---|---|---|---|
| 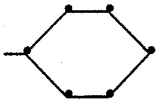 | $CH_3$ | $CH(CH_3)_2$ | H | H | H | 95.5-98 |
| $C_{18}H_{37}$—n | $CH_3$ | $CH(CH_3)_2$ | H | H | H | 77.3-79.2 |
| $CH_2C_6H_5$ | $CH_3$ | $CH(CH_3)_2$ | H | H | H | 116.5-119 |
| —$CH_2C_6H_5$ | $CH_3$ | $CH_2CH(CH_3)_2$ | H | H | H | 76-78.5 |
| $CH_3$ | $CH_3$ | $CH_2CH(CH_3)_2$ | H | H | H | 92-94 |
| —$C_4H_9$—n | $CH_3$ | $CH_2(CH_3)_2$ | H | H | H | 54-57 |
| $CH_2C{\equiv}CH$ | $CH_3$ | $CHCH(CH_3)_2$ | H | H | H | 128.5-131 |
| $CH_3$ | $CH_3$ | 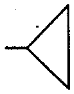 | H | H | H | 128-131 |
| $CH_2C_6H_5$ | $CH_3$ | 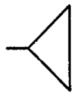 | H | H | H | 111-113 |
| $CH_3$ | $CH_3$ | $CH(CH_3)_2$ | H | H | $OCH_3$ | 154-155 |
| $CH_2$—CH=CH—$C_7H_{15}$—n | $CH_3$ | $CH(CH_3)_2$ | H | H | H | oil |
| $CH_2$—C(Cl)=$CH_2$ | $CH_3$ | $CH(CH_3)_2$ | H | H | H | 73-77 |
| $C_6H_{13}$—n | $CH_3$ | $CH(CH_3)_2$ | H | H | H | oil |
| $CH(CH_3)CH$=CH—$CH_3$ | $CH_3$ | $CH(CH_3)_2$ | H | H | H | oil |
| $CH_3$ | | —$(CH_2)_5$— | H | H | H | 146-148 |
| $CH_2CH$=$(CH_3)_2$ | $CH_3$ | $CH(CH_3)_2$ | H | H | H | 77.5-79 |
| $CH_2C_6H_5$ | | —$(CH_2)_5$— | H | H | H | 117-122 |
| $CH_2{\equiv}CCH_2OH$ | $CH_3$ | $CH(CH_3)_2$ | H | H | H | gum |
| $CH_2C_6H_5$ | $C_2H_5$ | $C_2H_5$ | H | H | H | 114.5-118 |
| $C(CH_3)C{\equiv}CH$ | $CH_3$ | $CH(CH_3)_2$ | H | H | H | 128-132 |
| $CH_2CH_2N^{\oplus}(CH_3)_3I^{\ominus}$ | $CH_3$ | $CH(CH_3)_2$ | H | H | H | 165-175 |
| $CH_3$ | $C_2H_5$ | $C_2H_5$ | H | H | H | 132.5-135.5 |
| $C(CH_3)_2C{\equiv}CH$ | $CH_3$ | $CH(CH_3)_2$ | H | H | H | 104-106 |
| $CH_2C{\equiv}CH$ | $CH_3$ | 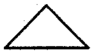 | H | H | H | 122-124 |
| $CH_2C{\equiv}CH$ | | —$(CH_2)$— | H | H | H | 164.5-166.5 |
| $CH_3$ | $CH_3$ | $CH(CH_3)_2$ | $CH_3$ | H | H | 114-115.5 |
| $CH_2C{\equiv}CH$ | $C_2H_5$ | $C_2H_5$ | H | H | H | 135.5-137 |
| 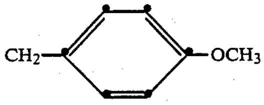 | $CH_3$ | $CH(CH_3)_2$ | H | H | H | 111-113 |
| 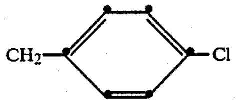 | $CH_3$ | $CH(CH_3)_2$ | H | H | H | 136-138 |
| 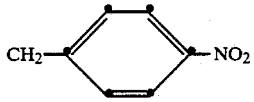 | $CH_3$ | $CH(CH_3)_2$ | H | H | H | 131.5-133 |
| $CH_2COOCH_3$ | $CH_3$ | $CH(CH_3)_2$ | H | H | H | 104-108 |

-continued

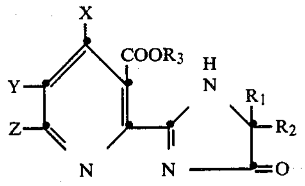

| $R_3$ | $R_1$ | $R_2$ | X | Y | Z | mp °C. |
|---|---|---|---|---|---|---|
| 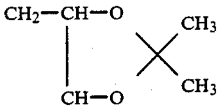 | $CH_3$ | $CH(CH_3)_2$ | H | H | H | 95-97 |
| $CH_2CH_2CH_2COOC_2H_5$ | $CH_3$ | $CH(CH_3)_2$ | H | H | H | oil |
| $CH(CH_3)COOCH_3$ | $CH_3$ | $CH(CH_3)_2$ | H | H | H | 133-135 |
| $CH_3$ | $CH_3$ | $CH(CH_3)_2$ | H | Br | H | 122.5-126 |
| $CH_2CH{=}CH{-}COOC_2H_5$ | $CH_3$ | $CH(CH_3)_2$ | H | H | H | oil |
| $(CH_2)_4COOCH_3$ | $CH_3$ | $CH(CH_3)_2$ | H | H | H | oil |
| 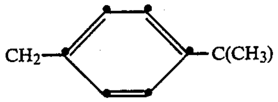 | $CH_3$ | $CH(CH_3)_2$ | H | H | H | 108-111 |
| 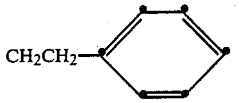 | $CH_3$ | $CH(CH_3)_2$ | H | H | H | 107-109 |
| 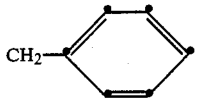 | $CH_3$ | $CH(CH_3)_2$ | $CH_3$ | H | H | 130-132 |
| 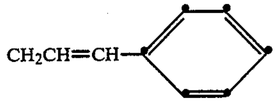 | $CH_3$ | $CH(CH_3)_2$ | H | H | H | 113-115 |
| $CH_2CH{=}C(CH_3){-}CH_2CH_2CH{=}C(CH_3)_2$ | $CH_3$ | $CH(CH_3)_2$ | H | H | H | oil |
| $CH_2CH(OH)CH_2OH$ | $CH_3$ | $CH(CH_3)_2$ | H | H | H | oil |
| $(CH_2)_3C{\equiv}CH$ | $CH_3$ | $CH(CH_3)_2$ | H | H | H | 73-75 |
| 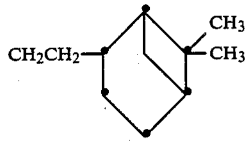 | $CH_3$ | $CH(CH_3)_2$ | H | H | H | oil |
| $CH(C_6H_5)COOCH_3$ | $CH_3$ | $CH(CH_3)_2$ | H | H | H | oil |
| $CH_2CH_2{-}C(CH_3){=}CH_2$ | $CH_3$ | $CH(CH_3)_2$ | H | H | H | oil |
| $(CH_2)_9CH{=}CH_2$ | $CH_3$ | $CH(CH_3)_2$ | H | H | H | oil |
| $CH(CH_3)C_6H_5$ | $CH_3$ | $CH(CH_3)_2$ | H | H | H | oil |
| $CH_3$ | 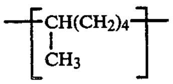 | | H | H | H | 122-124 |
| 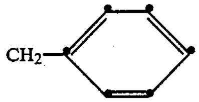 | 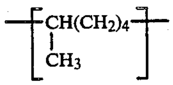 | | H | H | H | 123-125 |
| $CH_2C{\equiv}CH$ | 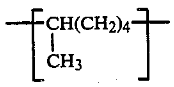 | | H | H | H | 132-134.5 |

-continued

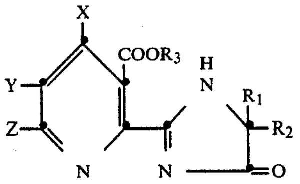

| $R_3$ | $R_1$ | $R_2$ | X | Y | Z | mp °C. |
|---|---|---|---|---|---|---|
| $CH_3$ | $CH_3$ | $CH(CH_3)_2$ | H | H | Cl | 102.5-104.5 |
| $CH_2COOCH_2CH_3$ | $CH_3$ | $CH(CH_3)_2$ | H | H | H | 86-90 |
| $CH_2COOH$ | $CH_3$ | $CH(CH_3)_2$ | H | H | H | 187-189 |
| $CH_2COOCH_2C_6H_5$ | $CH_3$ | $CH(CH_3)_2$ | H | H | H | 121.5-123 |
| $CH_2COOH$ | $CH_3$ | $CH(CH_3)_2$ | H | H | H | 106-110 |
| $CH_3$ | $CH_3$ | $CH(CH_3)_2$ | H | H | H | 110-112 $[\alpha]_D = -27.41°$ |
| $CH_3$ | $CH_3$ | $CH(CH_3)_2$ | H | H | H | 110.5-114 $[\alpha]_D = +27.28°$ |
| $CH_2C_6H_5$ | $CH_3$ | $CH(CH_3)_2$ | H | H | H | 102-105 $[\alpha]_D = +13.08°$ |
| $CH_2C_6H_5$ | $CH_3$ | $CH(CH_3)_2$ | H | H | H | 104-107 $[\alpha]_D = -12.76°$ |
| $CH_3$ | $CH_3$ | $CH(CH_3)_2$ | H | H | $N(CH_3)_2$ | 184.5-185.5 |
| $N{=}C(CH_3)_2$ | $CH_3$ | $CH(CH_3)_2$ | H | H | H | 117-119.5 |
| $CH_2CCl_3$ | $CH_3$ | $CH(CH_3)_2$ | H | H | H | 114-116 |
| $CH_3$ | $CH_3$ | $CH(CH_3)_2$ | H | H | $OC_6H_5$ | 128-131 |
| $CH_3$ | $CH_3$ | $CH(CH_3)_2$ | H | $C_4H_9$—n | H | 69-71.5 |
| $CH_3$ | $CH_3$ | $CH(CH_3)_2$ | Cl | H | H | 110-113 |
| $CH_3$ | $CH_3$ | $CH(CH_3)_2$ | H | H | $CF_3$ | 96.5-100 |
| $CH_3$ | $CH_3$ | $CH(CH_3)_2$ | H | H | 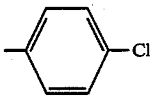 | |
| $CH_3$ | $CH_3$ | $CH(CH_3)_2$ | H | H | 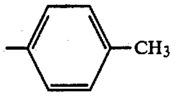 | 190-191 |
| $C_2H_5$ | $CH_3$ | $CH(CH_3)_2$ | H | H | n-$C_3H_7$ | 85-87 |
| $CH_3$ | $CH_3$ | $CH(CH_3)_2$ | H | H | n-$C_3H_7$ | 124-126 |
| $CH(CH_3)_2$ | $CH_3$ | $CH(CH_3)_2$ | H | H | n-$C_3H_7$ | 115-122 |
| $CH_3$ | $CH_3$ | $CH(CH_3)_2$ | H | H | i-$C_3H_7$ | 122-124.5 |
| $C_2H_5$ | $CH_3$ | $CH(CH_3)_2$ | H | H | i-$C_3H_7$ | |
| $CH(CH_3)_2$ | $CH_3$ | $CH(CH_3)_2$ | H | H | i-$C_3H_7$ | 106.5-110.5 |
| $CH_3$ | $CH_3$ | $CH(CH_3)_2$ | H | | $-(CH_2)_5-$ | 170-174 |
| $CH_3$ | $CH_3$ | $CH(CH_3)_2$ | H | $CH_3$ | H | 129-130.5 |
| $CH_3$ | $CH_3$ | $CH(CH_3)_2$ | H | H | $C_6H_5$ | 162-164 |
| $CH_3$ | $CH_3$ | $CH(CH_3)_2$ | H | H | $CH_3$ | 95.5-97.5 |
| $C_2H_5$ | $CH_3$ | $CH(CH_3)_2$ | H | H | $C_2H_5$ | 110-113 |
| $CH(CH_3)_2$ | $CH_3$ | $CH(CH_3)_2$ | H | H | $C_2H_5$ | 111-123 |
| $CH_3$ | $CH_3$ | $CH(CH_3)_2$ | H | H | $C_2H_5$ | 139-140 |

EXAMPLE 8

Preparation of the Hydrochloride salt of methyl-2-(5-isopropyl-5-methyl-4-oxo-2-imidazolin-2-yl)nicotinate To a stirred suspension of 3.0 g of the ester of Example 5 in 40 ml ether is added enough methylene chloride to obtain a solution. Dry hydrogen chloride is then passed into the solution for about 20 minutes. After 1 hour the mixture is filtered to remove the product which is washed with ether and dried to give 1.90 g of analytically pure hydrochloride salt and melting point equal to 195°-196° C.

EXAMPLE 9

Preparation of 2-(5-Isopropyl-5-methyl-4-oxo-2-imidazolin-2-yl)nicotinic acid To 22.63 g ester of Example 5 in 100 ml water is added a solution containing 3.29 g sodium hydroxide in 25 ml water and the mixture heated under reflux with stirring for 1.5 hours. After standing at room temperature overnight, 6.8 ml concentrated hydrochloric acid is added causing a heavy precipitate to form. This is removed by filtration, washed with 20 ml water, followed by 30 ml ether and dried to give 19.27 g acid, mp 168°-170° C. This material is dissolved in 350 ml methylene chloride, filtered (to remove a small amount of the isomeric 2-acid) and concentrated to give 17.91 g of pure acid, mp 170°-172° C. The analytically pure sample is prepared by recrystallization of the material from acetone-hexane, mp 170°-172.5°0 C. By substituting the appropriate methyl nicotinate for methyl 2-(5-isopropyl-5-methyl-4-oxo-2-imidazolin-2-yl)nicotinate in the above procedure, the following nicotinic acids are produced.

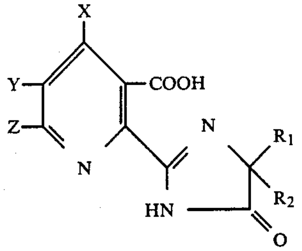

| $R_1$ | $R_2$ | X | Y | Z | mp °C. |
| --- | --- | --- | --- | --- | --- |
| $CH_3$ | $CH(CH_3)_2$ | H | H | $CF_3$ | 133-142 |
| $CH_3$ | $CH(CH_3)_2$ | H | H | 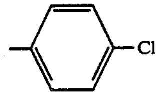 | 247-249 |
| $CH_3$ | $CH(CH_3)_2$ | H | H | 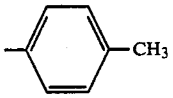 | 215.5-218.5 |
| $CH_3$ | $CH(CH_3)_2$ | H | H | n-$C_3H_7$ | 148.5-150.5 |
| $CH_3$ | $CH(CH_3)_2$ | H | H | i-$R_3H_7$ | 131-133.5 |
| $CH_3$ | $CH(CH_3)_2$ | H | $CH_3$ | $CH_3$ | 167-180 |
| $CH_3$ | $CH(CH_3)_2$ | H | | $-(CH_2)_5-$ | 141-148 |
| $CH_3$ | $CH(CH_3)_2$ | H | | $-(CH_2)_3-$ | 160-164 |
| $CH_3$ | $CH(CH_3)_2$ | H | H | $CH_3$ | 145-146.5 |
| $CH_3$ | $CH(CH_3)_2$ | H | H | $C_2H_5$ | 118-122 |
| $CH_3$ | $CH(CH_3)_2$ | H | | $-(CH_2)_4-$ | 159-162 |

EXAMPLE 10

Preparation of 2-(5-Isopropyl-5-methyl-4-oxo-2-imidazolin-2-yl)nicotinic acid To 1.0 g of the benzyl ester in 20 ml ethanol is added 50 mg 5% palladium on carbon catalyst and the mixture shaken in an atmosphere of hydrogen until one equivalent of hydrogen has been absorbed. The catalyst is removed by filtration, the solvent removed in vacuo and the residue crystallized from acetone-hexane to give the acid as described in Example 9.

The following acids are made by the above methods:

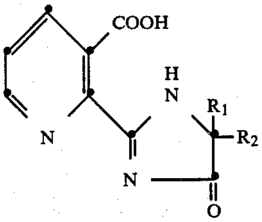

| $R_1$ | $R_2$ | mp °C. |
| --- | --- | --- |
| $CH_3$ | $C_2H_5$ | 124-126° |

-continued

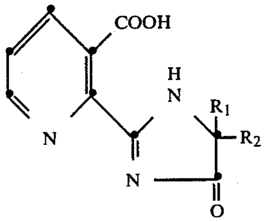

| $R_1$ | $R_2$ | mp °C. |
| --- | --- | --- |
| $-CH-(CH_2)_4-$<br>\|<br>CH | | 180-183° |
| $CH_3$ | $CH_3$ | 204-205.5° |
| $CH_3$ | 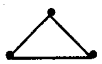 | 198-200° |
| $CH_3$ | $CH(CH_3)_2$ | 128-130° |
| $CH_3$ | $CH(CH_3)_2$ | 132-134 |

EXAMPLE 11

Preparation of Calcium 2-(5-isopropyl-5-methyl-4-oxo-2-imidazolin-2-yl)nicotinate To 0.98 g of the acid of Example 9 partially dissolved in 10 ml water is added, with stirring 0.18 g calcium carbonate. After 10 minutes,the solution is filtered, the filtrate concentrated and the residue treated with ether to give a crystalline product which is dried at 40° C. and 25 mm pressure to give 0.88 g of the calcium salt mp 265° C.

The sodium, diisopropylammonium, and triethylammonium salts are prepared in a similar manner.

The following salts can be prepared by the above procedure using the appropriate acid and the oxide, carbonate, bicarbonate or hydroxide of the selected metal, alkali metal, alkaline earth metal, ammonia or aliphatic amine.

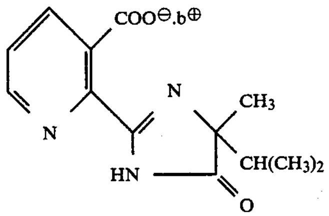

| $b^+$ | mp °C. |
| --- | --- |
| $NH_3CH(CH_3)C_6H_5$ | gum |
| $NH_4$ | sublines >168 |
| Ba/2 | >225 |
| Cu/2 | >225 |
| K | >225 |
| Li | >225 |
| Mg/2 | >225 |
| 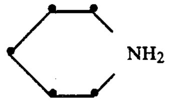 | — |

-continued

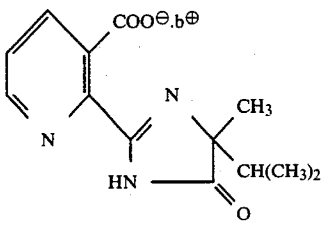

| b+ | mp °C. |
|---|---|
| 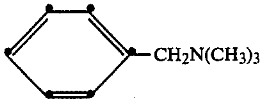 | oil |
| $H_2N-(CH_2)_6NH_3$ | oil |
| $C_{18}H_{35}$ | wax |
| n-$C_{12}H_{25}NH_3$ | 150-153 |
| $(CH_3)_3CCH_2C(CH_3)_2NH_3$ | — |
| $(n\text{-}C_4H_9)_2NH_2$ | — |
| $HOCH_2CH_2NH_2CH_3$ | — |
| 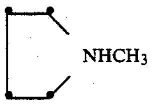 | — |
| n-$C_8H_{17}NH_3$ | — |
| 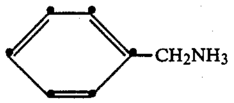 | — |
| Na | — |
| $CH(CH_3)_2NH$ | 160-180 (dec) |
| $(C_2H_5)_3N$ | — |
| 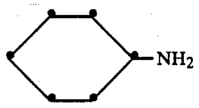 | — |
| 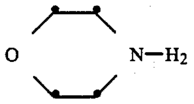 | — |
| 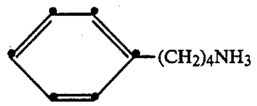 | — |
| 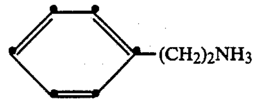 | — |
| $(CH_3O)_2CHCH_2NH_3$ | — |
| $(C_2H_5OCH_2CH_2)NH_3$ | — |
| $CH_3O(CH_2)_3NH_3$ | — |
| $(HOCH_2CH_2)_2NH_2$ | — |
| Fe/2 | >225 |
| Fe/3 | 155-158 |
| $HOCH_2CH_2NH_3$ | — |

-continued

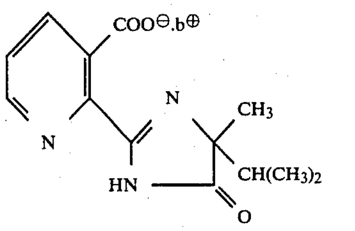

| b+ | mp °C. |
|---|---|
| 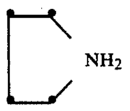 | — |
| $(C_2H_5)_2NH_2$ | — |
| $(CH_3)_2CHNH_3$ | — |
| $CH_2{=}C(CH_3)CH_2NH_3$ | — |
| $(CH_3)_2CHCH_2NH_3$ | — |
| $CH_3OCH_2CH(CH_3)NH_3$ | — |
| $(CH_3)_3CNH_3$ | — |
| $(CH_3)_2CHNH_3$ | 135-137 $[\alpha]_D^{25} = +39.13°$ (c = 0.0127 g/ml $H_2O$) |

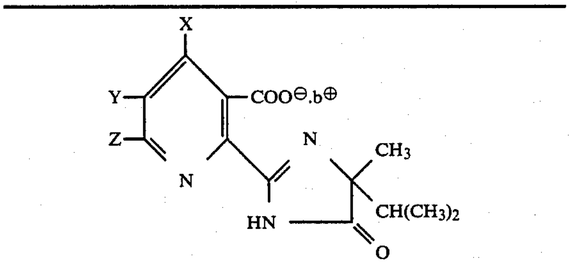

| X | Y | Z | b⊕ | mp °C. |
|---|---|---|---|---|
| H | $OCH(CH_3)_2$ | H | $(CH_3)_2CHNH_3$ | amorphous |
| H | $C_2H_5$ | H | Ca/2 | >250 |
| H | $C_2H_5$ | H | Na | 214-240 |
| H | $C_2H_5$ | H | $(CH_3)_2CHNH_3$ | |

EXAMPLE 12

Preparation of Methyl 2-[(carbamoyl-1,2-dimethylpropyl)carbamoyl]nicotinate

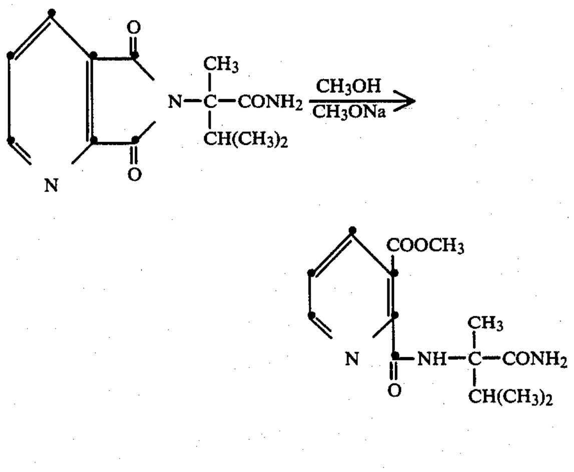

Sodium hydride (0.47 g of a 50% suspension in mineral oil) is reacted with 500 ml dry methanol under nitrogen. To this is added 51.4 g of the amide of Example 2 and the mixture stirred at room temperature overnight. The mixture is concentrated, the residue dissolved in methylene chloride and the solution washed first with 150 ml water followed by 150 ml brine. After drying ($Na_2SO_4$), the organic phase is concentrated and the residue crystallized from ether to give 47.85 g of product which is analytically pure mp 108°-145° C. with decomposition.

EXAMPLE 13

Preparation of Methyl 3-[1-carbamoyl-1,2-dimethylpropyl)carbamoyl]picolinate

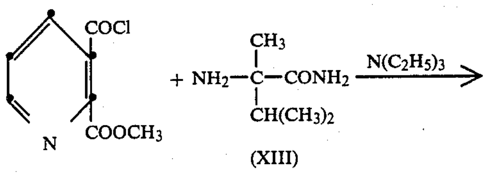

(XIV) (XIII)

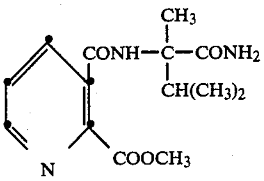

(XV)

To a stirred mixture containing 25.5 g acid chloride [(Helv. Chem. Acta, 34, 488 (1951)] and 29.7 ml triethylamine in 200 ml methylene chloride is added, under nitrogen, dropwise a solution containing 13.93 g amino amide as disclosed in (U.S. Pat. No. 4,017,510) at such a rate that the temperature of the reaction mixture remains below 30° C. After 1 hour, the mixture is filtered, the solid washed with methylene chloride and dried to give 19.8 g product, mp 176°-177° C. (decomp). A sample recrystallized from nitromethane had mp 196°-196.5° C. (decomp) and analytically pure.

EXAMPLE 14

Preparation of 5,7-Dihydro-α-isopropyl-α-methyl-5,7-dioxo-6-H-pyrrolo[3,4-b]pyridine-6-acetic acid (-isomer)

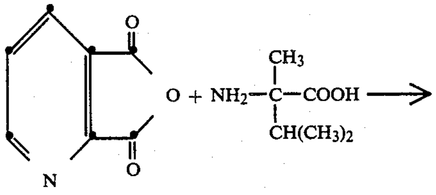

-continued

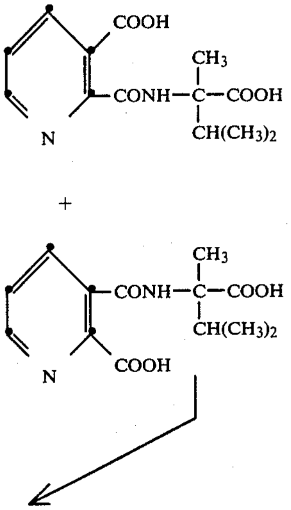

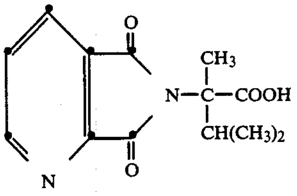

To a stirred suspension of 18.4 g of the anhydride in 760 ml of dry acetone is added, under nitrogen, 16.2 g of (+)-methylvaline. After stirring at room temperature for 48 hours, the mixture is filtered and the filtrate concentrated to give the crude intermediate. This material is dissolved in 500 ml acetic anhydride, a catalytic quantity of sodium acetate added and the mixture stirred at room temperature for 5 hours. After heating under reflux for 1.5 hours, the mixture is concentrated. The residue is dissolved in ethyl acetate and washed with water. The dried extract is concentrated to give a dark syrup. A sample is dissolved in ethyl acetate, treated with charcoal, filtered and concentrated. The residue is crystallized from methylene chloride to give the product, mp 122°-125° C. $[\alpha]_D^{25}=-7.73°$ C. (c=0.100, THF).

By essentially the same procedure and using the appropriate starting quinolinic anhydride and amino acid the following amides are prepared

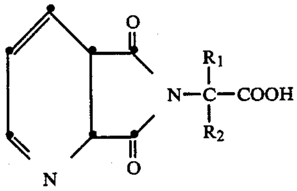

| $R_1$ | $R_2$ | mp °C. |
|---|---|---|
| $-CH_3$ | $-CH(CH_3)_2$ | 126-127<br>$[\alpha]_D^{25}$ = +6.93<br>(c = 0.100, THF) |
| $CH_3$ | $CH_2CH(CH_3)_2$ | 174-176 |
| $CH_3$ | $CH(CH_3)_2$ | 196.5-198.5 |
| $-\underset{CH_3}{CH}CH_2CH_2CH_2CH_2-$ | | 183-186 |

EXAMPLE 15

Preparation of 5,7-Dihydro-α-isopropyl-α-methyl-5,7-dioxo-6H-pyrrolo[3,4-b]pyridine-6-acetamide

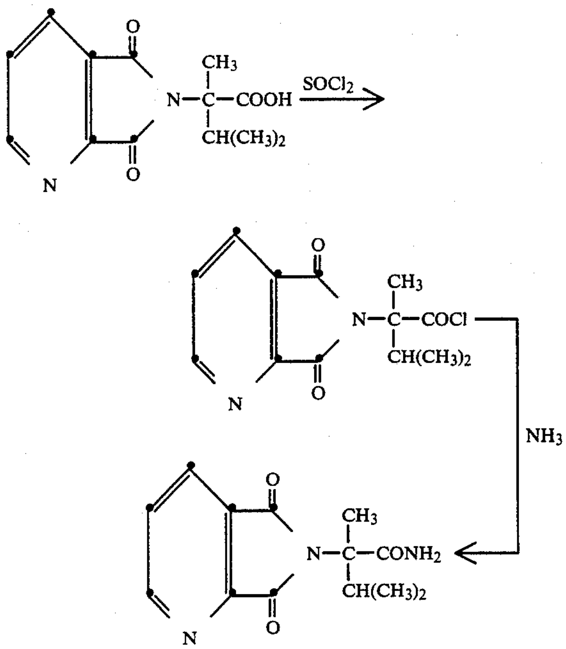

To a mixture containing 32 g of (−)-acid in 375 ml of toluene is added 2 ml of dimethylformamide followed by 13 ml of thionyl chloride. After heating at reflux for 1.25 hours, the mixture is concentrated in vacuo. The residue is dissolved in 350 ml of tetrahydrofuran, cooled to 0° C. and a slight excess of gaseous ammonia bubbled through the mixture. The solvent is removed in vacuo to leave a solid which is washed with water and air-dried. A portion of this solid is crystallized twice from ethyl acetate (with charcoal treatment) to give the desired product as a white crystalline solid, mp 188°-189° C. $[\alpha]_D^{25}=+3.59$ (c=0.791, DMSO)

By essentially the same procedure and using the appropriate acid, the following amides are prepared.

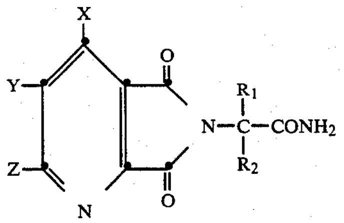

| $R_1$ | $R_2$ | X | Y | Z | mp °C. |
|---|---|---|---|---|---|
| $CH_3$ | $CH(CH_3)_2$ | H | H | H | 189.5-192 $[\alpha]_D^{25} = -3.02$ (c = 0.0744, DMSO) |
| $CH_3$ | $CH_2CH(CH_3)_2$ | H | H | H | 176-178 |
| $-\underset{\substack{\vert\\CH_3}}{C}HCH_2CH_2CH_2CH_2-$ | | H | H | H | 186-188 |

Trans ($CH_3$ to $CONH_2$)

-continued

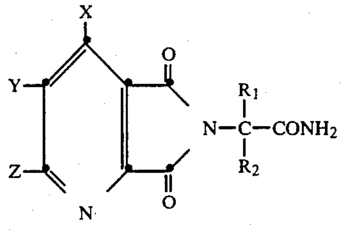

| $R_1$ | $R_2$ | X | Y | Z | mp °C. |
|---|---|---|---|---|---|
| $-\underset{\substack{\vert\\CH_3}}{C}H-CH_2CH_2CH_2CH_2-$ | | H | H | H | 241-247 |
| Cis ($CH_3$ to $CONH_2$) | | | | | |
| $CH_3$ | $CH(CH_3)_2$ | H | H | $OCH_3$ | 194-195 |
| $C_2H_5$ | $C_2H_5$ | H | H | H | 215-218 |
| $CH_3$ | $CH(CH_3)_2$ | $CH_3$ | H | H | 146.5-157 |
| $CH_3$ | $CH(CH_3)_2$ | H | Br | H | 192-198.5 |
| $-(CH_2)_5-$ | | H | H | H | 211-213 |
| $CH_3$ | $CH(CH_3)_2$ | H | H | Cl | 154-156 |
| $CH_3$ | $CH(CH_3)_2$ | H | H | H | 189.5-192 (− isomer) |
| $CH_3$ | $CH(CH_3)_2$ | H | H | H | 188-189 (+ isomer) |

EXAMPLE 16

Preparation of 5-Butyl-N-(1-carbamoyl-1,2-dimethylpropyl)picolinamide

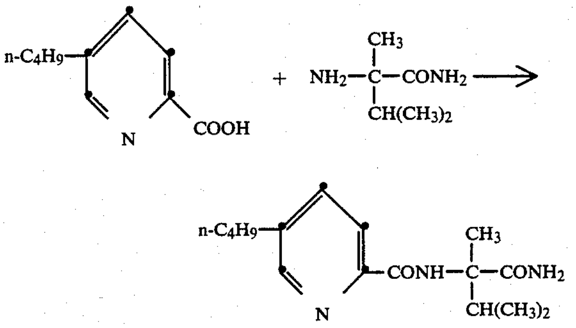

To a suspension of 20 g of acid in 200 ml of dry tetrahydrofuran is added with stirring 10.7 ml of ethyl chloroformate. The mixture is cooled to −10° C. and and 17.1 ml of triethylamine added dropwise so that the temperature does not exceed 0° C. After 10 minutes, a solution containing 14.3 g of the amino amide in 150 ml of dry tetrahydrofuran is added dropwise at 0° C. with stirring. The mixture is allowed to reach room temperature and after 2 hours, enough water added to dissolve the solid. The tetrahydrofuran is removed in vacuo. The aqueous residue is extracted with ethyl acetate, and after saturating with salt, extracted again. The organic phase are combined, washed with brine dried and concentrated. The residual oil crystallized. A portion was crystallized first from methylene chloride-hexane followed by ether-hexane to give analytically pure product mp 83°-86° C.

Using essentially the same procedures described above the following picolinic acids are prepared.

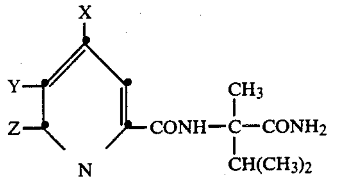

| X | Y | Z | mp °C. |
|---|---|---|---|
| H | $CH_3$ | H | 126-127.5° |
| H | H | $CH_3$ | |
| H | $C_2H_5$ | H | |
| H | $NO_2$ | H | 158-160 |
| H | $C_2H_5$ | H | 106-110 |
| H | $COOCH_3$ | H | 154-156 |
| H | $N(CH_3)_2$ | H | gum |
| H | $N(C_2H_5)$ | H | |
| H | F | H | 190-196 |
| H | $C_2H_5$ | H | oil $[\alpha]_D^{20} = -48.6°$ (c = 0.080 g/ml THF) |

EXAMPLE 17

Preparation of 2-(5-Butyl-2-pyridyl)-5-isopropyl-5-methyl-2-imidazolin-4-one

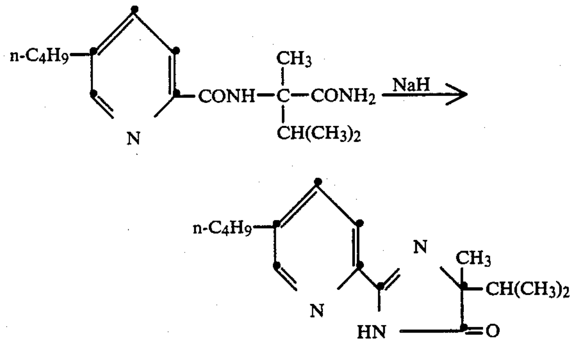

A stirred suspension of sodium hydride (2.4 g) in 250 ml of dry toluene is heated with stirring, under reflux under a Dean-Stark water Separator. To this mixture is added slowly 26.52 g of diamide. After the addition, heating is continued for 1.5 hours. After standing overnight, the reaction is quenched with water, the pH adjusted to 5 with hydrochloric acid and the phases separated. The aqueous phase is further extracted twice with ethyl acetate, the organic extracts combined, washed with brine, dried and concentrated.

The residue is recrystallized from hexane to give the pure product mp 60°-62° C.

Using essentially the same procedure, the following imidazolinones are prepared.

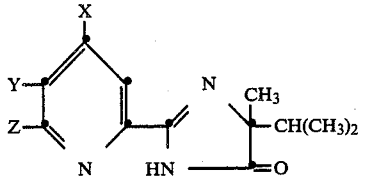

| X | Y | Z | mp °C. |
|---|---|---|---|
| H | $C_6H_5$ | H | 111-114 |

-continued

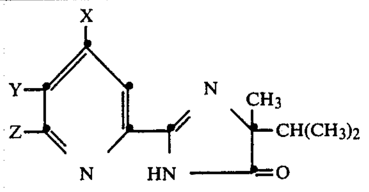

| X | Y | Z | mp °C. |
|---|---|---|---|
| H | H | $CH_3$ | — |
| H | $CH_3$ | H | 82.5-84 |
| H | $NO_2$ | H | 125-130 |
| H | $C_2H_5$ | H | 67-71 |
| H | $OCH_3$ | H | 166-167.5 |
| H | $COOCH_3$ | H | 133-134 |
| H | $N(CH_3)_2$ | H | 153-156 |
| H | $N(C_2H_5)_2$ | H | 120-124 |
| H | F | H | 88-98 |
| H | $C_2H_5$ | H | 64-66 $[\alpha]_D^{20} = +5.32°$ (c = 0.0500 g/ml THF) |

EXAMPLE 18

Preparation of 5-Butyl-2-(5-isopropyl-5-methyl-4-oxo-2-imidazolin-2-yl)nicotinic acid

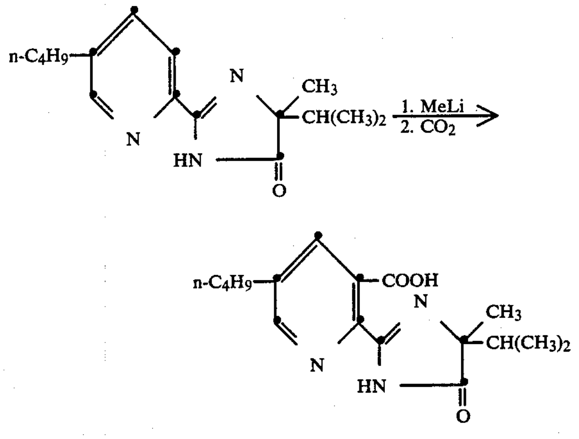

To a stirred solution containing 10.0 g imidazolinone in 100 ml dry tetrahydrofuran at −76° under nitrogen is added dropwise 47.3 ml of a 1.7M solution of methyl lithium in ether. The mixture becomes very thick and 2 ml hexamethylphosphoramide and about 150 ml tetrahydrofuran is added. The mixture is allowed to warm to −10° C. and held at this temperature for 0.75 hour. The mixture is cooled to −70° and added to slurry of carbon dioxide in tetrahydrofuran. After stirring for 0.5 hour, water is added to the mixture, the pH adjusted to 2 with dilute sulfuric acid, and the product extracted into methylene chloride. The extract is washed with brine, dried and concentrated to give the product as a yellow solid. Recrystallization from methylene-chloride-hexane gave an analytically pure sample, mp 152°-154°.

Using essentially the same procedure as described above but substituting the appropriate imidazolinone for 2-(5-butyl-2-pyridyl)-5-isopropyl-5-methyl-2-imidazolinone, and using dimethylformamide and methyl iodide as well as carbon dioxide as electrophiles, the following imidazolinones are prepared:

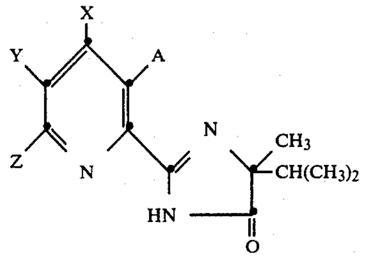

| A | X | Y | Z | mp °C. |
|---|---|---|---|---|
| COOH | Cl | H | H | 184–186 |
| COOH | H | $CH_3$ | H | 203.5–204.5 |
| COOH | H | $C_6H_5$ | H | 150–151.5 |
| $CH_3$ | H | H | H | 93–96 |
| CHO | H | H | H | 223–225 |
| COOH | H | H | $C_6H_5$ | 252–254 |
| COOH | H | $CH_3$<br>$CH_2O-Si-CH_3$<br>$C(CH_3)_3$ | H | 82–85 |
| COOH | H | $C_2H_5$ | H | 172–175 |
| COOH | H | $OCH_3$ | H | 166–167.5 |
| COOH | H | n-$C_3H_7$ | H | 147–150 |
| COOH | H | i-$C_3H_7$ | H | 180.5–183.5 |
| COOH | H | $C(OH)(CH_3)_2$ | H | 168–169 |
| COOH | H | $OC_2H_5$ | H | 140–144 |
| COOH | H | $OCH(CH_3)_2$ | H | 92–96 |
| *COOH | H | OH | H | 255–257 |
| COOH | H | $N(CH_3)_2$ | H | 192–195 |
| COOH | H | $N(C_2H_5)_2$ | H | 69–78 |
| COOH | H | F | H | — |
| COOH | H | $C_2H_5$ | H | 121–123<br>$[\alpha]_D^{20} = +13.41°$<br>(c = 0.0908 g/ml THF) |

*The starting material is the 5-tert-butyldimethylsilyloxy derivative of Example 26.

EXAMPLE 19

Preparation of 2-(5-Isopropyl-5-methyl-4-oxo-2-imidazolin-2-yl)-3-pyridineacetic acid

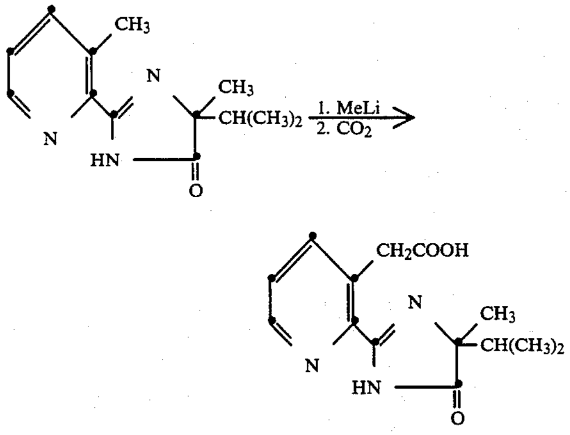

Using essentially the same procedure as described in Example 18 but substituting 5-isopropyl-5-methyl-2-(3-methyl-2-pyridyl)-2-imidazolin-4-one for 5-isopropyl-5-methyl-2-(5-n-butyl-2-pyridyl)-2-imidazolin-4-one, there is obtained the desired pyridine-acetic acid, mp 173° (dec.).

EXAMPLE 20

Preparation of Methyl 2-(5-isopropyl-5-methyl-4-oxo-2-imidazolin-2-yl)-6-phenoxynicotinate

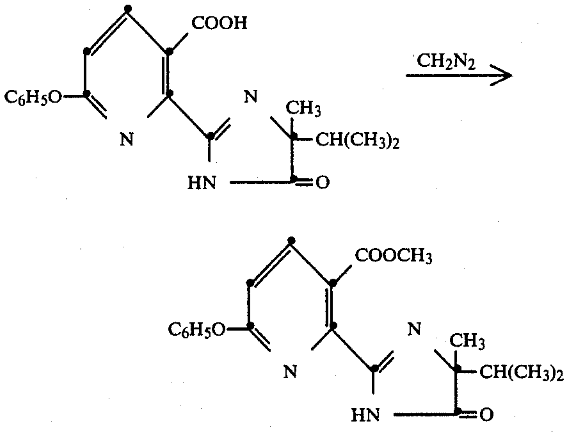

A solution of the acid in ether is treated with excess diazomethane. After a few minutes excess diazomethane is removed by warming. The solvent is removed and the residue crystallized from ether hexane to give the desired methyl ester mp 128°–131° C.

Using essentially the same conditions as those described above, the following methyl esters are prepared starting with the appropriate acid.

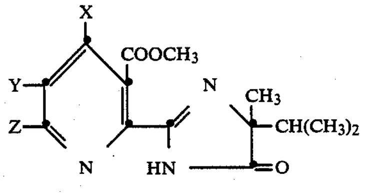

| X | Y | Z | mp °C. |
|---|---|---|---|
| H | H | $-OC_6H_5$ | 128–131 |
| H | $-C_4H_9-n$ | H | 69–71.5 |
| Cl | H | H | 110–113 |
| H | H | $OCH_2C_6H_5$ | 187–188 |
| H | H | $OC_2H_5$ | 126–129 |
| $OC_6H_5$ | H | H | 175–177 |
| H | $CH_3$ | H | 129–130.5 |
| H | $C_6H_5$ | H | — |
| H | H | $C_6H_5$ | 162–164 |
| $OCH_2C_6H_5$ | H | H | 164–171 |
| H | $C_2H_5$ | H | 96–99 |
| H | $CH_2OH$ | H | 146–147 |
| H | $OCH_3$ | H | 101–102.5 |
| H | $-C_3H_7-n$ | H | gum |
| H | $-CH(CH_3)_2$ | H | gum |
| H | $OC_2H_5$ | H | 47–50 |
| H | F | H | 92–101 |
| H | $N(CH_3)_2$ | H | 110–134 |
| H | $N(C_2H_5)_2$ | H | 118–120 |

EXAMPLE 21

Preparation of 4[2-(5-Isopropyl-5-methyl-4-oxo-2-imidazolin-2-yl)nicotinoyl]morpholine

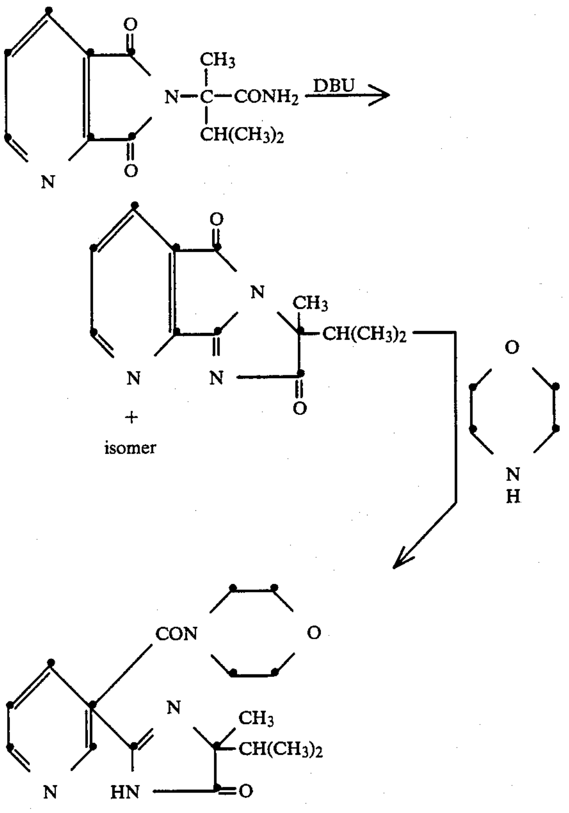

The cyclization of the amide is accomplished by heating 7.83 g of amide in 150 ml of toluene and 0.45 ml of 1,8-diazabicyclo[5,4,0]undec-7-ene under a Dean-Stark water Separator for 2 hours as described in Example 4. The separator is removed, 4 ml of morpholine is added and heating continued for 3 hours. The mixture is concentrated and the residue chromatographed on silica gel in ethyl acetate. The product is eluted first and this material is recrystallized from ether-hexane to give pure amide mp 143°-145.5° C.

By substituting the appropriate amine for morpholine, the following amides are prepared.

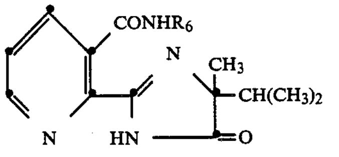

| $R_6$ | mp °C. |
|---|---|
| $-CH_2C{\equiv}CH$ | 171-173.5 |
| 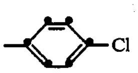 | 227.5-228.5 |
| $-CH_2CH_2OH$ | 174.5-175.5 |

EXAMPLE 22

Preparation of N-(2-chloroethyl)-2-(5-isopropyl-5-methyl-4-oxo-2-imidazolin-2-yl)nicotinamide

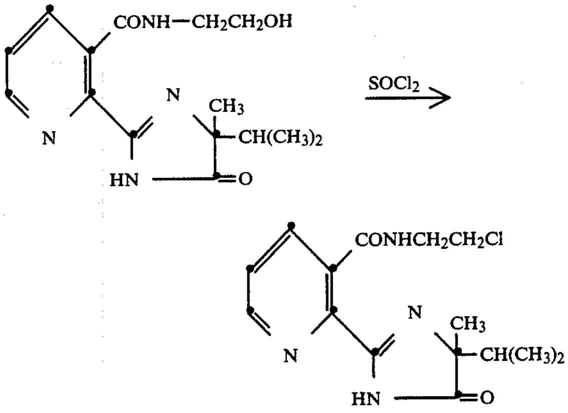

A mixture containing 4.04 g of hydroxyethylamide and 8.2 ml of thionyl chloride in 250 ml of methylene chloride is heated at reflux for 3.5 hours. The mixture is cooled, poured into water and the aqueous phase made basic with sodium carbonate. The mixture is shaken, the organic phase separated, washed with water, dried and concentrated to leave a white solid which is recrystallized from toluene to give the desired chloroethylamide as a white crystalline solid, melting partially at 128.5° C. with complete melting at 157° C.

EXAMPLE 23

Preparation of 2-(5-Isopropyl-5-methyl-4-oxo-2-imidazolin-2-yl)nicotinamide

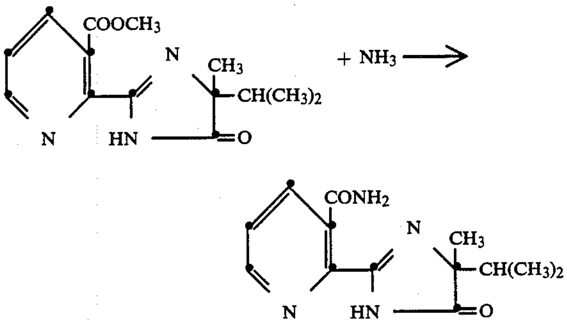

A solution containing 10.0 g of ester in 50 ml of tetrahydrofuran is added to 100 ml of liquid ammonia in a glass bomb. The bomb is sealed and the contents heated at 100° C. for 16 hours. After cooling, the ammonia is evaporated and the residue concentrated. This residue is combined with material from similar reactions using 5 g and 7 g of the ester. These are crystallized from ethyl acetate to give 5 g of product. The filtrate is concentrated after treatment with charcoal to give a further 15.7 g of product.

Two recrystallizations of a sample from ethyl acetate gives the pure nicotinamide as a white crystalline solid mp 178°~2° C.

EXAMPLE 24

Preparation of 2-(5-Isopropyl-5-methyl-4-oxo-2-imidazolin-2-yl)nicotinonitrile

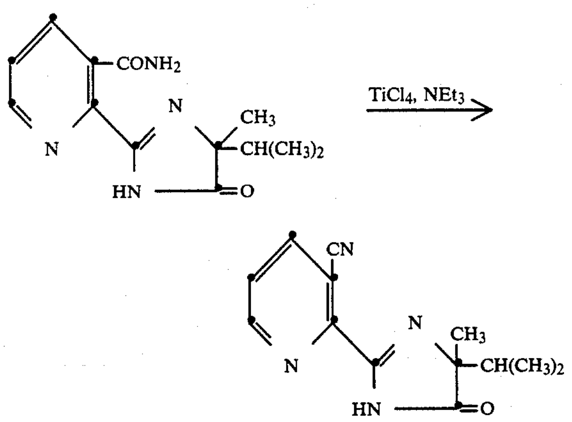

To 75 ml of ice-cold tetrahydrofuran under nitrogen is added with stirring 12 ml of titanium tetrachloride in 20 ml of carbon tetrachloride at such a rate that the temperature does not exceed 5° C. This is followed by the addition of 5.2 g of the amide in 75 ml of tetrahydrofuran again maintaining a temperature of <5° C. Finally, 17 ml of triethylamine in 5 ml of tetrahydrofuran is added to the mixture under the same conditions. After 1.5 hours at 5° C., the mixture is stirred overnight at room temperature. Water (100 ml) is cautiously added at 0° C., the upper organic phase is separated and the aqueous phase extracted with methylene chloride (4×100 ml). The combined extracts are washed with brine, dried and concentrated. The solid residue is recrystallized from hexane-methylene-chloride to give the nicotinonitrile as a tan solid, mp 144°-148° C. The analytically pure compound has mp 148°-150° C.

EXAMPLE 25

Preparation of 2-[5-(hydroxymethyl)-2-pyridyl]-5-isopropyl-5-methyl-2-imidazolin-4-one

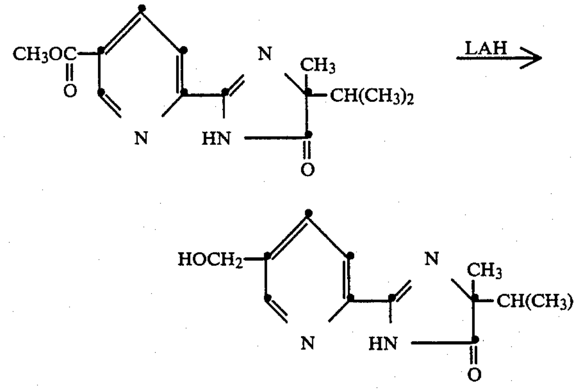

To a stirred slurry of 23 g lithium aluminum hydride in 250 ml tetrahydrofuran under nitrogen at −70° C. is added dropwise 46.8 g of the ester in 350 ml tetrahydrofuran. The mixture is warmed to room temperature, 73 ml of a saturated ammonium chloride solution added cautiously with vigorous stirring, the mixture filtered and the solid washed with tetrahydrofuran. The filtrate is concentrated to leave a gum. This is chromatographed on silica gel and the product eluted by ethyl acetate, mp 101°-104° C.

EXAMPLE 26

Preparation of 2-[5(tert-butyldimethylsiloxy)methyl-2-pyridyl]-5-isopropyl-5-methyl-2-imidazolin-4-one

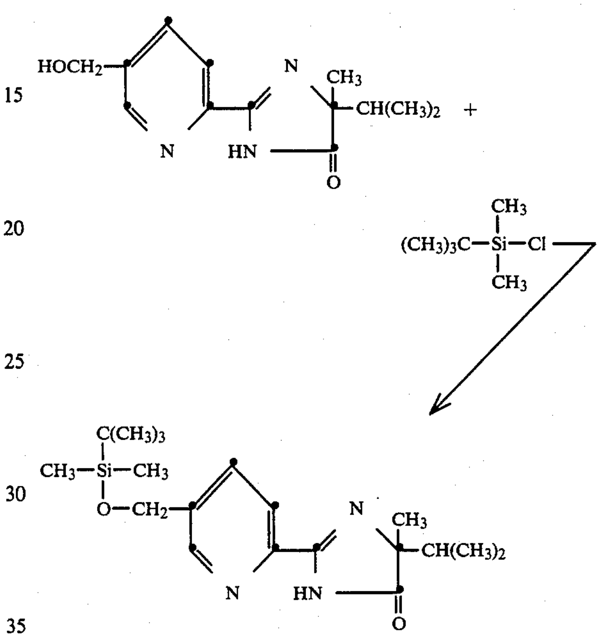

To a stirred solution containing 2.03 g alcohol in 3.5 ml dimethylformamide under nitrogen is added 0.68 g imidazole followed by 3.1 g t-butyldimethylsilyl chloride. The mixture is kept at 35° C. for 10 hours and room temperature for 10 hours. Saturated sodium sulfate is added and the aqueous mixture extracted with ether. The extract is washed with brine, dried and evaporated. The pure product is isolated as a gum by chromatography of the crude product on silica gel and elution with methylene chloride followed by ether.

By using essentially the same procedure but using 2-(5-hydroxy-2-pyridyl)-5-isopropyl-5-methyl-2-imidazolin-4-one as starting material, there is obtained 2-(5-tert-butyldimethylsiloxy-2-pyridyl)-5-isopropyl-5-methyl-2-imidazolin-4-one, mp 105°-109° C.

EXAMPLE 27

Preparation of 5-(Hydroxymethyl)-2-(5-isopropyl-5-methyl-4-oxo-2-imidazolin-2-yl)nicotinic acid

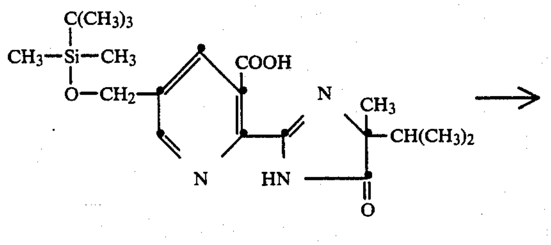

-continued

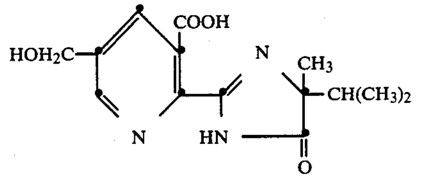

A solution containing 0.29 g silyl ether in 10 ml 80% aqueous acetic acid is heated on the steam bath for 0.5 hours. The mixture is concentrated and the residue dried azeotropically with toluene. The residue, a gum, is crystallized from methylene chloride-hexane. The pure product has mp 170°-171.5° C.

EXAMPLE 28

Preparation of Methyl 2-(1-acetyl-4-isopropyl-4-methyl-5-oxo-2-imidazolin-2-yl)nicotinate

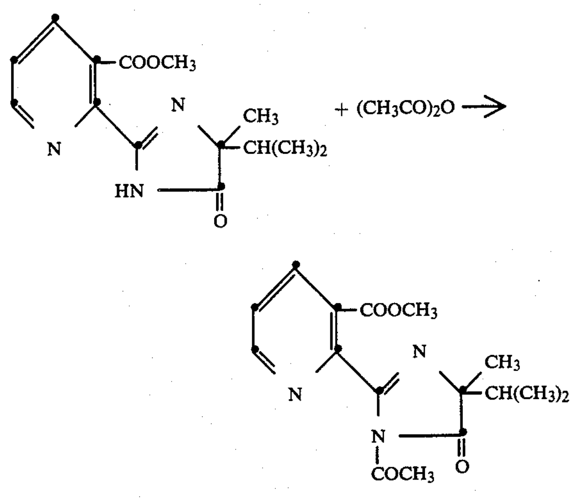

A solution containing 10 g methyl 2-(5-isopropyl-5-methyl-4-oxo-2-imidazolin-2-yl)nicotinate in 100 ml acetic anhydride is heated under reflux for 16 hours. The mixture is concentrated and the residue crystallized from ether-hexane to give the N-acetyl derivative, mp 88°-90° C. This is the mp of analytically pure material.

Using essentially the same conditions as those described above, the following N-substituted imidazolinones are prepared by reacting the appropriate imidazolinyl nicotinate with the appropriate acyl anhydride, acyl halide, sulfonyl halide, alkyl halide or sulfate either alone or in a solvent such as pyridine or toluene.

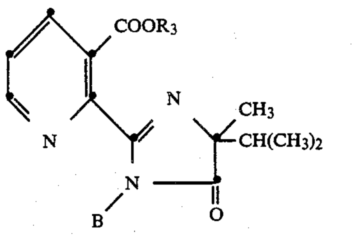

| $R_3$ | B | mp °C. |
|---|---|---|
| $CH_3$ | $CH_3$ | oil |

-continued

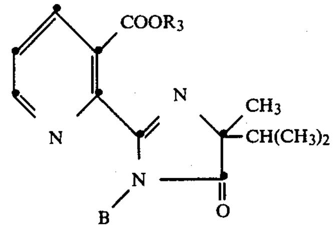

| $R_3$ | B | mp °C. |
|---|---|---|
| $CH_3$ | $COC(CH_3)_3$ | 85-87 |
| $CH_3$ | $COC_{11}H_{23}$—n | oil |
| $CH_3$ | $COC_6H_5$ | 104-107 |
| $CH_3$ | $COC_2H_5$ | 90-92.5 |
| $CH_3$ | $COCH_2Cl$ | 98-100 |
| $CH_2C_6H_5$ | $COC_2H_5$ | oil |
| $CH_2C_6H_5$ | $COC(CH_3)_3$ | oil |
| $CH_2C_6H_5$ | $COCH_2Cl$ | oil |
| $CH_3$ | $SO_2CH_3$ | 115-118 |
| $CH_2{\equiv}CH$ | $COCH_3$ | 125-127 |
| $CH_2C{\equiv}CH$ | $COCH_2Cl$ | 118-122 |
| $CH_2C{\equiv}CH$ | $COC_6H_5$ | 118-120 |
| $CH_2C{\equiv}CH$ | $COC(CH_3)_3$ | 101-104 |
| $CH_3$ | $COOC_2H_5$ | oil |
| $CH_3$ | 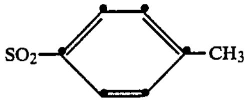 | 114-118 |
| $CH_2C_6H_5$ | $COC_6H_5$ | 117-125 |
| $CH_2C{\equiv}CH$ | $COC_2H_5$ | 85-88 |
| $CH_3$ | 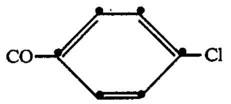 | 122-125 |
| $CH_3$ | 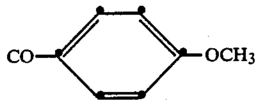 | 119.5-121.5 |
| $CH_3$ | 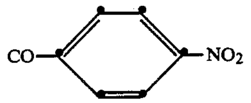 | 148-151 |

EXAMPLE 29

Preparation of Methyl 2-(1-acetyl-4-isopropyl-4-methyl-5-oxo-2-imidazolin-2-yl)nicotinate-1-oxide

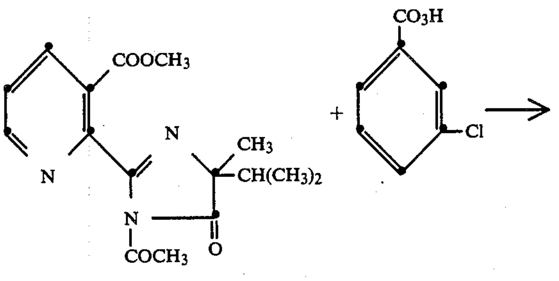

-continued

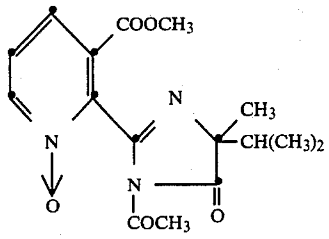

To a solution containing 40 g (126 mmoles) of the nicotinate in 500 ml methylene chloride is added 30 g of 80–90% pure (139 mmoles based on 80% purity) m-chloroperbenzoic acid. After heating at reflux overnight, excess peracid is destroyed by the addition of excess 1-hexene. The solution is washed with saturated sodium bicarbonate solution, dried and concentrated. The residue is crystallized from methylene chloride-hexane-ether to give 18.3 g of the desired N-oxide, mp 92°–100° C. The analytically pure N-oxide has mp 95°–99° C.

EXAMPLE 30

Preparation of Methyl 2-(5-isopropyl-5-methyl-4-oxo-2-imidazolin-2-yl)nicotinate-1-oxide

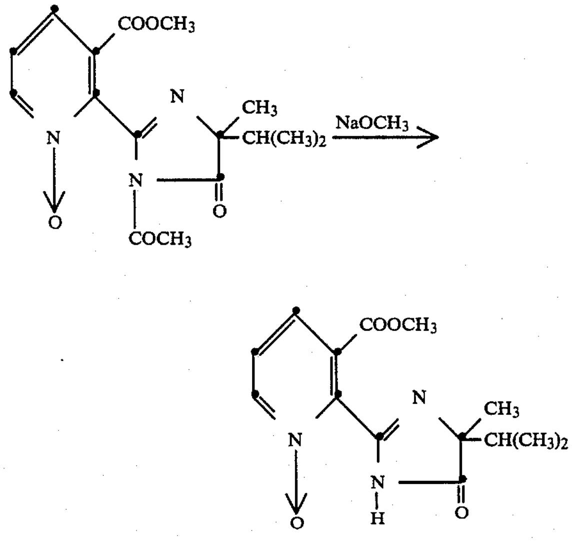

To a solution of 30 g of the N-acetyl compound in 200 ml methanol is added approximately 0.5 g sodium methoxide. After stirring for two hours, the product is removed by filtration and air dried, mp 197°–201° C. The analytically pure sample which had been recrystallized from acetone-hexane has mp 200°–201° C.

EXAMPLE 31

Preparation of Methyl 6-chloro-2-(5-isopropyl-5-methyl-4-oxo-2-imidazolin-2-yl)nicotinate

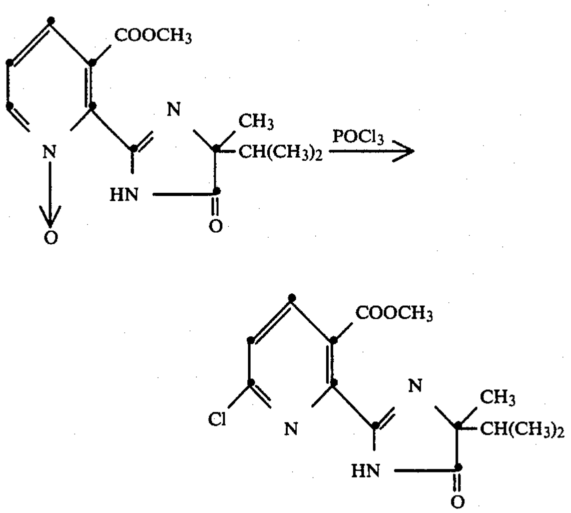

A solution containing 22.0 g N-oxide in 135 ml phosphorus oxychloride is heated under reflux for four hours. After standing at room temperature overnight, excess phosphorus oxychloride is removed in vacuo and the residue treated with xylene and again concentrated. The residue is dissolved in methylene chloride and treated with water, the pH adjusted to 5 with sodium carbonate and ether added to make the organic layer the upper layer. The layers are separated and the aqueous phase reextracted twice with ether. The combined organic extracts are washed with brine, dried and concentrated. The residue is chromatographed on 250 g of silica gel in a mixture of ether and hexane to give 10.6 g of the desired product. This is recrystallized from ether-hexane to give 8.95 g of the 6-chloro derivative, mp 104°–106° C. The analytically pure sample melted at 102.5°–104.5° C.

EXAMPLE 32

Preparation of 6-Chloro-2-(5-isopropyl-5-methyl-4-oxo-2-imidazolin-2-yl)nicotinic acid

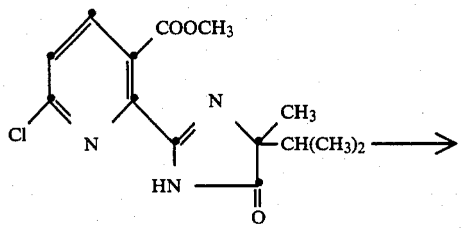

-continued

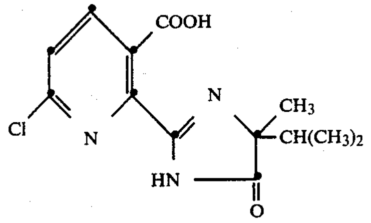

A suspension of 3.0 g of the ester in 5.8 ml of 2N sodium hydroxide, 5 ml water and 3 ml methanol is warmed to 35° C. to obtain a clear solution. After stirring the solution for three hours, it is cooled, extracted with ether and the organic phase discarded. The pH of the aqueous phase is adjusted to 2 with 6N hydrochloric acid and then sodium bicarbonate solution added to bring the pH to 4. The aqueous phase is extracted twice with methylene chloride, the pH of the aqueous phase adjusted to 2 and again extracted twice with methylene chloride. The organic phases are combined, dried and concentrated and the residue crystallized from methylene chloride-hexane to give the analytically pure acid, mp 154°-157° C.

Following the above procedure but substituting the 5-bromo ester for the 6-chloro ester yields 5-bromo-2-(5-isopropyl-5-methyl-4-oxo-2-imidazolin-2-yl)nicotinic acid, mp 211°-213° C.

EXAMPLE 33

Preparation of 6-(Benzyloxy)-2-(5-isopropyl-5-methyl-4-oxo-2-imidazolin-2-yl)nicotinic acid

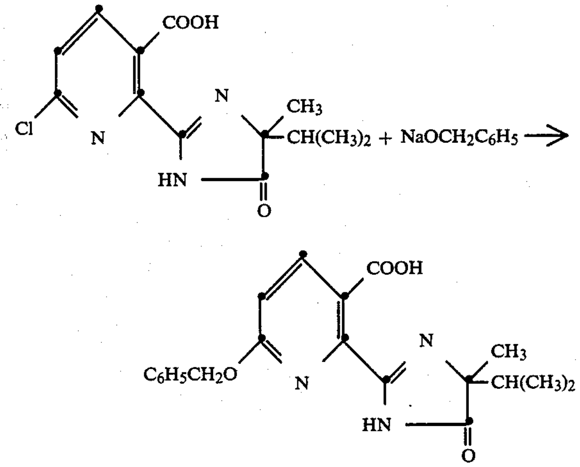

To sodium hydride (from 0.34 g 50% sodium hydride in oil) in 2 ml of N-methyl pyrolidone is added with stirring and under nitrogen 2 ml benzyl alcohol. After the formation of the alkoxide is complete, 0.6 g of the chloro acid is added and the mixture heated at 165°-175° for five hours.

After cooling, the mixture is diluted with water, the pH thereof adjusted to 1 with 1N hydrochloric acid and then back to pH 8 with saturated sodium bicarbonate. The mixture is extracted twice with ether and the ether discarded. The pH of the aqueous phase is adjusted to 5 and extracted several times with methylene chloride. The extracts are combined, dried and concentrated. Crystallization from ether-hexane gives the 6-benzyloxy derivative mp 205°-207° C.

Using essentially the same conditions as described above, and using the appropriate 4- or 6-chloro-2-(5-isopropyl-5-methyl-4-oxo-2-imidazolin-2-yl)nicotinic acid and appropriate sodium alkoxide, phenoxide or thioalkoxide, the following imidazolinyl nicotinic acids are prepared.

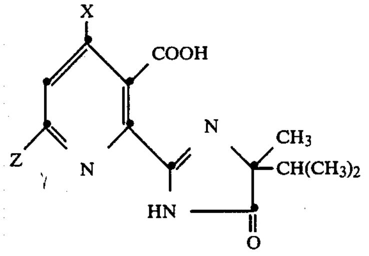

| X | Z | Mp °C. |
|---|---|---|
| H | $OCH_3$ | 190-191.5 |
| $OC_6H_5$ | H | 196-198 |
| H | $OC_6H_5$ | 182.5-185.5 |
| H | $OC_2H_5$ | 190-191.5 |
| H | $SCH_3$ | 188.5-190 |
| $OCH_2C_6H_5$ | H | 172-174 |
| H | $OCH_2C_6H_5$ | 205-207 |
| H | $OC_4H_9$—n | 147-151 |
| H | $OCH(CH_3)_2$ | 188-192 |
| H | $NHC_6H_5$ | 198-201 |
| H | $N(CH_3)_2$ | 245-248 |
| H | $OCH_2C{\equiv}CH$ | 195-198 |
| H | $OHNCH(CH_3)_2$ | 189-194 |

EXAMPLE 34

Preparation of 4-Hydroxy-2(5-isopropyl-5-methyl-4-oxo-2-imidazolin-2-yl)nicotinic acid

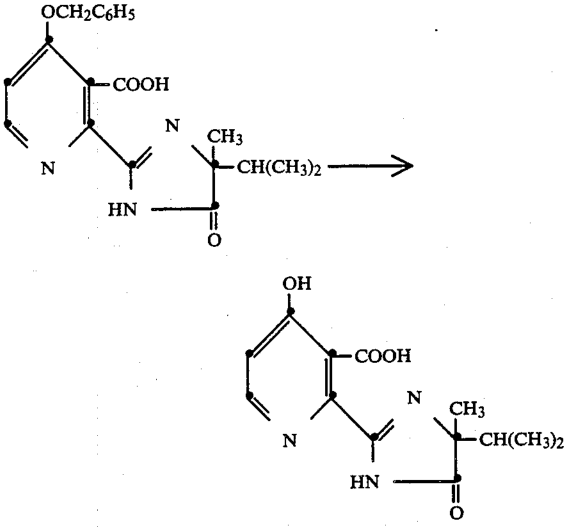

To 15 ml concentrated sulfuric acid is added slowly, with stirring 1.55 g of the benzyloxy derivative. To this mixture is added 7 ml ethylene-dichloride. After 16 hours at room temperature, the mixture is poured over ice, the pH adjusted to 4 with dilute sodium hydroxide and extracted with ethyl acetate. The extract was dried and concentrated to leave a tan solid which is recrystallized from methylene chloride-ether, mp 210°-211° C.

EXAMPLE 35

Preparation of 2-Isopropyl-2-methyl-5H-imidazo[1',2':1,2]pyrrolo[3,4-b]pyridine-3(2H), 5-dione

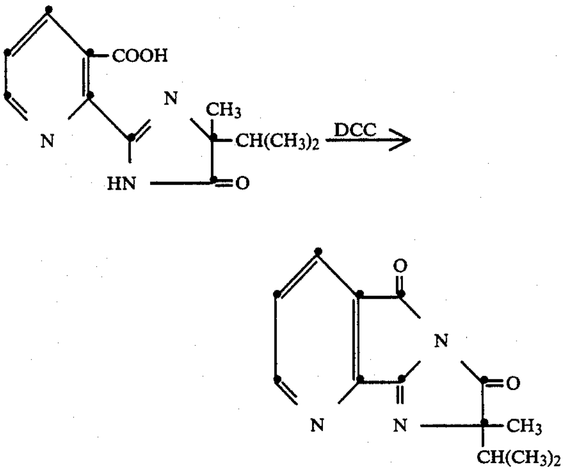

To a solution containing 50.9 g of dicyclohexylcarbodiimide in 600 ml of dry methylene chloride is added, while stirring, 60 g of the acid at such a rate that the temperature does not exceed 32° C. After stirring at room temperature for 2.5 hours, the mixture is filtered and the filtrate concentrated to give a white solid. This solid is recrystallized from methylene chloride to give 57.4 g of the dione, mp 125°-128.5° C. The analytically pure dione melts at 132°-134° C.

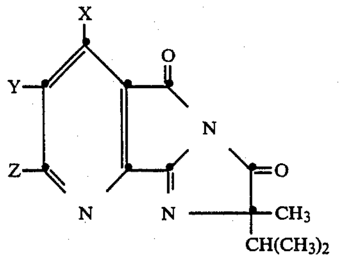

| X | Y | Z | mp °C. |
|---|---|---|---|
| H | H | $C_3H_7$ | 98.5-101 |
| H | H | $CH(CH_3)_2$ | 100-105 |
| H | $CH(CH_3)_2$ | H | 128-137 |
| H | $C_2H_5$ | H | 126-131 |
| H | H | $C_2H_5$ | 148-152.5 |
| H | $OCH(CH_3)_2$ | H | 157-161 |

EXAMPLE 36

Preparation of the Acetone oxime ester of 2-(5-isopropyl-5-methyl-4-oxo-2-imidazolin-2-yl)nicotinic acid

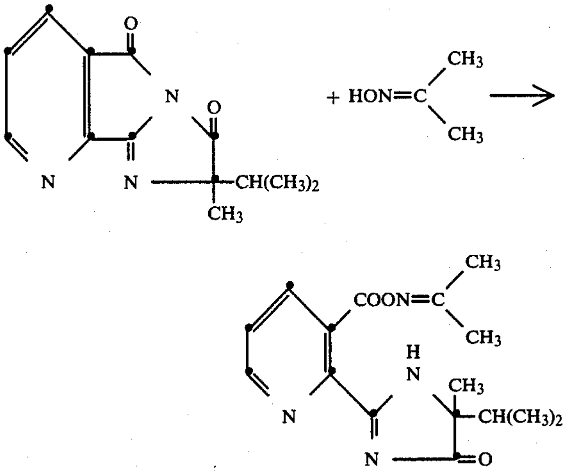

To a solution containing 2.0 g of the 3,5-dione in 15 ml of toluene is added 0.6 g of acetone oxime. The mixture is heated and stirred at 50°-60° C. for 2.75 hours. After stirring overnight at room temperature, the solvent is removed and the residue chromatographed on silica gel using 10% acetonitrile in methylene chloride followed by 30% acetonitrile in methylene chloride as the eluent. Toluene is removed from the fractions containing the product and the product collected. This is recrystallized from methylene chloride-hexane to give analytically pure oxime ester mp 117°-119.5° C. The ester from 2,2,2-trichloroethanol mp 114°-116° C. is prepared in essentially the same manner. Other esters prepared in the same manner are listed below.

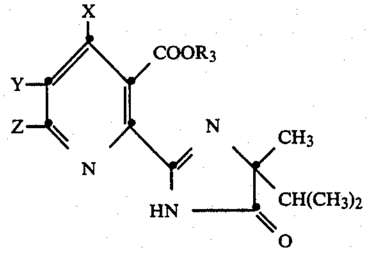

| $R_3$ | X | Y | Z | mp °C. |
|---|---|---|---|---|
| $CH_3$ | H | $C_2H_5$ | H | 96-99 |
| $CH(CH_3)_2$ | H | $C_2H_5$ | H | 106-108 |
| $CH_2C{\equiv}CH$ | H | $C_2H_5$ | H | 143-145 |
| $CH_2C_6H_5$ | H | $C_2H_5$ | H | 121-123.5 |
| $C_2H_5$ | H | $C_2H_5$ | H | 84.5-86.5 |
| 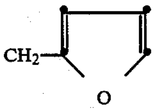 | H | $C_2H_5$ | H | gum |
| $CH_3$ | H | $OCH(CH_3)_2$ | H | gum |
| $C_2H_5$ | H | $OCH(CH_3)_2$ | H | 96-101 |
| $CH_2C{\equiv}CH$ | H | $OCH(CH_3)_2$ | H | 124-125 |
| $CH(CH_3)_2$ | H | $OCH(CH_3)_2$ | H | 95-99 |

-continued

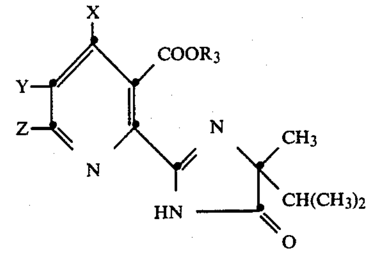

| R3 | X | Y | Z | mp °C. |
|---|---|---|---|---|
| 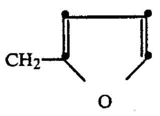 | H | $OCH(CH_3)_2$ | H | 123-125 |
| $CH_2—C_6H_5$ | H | $OCH(CH_3)_2$ | H | 145-146.5 |
| $CH_3$ | H | OH | H | 200.5-202 |

EXAMPLE 37

Preparation of 2-(3-Acetyl-2-pyridyl)-5-isopropyl-5-methyl-2-imidazolin-4-one

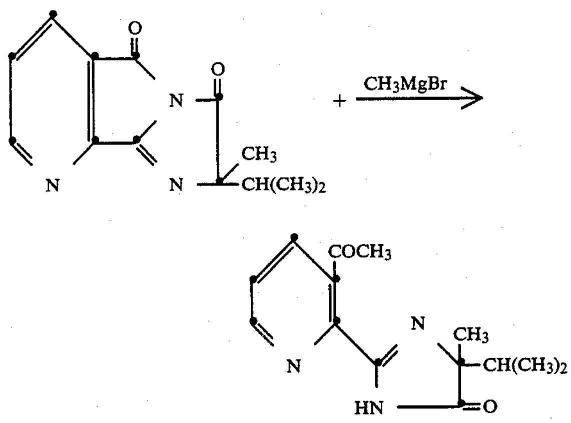

To a stirred solution containing 10.0 g of the dione in 100 ml of dry tetrahydrofuran under nitrogen and −78° C. is added dropwise 15.1 ml of a 3M solution of methyl magnesium bromide in ether. A temperature of <−60° C. is maintained during the addition. After the addition, stirring is continued at −78° C. and then the mixture warmed slowly to room temperature. The mixture is diluted with an equal volume of water, the pH adjusted to 4 with glacial acetic acid and extracted three times with methylene chloride. The combined extracts are dried and concentrated. The residue is chromatographed on silica gel with ether. Concentration of the appropriate fractions give 6.1 g of product as a crystalline solid mp 104°-108° C. An analytically pure sample has mp 103°-105° C.

Using essentially the same procedure as described above but substituting phenyl lithium or sodium trimethyl phosphonoacetate for methyl magnesium bromide, the following imidazolinones are prepared.

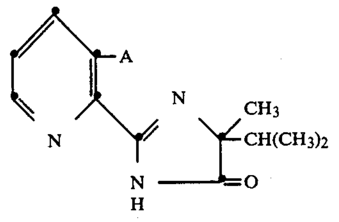

| A | mp °C. |
|---|---|
| $COC_6H_5$ | 138-140.5 |
| 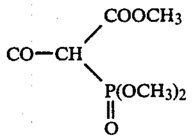 | 131.5-134 |

EXAMPLE 38

Preparation of 2-[3-(Hydroxymethyl)-2-pyridyl]-5-isopropyl-5-methyl-2-imidazolin-4-one

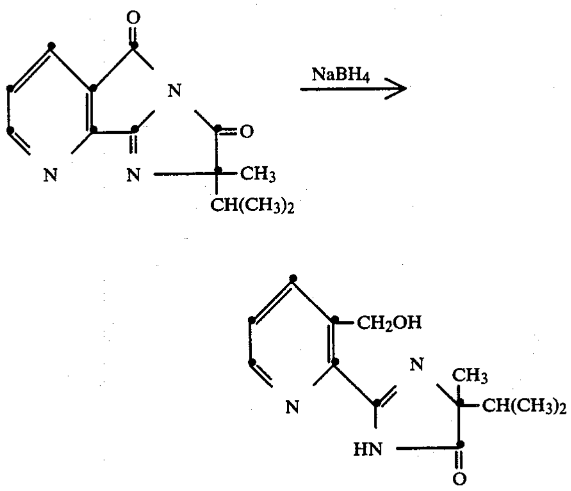

To a stirred solution of 0.32 g sodium borohydride in 25 ml absolute ethanol at 0° C. is added during 10 minutes with stirring a solution containing 2.0 g dione in 25 ml dry tetrahydrofuran. The mixture is then stirred a further three hours at room temperature. The mixture is poured into 200 ml ice water, extracted with methylene chloride, the extract dried and concentrated. The residue is crystallized from methylene-chloride-hexane to give the desired product. The analytically pure sample has mp 145°-149° C.

EXAMPLE 39

Preparation of 1,3-Dihydro-α-isopropyl-α-methyl-1,3-dioxo-2-H-pyrrolo-[3,4-b]quinoline-2-acetonitrile Procedure A

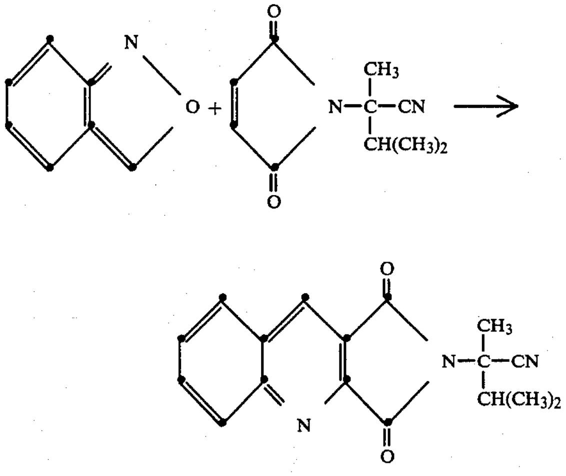

Anthranil (59.6 g, 0.5 mol) is added dropwise under nitrogen, with stirring, over a 45 minute period, to a refluxing solution of α-isopropyl-α-methyl-2,5-dioxo-3-pyrroline-1-acetonitrile in o-dichlorobenzene (450 ml). After 18 hours the reaction mixture is cooled and methylene chloride added. This solution is passed through a 3 inch silica gel column, by eluting with methylene chloride. The eluate is concentrated to 500 ml and hexane added. A precipitate forms and is filtered off and air dried, to yield the product 110.6 g, (75%) as a light brown solid. Crystallization from ethyl acetate-hexane gives pale yellow crystals, mp 195°-196° C. Anal. calcd. for $C_{17}H_{15}N_3O_2$: C, 69.61; H, 5.15; N, 14.33. Found: C, 69.37; H, 5.15; N, 14.43.

Employing similar conditions the compounds of Table I are prepared.

Procedure B

Cyclization of o-formylanilino-maleimides

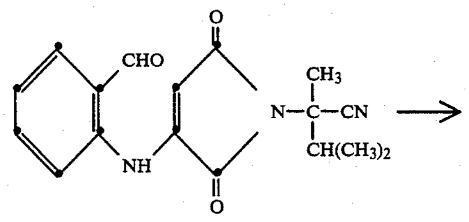

-continued

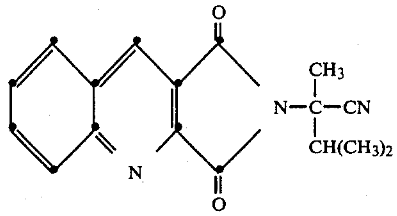

A solution of N-(1-cyano-1,2-dimethylpropyl)-2-(o-formylanilino)maleimide (7.19 g, 0.023 mol) in xylene (300 ml) containing p-toluenesulfonic acid (0.3 g, 0.0016 mol) is heated at reflux for 4 hours using a Dean-Stark trap to collect the eliminated water. The reaction is cooled, evaporated under reduced pressure and dissolved in hot ethyl acetate which is passed through a 3 inch silica gel column. The ethyl acetate fractions eluted are combined to give a solid, mp 195°-195.5° C., 5.51 g, (81%) of 1,3-dihydro-α-isopropyl-α-methyl-1,3-dioxo-2-H-pyrrolo[3,4-b]quinoline-2-acetonitrile.

Other compounds prepared by this procedure are listed in Table I.

EXAMPLE 40

Procedure C

Preparation of 1,3-Dihydro-α-isopropyl-α-methyl-1,3-dioxo-2-H-pyrrolo[3,4-b]4-acetoxyquinoline-2-acetonitrile

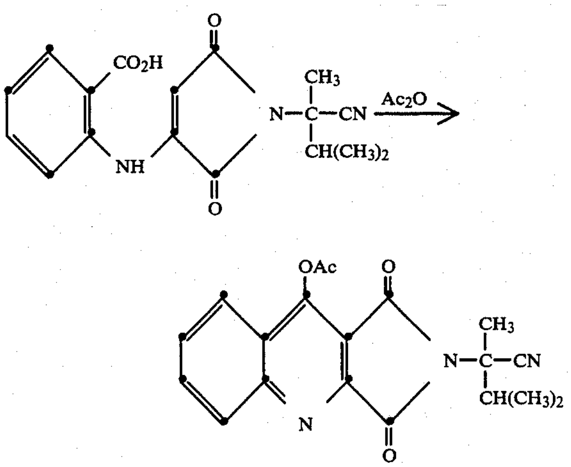

A solution of N-[1-(1-cyano-1,2-dimethylpropyl)-2,5-dioxo-3-pyrrolin-3-yl anthranilic]acid (3.27 g, 0.01 mol) in acetic anhydride (20 ml) is treated all at once with triethylamine (10 ml) and dimethylaminopyridine (0.122 g, 0.001 mol). After stirring under nitrogen for 1 hour at 25° the reaction is poured into ice-water. A solid forms and is filtered off. Purification is achieved by re-suspension in ether, filtering and drying. Yield 2.54 g (72%) of product, mp 145°-151° C., (m+1)/e=352.

TABLE I

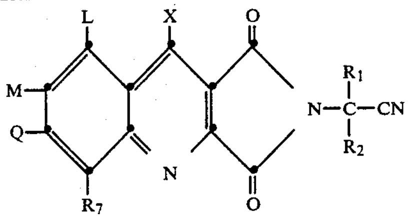

| $R_1$ | $R_2$ | X | L | M | Q | $R_7$ | Procedure | mp °C. |
|---|---|---|---|---|---|---|---|---|
| $CH_3$ | $CH(CH_3)_2$ | H | H | $NO_2$ | H | H | A | 230–232 |
| $CH_3$ | $CH(CH_3)_2$ | H | H | H | $NO_2$ | H | A | 260–261 |
| $CH_3$ | $CH(CH_3)_2$ | H | $NO_2$ | H | H | H | | |
| $CH_3$ | $CH(CH_3)_2$ | H | H | H | H | $NO_2$ | A | |
| $CH_3$ | $CH(CH_3)_2$ | H | Br | H | H | H | A | 161–167 |
| $CH_3$ | $CH(CH_3)_2$ | H | Cl | H | H | H | A,B | 139.5–142 |
| $CH_3$ | $CH(CH_3)_2$ | H | H | $CF_3$ | H | H | B | |
| $CH_3$ | $CH(CH_3)_2$ | H | H | H | Cl | H | B | 188 |
| $CH_3$ | $CH(CH_3)_2$ | H | H | $CH_3$ | H | H | B | |
| $CH_3$ | $CH(CH_3)_2$ | H | H | H | $CH_3$ | H | B | 186–190 |
| $CH_3$ | $CH(CH_3)_2$ | H | H | H | H | $CH_3$ | B | |
| $CH_3$ | $CH(CH_3)_2$ | H | H | $OCH_3$ | H | H | B | 241–247 |
| $CH_3$ | $CH(CH_3)_2$ | H | H | H | $CH_3$ | $CH_3$ | B | |
| $CH_3$ | $CH(CH_3)_2$ | H | H | $CH_3$ | H | $CH_3$ | B | 244 |
| $CH_3$ | $CH(CH_3)_2$ | H | $CH_3$ | H | H | $CH_3$ | B | |
| $CH_3$ | $CH(CH_3)_2$ | H | H | H | Cl | $CH_3$ | B | |
| $CH_3$ | $CH(CH_3)_2$ | H | Cl | H | H | $CH_3$ | B | |
| $CH_3$ | $CH(CH_3)_2$ | H | H | Cl | H | $CH_3$ | B | |
| $CH_3$ | $CH(CH_3)_2$ | H | Cl | H | H | $OCH_3$ | B | |
| $CH_3$ | $C_3H_7$ | H | H | H | H | H | A | |
| $CH_3$ | $C_2H_5$ | H | H | H | H | H | A | 147–149 |
| $CH_3$ | n-$C_4H_9$ | H | H | H | H | H | A | |
| $CH_3$ | s-$C_4H_9$ | H | H | H | H | H | A | |
| $CH_3$ | i-$C_4H_9$ | H | H | H | H | H | A | |
| $CH_3$ | t-$C_4H_9$ | H | H | H | H | H | A | |
| $CH_3$ | cyclopropyl | H | H | H | H | H | A | 182–185 |
| $CH_3$ | $CH_2CH{=}CH_2$ | H | H | H | H | H | A | |
| $CH_3$ | cyclohexyl | H | H | H | H | H | A | |
| | $(CH_2)_5$ | H | H | H | H | H | A | |
| $CH_3$ | $CH(CH_3)_2$ | Cl | H | H | H | H | | |
| $CH_3$ | $CH(CH_3)_2$ | $CH_3$ | H | H | H | H | B | 164–168 |
| $CH_3$ | $CH(CH_3)_2$ | F | H | H | H | H | | |
| $CH_3$ | $CH(CH_3)_2$ | $OCH_3$ | H | H | H | H | | |
| $CH_3$ | $CH(CH_3)_2$ | OH | H | H | H | H | | |
| $CH_3$ | $CH(CH_3)_2$ | H | H | Cl | | H | A | 202.5–203.5 |
| $CH_3$ | $CH(CH_3)_2$ | H | H | H | $CH_3$ | H | B | 186–189 |
| $CH_3$ | $CH(CH_3)_2$ | H | H | Br | H | H | A | 220–224 |
| $CH_3$ | $CH_3$ | H | H | H | H | H | A | 216–217 |
| $CH_3$ | $CH(CH_3)_2$ | H | H | Cl | Cl | H | A | 241–243 |
| $CH_3$ | $CH(CH_3)_2$ | H | H | H | H | Cl | A | 212.5–216.5 |
| $CH_3$ | $CH(CH_3)_2$ | H | H | $-O-CH_2-O-$ | | H | A | 251–253 |
| $CH_3$ | $CH(CH_3)_2$ | H | H | F | H | H | A | 212.5–215 |
| $CH_3$ | $CH(CH_3)_2$ | H | $CH_3$ | H | H | H | B | 191–193 |
| $CH_3$ | $CH(CH_3)_2$ | H | Br | H | H | H | A | 161–167 |
| $CH_3$ | $CH(CH_3)_2$ | H | H | H | $CH_3$ | H | B | 186–189 |
| $CH_3$ | $CH(CH_3)_2$ | H | H | Br | H | H | A | 220–224 |
| $CH_3$ | $CH_3$ | H | H | H | H | H | A | 216–217 |
| $CH_3$ | $CH(CH_3)_2$ | H | H | Cl | Cl | H | A | 241–243 |
| $CH_3$ | $CH(CH_3)_2$ | H | H | H | H | Cl | A | 212.5–216.5 |
| $CH_3$ | $CH(CH_3)_2$ | H | H | $-O-CH_2-O-$ | | H | A | 251–253 |
| $CH_3$ | $CH(CH_3)_2$ | H | H | F | H | H | A | 212.5–215 |

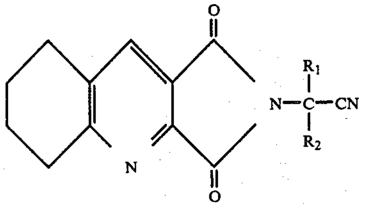

mp °C. 165-167

EXAMPLE 41

Preparation of 1,3-Dihydro-α-isopropyl-α-methyl-1,3-dioxo-2-H-pyrrolo[3,4-b]quinoline-2-acetamide

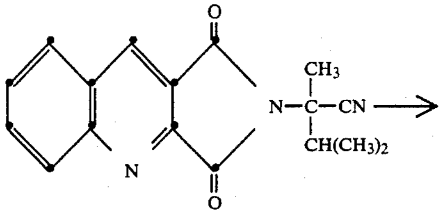

-continued

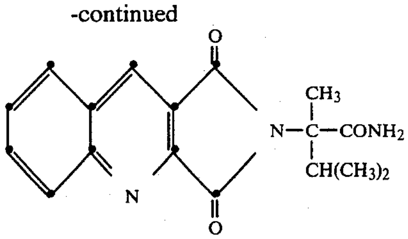

1,3-Dihydro-α-isopropyl-α-methyl-1,3-dioxo-2-H-pyrrolo[3,4-b]quinoline-2-acetonitrile (0.44 g, 0.0015 mol) is dissolved in conc. sulfuric acid (5 ml) at room temperature and stirred overnight. The reaction mixture is poured onto crushed ice (50 ml) and a white precipitate forms and is filtered off, washed with water, aqueous sodium bicarbonate and water and then vacuum dried. This gives 0.34 g (74%) of product, mp 237°-239° C. (dec.). Anal. calcd. for $C_{17}H_{17}N_3O_3$: C, 65.58; H, 5.50; N, 13.50. Found: C, 65.03; H, 5.63; N, 13.19.

The following compounds are prepared in the same manner as described above.

TABLE II

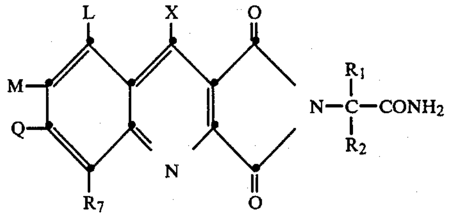

| $R_1$ | $R_2$ | X | L | M | Q | $R_7$ | mp °C. |
|---|---|---|---|---|---|---|---|
| $CH_3$ | $CH(CH_3)_2$ | H | H | $NO_2$ | H | H | 225-227 (dec.) |
| $CH_3$ | $CH(CH_3)_2$ | H | H | H | $NO_2$ | H | 237-238 |
| $CH_3$ | $CH(CH_3)_2$ | H | $NO_2$ | H | H | H | |
| $CH_3$ | $CH(CH_3)_2$ | H | Br | H | H | H | 197-198 |
| $CH_3$ | $CH(CH_3)_2$ | H | H | Cl | H | H | 216-217 |
| $CH_3$ | $CH(CH_3)_2$ | H | H | $CF_3$ | H | H | |
| $CH_3$ | $CH(CH_3)_2$ | H | H | H | $CF_3$ | H | |
| $CH_3$ | $CH(CH_3)_2$ | H | H | H | Cl | H | 232-234 |
| $CH_3$ | $CH(CH_3)_2$ | H | H | H | H | Cl | 207.5-208.5 |
| $CH_3$ | $CH(CH_3)_2$ | H | H | $CH_3$ | H | H | 226-227 |
| $CH_3$ | $CH(CH_3)_2$ | H | H | H | $CH_3$ | H | 256-260 |
| $CH_3$ | $CH(CH_3)_2$ | H | H | H | H | $CH_3$ | |
| $CH_3$ | $CH(CH_3)_2$ | H | H | $OCH_3$ | H | H | 225-280 |
| $CH_3$ | $CH(CH_3)_2$ | H | H | H | $CH_3$ | $CH_3$ | |
| $CH_3$ | $CH(CH_3)_2$ | H | H | $CH_3$ | H | $CH_3$ | 208-214 |
| $CH_3$ | $CH(CH_3)_2$ | H | $CH_3$ | H | H | $CH_3$ | |
| $CH_3$ | $CH(CH_3)_2$ | H | H | H | Cl | $CH_3$ | |
| $CH_3$ | $CH(CH_3)_2$ | H | Cl | H | H | $CH_3$ | |
| $CH_3$ | $CH(CH_3)_2$ | H | H | Cl | H | $CH_3$ | |
| $CH_3$ | $CH(CH_3)_2$ | H | Cl | H | H | $OCH_3$ | |
| $CH_3$ | $C_3H_7$ | H | H | H | H | H | |
| $CH_3$ | $C_2H_5$ | H | H | H | H | H | 222-224 |
| $CH_3$ | $C_4H_9$ | H | H | H | H | H | |
| $CH_3$ | s-$C_4H_9$ | H | H | H | H | H | |
| $CH_3$ | i-$C_4H_9$ | H | H | H | H | H | |
| $CH_3$ | t-$C_4H_9$ | H | H | H | H | H | |
| $CH_3$ | 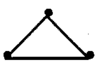 | H | H | H | H | H | 195-197 |
| $CH_3$ | $CH_2CH{=}CH_2$ | H | H | H | H | H | |
| $CH_3$ | 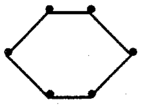 | H | H | H | H | H | |
| $(CH_2)_5$ | | H | H | H | H | H | 202-205 |

TABLE II-continued

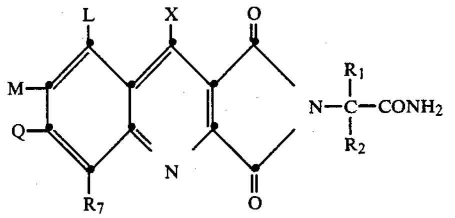

| R1 | R2 | X | L | M | Q | R7 | mp °C. |
|---|---|---|---|---|---|---|---|
| $CH_3$ | $CH(CH_3)_2$ | Cl | H | H | H | H | |
| $CH_3$ | $CH(CH_3)_2$ | $CH_3$ | H | H | H | H | |
| $CH_3$ | $CH(CH_3)_2$ | F | H | H | H | H | |
| $CH_3$ | $CH(CH_3)_2$ | $OCH_3$ | H | H | H | H | |
| $CH_3$ | $CH(CH_3)_2$ | OH | H | H | H | H | |
| $CH_3$ | $CH(CH_3)_2$ | OAc | H | H | H | H | |
| $CH_3$ | $CH(CH_3)_2$ | H | Cl | H | H | H | 198–199 (dec.) |
| $CH_3$ | $CH(CH_3)_2$ | H | Br | H | H | H | 197–198 |
| $CH_3$ | $CH(CH_3)_2$ | H | H | Br | H | H | 250–252 |
| $CH_3$ | $CH(CH_3)_2$ | H | H | Cl | Cl | H | 208–214 |
| $CH_3$ | $CH_3$ | H | H | H | H | H | 243–244 |
| $CH_3$ | $CH(CH_3)_2$ | H | $CH_3$ | H | H | H | 187–190 |
| $CH_3$ | $CH(CH_3)_2$ | H | H | $-O-CH_2-O-$ | | H | 213–217 |
| $CH_3$ | $CH(CH_3)_2$ | H | H | F | H | H | 219–222 |
| 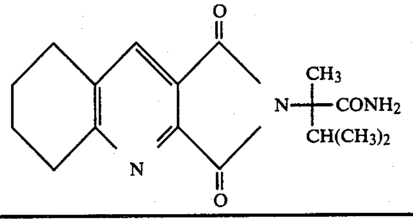 | | | | | | | 258–260 |

EXAMPLE 42

Preparation of 2-(5-Isopropyl-5-methyl-4-oxo-2-imidazolin-2-yl)-3-quinolinecarboxylic acid Procedure A

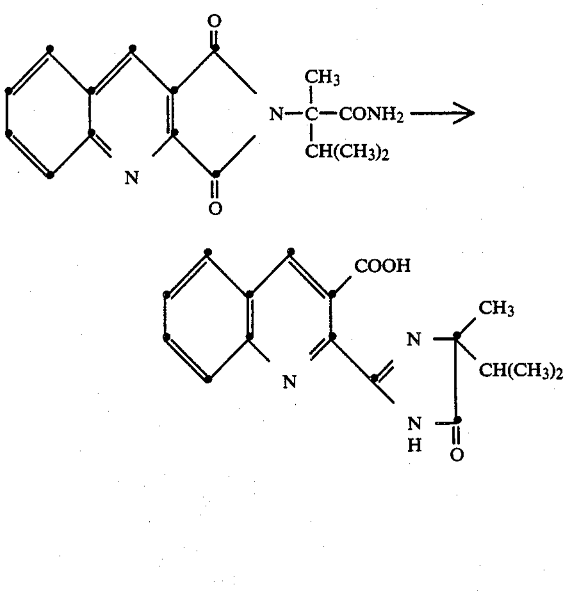

To a slurry of 1,3-dihydro-α-isopropyl-α-methyl-1,3-dioxo-2-H-pyrrolo[3,4-b]quinoline-2-acetamide (5.76 g, 0.0185 mol) in dry xylene (600 ml) is added a 50% oil dispersion of sodium hydride (1.33 g, 0.0278 mol) and the mixture is heated to reflux, whereupon the reaction mixture becomes homogeneous. After 3 hours at reflux the reaction is set aside at room temperature overnight and then methanol (15 ml) containing sodium methoxide (0.1 g) is slowly added and warmed at reflux for 1 hour. The mixture is filtered while hot and the organic solvents stripped to give an oil and solid. A methylene chloride-water mixture is shaken with the above residues, until they dissolve. The aqueous layer (200 ml) is separated and slowly acidified with acetic acid (5 ml). A precipitate of the product is formed and is collected by filtration to give 3.91 g (72%) of mp 219°–224° C. Recrystallization from hexane-ethyl acetate gives mp 219°–222° C. (dec.). Anal. calcd. for $C_{17}H_{17}N_3O_3$: C, 65.58; H, 5.50; N, 13.50. Found: C, 65.09; H, 5.50; N, 13.59.

The procedure described above is used to prepare the compounds reported in Table III below. However, to avoid ester formation, rather than filter off the insolubles and strip down the xylene, one may simply add methanol followed by water (caution, hydrogen may be evolved) to the xylene layer.

TABLE III

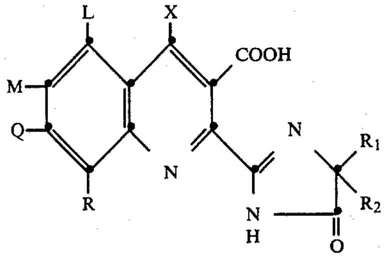

| R1 | R2 | X | L | M | Q | R7 | Procedure | mp° C. |
|---|---|---|---|---|---|---|---|---|
| $CH_3$ | $CH(CH_3)_2$ | H | H | H | $NO_2$ | H | A | 247-251 |
| $CH_3$ | $CH(CH_3)_2$ | H | H | $NO_2$ | H | H | A | 241.5-242 |
| $CH_3$ | $CH(CH_3)_2$ | H | $NO_2$ | H | H | H | A | |
| $CH_3$ | $CH(CH_3)_2$ | H | H | H | H | $NO_2$ | A | 255-257 (dec.) |
| $CH_3$ | $CH(CH_3)_2$ | H | Br | H | H | H | A | 263-264 |
| $CH_3$ | $CH(CH_3)_2$ | H | H | Cl | H | H | A | 225-226 |
| $CH_3$ | $CH(CH_3)_2$ | H | H | H | Cl | H | A | 238-240 |
| $CH_3$ | $CH(CH_3)_2$ | H | H | H | H | Cl | A | 241-245 |
| $CH_3$ | $CH(CH_3)_2$ | Cl | H | H | H | H | A | 223-224 |
| $CH_3$ | $CH(CH_3)_2$ | H | Cl | H | H | H | A | 255-256 (dec.) |
| $CH_3$ | $CH(CH_3)_2$ | H | H | $CF_3$ | H | H | A | 215-218 |
| $CH_3$ | $CH(CH_3)_2$ | H | H | H | $CF_3$ | H | A | |
| $CH_3$ | $CH(CH_3)_2$ | H | H | F | H | H | A | 244-246 |
| $CH_3$ | $CH(CH_3)_2$ | H | H | $CH_3$ | H | H | A | 218-225 |
| $CH_3$ | $CH(CH_3)_2$ | H | H | H | $CH_3$ | H | A | 265-270 (dec.) |
| $CH_3$ | $CH(CH_3)_2$ | H | H | H | H | $CH_3$ | A | |
| $CH_3$ | $CH(CH_3)_2$ | $CH_3$ | H | H | H | H | A | 236-238 |
| $CH_3$ | $CH(CH_3)_2$ | H | H | $OCH_3$ | H | H | A | 203.5-205 |
| $CH_3$ | $CH(CH_3)_2$ | H | H | $SCH_3$ | H | H | A | 264.5-265 |
| $CH_3$ | $CH(CH_3)_2$ | H | H | $SO_2CH_3$ | H | H | (peracid on above) | 254-255 |
| $CH_3$ | $CH(CH_3)_2$ | F | H | H | H | H | A | |
| $CH_3$ | $CH(CH_3)_2$ | H | H | H | $CH_3$ | $CH_3$ | A | 278-282 (dec.) |
| $CH_3$ | $CH(CH_3)_2$ | H | H | $CH_3$ | H | $CH_3$ | A | 258-260 |
| $CH_3$ | $CH(CH_3)_2$ | H | $CH_3$ | H | H | $CH_3$ | A | |
| $CH_3$ | $CH(CH_3)_2$ | H | H | H | Cl | $CH_3$ | A | |
| $CH_3$ | $CH(CH_3)_2$ | H | Cl | H | H | $CH_3$ | A | 188-190 |
| $CH_3$ | $CH(CH_3)_2$ | $OCH_3$ | H | H | H | H | A | |
| $CH_3$ | $CH(CH_3)_2$ | OH | H | H | H | H | | 220-222 |
| $CH_3$ | $CH(CH_3)_2$ | OAc | H | H | H | H | | 188-190 |
| $CH_3$ | $CH(CH_3)_2$ | H | H | Cl | H | $CH_3$ | A | |
| $CH_3$ | $CH(CH_3)_2$ | H | Cl | H | H | $OCH_3$ | A | |
| $CH_3$ | $C_3H_7$—n | H | H | H | H | H | A | |
| $CH_3$ | $C_2H_5$ | H | H | H | H | H | A | 248-253 |
| $CH_3$ | $C_4H_9$—n | H | H | H | H | H | A | |
| $CH_3$ | $C_4H_9$—sec | H | H | H | H | H | A | |
| $CH_3$ | $C_4H_9$—iso | H | H | H | H | H | A | |
| $CH_3$ | $C_4H_9$—tert | H | H | H | H | H | A | |
| $CH_3$ | 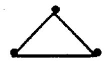 | H | H | H | H | H | A | |
| $CH_3$ | $CHCH{=}CH_2$ | H | H | H | H | H | A | |
| $CH_3$ | 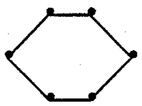 | H | H | H | H | H | A | |
| $—(CH_2)_5—$ | | H | H | H | H | H | A | 234-240 |
| $CH_3$ | $CH(CH_3)_2$ | H | H | H | F | H | A | |
| $CH_3$ | $CH(CH_3)_2$ | H | H | H | CN | H | | |
| $CH_3$ | $CH(CH_3)_2$ | H | H | H | $N(CH_3)_2$ | H | A | |
| $CH_3$ | $CH(CH_3)_2$ | H | H | H | $NH_2$ | H | (reduction Q = $NO_2$) | |
| $CH_3$ | $CH(CH_3)_2$ | H | H | H | I | H | A | |
| $CH_3$ | $CH(CH_3)_2$ | H | H | Br | H | H | A | 215-225 |
| $CH_3$ | $CH(CH_3)_2$ | H | H | $—O—CH_2—O—$ | | H | A | 252-257 |
| $CH_3$ | $CH(CH_3)_2$ | H | $OCH_3$ | H | H | $OCH_3$ | A | 249-250 |
| $CH_3$ | $CH(CH_3)_2$ | H | $CH_3$ | H | H | H | | 255-260 (dec.) |
| $CH_3$ | $CH(CH_3)_2$ | H | H | $OCHF_2$ | H | H | | 208-209 |
| $CH_3$ | $CH(CH_3)_2$ | H | H | H | H | $OCH_3$ | | 258.5-261 |
| $CH_3$ | $CH(CH_3)_2$ | H | H | $N(CH_3)_2$ | H | H | | 63-66 |
| $CH_3$ | $CH(CH_3)_2$ | H | H | H | $NO_2$ | $OCH_3$ | A | 209-211 |
| $CH_3$ | $CH(CH_3)_2$ | H | H | Cl | Cl | H | A | |
| $CH_3$ | $CH(CH_3)_2$ | H | H | $OC_2H_5$ | H | H | | 223 |

TABLE III-continued

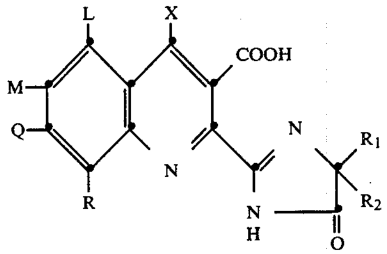

| $R_1$ | $R_2$ | X | L | M | Q | $R_7$ | Procedure | mp° C. |
|---|---|---|---|---|---|---|---|---|
| $CH_3$ | $CH(CH_3)_2$ | H | H | $SCH_3$ | H | H | | 264.5-265 |
| $CH_3$ | $CH(CH_3)_2$ | H | H | $C_6H_5$ | H | H | | |
| $CH_3$ | $CH(CH_3)_2$ | H | H | H | $NHCOCH_3$ | H | | 301-302 |
| $(-)CH_3$ | $CH(CH_3)_2$ | H | H | H | H | H | | 229-237 (dec.) $[\alpha]_D^{25} = -29.2°$ |
| $(+)CH_3$ | $CH(CH_3)_2$ | H | H | H | H | H | | 228-236.5 (dec.) $[\alpha]_D^{25} = +28.3°$ |
| $CH_3$ | $CH(CH_3)_2$ | H | H | $C_6H_5$ | H | H | | 209.5-212 |
| $CH_3$ | $CH(CH_3)_2$ | H | H | $CH_3$ | $CH_3$ | H | | 238-240 |
| $CH_3$ | $CH(CH_3)_2$ | H | H | $C_2H_5$ | H | H | | 179.5-180.5 |
| $CH_3$ | $CH(CH_3)_2$ | H | H | $NH-CH(CH_3)_2$ | H | H | | 246-248 |
| $CH_3$ | $CH(CH_3)_2$ | H | H | $C_4H_9$ | H | H | | 149-150.5 |
| $CH_3$ | $CH(CH_3)_2$ | H | H | $OC_4H_9$ | H | H | | 163-165 |
| $CH_3$ | $CH(CH_3)_2$ | H | H | $SO_2CH_3$ | H | H | (from $SCH_3$) | 254-255 |
| $CH_3$ | $CH(CH_3)_2$ | H | H | $SCH_3$ | H | H | | 264-265 |
| $CH_3$ | $CH(CH_3)_2$ | H | H | $OC_4H_9$ | H | H | | 163-165 |
| $CH_3$ | $CH(CH_3)_2$ | H | H | $CH(CH_2)_2CH_3$ | H | H | | 145-155 (Then 245-255) |
| $CH_3$ | $CH(CH_3)_2$ | H | H | $OC_2H_5$ | H | H | from 6-OH | 206-208 |
| $CH_3$ | $CH(CH_3)_2$ | H | H | OH | H | H | Demethylation of 6-MeO with HI | 261-265 |
| $CH_3$ | $CH(CH_3)_2$ | H | H | H | $OC_2H_5$ | H | | 237.5-239 |
| $(+)CH_3$ | $CH(CH_3)_2$ | H | H | Cl | H | H | | 235-237 |

EXAMPLE 43

Preparation of Ethyl-2-(5-isopropyl-5-methyl-4-oxo-2-imidazolin-2-yl)-3-quinolinecarboxylic acid Procedure A

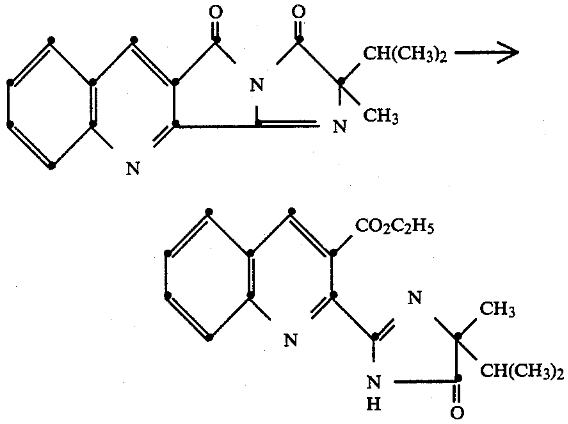

To 2-isopropyl-2-methyl-5-H-imidazo[1',2':1,2-]pyrazolo[3,4-b]quinoline-3H(2H),5-dione (2 g, 0.0068 mol) in absolute ethanol (40 ml) under nitrogen is added 50% sodium hydride (0.34 g, 0.00716 mol) with ice-cooling. Gas evolution is observed. After 10 minutes the reaction is neutralized with aqueous ammonium chloride, stripped and partitioned between water and ethyl acetate. The organic layer is separated and dried over anhydrous magnesium sulfate, filtered, stripped and the residue crystallized from ethyl acetate-hexane to give 1.38 g (60%) of a white solid, mp 146°-147.5° C.

In a similar manner, the following esters in Table IV may be prepared by Procedure A.

EXAMPLE 44

Preparation of Methyl-2-(5-isopropyl-5-methyl-4-oxo-2-imidazolin-2-yl)-3-quinolinecarboxylic acid Procedure B

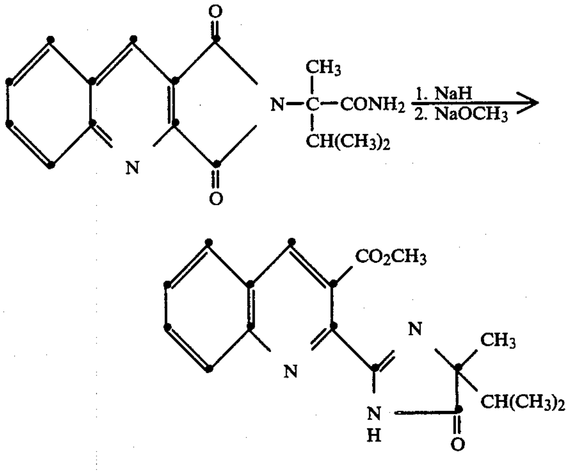

A 50% sodium hydride oil dispersion (1.4 g, 0.0292 mol) is added to azeotropically dried 1,3-dihydro-α-isopropyl-α-methyl-1,3-dioxo-2-H-pyrrolo[3,4-b]quinoline-2-acetamide (6 g, 0.0193 mol) in xylene, under nitrogen. The mixture is heated and stirred under reflux for six hours, cooled and slowly quenched with a solution of sodium methoxide (0.1 g) in methanol (20 ml). After heating at 60° C. for 3 hours the mixture is filtered and the filtrate stripped to give a white solid, which is dissolved in a methylene chloride-water mixture. Separation of the organic layer and stripping afforded a solid of 0.48 g, which is purified by passing through a silica gel pad with ethyl acetate as solvent. After removal of the solvent, the solid residue is crystallized from ethyl acetate-hexane to give white needles of the required ester, 0.4 g, mp 145°-154° C. Anal. calcd. for $C_{18}H_{19}N_3O_3$: C, 66.44; H, 5.89; N, 12.92. Found: C, 66.35; H, 5.93; N, 12.83.

EXAMPLE 45

Acid Salts of Quinolinecarboxylic acid esters

Preparation of the hydrochloride salt of methyl 2-(5-isopropyl-5-methyl-4-oxo-2-imidazolin-2-yl)-3-quinoline carboxylic acid A solution of the ester is dissolved in an ether-methylene chloride solution and dry hydrogen chloride is passed through the solution until all of the solid hydrochloride salt forms and is filtered off, ether washed and vacuum dried, with mp 226°-270° C. The following salts may be prepared in a similar manner, substituting the appropriate acid HX, although some are hygroscopic oils, and employing ethyl acetate as a preferred solvent for acid salts.

TABLE IV

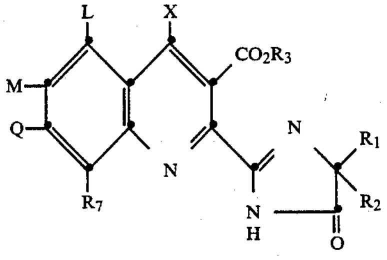

| $R_3$ | $R_1$ | $R_2$ | X | L | M | Q | $R_7$ | mp °C. | Example Procedure |
|---|---|---|---|---|---|---|---|---|---|
| $CH_3$ | $CH_3$ | $CH(CH_3)_2$ | H | H | H | H | H | 145-154 | B |
| $C_2H_5$ | $CH_3$ | $CH(CH_3)_2$ | H | H | H | H | H | 146-147.5 | A |
| $CH(CH_3)_2$ | $CH_3$ | $CH(CH_3)_2$ | H | H | H | H | H | | |
| $CH_2CH{=}CH_2$ | $CH_3$ | $CH(CH_3)_2$ | H | H | H | H | H | | |
| 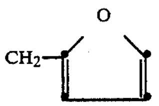 | $CH_3$ | $CH(CH_3)_2$ | H | H | H | H | H | 163-165.5 | A |
| $CH_2C_6H_5$ | $CH_3$ | $CH(CH_3)_2$ | H | H | H | H | H | 159-161 | A |
| $C_6H_5$ | $CH_3$ | $CH(CH_3)_2$ | H | H | H | H | H | | |
| $C_8H_{17}$ | $CH_3$ | $CH(CH_3)_2$ | H | H | H | H | H | | A |
| $CH_3$ | $CH_3$ | $C_2H_5$ | H | H | H | H | H | | |
| 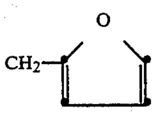 | $CH_3$ | $C_2H_5$ | H | H | H | H | H | | A |
| $CH_3$ | $CH_3$ | $CH(CH_3)_2$ | H | H | $CH_3$ | H | H | | |
| $CH_3$ | $CH_3$ | $CH(CH_3)_2$ | H | H | H | Cl | H | | |
| $CH_3$ | $CH_3$ | $CH(CH_3)_2$ | H | H | $N(CH_3)_2$ | H | H | 63-66 | |
| $C_4H_9$ | $CH_3$ | $CH(CH_3)_2$ | H | H | H | H | H | 133.5-134.5 | A |
| $CH_3$ | $CH_3$ | $C_2H_5$ | H | H | H | H | H | | |
| $CH_3$ | $CH_3$ | 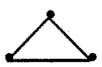 | H | H | H | H | H | | |
| $CH_3$ | $CH_3$ | sec-$C_4H_9$ | H | H | H | H | H | | |
| $CH_3$ | $-(CH_2)_5-$ | | H | H | H | H | H | | |
| $CH_3$ | $CH_3$ | $CH(CH_3)_2$ | H | H | H | $CH_3$ | H | 150-165 | |
| $CH_3$ | $CH_3$ | $CH(CH_3)_2$ | H | H | H | H | $NO_2$ | 243-245 | |
| $CH_3$ | $CH_3$ | $CH(CH_3)_2$ | H | H | H | H | $NH_2$ | 231-233 | |
| $CH_3$ | $CH_3$ | $CH(CH_3)_2$ | H | H | H | H | $N(CH_3)_2$ | 149-152 | |
| $CH_3$ | $CH_3$ | $CH(CH_3)_2$ | H | H | $NO_2$ | H | H | 206-208 | |
| $CH_3$ | $CH_3$ | $CH(CH_3)_2$ | H | H | $NO_2$ | H | H | 193-194.5 | |
| $CH_3$ | $CH_3$ | $CH(CH_3)_2$ | H | H | $NHCOCH_3$ | H | H | 239-240 | |

TABLE V

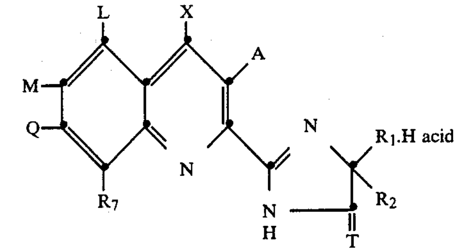

| R1 | R2 | T | A | L | M | Q | R7 | H Acid | mp °C. |
|---|---|---|---|---|---|---|---|---|---|
| $CH_3$ | $CH(CH_3)_2$ | O | $CO_2CH_3$ | H | H | H | H | HCl | |
| $CH_3$ | $CH(CH_3)_2$ | S | $CO_2CH_3$ | H | H | H | H | HCl | |
| $CH_3$ | $CH(CH_3)_2$ | O | $CO_2CH_3$ | H | H | H | H | HBr | |
| $CH_3$ | $CH(CH_3)_2$ | O | $CO_2CH_3$ | H | H | H | H | $HNO_3$ | |
| $CH_3$ | $CH(CH_3)_2$ | O | $CO_2CH_3$ | H | H | H | H | $H_2SO_4$ | |
| $CH_3$ | $CH(CH_3)_2$ | O | $CO_2H$ | H | H | H | H | HCl | 266–270 |
| $CH_3$ | $CH(CH_3)_2$ | O | CHO | H | H | H | H | HCl | |
| $CH_3$ | $CH(CH_3)_2$ | O | $CH_2OH$ | H | H | H | H | HCl | |
| $CH_3$ | $CH(CH_3)_2$ | O | $CO_2CH_3$ | H | H | Cl | H | HCl | |
| $CH_3$ | $CH(CH_3)_2$ | O | $CO_2CH_3$ | H | H | $CH_3$ | H | HCl | |
| $CH_3$ | $CH(CH_3)_2$ | O | $CO_2CH_3$ | H | $CH_3$ | H | H | HCl | |

EXAMPLE 46

Preparation of Sodium 2-(5-isopropyl-5-methyl-4-oxo-2-imidazolin-2-yl)-3-quinolinecarboxylic acid

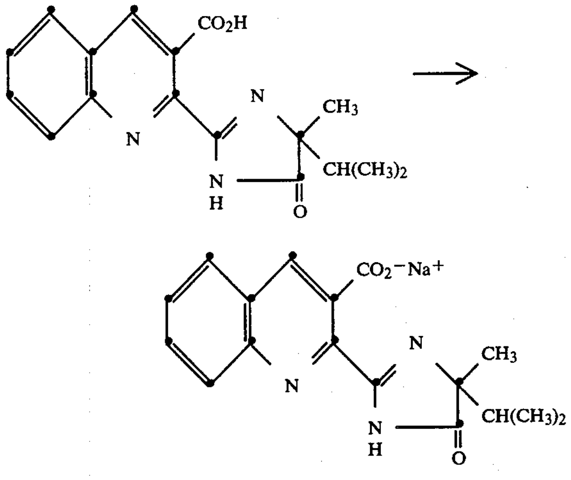

A solution of 2-(5-isopropyl-5-methyl-4-oxo-2-imidazolin-2-yl)-3-quinolinecarboxylic acid (2.33 g, 0.0075 mol) in water (22 ml) containing sodium hydroxide (0.3 g, 0.0075 mol) is stirred at room temperature overnight, then washed with methylene chloride and the aqueous layer separated and evaporated to an orange solid, which is washed with ether and air dried. The product as a dihydrate is obtained as a cream solid, mp 235°–250° C. (dec.). Anal. calcd. for $C_{17}H_{16}N_3O_3$-Na+2 $H_2O$: C, 55.27; H, 5.45; N, 11.37; Na, 6.22. Found: C, 55.56; H, 5.31; N, 11.35; Na, 6.30.

Substituting for sodium hydroxide the following salts are prepared in a similar manner. Compounds prepared in this manner are described in Table VI.

TABLE VI

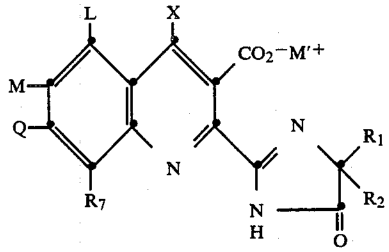

| R1 | R2 | X | L | M | Q | R7 | M' | mp °C. |
|---|---|---|---|---|---|---|---|---|
| $CH_3$ | $(CH_3)_2CH$ | H | H | H | H | H | Na | 235–250 |
| $CH_3$ | $(CH_3)_2CH$ | | | | | | K | |
| $CH_3$ | $(CH_3)_2CH$ | H | H | H | H | H | $NH_4$ | 128–137 |
| $CH_3$ | $(CH_3)_2CH$ | H | H | H | H | H | $H_3NCH_3$ | 193–196 (dec.) |
| $CH_3$ | $(CH_3)_2CH$ | H | H | H | H | H | $H_2N(CH_3)_2$ | 155–160 (dec.) |
| $CH_3$ | $(CH_3)_2CH$ | H | H | H | H | H | $HN(CH_3)_3$ | |
| $CH_3$ | $(CH_3)_2CH$ | H | H | H | H | H | $H_2N(C_3H_7{-}i)_2$ | 237–239 |
| $CH_3$ | $(CH_3)_2CH$ | H | H | H | H | H | $NH_3CH_2CH{=}CH_2$ | |
| $CH_3$ | $(CH_3)_2CH$ | H | H | H | H | H | $NH_3CH_2C{\equiv}CH$ | |
| $CH_3$ | $(CH_3)_2CH$ | H | H | H | H | H | $NH_3C_6H_5$ | |
| $CH_3$ | $(CH_3)_2CH$ | H | H | H | H | H | $NH_3C_8H_{17}$ | 76 |
| $CH_3$ | $(CH_3)_2CH$ | H | H | H | H | H | $NH_3C_{18}H_{37}$ | 111–113 |
| $CH_3$ | $(CH_3)_2CH$ | H | H | H | H | H | $NH_3C_3H_7{-}i$ | 133–134 |

TABLE VI-continued

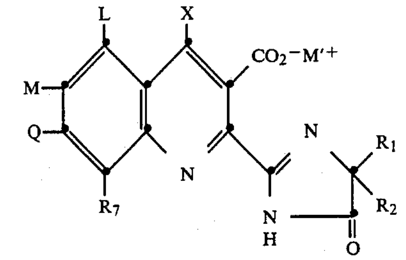

| R1 | R2 | X | L | M | Q | R7 | M' | mp °C. |
|---|---|---|---|---|---|---|---|---|
| $CH_3$ | $(CH_3)_2CH$ | H | H | H | H | H | 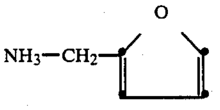 | |
| $CH_3$ | $(CH_3)_2CH$ | H | H | H | H | H | Ca | 270–290 |
| $CH_3$ | $(CH_3)_2CH$ | H | H | H | Cl | H | Ca | |
| $CH_3$ | $(CH_3)_2CH$ | H | H | H | $CH_3$ | H | $NH_2(C_3H_7i)_2$ | |
| $CH_3$ | $C_2H_5$ | H | H | H | H | H | $NH_3C_8H_{17}$ | |
| $-(CH_2)_5-$ | | H | H | H | H | H | $NH_3C_{18}H_{37}$ | |
| $CH_3$ | $(CH_3)_2CH$ | H | H | H | H | H | $NH_3C_2H_5$ | 170–175 (dec.) |
| $CH_3$ | $(CH_3)_2CH$ | H | H | H | H | H | 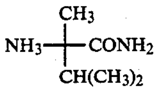 | 195–199 |

EXAMPLE 47

Preparation of 2-isopropyl-2-methyl-5H-imidazo[1',2':1,2]pyrrolo[3,4-b]quinoline-3(2H),5-dione.

Procedure A

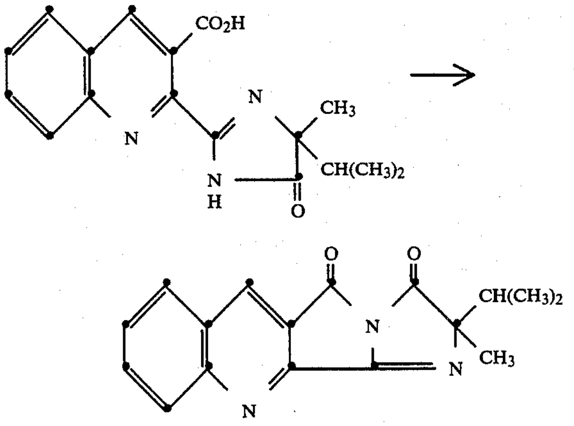

Dicyclohexylcarbodiimide (3.47 g, 0.0168 mol) in methylene chloride under nitrogen is added to a stirred suspension of 2-(5-isopropyl-5-methyl-4-oxo-2-imidazolin-2-yl)-3-quinolinecarboxylic acid, (5.24 g, 0.0168 mol) in methylene chloride at room temperature overnight. Since reaction was incomplete a further 0.3 g of dicyclohexylcarbodiimide was added and the mixture stirred for a further 48 hours. The reaction mixture is evaporated to a yellow solid and is purified by chromatography on a silica gel column. The product elutes with acetonitrile-methylene chloride as a white solid, which is crystallized from toluene as mp 225°–227° C. Anal. calcd. for $C_{17}H_{15}N_3O_2$: C, 69.61; H, 5.15; N, 14.33. Found: C, 69.76, H, 5.31; N, 14.13.

EXAMPLE 48

Procedure B

Preparation of cis and trans 1,11b-Dihydro-11b-hydroxy-3-isopropyl-3-methyl-5-H-imidazo[1',2':1,2]pyrrolo[3,4-b]quinoline-2(3H),5-dione

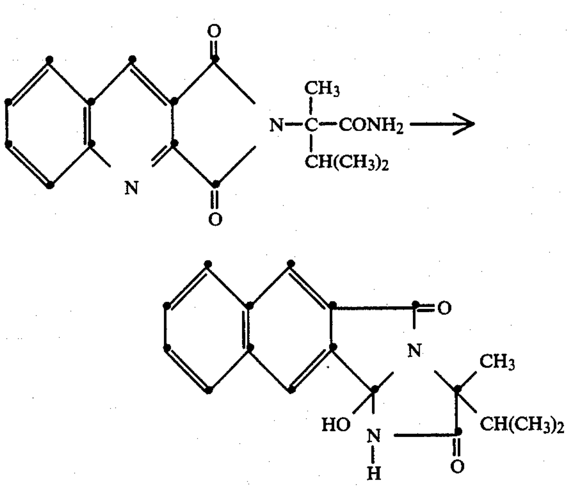

A solution of 1,3-dihydro-α-isopropyl-α-methyl-1,3-dioxo-2-H-pyrrolo[3,4-b]quinoline-2-acetamide (0.5 g, 0.0016 mol) was heated under reflux in xylene for 23 hours. On cooling, a white solid 0.17 g, mp 191°–192° C. precipitates and a further crop of 0.1 g, mp 187°–189° C. is formed by dilution of the filtrate by hexane. Anal. calcd. for $C_{17}H_{17}N_3O_3$: C, 65.58; H, 5.50; N, 13.50. Found: C, 66.08; H, 5.65; N, 13.00.

Other tricycles are obtained by procedures similar to Procedures A and B above.

Examples of Tricycles:

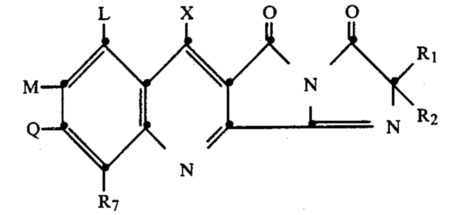

| | | | |
|---|---|---|---|
| Q = $CH_3$ | X,L,M,$R_7$ = H | $R_1$ = $CH_3$ | $R_2$ = $CH(CH_3)_2$ |
| Q = Cl | X,L,M,$R_7$ = H | $R_1$ = $CH_3$ | $R_2$ = $CH(CH_3)_2$ |
| M = $CH_3$ | X,L,Q,$R_7$ = H | $R_1$ = $CH_3$ | $R_2$ = $CH(CH_3)_2$ |
| M = Cl | X,L,Q,$R_7$ = H | $R_1$ = $CH_3$ | $R_2$ = $CH(CH_3)_2$ |
| Q = $CF_3$ | X,L,M,$R_7$ = H | $R_1$ = $CH_3$ | $R_2$ = $CH(CH_3)_2$ |
| M = $N(CH_3)_2$ | X,L,Q,$R_7$ = H | $R_1$ = $CH_3$ | $R_2$ = $CH(CH_3)_2$ |
| M = $OCH_3$ | X,L,Q,$R_7$ = H | $R_1$ = $CH_3$ | $R_2$ = $CH(CH_3)_2$ |
| X = OH | L,M,Q,$R_7$ = H | $R_1$ = $CH_3$ | $R_2$ = $CH(CH_3)_2$ |
| X,L,M,R,Q = H | | $R_1$ | $R_2$ |
| | | $CH_3$ | $C_2H_5$ |
| | | $CH_3$ | $C_3H_7$ |
| | | $CH_3$ | $C_4H_9$—n |
| | | $CH_3$ | $C_4H_9$—sec |
| | | $CH_3$ | $C_4H_9$—iso |
| | | $CH_3$ | 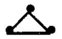 |
| | | $—(CH_2)_5—$ | |
| | | $CH_3$ | 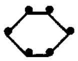 |

EXAMPLE 49

Preparation of N-(1-cyano-1,2-dimethylpropyl-2-(o-formylanilino)-maleimide

Procedure A

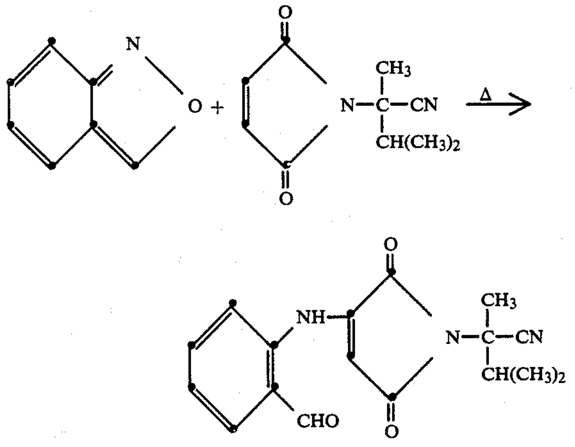

A solution of anthranil (3.55 g, 0.0298 mol) and α-isopropyl-α-methyl-2,5-dioxo-3-pyrroline-1-acetonitrile (5.73 g, 0.0298 mol) in xylene (20 ml) is heated at reflux for 39 hours under nitrogen. On cooling a yellow precipitate forms and is filtered off to give 2.78 g of mp 191°-192° C. product. Anal. calcd. for $C_{17}H_{17}N_3O_3$: C, 65.58; H, 5.50; N, 13.50. Found: C, 65.33; H, 5.44; N, 13.36.

EXAMPLE 50

Procedure B

Preparation of N-(1-cyano-1,2-dimethylpropyl)-2-(2-formyl-5-chloroanilino)maleimide

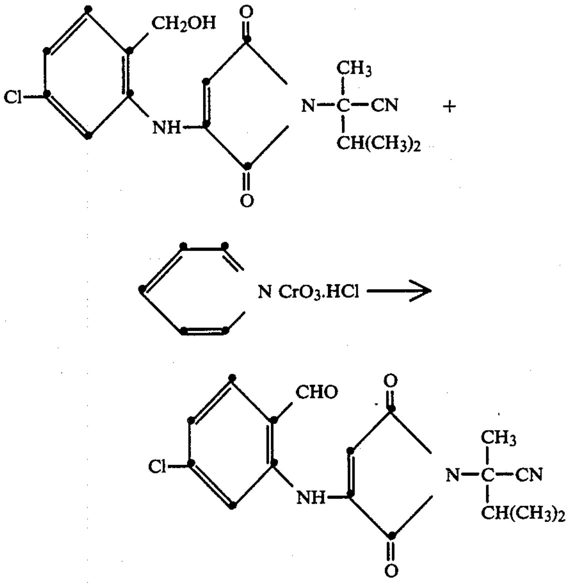

Pyridinium chlorochromate (4.4 g, 0.0204 mol) in methylene dichloride (20 ml) is added rapidly to a methylene chloride (20 ml) solution of N-(1-cyano-1,2-dimethylpropyl)-2-(5-chloro-2-hydroxymethylanilino)maleimide (4.75 g, 0.0136 mol). After 2 hours the dark reaction mixture is diluted with ether (20 ml) and a yellow precipitate is formed and is filtered off. This solid is redissolved in ethyl acetate:methylene chloride (1:1) and is passed through a silica gel column to give a yellow solid 4.31 g, (92%) with mp 80° C. (dec.).

The following aldehydes are prepared according to Procedures A or B as shown in Table VII.

TABLE VII

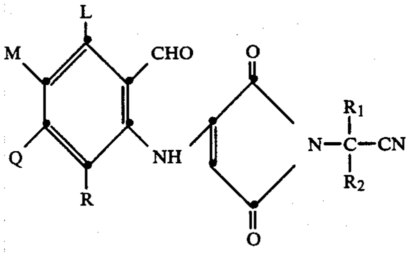

| $R_1$ | $R_2$ | L | M | Q | R | Example Method | mp °C. |
|---|---|---|---|---|---|---|---|
| $CH_3$ | $CH(CH_3)_2$ | Cl | H | H | H | | |
| $CH_3$ | $CH(CH_3)_2$ | H | Cl | H | H | 50B | |
| $CH_3$ | $CH(CH_3)_2$ | H | H | Cl | H | 49A | 80 |
| $CH_3$ | $CH(CH_3)_2$ | H | H | H | Cl | | |
| $CH_3$ | $CH(CH_3)_2$ | $CH_3$ | H | H | H | | 206-225 |
| $CH_3$ | $CH(CH_3)_2$ | H | $CH_3$ | H | H | 50B | 234-238 |
| $CH_3$ | $CH(CH_3)_2$ | H | H | $CH_3$ | H | 50B | 210-215 |
| $CH_3$ | $CH(CH_3)_2$ | H | H | H | $CH_3$ | | |
| $CH_3$ | $CH(CH_3)_2$ | H | H | H | $OCH_3$ | | |
| $CH_3$ | $CH(CH_3)_2$ | H | H | Cl | $CH_3$ | | |
| $CH_3$ | $CH(CH_3)_2$ | Cl | H | H | $CH_3$ | | |
| $CH_3$ | $CH(CH_3)_2$ | H | Cl | H | $CH_3$ | | |
| $CH_3$ | $CH(CH_3)_2$ | Cl | H | H | $OCH_3$ | | |

TABLE VII-continued

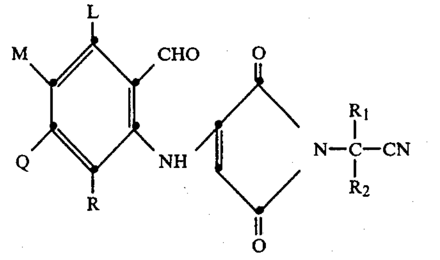

| $R_1$ | $R_2$ | L | M | Q | R | Example Method | mp °C. |
|---|---|---|---|---|---|---|---|
| $CH_3$ | $CH(CH_3)_2$ | $CH_3$ | H | H | $CH_3$ | | |
| $CH_3$ | $CH(CH_3)_2$ | H | $CH_3$ | H | $CH_3$ | | |
| $CH_3$ | $CH(CH_3)_2$ | H | H | $CH_3$ | $CH_3$ | | |
| $CH_3$ | $CH(CH_3)_2$ | H | $CF_3$ | H | H | | |
| $CH_3$ | $CH(CH_3)_2$ | H | H | $CF_3$ | H | | |
| $-(CH_2)_5-$ | | H | H | H | H | | |

In addition, the following compound can be prepared by the same procedure as described above using the appropriate starting materials

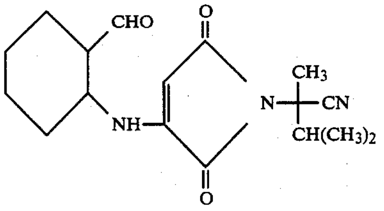

gum

EXAMPLE 51

Preparation of N-(1-cyano-1,2-dimethylpropyl)-2-(2-hydroxymethylanilino)maleimide

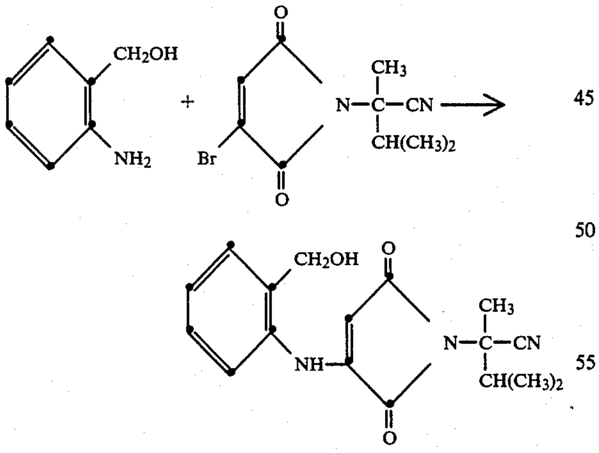

To o-aminobenzyl alcohol, (2 g, 0.0125 mol) and 3-bromo-α-isopropyl-α-methyl-2,5-dioxo-3-pyrroline-1-acetonitrile (2.7 g, 0.01 mol) is added absolute ethanol (100 ml) containing 3 g of 5 A pulverized sieves. The mixture is stirred for 20 hours at room temperature. The solvent is removed and the residue is purified through a silica gel dry column, eluant ether-hexane (2:1). Starting bromomaleimide is first recovered, followed by a bright yellow solid 1.89 g (60%), mp 39°–45° C. Anal. calcd. for $C_{17}H_{19}N_3O_3$: C, 65.16; H, 6.11; N, 13.41. Found: C, 65.94; H, 6.21; N, 12.87.

Other compounds are prepared by the above procedure with variously substituted o-aminobenzylalcohols. Employing i-propanol or t-butanol for ethanol generally improves the product yield and bases as acid acceptors may also be employed.

TABLE VIII

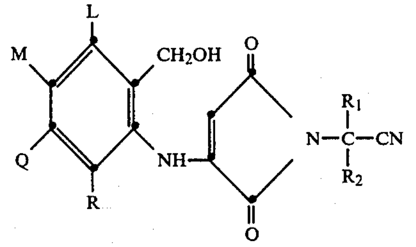

| $R_1$ | $R_2$ | L | M | Q | R | mp °C. |
|---|---|---|---|---|---|---|
| $CH_3$ | $CH(CH_3)_2$ | H | H | H | $CH_3$ | |
| $CH_3$ | $CH(CH_3)_2$ | H | H | $CH_3$ | H | gum |
| $CH_3$ | $CH(CH_3)_2$ | H | $CH_3$ | H | H | gum |
| $CH_3$ | $CH(CH_3)_2$ | $CH_3$ | H | H | H | gum |
| $CH_3$ | $CH(CH_3)_2$ | H | H | H | Cl | |
| $CH_3$ | $CH(CH_3)_2$ | H | H | Cl | H | 98-100 |
| $CH_3$ | $CH(CH_3)_2$ | H | Cl | H | H | |
| $CH_3$ | $CH(CH_3)_2$ | Cl | H | H | H | |
| $CH_3$ | $CH(CH_3)_2$ | H | H | H | $OCH_3$ | |
| $CH_3$ | $CH(CH_3)_2$ | H | H | Cl | $CH_3$ | |
| $CH_3$ | $CH(CH_3)_2$ | H | Cl | H | $CH_3$ | |
| $CH_3$ | $CH(CH_3)_2$ | Cl | H | H | $OCH_3$ | |
| $CH_3$ | $CH(CH_3)_2$ | $CH_3$ | H | H | $CH_3$ | |
| $CH_3$ | $CH(CH_3)_2$ | H | $CH_3$ | H | $CH_3$ | oil |
| $CH_3$ | $CH(CH_3)_2$ | H | H | $CH_3$ | $CH_3$ | |
| $CH_3$ | $CH(CH_3)_2$ | H | H | $CF_3$ | H | |
| $CH_3$ | $CH(CH_3)_2$ | H | $CF_3$ | H | H | |
| $-(CH_2)_5-$ | | H | H | H | H | |

EXAMPLE 52

Preparation of 3-Bromo-α-isopropyl-α-methyl-2,5-dioxo-3-pyrroline-1-acetonitrile

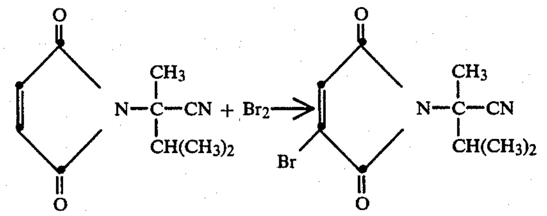

To a solution of α-isopropyl-α-methyl-2,5-dioxo-3-pyrroline-1-acetonitrile (50 g, 0.25 mol) in acetic acid (500 ml) heated at 75° C. is added bromine (40.76 g, 0.255 mol) in acetic acid (80 ml) dropwise with stirring. The reaction is maintained at 85° overnight and evaporated to a syrup, which is dissolved in methylene chloride (300 ml), is cooled to 5° C. to which triethylamine (34.78 ml) is added. After stirring for 2 hours the brown methylene chloride solution is diluted with ether and a white precipitate is formed. This is extracted with water (400 ml) and the organic layer is dried over anhydrous magnesium sulfate, then passed through a 2 inch bed of silica gel with methylene chloride to elute. The eluate is obtained as a dark brown oil. Anal. Calcd. for $C_{10}H_{10}N_2O_2Br$: C, 44.29; H, 4.09; N, 10.33. Found: C, 43.37; H, 4.05; N, 10.07.

Other bromomaleimides are prepared in a similar manner.

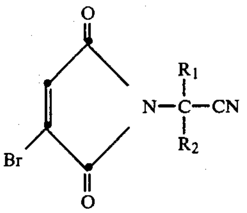

| $R_1$ | $R_2$ |
|---|---|
| $CH_3$ | $C_2H_5$ |
| $CH_3$ | $C_4H_9$ |
| $CH_3$ | $C_4H_9$—iso |
| $CH_3$ | $C_4H_9$—sec |
| $CH_3$ | $C_4H_9$—tert |
| $CH_3$ | 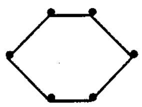 |
| $-(CH_2)_5-$ | |
| $CH_3$ | $CH_2CH{=}CH_2$ |
| $CH_3$ | 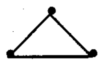 |

EXAMPLE 53

Preparation of α-isopropyl-α-methyl-2,5-dioxo-3-pyrroline-1-acetonitrile

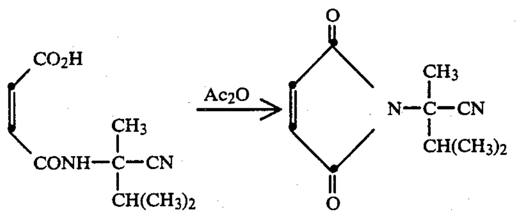

A solution of N-(1-cyano-1,2-dimethylpropyl)-maleamic acid (595 g, 2.83 mol) in acetic anhydride (3.96 liters) containing sodium acetate (13.72 g, 0.167 mol) is heated under reflux for one hour, cooled and the solvent removed in vacuo. The product is distilled* at 120°-130° C./0.1 mm to give 337 g (63%) of product.

*The pot temperature should not excede 200°.

Anal. calcd. for $C_{10}H_{12}N_2O_2$: C, 62.49; H, 6.29; N, 14.57. Found: C, 62.32; H, 6.36; N, 14.59.

In a similar manner the following compounds are prepared.

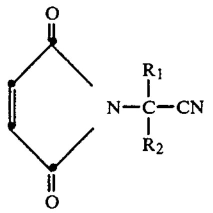

| $R_1$ | $R_2$ | mp °C. |
|---|---|---|
| $CH_3$ | $CH(CH_3)_2$ | |
| $CH_3$ | $C_2H_5$ | oil |
| $CH_3$ | $C_3H_7$ | |
| $CH_3$ | $C_4H_9$ | |
| $CH_3$ | $C_4H_9$—iso | |
| $CH_3$ | $C_4H_9$—sec | |
| $CH_3$ | $C_4H_9$—tert | |
| $CH_3$ | 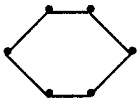 | |
| $CH_3$ | 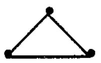 | oil |
| $-(CH_2)_5-$ | | oil |
| $CH_3$ | $CH_2CH{=}CH_2$ | |
| $CH_3$ | $CH_3$ | oil |

EXAMPLE 54

Preparation of N-[1-(1-cyano-1,2-dimethylpropyl)-2,5-dioxo-3-pyrrolin-3-yl]anthranilic acid

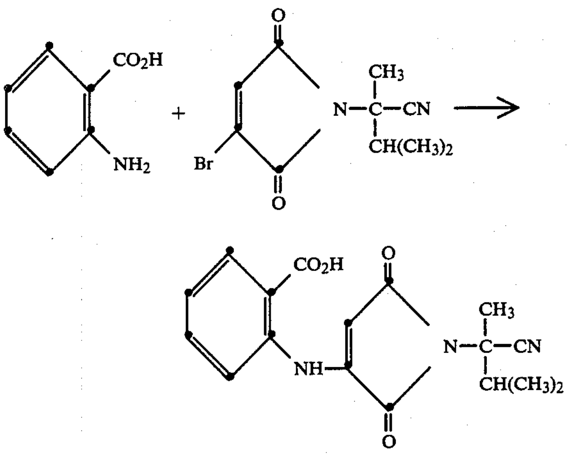

A mixture of anthranilic acid, (13.7 g, 0.1 mol), 3-bromo-α-isopropyl-α-methyl-2,5-dioxo-3-pyrroline-1-acetonitrile (27 g, 0.1 mol), isopropanol (200 ml) and sodium acetate (8.2 g) is stirred at room temperature 3 days and then is heated at reflux 1 hour. On cooling, and with the addition of ether, a yellow solid 31.6 g, (19.7%) is obtained, mp 262°-266° C. after crystallizing from acetic acid. Anal. calcd. for $C_{17}H_{17}N_3O_4$: C, 62.37; H, 5.24; N, 12.84. Found: C, 62.24; H, 5.19; N, 12.70.

In a similar manner other maleimides may be prepared.

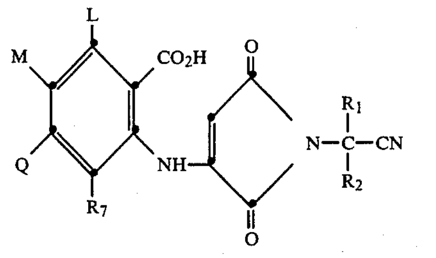

| R1 | R2 | L | M | Q | R7 |
|---|---|---|---|---|---|
| $CH_3$ | $CH(CH_3)_2$ | H | Cl | H | H |
| $CH_3$ | $CH(CH_3)_2$ | H | H | Cl | H |
| $CH_3$ | $CH(CH_3)_2$ | H | $CH_3$ | H | H |
| $CH_3$ | $CH(CH_3)_2$ | H | H | $CH_3$ | H |

EXAMPLE 55

Preparation of N-(1-carbamoyl-1,2-dimethylpropyl)quinaldamide

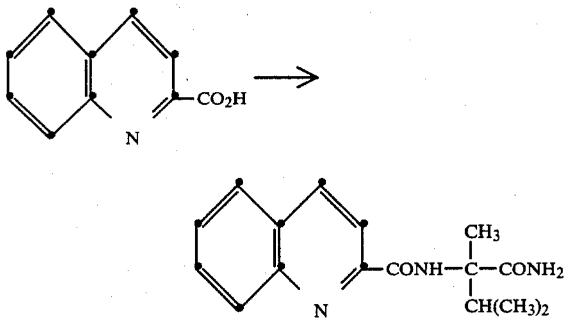

To a solution of quinaldic acid (20 g, 0.116 mol) in tetrahydrofuran (500 ml) cooled to −9° C. is added methyl chloroformate (8.92 ml, 0.116 mol) followed by triethylamine (18.4 ml, 0.139 mol). After 20 minutes 2-amino-2,3-dimethylbutyramide (15.1 g, 0.116 mol) is added and the mixture stirred overnight at room temperature. Water is added and the solution is reduced to 200 ml of a rotorvap. A white solid separates and is filtered off, water washed and dried. Recrystallization from absolute ethanol gives the product mp 179°-180° C., 26.86 g (87%). Anal. calcd. for $C_{16}H_{19}N_3O_2$: C, 67.34; H, 6.73; N, 14.72. Found: C, 67.14; H, 6.17; N, 14.72.

In a similar manner other quinolinecarboxamides may be prepared.

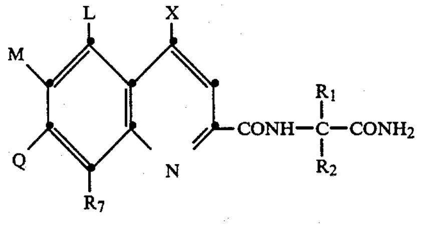

| R1 | R2 | X | L | M | Q | R7 | mp °C. |
|---|---|---|---|---|---|---|---|
| $CH_3$ | $CH(CH_3)_2$ | $OCH_3$ | H | H | H | H | 167-169 |
| $CH_3$ | $CH(CH_3)_2$ | $CH_3$ | H | H | H | H | |
| $CH_3$ | $CH(CH_3)_2$ | Cl | H | H | H | H | 188-195 |
| $CH_3$ | $CH(CH_3)_2$ | H | H | H | H | Cl | 223-224.5 |
| $CH_3$ | $CH(CH_3)_2$ | H | H | H | H | $NO_2$ | |

-continued

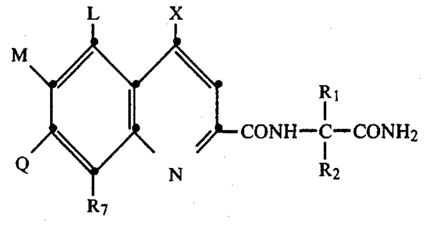

| R1 | R2 | X | L | M | Q | R7 | mp °C. |
|---|---|---|---|---|---|---|---|
| $CH_3$ | $C_2H_5$ | H | H | H | H | H | |
| $CH_3$ | $C_4H_9$—sec | H | H | H | H | H | |
| $(CH_2)_5$ | | H | H | H | H | H | |
| $CH_3$ | $CH(CH_3)_2$ | H | H | H | H | BR | |
| $CH_3$ | $CH(CH_3)_2$ | H | H | $OCH_3$ | H | H | 225-280 (dec.) |
| $CH_3$ (−) | $CH(CH_3)_2$ | H | H | H | H | H | 107-111 $[\alpha]_D^{25}$ = −62.7 |
| $CH_3$ (+) | $CH(CH_3)_2$ | H | H | H | H | H | 105-108 $[\alpha]_D^{25}$ = +62.2 |
| $CH_3$ | $CH(CH_3)_2$ | H | H | H | H | $OCH_3$ | foam |

EXAMPLE 56

Preparation of α-Isopropyl-α-methyl-2,5-dioxo-3-pyrroline-1-acetamide

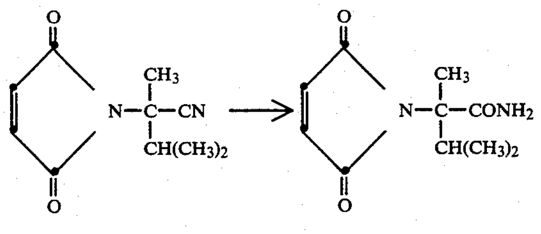

A solution of α-isopropyl-α-methyl-2,5-dioxo-3-pyrroline-1-acetonitrile (2.0 g, 0.104 mol) in methylene chloride (30 ml) is added in a fine stream to concentrated sulfuric acid at room temperature. After stirring overnight at room temperature for 16 hours the mixture is poured onto ice, containing sodium chloride and ethyl acetate. The organic layer is washed with aqueous sodium bicarbonate, brine and dried. Evaporation after washing with ether-pentane gives a solid (72%), mp 138.5°-140° C. Anal. calcd. for $C_{10}H_{14}N_2O_3$: C, 57.13; H, 6.71; N, 13.33. Found: C, 56.89; H, 6.64; N, 13.16.

In a similar manner other imideamides are prepared.

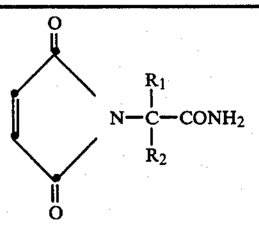

| R1 | R2 |
|---|---|
| $CH_3$ | $C_2H_5$ |
| $CH_3$ | $C_3H_7$ |
| $CH_3$ | $C_4H_9$—n |
| $CH_3$ | $C_4H_9$—iso |

-continued

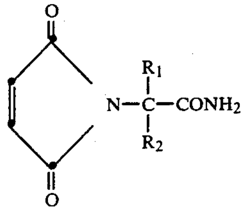

| $R_1$ | $R_2$ |
| --- | --- |
| $CH_3$ | $C_4H_9$—sec |
| $CH_3$ | $C_4H_9$—tert |
| $CH_3$ | 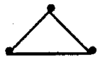 |
| $CH_3$ | $CH_2CH{=}CH_2$ |
| $CH_3$ | 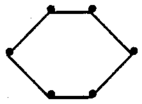 |
| —$(CH_2)_5$— | |

EXAMPLE 57

Preparation of 5-Isopropyl-5-methyl-2-(2-quinolyl)-2-imidazolin-4-one

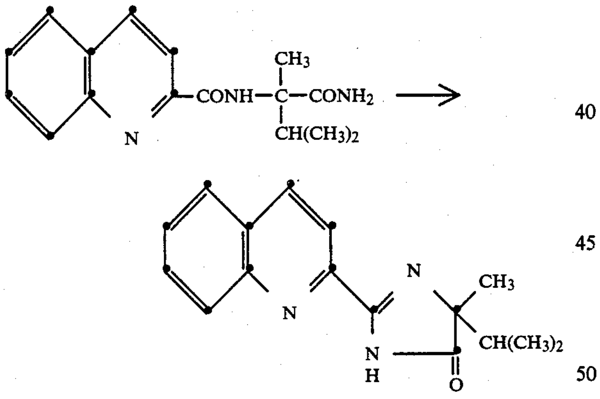

To a slurry of N-(1-carbamoyl-1,2-dimethylpropyl)-2-quinolinecarboxamide (16.04 g, 0.0562 mol) in xylene (610 ml) under nitrogen is added a 50% oil dispersion of sodium hydride (2.7 g, 0.056 mol) at 20° C. The reaction is heated to reflux for 2 hours, cooled and water (50 ml) added. The aqueous layer is extracted with methylene chloride and the organic layers combined and evaporated to give a yellow oil, 17 g. Purification is accomplished by passing through a silica gel column using hexane-ethyl acetate as solvent. A pale yellow solid is obtained and is recrystalized from ethyl acetate to give 11.77 g (78%) of white product, mp 112°-117° C. Anal. calcd. for $C_{16}H_{17}N_3O$: C, 71.88; H, 6.41; N, 15.72. Found: C, 71.91; H, 6.47; N, 15.70.

Other compounds prepared in a similar manner are shown in Table IX.

TABLE IX

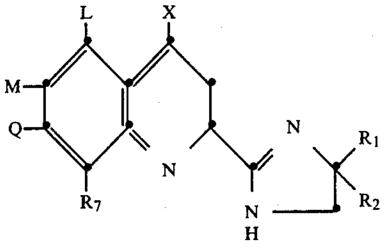

| $R_1$ | $R_2$ | X | L | M | Q | $R_7$ | mp °C. |
| --- | --- | --- | --- | --- | --- | --- | --- |
| $CH_3$ | $CH(CH_3)_2$ | $OCH_3$ | H | H | H | H | 157-161 |
| $CH_3$ | $CH(CH_3)_2$ | $CH_3$ | H | H | H | H | |
| $CH_3$ | $CH(CH_3)_2$ | Cl | H | H | H | H | 176-178 |
| $CH_3$ | $CH(CH_3)_2$ | H | H | H | H | Cl | |
| $CH_3$ | $CH(CH_3)_2$ | H | H | H | H | $NO_2$ | |
| $CH_3$ | $C_2H_5$ | H | H | H | H | H | |
| $CH_3$ | $C_3H_7$ | H | H | H | H | H | |
| $CH_3$ | $C_4H_9$—n | H | H | H | H | H | |
| $CH_3$ | $C_4H_9$—i | H | H | H | H | H | |
| $CH_3$ | $C_4H_9$—sec | H | H | H | H | H | |
| $CH_3$ | $C_4H_9$—t | H | H | H | H | H | |
| $CH_3$ | cyclopropyl | H | H | H | H | H | |
| $CH_3$ | $CH_2CH{=}CH_2$ | H | H | H | H | H | |
| $CH_3$ | cyclohexyl | H | H | H | H | H | |
| $(CH_2)_5$ | | H | H | H | H | H | |
| $CH_3$ | $CH(CH_3)_2$ | H | H | $OCH_3$ | H | H | 133-134 |
| $CH_3$ (+) | $CH(CH_3)_2$ | H | H | H | H | H | 113.5-115.5 $[\alpha]_D^{25}$ = +18.74 |
| $CH_3$ (−) | $CH(CH_3)_2$ | H | H | H | H | H | 114-115.5 $[\alpha]_D^{25}$ = −18.83 |
| $CH_3$ | $CH(CH_3)_2$ | H | H | H | H | $OCH_3$ | 112.5-115 |

EXAMPLE 58

Preparation of 2-(5-isopropyl-5-methyl-4-oxo-2-imidazolin-2-yl)-3-quinolinecarboxaldehyde

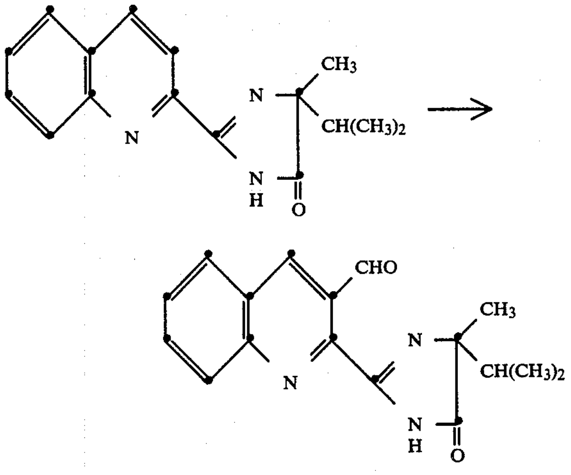

To a mixture of 5-isopropyl-5-methyl-2-(2-quinolyl)-2-imidazolin-4-one (3 g, 0.0112 mol) in ether (150 ml) is added tetramethylethylenediamine (3.4 g, 0.00225 mol). n-Butyllithium (17 ml, 0.027 mol) in hexane is added dropwise to the reaction mixture cooled to −63° C. An intense red color is generated and after the addition the mixture is maintained at −10° to −20° C. for 2½ hours.

Dry DMF (5 ml) is added at −10° C. and the mixture is allowed to attain room temperature, while stirring overnight. The mixture is diluted with water (75 ml) and is neutralized with acetic acid. A pale yellow solid 2.57 g (78%) is obtained with mp 226°-227° C. after crystallization* from 95% ethanol. Anal. calcd. for $C_{17}H_{17}N_3O_2$: C, 69.13; H, 5.80; N, 14.23. Found: C, 68.98; H, 5.88; N, 14.25. The oxime of this aldehyde, prepared in the usual way, has mp 255°-257° C.

*Dilution of the 95% ethanol with 5-10 ml of water gives a new solid which is filtered off. Washing the solid with 95% ethanol removes the yellow color and gives a material mp 168°-169° C. An (m+1)/e confirms either tricyclic structure A or B.

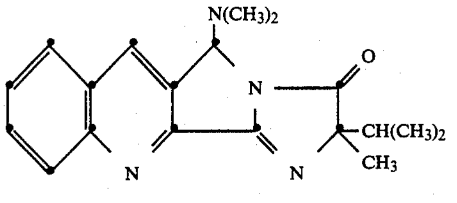

or

A

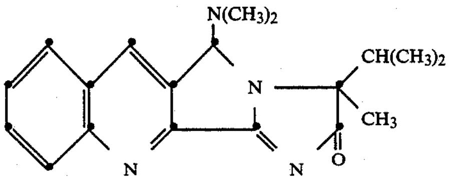

B

In a similar manner other A groups are prepared.

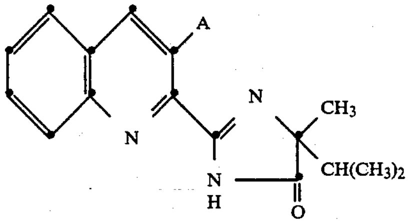

| A | mp °C. |
|---|---|
| COOH | |
| $CH_2CH_2OH$ | |
| $CH_3$ | 178-179 |
| $CH_2CO_2CH_3$ | |
| $CH_3CHOH$ | |
| $C_6H_5CHOH$ | |
| $(CH_3)_2COH$ | 181-184 |
| $C_6H_5C(CH_3)OH$ | 135-199 a diastereomeric mixture |

Compounds with other A groups are prepared as described in the Examples noted.

| | | |
|---|---|---|
| $CONH_2$ | 213-215 | (Example 23) |
| CN | 249-251 | (Example 24) |
| $CONHCH_2CH_2OH$ | 204.5-206 | (Example 21) |
| CONHOH | 187 | (Example 36) |

-continued

| | | |
|---|---|---|
| 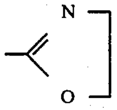 | 170-176 | (Example 70) |

EXAMPLE 59

Preparation of 2-3-(Hydroxymethyl)-2-quinolyl-5-isopropyl-5-methyl-2-imidazolin-4-one

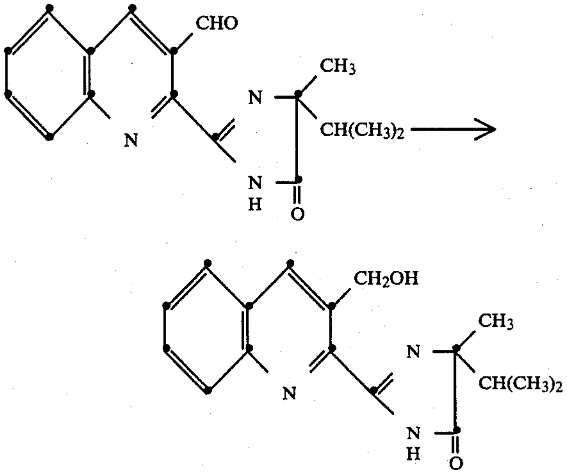

Powdered sodium borohydride (0.5 g, 0.013 mol) is added to 2-(5-isopropyl-5-methyl-4-oxo-2-imidazolin-2-yl)-3-quinolinecarboxaldehyde (0.78 g, 0.00264 mol) which is suspended in ethanol (150 ml) under nitrogen. A clear yellow solution results. After 20 minutes the reaction is concentrated to 40 ml, and is diluted with water (75 ml). Methylene chloride extraction and evaporation gives a solid which is crystallized from hexane-ethyl acetate to give pale yellow crystals, mp 138°-149° C., M/e 298.

Other compounds may be prepared by the above procedure using the appropriately substituted quinolinecarboxaldehyde. Such compounds are shown in Table X.

TABLE X

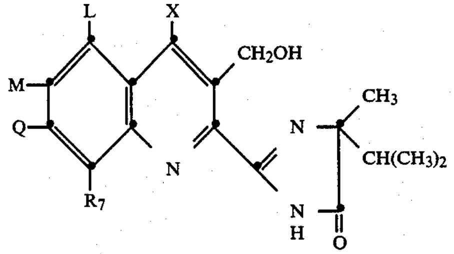

| | |
|---|---|
| X = Cl, Me | L, M, Q, $R_7$ = H |
| L = Me, Cl | X, M, Q, $R_7$ = H |
| M = Me, Cl | X, L, Q, $R_7$ = H |
| Q = Me, Cl | X, L, M, $R_7$ = H |
| $R_7$ = Me, Cl | X, L, M, Q = H |
| M = $CH(CH_3)_2$ | X, L, Q, $R_7$ = H mp 195-198° |

EXAMPLE 60

Preparation of methyl 5-aminopicolinate

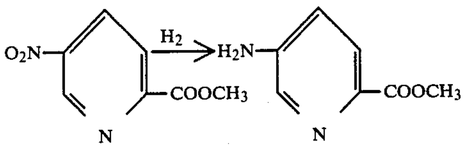

A solution containing 10 g methyl 5-nitropicolinate in 400 ml ethyl acetate is stirred under hydrogen in the presence of 1 g platinum oxide at room temperature and atmospheric pressure. When no further hydrogen uptake occurs, the catalyst is removed by filtration, the filtrate concentrated, and the product collected. This is recrystallized from ethyl acetate to give analytically pure methyl 5-aminopicolinate, mp 147°-150.5° C.

EXAMPLE 61

Preparation of methyl 5-diethylaminopicolinate

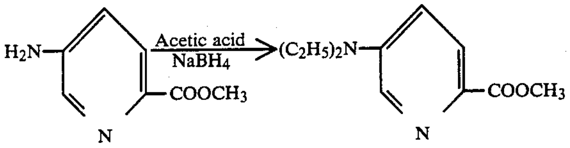

To a stirred solution of the amine (5 g) in acetic acid (100 ml) is added during four and one-half hours at 55° C. 12 pellets of sodium borohydride. (Each pellet weighs ~0.4 g). The mixture is then stirred overnight under nitrogen at 40°-45° C. A further 8 pellets of sodium borohydride is added during four and one-half hours and stirring again continued at 40°-45° C. overnight. The mixture is diluted with water and concentrated. The pH of the residue is adjusted to 6 with 2N NaOH, and the mixture extracted with ethyl acetate. The extract is dried and concentrated, and the residue chromatographed on silica gel with ethyl acetate. This gives 3.8 g of product which is crystallized from ether-hexane to give analytically pure methyl 5-diethylaminopicolinate, mp 52°-53.5° C.

Using essentially the same procedure, but substituting formic acid for the acetic acid, there is obtained methyl 5-dimethylaminopicolinate, mp 100°-103° C.

EXAMPLE 62

Preparation of methyl 5-fluoropicolinate

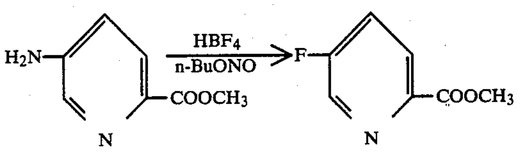

The methyl 5-aminopicolinate (2.2 g) is dissolved in 5.5 ml 48% fluoroboric acid and 20 ml 95% ethanol. This mixture is cooled, with stirring, to −3° C. and then 1.81 g n-butyl nitrite added dropwise. After a further one-half hour at −3° C., 0.5 ml n-butyl nitrite is added slowly and stirring continued for one-half hour at 0° C. After adding 20 ml ether carefully, the mixture is rapidly filtered, and the solid washed twice with cold hexane. The solid is suspended in 100 ml heptane, and the suspension slowly heated with stirring. At about 60° C., a vigorous exothermic reaction occurs. Heating is then continued to 80° C. A red oil separates on the sides of the flask. The heptane solution is filtered, and the filtrate concentrated to give the desired product. The red oil is dissolved in water, excess sodium bicarbonate solution added, and the solution extracted with ethyl acetate. The ethyl acetate extract is washed with saturated brine, dried and concentrated. The residue is chromatographed on silica gel and the product, methyl 5-fluoropicolinate, eluted with 1:1-ether:hexane. This material is used directly for the preparation of the picolinic acid.

EXAMPLE 63

Preparation of 5-diethylaminopicolinic acid

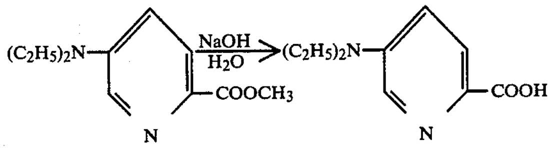

To a stirred solution containing 2.5 g of methyl 5-diethylaminopicolinate in 40 ml methanol is added 40 ml water and 1.04 g of a 50% solution of NaOH in water. The mixture is heated to reflux and allowed to cool to room temperature. This is repeated. The base is neutralized with concentrated HCl, and the solvents removed in vacuo. The residue is dried azeotropically with dioxane. The residue is then extracted into ethanol. Concentration of the ethanol gives 5-diethylaminopicolinic acid as a white crystalline solid, mp 145.5°-147.5° C.

Using essentially the same procedure but substituting the appropriate picolinate for the methyl 5-diethylaminopicolinate, there is obtained the following picolinic acids:

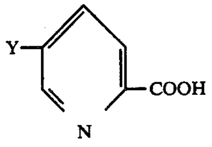

| Y | mp °C. |
|---|---|
| $N(CH_3)_2$ | 160-164 |
| F | 160-162 |

EXAMPLE 64

Preparation of
2-[5-(1-Hydroxy-1-methylethyl)-2-pyridyl]-5-isopropyl-5-methyl-2-imidazolin-4-one

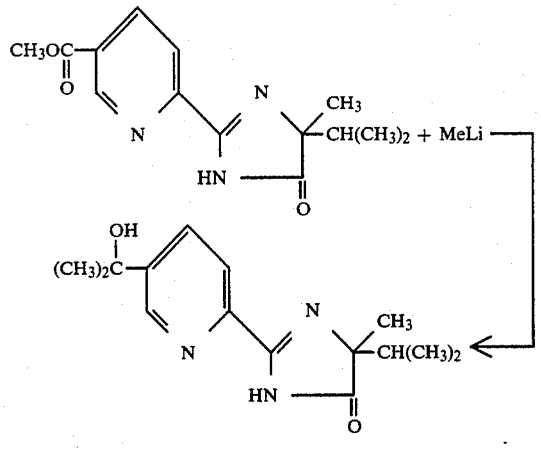

To a stirred solution of 2.1 g of the ester under nitrogen at −65° C. is added dropwise 12.7 ml of a 1.2M solution of methyl lithium in hexane. The mixture is allowed to warm slowly to −5° C. for one hour and then poured over a stirred slurry of solid carbon dioxide in hexane. After reaching room temperature, excess saturated aqueous ammonium chloride solution is added and ethyl acetate. The aqueous phase is separated and washed twice with ethyl acetate. The combined organic phases are washed with saturated brine, dried and concentrated to give 1.38 g of an orange solid. This is recrystallized from ethyl acetate to give 2-[5-(1-hydroxy-1-methylethyl)-2-pyridyl]-5-isopropyl-5-methyl-2-imidazolin-2-one, mp 166°–168° C.

EXAMPLE 65

Preparation of
2-(5-isopropenyl-2-pyridyl)-5-isopropyl-5-methyl-2-imidazolin-4-one

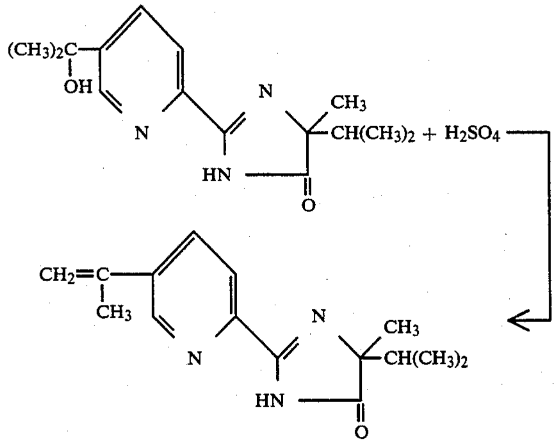

To 6.4 g of 2-[5-(1-hydroxy-1-methylethyl)-2-pyridyl]-5-isopropyl-5-methyl-2-imidazolin-4-one is added with stirring and cooling (ice) 30 ml concentrated sulfuric acid. The mixture is stirred at room temperature for a further 30 minutes, then poured onto 100 ml ice. The pH of this mixture is adjusted to 4 with concentrated ammonium hydroxide and extracted with 3×200 ml ether. The combined extracts were washed with saturated brine, dried and concentrated to give 5.71 g yellow solid. Recrystallized from ether-hexane gave analytically pure 2-(5-isopropenyl-2-pyridyl)-5-isopropenyl-5-methyl-2-imidazolin-4-one, mp 123°–125° C.

EXAMPLE 66

Preparation of
2-(5-isopropyl-2-pyridyl)-5-isopropyl-5-methyl-2-imidazolin-4-one

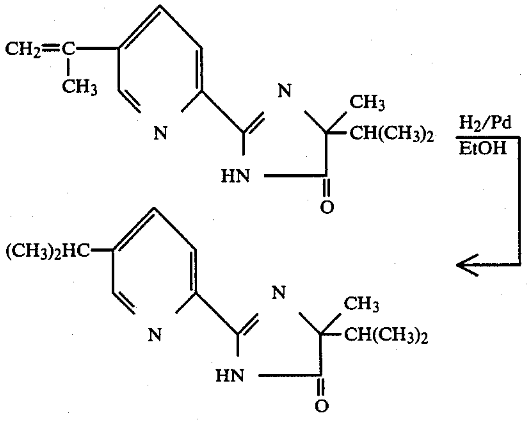

A stirred suspension of 1.36 g 5% palladium on carbon in 10 ml ethanol is pre-reduced with hydrogen. A solution containing 5.24 g of the isopropenyl pyridine in 50 ml ethanol is added and stirring under hydrogen continued. No reduction occurs. The catalyst is removed by filtration, and the same amount of fresh catalyst added. During one hour, 500 ml hydrogen is absorbed at atmospheric pressure. The catalyst is removed by filtration and the filtrate concentrated to leave an oil which was crystallized from ether-hexane and had the appropriate infrared and NMR spectra.

EXAMPLE 67

Preparation of
6-(5-isopropyl-5-methyl-4-oxo-2-imidazolin-2-yl)nicotinaldehyde

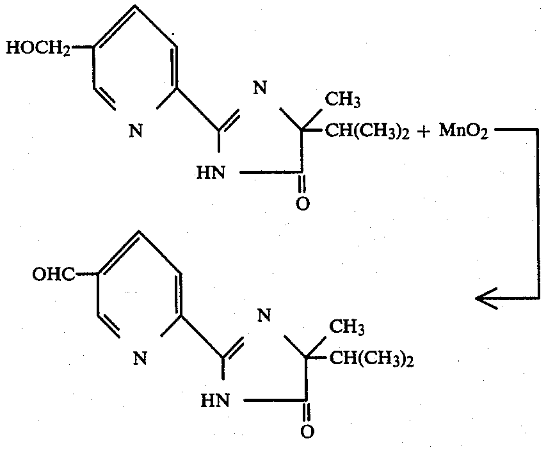

To a stirred solution containing 18 g hydroxymethyl pyridine in 180 ml dry methylene chloride under nitrogen is added 44.3 g of activated manganese dioxide. The mixture is heated under reflux for four hours. The mixture is filtered and the filtrate concentrated. Trituration of the residue with ether-hexane gave a crystalline solid. This is recrystallized from ether-hexane to give analytically pure 6-(5-isopropyl-5-methyl-4-oxo-2-imidazolin-2-yl)nicotinaldehyde, mp 105.5°-108° C.

EXAMPLE 68

Preparation of 2-(5-propenyl-2-pyridyl)-5-isopropyl-5-methyl-2-imidazolin-4-one

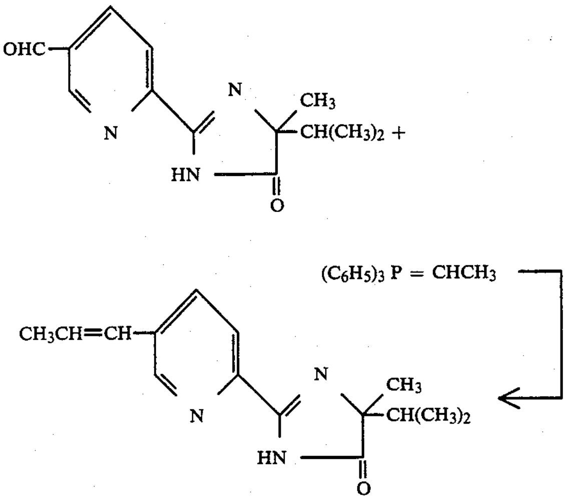

To 2.12 g of a 50% suspension of sodium hydride in mineral oil under nitrogen is added 30 ml dry dimethylsufoxide. The mixture is stirred and heated at 70° C. for 45 minutes. This is cooled and 16.4 g (ethyl) triphenylphosphonium bromide is added. A thick precipitate forms and more dry DMSO is added to allow efficient stirring. After 20 minutes, 5.42 g aldehyde in 30 ml DMSO is added all at once. The exotherm is controlled by cooling. After stirring at room temperature for three hours, the mixture is heated at 60° C. for one and one-half hours. The mixture is diluted with 200 ml water, the pH adjusted to 3 with concentrated $H_2SO_4$ and extracted with ethyl acetate. The extract is dried and concentrated. Chromatography of the residue on silica gel using ether-hexane as eluant gave 2.55 g of a gummy material whose NMR spectrum was consistent with the desired product, 2-(5-propenyl-2-pyridyl)-5-isopropyl-5-methyl-2-imidazolin-4-one as a mixture of cis and trans-isomers.

EXAMPLE 69

Preparation of 2-(5-propyl-2-pyridyl)-5-isopropyl-5-methyl-2-imidazolin-4-one

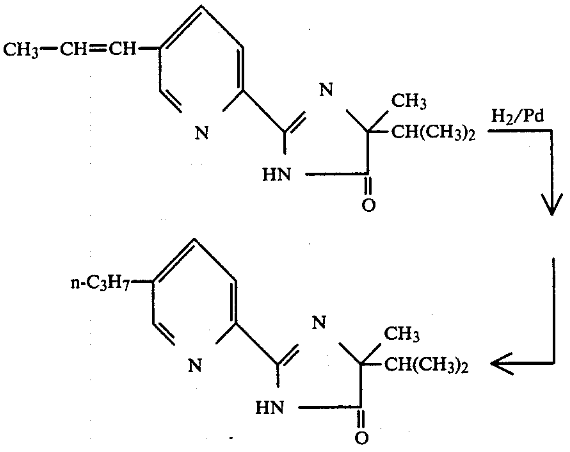

The reduction with hydrogen of the propenyl derivative (2.4 g) is carried out in ethanol (30 ml) in the presence of 0.62 g 5% palladium on carbon catalyst. The reduction takes six hours. The mixture is filtered, and the filtrate concentrated to give a gum whose NMR spectrum showed complete reduction of the propenyl group and formation of the product 2-(5-propyl-2-pyridyl)-5-isopropyl-5-methyl-2-imidazolin-4-one.

EXAMPLE 70

Preparation of 5-isopropyl-5-methyl-2-[3-(2-oxazolin-2-yl)-2-pyridyl]-2-imidazolin-4-one

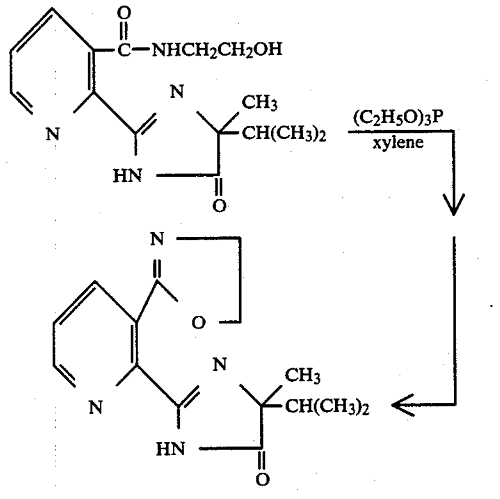

A mixture containing 1.87 g nicotinic acid amide and 1.12 ml triethylphosphite in 60 ml xylene is heated under reflux for 19 hours. After cooling and addition of 25 ml ethyl acetate, the mixture is extracted with a solution of 7 g KOH in 100 ml water. The aqueous phase is separated, acidified to pH 4 and extracted with ethyl acetate. The extract was concentrated. The residue was triturated with ether to give a solid which was collected and discarded. The filtrate was concentrated, and the residue chromatographed on silica gel using 1:1 and 3:1 acetone-hexane as eluant. The product fractions were combined and concentrated to give 5-isopropyl-5-methyl-2-[3-(2-oxazolin-2-yl)-2-pyridyl]-2-imidazolin-4-one as a foam with appropriate NMR and IR spectra.

EXAMPLE 71

Preparation of dimethyl 6-phenylpyridine-2,3-dicarboxylate

A

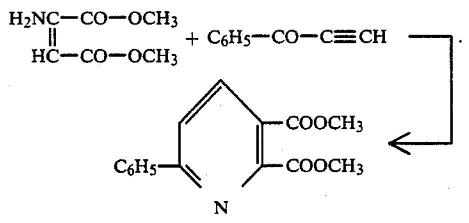

A suspension of 3.18 g (20 mmol) of dimethyl 2-aminomaleate and 2.6 g (20 mmol) of phenyl ethynyl ketone in 10 ml of methanol is heated at reflux overnight. The methanol is removed in vacuo, and the residue is digested in ether and filtered to give 2.52 g of the desired diester as a tan solid, mp 124.5°-127° C.

B

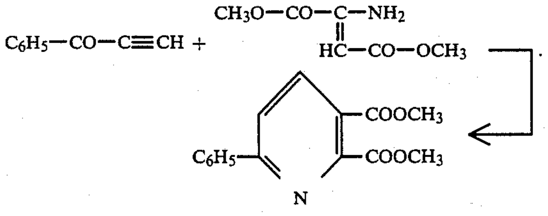

A solution of 11.66 g (73.5 mmol) of dimethyl 2-aminofumarate and 9.5 g (73 mmol) of phenyl ethynyl ketone in 35 ml of methanol is heated at reflux overnight. The reaction is allowed to cool to room temperature, and 10 g of crude diester is collected by filtration. The crude diester is dissolved in dichloromethane-methanol mixture and treated with charcoal, filtered, concentrated and the residue crystallized to give 9.1 g of the desired diester as a white solid, mp 124°-127° C.

The above experiments show that when either the aminofumarate or aminomaleate is used in this reaction, the same product is produced.

Using essentially the same procedure as described above, but substituting the appropriate ethynyl ketone for phenyl ethynyl ketone and using either the maleate, fumarate or mixture of these, the following pyridine-2,3-dimethyl esters are prepared.

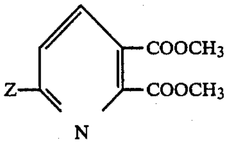

| Z | mp °C. or bp °C./pressure |
|---|---|
| 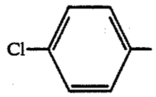 | 119.5–122° |

-continued

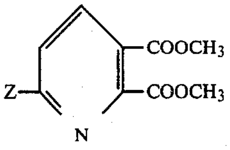

| Z | mp °C. or bp °C./pressure |
|---|---|
| 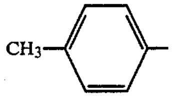 | 106–107.5° |
| $C_2H_5$ | 122–127°/0.25 mm |
| n-$C_3H_7$ | 151–155°/0.3 mm |
| i-$C_3H_7$ | 131–135°/0.15 mm |

EXAMPLE 72

Preparation of dimethyl 5,6-dimethylpyridine-2,3-dicarboxylate

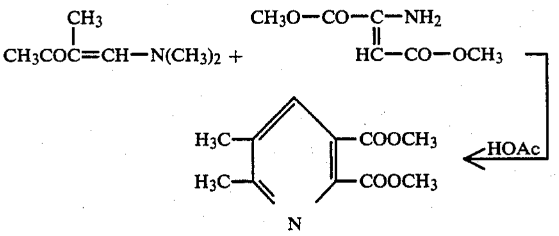

A solution of 6.0 g (47.2 mmol) of 4-dimethylaminomethylene-3-methyl-3-buten-2-one and 7.5 g (47.2 mmol) of dimethyl 2-aminofumarate in 140 ml of acetic acid is heated at 85° C. overnight. The reaction mixture is concentrated in vacuo, and the residue dissolved in ether. The ether layer is washed with saturated sodium bicarbonate, brine, dried over sodium sulfate, filtered, and concentrated in vacuo. The residue is filtered to remove some precipitate that forms. The solid precipitate is washed with ether, and the filtrate concentrated again and distilled at reduced pressure to give the desired diester as a yellow oil, bp 122°-140° C./0.2 mm.

By essentially the same procedure but substituting 2-(dimethylaminomethylene)cyclopentanone for 4-dimethylamino-3-methyl-buten-2-one there is obtained 6,7-dihydro-5H-1-pyrindene-2,3-dicarboxylic acid dimethyl ester as a yellow oil.

EXAMPLE 73

Preparation of dimethyl5,6,7,8-tetrahydroquinoline-2,3-dicarboxylate

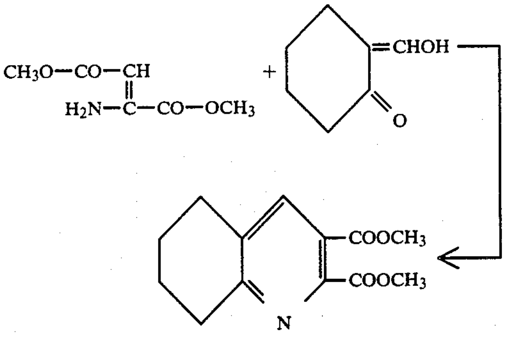

A mixture of 10.04 g dimethyl aminofumarate and 8.0 g 2-formylcyclohexanone is heated at 150° C. under a reflux condenser for one hour. The condenser is removed, and the volatile components allowed to escape. Material volatile at 0.5 mm and 150° C. is then removed. The residue is purified by flash chromatography on silica gel using hexane-ethyl acetate (4:1) as eluant. Fractions containing the product are combined to give 2.97 g dimethyl 5,6,7,8-tetrahydroquinoline-2,3-dicarboxylate as an amber oil having the appropriate NMR and IR spectra.

EXAMPLE 74

Preparation of 6-propylpyridine-2,3-dicarboxylic acid

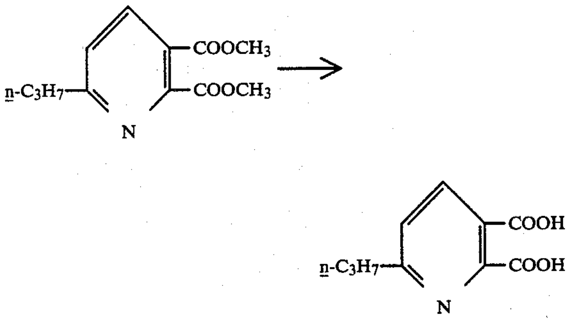

To a stirred solution under nitrogen containing 17.25 g of diester in 75 ml dry methanol is added 19.2 g potassium hydroxide with cooling to control the exotherm. The mixture is heated under reflux for one and one-half hours. Then a mixture of 10.4 ml concentrated $H_2SO_4$, 19.1 g ice, and 25 ml methanol is added. The mixture is cooled, diluted with 350 ml acetone, and solid sodium sulfate added. The mixture is filtered, and the filtrate concentrated. The residue is triturated with ether. The crystalline diacid is removed by filtration. A sample is recrystallized from acetone-hexane to give analytically pure 6-propylpyridine-2,3-dicarboxylic acid, mp 149°-153° C.

The following acids are prepared similarly by substituting the appropriate substituted pyridine diester for dimethyl 6-propylpyridine-2,3-dicarboxylate.

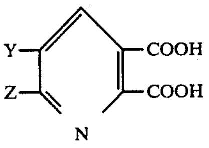

| Y | Z | mp °C. |
|---|---|---|
| H | i-$C_3H_7$ | 121.5-124° |
| H | 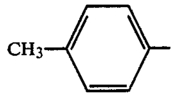 | 243-253° |
| H | 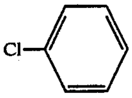 | >245° |
| H | $C_2H_5$ | 155.5-157° |
| H | 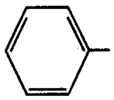 | 162-164° |
| $CH_3$ | $CH_3$ | 230-232° |
| | $-(CH_2)_3-$ | 180-181° |
| | $-(CH_2)_4-$ | 174 (decomposed) |

EXAMPLE 75

Preparation of 6-trifluoromethylpyridine-2,3-dicarboxylic acid

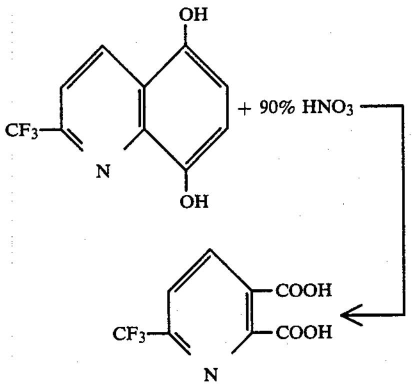

To a stirred 90% nitric acid solution (50 ml) at 5° C. is added 4.0 g of the quinoline [J. Med. Chem., 16, 134 (1973)]. The mixture is then stirred at room temperature for 0.5 hour followed by warming slowly to 100° C. After 15 minutes at 100° C., the mixture is cooled and poured into 100 ml ice water. The mixture is concentrated to one-half the volume, extracted twice with methylene chloride and the aqueous phase then concentrated in vacuo. The residue oil is crystallized to give the product, 6-trifluoromethylpyridine-2,3-dicarboxylic acid, mp 153°-157° C. (decomposed).

EXAMPLE 76

Preparation of 6-phenylpyridine-2,3-dicarboxylic acid anhydride

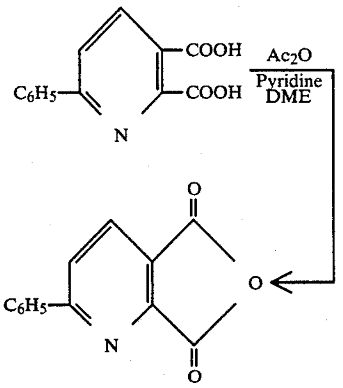

To a solution of 5.56 g (22.9 mmol) of 6-phenylpyridine-2,3-dicarboxylic acid and 7 ml (121.8 mmol) of acetic anhydride in 25 ml of dimethoxyethane (DME) is added 3.7 ml (45.7 mmol) of pyridine. A small exotherm ensues, and the anhydride begins to precipitate. After one hour, the reaction mixture is diluted with ether and hexane to the cloud point, chilled in an ice bath, and filtered. The solid is washed with ether to give 4.73 g of the desired anhydride as a white solid, mp 187°-192° C.

Using essentially the same procedure as described above but substituting the appropriate pyridine-2,3-dicarboxylic acid for 6-phenylpyridine-2,3-dicarboxylic acid, the following anhydrides are prepared. Many of these are used without full characterization since they are sensitive to atmospheric moisture.

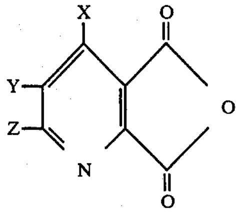

| X | Y | Z | mp °C. |
|---|---|---|---|
| H | H | Cl— | Solid |
| H | H | $CH_3$ | Solid |
| H | H | $C_2H_5$ | 65-67° |
| H | H | $C_3H_7$ | Oil |
| H | H | i-$C_3H_7$ | Oil |
| H | H | $CF_3$ | Oil |
| H | H | $CH_3$ | 106-108.5° |
| H | $-(CH_2)_3-$ | | Semi-solid |
| H | $CH_3$ | $CH_3$ | Semi-solid |
| H | $-(CH_2)_4-$ | | Oil |

EXAMPLE 77

Resolution of 2-amino-2,3-dimethylbutyronitrile

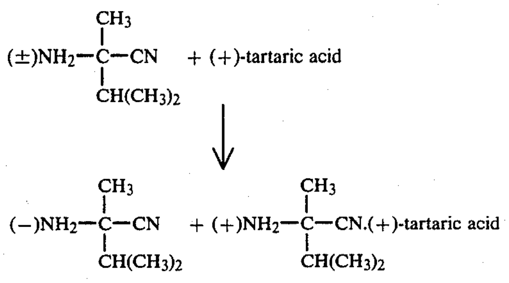

(A) (B)

To an ice-cold solution of 80 g (+)-tartaric acid in 200 ml water is added 56 g of (±)-2-amino-2,3-dimethylbutyronitrile. During the addition, the mixture is kept cold. The precipitate is collected by filtration, washed with a small amount of ice-cold water and dried to give 65.25 g of the tartrate salt (B).

The filtrate from (B) is treated with 56 ml concentrated ammonia and extracted three times with ether. The combined extracts are washed with brine, dried and concentrated to give 24 g (−)-2-amino-2,3-dimethylbutyronitrile (A) with $[\alpha]_D^{25}=-4.49°$ (c=0.0376 g/ml THF).

The (−)-aminonitrile is converted again to the salt with 39 g (−)-tartaric acid in 54 ml water, the salt collected, and the aminonitrile liberated from the salt with 26 ml concentrated ammonium hydroxide as described above. This process gives 19.3 g of (−)-2-amino-2,3-dimethylbutyronitrile with $[\alpha]_D^{25}=-5.89°$ (c=0.0353 g/ml THF).

Two further cycles of salt preparation and liberation of the aminonitrile with ammonia give 11.8 g of (−)-2-amino-2,3-dimethylbutyronitrile with $[\alpha]_D^{25}=-7.31°$ (c=0.0368 g/ml THF).

When salt derived from (+)-tartaric acid and (+)-2-amino-2,3-dimethylbutyronitrile obtained as described for (B) above is put through the same sequence of liberation of aminonitrile, salt formation with (+)-tartaric acid two times, the (+)-2-amino-2,3-dimethylbutyronitrile obtained has $[\alpha]_D^{25}=+6.93°$ (c=0.085 g/ml THF).

This process is disclosed in the application of Peter John Wepplo and William Henry Gastrock, Ser. No. 381,828, filed concurrently herewith and incorporated herein by reference thereto.

EXAMPLE 78

Preparation of 2-amino-2,3-dimethylbutyramide

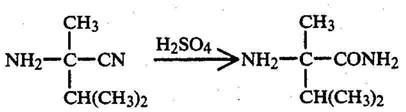

Concentrated sulfuric acid (29.7 ml) is cooled with stirring in an ice-acetone cooling bath. To the acid is added 11.8 g (−)-2-amino-2,3-dimethylbutyronitrile with $[\alpha]_D^{25}=-7.31°$ (C=0.0368 g/ml THF) at such a rate that the temperature does not go above 25° C. After the addition, the temperature of the reaction mixture is slowly raised to 100° C. and held at that temperature for one hour. After cooling the mixture in an ice-acetone bath, 85 ml concentrated ammonia is added at such a rate that the temperature does not exceed 75° C. The mixture is extracted five times with methylene chloride, the combined extracts dried and concentrated. This gives 11.95 g of white solid, mp 79°-81° C. and $[\alpha]_D^{25}=+57.43°$ (c=0.0213 g/ml THF). This solid is recrystallized from methylene chloride-hexane to give 11.2 g of (+)-2-amino-2,3-dimethylbutyramide, mp 81°-82° C. $[\alpha]_D^{25}=+59.38°$ (c=0.0162 g/ml THF).

In a similar way, hydrolysis of the (+)-2-amino-2,3-dimethylbutyronitrile with sulfuric acid yields the (−)-2-amino-2,3-dimethylbutyramide, mp 81°-82° C., $[\alpha]_D^{25}=-57.14°$ (c=0.0654 g/ml THF).

In a similar way, hydrolysis of the (±)-2-amino-2,3-dimethylbutyronitrile with sulfuric acid yields (±)-2-amino-2,3-dimethylbutyramide, mp 74.5°-76° C.

EXAMPLE 79

Preparation of 2-amino-2,3-dimethylthiobutyramide

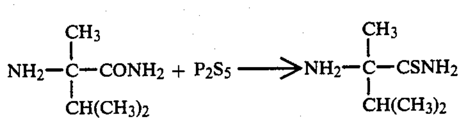

A stirred mixture containing 39 g of 2-amino-2,3-dimethylbutyramide and 73.3 g phosphorus pentasulfide in 1 L dry dioxane is heated at reflux for four hours. After stirring at room temperature for 72 hours, the mixture is again heated at reflux for two hours. The mixture is cooled; the mixture concentrated, and the residue distributed between water and methylene chloride. The aqueous phase is separated; the pH adjusted to 8 with concentrated ammonium hydroxide and extracted three times with methylene chloride. The organic phases were combined, dried and concentrated to give 22.47 g product mp 78°-85° C. Recrystallization of this material first from ethyl acetate and then methylene chloride-pentane gives analytically pure 2-amino-2,3-dimethylthiobutyramide with mp 98°-100° C.

EXAMPLE 80

Preparation of 6-isopropyl-2-(5-isopropyl-5-methyl-4-oxo-2-imidazolin-2-yl)nicotinic acid

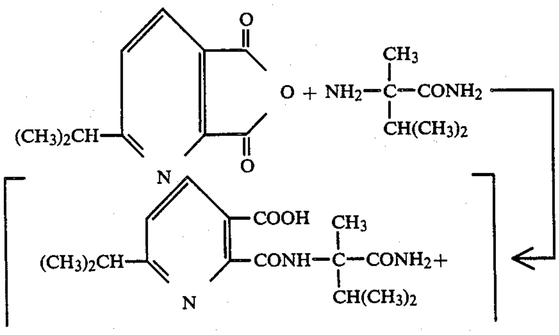

-continued

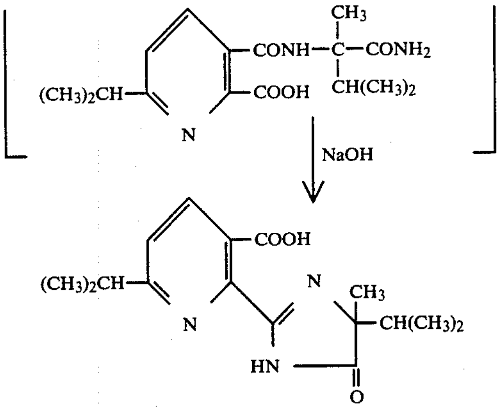

To a stirred solution of the anhydride (15.1 g) in 125 ml THF under nitrogen is added 11.4 g of 2-amino-2,3-dimethylbutyramide. The mixture is stirred overnight. The solvent is removed in vacuo, and the resulting oil (consisting of a mixture of the isomeric pyridine monoacid-monoamide products) dissolved in 66 ml of 6N NaOH. This solution is heated at 70° C. under nitrogen for three and one-half hours, then cooled and the pH of the solution adjusted to 9 with 6N $H_2SO_4$. The mixture is extracted twice with ether, and the organic extracts discarded. The pH of the aqueous phase is adjusted to 3 with 6N $H_2SO_4$. The resulting precipitate is removed by filtration, washed with water and dried to give 13.25 g of desired product. A sample is recrystallized from methylene chloride-hexane followed by ether-hexane to give an analytically pure sample of 6-isopropyl-2-(5-isopropyl-5-methyl-4-oxo-2-imidazolin-2-yl)nicotinic acid, mp 131°-133.5° C.

By using essentially the same procedure but substituting the appropriate substituted pyridine-2,3-dicarboxylic acid anhydride for 6-isopropylpyridine-2,3-dicarboxylic acid anhydride and also substituting, if necessary, the optically active 2-amino-2,3-dimethylbutyramide or the 2-amino-2,3-dimethylthiobutyramide for 2-amino-2,3-dimethylbutyramide, the following nicotinic acids were prepared.

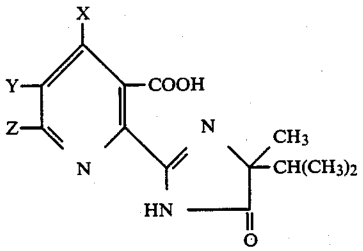

| X | Y | Z | mp° C. |
|---|---|---|---|
| H | H | $CH_3$ | 145-146.5 |
| H | H | $CF_3$ | 133-142 |
| H | H | H | 128-131 $[\alpha]_D^{25}=+18.37°$ (c = 0.0902 g/ml THF) |
| H | H | $C_3H_7$ | 148.5-150.5 |
| H | H | 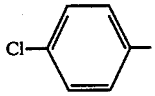 | 247-249 |

-continued

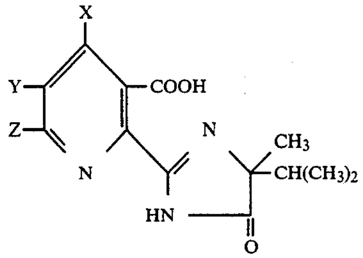

| X | Y | Z | mp° C. |
|---|---|---|---|
| H | H | 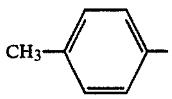 | 215.5–218.5 |
| H | H | 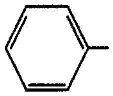 | 252–254 |
| H | H | $C_2H_5$ | 118–122 |
| H | $CH_3$ | $CH_3$ | 172–180 |
| H | $-(CH_2)_3-$ | | 160–164 |
| H | H | H | 170–172.5 |
| H | $-(CH_2)_4-$ | | 162–165 |

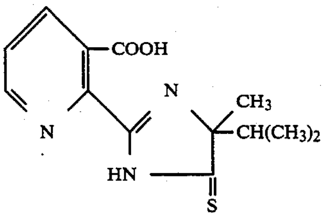

-continued

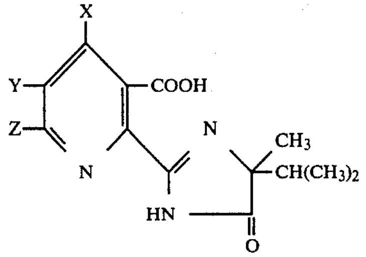

| X | Y | Z | mp° C. |
|---|---|---|---|
| | | mp 182–184° | |

EXAMPLE 81

Preparation of 2-(5-isopropyl-5-methyl-4-oxo-2-imidazolin-2-yl)nicotinic acid

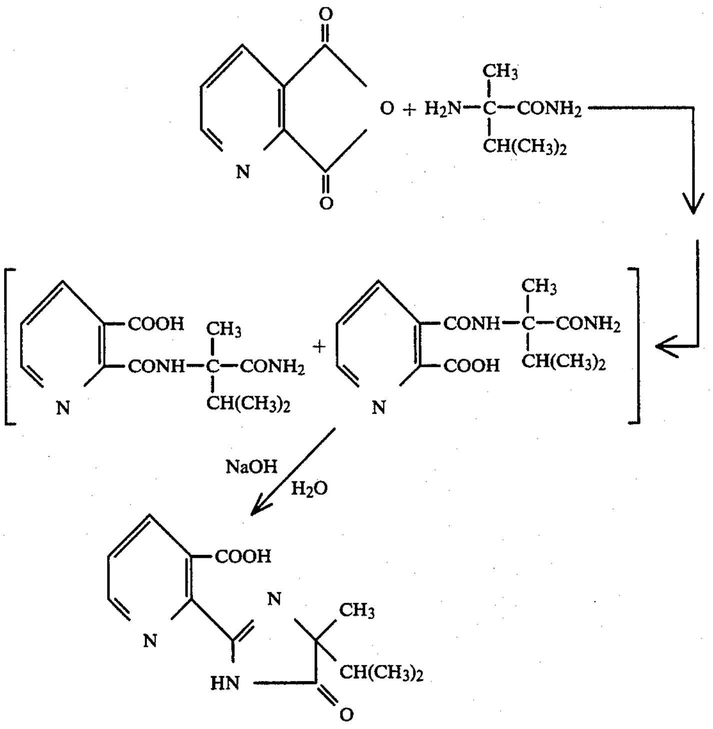

To a stirred suspension of 2,3-pyridinedicarboxylic anhydride (30 g) in 150 ml of acetonitrile is added a solution of 2-amino-2,3-dimethylbutyramide (28 g) in 140 ml of acetonitrile at 25°–30° C. The mixture is stirred for two hours. The solvent is removed at 50° C. and reduced pressure. The residual gum is dissolved in 230 ml of 2.6N sodium hydroxide and heated to 80° C. for one and one-half hours.

The mixture is cooled to 25° C. and acidified to a pH of 3 with 65 ml of 37% hydrochloric acid. The resulting solution is extracted with two 200 ml portions of methylene chloride. The extracts are concentrated to a residue of 33 g of the desired product, mp 160°–165° C.

After standing overnight, the aqueous layer deposits 3.8 g of the picolinic acid isomer, mp 155°–157° C. (dec.).

EXAMPLE 82

Preparation of 2-(4-oxo-1,3-diazaspiro[4.5]dec-2-en-2-yl)nicotinic acid

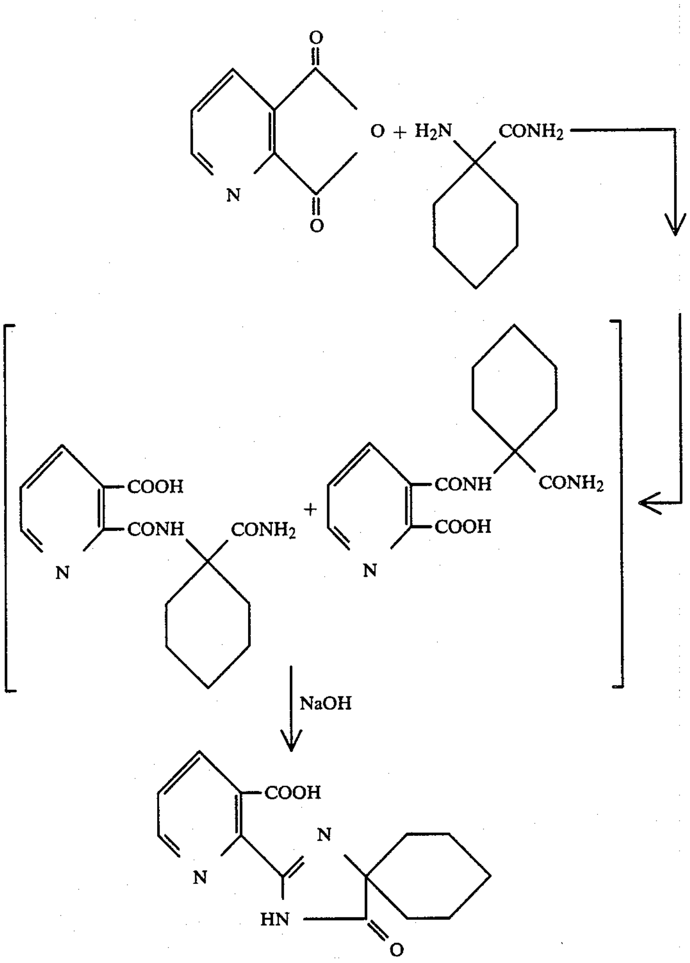

To a stirred solution of 7.1 g of 1-aminocyclohexanecarboxamide in 60 ml of methylene chloride was added 7.5 g of 2,3-pyridinedicarboxylic anhydride. The mixture becomes warm and forms a solution. Stirring is continued for two hours as colorless solid precipitates. The mixture of monoacid/diamides is collected, 12.0 g, mp 168°-178° C. (dec.).

This material is dissolved in 45 ml of 2.7N sodium hydroxide and heated for one hour at 80°-85° C. It is then cooled and acidified with 10.3 ml of 37% hydrochloric acid and extracted with two 25 ml portions of methylene chloride. The extracts are concentrated to give 7.5 g of the desired product. Recrystallization from aqueous methanol gives a product with a mp of 186°-189° C.

EXAMPLE 83

Preparation of 5-ethoxy-2-methylpyridine

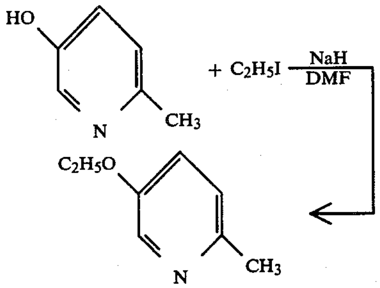

To a stirred suspension of 16.6 g sodium hydride in 500 ml dry dimethylformamide (DMF) under nitrogen at 0° C. is added 90 g 5-hydroxy-2-methylpyridine at such a rate that the temperature remains between 0°-5° C. When gas evolution ceases, 73.8 ml ethyl iodide in 100 ml DMF is added dropwise. After stirring at room temperature overnight, the mixture is diluted with water and extracted with ether. The ether extracts are washed with brine, dried and concentrated. This oil is distilled to give 62.5 g of 5-ethoxy-2-methylpyridine, bp 89°-91° C. at 12 mm.

Using the above procedure but substituting isopropyl iodide for ethyl iodide there is obtained 5-isopropoxy-2-methylpyridine, bp 95°-100° C./0.15 mm.

EXAMPLE 84

Preparation of 2-(5-ethoxy-2-pyridyl)-5-isopropyl-5-methyl-2-imidazolin-4-one

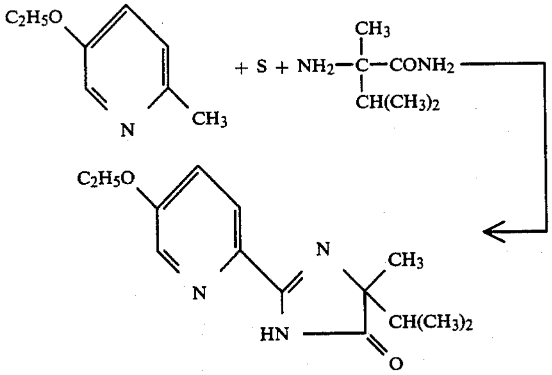

A mixture of 60.5 g 5-ethoxy-2-picoline, 38.3 g 2-amino-2,3-dimethylbutyramide and 28.5 g sulfur is heated with stirring under nitrogen. At 160° C. a liquid boils which is condensed and returned to the flask through a tube packed molecular sieves to absorb water formed in the reaction. The temperature of the mixture slowly rises to 185° C. and is held there for 2.5 hours. The mixture is cooled, dissolved in 500 ml ethyl acetate and filtered. The filtrate is extracted with 6×100 ml portions of 2N hydrochloric acid. The aqueous phases are combined, the pH adjusted to 7 with 50% aqueous sodium hydroxide. A solid precipitate forms which is collected. The mother liquor is extracted with methylene chloride, the extracts dried and concentrated. The residue is triturated with ether hexane to give a crystalline solid which is removed and thoroughly washed with hexane and dried. Both solids are combined to give 23.7 g product. Two recrystallizations of a sample from methylene chloride-hexane gave analytically pure 2-(5-ethoxy-2-pyridyl)-5-isopropyl-5-methyl-2-imidazolin-4-one, mp 143°-145° C.

Using essentially the same procedure described above but substituting the appropriate substituted α-picoline or quinaldine for 5-ethoxy-2-picoline. The following imidazolinones are prepared:

| Substituent | mp° C. |
|---|---|
| 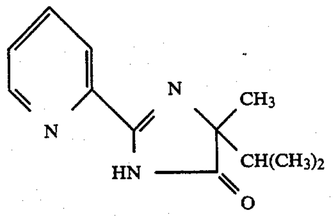 | |
| none | 90-93 |
| 5-$C_2H_5$ | 67-71 |
| 5-$OCH_3$ | 166-167.5 |
| 5-$C_6H_5$ | 150-151.6 |
| 3-$CH_3$ | 93-96 |
| 3-$COOC_2H_5$ | 72-75 |

-continued

| Substituent | mp° C. |
|---|---|
| 5-$OCH(CH_3)_2$ | 126-128 |
| 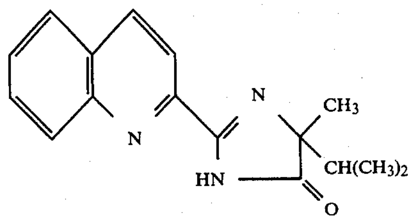 | |
| none | 143-144 |
| 3-$COOC_2H_5$ | 146-147.5 |

EXAMPLE 85

Preparation of dimethyl 3-phenylaminobut-2-ene-dioate

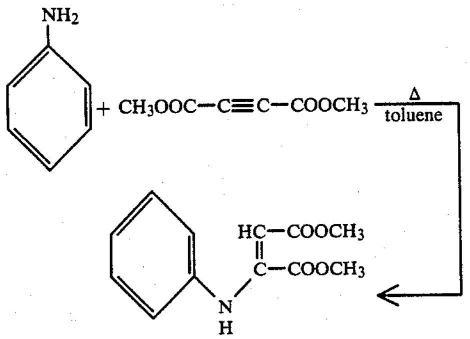

To a stirred solution of dimethylacetylenedicarboxylate (DMAD, 0.10 mol) in 50 ml of ethylenedichloride (EDC), is slowly added a solution of aniline (0.10 mole) in 15 ml of EDC. The temperature of the reaction mixture is maintained below 30° C. and stirring is continued for about one hour until the reaction is essentially complete. The toluene is then removed under vacuum to afford the dimethyl 3-phenylaminobut-2-ene-dioate.

EXAMPLE 86

Preparation of diethyl 3-phenylaminobut-2-ene-dioate

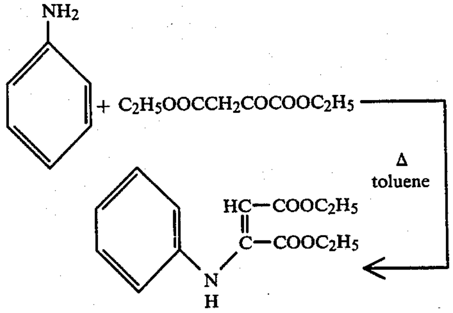

Aniline (0.217 mol) and diethyl oxalacetate (0.217 mol) are mixed in toluene (500 ml) and heated to reflux, i.e., about 100° C., under a water separator for approximately one hour. The toluene is then removed under vacuum to afford the desired product, i.e., diethyl 3-phenylaminobut-2-ene-dioate.

Following the above procedure, but utilizing a substituted aniline for aniline and/or dimethyl oxalacetate for diethyl oxalacetate, yields the (anilino) maleic acid esters illustrated below.

Preparation and properties of substituted-phenylaminobut-2-ene-dioates.

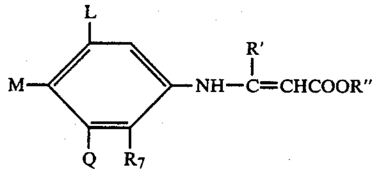

| L | M | Q | R7 | R' | R" | mp °C. |
|---|---|---|---|---|---|---|
| H | H | H | H | $CO_2C_2H_5$ | $C_2H_5$ | oil |
| H | $NO_2$ | H | H | $CO_2CH_3$ | $CH_3$ | 119.5-120.5 |
| H | H | H | $OCH_3$ | $CO_2CH_3$ | $CH_3$ | 71-73 |
| H | CN | H | H | $CO_2CH_3$ | $CH_3$ | 107-109 |
| H | $SCH_3$ | H | H | $CO_2CH_3$ | $CH_3$ | 50-54 |
| H | $C_6H_5$ | H | H | $CO_2CH_3$ | $CH_3$ | 60-63 |
| H | $CF_3$ | H | H | $CO_2CH_3$ | $CH_3$ | oil |
| H | H | $CH_3$ | $CH_3$ | $CO_2CH_3$ | $CH_3$ | 127-129.5 |
| H | $OCH_3$ | H | H | $CO_2CH_3$ | $CH_3$ | — |
| H | $CH_3$ | $CH_3$ | H | $CO_2CH_3$ | $CH_3$ | — |
| $OCH_3$ | H | H | $OCH_3$ | $CO_2C_2H_5$ | $C_2H_5$ | oil |
| H | $C_2H_5$ | H | H | $CO_2CH_3$ | $CH_3$ | oil |
| H | Br | H | H | $CO_2CH_3$ | $CH_3$ | 83-86 |
| H | H | $OC_2H_5$ | H | $CO_2CH_3$ | $CH_3$ | — |
| H | $C_4H_9$ | H | H | $CO_2CH_3$ | $CH_3$ | oil |

EXAMPLE 87

Preparation of dimethyl 2,3-quinolinedicarboxylate

To a solution of dimethylformamide (DMF, 0.1 mol) in ethylenedichloride (EDC, 100 ml), cooled in an ice bath, is added dropwise with stirring phosphorous oxychloride ($POCl_3$, 0.10 mol). The resulting solution is stirred for one and one-half hours at room temperature and then cooled in an ice bath. To the cooled solution is then added, in small increments, a solution of dimethyl 3-phenylaminobut-2-ene-dioate in ethylene dichloride. The resulting mixture is thereafter heated to reflux for three hours, cooled, and washed with half saturated brine. The organic phase is separated from the aqueous phase and dried. The solvent is removed under vacuum, and the residue recrystallized from methanol to afford 18.2 g (0.074 mol) of dimethyl 2,3-quinolinedicarboxylate, mp 105°-106.5° C.

Using the above procedure and the appropriate 3-phenylaminobut-2-ene-dioate or 3-phenylaminobut-2-eneoate yields the dialkyl 2,3-quinolinedicarboxylates or 2-methyl-3-quinolinecarboxylates reported below.

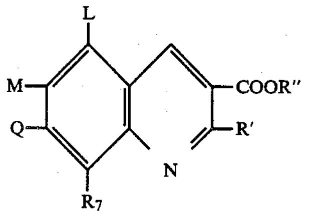

| L | M | Q | R7 | R' | R" | mp° C. |
|---|---|---|---|---|---|---|
| H | H | H | H | $CH_3$ | $C_2H_5$ | 65-69 |
| H | H | H | H | $CO_2CH_3$ | $C_2H_5$ | 53-54.5 |
| H | $NO_2$ | H | H | $CO_2CH_3$ | $CH_3$ | 174-174.5 |
| H | H | H | $OCH_3$ | $CO_2CH_3$ | $CH_3$ | 95-96 |
| H | CN | H | H | $CO_2CH_3$ | $CH_3$ | 185.5-187.5 |

-continued

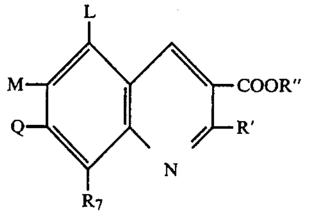

| L | M | Q | R7 | R' | R" | mp° C. |
|---|---|---|---|---|---|---|
| H | $SCH_3$ | H | H | $CO_2CH_3$ | $CH_3$ | 136-138 |
| H | $C_6H_5$ | H | H | $CO_2CH_3$ | $CH_3$ | 300 |
| H | $CF_3$ | H | H | $CO_2CH_3$ | $CH_3$ | 123.5-125 |
| H | H | $CH_3$ | $CH_3$ | $CO_2CH_3$ | $CH_3$ | 150.5-152 |
| H | $OCH_3$ | H | H | $CO_2CH_3$ | $CH_3$ | 129-131 |
| H | $CH_3$ | $CH_3$ | H | $CO_2CH_3$ | $CH_3$ | 116-118 |
| $OCH_3$ | H | H | $OCH_3$ | $CO_2C_2H_5$ | $C_2H_5$ | 82-85 |
| H | $OC_6H_5$ | H | H | $CO_2CH_3$ | $CH_3$ | 138-140 |
| H | $C_2H_5$ | H | H | $CO_2CH_3$ | $CH_3$ | 60-61.5 |
| H | $C_4H_9$ | H | H | $CO_2CH_3$ | $CH_3$ | oil |
| H | Br | H | H | $CO_2CH_3$ | $CH_3$ | 157-158 |
| H | H | $OC_2H_5$ | H | $CO_2CH_3$ | $CH_3$ | — |

EXAMPLE 88

Preparation of 2,3-quinolinedicarboxylic acid

To a solution of diethyl 2,3-quinolinedicarboxylate (0.162 mol) in ethanol (150 ml) is added a solution of sodium hydroxide (0.50 mol) in water (400 ml). The mixture is heated at reflux for 5 hours, and the ethanol then removed by distillation at atmospheric pressure. The solution is cooled in an ice bath, diluted with water (100 ml), and acidified with concentrated hydrochloric acid, added in small increments. The precipitate is filtered, washed with water, and air dried to afford the desired 2,3-quinolinedicarboxylic acid as the trihydrate; mp 271°-277° C.

Utilizing the above procedure, but substituting the appropriate substituted or unsubstituted dialkyl 2,3-quinolinedicarboxylate, yields the substituted or unsubstituted 2,3-quinolinedicarboxylic acids reported below.

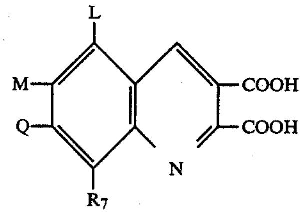

| L | M | Q | R7 | mp° C. |
|---|---|---|---|---|
| H | $NO_2$ | H | H | 295-297(dec) |
| H | H | H | $OCH_3$ | 270-275 |
| H | $CF_3$ | H | H | 165-167 |
| H | CN | H | H | >300 |
| H | $C_6H_5$ | H | H | >30 |
| H | $SCH_3$ | H | H | >305 |
| H | H | $CH_3$ | $CH_3$ | 148-150 |
| H | $OCH_3$ | H | H | |
| $OCH_3$ | H | H | $OCH_3$ | 274-276 |
| H | $C_2H_5$ | H | H | 190-195 |
| H | $C_4H_9$—n | H | H | |
| H | $OC_6H_5$ | H | H | |

EXAMPLE 89

Preparation of 3-methyl-2-quinolinecarboxylic acid

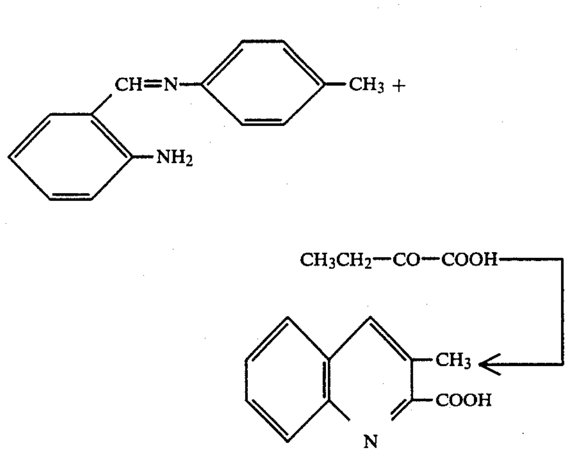

To 100 ml of absolute ethanol is added 4.0 g (0.02 mol) of N-o-aminobenzylidine-p-toluidine, 10 drops of piperidine and 3.89 g (0.04 mol) of 2-ketobutyric acid. The mixture is stirred and heated to reflux temperature for three hours, then cooled and concentrated in vacuo. The residue is taken up in 10% aqueous sodium carbonate solution and washed with an ether/petroleum ether (2:1) solution. Acidification of the aqueous layer followed by concentration in vacuo to 15 ml gives an off-white solid having a melting point of 141°-142° C.

EXAMPLE 90

Preparation of 2,3-quinolinedicarboxylic acid

Three grams of 2-methylquinoline-3-carboxylic acid (0.012 mol of 3.5 hydrate) is dissolved in 100 ml 15% sodium hydroxide solution and an additional 100 ml $H_2O$ is added. The mixture becomes homogenous. At room temperature is added, all at once, 12.0 g nickel peroxide, (0.044 mol, 3.6 eq, 20% excess) and the mixture is stirred magnetically for 12 hours. The insolubles are removed by vacuum filtration and washed with water. The filtrate is acidified to pH of 2 and a solid fluffy precipitate forms. It is filtered and dried to give 2.48 g of quinoline-2,3-dicarboxylic acid which is hydrated with 1.3 moles $H_2O$/mole compound as determined by NMR. Additional product is isolated from the aqueous filtrate by concentration and filtration. This brings the total actual product yield to 2.88 g of product having a melting point of 271°-277° C. Product yield is better than 99% of theory.

Following the above procedure but substituting the appropriate substituted 2-methylquinoline-3-carboxylic acid for 2-methylquinoline-3-carboxylic acid yields the following substituted 2,3-quinolinedicarboxylic acids.

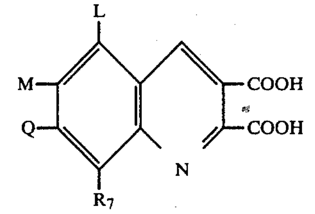

| L | M | Q | $R_7$ | mp °C. |
|---|---|---|---|---|
| H | $NO_2$ | H | H | 295-297 (dec.) |
| H | H | H | $OCH_3$ | 270 275 |
| H | $CF_3$ | H | H | 165-167 |
| H | CN | H | H | 300 |
| H | $C_6H_5$ | H | H | 300 |
| H | H | $CH_3$ | $CH_3$ | 148-150 |
| H | $OCH_3$ | H | H | — |
| $OCH_3$ | H | H | $OCH_3$ | 274-276 |
| H | $C_2H_5$ | H | H | 190-195 |
| H | $C_4H_9$—n | H | H | — |
| H | $OC_6H_5$ | H | H | — |
| H | $OCHF_2$ | H | H | 226 |
| H | H | $OC_2H_5$ | H | 197-198 (dec.) |
| H | Br | H | H | 254-255 |
| H | Cl | H | H | 251-253 |

EXAMPLE 91

Preparation of 2,3-quinolinedicarboxylic acid

Following the procedure of Example 90 but substituting 3-methylquinoline-2-carboxylic acid for 2-methylquinoline-3-carboxylic acid affords the title compound, mp 271°-277° C., in 70% yield.

EXAMPLE 92

Preparation of 2,3-quinolinedicarboxylic acid

2-Methylquinoline-3-carboxylic acid (1.25 g, 0.005 mol) is dissolved in a mixture of 40 ml of water and 20 ml of 15% sodium hydroxide. To this mixture is added nickel (II) chloride (hexahydrate) (0.23 g, 0.001 mol). The resulting mixture is stirred while 20 ml of 5.25% sodium hypochlorite solution, in 30 ml $H_2O$, is added at the rate of 5-7 drops per minute. After stirring for 14 hours, the solids are removed by filtration, and the filtrate acidified to $pH_2$ with HCl and concentrated to a volume of 25 ml in vacuo. A yellow solid separates which weighs 0.70 g and is recovered starting material. Further concentration of the aqueous phase gives 0.37 g of the 2,3-quinolinedicarboxylic acid, mp 271°-277° C.

EXAMPLE 93

Preparation of 2,3-quinolinedicarboxylic anhydride

A mixture of 2,3-quinolinedicarboxylic acid-trihydrate (0.141 mol) in acetic anhydride (125 ml) is heated at 85° C. for ½ hour and then at 100° C. for 1 hour. The reaction mixture is then cooled to room temperature, filtered and the solids washed with ethyl ether to afford the desired 2,3-quinolinedicarboxylic anhydride, mp 225°-228° C.

Utilizing the above procedure but substituting the appropriately substituted 2,3-quinolinedicarboxylic acid for 2,3-quinolinedicarboxylic acid-trihydrate, yields the following substituted 2,3-quinolinedicarboxylic anhydrides.

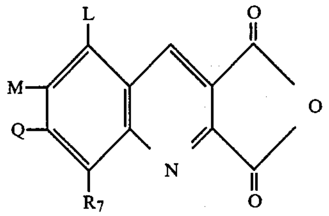

| L | M | Q | $R_7$ | mp °C. |
|---|---|---|---|---|
| H | $OC_6H_5$ | H | H | 187–188 |
| H | $NO_2$ | H | H | 225–228 (dec) |
| H | $C_6H_5$ | H | H | 258.5–261 |
| H | H | $CH_3$ | $CH_3$ | 270–272 |
| H | $OCH_3$ | H | H | 208–210 |
| H | $CH_3$ | $CH_3$ | H | |
| H | $SCH_3$ | H | H | 247–251 |
| H | CN | H | H | 190–192 |
| H | H | H | $OCH_3$ | |
| H | $C_2H_5$ | H | H | |
| H | $C_4H_9$—n | H | H | ~160–210 |
| $OCH_3$ | H | H | H | 266–267 |

EXAMPLE 94

Preparation of quinoline-2,3-dicarboxylic acid anhydride

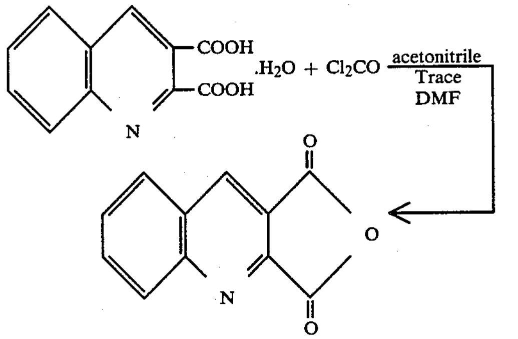

Procedure

To 4.7 g (0.02 moles) of quinoline-2,3-dicarboxylic acid monohydrate in 75 ml of acetonitrile is added 0.5 ml of dimethylformamide. 17.4 g (0.022 moles) of a 12.5% solution of phosgene in toluene is then added, dropwise, keeping the temperature at 20° C. The mixture is stirred at room temperature for two-three hours. The mixture is stripped to yield 4.0 g (theoretical yield) of a cream-colored solid having a mp: 218°–221° C. An infrared spectrum confirms that the desired anhydride has been obtained. The sample contains no residual starting dicarboxylic acid.

This process is described in the application for United States Letters Patent of Thomas Walter Drabb, Jr., Ser. No. 381,816, now U.S. Pat. No. 4,439,607 filed concurrently herewith and incorporated herein by reference thereto. By using essentially this procedure, the following anhydrides have been prepared.

| Structure | Yield | Comments |
|---|---|---|
| 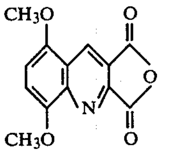 | 68%* | Could not be prepared by heating in acetic anhydride; diacid decarboxylated. |
| 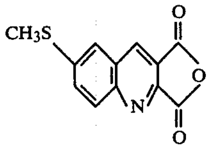 | 68%* | Recovered starting material when acetic anhydride was used instead of phosgene. |
| 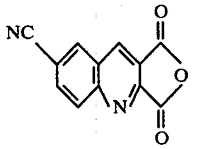 | * | Recovered starting material when acetic anhydride was used instead of phosgene. |
| 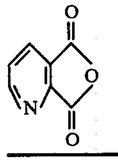 | 98.4%* | mp: 135–137° C. Toluene used as a solvent. |

*Obtained by filtration of reaction mixture instead of concentration.

EXAMPLE 95

Preparation of 2-[(1-carbamoyl-1,2-dimethylpropyl)carbamoyl]-3-quinolinecarboxylic acid A solution of 2,3-quinolinedicarboxylic anhydride (0.037 mol) in tetrahydrofuran (THF, 250 ml) is stirred at 5° C. under a drying tube, and a solution of 2-amino-2,3-dimethylbutyramide (0.037 mol) in THF (50 ml) added thereto, in small increments, over a 15 minute period. The reaction mixture is allowed to warm slowly to room temperature for an extended period of time, i.e. about 17 hours. The solvent is evaporated in vacuo to afford a gummy residue, which is triturated with hot ethyl acetate (400 ml) and then filtered to afford the desired 2-[(1-carbamoyl-1,2-dimethylpropyl)carbamoyl]-3-quinolinecarboxylic acid, mp 172.5°–173.5° C.

Utilizing the above procedure but substituting the appropriately substituted 2,3-quinolinedicarboxylic anhydride for 2,3-quinolinedicarboxylic anhydride yields the following 2-[(1-carbamoyl-1,2-dimethylpropyl)carbamoyl]-1,2-dimethylpropyl)carbamoyl]-3-quinolinecarboxylic acids.

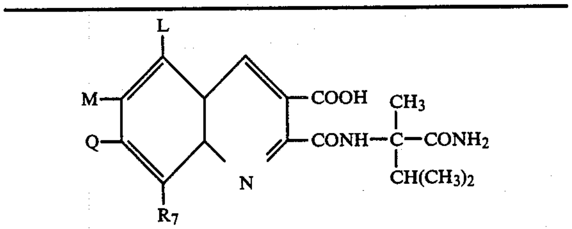

| L | M | Q | $R_7$ | mp °C. |
|---|---|---|---|---|
| H | $OC_5H_5$ | H | H | 189–190 |
| H | $NO_2$ | H | H | 225–227 (dec) |

-continued

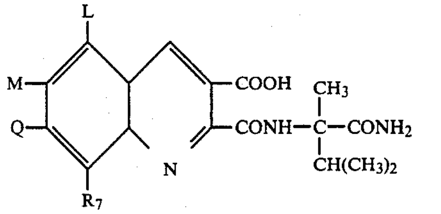

| L | M | Q | $R_7$ | mp °C. |
|---|---|---|---|---|
| H | H | H | $OCH_3$ | foam |
| H | $CF_3$ | H | H | 222-224 |
| H | CN | H | H | |
| H | $SCH_3$ | H | H | |
| H | $C_6H_5$ | H | H | 189.5-192 |
| H | H | $CH_3$ | $CH_3$ | 246-250 |
| H | $OCH_3$ | H | H | |
| H | $CH_3$ | $CH_3$ | H | |
| H | $C_2H_5$ | H | H | |
| H | $C_4H_9$ | H | H | |
| $OCH_3$ | H | H | $OCH_3$ | 209-209.5 |

EXAMPLE 96

Preparation of 2-(5-isopropyl-5-methyl-4-oxo-2-imidazolin-2-yl)-3-quinolinecarboxylic acid A solution of 2-[(1-carbamoyl-1,2-dimethylpropyl)-carbamoyl]-3-quinolinecarboxylic acid (0.152 mol), in water (50 ml) containing sodium hydroxide (0.06 mol) is heated at 75° to 80° C. for 2 hours. The solution is cooled in an ice bath and acidified with concentrated hydrochloric acid, added in small increments. The resulting precipitate is filtered, washed with water, air dried, and recrystallized from acetone to afford the 2-(5-isopropyl-5-methyl-4-oxo-2-imidazolin-2-yl)-3-quinolinecarboxylic acid, mp 239°-243.5° C.

Utilizing the above procedure and substituting the appropriate 3-quinolinecarboxylic acid for 2-(1-carbamoyl-1,2-dimethylpropyl)carbamoyl]-3-quinolinecarboxylic acid yields the compounds illustrated below.

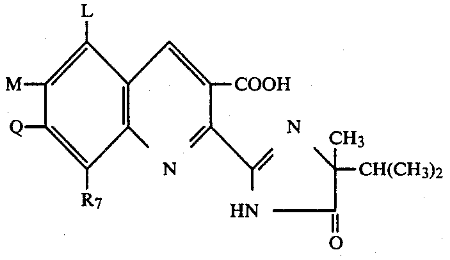

| L | M | Q | $R_7$ | mp °C. |
|---|---|---|---|---|
| H | $NO_2$ | H | H | 241.5-242 |
| H | $OC_6H_5$ | H | H | 223 |
| H | H | H | $OCH_3$ | 258.5-261 |
| H | $CF_3$ | H | H | 215-218 |
| H | $C_6H_5$ | H | H | 209.5-212 |
| H | $CH_3$ | $CH_3$ | H | 238-240 |
| $OCH_3$ | H | H | $OCH_3$ | 249-250 |
| H | $SCH_3$ | H | H | |
| H | $C_2H_5$ | H | H | |
| H | $C_4H_9$ | H | H | |
| H | H | $CH_3$ | $CH_3$ | |

EXAMPLE 97

Preparation of 2-(5-isopropyl-5-methyl-4-oxo-2-imidazolin-2-yl)-3-quinolinecarboxylic acid

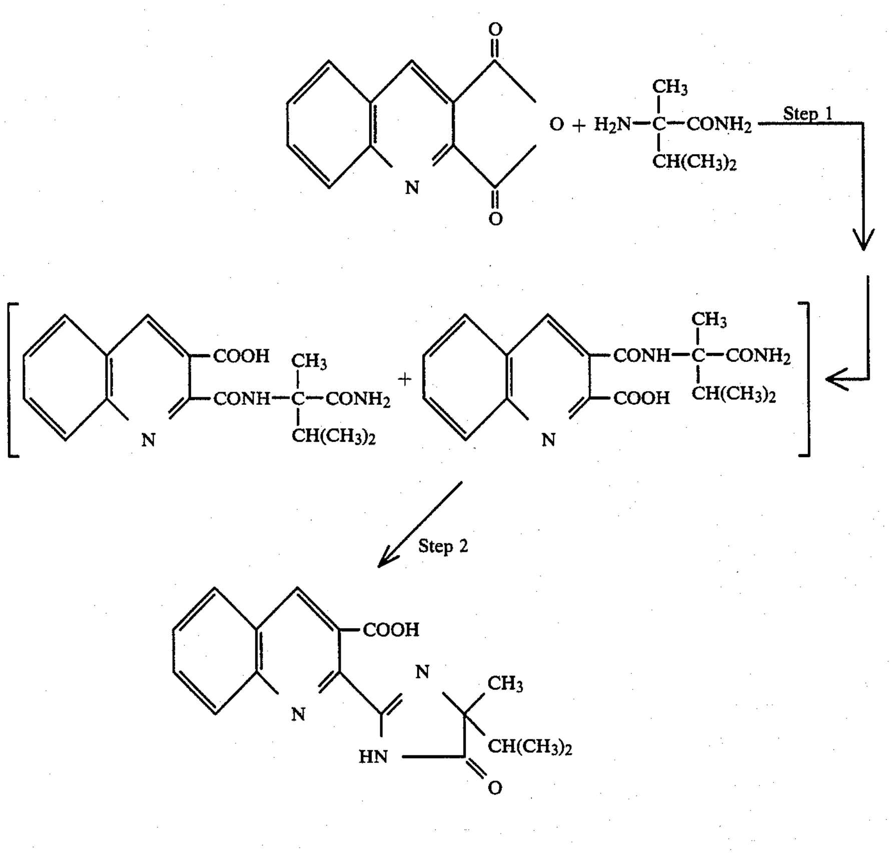

To a stirred solution of 2-amino-2,3-dimethylbutyramide (40 g) in 500 ml of acetonitrile is added 60 g of 2,3-quinolinedicarboxylic acid anhydride in portions during about 45 minutes. The mixture is heated to 50°-60° C. for two hours, cooled to room temparature and filtered to give 73.7 g of the mixture of carbamoyl quinolinecarboxylic acids.

This solid is dissolved in 435 ml of 1.5N sodium hydroxide and heated for two hours at 80°-85° C. The solution is then cooled and acidified with 57 ml of 37% hydrochloric acid. The desired product is removed by filtration and dried. Recrystallization from methanol gives 49 g 2-(5-isopropyl-5-methyl-4-oxo-2-imidazolin-2-yl)-3-quinolinecarboxylic acid, melting at 240°-242° C.

Following step 1 of the above procedure yields the following 2-carbamoyl-3-quinolinecarboxylic acids having the structure:

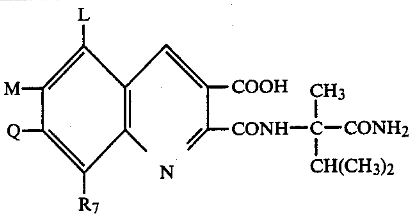

wherein L, M, Q and $R_7$ are as reported below.

| L | M | Q | $R_7$ | mp° C. |
|---|---|---|---|---|
| H | H | H | H | 172.5-173.5 |
| H | H | H | H | 183-185 $[\alpha_D] = -90.5°$ in $CH_2Cl_2$ |
| H | $OC_2H_5$ | H | H | — |
| H | $NO_2$ | H | H | 225-227 |
| H | H | H | $OCH_3$ | Foam |
| H | $CF_3$ | H | H | 222-224 |
| H | CN | H | H | — |
| H | $C_6H_5$ | H | H | 189.5-192 |
| H | H | $CH_3$ | $CH_3$ | 246-250 |
| H | $OCH_3$ | H | H | — |
| H | $CH_3$ | $CH_3$ | H | — |
| H | $C_2H_5$ | H | H | 198-199 |
| H | $C_4H_9$ | H | H | 163-164 |
| H | Br | H | H | — |
| $OCH_3$ | H | H | $OCH_3$ | 209-209.5 |
| H | $SCH_3$ | H | H | — |
| H | $OC_6H_5$ | H | H | 189-190 |

Following step 2 of the above procedure, i.e., the base catalyzed cyclication of a 2-carbamoyl-3-quinolinecarboxylic acid, yields the 2-(5-isopropyl-5-methyl-4-oxo-2-imidazolin-2-yl)-3-quinolinecarboxylic acids having the formula:

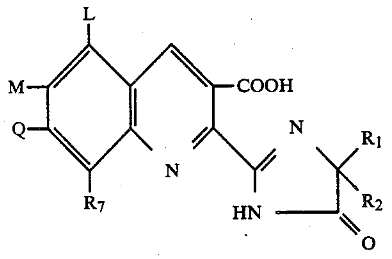

wherein L, M, Q and $R_7$ are as reported below.

| L | M | Q | $R_7$ | mp °C. |
|---|---|---|---|---|
| H | H | H | H | 241-244 |

-continued

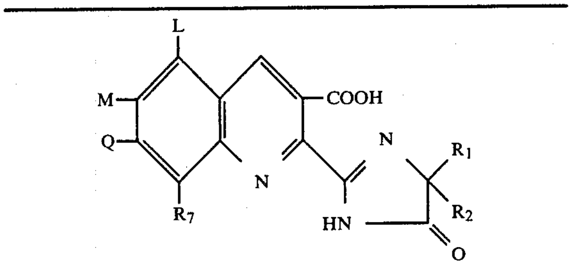

wherein L, M, Q and $R_7$ are as reported below.

| L | M | Q | $R_7$ | mp °C. |
|---|---|---|---|---|
| H | H | H | H | 228-236.5 $[\alpha]_D^{25} = +28.3°$ (c = 0.0105 g/ml $CH_2Cl_2$) |
| H | $OC_2H_5$ | H | H | 206-208 |
| H | $NO_2$ | H | H | 241.5-242 |
| H | H | H | $OCH_3$ | 258-261 |
| H | $CF_3$ | H | H | 215-218 |
| H | CN | H | H | — |
| H | $C_6H_5$ | H | H | 209.5-212 |
| H | H | $CH_3$ | $CH_3$ | 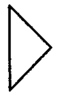 280 |
| H | $OCH_3$ | H | H | 203.5-205 |
| H | $CH_3$ | $CH_3$ | H | 238-240 |
| H | $C_2H_5$ | H | H | 179-180.5 |
| H | $C_4H_9$ | H | H | 149-150.5 |
| H | Br | H | H | 215-225 |
| $OCH_3$ | H | H | $OCH_3$ | 249-250 |
| H | $SCH_3$ | H | H | 264-265 |
| H | H | $OC_2H_5$ | H | — |
| H | $OC_6H_5$ | H | H | 223 |

EXAMPLE 98

Post-Emergence Herbicidal Evaluation of Test Compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.016 kg of 10 kg per hectare of active compound when applied for the plants through a spray nozzle operating at 40 psi for a predetermined time. After spraying, the plants are placed on greenhouse benches and are cared for in the usual manner, commensurate with conventional greenhouse practices. From 4 to 5 weeks after treatment, the seedling plants, are examined and rated according to the rating system provided below. The data obtained are recorded in Table XI below.

| Rating System | % Difference in Growth from the Check* |
|---|---|
| 0 - No effect | 0 |
| 1 - Possible effect | 1-10 |
| 2 - Slight effect | 11-25 |
| 3 - Moderate effect | 26-40 |
| 5 - Definite injury | 41-60 |

-continued

| Rating System | % Difference in Growth from the Check* |
|---|---|
| 6 - Herbicidal effect | 61–75 |
| 7 - Good Herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (*Echinochloa crusgalli*) |
| Green foxtail | (*Setaria viridis*) |
| Purple Nutsedge | (*Cyperus rotundus* L.) |
| Wild Oats | (*Avena Fatua*) |
| Quackgrass | (*Agropyron repens*) |
| Field Bindweed | (*Convolvulus arvensis* L.) |
| Cocklebur | (*Xanthium pensylvanicum*) |
| Morningglory | (*Ipomoea purpurea*) |
| Ragweed | (*Ambrosia artemisiifolia*) |
| Velvetleaf | (*Abutilon Theophrasti*) |
| Barley | (*Hordeum vulgare*) |
| Corn | (*Zea mays*) |
| Rice | (*Oryza Sativa*) |
| Soybean | (*Glycine max*) |
| Sunflower | (*Helianthus annus*) |
| Wheat | (*Triticum aestivum*) |

TABLE XI

POST-EMERGENCE TESTS - RATES IN KG/HA

| Compounds | RATE | BARNY ARDGR | GREEN FOX | P NUT SEDGE | WILD OATS | QUACK GRASS | FLD B INDWD | COCKL EBUR | XXX M RNGLY | RAGWE ED | VELVE TLEAF | S BAR LY LA | CORN FIELD | RICE, NATO | SOYBE AN WI | SUNFL R XXX | S WHE AT ER |
|---|---|---|---|---|---|---|---|---|---|---|---|---|---|---|---|---|---|
| Triethylammonium 2-(5-isopropyl-5-methyl-4-oxo-2-imidazolin-2-yl)-nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 0.0 | 9.0 | 9.0 | 9.0 | 9.0 | 9.0 | 9.0 | 9.0 | 9.0 | 9.0 | 9.0 | 9.0 | 9.0 | 9.0 |
| | 0.063 | 9.0 | 9.0 | 8.0 | 9.0 | 9.0 | 9.0 | 9.0 | 9.0 | 7.0 | 9.0 | 9.0 | 9.0 | 9.0 | 8.0 | 9.0 | 9.0 |
| | .032 | 9.0 | 9.0 | 8.0 | 9.0 | 9.0 | 9.0 | 7.0 | 9.0 | 5.0 | 9.0 | 7.0 | 9.0 | 9.0 | 8.0 | 9.0 | 9.0 |
| Sodium 2-(5-isopropyl-5-methyl-4-oxo-2-imidazolin-2-yl)nicotinate | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 9.0 | 9.0 | 8.0 | 9.0 | 9.0 | 9.0 | 8.0 | 9.0 | 8.0 | 9.0 | 9.0 | 9.0 | 9.0 | 9.0 | 9.0 | 9.0 |
| | .032 | 9.0 | 9.0 | 7.0 | 9.0 | 9.0 | 9.0 | 8.0 | 9.0 | 7.0 | 9.0 | 9.0 | 9.0 | 9.0 | 8.0 | 9.0 | 9.0 |
| Methyl 2-(5-isopropyl-5-methyl-4-oxo-2-imidazolin-2-yl)nicotinate | 10.000 | 9.0 | 9.0 | 9.0 | 9.0 | | | | 9.0 | 9.0 | 9.0 | | | | | | |
| | 2.000 | 9.0 | 9.0 | 9.0 | 9.0 | | 9.0 | 9.0 | 9.0 | 9.0 | 9.0 | | 9.0 | 9.0 | 9.0 | | |
| | 1.000 | 9.0 | 9.0 | 8.9 | 9.0 | 9.0 | 9.0 | 9.0 | 9.0 | 8.6 | 9.0 | 8.8 | 8.8 | 8.8 | 9.0 | 9.0 | 8.8 |
| | .500 | 9.0 | 9.0 | 8.2 | 9.0 | 9.0 | 9.0 | 9.0 | 8.9 | 8.0 | 9.0 | 8.7 | 8.9 | 7.8 | 9.0 | 9.0 | 7.9 |
| | .250 | 0.8 | 9.0 | 7.6 | 8.9 | 8.5 | 9.0 | 8.4 | 8.4 | 7.1 | 9.0 | 8.5 | 0.4 | 7.5 | 8.7 | 9.0 | 7.5 |
| | .125 | 6.9 | 8.8 | 5.2 | 0.9 | 8.3 | 8.6 | 7.4 | 8.2 | 5.7 | 8.8 | 8.0 | 8.4 | 6.8 | 8.3 | 8.7 | 6.8 |
| | .063 | 4.4 | 8.0 | 3.3 | 8.0 | 5.5 | 7.8 | 6.2 | 7.6 | 2.8 | 8.8 | 6.7 | 8.1 | 4.3 | 7.6 | 7.5 | 5.5 |
| | .032 | 2.3 | 7.4 | 1.9 | 5.4 | 4.0 | 4.6 | 6.5 | 7.1 | 0.6 | 7.7 | 6.1 | 6.7 | 2.0 | 7.2 | 5.5 | 3.0 |
| | .016 | | | | | | | | | | | 7.5 | 6.0 | 3.0 | 4.5 | 7.5 | 1.0 |
| 2-(5-Isopropyl-5-methyl 4-oxo-2-imidazolin-2-yl)nicotinic acid | 10.000 | 9.0 | 9.0 | 9.0 | 9.0 | | | | 7.0 | 9.0 | 9.0 | | | | | | |
| | 2.000 | 9.0 | 9.0 | 9.0 | 9.0 | | | | 0.0 | 8.0 | 9.0 | | 9.0 | 9.0 | 9.0 | | |
| | 1.000 | 9.0 | 9.0 | 9.0 | 9.0 | 9.0 | 9.0 | 9.0 | 8.7 | 8.7 | 9.0 | 9.0 | 9.0 | 9.0 | 9.0 | 9.0 | 9.0 |
| | .500 | 9.0 | 9.0 | 8.7 | 9.0 | 9.0 | 9.0 | 9.0 | 8.7 | 8.3 | 8.7 | 9.0 | 9.0 | 8.7 | 9.0 | 9.0 | 9.0 |
| | .250 | 8.7 | 9.0 | 0.3 | 9.0 | 9.0 | 9.0 | 9.0 | 8.7 | 8.3 | 8.7 | 9.0 | 9.0 | 8.7 | 9.0 | 9.0 | 9.0 |
| | .125 | 9.0 | 9.0 | 7.7 | 9.0 | 9.0 | 9.0 | 9.0 | 8.7 | 7.3 | 8.7 | 9.0 | 9.0 | 8.3 | 8.5 | 9.0 | 9.0 |
| | .063 | 9.0 | 9.0 | 7.3 | 9.0 | 9.0 | 9.0 | 9.0 | 8.7 | 7.3 | 8.7 | 8.5 | 9.0 | 8.0 | 8.5 | 9.0 | 9.0 |
| | .032 | 8.3 | 9.0 | 5.7 | 9.0 | 9.0 | 9.0 | 8.5 | 8.7 | 5.7 | 8.7 | 8.5 | 9.0 | 7.3 | 7.5 | 9.0 | 9.0 |
| | .016 | 5.0 | 9.0 | 0.0 | 9.0 | | | | 6.0 | 0.0 | 6.0 | | 9.0 | 8.0 | 8.0 | | |
| Methyl 2-(5-ethyl-5-methyl-4-oxo-2-imidazolin-2-yl)nicotinate | 1.000 | 3.0 | 9.0 | 0.0 | 7.0 | | | | 8.0 | 4.0 | 9.0 | | 1.0 | 7.0 | 7.0 | | |
| | .500 | 3.0 | 8.0 | 2.0 | 6.0 | | | | 8.0 | 3.0 | 9.0 | | 1.0 | 4.0 | 6.0 | | |
| | .250 | 1.0 | 7.0 | 0.0 | 5.0 | | | | 8.0 | 0.0 | 9.0 | | 0.0 | 4.0 | 6.0 | | |
| | .125 | 0.0 | 7.0 | 0.0 | 0.0 | | | | 7.0 | 0.0 | 9.0 | | 0.0 | 2.0 | 2.0 | | |
| | .063 | 0.0 | 3.0 | 0.0 | 0.0 | | | | 4.0 | 0.0 | 9.0 | | 0.0 | 0.0 | 2.0 | | |
| 2-Propynyl 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 0.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 8.0 | 9.0 | 7.0 | 9.0 | 9.0 | 9.0 | 8.0 | 9.0 | 8.0 | 9.0 | 9.0 | 9.0 | 7.0 | 8.0 | 9.0 | 9.0 |
| | .032 | 4.9 | 9.0 | 4.0 | 9.0 | 5.0 | 9.0 | 2.0 | 9.0 | 4.0 | 9.0 | 9.0 | 9.0 | 6.0 | 4.0 | 9.0 | 8.0 |
| 2-Propynyl 2-(5,5-dimethyl-4-oxo-2-imidazolin-2-yl)-nicotinate | 1.000 | 5.0 | 9.0 | 0.0 | 1.0 | 8.0 | 8.0 | 4.0 | 8.0 | 1.0 | 8.0 | 5.0 | 1.0 | 8.0 | 4.0 | 5.0 | 5.0 |
| | .500 | 1.0 | 8.0 | 0.0 | 0.0 | 6.0 | 6.0 | 0.0 | 6.0 | 0.0 | 8.0 | 1.0 | 0.0 | 7.0 | 2.0 | 1.0 | 2.0 |
| | .250 | 0.0 | 8.0 | 0.0 | 0.0 | 2.0 | 8.0 | 0.0 | 4.0 | 0.0 | 0.0 | 0.0 | 0.0 | 4.0 | 0.0 | 0.0 | 0.0 |
| | .125 | 0.0 | 6.0 | 0.0 | 0.0 | 1.0 | 1.0 | 0.0 | 1.0 | 0.0 | 4.0 | 0.0 | 0.0 | 1.0 | 0.0 | 0.0 | 0.0 |
| | .063 | 0.0 | 4.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| | .032 | 0.0 | 2.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Tert-Butyl-2-(5-isopropyl-5-methyl-4-oxo-2- | 1.000 | | 7.0 | 8.0 | 9.0 | | 9.0 | 9.0 | 8.0 | 8.0 | 9.0 | 9.0 | 9.0 | 8.0 | 9.0 | 9.0 | 9.0 |
| | .500 | | | 8.0 | 8.0 | 9.0 | 9.0 | 8.0 | 8.0 | 7.0 | 9.0 | 9.0 | 8.0 | 8.0 | 8.0 | 9.0 | 9.0 |

TABLE XI-continued

| POST-EMERGENCE TESTS - RATES IN KG/HA | | | | | | | | | | | | | | | | | |
|---|---|---|---|---|---|---|---|---|---|---|---|---|---|---|---|---|---|
| imidazolin-2-yl)nicotinate | .250 | | | 6.0 | 3.0 | 8.0 | 9.0 | 7.0 | 7.0 | 1.0 | 9.0 | 9.0 | 7.0 | 4.0 | 7.0 | 9.0 | 8.0 |
| | .125 | | | 3.0 | 3.0 | 7.0 | 8.0 | 3.0 | 6.0 | 0.0 | 8.0 | 8.0 | 7.0 | 3.0 | 7.0 | 8.0 | 7.0 |
| | .063 | | | 1.0 | 0.0 | 1.0 | 2.0 | 2.0 | 3.0 | 0.0 | 6.0 | 2.0 | 0.0 | 1.0 | | 4.0 | 4.0 |
| | .032 | | | 0.0 | 0.0 | 0.0 | 0.0 | | 2.0 | 0.0 | 2.0 | 1.0 | 0.0 | 0.0 | 0.0 | 1.0 | 1.0 |
| Cyclohexyl-2-(5-isopropyl-5-methyl-4-oxo-2-imidazolin-2-yl)nicotinate | 1.000 | | | 6.0 | 0.0 | 9.0 | 8.0 | 9.0 | 8.0 | 1.0 | 8.0 | 7.0 | 1.0 | 4.0 | 6.0 | 8.0 | 9.0 |
| | .500 | | | 2.0 | 0.0 | 6.0 | 7.0 | 3.0 | 7.0 | 0.0 | 0.0 | 4.0 | 0.0 | 3.0 | 2.0 | 6.0 | 7.0 |
| | .250 | | | 1.0 | 0.0 | 1.0 | 2.0 | 0.0 | 3.0 | 0.0 | 6.0 | 2.0 | 0.0 | 2.0 | 0.0 | 2.0 | 3.0 |
| | .125 | | | 0.0 | 0.0 | 0.0 | 1.0 | 0.0 | 0.0 | 0.0 | 3.0 | 1.0 | 0.0 | 0.0 | | 0.0 | 0.0 |
| | .063 | | | 0.0 | 0.0 | 0.0 | 0.0 | 0.0 | 0.0 | 0.0 | 1.0 | 0.0 | 0.0 | 0.0 | 0.0 | 0.0 | 0.0 |
| | .032 | | | 0.0 | 0.0 | 0.0 | 0.0 | 0.0 | 0.0 | 0.0 | 0.0 | 0.0 | 0.0 | 0.0 | 0.0 | 0.0 | 0.0 |
| Methyl 2-(5,5-dimethyl-4-oxo-2-imidazolin-2-yl)nicotinate | 1.000 | 2.0 | 9.0 | 0.0 | 0.0 | 2.0 | 4.0 | 4.0 | 7.0 | 2.0 | 9.0 | 0.0 | 9.0 | 7.0 | 2.0 | 0.0 | 1.0 |
| | .500 | 1.0 | 0.0 | 0.0 | 0.0 | 0.0 | 8.0 | 2.0 | 7.0 | 3.0 | 0.0 | 0.0 | 0.0 | 7.0 | 2.0 | 0.0 | 0.0 |
| | .250 | 0.0 | 8.0 | 0.0 | 0.0 | 0.0 | 7.0 | 0.0 | 8.0 | 0.0 | 8.0 | 0.0 | 0.0 | 6.0 | 0.0 | 0.0 | 0.0 |
| | .125 | 0.0 | 8.0 | 0.0 | 0.0 | 0.0 | 4.0 | 0.0 | 6.0 | 0.0 | 3.0 | 0.0 | 0.0 | 1.0 | 0.0 | 0.0 | 0.0 |
| | .063 | 0.0 | 4.0 | 0.0 | 0.0 | 0.0 | 0.0 | 0.0 | 1.0 | 0.0 | 2.0 | 0.0 | 0.0 | 2.0 | 0.0 | 0.0 | 0.0 |
| | .032 | 0.0 | 2.0 | 0.0 | 0.0 | 0.0 | 0.0 | 0.0 | 0.0 | 0.0 | 1.0 | 0.0 | 0.0 | 0.0 | 0.0 | 0.0 | 0.0 |
| Benzyl 2-(5,5-dimethyl-4-oxo-2-imidazolin-2-yl)nicotinate | 1.000 | 1.0 | 8.0 | 0.0 | 0.0 | 0.0 | 9.0 | 8.0 | 6.0 | 0.0 | 7.0 | 1.0 | 0.0 | 2.0 | 3.0 | 1.0 | 0.0 |
| | .500 | 1.0 | 8.0 | 0.0 | 0.0 | 0.0 | 4.0 | 0.0 | 6.0 | 0.0 | 7.0 | 0.0 | 0.0 | 1.0 | 2.0 | 0.0 | 0.0 |
| | .250 | 0.0 | 7.0 | 0.0 | 0.0 | 0.0 | 2.0 | 0.0 | 4.0 | 0.0 | 3.0 | 0.0 | 0.0 | 1.0 | 0.0 | 0.0 | 0.0 |
| | .125 | 8.0 | 2.0 | 0.0 | 0.0 | 0.0 | 2.0 | 0.0 | 4.0 | 0.0 | 1.0 | 0.0 | 0.0 | 0.0 | 0.0 | 0.0 | 0.0 |
| | .063 | 0.0 | 0.0 | 0.0 | 0.0 | 0.0 | 1.0 | 0.0 | 8.0 | 0.0 | 0.0 | 0.0 | 0.0 | 0.0 | 0.0 | 0.0 | 0.0 |
| | .032 | 0.0 | 0.0 | 0.0 | 0.0 | 0.0 | 0.0 | 0.0 | 1.0 | 0.0 | 0.0 | 0.0 | 0.0 | 0.0 | 0.0 | 0.0 | 0.0 |
| Calcium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 9.0 | 9.0 | 8.0 | 9.0 | 9.0 | 9.0 | 9.0 | 9.0 | 8.0 | 9.0 | 9.0 | 9.0 | 9.0 | 9.0 | 9.0 | 9.0 |
| | .032 | 8.0 | 9.0 | 8.0 | 9.0 | 9.0 | 9.0 | 6.0 | 9.0 | 6.0 | 9.0 | 9.0 | 9.0 | 9.0 | 8.0 | 9.0 | 9.0 |
| Benzyl 2-(5-ethyl-5-methyl-4-oxo-2-imidazolin-2-yl)-nicotinate | 1.000 | 7.0 | 9.0 | 3.0 | 8.0 | 6.0 | 0.0 | 9.0 | 9.0 | 7.0 | 9.0 | 7.0 | 9.0 | 0.0 | 0.0 | 0.0 | 0.0 |
| | .500 | 2.0 | 9.0 | 2.0 | 7.0 | 5.0 | 0.0 | 9.0 | 9.0 | 3.0 | 9.0 | 6.0 | 0.0 | 4.0 | 9.0 | 1.0 | 4.0 |
| | .250 | 1.0 | 9.0 | 2.0 | 1.0 | 4.0 | 7.0 | 1.0 | 9.0 | 1.0 | 9.0 | 3.0 | 8.0 | 3.0 | 9.0 | 0.0 | 1.0 |
| | .125 | 0.0 | 7.0 | 1.0 | 0.0 | 0.0 | 7.0 | 0.0 | 8.0 | 0.0 | 7.0 | 0.0 | 1.0 | 1.0 | 3.0 | 0.0 | 0.0 |
| | .063 | 0.0 | 2.0 | 0.0 | 0.0 | 0.0 | 8.0 | 0.0 | 7.0 | 0.0 | 7.0 | 0.0 | 1.0 | 0.0 | 1.0 | 0.0 | 0.0 |
| | .032 | 0.0 | 1.0 | 0.0 | 0.0 | 0.0 | 4.0 | 0.0 | 4.0 | 0.0 | 4.0 | 0.0 | 1.0 | 0.0 | 1.0 | 0.0 | 0.0 |
| 2-Propynyl 2-(5-ethyl-5-methyl-4-oxo-2-imidazolin-2-yl)nicotinate | 1.000 | 9.0 | 9.0 | 8.0 | 9.0 | 9.0 | 9.0 | 0.0 | 9.0 | 9.0 | 9.0 | 9.0 | 9.0 | 9.0 | 9.0 | 9.0 | 9.0 |
| | .500 | 7.0 | 9.0 | 6.0 | 9.0 | 0.0 | 9.0 | 3.0 | 9.0 | 7.0 | 9.0 | 9.0 | 9.0 | 9.0 | 9.0 | 9.0 | 9.0 |
| | .250 | 6.0 | 9.0 | 2.0 | 9.0 | 4.0 | 9.0 | 5.0 | 9.0 | 3.0 | 9.0 | 8.0 | 9.0 | 9.0 | 7.0 | 9.0 | 8.0 |
| | .125 | 5.0 | 9.0 | 1.0 | 4.0 | 2.0 | 9.0 | 8.0 | 8.0 | 0.0 | 9.0 | 7.0 | 4.0 | 8.0 | 8.0 | 8.0 | 4.0 |
| | .063 | 1.0 | 9.0 | 0.0 | 0.0 | 0.0 | 8.0 | 1.0 | 7.0 | 0.0 | 8.0 | 1.0 | 0.0 | 4.0 | 5.0 | 1.0 | 1.0 |
| | .032 | 0.0 | 4.0 | 0.0 | 0.0 | 0.0 | 5.0 | 0.0 | 6.0 | 0.0 | 5.0 | 0.0 | 0.0 | 1.0 | 1.0 | 0.0 | 0.0 |
| 2-(5-Ethyl-5-methyl-4-oxo-2-imidazolin-2-yl)nicotinic acid | 1.000 | 9.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .250 | 9.0 | 9.0 | 7.0 | 9.0 | 9.0 | 9.0 | 9.0 | 9.0 | 6.0 | 9.0 | 9.0 | 9.0 | 9.0 | 9.0 | 9.0 | 9.0 |
| | .125 | 9.0 | 9.0 | 4.0 | 9.0 | 9.0 | 9.0 | 8.0 | 9.0 | 3.0 | 9.0 | 9.0 | 7.0 | 9.0 | 9.0 | 9.0 | 9.0 |
| | .063 | 8.0 | 9.0 | 1.0 | 8.0 | 4.0 | 0.0 | 7.0 | 9.0 | 0.0 | 9.0 | 0.0 | 7.0 | 7.0 | 7.0 | 9.0 | 8.0 |
| | .032 | 3.0 | 7.0 | 1.0 | 1.0 | 2.0 | 8.0 | 2.0 | 0.0 | 0.0 | 9.0 | 1.0 | 0.0 | 6.0 | 6.0 | 0.0 | 4.0 |
| Diisopropylammonium-2-(5-isopropyl-5-methyl-4-oxo-2-imidazolin-2-yl)nicotinic acid | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 5.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 8.0 | 9.0 | 8.0 | 9.0 | 9.0 | 9.0 | 6.0 | 9.0 | 8.0 | 9.0 | 9.0 | 9.0 | 9.0 | 8.0 | 9.0 | 9.0 |
| | .032 | 8.0 | 9.0 | 7.0 | 9.0 | 9.0 | 8.0 | 5.0 | 8.0 | 5.0 | 9.0 | 9.0 | 9.0 | 8.0 | 8.0 | 9.0 | 9.0 |

TABLE XI-continued

POST-EMERGENCE TESTS - RATES IN KG/HA

| | | | | | | | | | | | | | | | | | |
|---|---|---|---|---|---|---|---|---|---|---|---|---|---|---|---|---|---|
| Dodecyl 2-(5-isopropyl-5-methyl-4-oxo-2-imidazolin-2-yl)nicotinate | 1.000 | 6.0 | 0.0 | 7.0 | 0.0 | 9.0 | 9.0 | 9.0 | 0.0 | 6.0 | 9.0 | 8.0 | 7.0 | 2.0 | 7.0 | 9.0 | 8.0 |
| | .500 | 3.0 | 8.0 | 3.0 | 0.0 | 0.0 | 9.0 | 9.0 | 7.0 | 2.0 | 9.0 | 0.0 | 4.0 | 2.0 | 7.0 | 9.0 | 7.0 |
| | .250 | 3.0 | 7.0 | 1.0 | 6.0 | 3.0 | 7.0 | 9.0 | 7.0 | 0.0 | 9.0 | 7.0 | 2.0 | 0.0 | 3.0 | 3.0 | 3.0 |
| | .125 | 1.0 | 6.0 | 0.0 | 4.0 | 1.0 | 4.0 | 6.0 | 7.0 | 0.0 | 7.0 | 4.0 | 0.0 | 0.0 | 3.0 | 0.0 | 1.0 |
| | .063 | 0.0 | 3.0 | 0.0 | 4.0 | 0.0 | 3.0 | 1.0 | 7.0 | 0.0 | 7.0 | 4.0 | 0.0 | 0.0 | 1.0 | 0.0 | 0.0 |
| 2-Decynyl 2-(5-isopropyl-5-methyl-4-oxo-2-imidazolin-2-yl)nicotinate | 1.000 | | 9.0 | 8.0 | 9.0 | | 9.0 | 9.0 | 9.0 | 9.0 | 9.0 | 9.0 | 9.0 | 9.0 | 9.0 | 9.0 | 9.0 |
| | .500 | | 9.0 | 7.0 | 9.0 | | 9.0 | 9.0 | 9.0 | 9.0 | 9.0 | 9.0 | 9.0 | 8.0 | 9.0 | 9.0 | 9.0 |
| | .250 | | 9.0 | 7.0 | 9.0 | | 9.0 | 8.0 | 8.0 | 4.0 | 9.0 | 9.0 | 9.0 | 8.0 | 9.0 | 9.0 | 9.0 |
| | .125 | | 9.0 | 6.0 | 9.0 | | 9.0 | 6.0 | 8.0 | 4.0 | 8.0 | 8.0 | 9.0 | 7.0 | 9.0 | 9.0 | 9.0 |
| | .063 | | 7.0 | 2.0 | 9.0 | | 0.0 | 3.0 | 7.0 | 2.0 | 8.0 | 8.0 | 7.0 | 4.0 | 9.0 | 8.0 | 8.0 |
| | .032 | | 1.0 | 0.0 | 7.0 | | 8.0 | 1.0 | 4.0 | 0.0 | 6.0 | 7.0 | 4.0 | 2.0 | 9.0 | 2.0 | 7.0 |
| 2-Methyoxyethyl 2-(5-isopropyl-5-methyl-4-oxo-2-imidazolin-2-yl)nicotinate | 1.000 | | 9.0 | 9.0 | 9.0 | | 9.0 | 9.0 | 9.0 | 9.0 | 9.0 | 9.0 | 9.0 | 8.0 | 9.0 | 9.0 | 9.0 |
| | .500 | | 9.0 | 8.0 | 9.0 | | 9.0 | 9.0 | 9.0 | 9.0 | 9.0 | 9.0 | 9.0 | 8.0 | 9.0 | 9.0 | 9.0 |
| | .250 | | 9.0 | 8.0 | 9.0 | | 8.0 | 3.0 | 9.0 | 9.0 | 9.0 | 9.0 | 9.0 | 4.0 | 9.0 | 9.0 | 9.0 |
| | .125 | | 9.0 | 2.0 | 9.0 | | 8.0 | 2.0 | 8.0 | 6.0 | 8.0 | 9.0 | 9.0 | 4.0 | 9.0 | 9.0 | 9.0 |
| | .063 | | 2.0 | 0.0 | 9.0 | | 7.0 | 0.0 | 7.0 | 1.0 | 8.0 | 8.0 | 7.0 | 2.0 | 0.0 | 4.0 | 8.0 |
| | .032 | | 1.0 | 0.0 | 4.0 | | 3.0 | 0.0 | 4.0 | 0.0 | 6.0 | 7.0 | 0.0 | 1.0 | 7.0 | 3.0 | 4.0 |
| Allyl-2-(5-isopropyl-5-methyl-4-oxo-2-imidazolin-2-yl)nicotinate | 1.000 | | 9.0 | 8.0 | 9.0 | | 9.0 | 9.0 | 9.0 | 9.0 | 9.0 | 9.0 | 9.0 | 0.0 | 9.0 | 9.0 | 9.0 |
| | .500 | | 9.0 | 8.0 | 9.0 | | 9.0 | 9.0 | 9.0 | 9.0 | 9.0 | 9.0 | 9.0 | 8.0 | 9.0 | 9.0 | 9.0 |
| | .250 | | 9.0 | 2.0 | 9.0 | | 9.0 | 8.0 | 9.0 | 8.0 | 9.0 | 9.0 | 9.0 | 0.0 | 9.0 | 9.0 | 9.0 |
| | .125 | | 8.0 | 1.0 | 9.0 | | 9.0 | 4.0 | 9.0 | 7.0 | 9.0 | 9.0 | 9.0 | 0.0 | 9.0 | 9.0 | 9.0 |
| | .063 | | 7.0 | 0.0 | 9.0 | | 8.0 | 1.0 | 8.0 | 4.0 | 8.0 | 8.0 | 7.0 | 6.0 | 8.0 | 8.0 | 8.0 |
| | .032 | | 2.0 | 0.0 | 7.0 | | 7.0 | 0.0 | 7.0 | 1.0 | 6.0 | 7.0 | 0.0 | 3.0 | 7.0 | 7.0 | 4.0 |
| 1-Methylally 2-(5-isopropyl-5-methyl-4-oxo-2-imidazolin-2-yl)nicotinate | 1.000 | | 9.0 | 8.0 | 9.0 | | 9.0 | 9.0 | 9.0 | 9.0 | 9.0 | 9.0 | 9.0 | 7.0 | 9.0 | 9.0 | 9.0 |
| | .500 | | 9.0 | 8.0 | 9.0 | | 8.0 | 9.0 | 9.0 | 8.0 | 9.0 | 9.0 | 9.0 | 6.0 | 9.0 | 9.0 | 9.0 |
| | .250 | | 8.0 | 1.0 | 9.0 | | 8.0 | 5.0 | 8.0 | 7.0 | 8.0 | 9.0 | 7.0 | 5.0 | 8.0 | 9.0 | 9.0 |
| | .125 | | 4.0 | 0.0 | 9.0 | | 7.0 | 1.0 | 8.0 | 1.0 | 8.0 | 9.0 | 4.0 | 3.0 | | 7.0 | 8.0 |
| | .063 | | 1.0 | 0.0 | 0.0 | | 7.0 | 1.0 | 7.0 | 0.0 | 7.0 | 7.0 | 0.0 | 1.0 | 7.0 | 7.0 | 7.0 |
| | .032 | | 0.0 | 0.0 | 3.0 | | 4.0 | 0.0 | 6.0 | 0.0 | 6.0 | 2.0 | 0.0 | 0.0 | 1.0 | 1.0 | 4.0 |
| 1-Methyl 2-propynyl-2-(5-isopropyl-5-methyl-4-oxo-2-imidazolin-2-yl)nicotinate | 1.000 | | 9.0 | 8.0 | 9.0 | | 9.0 | 9.0 | 9.0 | 9.0 | 9.0 | 9.0 | 9.0 | 9.0 | 9.0 | 9.0 | 9.0 |
| | .500 | | 9.0 | 8.0 | 9.0 | | 9.0 | 9.0 | 9.0 | 9.0 | 9.0 | 9.0 | 9.0 | 9.0 | 9.0 | 9.0 | 9.0 |
| | .250 | | 9.0 | 8.0 | 9.0 | | 9.0 | 7.0 | 9.0 | 9.0 | 9.0 | 9.0 | 9.0 | 8.0 | 9.0 | 9.0 | 9.0 |
| | .125 | | 9.0 | 7.0 | 9.0 | | 9.0 | 4.0 | 9.0 | 6.0 | 8.0 | 9.0 | 9.0 | 7.0 | 7.0 | 9.0 | 9.0 |
| | .063 | | 7.0 | 5.0 | 9.0 | | 8.0 | 4.0 | 8.0 | 4.0 | 7.0 | 9.0 | 7.0 | 6.0 | 6.0 | 8.0 | 9.0 |
| | .032 | | 4.0 | 2.0 | 7.0 | | 0.0 | 1.0 | 7.0 | 1.0 | 7.0 | 7.0 | 7.0 | 5.0 | | 7.0 | 7.0 |
| Ethyl 2-(5-isopropyl-5-methyl-4-oxo-2-imidazolin-2-yl)nicotinate | 1.000 | 8.0 | 9.0 | 0.0 | 9.0 | 9.0 | 9.0 | 9.0 | 9.0 | 9.0 | 9.0 | 9.0 | 9.0 | 8.0 | 9.0 | 9.0 | 9.0 |
| | .500 | 7.0 | 9.0 | 7.0 | 9.0 | 9.0 | 9.0 | 9.0 | 9.0 | 8.0 | 9.0 | 9.0 | 8.0 | 8.0 | 9.0 | 9.0 | 9.0 |
| | .250 | 3.0 | 9.0 | 7.0 | 9.0 | 8.0 | 9.0 | 9.0 | 9.0 | 0.0 | 9.0 | 9.0 | 8.0 | 4.0 | 8.0 | 9.0 | 8.0 |
| | .125 | 0.0 | 0.0 | 2.0 | 8.0 | 7.0 | 8.0 | 9.0 | 9.0 | 8.0 | 9.0 | 3.0 | 0.0 | 2.0 | 5.0 | 9.0 | 7.0 |
| | .063 | 0.0 | 4.0 | 0.0 | 2.0 | 3.0 | 8.0 | 8.0 | 7.0 | 4.0 | 0.0 | 0.0 | 0.0 | 0.0 | 0.0 | 1.0 | 3.0 |
| | .032 | 0.0 | 3.0 | 0.0 | 1.0 | 1.0 | 7.0 | 0.0 | 3.0 | 0.0 | 8.0 | 0.0 | 0.0 | 0.0 | 0.0 | 0.0 | 2.0 |
| 2-(Benzyloxy)ethyl 2-(5-isopropyl-5-methyl-4-oxy-2-imidazolin-2-yl)nicotinate | 1.000 | 9.0 | 9.0 | 8.0 | 9.0 | 9.0 | 9.0 | 9.0 | 9.0 | 0.0 | 9.0 | 8.0 | 8.0 | 0.0 | 9.0 | 9.0 | 0.0 |
| | .500 | 8.0 | 8.0 | 1.0 | 9.0 | 9.0 | 9.0 | 7.0 | 9.0 | 8.0 | 9.0 | 8.0 | 8.0 | 8.0 | 9.0 | 9.0 | 0.0 |
| | .250 | 3.0 | 9.0 | 0.0 | 0.0 | 7.0 | 9.0 | 9.0 | 0.0 | 7.0 | 8.0 | 7.0 | 2.0 | 4.0 | 0.0 | 8.0 | 0.0 |
| | .125 | 1.0 | 7.0 | 0.0 | 6.0 | 4.0 | 9.0 | 1.0 | 8.0 | 1.0 | 0.0 | 7.0 | 2.0 | 1.0 | 0.0 | 1.0 | 6.0 |
| | .063 | 0.0 | 3.0 | 0.0 | 0.0 | 0.0 | 4.0 | 0.0 | 0.0 | 0.0 | 3.0 | 0.0 | 0.0 | 0.0 | 2.0 | 0.0 | 0.0 |
| | .032 | 0.0 | 2.0 | 0.0 | 0.0 | 0.0 | 0.0 | 0.0 | 4.0 | 0.0 | 1.0 | 0.0 | 0.0 | 0.0 | | 0.0 | 0.0 |
| 3-Isopropyl-3-methyl-[3H]—imidazo[1',2:1,2]pyrrolo-[3,4-b]pyridine-2-(3H),5-dione | 1.000 | 9.0 | 9.0 | 8.0 | 9.0 | 9.0 | 9.0 | 9.0 | 9.0 | 9.0 | 9.0 | 9.0 | 9.0 | 8.0 | 9.0 | 9.0 | 9.0 |
| | .500 | 9.0 | 9.0 | 7.0 | 9.0 | 9.0 | 9.0 | 4.0 | 9.0 | 9.0 | 7.0 | 9.0 | 9.0 | 8.0 | 9.0 | 9.0 | 9.0 |
| | .250 | 9.0 | 8.0 | 7.0 | 9.0 | 8.0 | 9.0 | 3.0 | 9.0 | 6.0 | 6.0 | 9.0 | 9.0 | 7.0 | 8.0 | 9.0 | 0.0 |
| | .125 | 4.0 | 8.0 | 3.0 | 4.0 | 4.0 | 9.0 | 3.0 | 9.0 | 1.0 | 6.0 | 0.0 | 9.0 | 7.0 | 8.0 | 8.0 | 0.0 |
| | .063 | 3.0 | 4.0 | 6.0 | 2.0 | 0.0 | 8.0 | 2.0 | 7.0 | 0.0 | 3.0 | 2.0 | 9.0 | 2.0 | 7.0 | 4.0 | 3.0 |

TABLE XI-continued

POST-EMERGENCE TESTS - RATES IN KG/HA

| | | | | | | | | | | | | | | | | |
|---|---|---|---|---|---|---|---|---|---|---|---|---|---|---|---|---|
| | .032 | 1.0 | 4.0 | | 1.0 | 0.0 | | 1.0 | 7.0 | 0.0 | 2.0 | 4.0 | 0.0 | 2.0 | 6.0 | 1.0 | 1.0 |
| Methyl-2-(5-isopropyl-5- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 8.0 |
| methyl-4-oxo-2-imidazolin- | .500 | 9.0 | 9.0 | 9.0 | 9.0 | 8.0 | 9.0 | 9.0 | 9.0 | 9.0 | 9.0 | 9.0 | 9.0 | 8.0 | 9.0 | 9.0 | 8.0 |
| 2-yl)nicotinate hydrochlo- | .250 | 9.0 | 9.0 | 9.0 | 9.0 | 9.0 | 9.0 | 9.0 | 9.0 | 8.0 | 9.0 | 9.0 | 9.0 | 0.0 | 9.0 | 9.0 | 8.0 |
| ride | .125 | 9.0 | 9.0 | 8.0 | 9.0 | 8.0 | 9.0 | 8.0 | 8.0 | 7.0 | 9.0 | 0.0 | 9.0 | 8.0 | 9.0 | 9.0 | 7.0 |
| | .063 | 4.0 | 9.0 | 7.0 | 7.0 | 4.0 | 8.0 | 9.0 | 8.0 | 4.0 | 8.0 | 8.0 | 9.0 | 7.0 | 9.0 | 6.0 | 6.0 |
| | .032 | 2.0 | 6.0 | 6.0 | 6.0 | 4.0 | | 8.0 | 8.0 | 4.0 | 7.0 | 8.0 | 9.0 | 4.0 | 8.0 | 4.0 | 4.0 |
| Furfuryl 2-(5-isopropyl- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| 5-methyl-4-oxo-2-imidazo- | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| lin-2-yl)nicotinate | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 9.0 | 8.0 | 9.0 | 9.0 | 9.0 | 9.0 | 9.0 | 9.0 | 9.0 |
| | .063 | 8.0 | 8.0 | 7.0 | 9.0 | 0.0 | 9.0 | 9.0 | 9.0 | 0.0 | 0.0 | 0.0 | 9.0 | 7.0 | 0.0 | 9.0 | 9.0 |
| | .032 | 7.0 | 7.0 | 3.0 | 9.0 | 6.0 | 9.0 | 4.0 | 9.0 | 3.0 | 7.0 | 0.0 | 9.0 | 7.0 | 7.0 | 9.0 | 9.0 |
| Isopropyl 2-(5-isopropyl- | 1.000 | 8.0 | 7.0 | 2.0 | 9.0 | 0.0 | 9.0 | 9.0 | 9.0 | 9.0 | 9.0 | 0.0 | 1.0 | 8.0 | 0.0 | 9.0 | 0.0 |
| 5-methyl-4-oxo-2-imidazo- | .500 | 1.0 | 7.0 | 1.0 | 0.0 | 0.0 | 9.0 | 6.0 | 9.0 | 0.0 | 9.0 | 7.0 | 1.0 | 2.0 | 8.0 | 9.0 | 2.0 |
| lin-2-yl)nicotinate | .250 | 1.0 | 3.0 | 0.0 | 6.0 | 1.0 | 8.0 | 4.0 | 0.0 | 6.0 | 9.0 | 3.0 | 0.0 | 2.0 | 7.0 | 4.0 | 1.0 |
| | .125 | 1.0 | 8.0 | 0.0 | 2.0 | 0.0 | 6.0 | 0.0 | 9.0 | 6.0 | 7.0 | 2.0 | 0.0 | 0.0 | 7.0 | 1.0 | 0.0 |
| | .063 | 0.0 | 2.0 | 0.0 | 1.0 | 0.0 | 3.0 | | 4.0 | 1.0 | 6.0 | 3.0 | 0.0 | 0.0 | 3.0 | 1.0 | 0.0 |
| | .032 | 0.0 | 2.0 | 0.0 | 0.0 | 0.0 | 2.0 | 0.0 | 4.0 | 0.0 | 6.0 | 1.0 | 0.0 | 0.0 | 1.0 | 1.0 | 0.0 |
| Benzyl 2-(5-isopropyl-5- | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 | 9.0 | 9.0 |
| methyl-4-oxo-2-imidazolin- | .500 | 9.0 | 9.0 | 8.0 | 9.0 | 9.0 | 9.0 | 9.0 | 9.0 | 8.0 | 9.0 | 9.0 | 9.0 | 9.0 | 9.0 | 9.0 | 9.0 |
| 2-yl)nicotinate | .250 | 7.0 | 9.0 | 7.0 | 9.0 | 9.0 | 8.0 | 9.0 | 9.0 | 6.0 | 9.0 | 9.0 | 9.0 | 0.0 | 9.0 | 9.0 | 9.0 |
| | .125 | 6.0 | 9.0 | 6.0 | 9.0 | | 8.0 | 2.0 | 9.0 | 1.0 | 9.0 | 8.0 | 9.0 | 7.0 | 9.0 | 9.0 | 0.0 |
| | .063 | 4.0 | 7.0 | 1.0 | 9.0 | | 7.0 | 0.0 | 8.0 | 1.0 | 2.0 | 2.0 | 9.0 | 7.0 | 4.0 | 9.0 | 6.0 |
| | .032 | 1.0 | 6.0 | 1.0 | 6.0 | 0.0 | 4.0 | 0.0 | 8.0 | 0.0 | 1.0 | 2.0 | 1.0 | 2.0 | 1.0 | 9.0 | 2.0 |

| Compound | RATE | BARNY ARDGR | GREEN FOX | P NUTSEDGE | WILD OATS | QUACK GRASS | FLD BINDWD | MRNGL RY SP | RAGWEED | VELVE TLEAF | S BARLY LA | CORN FIELD | COTTON | RICE, NATO | SOYBEAN AD |
|---|---|---|---|---|---|---|---|---|---|---|---|---|---|---|---|
| 2-Methylallyl 2-(5- | 1.000 | 9.0 | 9.0 | 9.0 | 9.0 | 8.0 | 9.0 | 9.0 | 9.0 | 9.0 | 9.0 | 9.0 | 9.0 | 9.0 | 9.0 |
| isopropyl-5-methyl- | .500 | 9.0 | 9.0 | 8.0 | 9.0 | 8.0 | 9.0 | 9.0 | 9.0 | 9.0 | 9.0 | 9.0 | 9.0 | 8.0 | 9.0 |
| 4-oxo-2-imidazolin- | .250 | 8.0 | 8.0 | 7.0 | 8.0 | 8.0 | 9.0 | 8.0 | 6.0 | 8.0 | 9.0 | 9.0 | 9.0 | 8.0 | 9.0 |
| 2-yl)nicotinate | .125 | 3.0 | 8.0 | 6.0 | 7.0 | 7.0 | 7.0 | 8.0 | 5.0 | 8.0 | 8.0 | 7.0 | 9.0 | 8.0 | 8.0 |
| | .063 | 1.0 | 7.0 | 1.0 | 6.0 | 6.0 | 7.0 | 8.0 | 1.0 | 7.0 | 7.0 | 3.0 | | 4.0 | 7.0 |
| | .032 | 0.0 | 4.0 | 0.0 | 1.0 | 3.0 | 7.0 | 7.0 | 0.0 | 6.0 | 2.0 | 1.0 | 9.0 | 3.0 | 3.0 |
| 2-Butenyl 2-(5-isopropyl- | 1.000 | 9.0 | 9.0 | 8.0 | 9.0 | 7.0 | 8.0 | 9.0 | 9.0 | 9.0 | 9.0 | 9.0 | 9.0 | 8.0 | 9.0 |
| 5-methyl-4-oxo-2- | .500 | 9.0 | 9.0 | 7.0 | 9.0 | 7.0 | 8.0 | 9.0 | 8.0 | 9.0 | 9.0 | 9.0 | 9.0 | 8.0 | 9.0 |
| imidazolin-2-yl)nicotinate | .250 | 7.0 | 9.0 | 6.0 | 9.0 | 7.0 | 8.0 | 9.0 | 7.0 | 9.0 | 9.0 | 8.0 | 9.0 | 8.0 | 8.0 |
| | .125 | 4.0 | 8.0 | 5.0 | 7.0 | 7.0 | 8.0 | 9.0 | 7.0 | 8.0 | 9.0 | 8.0 | 9.0 | 7.0 | 8.0 |
| | .063 | 3.0 | 7.0 | 4.0 | 6.0 | 6.0 | 7.0 | 9.0 | 1.0 | 7.0 | 8.0 | 1.0 | 9.0 | 6.0 | 6.0 |
| | .032 | 1.0 | 5.0 | 1.0 | 2.0 | 4.0 | 7.0 | 7.0 | 0.0 | 6.0 | 3.0 | 0.0 | 9.0 | 1.0 | 3.0 |
| Octadecyl 2-(5-isopropyl- | 8.000 | 7.0 | 1.0 | 7.0 | 9.0 | 9.0 | 9.0 | 6.0 | 3.0 | 9.0 | | | | | |
| 5-methyl-4-oxo-2- | 1.000 | | 0.0 | 0.0 | 4.0 | | 0.0 | 0.0 | 0.0 | 3.0 | 2.0 | 0.0 | 0.0 | 0.0 | |
| imidazolin-2-yl)nicotinate | | | | | | | | | | | | | | | |
| Propyl 2-(5-isopropyl- | 8.000 | 9.0 | 9.0 | 9.0 | 9.0 | 9.0 | 9.0 | 9.0 | 9.0 | 9.0 | | | | | |
| 5-methyl-4-imidazolin- | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 |
| 2-yl)nicotinate | .500 | 7.0 | 9.0 | 8.0 | 9.0 | 8.0 | 9.0 | 9.0 | 9.0 | 9.0 | 9.0 | 9.0 | 9.0 | 9.0 | 9.0 |
| | .250 | 8.0 | 9.0 | 7.0 | 9.0 | 7.0 | 9.0 | 9.0 | 9.0 | 9.0 | 9.0 | 9.0 | 9.0 | 8.0 | 8.0 |
| | .125 | 2.0 | 9.0 | 5.0 | 7.0 | 5.0 | 7.0 | 9.0 | 6.0 | 9.0 | 8.0 | 7.0 | 9.0 | 4.0 | 8.0 |
| | .063 | 0.0 | 7.0 | 1.0 | 2.0 | 4.0 | 5.0 | 8.0 | 3.0 | 8.0 | 7.0 | 2.0 | 9.0 | 2.0 | 7.0 |
| | .032 | 0.0 | 6.0 | 0.0 | 1.0 | 3.0 | 4.0 | 6.0 | 0.0 | 6.0 | 3.0 | 0.0 | 9.0 | 1.0 | 6.0 |
| Butyl 2-(5-isopropyl- | 8.000 | 9.0 | 9.0 | 9.0 | 9.0 | 9.0 | 9.0 | 9.0 | 9.0 | 9.0 | | | | | |
| 5-methyl-4-oxo-2- | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| imidazolin-2-yl)- | .500 | 9.0 | 9.0 | 7.0 | 9.0 | 7.0 | 9.0 | 9.0 | 9.0 | 9.0 | 9.0 | 9.0 | 9.0 | 9.0 | 8.0 |
| nicotinate | .250 | 6.0 | 9.0 | 7.0 | 9.0 | 6.0 | 9.0 | 9.0 | 8.0 | 9.0 | 9.0 | 9.0 | 9.0 | 9.0 | 8.0 |
| | .125 | 2.0 | 8.0 | 2.0 | 7.0 | 5.0 | 7.0 | 4.0 | 3.0 | 9.0 | 9.0 | 6.0 | 9.0 | 7.0 | 7.0 |
| Methyl 2-(5-isopropyl- | 8.000 | 9.0 | 9.0 | 9.0 | 9.0 | 9.0 | 7.0 | 9.0 | 8.0 | 9.0 | | | | | |
| 5-methyl-4-oxo-2- | 1.000 | 9.0 | 9.0 | 7.0 | 9.0 | 8.0 | 7.0 | 8.0 | 2.0 | 7.0 | 9.0 | 9.0 | 9.0 | 7.0 | 9.0 |
| imidazolin-2-yl)-6- | .500 | 9.0 | 9.0 | 7.0 | 8.0 | 7.0 | 7.0 | 9.0 | 7.0 | 7.0 | 8.0 | 9.0 | 8.0 | 7.0 | 9.0* |
| methoxynicotinate | .250 | 7.0 | 9.0 | 7.0 | 8.0 | 7.0 | 6.0 | 9.0 | 0.0 | 4.0 | 8.0 | 9.0 | 6.0 | 6.0 | 7.0 |
| | .125 | 7.0 | 8.0 | 6.0 | 7.0 | 6.0 | 6.0 | 8.0 | 0.0 | 2.0 | 7.0 | 8.0 | 4.0 | 6.0 | |
| | .063 | 6.0 | 7.0 | 6.0 | 7.0 | 4.0 | 2.0 | 7.0 | 0.0 | 1.0 | 4.0 | 4.0 | 1.0 | 4.0 | 4.0 |
| | .032 | 2.0 | 4.0 | 0.0 | 6.0 | 1.0 | 1.0 | 2.0 | 0.0 | 0.0 | 1.0 | 7.0 | 1.0 | 3.0 | 3.0 |
| 2-Decenyl 2-(5- | 1.000 | 9.0 | 9.0 | 8.0 | 9.0 | 9.0 | 9.0 | 9.0 | 9.0 | 9.0 | 9.0 | 9.0 | 9.0 | 8.0 | 9.0 |
| isopropyl-5-methyl- | .500 | 9.0 | 9.0 | 7.0 | 9.0 | 8.0 | 9.0 | 9.0 | 7.0 | 9.0 | 9.0 | 9.0 | 9.0 | 8.0 | 7.0 |
| 4-oxo-2-imidazolin- | .250 | 7.0 | 9.0 | 7.0 | 9.0 | 7.0 | 9.0 | 9.0 | 6.0 | 9.0 | 9.0 | 7.0 | 8.0 | 8.0 | 7.0 |
| 2-yl)nicotinate | .125 | 3.0 | 9.0 | 6.0 | 8.0 | 7.0 | 7.0 | 3.0 | 1.0 | 8.0 | 8.0 | 2.0 | 7.0 | 6.0 | 5.0 |
| | .063 | 2.0 | 4.0 | 2.0 | 7.0 | 7.0 | 7.0 | | 0.0 | 8.0 | 8.0 | 1.0 | 7.0 | 2.0 | 3.0 |
| | .032 | 0.0 | 2.0 | 0.0 | 0.0 | 4.0 | 2.0 | 2.0 | 0.0 | 3.0 | 3.0 | 1.0 | 5.0 | 1.0 | 2.0 |
| N,N—diethyl 2-(5-isopropyl-5-methyl-4-oxo-2-imidazolin-2-yl)nicotinamide | 8.000 | 8.0 | 9.0 | 9.0 | 9.0 | 9.0 | 1.0 | 9.0 | 6.0 | 8.0 | | | | | |
| 3-Isopropyl-8-methoxy- | 8.000 | 9.0 | 9.0 | 9.0 | 9.0 | 9.0 | 0.0 | 8.0 | 8.0 | 9.0 | | | | | |
| 3-methyl-5H—imidazo- | 1.000 | 6.0 | 8.0 | 8.0 | 9.0 | 8.0 | 7.0 | 8.0 | 2.0 | 2.0 | 8.0 | 6.0 | 9.0 | 7.0 | 4.0 |
| [1',2':1,2]pyrrolo- | .500 | 6.0 | 8.0 | 7.0 | 3.0 | 6.0 | 7.0 | 2.0 | 0.0 | 2.0 | 4.0 | 2.0 | 7.0 | 7.0 | 1.0 |
| [3,4-b]pyridine-2- | .250 | 4.0 | 7.0 | 4.0 | 1.0 | 4.0 | 3.0 | 2.0 | 0.0 | 1.0 | 1.0 | 1.0 | 6.0 | 7.0 | 1.0 |
| (3H),5-dione | .125 | 2.0 | 4.0 | 1.0 | 0.0 | 2.0 | 2.0 | 1.0 | 0.0 | 0.0 | 0.0 | 1.0 | 6.0 | 6.0 | 1.0 |
| | .063 | 2.0 | 4.0 | 1.0 | 0.0 | 2.0 | 1.0 | | 0.0 | 0.0 | 0.0 | | 2.0 | 4.0 | 1.0 |
| | .032 | 0.0 | 3.0 | 1.0 | 0.0 | 1.0 | 1.0 | | 0.0 | 0.0 | 0.0 | 0.0 | 1.0 | 3.0 | 0.0 |
| 2-Chloroallyl 2-(5- | 1.000 | 9.0 | 9.0 | 9.0 | 9.0 | 8.0 | 9.0 | 9.0 | 9.0 | 9.0 | 9.0 | 9.0 | 9.0 | 9.0 | 9.0 |
| isopropyl-5-methyl- | .500 | 9.0 | 9.0 | 8.0 | 9.0 | 8.0 | 9.0 | 9.0 | 9.0 | 9.0 | 9.0 | 9.0 | 9.0 | 9.0 | 9.0 |
| 4-oxo-2-imidazolin- | .250 | 9.0 | 9.0 | 7.0 | 9.0 | 8.0 | 9.0 | 9.0 | 9.0 | 9.0 | 9.0 | 9.0 | 9.0 | 9.0 | 9.0 |
| 2-yl)nicotinate | .125 | 9.0 | 9.0 | 7.0 | 9.0 | 7.0 | 9.0 | 9.0 | 8.0 | 9.0 | 9.0 | 9.0 | 9.0 | 9.0 | 8.0 |
| | .063 | 9.0 | 9.0 | 7.0 | 9.0 | 7.0 | 9.0 | 8.0 | 6.0 | 9.0 | 9.0 | 9.0 | 9.0 | 9.0 | 8.0 |
| | .032 | 6.0 | 9.0 | 6.0 | 7.0 | 6.0 | 7.0 | 6.0 | 2.0 | 9.0 | 9.0 | 8.0 | 9.0 | 8.0 | 6.0 |
| Methyl 2-(1-acetyl-4- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| isopropyl-4-methyl-5- | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| oxo-2-imidazolin-2-yl)- | .250 | 9.0 | 9.0 | 8.0 | 9.0 | 8.0 | 9.0 | 9.0 | 9.0 | 9.0 | 9.0 | 9.0 | 9.0 | 9.0 | 9.0 |
| nicotinate | .125 | 7.0 | 9.0 | 7.0 | 9.0 | 8.0 | 9.0 | 8.0 | 2.0 | 9.0 | 9.0 | 9.0 | 9.0 | 8.0 | 8.0 |
| | .063 | 4.0 | 9.0 | 7.0 | 7.0 | 7.0 | 7.0 | 7.0 | 1.0 | 9.0 | 8.0 | 9.0 | 8.0 | 7.0 | 8.0 |
| | .032 | 1.0 | 7.0 | 3.0 | 3.0 | 6.0 | 7.0 | 4.0 | 0.0 | 9.0 | 6.0 | 8.0 | 7.0 | 2.0 | 7.0 |
| Methyl 2-(5-cyclopropyl- | 1.000 | 9.0 | 9.0 | 8.0 | 9.0 | 7.0 | 8.0 | 8.0 | 8.0 | 9.0 | 9.0 | 8.0 | 8.0 | 9.0 | 9.0 |
| 5-methyl-4-oxo-2- | .500 | 7.0 | 9.0 | 7.0 | 4.0 | 4.0 | 8.0 | 8.0 | 4.0 | 9.0 | 8.0 | 7.0 | 8.0 | 9.0 | 9.0 |
| imidazolin-2-yl)- | .250 | 2.0 | 8.0 | 3.0 | 1.0 | 3.0 | 6.0 | 8.0 | 2.0 | 7.0 | 4.0 | 7.0 | 8.0 | 7.0 | 9.0 |
| nicotinate | .125 | 0.0 | 8.0 | 1.0 | 0.0 | 1.0 | 5.0 | 6.0 | 0.0 | 7.0 | 3.0 | 2.0 | 4.0 | 4.0 | 9.0 |
| | .063 | 0.0 | 6.0 | 0.0 | 0.0 | 1.0 | 4.0 | 4.0 | 0.0 | 4.0 | 2.0 | 0.0 | | 1.0 | 7.0 |
| | .032 | 0.0 | 2.0 | 0.0 | 0.0 | 1.0 | 3.0 | 3.0 | 0.0 | 3.0 | 0.0 | 0.0 | 2.0 | 1.0 | 2.0 |
| Hexyl 2-(5-isopropyl- | 8.000 | 9.0 | 9.0 | 9.0 | 9.0 | 9.0 | 2.0 | 8.0 | 8.0 | 9.0 | | | | | |
| 5-methyl-4-oxo-2- | 1.000 | 3.0 | 6.0 | 8.0 | 9.0 | 9.0 | 9.0 | 8.0 | 6.0 | 9.0 | 9.0 | 7.0 | 8.0 | 8.0 | 8.0 |
| imidazolin-2-yl)- | .500 | 1.0 | 4.0 | 6.0 | 6.0 | 8.0 | 8.0 | 8.0 | 2.0 | 8.0 | 9.0 | 6.0 | 8.0 | 4.0 | 7.0 |
| nicotinate | .250 | 1.0 | 4.0 | 3.0 | 6.0 | 8.0 | 6.0 | 7.0 | 1.0 | 8.0 | 9.0 | 3.0 | 8.0 | 4.0 | 7.0 |
| | .125 | 1.0 | 2.0 | 1.0 | 4.0 | 8.0 | 4.0 | 4.0 | 0.0 | 6.0 | 9.0 | 1.0 | 7.0 | 1.0 | 6.0 |
| | .063 | 0.0 | 1.0 | 1.0 | 0.0 | 6.0 | 3.0 | 3.0 | 0.0 | 4.0 | 8.0 | 1.0 | 4.0 | 1.0 | 2.0 |
| | .032 | 0.0 | 0.0 | 0.0 | 0.0 | 2.0 | 1.0 | 1.0 | 0.0 | 2.0 | 3.0 | 1.0 | 2.0 | 1.0 | 1.0 |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| 1-Methyl-2-butenyl 2-(5-isopropyl-5-methyl-4-oxo-2-imidazolin-2-yl)nicotinate | 8.000 | 9.0 | 9.0 | 9.0 | 9.0 | 9.0 | 7.0 | 9.0 | 9.0 | 9.0 | | | | | |
| | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 8.0 | 9.0 | 9.0 | 8.0 | 9.0 | 9.0 | 9.0 | 9.0 | 9.0 | 9.0 |
| | .063 | 9.0 | 9.0 | 8.0 | 9.0 | 8.0 | 9.0 | 9.0 | 8.0 | 9.0 | 9.0 | 9.0 | 9.0 | 8.0 | 8.0 |
| | .032 | 9.0 | 9.0 | 7.0 | 9.0 | 7.0 | 7.0 | 9.0 | 4.0 | 7.0 | 9.0 | 9.0 | 9.0 | 7.0 | 8.0 |
| Methyl 2-(4-isopropyl-1,4-dimethyl-5-oxo-2-imidazolin-2-yl)-nicotinate | 5.000 | 8.0 | 9.0 | 8.0 | 9.0 | 9.0 | 1.0 | 8.0 | 7.0 | 9.0 | | | | | |
| | 1.000 | 7.0 | 9.0 | 6.0 | 8.0 | 7.0 | 6.0 | 7.0 | 3.0 | 8.0 | 9.0 | 9.0 | 7.0 | 8.0 | 7.0 |
| | .500 | 1.0 | 8.0 | 2.0 | 6.0 | 4.0 | 6.0 | 7.0 | 1.0 | 7.0 | 4.0 | 9.0 | 6.0 | 7.0 | 7.0 |
| | .250 | 1.0 | 8.0 | 0.0 | 2.0 | 4.0 | 4.0 | 7.0 | 0.0 | 6.0 | 4.0 | 6.0 | 6.0 | 6.0 | 7.0 |
| | .125 | 1.0 | 6.0 | 0.0 | 0.0 | 4.0 | 2.0 | 4.0 | 0.0 | 4.0 | 2.0 | 2.0 | 6.0 | 4.0 | 3.0 |
| | .063 | 1.0 | 2.0 | 0.0 | 0.0 | 2.0 | 2.0 | 4.0 | 0.0 | 1.0 | 1.0 | 1.0 | 3.0 | 0.0 | 2.0 |
| | .032 | 0.0 | 1.0 | 0.0 | 0.0 | 1.0 | 1.0 | 1.0 | 0.0 | 0.0 | 0.0 | 0.0 | 2.0 | 0.0 | 2.0 |
| Methyl 2-(4-isopropyl-4-methyl-5-oxo-1-pivaloyl-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 8.0 | 9.0 |
| | .500 | 9.0 | 9.0 | 8.0 | 9.0 | 7.0 | 9.0 | 9.0 | 8.0 | 9.0 | 9.0 | 9.0 | 9.0 | 9.0 | 9.0 |
| | .250 | 9.0 | 9.0 | 8.0 | 9.0 | 7.0 | 9.0 | 6.0 | 4.0 | 9.0 | 9.0 | 9.0 | 9.0 | 9.0 | 9.0 |
| | .125 | 8.0 | 9.0 | 7.0 | 8.0 | 7.0 | 9.0 | 7.0 | 4.0 | 9.0 | 9.0 | 9.0 | 9.0 | 7.0 | 8.0 |
| | .063 | 6.0 | 9.0 | 2.0 | 6.0 | 7.0 | 7.0 | 3.0 | 1.0 | 8.0 | 8.0 | 8.0 | 9.0 | 6.0 | 7.0 |
| | .032 | 1.0 | 8.0 | 1.0 | 2.0 | 3.0 | 7.0 | 1.0 | 0.0 | 6.0 | 7.0 | 8.0 | 7.0 | 3.0 | 6.0 |
| Methyl 2-(4-oxo-1,3-diazaspiro[4.5]dec-2-en-2-yl)nicotinate | 8.000 | 9.0 | 9.0 | 8.0 | 9.0 | 9.0 | 0.0 | 8.0 | 4.0 | 9.0 | | | | | |
| | 1.000 | 3.0 | 9.0 | 7.0 | 9.0 | 6.0 | 7.0 | 1.0 | 2.0 | 9.0 | 9.0 | 1.0 | 7.0 | 8.0 | 4.0 |
| | .500 | 2.0 | 8.0 | 3.0 | 7.0 | 3.0 | 4.0 | 0.0 | 0.0 | 8.0 | 2.0 | 1.0 | 4.0 | 6.0 | 2.0 |
| | .250 | 0.0 | 8.0 | 2.0 | 2.0 | 3.0 | 4.0 | 0.0 | 0.0 | 9.0 | 1.0 | 0.0 | 4.0 | 3.0 | 0.0 |
| | .125 | 0.0 | 4.0 | 0.0 | 1.0 | 1.0 | 2.0 | 0.0 | 0.0 | 3.0 | 0.0 | 0.0 | 2.0 | 3.0 | 0.0 |
| | .063 | 0.0 | 1.0 | 0.0 | 0.0 | 1.0 | 1.0 | 0.0 | 0.0 | 2.0 | 0.0 | 0.0 | 0.0 | 1.0 | 0.0 |
| | .032 | 0.0 | 0.0 | 0.0 | 0.0 | 0.0 | 0.0 | 0.0 | 0.0 | 1.0 | 0.0 | 0.0 | 0.0 | 0.0 | 0.0 |
| 3-Methyl-2-butenyl 2-(5-isopropyl-5-methyl-4-oxo-2-imidazolin-2-yl)nicotinate | 8.000 | 9.0 | 9.0 | 9.0 | 9.0 | 9.0 | 9.0 | 9.0 | 9.0 | 9.0 | | | | | |
| | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .063 | 7.0 | 9.0 | 7.0 | 9.0 | 7.0 | 9.0 | 7.0 | 3.0 | 7.0 | 9.0 | 9.0 | 9.0 | 8.0 | 7.0 |
| | .032 | 2.0 | 7.0 | 7.0 | 7.0 | 6.0 | 8.0 | 7.0 | 1.0 | 6.0 | 8.0 | 2.0 | 8.0 | 7.0 | 6.0 |
| Benzyl 2-(4-oxo-1,3-diazaspiro[4.5]dec-2-en-2-yl)nicotinate | 8.000 | 9.0 | 9.0 | 9.0 | 9.0 | 9.0 | 3.0 | 9.0 | 7.0 | 9.0 | | | | | |
| | 1.000 | 0.0 | 7.0 | 2.0 | 0.0 | 3.0 | 7.0 | 2.0 | 0.0 | 2.0 | 4.0 | 1.0 | 3.0 | 3.0 | 0.0 |
| | .500 | 0.0 | 1.0 | 1.0 | 0.0 | 0.0 | 2.0 | 1.0 | 0.0 | 0.0 | 1.0 | 0.0 | 3.0 | 1.0 | 0.0 |
| | .250 | 0.0 | 0.0 | 0.0 | 0.0 | 0.0 | 0.0 | 0.0 | 0.0 | 0.0 | 0.0 | 0.0 | 2.0 | 0.0 | 0.0 |
| | .125 | 0.0 | 0.0 | 0.0 | 0.0 | 0.0 | 0.0 | 0.0 | 0.0 | 0.0 | 0.0 | 0.0 | 1.0 | 0.0 | 0.0 |
| | .063 | 0.0 | 0.0 | 0.0 | 0.0 | 0.0 | 0.0 | 0.0 | 0.0 | 0.0 | 0.0 | 0.0 | 0.0 | 0.0 | 0.0 |
| | .032 | 0.0 | 0.0 | 0.0 | 0.0 | 0.0 | 0.0 | 0.0 | 0.0 | 0.0 | 0.0 | 0.0 | 0.0 | 0.0 | 0.0 |
| 2-(5-Isopropyl-5-methyl-4-oxo-2-imidazolin-2-yl)-nicotinohydroxamic acid | 8.000 | 9.0 | 9.0 | 9.0 | 9.0 | 9.0 | 3.0 | 9.0 | 9.0 | 9.0 | | | | | |
| | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 8.0 | 9.0 | 9.0 | 9.0 | 8.0 | 9.0 | 9.0 | 9.0 | 9.0 | 8.0 |
| | .125 | 8.0 | 9.0 | 9.0 | 9.0 | 7.0 | 8.0 | 9.0 | 4.0 | 7.0 | 9.0 | 9.0 | 9.0 | 9.0 | 8.0 |
| | .063 | 6.0 | 9.0 | 2.0 | 9.0 | 7.0 | 8.0 | 8.0 | 2.0 | 7.0 | 7.0 | 9.0 | 8.0 | 9.0 | 7.0 |
| | .032 | 1.0 | 6.0 | 1.0 | 5.0 | 7.0 | 7.0 | 4.0 | 1.0 | 4.0 | 7.0 | 7.0 | 7.0 | 8.0 | 4.0 |
| Benzyl 2-(5-isopropyl-5-methyl-4-oxo-2-imidazolin-2-yl) nicotinate | 8.000 | 9.0 | 9.0 | 9.0 | 9.0 | 9.0 | 3.0 | 9.0 | 9.0 | 9.0 | | | | | |
| | 1.000 | 9.0 | 9.0 | 6.0 | 8.0 | 6.0 | 9.0 | 9.0 | 7.0 | 9.0 | 8.0 | 4.0 | 9.0 | 8.0 | 9.0 |
| | .500 | 9.0 | 9.0 | 1.0 | 8.0 | 6.0 | 8.0 | 8.0 | 5.0 | 9.0 | 9.0 | 4.0 | 9.0 | 7.0 | 7.0 |
| | .250 | 4.0 | 6.0 | 1.0 | 7.0 | 5.0 | 8.0 | 8.0 | 0.0 | 9.0 | 7.0 | 4.0 | 9.0 | 4.0 | 6.0 |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| | .125 | 1.0 | 5.0 | 0.0 | 3.0 | 2.0 | 7.0 | 8.0 | 0.0 | 7.0 | 6.0 | 3.0 | 9.0 | 3.0 | 4.0 |
| | .063 | 0.0 | 2.0 | 0.0 | 1.0 | 2.0 | 7.0 | 7.0 | 0.0 | 6.0 | 3.0 | 1.0 | 8.0 | 0.0 | 3.0 |
| | .032 | 0.0 | 1.0 | 0.0 | 0.0 | 1.0 | 4.0 | 6.0 | 0.0 | 3.0 | 1.0 | 0.0 | 7.0 | 0.0 | 1.0 |
| 6-methoxy-2-(5- | 5.000 | 9.0 | 9.0 | 9.0 | 9.0 | 9.0 | 2.0 | 8.0 | 9.0 | 9.0 | | | | | |
| isopropyl-5-methyl- | 1.000 | 9.0 | 9.0 | 9.0 | 9.0 | 9.0 | 9.0 | 9.0 | 8.0 | 9.0 | 9.0 | 9.0 | 9.0 | 9.0 | 9.0 |
| 4-oxo-2-imidazolin- | .500 | 9.0 | 9.0 | 9.0 | 9.0 | 9.0 | 9.0 | 9.0 | 7.0 | 9.0 | 9.0 | 9.0 | 9.0 | 9.0 | 9.0 |
| 2-yl)nicotinic acid | .250 | 9.0 | 9.0 | 9.0 | 9.0 | 9.0 | 9.0 | 9.0 | 8.0 | 8.0 | 9.0 | 9.0 | 9.0 | 9.0 | 9.0 |
| | .125 | 9.0 | 9.0 | 9.0 | 9.0 | 8.0 | 9.0 | 9.0 | 6.0 | 7.0 | 9.0 | 9.0 | 9.0 | 9.0 | 8.0 |
| | .063 | 9.0 | 8.0 | 8.0 | 9.0 | 7.0 | 8.0 | 9.0 | 3.0 | 3.0 | 7.0 | 9.0 | 7.0 | 9.0 | 8.0 |
| | .032 | 7.0 | 8.0 | 7.0 | 9.0 | 7.0 | 8.0 | 6.0 | 3.0 | 3.0 | 7.0 | 9.0 | 6.0 | 8.0 | 6.0 |
| 2-(4-oxo-1,3- | 1.000 | 9.0 | 9.0 | 7.0 | 9.0 | 7.0 | 9.0 | 4.0 | 6.0 | 9.0 | 9.0 | 9.0 | 9.0 | 9.0 | 5.0 |
| diazaspiro[4.5]- | .500 | 8.0 | 9.0 | 7.0 | 9.0 | 7.0 | 9.0 | 3.0 | | 9.0 | 9.0 | 9.0 | 8.0 | 8.0 | 4.0 |
| dec-2-en-2-yl) | .250 | 6.0 | 9.0 | 7.0 | 9.0 | 7.0 | 9.0 | 1.0 | 5.0 | 6.0 | 9.0 | 9.0 | 7.0 | 8.0 | 3.0 |
| nicotinic acid | .125 | 6.0 | 9.0 | 1.0 | 9.0 | 4.0 | 9.0 | 1.0 | 3.0 | 4.0 | 8.0 | 8.0 | 7.0 | 7.0 | 1.0 |
| | .063 | 1.0 | 4.0 | 1.0 | 1.0 | 3.0 | 4.0 | 1.0 | 0.0 | 1.0 | 3.0 | 3.0 | 3.0 | 2.0 | 1.0 |
| | .032 | 0.0 | 1.0 | 0.0 | 0.0 | 0.0 | 0.0 | 0.0 | 0.0 | 0.0 | 1.0 | 0.0 | 1.0 | 0.0 | 0.0 |
| α-Methylbenzylammonium | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-(5-isopropyl-5-methyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin-2- | .250 | 9.0 | 9.0 | 9.0 | 9.0 | 8.0 | 9.0 | 9.0 | 9.0 | 9.0 | 9.0 | 9.0 | 9.0 | 9.0 | 9.0 |
| yl)nicotinate | .125 | 9.0 | 9.0 | 9.0 | 9.0 | 8.0 | 9.0 | 9.0 | 9.0 | 9.0 | 9.0 | 9.0 | 9.0 | 9.0 | 8.0 |
| | .063 | 9.0 | 9.0 | 7.0 | 9.0 | 8.0 | 9.0 | 9.0 | 9.0 | 9.0 | 9.0 | 9.0 | 9.0 | 9.0 | 8.0 |
| | .032 | 9.0 | 8.0 | 7.0 | 9.0 | 8.0 | 9.0 | 8.0 | 2.0 | 9.0 | 9.0 | 9.0 | 9.0 | 9.0 | 8.0 |
| α-Cyclopropyl-5,7- | 5.000 | 9.0 | 9.0 | 9.0 | 9.0 | 9.0 | 1.0 | 9.0 | 9.0 | 9.0 | | | | | |
| dihydro-α-methyl-5,7- | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 |
| dioxo-6H—pyrrolo[3,4-b]- | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| pyridine-6-acetamide | .250 | 9.0 | 9.0 | 8.0 | 9.0 | 8.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 8.0 | 9.0 | 9.0 | 3.0 | 8.0 | 9.0 | 8.0 | 9.0 | 8.0 | 8.0 |
| | .063 | 7.0 | 9.0 | 2.0 | 7.0 | 7.0 | 9.0 | 7.0 | 2.0 | 8.0 | 9.0 | 4.0 | 9.0 | 8.0 | 8.0 |
| | .032 | 2.0 | 7.0 | 1.0 | 3.0 | 6.0 | 9.0 | 7.0 | 1.0 | 8.0 | 9.0 | 3.0 | 8.0 | 3.0 | 7.0 |
| 2-(5-cyclopropyl-5- | 8.000 | 9.0 | 9.0 | 9.0 | 9.0 | 9.0 | 7.0 | 9.0 | 9.0 | 9.0 | | | | | |
| methyl-4-oxo-2- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| imidazolin-2-yl)- | .500 | 9.0 | 9.0 | 9.0 | 9.0 | 9.0 | | 9.0 | 7.0 | 9.0 | 9.0 | 9.0 | 9.0 | 9.0 | 8.0 |
| nicotinic acid | .250 | 9.0 | 9.0 | 9.0 | 9.0 | 9.0 | 9.0 | 9.0 | 3.0 | 9.0 | 9.0 | 9.0 | 9.0 | 9.0 | 8.0 |
| | .125 | 9.0 | 9.0 | 8.0 | 8.0 | 9.0 | 9.0 | 9.0 | 3.0 | 9.0 | 9.0 | 9.0 | 9.0 | 8.0 | 7.0 |
| | .063 | 9.0 | 8.0 | 7.0 | 8.0 | 7.0 | 9.0 | 9.0 | 0.0 | 8.0 | 9.0 | 8.0 | 8.0 | 7.0 | 6.0 |
| | .032 | 7.0 | 6.0 | 0.0 | 3.0 | 2.0 | 9.0 | 6.0 | 0.0 | 8.0 | 4.0 | 7.0 | 8.0 | 6.0 | 4.0 |
| 1,1-Dimethyl-2-propynyl | 1.000 | 9.0 | 9.0 | 8.0 | 9.0 | 8.0 | 9.0 | 9.0 | 9.0 | 9.0 | 9.0 | 9.0 | 9.0 | 9.0 | 9.0 |
| 2-(5-isopropyl-5-methyl- | .500 | 9.0 | 9.0 | 8.0 | 9.0 | 8.0 | 9.0 | 9.0 | 8.0 | 9.0 | 9.0 | 9.0 | 9.0 | 9.0 | 8.0 |
| 4-oxo-2-imidazolin-2- | .250 | 9.0 | 8.0 | 8.0 | 9.0 | 7.0 | 9.0 | 9.0 | 8.0 | 9.0 | 9.0 | 9.0 | 9.0 | 9.0 | 8.0 |
| yl)nicotinate | .125 | 7.0 | 9.0 | 8.0 | 9.0 | 7.0 | 8.0 | 9.0 | 6.0 | 9.0 | 9.0 | 9.0 | 8.0 | 8.0 | 8.0 |
| | .063 | 7.0 | 7.0 | 7.0 | 9.0 | 7.0 | 8.0 | 9.0 | 6.0 | 9.0 | 9.0 | 8.0 | 8.0 | 8.0 | 8.0 |
| | .032 | 4.0 | 8.0 | 3.0 | 8.0 | 7.0 | 7.0 | 9.0 | 1.0 | 8.0 | 8.0 | 7.0 | 8.0 | 6.0 | 5.0 |
| 2-trimethylammoniumethyl | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-(5-isopropyl-5-methyl- | .500 | 9.0 | 9.0 | 8.0 | 9.0 | 8.0 | 9.0 | 9.0 | 9.0 | 9.0 | 9.0 | 9.0 | 9.0 | 9.0 | 9.0 |
| 4-oxo-2-imidazolin-2-yl)- | .250 | 9.0 | 9.0 | 8.0 | 9.0 | 7.0 | 9.0 | 9.0 | 8.0 | 9.0 | 9.0 | 9.0 | 9.0 | 9.0 | 9.0 |
| nicotinate iodide | .125 | 8.0 | 8.0 | 8.0 | 9.0 | 7.0 | 9.0 | 8.0 | 4.0 | 9.0 | 9.0 | 8.0 | 9.0 | 8.0 | 8.0 |
| | .063 | 7.0 | 8.0 | 8.0 | 9.0 | 6.0 | 8.0 | 8.0 | 1.0 | 9.0 | 9.0 | 8.0 | 9.0 | 9.0 | 7.0 |
| | .032 | 6.0 | 7.0 | 7.0 | 9.0 | 5.0 | 8.0 | 8.0 | 0.0 | 7.0 | 8.0 | 7.0 | 7.0 | 6.0 | 6.0 |
| N—(2-Hydroxyethyl)-2-(5-isopropyl-5-methyl-4-oxo-2-imidazolin-2-yl)nicotinamide | 8.000 | 7.0 | 9.0 | 9.0 | 9.0 | 9.0 | 0.0 | 7.0 | 6.0 | 7.0 | | | | | |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| Ammonium 2-(5-Isopropyl-5-methyl-4-oxo-2-imidazolin-2-yl)-nicotinate | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 7.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 7.0 | 9.0 | 9.0 | 9.0 | 9.0 | 7.0 | 9.0 | 9.0 | 9.0 | 9.0 | 9.0 | 9.0 |
| | .063 | 9.0 | 9.0 | 7.0 | 9.0 | 9.0 | 9.0 | 7.0 | 9.0 | 9.0 | 9.0 | 9.0 | 9.0 | 9.0 | 9.0 |
| | .032 | 8.0 | 8.0 | 6.0 | 9.0 | 8.0 | 9.0 | 9.0 | 7.0 | 9.0 | 9.0 | 9.0 | 9.0 | 8.0 | 8.0 |
| Methyl 2-(4-isopropyl-1-lauroyl-4-methyl-5-oxo-2-imidazolin-2-yl)-nicotinate | 8.000 | 9.0 | 9.0 | 9.0 | 9.0 | 9.0 | 3.0 | 9.0 | 9.0 | 9.0 | | | | | |
| | 1.000 | 9.0 | 9.0 | 9.0 | 9.0 | 8.0 | 9.0 | 9.0 | 8.0 | 9.0 | 9.0 | 9.0 | 9.0 | 8.0 | 9.0 |
| | .500 | 9.0 | 9.0 | 9.0 | 9.0 | 7.0 | 9.0 | 9.0 | 7.0 | 9.0 | 9.0 | 9.0 | 9.0 | 9.0 | 9.0 |
| | .250 | 9.0 | 9.0 | 7.0 | 9.0 | 7.0 | 9.0 | 3.0 | 7.0 | 9.0 | 9.0 | 9.0 | 9.0 | 8.0 | 8.0 |
| | .125 | 4.0 | 9.0 | 3.0 | 8.0 | 7.0 | 9.0 | 6.0 | 1.0 | 9.0 | 9.0 | 9.0 | 8.0 | 7.0 | 7.0 |
| | .063 | 4.0 | 9.0 | 0.0 | 6.0 | 4.0 | 7.0 | 6.0 | 0.0 | 6.0 | 3.0 | 8.0 | 7.0 | 3.0 | 7.0 |
| | .032 | 0.0 | 6.0 | 0.0 | 0.0 | 1.0 | 6.0 | 0.0 | 0.0 | 4.0 | 2.0 | 2.0 | 5.0 | 2.0 | 6.0 |
| 1,1-Dimethylallyl 2-(5-isopropyl-5-methyl-4-oxo-2-imidazolin-2-yl)-nicotinate | 8.000 | 9.0 | 9.0 | 9.0 | 9.0 | 9.0 | 7.0 | 9.0 | 9.0 | 9.0 | | | | | |
| | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 8.0 | 9.0 | 9.0 | 9.0 | 9.0 | 9.0 | 9.0 | 9.0 |
| 2-Propynyl 2-(5-cyclopropyl-5-methyl-4-oxo-2-imidazolin-2-yl)nicotinate | 8.000 | 9.0 | 9.0 | 9.0 | 9.0 | 9.0 | 9.0 | 7.0 | 2.0 | 9.0 | | | | | |
| | 1.000 | 9.0 | 8.0 | 7.0 | 9.0 | 8.0 | 9.0 | 9.0 | 9.0 | 9.0 | 9.0 | 9.0 | 9.0 | 9.0 | 8.0 |
| | .500 | 8.0 | 8.0 | 7.0 | 9.0 | 7.0 | 9.0 | 9.0 | 8.0 | 9.0 | 9.0 | 9.0 | 9.0 | 9.0 | 7.0 |
| | .250 | 6.0 | 7.0 | 4.0 | 9.0 | 6.0 | 9.0 | 9.0 | 6.0 | 5.0 | 9.0 | 8.0 | 9.0 | 8.0 | 6.0 |
| | .125 | 1.0 | 7.0 | 1.0 | 8.0 | 5.0 | 9.0 | 8.0 | 3.0 | 5.0 | 8.0 | 7.0 | 8.0 | 7.0 | 5.0 |
| | .063 | 1.0 | 3.0 | 0.0 | 4.0 | 4.0 | 6.0 | 4.0 | 3.0 | 3.0 | 7.0 | 7.0 | 7.0 | 4.0 | 5.0 |
| | .032 | 0.0 | 3.0 | 0.0 | 4.0 | 1.0 | 4.0 | 2.0 | 3.0 | 2.0 | 7.0 | 1.0 | 7.0 | 4.0 | 4.0 |
| 2-Propynyl 2-(4-oxo-1,3-diazaspiro[4.5]-dec-2-en-2-yl)nicotinate | 5.000 | 9.0 | 9.0 | 8.0 | 9.0 | 9.0 | 9.0 | 8.0 | 3.0 | 9.0 | | | | | |
| | 1.000 | 6.0 | 7.0 | 7.0 | 9.0 | 7.0 | 9.0 | 3.0 | 2.0 | 7.0 | 6.0 | 2.0 | 7.0 | 9.0 | 3.0 |
| | .500 | 6.0 | 6.0 | 2.0 | 9.0 | 3.0 | 9.0 | 1.0 | 2.0 | 6.0 | 9.0 | 1.0 | 6.0 | 9.0 | 2.0 |
| | .250 | 2.0 | 5.0 | 0.0 | 9.0 | 1.0 | 9.0 | 1.0 | 0.0 | 3.0 | 6.0 | 1.0 | 6.0 | 8.0 | 2.0 |
| | .125 | 0.0 | 4.0 | 0.0 | 7.0 | 1.0 | 7.0 | 0.0 | 0.0 | 1.0 | 8.0 | 1.0 | 4.0 | 8.0 | 2.0 |
| N—(2-Chloroethyl)-2-(5-isopropyl-5-methyl-4-oxo-2-imidazolin-2-yl)nicotinamide | 8.000 | 9.0 | 9.0 | 9.0 | 9.0 | 9.0 | 3.0 | 9.0 | 8.0 | 9.0 | | | | | |
| | 1.000 | 8.0 | 7.0 | 8.0 | 9.0 | 8.0 | 9.0 | 8.0 | 7.0 | 9.0 | 9.0 | 9.0 | 8.0 | 9.0 | 7.0 |
| | .500 | 6.0 | 6.0 | 7.0 | 9.0 | 7.0 | 9.0 | 7.0 | 7.0 | 8.0 | 9.0 | 8.0 | 8.0 | 7.0 | 7.0 |
| | .250 | 4.0 | 5.0 | 6.0 | 7.0 | 7.0 | 8.0 | 7.0 | | 6.0 | 8.0 | 8.0 | 8.0 | 6.0 | 6.0 |
| | .125 | 1.0 | 3.0 | 4.0 | 6.0 | 4.0 | 7.0 | 7.0 | 6.0 | 6.0 | 7.0 | 6.0 | 7.0 | 5.0 | 4.0 |
| | .063 | 1.0 | 3.0 | 2.0 | 6.0 | 4.0 | 6.0 | 4.0 | 1.0 | 6.0 | 9.0 | 6.0 | 6.0 | 4.0 | 3.0 |
| | .032 | 0.0 | 2.0 | 1.0 | 5.0 | 4.0 | 6.0 | 3.0 | 1.0 | 6.0 | 7.0 | 3.0 | 5.0 | 3.0 | 3.0 |
| p-Methoxybenzyl 2-(5-isopropyl-5-methyl-4-oxo-2-imidazolin-2-yl)nicotinate | 8.000 | 9.0 | 9.0 | 9.0 | 9.0 | 9.0 | 9.0 | 6.0 | 8.0 | 9.0 | | | | | |
| | 1.000 | 9.0 | 8.0 | 8.0 | 9.0 | 9.0 | 9.0 | 9.0 | 9.0 | 9.0 | 9.0 | 9.0 | 9.0 | 9.0 | 9.0 |
| | .500 | 9.0 | 8.0 | 7.0 | 9.0 | 9.0 | 9.0 | 9.0 | 9.0 | 9.0 | 9.0 | 9.0 | 9.0 | 9.0 | 9.0 |
| | .250 | 7.0 | 8.0 | 7.0 | 9.0 | 8.0 | 9.0 | 9.0 | 9.0 | 9.0 | 9.0 | 8.0 | 9.0 | 9.0 | 9.0 |
| | .125 | 6.0 | 8.0 | 7.0 | 9.0 | 8.0 | 9.0 | 9.0 | 3.0 | 9.0 | 9.0 | 8.0 | 8.0 | 8.0 | 7.0 |
| | .063 | 4.0 | 9.0 | 5.0 | 9.0 | 7.0 | 9.0 | 8.0 | 3.0 | 9.0 | 8.0 | 8.0 | 8.0 | 7.0 | 6.0 |
| | .032 | 2.0 | 7.0 | 2.0 | 7.0 | 7.0 | 9.0 | 7.0 | 0.0 | 7.0 | 8.0 | 8.0 | 7.0 | 7.0 | 4.0 |
| Barium 2-(5-isopropyl-5-methyl-4-oxo-2-imidazolin-2-yl)-nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 8.0 | 9.0 | 9.0 | 9.0 | 9.0 | 9.0 | 9.0 |
| | .250 | 9.0 | 9.0 | 8.0 | 9.0 | 9.0 | 9.0 | 9.0 | 7.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 7.0 | 9.0 | 9.0 | 9.0 | 9.0 | 8.0 | 8.0 |
| | .063 | 9.0 | 9.0 | 7.0 | 9.0 | 8.0 | 9.0 | 9.0 | 3.0 | 9.0 | 9.0 | 9.0 | 9.0 | 8.0 | 8.0 |
| | .032 | 8.0 | 8.0 | 7.0 | 9.0 | 8.0 | 9.0 | 8.0 | 3.0 | 9.0 | 9.0 | 9.0 | 9.0 | 7.0 | 7.0 |
| Cupric 2-(5-isopropyl-5-methyl-4-oxo-imidazolin-2-yl)nicotinate | 1.000 | 9.0 | 9.0 | 9.0 | 9.0 | 8.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 8.0 | 9.0 | 9.0 | 9.0 | 9.0 | 9.0 | 9.0 | 9.0 | 9.0 | 9.0 |
| | .250 | 9.0 | 8.0 | 7.0 | 9.0 | 7.0 | 9.0 | 9.0 | 8.0 | 9.0 | 9.0 | 9.0 | 9.0 | 9.0 | 9.0 |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| | .125 | 9.0 | 8.0 | 7.0 | 9.0 | 8.0 | 9.0 | 9.0 | 7.0 | 9.0 | 9.0 | 8.0 | 9.0 | 9.0 | 9.0 |
| | .063 | 9.0 | 8.0 | 6.0 | 9.0 | 7.0 | 9.0 | 8.0 | 7.0 | 9.0 | 9.0 | 8.0 | 9.0 | 9.0 | 8.0 |
| | .032 | 9.0 | 8.0 | 5.0 | 9.0 | 7.0 | 8.0 | 8.0 | 2.0 | 9.0 | 9.0 | 7.0 | 8.0 | 8.0 | 7.0 |
| Potassium 2-(5-isopropyl-5-methyl-4-oxo-2-imidazolin-2-yl)-nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 8.0 | 9.0 | 9.0 | 8.0 | 9.0 | 9.0 | 9.0 | 9.0 | 9.0 | 9.0 |
| | .125 | 9.0 | 9.0 | 7.0 | 9.0 | 7.0 | 9.0 | 9.0 | 8.0 | 9.0 | 9.0 | 9.0 | 9.0 | 9.0 | 9.0 |
| | .063 | 9.0 | 9.0 | 7.0 | 9.0 | 9.0 | 9.0 | 9.0 | 4.0 | 9.0 | 9.0 | 9.0 | 9.0 | 9.0 | 9.0 |
| | .032 | 9.0 | 9.0 | 7.0 | 9.0 | 8.0 | 9.0 | 9.0 | 2.0 | 9.0 | 9.0 | 9.0 | 9.0 | 8.0 | 7.0 |
| Lithium 2-(5-isopropyl-5-methyl-4-oxo-2-imidazolin-2-yl)nicotinate | 1.000 | 9.0 | 9.0 | 9.0 | 9.0 | 8.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 8.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 8.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 7.0 | 9.0 | 9.0 | 8.0 | 9.0 | 9.0 | 9.0 | 9.0 | 9.0 | 9.0 |
| | .063 | 9.0 | 9.0 | 7.0 | 9.0 | 8.0 | 9.0 | 9.0 | 6.0 | 9.0 | 9.0 | 9.0 | 9.0 | 9.0 | 8.0 |
| | .032 | 9.0 | 9.0 | 7.0 | 9.0 | 7.0 | 9.0 | 9.0 | 5.0 | 8.0 | 9.0 | 9.0 | 9.0 | 8.0 | 9.0 |
| Magnesium 2-(5-isopropyl-5-methyl-4-oxo-2-imidazolin-2-yl)nicotinate | 1.000 | 9.0 | 9.0 | 8.0 | 9.0 | 8.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .125 | 9.0 | 8.0 | 7.0 | 9.0 | 7.0 | 9.0 | 9.0 | 8.0 | 9.0 | 9.0 | 9.0 | 9.0 | 9.0 | 8.0 |
| | .063 | 9.0 | 8.0 | 8.0 | 9.0 | 8.0 | 9.0 | 9.0 | 7.0 | 9.0 | 9.0 | 9.0 | 9.0 | 9.0 | 8.0 |
| | .032 | 9.0 | 8.0 | 7.0 | 9.0 | 7.0 | 9.0 | 8.0 | 6.0 | 9.0 | 9.0 | 9.0 | 9.0 | 9.0 | 8.0 |
| Piperidinium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 7.0 | 9.0 | 9.0 | 9.0 | 9.0 | 9.0 | 8.0 |
| | .063 | 9.0 | 9.0 | 8.0 | 9.0 | 9.0 | 9.0 | 9.0 | 8.0 | 9.0 | 9.0 | 9.0 | 9.0 | 9.0 | 8.0 |
| | .032 | 9.0 | 9.0 | 7.0 | 9.0 | 9.0 | 9.0 | 9.0 | 3.0 | 9.0 | 9.0 | 9.0 | 9.0 | 9.0 | 7.0 |
| p-Chlorobenzyl 2-(5-isopropyl-5-methyl-4-oxo-2-imidazolin-2-yl)nicotinate | 8.000 | 9.0 | 9.0 | 9.0 | 9.0 | 9.0 | 9.0 | 6.0 | 9.0 | | | | | | |
| | 1.000 | 9.0 | 9.0 | 7.0 | 9.0 | 7.0 | 9.0 | 9.0 | 8.0 | 9.0 | 9.0 | 8.0 | 9.0 | 9.0 | 9.0 |
| | .500 | 7.0 | 7.0 | 7.0 | 9.0 | 7.0 | 8.0 | 9.0 | 8.0 | 9.0 | 9.0 | 8.0 | 8.0 | 7.0 | 8.0 |
| | .250 | 5.0 | 7.0 | 4.0 | 9.0 | 6.0 | 8.0 | 7.0 | 7.0 | 9.0 | 9.0 | 8.0 | 7.0 | 7.0 | 7.0 |
| | .125 | 4.0 | 6.0 | 3.0 | 8.0 | 6.0 | 8.0 | 7.0 | 4.0 | 7.0 | 8.0 | 6.0 | 7.0 | 5.0 | 7.0 |
| | .063 | 1.0 | 6.0 | 2.0 | 4.0 | 3.0 | 7.0 | 4.0 | 0.0 | 6.0 | 7.0 | 5.0 | 6.0 | 4.0 | 5.0 |
| | .032 | 0.0 | 3.0 | 0.0 | 4.0 | 1.0 | 4.0 | 3.0 | 0.0 | 5.0 | 6.0 | 4.0 | 5.0 | 1.0 | 3.0 |
| p-Nitrobenzyl 2-(5-isopropyl-5-methyl-4-oxo-2-imidazolin-2-yl)nicotinate | 8.000 | 9.0 | 9.0 | 9.0 | 9.0 | 9.0 | 9.0 | 8.0 | 9.0 | 9.0 | | | | | |
| | 1.000 | 9.0 | 9.0 | 7.0 | 9.0 | 9.0 | 9.0 | 9.0 | 9.0 | 9.0 | 9.0 | 9.0 | 9.0 | 9.0 | 9.0 |
| | .500 | 9.0 | 8.0 | 7.0 | 9.0 | 9.0 | 9.0 | 9.0 | 9.0 | 9.0 | 9.0 | 9.0 | 9.0 | 9.0 | 9.0 |
| | .250 | 9.0 | 8.0 | 7.0 | 9.0 | 8.0 | 9.0 | 9.0 | 6.0 | 9.0 | 9.0 | 9.0 | 9.0 | 9.0 | 9.0 |
| | .125 | 9.0 | 8.0 | 4.0 | 9.0 | 8.0 | 9.0 | 9.0 | 5.0 | 9.0 | 9.0 | 9.0 | 9.0 | 9.0 | 9.0 |
| | .063 | 7.0 | 7.0 | 4.0 | 9.0 | 7.0 | 9.0 | 8.0 | 4.0 | 8.0 | 9.0 | 9.0 | 8.0 | 8.0 | 6.0 |
| | .032 | 5.0 | 7.0 | 3.0 | 7.0 | 4.0 | 8.0 | 8.0 | 1.0 | 7.0 | 8.0 | 8.0 | 7.0 | 6.0 | 5.0 |
| Benzyltrimethyl-ammonium 2-(5-isopropyl-5-methyl-4-oxo-2-imidazolin-2-yl)nicotinate | 1.000 | 9.0 | 9.0 | 9.0 | | 9.0 | 9.0 | 9.0 | | 9.0 | 9.0 | 9.0 | | 9.0 | |
| | .500 | 3.0 | 9.0 | 6.0 | | 8.0 | 9.0 | 8.0 | 2.0 | 7.0 | | 9.0 | 8.0 | 8.0 | |
| | .250 | 3.0 | 8.0 | 1.0 | 7.0 | 4.0 | 7.0 | 7.0 | | 7.0 | 5.0 | 9.0 | 7.0 | 7.0 | 4.0 |
| | .125 | | 7.0 | 0.0 | 5.0 | 1.0 | 7.0 | 3.0 | 1.0 | 3.0 | 5.0 | 8.0 | 7.0 | 6.0 | 3.0 |
| | .063 | 2.0 | 7.0 | 0.0 | 5.0 | 1.0 | 6.0 | 3.0 | | 3.0 | 5.0 | 5.0 | 7.0 | 6.0 | 3.0 |
| Omega-Aminohexyl-ammonium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 8.0 | 9.0 | 9.0 | 9.0 | 8.0 | 8.0 | 9.0 | 9.0 | 9.0 | 9.0 | 9.0 | 8.0 |
| | .063 | 9.0 | 8.0 | 8.0 | 9.0 | 9.0 | 9.0 | 8.0 | 6.0 | 9.0 | 9.0 | 9.0 | 8.0 | 9.0 | 7.0 |
| | .032 | 8.0 | 8.0 | 1.0 | 9.0 | 9.0 | 9.0 | 6.0 | 3.0 | 9.0 | 9.0 | 9.0 | 8.0 | 9.0 | 7.0 |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| Tallowammonium 2-(5-isopropyl-5-methyl-4-oxo-2-imidazolin-2-yl)nicotinate | 8.000 | 9.0 | 9.0 | 9.0 | 9.0 | 9.0 | 1.0 | 9.0 | 9.0 | 9.0 | | | | | |
| | 1.000 | 9.0 | 9.0 | 9.0 | 9.0 | 9.0 | 9.0 | 9.0 | | 9.0 | 9.0 | 9.0 | 9.0 | 9.0 | 9.0 |
| | .500 | | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 8.0 |
| | .063 | 9.0 | 9.0 | 9.0 | 9.0 | 9.0 | 9.0 | 9.0 | 4.0 | 9.0 | 9.0 | 9.0 | 9.0 | 9.0 | 8.0 |
| | .032 | 9.0 | 9.0 | 7.0 | 9.0 | 9.0 | 9.0 | 9.0 | 3.0 | 9.0 | 9.0 | 9.0 | 9.0 | 9.0 | |
| Carbomethoxymethyl 2-(5-isopropyl-5-methyl-4-oxo-2-imidazolin-2-yl)-nicotinate | 8.000 | 9.0 | 9.0 | 9.0 | 9.0 | 9.0 | 9.0 | 8.0 | 9.0 | 9.0 | | | | | |
| | 1.000 | 9.0 | 8.0 | 8.0 | 9.0 | 9.0 | 9.0 | 9.0 | 9.0 | 9.0 | 9.0 | 9.0 | 9.0 | 9.0 | 9.0 |
| | .500 | 8.0 | 9.0 | 8.0 | 9.0 | 8.0 | 9.0 | 9.0 | 7.0 | 9.0 | 9.0 | 9.0 | 9.0 | 9.0 | 9.0 |
| | .250 | 9.0 | 9.0 | 8.0 | 9.0 | 8.0 | 9.0 | 9.0 | 7.0 | 9.0 | 9.0 | 8.0 | 8.0 | 8.0 | 7.0 |
| | .125 | 7.0 | 7.0 | 7.0 | 9.0 | 6.0 | 9.0 | 9.0 | 3.0 | 9.0 | 8.0 | 8.0 | 8.0 | 8.0 | 7.0 |
| | .063 | 6.0 | 6.0 | 6.0 | 8.0 | 6.0 | 8.0 | 8.0 | 1.0 | 7.0 | 7.0 | 8.0 | 7.0 | 7.0 | 5.0 |
| | .032 | 4.0 | 6.0 | 3.0 | 7.0 | 3.0 | 8.0 | 7.0 | 0.0 | 7.0 | 7.0 | 7.0 | 7.0 | 4.0 | 4.0 |
| Dodecylammonium 2-(5-isopropyl-5-methyl-4-oxo-2-imidazolin-2-yl)nicotinate | 8.000 | 9.0 | 9.0 | 9.0 | 9.0 | 9.0 | 1.0 | 9.0 | 9.0 | 9.0 | | | | | |
| | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | | 9.0 | 9.0 | 9.0 | 9.0 | 9.0 | 9.0 |
| | .125 | 9.0 | 8.0 | 9.0 | 9.0 | 9.0 | 9.0 | 9.0 | 4.0 | 9.0 | 9.0 | 9.0 | | 9.0 | 9.0 |
| | .063 | 9.0 | 8.0 | 9.0 | 9.0 | 9.0 | 9.0 | 9.0 | 3.0 | 8.0 | 9.0 | 9.0 | 9.0 | 9.0 | 9.0 |
| | .032 | 6.0 | 8.0 | 6.0 | 9.0 | 9.0 | 9.0 | 7.0 | 1.0 | 7.0 | 9.0 | 9.0 | 7.0 | 9.0 | 9.0 |
| 1,1,3,3-Tetramethyl-butylammonium 2-(5-isopropyl-5-methyl-4-oxo-2-imidazolin-2-yl)nicotinate | 8.000 | 9.0 | 9.0 | 9.0 | 9.0 | 9.0 | 1.0 | 9.0 | 9.0 | 9.0 | | | | | |
| | 1.000 | | 9.0 | 9.0 | 9.0 | 9.0 | 9.0 | 9.0 | 1.0 | 9.0 | | 9.0 | 9.0 | 9.0 | 8.0 |
| | .500 | | 9.0 | 7.0 | 9.0 | 8.0 | 9.0 | 9.0 | | 9.0 | 9.0 | 9.0 | 9.0 | 9.0 | 7.0 |
| | .250 | 3.0 | 9.0 | 6.0 | 9.0 | 8.0 | 9.0 | 8.0 | | 9.0 | 9.0 | 9.0 | 8.0 | 8.0 | |
| | .125 | 2.0 | 8.0 | 3.0 | | 7.0 | 9.0 | 8.0 | | 8.0 | 9.0 | 9.0 | | 7.0 | |
| | .063 | 1.0 | 7.0 | 0.0 | 4.0 | 2.0 | 4.0 | 3.0 | 0.0 | 3.0 | 3.0 | 7.0 | 7.0 | 3.0 | 4.0 |
| | .032 | 1.0 | 4.0 | 0.0 | 4.0 | 0.0 | 0.0 | 1.0 | 0.0 | 0.0 | 2.0 | 4.0 | 5.0 | 3.0 | 2.0 |
| Dibutylammonium 2-(5-isopropyl-5-methyl-4-oxo-2-imidazolin-2-yl)nicotinate | 8.000 | 9.0 | 9.0 | 9.0 | 9.0 | 9.0 | 6.0 | 9.0 | 9.0 | 9.0 | | | | | |
| | 1.000 | | 9.0 | 9.0 | 9.0 | 9.0 | 9.0 | 9.0 | 1.0 | 9.0 | 9.0 | 9.0 | 9.0 | 9.0 | 9.0 |
| | .500 | 9.0 | 9.0 | 7.0 | 9.0 | 9.0 | 9.0 | 9.0 | 0.0 | 9.0 | 9.0 | 9.0 | 9.0 | 9.0 | 7.0 |
| | .250 | 9.0 | 9.0 | 6.0 | 9.0 | 8.0 | 9.0 | 9.0 | | 9.0 | 9.0 | 9.0 | 9.0 | 7.0 | 5.0 |
| | .125 | | 8.0 | 3.0 | 9.0 | 7.0 | 9.0 | 8.0 | | 6.0 | 9.0 | 9.0 | 8.0 | 7.0 | 4.0 |
| | .063 | 4.0 | 8.0 | 1.0 | 8.0 | 5.0 | 8.0 | 6.0 | | 3.0 | 8.0 | 7.0 | 7.0 | 6.0 | 4.0 |
| | .032 | 4.0 | 6.0 | 0.0 | 7.0 | 0.0 | 6.0 | 2.0 | 0.0 | 0.0 | 6.0 | 4.0 | 6.0 | 4.0 | 2.0 |
| 2-(Methylamino)ethyl 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | | 9.0 | 9.0 | 9.0 | 9.0 | 9.0 | 9.0 |
| | .500 | 9.0 | 9.0 | 9.0 | 9.0 | | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 7.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 9.0 | 9.0 | 7.0 | 9.0 | 9.0 | 9.0 | 7.0 | 6.0 | 9.0 | 9.0 | 9.0 | 9.0 | 9.0 | 8.0 |
| | .032 | 4.0 | 9.0 | 7.0 | 9.0 | 9.0 | 9.0 | 6.0 | 2.0 | 9.0 | 9.0 | 9.0 | 8.0 | 9.0 | 7.0 |
| 1-Methylpyrrolidinium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 9.0 | 9.0 | 9.0 | 9.0 | 9.0 | 9.0 | 9.0 | 9.0 | 9.0 | 8.0 |
| | .125 | 9.0 | 9.0 | 8.0 | 9.0 | 9.0 | 9.0 | 9.0 | 8.0 | 9.0 | 9.0 | 9.0 | 9.0 | 9.0 | 7.0 |
| | .063 | 8.0 | 9.0 | 8.0 | 9.0 | 9.0 | 9.0 | 7.0 | 5.0 | 9.0 | 9.0 | 9.0 | 9.0 | 9.0 | 7.0 |
| | .032 | 8.0 | 8.0 | 7.0 | 9.0 | 7.0 | 9.0 | 6.0 | 3.0 | 9.0 | 9.0 | 9.0 | 9.0 | 9.0 | 7.0 |
| Octylammonium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .380 | 9.0 | 9.0 | 8.0 | 9.0 | 9.0 | 9.0 | 9.0 | 8.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .190 | 9.0 | 9.0 | 7.0 | 9.0 | 9.0 | 9.0 | 9.0 | 7.0 | 9.0 | 9.0 | 9.0 | 9.0 | 9.0 | 8.0 |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .095 | 9.0 | 9.0 | 6.0 | 9.0 | 9.0 | 9.0 | 9.0 | 5.0 | 9.0 | 9.0 | 9.0 | 9.0 | 9.0 | 9.0 |
| Benzylammonium 2-(5-isopropyl-5-methyl-4-oxo-2-imidazolin-2-yl)nicotinate | 8.000 | 9.0 | 9.0 | 9.0 | 9.0 | 9.0 | 1.0 | 9.0 | 9.0 | 9.0 | | | | | |
| | 1.000 | | 9.0 | 9.0 | 9.0 | 9.0 | 9.0 | 9.0 | 9.0 | 9.0 | 9.0 | 9.0 | 9.0 | 9.0 | 9.0 |
| | .500 | 4.0 | 7.0 | 8.0 | 9.0 | 9.0 | 9.0 | 9.0 | | 7.0 | 9.0 | 9.0 | 9.0 | 9.0 | 7.0 |
| | .250 | | 9.0 | 8.0 | 9.0 | 9.0 | 9.0 | 7.0 | 4.0 | 9.0 | 9.0 | 9.0 | 9.0 | 9.0 | 5.0 |
| | .125 | | 8.0 | 1.0 | 8.0 | 6.0 | 8.0 | 7.0 | 1.0 | 3.0 | 7.0 | 9.0 | 8.0 | 9.0 | 4.0 |
| | .063 | | 8.0 | 0.0 | 9.0 | 1.0 | 4.0 | 6.0 | 0.0 | 1.0 | 7.0 | 7.0 | 7.0 | 7.0 | 3.0 |
| | .032 | 0.0 | 7.0 | 0.0 | 6.0 | 0.0 | 1.0 | 4.0 | 0.0 | 1.0 | 7.0 | 2.0 | 5.0 | 5.0 | 2.0 |
| Cyclohexlammonium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .350 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .175 | 9.0 | 9.0 | 8.0 | 9.0 | 9.0 | 9.0 | 9.0 | 7.0 | 9.0 | 9.0 | 9.0 | 9.0 | 9.0 | 8.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| Morpholinium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .063 | 9.0 | 9.0 | 8.0 | 9.0 | 9.0 | 9.0 | 8.0 | 7.0 | 9.0 | 9.0 | 9.0 | 9.0 | 9.0 | 9.0 |
| | .032 | 9.0 | 9.0 | 7.0 | 9.0 | 9.0 | 9.0 | 7.0 | 6.0 | 9.0 | 9.0 | 9.0 | 9.0 | 9.0 | 8.0 |
| 4-Phenylbutylammonium 2-(5-isopropyl-methyl-4-oxo-2-imidazolin-2-yl)nicotinate | 8.000 | 9.0 | 9.0 | 9.0 | 9.0 | 9.0 | 4.0 | 9.0 | 9.0 | 9.0 | | | | | |
| | 1.000 | 9.0 | 9.0 | 9.0 | 9.0 | 9.0 | 9.0 | 9.0 | | 9.0 | 9.0 | 9.0 | 9.0 | 9.0 | 8.0 |
| | .500 | 9.0 | 9.0 | 9.0 | 9.0 | 9.0 | 9.0 | 9.0 | 7.0 | 9.0 | 9.0 | 9.0 | 9.0 | 9.0 | 8.0 |
| | .250 | | 9.0 | 8.0 | 9.0 | 8.0 | 9.0 | 7.0 | | 9.0 | 9.0 | 9.0 | 8.0 | 8.0 | 6.0 |
| | .125 | 4.0 | 7.0 | 2.0 | 9.0 | 5.0 | 8.0 | 7.0 | 3.0 | 3.0 | 7.0 | 8.0 | | 8.0 | 4.0 |
| | .063 | 4.0 | 9.0 | 0.0 | 7.0 | 7.0 | 7.0 | 4.0 | 0.0 | 4.0 | 7.0 | 7.0 | 7.0 | 8.0 | 6.0 |
| | .032 | 2.0 | 6.0 | 0.0 | 7.0 | 5.0 | 3.0 | 2.0 | 0.0 | 3.0 | 7.0 | 2.0 | | 7.0 | 3.0 |
| Phenethylammonium 2-(5-isopropyl-5-methyl-4-oxo-2-imidazolin-2-yl) nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .370 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .185 | 9.0 | 9.0 | 8.0 | 9.0 | 9.0 | 9.0 | 9.0 | 8.0 | 9.0 | 9.0 | 9.0 | 9.0 | 9.0 | 8.0 |
| | .125 | 9.0 | 9.0 | 8.0 | 9.0 | 9.0 | 9.0 | 9.0 | 9.0 | 9.0 | 9.0 | 9.0 | 9.0 | 9.0 | 8.0 |
| | .093 | 9.0 | 9.0 | 8.0 | 9.0 | 9.0 | 9.0 | 7.0 | 4.0 | 9.0 | 9.0 | 9.0 | 9.0 | 9.0 | 8.0 |
| Dimethoxymethyl-ammonium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 8.0 | 9.0 | 9.0 | 9.0 | 9.0 | 9.0 | 9.0 | 8.0 | 9.0 | 9.0 | 9.0 | 9.0 | 9.0 | 8.0 |
| | .032 | 7.0 | 9.0 | 7.0 | 9.0 | 9.0 | 9.0 | 5.0 | 4.0 | 9.0 | 9.0 | 9.0 | 9.0 | 9.0 | 8.0 |
| 2,2'-Diethoxydiethyl-ammonium 2-(5-isopropyl-5-methyl-4-oxo-2-imidazolin-2-yl)-nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 7.0 | 9.0 | 8.0 | 9.0 | 9.0 | 9.0 | 9.0 | 9.0 | 9.0 | 9.0 | 9.0 | 9.0 | 9.0 | 8.0 |
| | .063 | 7.0 | 9.0 | 8.0 | 9.0 | 9.0 | 9.0 | 9.0 | 5.0 | 9.0 | 9.0 | 9.0 | 9.0 | 9.0 | 8.0 |
| | .032 | 3.0 | 9.0 | 8.0 | 9.0 | 9.0 | 9.0 | 9.0 | 2.0 | 9.0 | 9.0 | 9.0 | 9.0 | 9.0 | 8.0 |
| 3-Methoxypropylammonium 2-(5-isopropyl-5-methyl-4-oxo-2-imidazolin-2-yl)-nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .340 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .170 | 9.0 | 9.0 | 9.0 | 9.0 | 9.0 | 9.0 | 9.0 | 9.0 | 9.0 | 9.0 | 9.0 | 9.0 | 9.0 | 9.0 |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| | .125 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .085 | 9.0 | 9.0 | 7.0 | 9.0 | 9.0 | 9.0 | 9.0 | 5.0 | 9.0 | 9.0 | 9.0 | 9.0 | 9.0 | 8.0 |
| 3-Carboethoxypropyl 2- | 8.000 | 9.0 | 8.0 | 9.0 | 9.0 | 9.0 | 9.0 | 9.0 | 9.0 | 9.0 | | | | | |
| (5-isopropyl-5-methyl- | 1.000 | 9.0 | 9.0 | 7.0 | 9.0 | 9.0 | 9.0 | 9.0 | 9.0 | 9.0 | 9.0 | 9.0 | 9.0 | 9.0 | 9.0 |
| 4-oxo-2-imidazolin-2- | .500 | 7.0 | 7.0 | 7.0 | 9.0 | 7.0 | 9.0 | 9.0 | 7.0 | 9.0 | 9.0 | 8.0 | 9.0 | 8.0 | 8.0 |
| yl)nicotinate | .250 | 7.0 | 7.0 | 6.0 | 9.0 | 6.0 | 9.0 | 9.0 | 7.0 | 9.0 | 8.0 | 7.0 | 8.0 | 7.0 | 7.0 |
| | .125 | 4.0 | 6.0 | 4.0 | 7.0 | 3.0 | 8.0 | 6.0 | 3.0 | 9.0 | 8.0 | 7.0 | 7.0 | 6.0 | 6.0 |
| | .063 | 1.0 | 6.0 | 2.0 | 5.0 | 2.0 | 8.0 | 4.0 | 0.0 | 7.0 | 6.0 | 6.0 | 5.0 | 3.0 | 5.0 |
| | .032 | 1.0 | 3.0 | 1.0 | 2.0 | 1.0 | 5.0 | 3.0 | 0.0 | 6.0 | 5.0 | 3.0 | | 2.0 | 2.0 |
| 1-Carbomethoxyethyl 2- | 8.000 | 9.0 | 9.0 | 9.0 | 9.0 | 9.0 | 9.0 | 8.0 | 9.0 | 9.0 | | | | | |
| (5-isopropyl-5-methyl- | 1.000 | 9.0 | 8.0 | 8.0 | 9.0 | 8.0 | 9.0 | 9.0 | 9.0 | 9.0 | 9.0 | 8.0 | 9.0 | 8.0 | 9.0 |
| 4-oxo-2-imidazolin-2- | .500 | 8.0 | 8.0 | 7.0 | 9.0 | 7.0 | 8.0 | 8.0 | 7.0 | 9.0 | 9.0 | 8.0 | 9.0 | 9.0 | 8.0 |
| yl)nicotinate | .250 | 7.0 | 9.0 | 6.0 | 8.0 | 6.0 | 8.0 | 7.0 | 1.0 | 8.0 | 9.0 | 8.0 | 9.0 | 9.0 | 8.0 |
| | .125 | 6.0 | 7.0 | 3.0 | 8.0 | 5.0 | 7.0 | 7.0 | 1.0 | | 7.0 | 8.0 | 8.0 | 7.0 | 8.0 |
| | .063 | 3.0 | 6.0 | 2.0 | 7.0 | 4.0 | 6.0 | 6.0 | 1.0 | | 6.0 | 5.0 | 7.0 | 4.0 | 7.0 |
| | .032 | 2.0 | 3.0 | 0.0 | 2.0 | 1.0 | 4.0 | 3.0 | 0.0 | 4.0 | 5.0 | 3.0 | 6.0 | 1.0 | 4.0 |
| Methyl 5-bromo-2-(5- | 8.000 | 9.0 | 9.0 | 9.0 | 9.0 | 9.0 | 9.0 | 9.0 | 9.0 | 9.0 | | | | | |
| isopropyl-5-methyl- | 1.000 | 4.0 | 5.0 | 7.0 | 8.0 | 5.0 | 3.0 | 4.0 | 6.0 | 5.0 | 6.0 | 8.0 | 7.0 | 8.0 | 6.0 |
| 4-oxo-2-imidazolin- | .500 | 3.0 | 3.0 | 6.0 | 7.0 | 3.0 | 2.0 | 3.0 | 8.0 | 3.0 | 7.0 | 8.0 | 6.0 | 6.0 | 5.0 |
| 2-yl)nicotinate | .250 | 2.0 | 3.0 | 3.0 | 7.0 | 3.0 | 0.0 | 2.0 | 7.0 | 3.0 | 3.0 | 5.0 | 3.0 | 6.0 | 2.0 |
| | .125 | 1.0 | 2.0 | 1.0 | 7.0 | 2.0 | 0.0 | 0.0 | 6.0 | 1.0 | 3.0 | 3.0 | 2.0 | 6.0 | 2.0 |
| | .063 | 0.0 | 2.0 | 1.0 | 6.0 | 1.0 | 0.0 | 0.0 | 6.0 | 1.0 | 2.0 | 3.0 | 1.0 | 4.0 | 2.0 |
| | .032 | 0.0 | 1.0 | 0.0 | 2.0 | 1.0 | 0.0 | 0.0 | 0.0 | 0.0 | 2.0 | 3.0 | 1.0 | 3.0 | 1.0 |
| 3-Carboethoxy-2- | 8.000 | 9.0 | 9.0 | 9.0 | 9.0 | 9.0 | 9.0 | 8.0 | 9.0 | 9.0 | | | | | |
| propenyl 2-(5- | 1.000 | 9.0 | 9.0 | 7.0 | 9.0 | 8.0 | 9.0 | 9.0 | 8.0 | 9.0 | 9.0 | 9.0 | 9.0 | 9.0 | 9.0 |
| isopropyl-5-methyl- | .500 | 9.0 | 9.0 | 7.0 | 9.0 | 8.0 | 9.0 | 9.0 | 8.0 | 9.0 | 9.0 | 9.0 | 9.0 | 9.0 | 9.0 |
| 4-oxo-2-imidazolin- | .250 | 9.0 | 8.0 | 7.0 | 9.0 | 8.0 | 9.0 | 9.0 | 6.0 | 9.0 | 9.0 | 9.0 | 8.0 | 9.0 | 9.0 |
| 2-yl)nicotinate | .125 | 7.0 | 7.0 | 7.0 | 9.0 | 7.0 | 9.0 | 9.0 | 2.0 | 9.0 | 9.0 | 8.0 | 9.0 | 9.0 | 8.0 |
| | .063 | 5.0 | 6.0 | 4.0 | 8.0 | 6.0 | 8.0 | 8.0 | 1.0 | 9.0 | 7.0 | 8.0 | 7.0 | 7.0 | 7.0 |
| | .032 | 3.0 | 4.0 | 2.0 | 7.0 | 3.0 | 8.0 | 6.0 | 0.0 | 6.0 | 8.0 | 6.0 | 6.0 | 6.0 | 4.0 |
| 3-Butenyl 2-(5- | 8.000 | 9.0 | 9.0 | 9.0 | 9.0 | 9.0 | 9.0 | 8.0 | 9.0 | 9.0 | | | | | |
| isopropyl-5-methyl | 1.000 | 9.0 | 8.0 | 8.0 | 9.0 | 8.0 | 9.0 | 9.0 | 9.0 | 9.0 | 9.0 | 9.0 | 9.0 | 9.0 | 9.0 |
| 4-oxo-2-imidazolin- | .500 | 9.0 | 9.0 | 8.0 | 9.0 | 8.0 | 9.0 | 9.0 | 9.0 | 9.0 | 9.0 | 9.0 | 9.0 | 9.0 | 9.0 |
| 2-yl)nicotinate | .250 | 9.0 | 8.0 | 7.0 | 9.0 | 8.0 | 9.0 | 9.0 | 4.0 | 9.0 | 9.0 | 9.0 | 9.0 | 8.0 | 9.0 |
| | .125 | 9.0 | 8.0 | 6.0 | 9.0 | 7.0 | 9.0 | 9.0 | 2.0 | 8.0 | 9.0 | 9.0 | 9.0 | 9.0 | 7.0 |
| | .063 | 8.0 | 7.0 | 4.0 | 9.0 | 7.0 | 8.0 | 8.0 | 1.0 | 7.0 | 8.0 | 8.0 | 8.0 | 9.0 | 7.0 |
| | .032 | 1.0 | 6.0 | 1.0 | 8.0 | 4.0 | 6.0 | 8.0 | 0.0 | 6.0 | 7.0 | 8.0 | 7.0 | 7.0 | 2.0 |
| 4-Carbomethoxybutyl | 8.000 | 9.0 | 9.0 | 9.0 | 9.0 | 9.0 | 9.0 | 8.0 | 9.0 | 9.0 | | | | | |
| 2-(5-isopropyl-5- | 1.000 | 8.0 | 9.0 | 6.0 | 9.0 | 7.0 | 8.0 | 9.0 | 8.0 | 9.0 | 9.0 | 8.0 | 8.0 | 8.0 | 9.0 |
| methyl-4-oxo-2- | .500 | 7.0 | 8.0 | 6.0 | 9.0 | 6.0 | 9.0 | 8.0 | 7.0 | 9.0 | 9.0 | 8.0 | 8.0 | 8.0 | 9.0 |
| imidazolin-2-yl)- | .250 | 6.0 | 7.0 | 5.0 | 9.0 | 4.0 | 8.0 | 8.0 | 2.0 | 7.0 | 7.0 | 6.0 | 8.0 | 7.0 | 7.0 |
| nicotinate | .125 | 3.0 | 6.0 | 0.0 | 7.0 | 3.0 | 8.0 | 7.0 | 0.0 | 7.0 | 7.0 | 4.0 | 7.0 | 6.0 | 7.0 |
| | .063 | 1.0 | 3.0 | 0.0 | 6.0 | 0.0 | 7.0 | 6.0 | 0.0 | 6.0 | 5.0 | 3.0 | 6.0 | 3.0 | 3.0 |
| | .032 | 0.0 | 2.0 | 0.0 | 5.0 | 0.0 | 6.0 | 4.0 | 0.0 | 4.0 | 4.0 | 2.0 | 2.0 | 2.0 | 2.0 |
| Ferrous 2-(5- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| isopropyl-5-methyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin- | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-yl)nicotinate | .125 | 9.0 | 9.0 | 9.0 | 9.0 | 9.0 | 9.0 | 9.0 | | 9.0 | 9.0 | 9.0 | 9.0 | 9.0 | 9.0 |
| | .063 | 9.0 | 9.0 | 9.0 | 9.0 | 9.0 | 9.0 | 9.0 | | 9.0 | 9.0 | 9.0 | 9.0 | 9.0 | 8.0 |
| | .032 | 9.0 | 9.0 | 9.0 | 9.0 | 9.0 | 9.0 | 9.0 | 6.0 | 9.0 | 9.0 | 9.0 | 9.0 | 9.0 | 7.0 |
| Ferric 2-(5-isopropyl- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| 5-methyl-4-oxo-2- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| imidazolin-2-yl)- | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| nicotinate | .125 | 9.0 | 9.0 | 9.0 | 9.0 | 9.0 | 9.0 | 9.0 | 9.0 | 9.0 | 9.0 | 9.0 | 9.0 | 9.0 | 8.0 |
| | .063 | 9.0 | 9.0 | 9.0 | 9.0 | 9.0 | 9.0 | 9.0 | 9.0 | 9.0 | 9.0 | 9.0 | 9.0 | 9.0 | 8.0 |
| | .032 | 9.0 | 9.0 | 9.0 | 9.0 | 9.0 | 9.0 | 9.0 | 9.0 | 9.0 | 9.0 | 9.0 | 9.0 | 9.0 | 8.0 |
| Diethanolammonium 2- | 8.000 | 9.0 | 9.0 | 9.0 | 9.0 | 9.0 | 7.0 | 9.0 | 9.0 | 9.0 | | | | | |
| (5-isopropyl-5-methyl- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-yl)nicotinate | .250 | 9.0 | 9.0 | 9.0 | 9.0 | 9.0 | 9.0 | 9.0 | 3.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 8.0 | 9.0 | 9.0 | 9.0 | 9.0 | 9.0 | 8.0 |
| | .063 | 9.0 | 9.0 | 8.0 | 9.0 | 9.0 | 9.0 | 9.0 | 4.0 | 9.0 | 9.0 | 9.0 | 9.0 | 9.0 | 7.0 |
| | .032 | 9.0 | 9.0 | 7.0 | 9.0 | 9.0 | 9.0 | 9.0 | | 9.0 | 9.0 | 9.0 | 9.0 | 9.0 | 7.0 |
| p-tert-Butylbenzyl | 8.000 | 9.0 | 9.0 | 9.0 | 9.0 | 9.0 | 9.0 | 8.0 | 9.0 | 9.0 | | | | | |
| 2-(5-isopropyl-5- | 1.000 | 6.0 | 7.0 | 6.0 | 9.0 | 8.0 | 9.0 | 9.0 | 7.0 | 9.0 | 8.0 | 8.0 | 7.0 | 8.0 | 8.0 |
| methyl-4-oxo-2- | .500 | 6.0 | 6.0 | 4.0 | 8.0 | 8.0 | 9.0 | 9.0 | 5.0 | 9.0 | 7.0 | 8.0 | 7.0 | 7.0 | 7.0 |
| imidazolin-2-yl)- | .250 | 4.0 | 6.0 | 2.0 | 8.0 | 6.0 | 7.0 | 8.0 | 5.0 | 7.0 | 7.0 | 6.0 | 6.0 | 5.0 | 7.0 |
| nicotinate | | | | | | | | | | | | | | | |
| Phenethyl 2-(5- | 8.000 | 9.0 | 9.0 | 9.0 | 9.0 | 9.0 | 9.0 | 9.0 | 8.0 | 9.0 | | | | | |
| isopropyl-5-methyl- | 1.000 | 9.0 | 9.0 | 7.0 | 9.0 | 8.0 | 9.0 | 9.0 | 7.0 | 9.0 | 9.0 | 9.0 | 8.0 | 9.0 | 8.0 |
| 4-oxo-2-imidazolin- | .500 | 9.0 | 8.0 | 7.0 | 9.0 | 7.0 | 9.0 | 9.0 | 7.0 | 9.0 | 9.0 | 9.0 | 8.0 | 9.0 | 8.0 |
| 2-yl)nicotinate | .250 | 9.0 | 7.0 | 7.0 | 9.0 | 6.0 | 7.0 | 8.0 | 6.0 | 9.0 | 9.0 | 8.0 | 7.0 | 8.0 | 8.0 |
| | .125 | 3.0 | 7.0 | 2.0 | 9.0 | 6.0 | 7.0 | 8.0 | 2.0 | 9.0 | 9.0 | 8.0 | 6.0 | 6.0 | 6.0 |
| | .063 | 1.0 | 3.0 | 2.0 | 7.0 | 6.0 | 7.0 | 7.0 | 0.0 | 7.0 | 8.0 | 5.0 | 5.0 | 3.0 | 4.0 |
| | .032 | 0.0 | 1.0 | 0.0 | 5.0 | 5.0 | 4.0 | 5.0 | 0.0 | 3.0 | 7.0 | 4.0 | 5.0 | 2.0 | |
| Cinnamyl 2-(5- | 8.000 | 9.0 | 9.0 | 9.0 | 9.0 | 9.0 | 3.0 | 9.0 | 9.0 | 9.0 | | | | | |
| isopropyl-5-methyl- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin- | .500 | 9.0 | 9.0 | 6.0 | 9.0 | 9.0 | 9.0 | 9.0 | 9.0 | 9.0 | 9.0 | 9.0 | 9.0 | 9.0 | 9.0 |
| 2-yl)nicotinate | .250 | 9.0 | 9.0 | 8.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 7.0 | 9.0 | 9.0 | 9.0 | 9.0 | 6.0 | 9.0 | 9.0 | 9.0 | 9.0 | 9.0 | 8.0 |
| | .063 | 8.0 | 7.0 | 5.0 | 9.0 | 9.0 | 9.0 | 8.0 | 4.0 | 8.0 | 9.0 | 9.0 | 9.0 | 8.0 | 7.0 |
| | .032 | 7.0 | 6.0 | 4.0 | 7.0 | 7.0 | 9.0 | 7.0 | 3.0 | 8.0 | 9.0 | 7.0 | 7.0 | 8.0 | 6.0 |
| 5-α-Hydroxy-3α- | 8.000 | 9.0 | 9.0 | 9.0 | 9.0 | 9.0 | 3.0 | 9.0 | 9.0 | 9.0 | | | | | |
| isopropyl-3-methyl | 1.000 | 9.0 | 9.0 | 8.0 | 9.0 | 9.0 | 9.0 | 9.0 | 9.0 | 9.0 | 9.0 | 9.0 | 8.0 | 9.0 | 9.0 |
| 5H—imidazo[1',2':1,2]- | .500 | 9.0 | 9.0 | 7.0 | 9.0 | 9.0 | 9.0 | 9.0 | 9.0 | 9.0 | 9.0 | 9.0 | 8.0 | 9.0 | 9.0 |
| pyrrolo[3,4-b]pyridin- | .250 | 7.0 | 7.0 | 6.0 | 9.0 | 9.0 | 9.0 | 8.0 | 8.0 | 9.0 | 8.0 | 7.0 | 8.0 | 7.0 | 9.0 |
| 2-(3H)dione | .125 | 8.0 | 7.0 | 6.0 | 7.0 | 7.0 | 9.0 | 8.0 | 8.0 | 6.0 | 8.0 | 4.0 | 7.0 | 7.0 | 7.0 |
| | .063 | 3.0 | 7.0 | 4.0 | 7.0 | 7.0 | 8.0 | 8.0 | 7.0 | 7.0 | 6.0 | 4.0 | 7.0 | 5.0 | 7.0 |
| | .032 | 0.0 | 4.0 | 1.0 | 4.0 | 6.0 | 7.0 | 7.0 | 6.0 | 2.0 | 1.0 | 3.0 | 4.0 | 3.0 | 3.0 |
| 5-Isopropyl-5-methyl- | 8.000 | 0.0 | 7.0 | 9.0 | 9.0 | 9.0 | 5.0 | 8.0 | 7.0 | 8.0 | | | | | |
| 2-(3-methyl-2-pyridyl)- | 1.000 | 0.0 | 0.0 | 0.0 | 0.0 | 6.0 | 4.0 | 2.0 | 0.0 | 4.0 | 0.0 | 0.0 | 0.0 | 0.0 | 2.0 |
| 2-imidazolin-4-one | .500 | 0.0 | 0.0 | 0.0 | 0.0 | 2.0 | 3.0 | 0.0 | 0.0 | 3.0 | 0.0 | 0.0 | 0.0 | 0.0 | 1.0 |
| | .250 | 0.0 | 0.0 | 0.0 | 0.0 | 0.0 | 3.0 | 0.0 | 0.0 | 2.0 | 0.0 | 0.0 | 0.0 | 0.0 | 1.0 |
| | .125 | 0.0 | 0.0 | 0.0 | 0.0 | 0.0 | 1.0 | 0.0 | 0.0 | 1.0 | 0.0 | 0.0 | 0.0 | 0.0 | 1.0 |
| | .063 | 0.0 | 0.0 | 0.0 | 0.0 | 0.0 | 0.0 | 0.0 | 0.0 | 1.0 | 0.0 | 0.0 | 0.0 | 0.0 | 0.0 |
| | .032 | 0.0 | 0.0 | 0.0 | 0.0 | 0.0 | 0.0 | 0.0 | 0.0 | 1.0 | 0.0 | 0.0 | 0.0 | 0.0 | 0.0 |
| 3,7-Dimethyl-2,6- | 8.000 | 9.0 | 9.0 | 9.0 | 9.0 | 9.0 | 2.0 | 9.0 | 9.0 | 9.0 | | | | | |
| octadienyl 2-(5- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| isopropyl-5-methyl- | .500 | 9.0 | 9.0 | 8.0 | 9.0 | 9.0 | 9.0 | 9.0 | 8.0 | 9.0 | 9.0 | 9.0 | 9.0 | 9.0 | 9.0 |
| 4-oxo-2-imidazolin- | .250 | 9.0 | 9.0 | 8.0 | 9.0 | | | 9.0 | 8.0 | 9.0 | 9.0 | 9.0 | 9.0 | 9.0 | 9.0 |
| 2-yl)nicotinate | .125 | 9.0 | 8.0 | 7.0 | 9.0 | 8.0 | 9.0 | 7.0 | 7.0 | 9.0 | 9.0 | 9.0 | 9.0 | 8.0 | 8.0 |
| | .063 | 8.0 | 7.0 | 7.0 | 8.0 | 8.0 | 9.0 | 7.0 | 6.0 | 9.0 | 9.0 | 7.0 | 9.0 | 7.0 | 7.0 |
| | .032 | 2.0 | 4.0 | 1.0 | 7.0 | 2.0 | 9.0 | 6.0 | 4.0 | 6.0 | 7.0 | 6.0 | 7.0 | 7.0 | 6.0 |
| 2,3-Dihydroxypropyl | 8.000 | 6.0 | 5.0 | 2.0 | 2.0 | | | 5.0 | 8.0 | 0.0 | | | | | |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| 2-(5-isopropyl-5- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| methyl-4-oxo-2- | .250 | 9.0 | 9.0 | 7.0 | 9.0 | 9.0 | 9.0 | 8.0 | 8.0 | 9.0 | 9.0 | 9.0 | 9.0 | 9.0 | 9.0 |
| imidazolin-2-yl)- | .125 | 7.0 | 8.0 | 7.0 | 9.0 | 9.0 | 9.0 | 8.0 | 6.0 | 8.0 | 9.0 | 9.0 | 8.0 | 8.0 | 7.0 |
| nicotinate | .063 | 5.0 | 6.0 | 4.0 | 9.0 | 8.0 | 9.0 | 8.0 | 6.0 | 8.0 | 9.0 | 9.0 | 7.0 | 8.0 | 7.0 |
| | .032 | 1.0 | 4.0 | 0.0 | 7.0 | 7.0 | 9.0 | 7.0 | 3.0 | 6.0 | 7.0 | 4.0 | 7.0 | 7.0 | 5.0 |
| 4-Pentynyl 2-(5- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| isopropyl-5-methyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin- | .250 | 8.0 | 8.0 | 6.0 | 9.0 | 7.0 | 9.0 | 9.0 | 9.0 | | 9.0 | 9.0 | 9.0 | 8.0 | 8.0 |
| 2-yl)nicotinate | .125 | 8.0 | 8.0 | 6.0 | 9.0 | 7.0 | 9.0 | 9.0 | | 8.0 | 9.0 | 9.0 | 9.0 | 8.0 | 8.0 |
| | .063 | 3.0 | 7.0 | 2.0 | 9.0 | 7.0 | 7.0 | 8.0 | 6.0 | 9.0 | 9.0 | 7.0 | 8.0 | 8.0 | 8.0 |
| | .032 | 2.0 | 5.0 | 1.0 | 8.0 | 7.0 | 6.0 | 7.0 | 0.0 | 7.0 | 9.0 | 6.0 | 8.0 | 6.0 | 7.0 |
| 2-(5-Isopropyl-5 | 1.000 | 9.0 | 9.0 | 9.0 | 9.0 | 9.0 | 8.5 | 9.0 | 9.0 | 8.0 | 9.0 | 9.0 | 9.0 | 9.0 | 6.0 |
| methyl-4-oxo-2- | .500 | 8.7 | 9.0 | 8.3 | 9.0 | 8.5 | 8.0 | 8.5 | 8.3 | 6.0 | 9.0 | 9.0 | 9.0 | 9.0 | 4.7 |
| imidazolin-2-yl)-3- | .250 | 8.3 | 8.3 | 7.3 | 9.0 | 7.5 | 8.0 | 8.5 | 8.0 | 4.7 | 9.0 | 9.0 | 9.0 | 9.0 | 3.0 |
| quinolinecarboxylic | .125 | 9.0 | 7.3 | 5.3 | 6.5 | 6.0 | 6.5 | 5.0 | 5.0 | 3.7 | 9.0 | 9.0 | 9.0 | 9.0 | 2.3 |
| acid | .063 | 4.3 | 6.3 | 3.7 | 4.5 | 5.0 | 5.0 | 6.0 | 1.3 | 3.0 | 9.0 | 9.0 | 8.5 | 7.0 | 2.0 |
| | .032 | 1.0 | 6.0 | 1.0 | 3.0 | 4.5 | 4.0 | 4.0 | 0.5 | 2.0 | 8.5 | 9.0 | 9.0 | 3.0 | 2.0 |
| 6,6-Dimethyl-2- | 1.000 | 9.0 | 9.0 | 9.0 | 9.0 | 9.0 | 9.0 | 9.0 | 9.0 | | 9.0 | 9.0 | 9.0 | 9.0 | 9.0 |
| norpinene-2-ethyl | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| 2-(5-isopropyl-5- | .250 | 9.0 | 9.0 | 8.0 | 9.0 | 9.0 | 9.0 | 9.0 | | 9.0 | 9.0 | 9.0 | 9.0 | 9.0 | 8.0 |
| methyl-4-oxo-2-yl)- | .125 | 8.0 | 9.0 | 7.0 | 9.0 | 8.0 | 9.0 | 9.0 | | 9.0 | 9.0 | 9.0 | 7.0 | 7.0 | 7.0 |
| nicotinate | .063 | 7.0 | 7.0 | 4.0 | 9.0 | 7.0 | 9.0 | 9.0 | 6.0 | 7.0 | 9.0 | 9.0 | 7.0 | 7.0 | 7.0 |
| | .032 | 2.0 | 6.0 | 1.0 | 9.0 | 6.0 | 9.0 | 9.0 | | 7.0 | 9.0 | 7.0 | 7.0 | 6.0 | 5.0 |
| α-Carbomethoxy- | 8.000 | 9.0 | 9.0 | 9.0 | 9.0 | 9.0 | 9.0 | 9.0 | | 9.0 | | | | | |
| benzyl 2-(5-isopropyl- | 1.000 | 9.0 | 9.0 | 9.0 | 9.0 | 9.0 | 9.0 | 9.0 | 7.0 | 9.0 | 9.0 | 9.0 | 9.0 | 9.0 | 9.0 |
| 5-methyl-4-oxo- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-imidazolin-2-yl)- | .250 | 9.0 | 9.0 | 9.0 | 9.0 | 9.0 | 9.0 | 9.0 | 6.0 | 9.0 | 9.0 | 9.0 | 9.0 | 9.0 | 8.0 |
| nicotinate | .125 | 7.0 | 9.0 | 8.0 | 9.0 | 9.0 | 9.0 | 9.0 | 1.0 | 9.0 | 9.0 | 9.0 | 9.0 | 9.0 | 8.0 |
| | .063 | 6.0 | 9.0 | 8.0 | 9.0 | 6.0 | 9.0 | 8.0 | 0.0 | 9.0 | 9.0 | 9.0 | 8.0 | 9.0 | 7.0 |
| | .032 | 5.0 | 8.0 | 8.0 | 9.0 | 8.0 | 7.0 | 6.0 | 0.0 | 8.0 | 9.0 | 8.0 | 7.0 | 6.0 | 7.0 |
| Methyl 2-(1-acetyl- | 8.000 | 9.0 | 9.0 | 9.0 | 9.0 | 9.0 | 9.0 | 8.0 | | 9.0 | | | | | |
| 4-isopropyl-4-methyl- | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 |
| 5-oxo-2-imidazolin-2- | .500 | 9.0 | 9.0 | 7.0 | 9.0 | 9.0 | 9.0 | 9.0 | 9.0 | 9.0 | 9.0 | 9.0 | 9.0 | 9.0 | 9.0 |
| yl)nicotinate-1-oxide | .250 | 1.0 | 9.0 | 7.0 | 8.0 | 9.0 | 9.0 | 9.0 | 0.0 | 9.0 | 9.0 | 9.0 | 9.0 | 8.0 | 7.0 |
| | .125 | 0.0 | 8.0 | 7.0 | 8.0 | 8.0 | 8.0 | 7.0 | 0.0 | 9.0 | 9.0 | 9.0 | 8.0 | 7.0 | 7.0 |
| | .063 | 0.0 | 7.0 | 0.0 | 8.0 | 8.0 | 7.0 | | 0.0 | 7.0 | 3.0 | 7.0 | 7.0 | 4.0 | 7.0 |
| | .032 | 0.0 | 3.0 | 0.0 | 2.0 | 3.0 | 7.0 | 2.0 | 0.0 | 6.0 | 2.0 | 3.0 | 6.0 | 2.0 | 5.0 |
| 3-Methyl-3-butenyl | 1.000 | 9.0 | 9.0 | 9.0 | 9.0 | 9.0 | 9.0 | 9.0 | | 9.0 | 9.0 | 9.0 | 9.0 | 9.0 | 9.0 |
| 2-(5-isopropyl-5- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| methyl-4-oxo-2- | .250 | 9.0 | 9.0 | 7.0 | 9.0 | 9.0 | 9.0 | 9.0 | 9.0 | 9.0 | 9.0 | 9.0 | 9.0 | 9.0 | 9.0 |
| imidazolin-2-yl)- | .125 | 7.0 | 9.0 | 7.0 | 9.0 | 9.0 | 9.0 | 9.0 | 8.0 | 9.0 | 9.0 | 9.0 | 9.0 | 8.0 | 8.0 |
| nicotinate | .063 | 3.0 | 9.0 | 7.0 | 9.0 | 9.0 | 9.0 | 9.0 | 8.0 | 8.0 | 9.0 | 9.0 | 8.0 | 7.0 | 7.0 |
| | .032 | 1.0 | 6.0 | 6.0 | 8.0 | 6.0 | 7.0 | 8.0 | | 8.0 | 9.0 | 9.0 | 7.0 | 7.0 | 6.0 |
| 10-Undecenyl 2- | 1.000 | 9.0 | 9.0 | 9.0 | 9.0 | 9.0 | 9.0 | 9.0 | 9.0 | | 9.0 | 9.0 | 9.0 | 9.0 | 9.0 |
| (5-isopropyl-5- | .500 | 9.0 | 9.0 | 8.0 | 9.0 | 9.0 | 9.0 | 9.0 | 9.0 | | 9.0 | 9.0 | 9.0 | 9.0 | 8.0 |
| methyl-4-oxo-2- | .250 | 7.0 | 7.0 | 7.0 | 9.0 | 9.0 | 9.0 | 9.0 | | 9.0 | 9.0 | 9.0 | 8.0 | 9.0 | 8.0 |
| imidazolin-2-yl)- | .125 | 4.0 | 6.0 | 7.0 | 9.0 | 8.0 | 9.0 | 8.0 | | 8.0 | 9.0 | 8.0 | 7.0 | 8.0 | 8.0 |
| nicotinate | .063 | 2.0 | 6.0 | 4.0 | 8.0 | 6.0 | 9.0 | 8.0 | 4.0 | 7.0 | 8.0 | 7.0 | 7.0 | 7.0 | 7.0 |
| | .032 | 1.0 | 6.0 | 1.0 | 6.0 | 4.0 | 4.0 | 7.0 | | 5.0 | 8.0 | 6.0 | 6.0 | 4.0 | 6.0 |
| 5-Bromo-2-(5- | 1.000 | 9.0 | 9.0 | 9.0 | 9.0 | 9.0 | 9.0 | 9.0 | 9.0 | 9.0 | 9.0 | 9.0 | 9.0 | 9.0 | 7.5 |
| isopropyl-5-methyl- | .500 | 9.0 | 9.0 | 9.0 | 9.0 | 9.0 | 8.0 | 9.0 | 9.0 | 9.0 | 9.0 | 9.0 | 9.0 | 9.0 | 7.5 |
| 4-oxo-2-imidazolin- | .250 | 9.0 | 9.0 | 9.0 | 9.0 | 9.0 | 7.0 | 9.0 | 9.0 | 9.0 | 9.0 | 9.0 | 9.0 | 9.0 | 5.5 |

TABLE XI-continued

| | | POST-EMERGENCE TESTS - RATES IN KG/HA | | | | | | | | | | | | | |
|---|---|---|---|---|---|---|---|---|---|---|---|---|---|---|---|
| 2-yl)nicotinic acid | .125 | 9.0 | 9.0 | 7.0 | 9.0 | 9.0 | 7.0 | 9.0 | 8.0 | 7.0 | 9.0 | 9.0 | 9.0 | 9.0 | 5.5 |
| | .063 | 8.0 | 9.0 | 7.0 | 3.0 | 7.0 | 7.0 | 6.0 | 8.0 | 7.0 | 8.0 | 8.5 | 8.0 | 9.0 | 3.5 |
| | .032 | 5.0 | 9.0 | 6.0 | 2.0 | 7.0 | 6.0 | 6.0 | 7.0 | 6.0 | 7.0 | 9.0 | 6.0 | 8.0 | 3.0 |
| α-methylbenzyl 2- | 8.000 | 9.0 | 9.0 | 9.0 | 9.0 | 9.0 | 9.0 | 9.0 | | 9.0 | | | | | |
| (5-isopropyl-5- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| methyl-4-oxo-2- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| imidazolin-2-yl)- | .250 | 8.0 | 9.0 | 8.0 | 9.0 | 9.0 | 9.0 | 9.0 | 7.0 | 9.0 | 9.0 | 9.0 | 9.0 | 9.0 | 8.0 |
| nicotinate | .125 | 8.0 | 9.0 | 8.0 | 9.0 | 9.0 | 9.0 | 9.0 | 6.0 | 8.0 | 9.0 | 9.0 | 9.0 | 9.0 | 8.0 |
| | .063 | 8.0 | 9.0 | 7.0 | 9.0 | 9.0 | 8.0 | 8.0 | 4.0 | 9.0 | 9.0 | 9.0 | 9.0 | 9.0 | 7.0 |
| | .032 | 8.0 | 8.0 | 7.0 | 7.0 | 8.0 | 7.0 | 8.0 | 0.0 | 4.0 | 6.0 | 9.0 | 7.0 | 8.0 | 6.0 |
| Methyl 2-(5-isopropyl- | 8.000 | 9.0 | 9.0 | 8.0 | 9.0 | 9.0 | 9.0 | 9.0 | | 9.0 | | | | | |
| 5-methyl-4-oxo-2- | 1.000 | 9.0 | 9.0 | 9.0 | 9.0 | 9.0 | 9.0 | 9.0 | 8.0 | 9.0 | 9.0 | 9.0 | 9.0 | 9.0 | 9.0 |
| imidazolin-2-yl)- | .500 | 8.0 | 9.0 | 7.0 | 9.0 | 7.0 | 8.0 | 9.0 | 3.0 | 9.0 | 9.0 | 9.0 | 9.0 | 8.0 | 9.0 |
| nicotinate-1-oxide | .250 | 7.0 | 9.0 | 7.0 | 9.0 | 9.0 | 9.0 | 9.0 | 1.0 | 9.0 | 6.0 | 9.0 | 8.0 | 8.0 | 9.0 |
| Methyl 6-chloro-2- | 8.000 | 9.0 | 9.0 | 9.0 | 9.0 | 9.0 | 9.0 | 9.0 | | 9.0 | | | | | |
| (5-isopropyl-5- | 1.000 | 9.0 | 9.0 | 9.0 | 9.0 | 9.0 | 9.0 | 9.0 | 9.0 | 8.0 | 9.0 | 9.0 | 9.0 | 9.0 | 7.5 |
| methyl-4-oxo-2- | .500 | 9.0 | 9.0 | 7.0 | 9.0 | 9.0 | 6.0 | 9.0 | 9.0 | 4.0 | 9.0 | 8.5 | 9.0 | 9.0 | 6.5 |
| imidazolin-2-yl)- | .250 | 9.0 | 9.0 | 8.0 | 9.0 | 8.0 | 5.0 | 9.0 | 9.0 | 3.0 | 9.0 | 7.0 | 9.0 | 9.0 | 6.0 |
| nicotinate | .125 | 7.0 | 9.0 | 4.0 | 9.0 | 8.0 | 5.0 | 6.0 | 8.0 | 2.0 | 6.5 | 4.5 | 6.0 | 8.0 | 5.0 |
| | .063 | 7.0 | 9.0 | 4.0 | 9.0 | 8.0 | 4.0 | 6.0 | 7.0 | 2.0 | 6.5 | 4.5 | 5.5 | 9.0 | 4.5 |
| | .032 | 6.0 | 9.0 | 0.0 | 9.0 | 8.0 | 4.0 | 5.0 | 4.0 | 0.0 | 4.5 | 2.5 | 3.0 | 8.0 | 4.0 |
| 2-Isopropyl-2-methyl- | 8.000 | 9.0 | 9.0 | 9.0 | 9.0 | 9.0 | 9.0 | 9.0 | 9.0 | 9.0 | | | | | |
| 5-H—imidazo[1',2':1,2]- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| pyrrolo[3,4-b]pyridine- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 3(2H),5-dione | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 9.0 | 9.0 | 8.0 | 9.0 | 9.0 | 9.0 | 9.0 | 0.0 | 9.0 | 9.0 | 9.0 | 9.0 | 9.0 | 9.0 |
| | .032 | 9.0 | 9.0 | 8.0 | 9.0 | 9.0 | 9.0 | 9.0 | 0.0 | 9.0 | 9.0 | 9.0 | 9.0 | 9.0 | 7.0 |
| 2-[3-(Hydroxymethyl)- | 1.000 | 9.0 | 9.0 | 9.0 | 9.0 | 9.0 | 9.0 | 9.0 | 9.0 | 9.0 | 9.0 | 9.0 | 7.0 | 9.0 | 8.0 |
| 2-pyridyl]-5-isopropyl- | .500 | 8.0 | 9.0 | 8.0 | 9.0 | 9.0 | 9.0 | 9.0 | 4.0 | 9.0 | 9.0 | 9.0 | 7.0 | 9.0 | 7.0 |
| 5-methyl-2-imidazo- | .250 | 7.0 | 8.0 | 8.0 | 9.0 | 7.0 | 9.0 | 8.0 | 1.0 | 9.0 | 9.0 | 8.0 | 7.0 | 8.0 | 7.0 |
| 4-one | .125 | 3.0 | 6.0 | 3.0 | 7.0 | 5.0 | 4.0 | 7.0 | | 8.0 | 9.0 | 7.0 | 6.0 | 7.0 | 3.0 |
| | .063 | 1.0 | 6.0 | 2.0 | 5.0 | 4.0 | 4.0 | 4.0 | | 7.0 | 9.0 | 4.0 | 6.0 | 7.0 | 3.0 |
| | .032 | 1.0 | 4.0 | 0.0 | 2.0 | 2.0 | 3.0 | 2.0 | 0.0 | 6.0 | 8.0 | 3.0 | 3.0 | 4.0 | 3.0 |
| Carboethoxymethyl | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 |
| 2-(5-isopropyl-5- | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| methyl-4-oxo-2- | .250 | 9.0 | 9.0 | 8.0 | 9.0 | 9.0 | 9.0 | 9.0 | 9.0 | 9.0 | 9.0 | 9.0 | 9.0 | 9.0 | 9.0 |
| imidazolin-2-yl)- | .125 | 9.0 | 9.0 | 8.0 | 9.0 | 9.0 | 9.0 | 9.0 | 9.0 | 9.0 | 9.0 | 9.0 | 9.0 | 9.0 | 8.0 |
| nicotinate | .063 | 7.0 | 8.0 | 7.0 | 9.0 | 9.0 | 9.0 | 9.0 | 7.0 | 9.0 | 9.0 | 9.0 | 9.0 | 9.0 | 8.0 |
| | .032 | 7.0 | 7.0 | 3.0 | 9.0 | 7.0 | 9.0 | 9.0 | 4.0 | 9.0 | 9.0 | 7.0 | 8.0 | 9.0 | 7.0 |
| Carbobenzyloxymethyl | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-(5-isopropyl-5- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| methyl-4-oxo-2- | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| imidazolin-2-yl)- | .125 | 9.0 | 9.0 | 7.0 | 9.0 | 7.0 | 9.0 | 9.0 | 3.0 | 9.0 | 9.0 | 9.0 | 9.0 | 9.0 | 9.0 |
| nicotinate | .063 | 7.0 | 7.0 | 4.0 | 9.0 | 4.0 | 9.0 | 9.0 | 3.0 | 9.0 | 9.0 | 8.0 | 8.0 | 9.0 | 7.0 |
| | .032 | 5.0 | 5.0 | 0.0 | 7.0 | 4.0 | 8.0 | 8.0 | 1.0 | 7.0 | 9.0 | 5.0 | 7.0 | 8.0 | 7.0 |
| Carboxymethyl 2-(5- | 1.000 | 9.0 | 9.0 | 8.0 | 9.0 | 9.0 | 9.0 | 9.0 | 9.0 | 9.0 | 9.0 | 9.0 | 9.0 | 9.0 | 9.0 |
| isopropyl-5-methyl- | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| 4-oxo-2-imidazolin- | .250 | 9.0 | 9.0 | 9.0 | 9.0 | 9.0 | 9.0 | 9.0 | 9.0 | | 9.0 | 9.0 | 9.0 | 9.0 | 9.0 |
| 2-yl)nicotinate | .125 | 9.0 | 9.0 | 6.0 | 9.0 | 9.0 | 9.0 | 9.0 | 9.0 | 9.0 | 9.0 | 9.0 | 8.0 | 9.0 | 9.0 |
| | .063 | 9.0 | 8.0 | 4.0 | 9.0 | 7.0 | 9.0 | 7.0 | 4.0 | 8.0 | 9.0 | 8.0 | 7.0 | 9.0 | 8.0 |
| | .032 | 6.0 | 4.0 | 0.0 | 7.0 | 5.0 | 4.0 | 6.0 | 1.0 | 7.0 | 9.0 | 6.0 | 7.0 | 8.0 | 8.0 |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| Cyanomethyl 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 7.0 | 9.0 | 9.0 | 9.0 | 9.0 | 9.0 | 9.0 | 9.0 | 9.0 | 9.0 | 9.0 | 9.0 |
| | .125 | 8.0 | 9.0 | 7.0 | 9.0 | 9.0 | 9.0 | 9.0 | 7.0 | 9.0 | 9.0 | 9.0 | 9.0 | 9.0 | 8.0 |
| | .063 | 8.0 | 9.0 | 5.0 | 9.0 | 9.0 | 9.0 | 9.0 | 6.0 | 9.0 | 9.0 | 9.0 | 9.0 | 9.0 | 8.0 |
| | .032 | 9.0 | 9.0 | 4.0 | 9.0 | 8.0 | 9.0 | 9.0 | 4.0 | 9.0 | 9.0 | 9.0 | 9.0 | 7.0 | 7.0 |
| Methyl (−)-2-(5-isopropyl-5-methyl-4-oxo-2-imidazolin-2-yl)nicotinate | 1.000 | 9.0 | 9.0 | 8.0 | 9.0 | 8.0 | 9.0 | 9.0 | 9.0 | 9.0 | 9.0 | 9.0 | 9.0 | 9.0 | 9.0 |
| | .500 | 8.0 | 9.0 | 6.0 | 9.0 | 8.0 | 9.0 | 9.0 | 8.0 | 9.0 | 9.0 | 9.0 | 9.0 | 9.0 | 7.0 |
| | .250 | 8.0 | 9.0 | 4.0 | 9.0 | 7.0 | 9.0 | 7.0 | 7.0 | 9.0 | 9.0 | 8.0 | 8.0 | 9.0 | 6.0 |
| | .125 | 3.0 | 9.0 | 2.0 | 6.0 | 5.0 | 6.0 | 7.0 | 4.0 | 9.0 | 7.0 | 6.0 | 7.0 | 8.0 | 6.0 |
| | .063 | 1.0 | 7.0 | 1.0 | 2.0 | 3.0 | 3.0 | 6.0 | 1.0 | 9.0 | 5.0 | 3.0 | 7.0 | 7.0 | 4.0 |
| | .032 | 0.0 | 7.0 | 0.0 | 0.0 | 0.0 | 2.0 | 4.0 | 0.0 | 6.0 | 3.0 | 2.0 | 7.0 | 7.0 | 4.0 |
| Methyl (+)-2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 8.0 | 9.0 | 9.0 | 6.0 | 9.0 | 9.0 | 9.0 | 9.0 | 9.0 | 9.0 |
| | .063 | 9.0 | 9.0 | 6.0 | 9.0 | 8.0 | 8.0 | 9.0 | 5.0 | 9.0 | 9.0 | 9.0 | 9.0 | 9.0 | 9.0 |
| | .032 | 7.0 | 9.0 | 6.0 | 9.0 | 8.0 | 8.0 | 8.0 | 3.0 | 9.0 | 9.0 | 9.0 | 8.0 | 9.0 | 9.0 |
| Benzyl (+)-2-(5-isopropyl-5-methyl-4-oxo-2-imidazolin-2-yl)nicotinate | 1.000 | 9.0 | 9.0 | 4.0 | 9.0 | 8.0 | 9.0 | 9.0 | 9.0 | 9.0 | 9.0 | 9.0 | 9.0 | 9.0 | 9.0 |
| | .500 | 8.0 | 9.0 | 4.0 | 9.0 | 8.0 | 9.0 | 9.0 | 7.0 | 9.0 | 9.0 | 9.0 | 9.0 | 9.0 | 7.0 |
| | .250 | 6.0 | 9.0 | 3.0 | 9.0 | 8.0 | 9.0 | 9.0 | 7.0 | 9.0 | 8.0 | 9.0 | 9.0 | 9.0 | 7.0 |
| | .125 | 2.0 | 7.0 | 1.0 | 7.0 | 7.0 | 7.0 | 8.0 | 3.0 | 9.0 | 7.0 | 8.0 | 9.0 | 8.0 | 6.0 |
| | .063 | 2.0 | 8.0 | 1.0 | 6.0 | 2.0 | 9.0 | 4.0 | 1.0 | 9.0 | 7.0 | 6.0 | 8.0 | 7.0 | 5.0 |
| | .032 | 0.0 | 6.0 | 0.0 | 2.0 | 1.0 | 8.0 | 3.0 | 0.0 | 8.0 | 5.0 | 5.0 | 8.0 | 6.0 | 5.0 |
| Benzyl (−)-2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 7.0 | 9.0 | 8.0 | 9.0 | 9.0 | 9.0 | 9.0 | 9.0 | 9.0 | 9.0 | 9.0 | 9.0 |
| | .125 | 9.0 | 9.0 | 7.0 | 9.0 | 9.0 | 9.0 | 9.0 | 7.0 | 9.0 | 9.0 | 9.0 | 9.0 | 9.0 | 9.0 |
| | .063 | 9.0 | 9.0 | 6.0 | 9.0 | 8.0 | 9.0 | 9.0 | 5.0 | 9.0 | 9.0 | 9.0 | 9.0 | 9.0 | 9.0 |
| | .032 | 6.0 | 9.0 | 3.0 | 9.0 | 8.0 | 9.0 | 4.0 | 1.0 | 9.0 | 9.0 | 9.0 | 9.0 | 8.0 | 7.0 |
| (−)-2-(5-Isopropyl-5-methyl-4-oxo-2-imidazolin-2-yl)-nicotinic acid | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 9.0 | 9.0 | 9.0 | 3.0 | 9.0 | 9.0 | 9.0 | 9.0 | 9.0 | 9.0 |
| | .125 | 9.0 | 9.0 | 6.0 | 9.0 | 8.0 | 9.0 | 9.0 | 7.0 | 9.0 | 9.0 | 9.0 | 9.0 | 9.0 | 7.0 |
| | .063 | 6.0 | 9.0 | 5.0 | 9.0 | 9.0 | 9.0 | 9.0 | 4.0 | 9.0 | 9.0 | 9.0 | 9.0 | 9.0 | 6.0 |
| | .032 | 6.0 | 9.0 | 2.0 | 8.0 | 8.0 | 9.0 | 4.0 | 1.0 | 9.0 | 8.0 | 9.0 | 9.0 | 9.0 | 5.0 |
| (+)-2-(5-Isopropyl-5-methyl-4-oxo-2-imidazolin-2-yl)-nicotinic acid | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 9.0 | 9.0 | 8.0 | 9.0 | 9.0 | 9.0 | 9.0 | 8.0 | 9.0 | 9.0 | 9.0 | 9.0 | 9.0 | 9.0 |
| | .032 | 9.0 | 9.0 | 9.0 | 9.0 | 9.0 | 9.0 | 8.0 | 8.0 | 9.0 | 9.0 | 9.0 | 9.0 | 9.0 | 8.0 |
| 2-(5-Isopropyl-5-methyl-4-oxo-2-imidazolin-2-yl)-nicotinic acid hydrochloride | 8.000 | 9.0 | 9.0 | 9.0 | 9.0 | 9.0 | 2.0 | 9.0 | 9.0 | 9.0 | | | | | |
| | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 8.0 | 9.0 |
| | .125 | 9.0 | 9.0 | 8.0 | 9.0 | 9.0 | 9.0 | 9.0 | 8.0 | 9.0 | 9.0 | 9.0 | 9.0 | 8.0 | 8.0 |
| | .063 | 9.0 | 9.0 | 8.0 | 9.0 | 9.0 | 9.0 | 9.0 | 7.0 | 9.0 | 9.0 | 9.0 | 9.0 | 8.0 | 8.0 |
| | .032 | 9.0 | 9.0 | 7.0 | 9.0 | 9.0 | 9.0 | 9.0 | 4.0 | 9.0 | 9.0 | 9.0 | 9.0 | 8.0 | 7.0 |
| Methyl 2-(1-benzoyl-4-isopropyl-4-methyl-5-oxo-2- | 8.000 | 9.0 | 9.0 | 9.0 | 9.0 | 9.0 | 1.0 | 8.0 | 9.0 | 9.0 | | | | | |
| | 1.000 | 9.0 | 9.0 | 7.0 | 9.0 | 9.0 | 9.0 | 9.0 | 9.0 | 9.0 | 9.0 | 9.0 | 9.0 | 8.0 | 9.0 |
| | .500 | 9.0 | 9.0 | 7.0 | 9.0 | 8.0 | 9.0 | 9.0 | 9.0 | 9.0 | 9.0 | 9.0 | 9.0 | 8.0 | 9.0 |

TABLE XI-continued

POST-EMERGENCE TESTS - RATES IN KG/HA

| | | | | | | | | | | | | | | |
|---|---|---|---|---|---|---|---|---|---|---|---|---|---|---|
| imidazolin-2-yl)- | .250 | 9.0 | 9.0 | 6.0 | 9.0 | 8.0 | 9.0 | 9.0 | 7.0 | 9.0 | 9.0 | 9.0 | 9.0 | 7.0 | 9.0 |
| nicotinate | .125 | 8.0 | 9.0 | 5.0 | 9.0 | 7.0 | 9.0 | 9.0 | 5.0 | 9.0 | 9.0 | 9.0 | | 6.0 | 8.0 |
| | .063 | 6.0 | 8.0 | 3.0 | 9.0 | 7.0 | 3.0 | 9.0 | 2.0 | 9.0 | 8.0 | 9.0 | 8.0 | 5.0 | 8.0 |
| | .032 | 1.0 | 8.0 | 2.0 | 7.0 | 7.0 | 3.0 | 7.0 | 1.0 | 7.0 | 7.0 | 9.0 | 7.0 | 5.0 | 8.0 |
| Methyl 6-dimethyl- | 1.000 | 9.0 | 6.0 | 0.0 | 6.0 | 3.0 | 0.0 | 9.0 | 0.0 | 2.0 | 6.0 | 9.0 | 5.0 | 6.0 | 3.0 |
| amino-2-(5-isopropyl- | .500 | 9.0 | 5.0 | 0.0 | 3.0 | 1.0 | 0.0 | 9.0 | 0.0 | 2.0 | 4.0 | 9.0 | 5.0 | 5.0 | 3.0 |
| 5-methyl-4-oxo-2- | .250 | 9.0 | 4.0 | 0.0 | 0.0 | 0.0 | 0.0 | 9.0 | 0.0 | 0.0 | 2.0 | 9.0 | 2.0 | 5.0 | 2.0 |
| imidazolin-2-yl)- | .125 | 6.0 | 3.0 | 0.0 | 0.0 | 0.0 | 0.0 | 7.0 | 0.0 | 0.0 | 2.0 | 9.0 | 2.0 | 4.0 | 2.0 |
| nicotinate | .063 | 2.0 | 3.0 | 0.0 | 0.0 | 0.0 | 0.0 | 7.0 | 0.0 | 0.0 | | 9.0 | 2.0 | 3.0 | 1.0 |
| | .032 | 0.0 | 3.0 | 0.0 | 0.0 | 0.0 | 0.0 | | 0.0 | 0.0 | | 7.0 | 1.0 | 3.0 | 1.0 |
| Methyl 2-(1-Chloro- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| acetyl-4-isopropyl- | .500 | 9.0 | 9.0 | 9.0 | 9.0 | 8.0 | 9.0 | 9.0 | 9.0 | 9.0 | 9.0 | 9.0 | 9.0 | 8.0 | 9.0 |
| 4-methyl-5-oxo-2- | .250 | 9.0 | 9.0 | 7.0 | 9.0 | 8.0 | 8.0 | 9.0 | 8.0 | 9.0 | 9.0 | 9.0 | 9.0 | 8.0 | 9.0 |
| imidazolin-2-yl)- | .125 | 8.0 | 9.0 | 8.0 | 9.0 | 8.0 | 8.0 | 9.0 | 6.0 | 9.0 | 9.0 | 9.0 | 9.0 | 8.0 | 9.0 |
| nicotinate | .063 | 7.0 | 8.0 | 3.0 | 9.0 | 7.0 | 8.0 | 4.0 | 3.0 | 9.0 | 9.0 | 9.0 | 8.0 | 8.0 | 8.0 |
| | .032 | 4.0 | 8.0 | 1.0 | 7.0 | 6.0 | 7.0 | 4.0 | 1.0 | 8.0 | 8.0 | 9.0 | 7.0 | 6.0 | 7.0 |
| Methyl 2-(4-isopropyl- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-methyl-5-oxo-1- | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| propionyl-2-imidazolin- | .250 | 9.0 | 9.0 | 8.0 | 9.0 | 9.0 | 9.0 | 9.0 | 8.0 | 9.0 | 9.0 | 9.0 | 9.0 | 9.0 | 9.0 |
| 2-yl)nicotinate | .125 | 9.0 | 9.0 | 7.0 | 9.0 | 9.0 | 9.0 | 8.0 | 6.0 | 9.0 | 9.0 | 9.0 | 8.0 | 9.0 | 9.0 |
| | .063 | 9.0 | 9.0 | 6.0 | 9.0 | 7.0 | 6.0 | | 3.0 | 9.0 | 9.0 | 9.0 | 8.0 | 9.0 | 8.0 |
| | .032 | 7.0 | 9.0 | 4.0 | 7.0 | 7.0 | 9.0 | 7.0 | 0.0 | 9.0 | 9.0 | 9.0 | 7.0 | 7.0 | 8.0 |
| O—[2-(5-Isopropyl-5- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| methyl-4-oxo-2- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| imidazolin-2-yl)- | .250 | 9.0 | 9.0 | 8.0 | 9.0 | 9.0 | 9.0 | 9.0 | 9.0 | 9.0 | 9.0 | 9.0 | 9.0 | 9.0 | 9.0 |
| nicotinoyl]acetone | .125 | 9.0 | 9.0 | 7.0 | 9.0 | 9.0 | 9.0 | 9.0 | 9.0 | 9.0 | 9.0 | 9.0 | 9.0 | 9.0 | 9.0 |
| oxime | .063 | 9.0 | 9.0 | 6.0 | 9.0 | 9.0 | 9.0 | 9.0 | 7.0 | 9.0 | 9.0 | 9.0 | 9.0 | 8.0 | 7.0 |
| | .032 | 9.0 | 9.0 | 6.0 | 9.0 | 8.0 | 9.0 | 7.0 | 0.0 | 8.0 | 9.0 | 9.0 | 9.0 | 7.0 | 7.0 |
| 2-(3-Acetyl-2-pyridyl)- | 1.000 | 4.0 | 8.0 | 8.0 | 9.0 | 7.0 | 8.0 | 9.0 | 7.0 | 9.0 | 9.0 | 9.0 | 7.0 | 8.0 | 8.0 |
| 5-isopropyl-5-methyl- | .500 | 2.0 | 8.0 | 4.0 | 7.0 | 6.0 | 8.0 | 9.0 | 4.0 | 9.0 | 9.0 | 9.0 | 7.0 | 8.0 | 7.0 |
| 2-imidazolin-4-one | .250 | 2.0 | 6.0 | 1.0 | 6.0 | 6.0 | 6.0 | 9.0 | 0.0 | 4.0 | 7.0 | 9.0 | 7.0 | 6.0 | 7.0 |
| | .125 | 0.0 | 5.0 | 0.0 | 4.0 | 2.0 | 2.0 | 7.0 | 0.0 | 1.0 | 6.0 | 7.0 | 6.0 | 6.0 | 5.0 |
| | .063 | 0.0 | 0.0 | 0.0 | 0.0 | 0.0 | 0.0 | | 0.0 | 1.0 | 2.0 | 2.0 | 2.0 | 3.0 | 4.0 |
| | .032 | 0.0 | 0.0 | 0.0 | 0.0 | 0.0 | 0.0 | 0.0 | 0.0 | 0.0 | 0.0 | 2.0 | 0.0 | 1.0 | 4.0 |
| Benzyl 2-(4-isopropyl- | 1.000 | 9.0 | 9.0 | 8.0 | 9.0 | 8.0 | 9.0 | 9.0 | 8.0 | 9.0 | 9.0 | 9.0 | 9.0 | 9.0 | 9.0 |
| 4-methyl-5-oxo-1- | .500 | 9.0 | 9.0 | 7.0 | 9.0 | 9.0 | 9.0 | 9.0 | 8.0 | 9.0 | 9.0 | 9.0 | 9.0 | 9.0 | 9.0 |
| propionyl-2-imidazolin- | .250 | 9.0 | 9.0 | 5.0 | 9.0 | 7.0 | 7.0 | 9.0 | 7.0 | 9.0 | 9.0 | 9.0 | 9.0 | 9.0 | 8.0 |
| 2-yl)nicotinate | .125 | 9.0 | 9.0 | 5.0 | 9.0 | 6.0 | 9.0 | 9.0 | 6.0 | 9.0 | 9.0 | 9.0 | 9.0 | 8.0 | 7.0 |
| | .063 | 9.0 | 7.0 | 1.0 | 9.0 | 3.0 | 9.0 | 9.0 | 1.0 | 9.0 | 9.0 | 9.0 | 9.0 | 7.0 | 7.0 |
| | .032 | 1.0 | 6.0 | 0.0 | 7.0 | 0.0 | 9.0 | 9.0 | 0.0 | 8.0 | 8.0 | 8.0 | 8.0 | 6.0 | 6.0 |
| Benzyl 2-(4-isopropyl- | 1.000 | 9.0 | 9.0 | 9.0 | 9.0 | 8.0 | 8.0 | 9.0 | 8.0 | 9.0 | 9.0 | 9.0 | 9.0 | 9.0 | 9.0 |
| 4-methyl-5-oxo-1- | .500 | 9.0 | 9.0 | 8.0 | 9.0 | 7.0 | 9.0 | 9.0 | 8.0 | 9.0 | 9.0 | 9.0 | 9.0 | 9.0 | 9.0 |
| pivaloyl-2-imidazolin- | .250 | 9.0 | 9.0 | 3.0 | 9.0 | 8.0 | 7.0 | 9.0 | 7.0 | 9.0 | 9.0 | 9.0 | 9.0 | 8.0 | 9.0 |
| 2-yl)nicotinate | .125 | 9.0 | 9.0 | 2.0 | 9.0 | 7.0 | 9.0 | 9.0 | 2.0 | 9.0 | 9.0 | 9.0 | 9.0 | 8.0 | 8.0 |
| | .063 | 9.0 | 9.0 | 0.0 | 9.0 | 7.0 | 0.0 | 9.0 | 0.0 | 7.0 | 9.0 | 9.0 | 9.0 | 8.0 | 7.0 |
| | .032 | 1.0 | 7.0 | 0.0 | 6.0 | 2.0 | 0.0 | 7.0 | 0.0 | 8.0 | 7.0 | 5.0 | 9.0 | 6.0 | 6.0 |
| Trimethyl 2-(5- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| isopropyl-5-methyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin- | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-yl)-β-oxo-α-phosphino. | .125 | 9.0 | 9.0 | 8.0 | 9.0 | 9.0 | 9.0 | 9.0 | 9.0 | 9.0 | 9.0 | 9.0 | 9.0 | 9.0 | 9.0 |
| 3-pyridinepropionic | .063 | 9.0 | 9.0 | 8.0 | 9.0 | 9.0 | 8.0 | 8.0 | 4.0 | 7.0 | 9.0 | 9.0 | 8.0 | 8.0 | 9.0 |
| acid | .032 | 9.0 | 9.0 | 6.0 | 7.0 | 9.0 | 8.0 | 6.0 | 1.0 | 1.0 | 9.0 | 9.0 | 7.0 | 7.0 | 6.0 |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| Methyl 2-[4-isopropyl-4-methyl-1-(methylsulfonyl)-5-oxo-2-imidazolin-2-yl)-nicotinate | 1.000 | 2.0 | 5.0 | 4.0 | 1.0 | 7.0 | 7.0 | 4.0 | 0.0 | 9.0 | 3.0 | 3.0 | 4.0 | 3.0 | 8.0 |
| 2-Propynyl 2-(1-Acetyl-4-isopropyl-4-methyl-5-oxo-2-imidazolin-2-yl)-nicotinate | 4.000 | 9.0 | 9.0 | 8.0 | 9.0 | 9.0 | 8.0 | 9.0 | 8.0 | 8.0 | 9.0 | 7.0 | 4.0 | 7.0 | 9.0 |
| | 1.000 | 9.0 | 7.0 | 1.0 | 9.0 | 3.0 | 0.0 | 4.0 | 5.0 | 3.0 | 9.0 | 7.0 | 4.0 | 7.0 | 9.0 |
| 2-Ethanolammonium 2-(5-isopropyl-5-methyl-4-oxo-2-imidazolin-2-yl)-nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 9.0 | 9.0 | 8.0 | 9.0 | 9.0 | 9.0 | 9.0 | 6.0 | 9.0 | 9.0 | 9.0 | 9.0 | 9.0 | 8.0 |
| | .032 | 9.0 | 9.0 | 7.0 | 9.0 | 8.0 | 9.0 | 9.0 | 4.0 | 9.0 | 9.0 | 9.0 | 9.0 | 9.0 | 8.0 |
| Pyrrolidinium 2-(5-isopropyl-5-methyl-4-oxo-2-imidazolin-2-yl)-nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 8.0 | 9.0 | 9.0 | 9.0 | 9.0 | 9.0 | 9.0 |
| | .063 | 9.0 | 9.0 | 7.0 | 9.0 | 9.0 | 9.0 | 9.0 | 6.0 | 9.0 | 9.0 | 9.0 | 9.0 | 9.0 | 9.0 |
| | .032 | 9.0 | 9.0 | 5.0 | 9.0 | 9.0 | 9.0 | 9.0 | 1.0 | 9.0 | 9.0 | 9.0 | 9.0 | 9.0 | 9.0 |
| Diethylammonium 2-(5-isopropyl-5-methyl-4-oxo-2-imidazolin-2-yl)-nicotinate | 1.000 | 9.0 | 9.0 | 9.0 | 9.0 | 9.0 | 9.0 | | 9.0 | 9.0 | 9.0 | 9.0 | 9.0 | 9.0 | 9.0 |
| | .500 | | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 8.0 | 9.0 | 9.0 | 9.0 | | 9.0 | 9.0 | 9.0 | 9.0 | 9.0 | 9.0 | |
| | .063 | 9.0 | 9.0 | 8.0 | 9.0 | 9.0 | 9.0 | 9.0 | 4.0 | 9.0 | 9.0 | 9.0 | 9.0 | 9.0 | 9.0 |
| | .032 | 3.0 | 9.0 | 7.0 | 9.0 | 9.0 | 9.0 | | 4.0 | 9.0 | 9.0 | 9.0 | 9.0 | 9.0 | 9.0 |
| Isopropylammonium 2-(5-isopropyl-5-methyl-4-oxo-2-imidazolin-2-yl)-nicotinate | 1.000 | 9.0 | 9.0 | 9.0 | 9.0 | 9.0 | 9.0 | | 9.0 | 9.0 | 9.0 | 9.0 | 9.0 | 9.0 | 9.0 |
| | .500 | 9.0 | 9.0 | 9.0 | 9.0 | 9.0 | 9.0 | | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 9.0 | 9.0 | 7.0 | 9.0 | 9.0 | 9.0 | 9.0 | 6.0 | 9.0 | 9.0 | 9.0 | 9.0 | 9.0 | 8.0 |
| | .032 | 9.0 | 9.0 | 7.0 | 9.0 | 9.0 | 9.0 | 9.0 | 1.0 | 8.0 | 9.0 | 9.0 | 8.0 | 9.0 | 9.0 |
| 2-Methylallyl-ammonium 2-(5-isopropyl-5-methyl-4-oxo-2-imidazolin-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | | 9.0 | | 9.0 | 9.0 | 9.0 | 9.0 | 9.0 |
| | .063 | 9.0 | 9.0 | 8.0 | 9.0 | 9.0 | 9.0 | 9.0 | 9.0 | 9.0 | 9.0 | 9.0 | 9.0 | 9.0 | 8.0 |
| | .032 | 9.0 | 9.0 | 7.0 | 9.0 | 9.0 | 9.0 | 9.0 | 2.0 | 9.0 | 9.0 | 9.0 | 9.0 | 8.0 | 7.0 |
| Isobutylammonium 2-(5-isopropyl-5-methyl-4-oxo-2-imidazolin-2-yl)-nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | | 9.0 | 9.0 | 9.0 | 9.0 | 9.0 | 9.0 | 9.0 |
| | .250 | 9.0 | 9.0 | 8.0 | 9.0 | 9.0 | 9.0 | | 9.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .063 | 9.0 | 9.0 | 7.0 | 9.0 | 9.0 | 9.0 | 9.0 | 6.0 | 9.0 | 9.0 | 9.0 | 9.0 | 9.0 | 9.0 |
| | .032 | 9.0 | 9.0 | 7.0 | 9.0 | 9.0 | 9.0 | 9.0 | 4.0 | 9.0 | 9.0 | 9.0 | 8.0 | 9.0 | 9.0 |
| 2-Methoxy-1-methyl-ethylammonium 2-(5-isopropyl-5-methyl-4-oxo-2-imidazolin-2-yl)nicotinate | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 7.0 | 9.0 | 9.0 | 9.0 | 9.0 | 9.0 | 9.0 |
| | .063 | 9.0 | 9.0 | 6.0 | 9.0 | 9.0 | 9.0 | | 4.0 | 9.0 | 9.0 | 9.0 | 9.0 | 9.0 | 9.0 |
| | .032 | 9.0 | 9.0 | 6.0 | 9.0 | 9.0 | 9.0 | 2.0 | 9.0 | 9.0 | 9.0 | 9.0 | 9.0 | 9.0 | |

TABLE XI-continued

POST-EMERGENCE TESTS - RATES IN KG/HA

| Compound | RATE | BARNY ARDGR | GREEN FOX | P NUTSEDGE | WILD OATS | QUACK GRASS | FLD BINDWD | MRNGL RY SP | RAGWEED | VELVE TLEAF | S BARLY LA | CORN FIELD | RICE, NATO | SOY-BEAN AD | SUNFLR XXX |
|---|---|---|---|---|---|---|---|---|---|---|---|---|---|---|---|
| tert-Butylammonium | 1.000 | 9.0 | 9.0 | 9.0 | 9.0 | 9.0 | 9.0 | | 9.0 | 9.0 | 9.0 | 9.0 | 9.0 | 9.0 | 9.0 |
| 2-(5-isopropyl-5- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| methyl-4-oxo-2- | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| imidazolin-2-yl)- | .125 | 9.0 | 9.0 | 8.0 | 9.0 | 9.0 | 9.0 | 9.0 | 7.0 | 9.0 | 9.0 | 9.0 | 9.0 | 9.0 | 9.0 |
| nicotinate | .063 | 9.0 | 9.0 | 6.0 | 9.0 | 9.0 | 9.0 | 9.0 | 7.0 | 9.0 | 9.0 | 9.0 | 9.0 | 9.0 | 9.0 |
| | .032 | 9.0 | 9.0 | 5.0 | 9.0 | 9.0 | 9.0 | | 1.0 | 9.0 | 9.0 | 9.0 | 8.0 | 8.0 | 9.0 |
| 2,2,2-Trichloro- | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| ethyl 2-(5-isopropyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 5-methyl-4-oxo-2- | .250 | 9.0 | 9.0 | 8.0 | 9.0 | 9.0 | 9.0 | 9.0 | 8.0 | 9.0 | 9.0 | 9.0 | 9.0 | 9.0 | 9.0 |
| imidazolin-2-yl)- | .125 | 9.0 | 9.0 | 7.0 | 9.0 | 9.0 | 9.0 | 9.0 | 6.0 | 9.0 | 9.0 | 9.0 | 9.0 | 9.0 | 8.0 |
| nicotinate | .063 | 9.0 | 9.0 | 7.0 | 9.0 | 9.0 | 9.0 | 9.0 | 6.0 | 9.0 | 9.0 | 9.0 | 8.0 | 8.0 | 7.0 |
| | .032 | 9.0 | 9.0 | 6.0 | 9.0 | 9.0 | 9.0 | 9.0 | 2.0 | 6.0 | 9.0 | 9.0 | 6.0 | 8.0 | 6.0 |
| 6-Chloro-2-(5- | 1.000 | 9.0 | 9.0 | 9.0 | 9.0 | 9.0 | 9.0 | 9.0 | 9.0 | 9.0 | 9.0 | 9.0 | 9.0 | 9.0 | 8.0 |
| isopropyl-5-methyl- | .500 | 9.0 | 9.0 | 9.0 | 9.0 | 9.0 | 9.0 | 9.0 | 9.0 | 9.0 | 9.0 | 9.0 | 9.0 | 9.0 | 7.0 |
| 4-oxo-2-imidazolin- | .250 | 9.0 | 9.0 | 9.0 | 9.0 | 9.0 | 9.0 | 9.0 | 8.0 | 9.0 | 9.0 | 9.0 | 9.0 | 9.0 | 7.0 |
| 2-yl)nicotinic acid | .125 | 9.0 | 9.0 | 8.0 | 9.0 | 9.0 | 9.0 | 9.0 | 9.0 | 9.0 | 9.0 | 9.0 | 9.0 | 8.0 | 7.0 |
| | .063 | 9.0 | 9.0 | 7.0 | 9.0 | 9.0 | 8.0 | 7.0 | 7.0 | 3.0 | 9.0 | 9.0 | 9.0 | 7.0 | 4.0 |
| | .032 | 4.0 | 9.0 | 7.0 | 9.0 | 7.0 | 7.0 | 7.0 | 6.0 | 1.0 | 9.0 | 7.0 | 5.0 | 6.0 | 4.0 |
| 1-Ethylmethyl 2-(1- | .500 | 9.0 | 9.0 | 8.0 | 9.0 | 9.0 | 9.0 | 9.0 | 6.0 | 9.0 | 9.0 | 9.0 | 9.0 | 8.0 | 9.0 |
| carboxy-4-isopropyl- | .250 | 9.0 | 9.0 | 8.0 | 9.0 | 9.0 | 9.0 | 9.0 | 7.0 | 9.0 | 9.0 | 9.0 | 9.0 | 6.0 | 7.0 |
| 4-methyl-5-oxo-2- | .125 | 6.0 | 8.0 | 7.0 | 8.0 | 7.0 | 9.0 | 6.0 | 4.0 | 9.0 | 7.0 | 9.0 | 7.0 | 3.0 | 6.0 |
| imidazolin-2-yl)- | .063 | 3.0 | 8.0 | 1.0 | 5.0 | 7.0 | 7.0 | 6.0 | 0.0 | 9.0 | 6.0 | 9.0 | 7.0 | 1.0 | |
| nicotinate | .032 | 1.0 | 7.0 | 1.0 | 4.0 | 4.0 | 7.0 | 5.0 | 0.0 | 4.0 | 6.0 | 9.0 | | 1.0 | 4.0 |
| Methyl 2-[4-isopropyl- | 1.000 | 9.0 | 7.0 | 7.0 | 6.0 | 9.0 | 9.0 | 7.0 | 8.0 | 9.0 | 9.0 | 9.0 | 8.0 | 6.0 | 9.0 |
| 4-methyl-5-oxo-1-(p- | .500 | 4.0 | 6.0 | 4.0 | 4.0 | 7.0 | 7.0 | 6.0 | 7.0 | 9.0 | 9.0 | 9.0 | 7.0 | 5.0 | 9.0 |
| tolysulfonyl)-2- | .250 | 2.0 | 9.0 | 2.0 | 0.0 | 7.0 | 7.0 | 3.0 | 0.0 | 3.0 | 7.0 | 9.0 | 4.0 | 4.0 | 7.0 |
| imidazolin-2-yl)- | .125 | 1.0 | 6.0 | 0.0 | 0.0 | 6.0 | 6.0 | 1.0 | 0.0 | 1.0 | 5.0 | 9.0 | 3.0 | 2.0 | 7.0 |
| nicotinate | .063 | 0.0 | 5.0 | 0.0 | 0.0 | 5.0 | 0.0 | 0.0 | 0.0 | 0.0 | 2.0 | 9.0 | 3.0 | 2.0 | 6.0 |
| | .032 | 0.0 | 3.0 | 0.0 | 0.0 | 4.0 | 0.0 | 0.0 | 0.0 | 0.0 | 2.0 | 8.0 | 3.0 | 1.0 | 4.0 |
| 5-Butyl-2-(5- | 4.000 | 8.0 | 9.0 | 7.0 | 9.0 | 8.0 | 9.0 | 4.0 | 2.0 | 9.0 | 4.0 | 6.0 | 9.0 | 7.0 | 1.0 |
| isopropyl-5-methyl- | 1.000 | 3.0 | 6.0 | 2.0 | 3.0 | 2.0 | 7.0 | 3.0 | 0.0 | 9.0 | 2.0 | 0.0 | 5.0 | 7.0 | 0.0 |
| 4-oxo-2-imidazolin- 2-yl)nicotinic acid | .500 | 0.0 | 6.0 | 2.0 | 0.0 | 2.0 | 2.0 | 2.0 | 0.0 | 2.0 | 3.0 | 0.0 | 0.0 | 7.0 | 0.0 |
| 2-Isopropyl-2-methyl- | 1.000 | 9.0 | | 7.0 | 8.0 | 9.0 | 9.0 | 9.0 | 6.0 | 9.0 | 9.0 | 9.0 | 7.0 | 9.0 | 9.0 |
| 8-propyl-5H—imidazo- | .500 | 6.0 | | 7.0 | 6.0 | 9.0 | 9.0 | 9.0 | 5.0 | 8.0 | 9.0 | 9.0 | 7.0 | 9.0 | 9.0 |
| [1',2':1,2]pyrrolo- | .250 | 3.0 | | 7.0 | 4.0 | 8.0 | 7.0 | 7.0 | 3.0 | 3.0 | 9.0 | 8.0 | 3.0 | 9.0 | 8.0 |
| [3,4-b]pyridine-3- | .125 | 3.0 | 1.0 | 1.0 | 6.0 | 5.0 | 4.0 | 1.0 | 1.0 | 9.0 | 6.0 | 3.0 | 5.0 | 6.0 | |
| (2H), 5-dione | .063 | 2.0 | | 0.0 | 1.0 | 2.0 | 4.0 | 2.0 | 0.0 | 0.0 | 5.0 | 4.0 | 3.0 | 2.0 | 3.0 |
| | .032 | 2.0 | | 0.0 | 1.0 | 0.0 | 2.0 | 1.0 | 0.0 | 0.0 | 3.0 | 2.0 | 2.0 | 1.0 | 3.0 |
| 2,8-Diisopropyl-2-methyl-5H—imidazo-[1',2':1,2]pyrrolo-[3,4-b]pyridine-3-(2H), 5-dione | 8.000 | 9.0 | 9.0 | 7.0 | 9.0 | 5.0 | 2.0 | 9.0 | 9.0 | 7.0 | | | | | |
| 2-(5-Isopropyl-5-methyl- | 1.000 | 7.0 | 7.0 | 0.0 | 3.0 | 4.0 | 2.0 | 4.0 | 0.0 | 0.0 | 5.0 | 9.0 | 4.0 | 3.0 | 9.0 |
| 4-oxo-2-imidazolin-2- | .500 | 5.0 | 7.0 | 0.0 | 2.0 | 2.0 | 1.0 | 2.0 | 0.0 | 0.0 | 4.0 | 9.0 | 3.0 | 2.0 | 6.0 |
| yl)-6-phenoxynicotinic | .250 | 3.0 | 7.0 | 0.0 | 0.0 | 1.0 | 1.0 | 1.0 | 0.0 | 0.0 | 2.0 | 9.0 | 3.0 | 1.0 | 6.0 |
| acid | .125 | 1.0 | 5.0 | 0.0 | 0.0 | 0.0 | 0.0 | 0.0 | 0.0 | 0.0 | 1.0 | 7.0 | 0.0 | 0.0 | 6.0 |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| | .063 | 1.0 | 1.0 | 0.0 | 0.0 | 0.0 | 0.0 | 0.0 | 0.0 | 0.0 | 0.0 | 3.0 | 0.0 | 0.0 | 5.0 |
| | .032 | 0.0 | 0.0 | 0.0 | 0.0 | 0.0 | 0.0 | 0.0 | 0.0 | 0.0 | 0.0 | 2.0 | 0.0 | 0.0 | 4.0 |
| Methyl 2-[1-(p-chloro- | 1.000 | 9.0 | 9.0 | 8.0 | 9.0 | 8.0 | 9.0 | 9.0 | 9.0 | 9.0 | 9.0 | 9.0 | 9.0 | 9.0 | 9.0 |
| benzoyl)-4-isopropyl- | .500 | 9.0 | 9.0 | 8.0 | 9.0 | 8.0 | 9.0 | 9.0 | 9.0 | 9.0 | 9.0 | 9.0 | 9.0 | 9.0 | 9.0 |
| 4-methyl-5-oxo-2- | .250 | 7.0 | 9.0 | 8.0 | 9.0 | 8.0 | 9.0 | 9.0 | 7.0 | 9.0 | 9.0 | 9.0 | 7.0 | 8.0 | 9.0 |
| imidazolin-2-yl)- | .125 | 2.0 | 7.0 | 7.0 | 8.0 | 8.0 | 7.0 | 7.0 | 3.0 | 9.0 | 9.0 | 9.0 | 7.0 | | 9.0 |
| nicotinoate | .063 | 1.0 | 4.0 | 3.0 | 7.0 | 7.0 | 5.0 | 5.0 | 1.0 | 8.0 | 8.0 | 8.0 | 5.0 | 7.0 | 8.0 |
| | .032 | 1.0 | 2.0 | 1.0 | 5.0 | 7.0 | 4.0 | 4.0 | 0.0 | 8.0 | 7.0 | 5.0 | 3.0 | 6.0 | 6.0 |
| Methyl 2-(1-p-anisoyl-4- | 1.000 | 9.0 | 9.0 | 7.0 | 9.0 | 9.0 | 9.0 | 9.0 | 9.0 | 9.0 | 9.0 | 9.0 | 9.0 | 9.0 | 9.0 |
| isopropyl-4-methyl-5-oxo- | .500 | 9.0 | 9.0 | 9.0 | 9.0 | 9.0 | 9.0 | 9.0 | 7.0 | 9.0 | 9.0 | 9.0 | 9.0 | 8.0 | 9.0 |
| 2-imidazolin-2-yl)- | .250 | 8.0 | 9.0 | 8.0 | 9.0 | 7.0 | 7.0 | 7.0 | 7.0 | 9.0 | 9.0 | 9.0 | 7.0 | 7.0 | 9.0 |
| nicotinate | .125 | 2.0 | 6.0 | 2.0 | 9.0 | 7.0 | 7.0 | 7.0 | 1.0 | 9.0 | 9.0 | 7.0 | 5.0 | | 9.0 |
| | .063 | 1.0 | 5.0 | 1.0 | 3.0 | 7.0 | 6.0 | 4.0 | 0.0 | 6.0 | 8.0 | 7.0 | 3.0 | 6.0 | 8.0 |
| Methyl 2-[4-isopropyl-4- | 1.000 | 9.0 | 9.0 | 8.0 | 9.0 | 9.0 | 9.0 | 9.0 | 9.0 | 9.0 | 9.0 | 9.0 | 8.0 | 9.0 | 9.0 |
| methyl-1-p-nitrobenzoyl)- | .500 | 9.0 | 9.0 | 8.0 | 9.0 | 9.0 | 9.0 | 9.0 | 7.0 | 9.0 | 9.0 | 9.0 | 8.0 | 8.0 | 9.0 |
| 5-oxo-2-imidazolin-2-yl)- | .250 | 6.0 | 9.0 | 7.0 | 9.0 | 8.0 | 9.0 | 9.0 | 7.0 | 9.0 | 9.0 | 9.0 | 7.0 | 8.0 | 9.0 |
| nicotinate | .125 | 1.0 | 9.0 | 7.0 | 9.0 | 7.0 | 8.0 | 4.0 | 0.0 | 8.0 | 9.0 | 8.0 | 5.0 | 7.0 | 9.0 |
| | .063 | 1.0 | 3.0 | 3.0 | 6.0 | 6.0 | 6.0 | 3.0 | 0.0 | 8.0 | 7.0 | 3.0 | 3.0 | 7.0 | 7.0 |
| | .032 | 0.0 | 1.0 | 0.0 | 0.0 | 4.0 | 1.0 | 3.0 | 0.0 | 6.0 | 6.0 | 2.0 | 2.0 | 5.0 | 3.0 |
| 6-Ethoxy-2-(5-iso- | 1.000 | 9.0 | 9.0 | 9.0 | 9.0 | 9.0 | 9.0 | 9.0 | 7.0 | 8.0 | 9.0 | 9.0 | 9.0 | 8.0 | 9.0 |
| propyl-5-methyl-4- | .500 | 9.0 | 9.0 | 9.0 | 9.0 | 9.0 | 8.0 | 7.0 | 6.0 | 8.0 | 9.0 | 9.0 | 8.0 | 7.0 | 9.0 |
| oxo-2-imidazolin-2- | .250 | 9.0 | 9.0 | 9.0 | 9.0 | 9.0 | 8.0 | 8.0 | 2.0 | 7.0 | 9.0 | 9.0 | 8.0 | | 9.0 |
| yl)nicotinic acid | .125 | 8.0 | 9.0 | 9.0 | 9.0 | 8.0 | 8.0 | 4.0 | 1.0 | 1.0 | 7.0 | 9.0 | 8.0 | 6.0 | 9.0 |
| | .063 | 4.0 | 7.0 | 9.0 | 8.0 | 6.0 | 6.0 | 3.0 | 0.0 | 0.0 | 6.0 | 8.0 | 5.0 | 4.0 | 9.0 |
| | .032 | 3.0 | 6.0 | 8.0 | 1.0 | 6.0 | 5.0 | 1.0 | 0.0 | 0.0 | 5.0 | 7.0 | | 3.0 | 8.0 |
| 2-(5-Isopropyl-5- | 1.000 | 9.0 | 9.0 | 9.0 | 9.0 | 9.0 | 9.0 | 9.0 | 3.0 | 8.0 | 9.0 | 9.0 | 9.0 | 5.0 | 9.0 |
| methyl-4-oxo-2- | .500 | 7.0 | 8.0 | 9.0 | 9.0 | 9.0 | 9.0 | 6.0 | 0.0 | 6.0 | 9.0 | 9.0 | 9.0 | 4.0 | 9.0 |
| imidazolin-2-yl)- | .125 | 3.0 | 7.0 | 7.0 | 6.0 | 6.0 | 7.0 | 4.0 | 0.0 | 0.0 | 7.0 | 8.0 | 5.0 | 2.0 | 7.0 |
| 6-(methylthio)- | .125 | 3.0 | 7.0 | 7.0 | 6.0 | 6.0 | 7.0 | 4.0 | 0.0 | 0.0 | 7.0 | 8.0 | 5.0 | 2.0 | 7.0 |
| nicotinic acid | .063 | 1.0 | 7.0 | 7.0 | 3.0 | 5.0 | 6.0 | 1.0 | 0.0 | 0.0 | 7.0 | 7.0 | 4.0 | 2.0 | 7.0 |
| | .032 | 0.0 | 5.0 | 1.0 | 1.0 | 3.0 | 5.0 | 0.0 | 0.0 | 0.0 | 7.0 | 6.0 | 2.0 | 1.0 | 7.0 |
| 2-(5-Isopropyl-5- | 1.000 | 9.0 | 9.0 | 9.0 | 9.0 | 9.0 | 9.0 | 9.0 | 9.0 | 9.0 | | 9.0 | 9.0 | 9.0 | 9.0 |
| methyl-4-oxo-2- | .500 | 9.0 | | 9.0 | 9.0 | 9.0 | 9.0 | 9.0 | 9.0 | 9.0 | | 9.0 | 9.0 | 8.0 | 9.0 |
| imidazolin-2-yl)- | .250 | 9.0 | | 8.0 | 9.0 | 9.0 | | 9.0 | 9.0 | 9.0 | | 9.0 | 9.0 | 7.0 | 9.0 |
| 5-methylnicotinic | .125 | 9.0 | | 8.0 | 9.0 | 8.0 | 9.0 | 9.0 | 9.0 | 9.0 | | 9.0 | 8.0 | 7.0 | 9.0 |
| acid | .063 | 9.0 | | 8.0 | 9.0 | 7.0 | | 9.0 | 7.0 | 9.0 | | 9.0 | 8.0 | 6.0 | 9.0 |
| | .032 | 9.0 | | 7.0 | 9.0 | 8.0 | | 9.0 | 3.0 | 9.0 | | 9.0 | 6.0 | 5.0 | 9.0 |
| Methyl 2-(5-isopropyl- | 2.000 | 9.0 | 9.0 | 9.0 | 9.0 | 9.0 | 9.0 | 9.0 | 9.0 | 9.0 | | 9.0 | 9.0 | | 9.0 |
| 5-methyl-4-oxo-2- | 1.000 | 9.0 | 9.0 | 9.0 | 9.0 | 9.0 | 9.0 | 8.0 | 9.0 | 9.0 | | 9.0 | 9.0 | | 9.0 |
| imidazolin-2-yl)-5- | | | | | | | | | | | | | | | |
| methylnicotinate | | | | | | | | | | | | | | | |
| Methyl 5-(hydroxy- | 1.000 | 0.0 | 4.0 | 7.0 | 0.0 | 7.0 | 9.0 | 4.0 | 0.0 | 4.0 | | 3.0 | 3.0 | 2.0 | 5.0 |
| methyl)-2-(5-iso- | | | | | | | | | | | | | | | |
| propyl-5-methyl-4- | | | | | | | | | | | | | | | |
| oxo-2-imidazolin- | | | | | | | | | | | | | | | |
| 2-yl)nicotinate | | | | | | | | | | | | | | | |
| 5-(Hydroxymethyl)-2- | 2.000 | 9.0 | 9.0 | 7.0 | 3.0 | 3.0 | 9.0 | 9.0 | 0.0 | 9.0 | | 6.0 | 8.0 | 5.0 | 9.0 |
| (5-isopropyl-5-methyl- | 1.000 | 1.0 | 8.0 | 7.0 | 1.0 | | 9.0 | 9.0 | 0.0 | 9.0 | | 6.0 | 8.0 | 5.0 | 8.0 |
| 4-oxo-2-imidazolin-2- | .500 | 0.0 | 7.0 | 6.0 | 0.0 | 3.0 | 9.0 | 9.0 | 0.0 | 9.0 | | 6.0 | 8.0 | 5.0 | 7.0 |
| yl)nicotinic acid | | | | | | | | | | | | | | | |
| 2-(5-Isopropyl-5- | 2.000 | 9.0 | 9.0 | 4.0 | 9.0 | 4.0 | 9.0 | 6.0 | 7.0 | 9.0 | | 9.0 | 7.0 | 5.0 | 9.0 |
| methyl-4-oxo-2- | 1.000 | 8.5 | 8.0 | 1.5 | 9.0 | 1.5 | 7.0 | 7.0 | 4.5 | 9.0 | | 9.0 | 7.5 | 4.5 | 8.0 |

TABLE XI-continued

| POST-EMERGENCE TESTS - RATES IN KG/HA | | | | | | | | | | | | | | |
|---|---|---|---|---|---|---|---|---|---|---|---|---|---|---|
| imidazolin-2-yl)-5-phenylnicotinic acid | .500 | 8.5 | 7.0 | 1.0 | 9.0 | 0.0 | 6.5 | 6.5 | 4.0 | 9.0 | 9.0 | 6.5 | 4.5 | 7.5 |
| | .250 | 7.5 | 7.0 | 0.0 | 8.0 | 1.0 | 4.0 | 5.0 | 1.0 | 5.5 | 9.0 | 6.5 | 4.5 | 8.0 |
| | .125 | 4.0 | | 0.0 | 7.0 | 0.0 | 0.0 | 4.0 | 0.0 | 7.0 | 9.0 | 6.0 | 3.0 | 8.0 |
| | .063 | 4.0 | | 0.0 | 9.0 | 0.0 | | 2.0 | 0.0 | 6.0 | 9.0 | 5.0 | 2.0 | 1.0 |
| | .032 | 2.0 | | 0.0 | 7.0 | 0.0 | 0.0 | 0.0 | 0.0 | 6.0 | 9.0 | 4.0 | 1.0 | 1.0 |
| 2-(5-Isopropyl-5-methyl-4-oxo-2-imidazolin-2-yl)-6-phenylnicotinic acid | 4.000 | 9.0 | 9.0 | 7.0 | 9.0 | 9.0 | 9.0 | 6.0 | 6.0 | 7.0 | 9.0 | 8.0 | 7.0 | 9.0 |
| | 1.000 | 9.0 | 9.0 | 3.0 | 7.0 | 2.0 | 6.0 | 4.0 | 4.0 | 2.0 | 9.0 | 4.0 | 5.0 | 9.0 |
| | .500 | 8.0 | 9.0 | 3.0 | 3.0 | | 8.0 | 3.0 | 1.0 | 2.0 | 6.0 | | 5.0 | 9.0 |
| | .250 | 8.0 | 7.0 | 2.0 | 2.0 | 2.0 | 5.0 | 1.0 | 0.0 | 0.0 | 6.0 | 3.0 | 5.0 | 9.0 |
| 2-(5-Isopropyl-5-methyl-4-oxo-2-imidazolin-2-yl)-6-methylnicotinic acid | 4.000 | 9.0 | 9.0 | 9.0 | 9.0 | 9.0 | 9.0 | 9.0 | 9.0 | 9.0 | 9.0 | 9.0 | 9.0 | 9.0 |
| | 1.000 | 9.0 | 9.0 | 9.0 | 9.0 | 9.0 | 9.0 | 9.0 | 9.0 | 9.0 | 9.0 | 9.0 | 8.5 | 9.0 |
| | .500 | 9.0 | 9.0 | 9.0 | 9.0 | 9.0 | 9.0 | 9.0 | 8.5 | 9.0 | 9.0 | 9.0 | 8.0 | 9.0 |
| | .250 | 9.0 | 9.0 | 9.0 | 9.0 | 9.0 | 9.0 | 9.0 | 7.0 | 9.0 | 9.0 | 8.0 | 8.0 | 9.0 |
| | .125 | 9.0 | | 8.0 | 9.0 | 9.0 | | 9.0 | 5.0 | 9.0 | 9.0 | 7.0 | 9.0 | 9.0 |
| | .063 | 9.0 | | 6.0 | 9.0 | 9.0 | | 9.0 | 5.0 | 9.0 | 9.0 | 7.0 | 6.0 | 9.0 |
| | .032 | 9.0 | | 6.0 | 9.0 | 9.0 | | 9.0 | 5.0 | 9.0 | 9.0 | 7.0 | 5.0 | 9.0 |
| Methyl 2-(5-isopropyl-5-methyl-4-oxo-2-imidazolin-2-yl)-6-phenylnicotinate | 1.000 | 8.0 | | 0.0 | 2.0 | 4.0 | 2.0 | 4.0 | 0.0 | 0.0 | 9.0 | 1.0 | 3.0 | 7.0 |
| | .500 | 9.0 | | 0.0 | 1.0 | 1.0 | 1.0 | 1.0 | 0.0 | 0.0 | 9.0 | 0.0 | 3.0 | 7.0 |
| | .250 | 6.0 | | 0.0 | 1.0 | 1.0 | 1.0 | 1.0 | 0.0 | 0.0 | 9.0 | 0.0 | 1.0 | 6.0 |
| | .125 | 5.0 | | 0.0 | 0.0 | 0.0 | 1.0 | 0.0 | 0.0 | 0.0 | 9.0 | 0.0 | 1.0 | 5.0 |
| | .063 | 4.0 | | 0.0 | 0.0 | 0.0 | 0.0 | 0.0 | 0.0 | 0.0 | 9.0 | 0.0 | 1.0 | 4.0 |
| | .032 | 3.0 | | 0.0 | 0.0 | 0.0 | 0.0 | 0.0 | 0.0 | 0.0 | 7.0 | 0.0 | 1.0 | 4.0 |
| 5-Isopropyl-5-methyl-2-[3-(2-oxazolin-2-yl)-2-pyridyl]-2-imidazolin-4-one | 1.000 | 9.0 | | 9.0 | 9.0 | 9.0 | 9.0 | 9.0 | 9.0 | 9.0 | 9.0 | 9.0 | 9.0 | 9.0 |
| | .500 | 9.0 | | 8.0 | 9.0 | 9.0 | 9.0 | 9.0 | 8.0 | 9.0 | 9.0 | 8.0 | 8.0 | 9.0 |
| | .250 | 8.0 | | 8.0 | 9.0 | 9.0 | 9.0 | 9.0 | 7.0 | 8.0 | 9.0 | 8.0 | 8.0 | 9.0 |
| | .125 | 6.0 | | 8.0 | 8.0 | 9.0 | 8.0 | 7.0 | 5.0 | 8.0 | 9.0 | 8.0 | 8.0 | 8.0 |
| 5-Ethyl-2-(5-isopropyl-5-methyl-4-oxo-2-imidazolin-2-yl)nicotinic acid | 1.000 | 9.0 | | 8.7 | 9.0 | 8.7 | 9.0 | 9.0 | 9.0 | 9.0 | 9.0 | 9.0 | 6.0 | 9.0 |
| | .500 | 9.0 | | 8.0 | 9.0 | 8.3 | 9.0 | 9.0 | 9.0 | 9.0 | 9.0 | 8.7 | 5.0 | 9.0 |
| | .250 | 9.0 | | 8.0 | 9.0 | 8.7 | 8.7 | 8.7 | 8.7 | 9.0 | 9.0 | 8.7 | 4.0 | 9.0 |
| | .125 | 9.0 | | 6.7 | 8.7 | 7.0 | 8.7 | 8.0 | 8.3 | 9.0 | 9.0 | 7.7 | 3.0 | 9.0 |
| | .063 | 7.7 | | 6.0 | 8.3 | 6.0 | 8.5 | 7.7 | 5.0 | 9.0 | 8.7 | 7.0 | 2.0 | 9.0 |
| | .032 | 7.0 | | 4.7 | 6.3 | 2.3 | 8.5 | 6.3 | 2.0 | 8.7 | 6.7 | 6.0 | 1.7 | 9.0 |
| Methyl 5-ethyl-2-(5-isopropyl-5-methyl-4-oxo-2-imidazolin-2-yl)-nicotinate | 1.000 | 9.0 | | 9.0 | 8.0 | 8.0 | 9.0 | 7.0 | 8.0 | 9.0 | 7.0 | 8.0 | 2.0 | 9.0 |
| | .500 | 8.0 | | 8.0 | 5.0 | 8.0 | 9.0 | 6.0 | 8.0 | 9.0 | 6.0 | 8.0 | 0.0 | 9.0 |
| | .250 | 3.0 | | 4.0 | 4.0 | 3.0 | 8.0 | 5.0 | 4.0 | 7.0 | 1.0 | 7.0 | 3.0 | 9.0 |
| | .125 | 3.0 | | 1.0 | 2.0 | 2.0 | 8.0 | 3.0 | 4.0 | 4.0 | 1.0 | 4.0 | 1.0 | 7.0 |
| | .063 | 0.0 | | 0.0 | 0.0 | | 5.0 | 2.0 | | 3.0 | 0.0 | 4.0 | 1.0 | 7.0 |
| | .032 | 0.0 | | 0.0 | 0.0 | | 3.0 | 1.0 | | 2.0 | 0.0 | 3.0 | 1.0 | 4.0 |
| 6-Ethyl-2-(5-isopropyl-5-methyl-4-oxo-2-imidazolin-2-yl)nicotinic acid | 1.000 | 9.0 | | 9.0 | 9.0 | 9.0 | 9.0 | 9.0 | 9.0 | 9.0 | 9.0 | 9.0 | 8.0 | 9.0 |
| | .500 | 8.0 | | 9.0 | 9.0 | 9.0 | 9.0 | 9.0 | 7.0 | 9.0 | 9.0 | 9.0 | 7.0 | 9.0 |
| | .250 | 8.0 | | 9.0 | 8.0 | 9.0 | 9.0 | 9.0 | 5.0 | 8.0 | 9.0 | 8.0 | 6.0 | 9.0 |
| | .125 | 8.0 | | 7.0 | 5.0 | 8.0 | 9.0 | 8.0 | 3.0 | 3.0 | 9.0 | 7.0 | 5.0 | 9.0 |
| | .063 | 8.0 | | 7.0 | 4.0 | 4.0 | 9.0 | 8.0 | 0.0 | 1.0 | 9.0 | 5.0 | 3.0 | 9.0 |
| | .032 | 2.0 | | 4.0 | 4.0 | 1.0 | 0.0 | 6.0 | 0.0 | 0.0 | 9.0 | 5.0 | 3.0 | 9.0 |
| Ethyl 2-(5-isopropyl-5-methyl-4-oxo-2-imidazolin-2-yl)-6-propylnicotinate | 1.000 | 4.0 | | 3.0 | 2.0 | | 6.0 | 5.0 | 0.0 | 4.0 | 3.0 | 3.0 | 4.0 | 3.0 |
| | .500 | 1.0 | | 0.0 | 2.0 | 2.0 | 4.0 | 4.0 | 0.0 | 3.0 | 2.0 | 2.0 | 3.0 | 1.0 |
| | .250 | 1.0 | | 0.0 | 2.0 | 0.0 | 2.0 | 3.0 | 0.0 | 2.0 | 2.0 | 2.0 | 3.0 | 1.0 |
| | .125 | 0.0 | | 0.0 | 2.0 | 0.0 | 1.0 | 2.0 | 0.0 | 0.0 | 2.0 | 2.0 | 2.0 | 1.0 |
| | .063 | 0.0 | | 0.0 | 1.0 | 0.0 | 0.0 | 0.0 | 0.0 | 0.0 | 2.0 | 2.0 | 2.0 | 0.0 |
| | .032 | 0.0 | | 0.0 | 0.0 | 0.0 | 0.0 | 0.0 | 0.0 | 0.0 | 2.0 | 1.0 | 1.0 | 0.0 |
| 2-(5-Isopropyl-5-methyl-4-oxo-2-imida- | 1.000 | 9.0 | | 8.0 | 9.0 | 9.0 | 8.0 | 9.0 | 9.0 | 9.0 | 9.0 | 9.0 | 7.0 | 9.0 |
| | .500 | 8.0 | | 7.0 | 8.0 | 9.0 | 9.0 | 9.0 | 8.0 | 9.0 | 9.0 | 9.0 | 7.0 | 9.0 |

TABLE XI-continued

POST-EMERGENCE TESTS - RATES IN KG/HA

| Compound | RATE | BARNY ARDGR | GREEN FOX | P NUTSEDGE | WILD OATS | QUACK GRASS | FLD BINDWD | MRNGLRY SP | RAGWEED | VELVE TLEAF | CORN FIELD | RICE, NATO | SOYBEAN AD | SUNFLR XXX | S WHE AT ER |
|---|---|---|---|---|---|---|---|---|---|---|---|---|---|---|---|
| zolin-2-yl)-6-propyl-nicotinic acid | .250 | 8.0 | | 7.0 | 7.0 | 9.0 | 9.0 | 8.0 | 3.0 | 3.0 | | 9.0 | 8.0 | 5.0 | 9.0 |
| | .125 | 8.0 | | 4.0 | 3.0 | 7.0 | 6.0 | 5.0 | 1.0 | 3.0 | | 9.0 | 6.0 | 4.0 | 9.0 |
| | .063 | 5.0 | | 3.0 | 1.0 | 4.0 | 6.0 | 2.0 | 0.0 | 2.0 | | 9.0 | 3.0 | 3.0 | 8.0 |
| | .032 | 5.0 | | 1.0 | 0.0 | 1.0 | | 0.0 | 0.0 | 1.0 | | 9.0 | 3.0 | 1.0 | 6.0 |
| Methyl 2-(5-iso-propyl-5-methyl-4-oxo-2-imidazolin-2-yl)-6-propyl-nicotinate | 1.000 | 8.0 | | 4.0 | 4.0 | 7.0 | 4.0 | 6.0 | 0.0 | 3.0 | | 6.0 | 3.0 | 3.0 | 3.0 |
| | .500 | 7.0 | | 3.0 | 2.0 | 6.0 | 3.0 | 5.0 | 0.0 | 1.0 | | 3.0 | 2.0 | 2.0 | 3.0 |
| | .250 | 4.0 | | 1.0 | 1.0 | 3.0 | 3.0 | 3.0 | 0.0 | 0.0 | | 3.0 | 2.0 | 2.0 | 1.0 |
| | .125 | 3.0 | | 0.0 | 0.0 | 1.0 | 1.0 | 2.0 | 0.0 | 0.0 | | 2.0 | 1.0 | 1.0 | 1.0 |
| | .063 | 2.0 | | 0.0 | 0.0 | 0.0 | 0.0 | 2.0 | 0.0 | 0.0 | | 2.0 | 0.0 | 1.0 | 0.0 |
| Ethyl 6-ethyl-2-(5-isopropyl-5-methyl-4-oxo-2-imidazolin-2-yl)-nicotinate | 1.000 | 8.0 | | 7.0 | 6.0 | 8.0 | 9.0 | 6.0 | 0.0 | 7.0 | | 6.0 | 8.0 | 6.0 | 7.0 |
| | .500 | 6.0 | | 7.0 | 3.0 | 7.0 | 9.0 | 5.0 | 0.0 | 5.0 | | 2.0 | 6.0 | 3.0 | 7.0 |
| | .250 | 5.0 | | 6.0 | 2.0 | 7.0 | 9.0 | 4.0 | 0.0 | 4.0 | | 2.0 | 4.0 | 3.0 | 7.0 |
| | .125 | 3.0 | | 4.0 | 2.0 | 1.0 | 7.0 | 2.0 | 0.0 | 1.0 | | 3.0 | 3.0 | 1.0 | 3.0 |
| | .063 | 1.0 | | 2.0 | 1.0 | 1.0 | 6.0 | 2.0 | 0.0 | 0.0 | | 3.0 | 3.0 | 1.0 | 3.0 |
| | .032 | 0.0 | | 0.0 | 1.0 | 0.0 | 2.0 | 1.0 | 0.0 | 0.0 | | 3.0 | 2.0 | 0.0 | 1.0 |
| Isopropyl 6-ethyl-2-(5-isopropyl-5-methyl-4-oxo-2-imidazolin-2-yl)-nicotinate | 1.000 | 7.0 | | 7.0 | 4.0 | 6.0 | 7.0 | 7.0 | 0.0 | 4.0 | | 4.0 | 5.0 | 4.0 | 5.0 |
| | .500 | 4.0 | | 3.0 | 3.0 | 2.0 | 6.0 | 4.0 | 0.0 | 2.0 | | 4.0 | 5.0 | 2.0 | 7.0 |
| | .250 | 2.0 | | 1.0 | 3.0 | 2.0 | 6.0 | 4.0 | 0.0 | 1.0 | | 2.0 | 3.0 | 1.0 | 4.0 |
| | .125 | 1.0 | | 0.0 | 2.0 | 1.0 | 3.0 | 2.0 | 0.0 | 0.0 | | 2.0 | 3.0 | 1.0 | 3.0 |
| | .063 | 0.0 | | 0.0 | 2.0 | 0.0 | 1.0 | 1.0 | 0.0 | 0.0 | | 2.0 | 0.0 | 1.0 | 3.0 |
| | .032 | 0.0 | | 0.0 | 1.0 | 0.0 | 0.0 | 0.0 | 0.0 | 0.0 | | 1.0 | 0.0 | 1.0 | 2.0 |
| 6-Isopropyl-2-(5-isopropyl-5-methyl-4-oxo-2-imidazolin-2-yl)nicotinic acid | 1.000 | 9.0 | | 9.0 | 9.0 | 9.0 | 8.0 | 9.0 | 6.0 | 9.0 | | 9.0 | 9.0 | 7.0 | 9.0 |
| | .500 | 9.0 | | 9.0 | 4.0 | 8.0 | 9.0 | 8.0 | 2.0 | 8.0 | | 9.0 | 8.0 | 7.0 | 9.0 |
| | .250 | 9.0 | | 7.0 | 3.0 | 8.0 | 9.0 | 7.0 | 2.0 | 3.0 | | 9.0 | 9.0 | 6.0 | 9.0 |
| | .125 | 4.0 | | 5.0 | 1.0 | 3.0 | 8.0 | 7.0 | 0.0 | 2.0 | | 9.0 | 6.0 | 4.0 | 7.0 |
| | .063 | 3.0 | | 1.0 | 1.0 | 2.0 | 4.0 | 3.0 | 0.0 | 2.0 | | 7.0 | 4.0 | 4.0 | 7.0 |
| | .032 | 1.0 | | 0.0 | 0.0 | 0.0 | 4.0 | 0.0 | 0.0 | 1.0 | | 5.0 | 2.0 | 2.0 | 3.0 |
| Methyl 6-isopropyl-2-(5-isopropyl-5-methyl-4-oxo-2-imidazolin-2-yl)-nicotinate | 8.000 | 9.0 | 9.0 | 3.0 | 9.0 | 6.0 | 6.0 | 6.0 | 8.0 | 8.0 | | | | | |
| | 1.000 | 9.0 | | 7.0 | 7.0 | 9.0 | 9.0 | 7.0 | 0.0 | 3.0 | | 9.0 | 8.0 | 7.0 | 7.0 |
| | .500 | 9.0 | | 6.0 | 3.0 | 8.0 | 4.0 | 6.0 | 0.0 | 3.0 | | 9.0 | 7.0 | 6.0 | 5.0 |
| | .250 | 8.0 | | 5.0 | 0.0 | 2.0 | 4.0 | 3.0 | 0.0 | 2.0 | | 9.0 | 4.0 | 6.0 | 5.0 |
| | .125 | 4.0 | | 2.0 | 0.0 | 2.0 | 3.0 | 0.0 | 0.0 | 1.0 | | 4.0 | 1.0 | 2.0 | 2.0 |
| | .063 | 2.0 | | 0.0 | 0.0 | 0.0 | 1.0 | 0.0 | 0.0 | 1.0 | | 4.0 | 0.0 | 2.0 | 2.0 |
| | .032 | 1.0 | | 0.0 | 0.0 | 0.0 | 1.0 | 0.0 | 0.0 | 1.0 | | 3.0 | 0.0 | 2.0 | 2.0 |
| Methyl 6-ethyl-2-(5-isopropyl-5-methyl-4-oxo-2-imidazolin-2-yl)nicotinate | 5.000 | 9.0 | 8.0 | 8.0 | 9.0 | 8.0 | 6.0 | 8.0 | 3.0 | 7.0 | | | | | |
| | 1.000 | 8.0 | | 8.0 | 7.0 | 7.0 | 9.0 | 9.0 | 0.0 | 4.0 | | 8.0 | 8.0 | 6.0 | 8.0 |
| | .500 | 8.0 | | 8.0 | 6.0 | | 9.0 | 6.0 | 0.0 | 3.0 | | 4.0 | 4.0 | 4.0 | 8.0 |
| | .250 | 6.0 | | 6.0 | 5.0 | 7.0 | 8.0 | 6.0 | 0.0 | 1.0 | | 2.0 | 2.0 | 3.0 | 7.0 |
| | .125 | 4.0 | | 6.0 | 3.0 | 3.0 | 7.0 | 3.0 | 0.0 | 0.0 | | 2.0 | 1.0 | 3.0 | 4.0 |
| | .063 | 2.0 | | 4.0 | 3.0 | 1.0 | 5.0 | 2.0 | 0.0 | 0.0 | | 3.0 | 1.0 | 2.0 | 3.0 |
| | .032 | 1.0 | | 0.0 | 1.0 | 0.0 | 3.0 | 1.0 | 0.0 | 0.0 | | 2.0 | 1.0 | 1.0 | 1.0 |
| Ethyl 6-isopropyl-2-(5-isopropyl-5-methyl-4-oxo-2-imidazolin-2-yl)nicotinate | 8.000 | 8.0 | 9.0 | 0.0 | 9.0 | 3.0 | 9.0 | 9.0 | 6.0 | 8.0 | | | | | |
| Isopropyl 6-isopropyl-2-(5-isopropyl-5-methyl-4-oxo-2-imidazolin-2-yl)nicotinate | 5.000 | 8.0 | | 0.0 | 7.0 | 1.0 | 6.0 | 5.0 | 0.0 | 4.0 | | | | | |

TABLE XI-continued

POST-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGLRY SP | RAGWEED | VELVE TLEAF | S BAR LY LA | CORN FIELD | RICE, NATO | SOYBEAN AD | SUNFLR XXX | S WHE AT ER |
|---|---|---|---|---|---|---|---|---|---|---|---|---|---|---|---|---|
| 2-(5-Isopropyl-5-methyl-4-oxo-2-imidazolin-2-yl)-5-propylnicotinic acid | 1.000 | 9.0 | | 4.5 | 9.0 | 9.0 | 9.0 | 9.0 | 9.0 | 9.0 | | | 9.0 | 9.0 | 7.5 | 9.0 |
| | .500 | 9.0 | | 2.0 | 9.0 | 9.0 | 9.0 | 7.5 | 7.5 | 9.0 | | | 9.0 | 9.0 | 5.5 | 9.0 |
| | .250 | 9.0 | | 1.0 | 9.0 | 8.0 | 9.0 | 5.5 | 4.5 | 9.0 | | | 9.0 | 8.5 | 4.5 | 9.0 |
| | .125 | 8.5 | | 0.5 | 8.0 | 8.0 | 9.0 | 4.5 | 2.5 | 8.5 | | | 9.0 | 7.5 | 4.0 | 9.0 |
| | .063 | 9.0 | | 0.0 | 4.5 | 8.0 | 4.5 | 3.0 | 0.0 | 4.5 | | | 8.5 | 5.5 | 2.5 | 7.0 |
| | .032 | 3.5 | | 0.0 | 2.0 | 3.0 | 4.5 | 2.0 | 0.0 | 3.0 | | | 8.5 | 4.0 | 2.0 | 5.5 |
| 2-(5-Isopropyl-5-methyl-4-oxo-2-imidazolin-2-yl)-5,6-dimethyl-nicotinic acid | 5.000 | 9.0 | 8.0 | 8.0 | 6.0 | 0.0 | 0.0 | | 8.0 | | | | | | | |
| | 1.000 | 4.0 | | 9.0 | 9.0 | 9.0 | 9.0 | 9.0 | 9.0 | 9.0 | | | 9.0 | 9.0 | 6.0 | 9.0 |
| | .500 | 4.0 | | 9.0 | 9.0 | 9.0 | 9.0 | 9.0 | 8.0 | 9.0 | | | 9.0 | 9.0 | 4.0 | 9.0 |
| | .250 | 4.0 | | 9.0 | 9.0 | 9.0 | 9.0 | 9.0 | 8.0 | 9.0 | | | 9.0 | 9.0 | 4.0 | 9.0 |
| | .125 | 3.0 | | 9.0 | 9.0 | 9.0 | 9.0 | 8.0 | 2.0 | 9.0 | | | 9.0 | 9.0 | 3.0 | 9.0 |
| | .063 | 2.0 | | 9.0 | 9.0 | 9.0 | 9.0 | 6.0 | 2.0 | 7.0 | | | 9.0 | 9.0 | 2.0 | 9.0 |
| | .032 | 2.0 | | 3.0 | 9.0 | 3.0 | 4.0 | 5.0 | 2.0 | 3.0 | | | 9.0 | 8.0 | 2.0 | 9.0 |
| 6-Isopropyl-2-(5-isopropyl-5-methyl-4-oxo-2-imidazolin-2-yl)nicotinic acid | 1.000 | 9.0 | | 8.0 | 9.0 | 9.0 | 9.0 | 9.0 | 5.0 | 8.0 | | | 9.0 | 9.0 | 8.0 | 9.0 |
| | .500 | 9.0 | | 8.0 | 9.0 | 9.0 | 8.0 | 9.0 | 2.0 | 6.0 | | | 9.0 | 9.0 | 8.0 | 9.0 |
| | .250 | 9.0 | | 8.0 | 9.0 | 9.0 | 9.0 | 9.0 | 0.0 | 6.0 | | | 9.0 | 9.0 | 7.0 | 9.0 |
| | .125 | 9.0 | | 7.0 | 8.0 | 8.0 | 6.0 | 9.0 | 0.0 | 3.0 | | | 9.0 | 9.0 | 6.0 | 9.0 |
| | .063 | 7.0 | | 6.0 | 4.0 | 4.0 | 5.0 | 9.0 | 0.0 | 3.0 | | | 9.0 | 3.0 | 5.0 | 7.0 |
| | .032 | 4.0 | | 3.0 | 2.0 | 2.0 | 2.0 | 3.0 | 0.0 | 2.0 | | | 8.0 | 3.0 | 4.0 | 5.0 |
| Methyl 2-(5-isopropyl-5-methyl-4-oxo-2-imidazolin-2-yl)nicotinate | 1.000 | 9.0 | | 7.0 | 9.0 | 9.0 | 7.0 | 8.0 | 9.0 | 3.0 | | | 9.0 | 8.0 | 7.0 | 9.0 |
| | .500 | 7.0 | | 7.0 | 9.0 | 9.0 | 9.0 | 7.0 | 8.0 | 3.0 | | | 9.0 | 8.0 | 6.0 | 9.0 |
| | .250 | 9.0 | | 7.0 | 9.0 | 9.0 | 7.0 | 7.0 | 8.0 | 2.0 | | | 9.0 | 7.0 | 6.0 | 9.0 |
| | .125 | 2.0 | | 5.0 | 8.0 | 9.0 | 6.0 | 5.0 | 7.0 | 1.0 | | | 9.0 | 5.0 | 5.0 | 9.0 |
| | .063 | 2.0 | | 2.0 | 6.0 | 5.0 | 4.0 | 3.0 | 6.0 | 1.0 | | | 9.0 | 2.0 | 4.0 | 9.0 |
| | .032 | 1.0 | | 0.0 | 3.0 | 4.0 | 4.0 | 0.0 | 3.0 | 0.0 | | | 9.0 | 1.0 | 4.0 | 7.0 |
| 5-Isopropyl-2-(5-isopropyl-5-methyl-4-oxo-2-imidazolin-2-yl)nicotinic acid | 1.000 | 9.0 | | 4.0 | 9.0 | 9.0 | 9.0 | 9.0 | 9.0 | 9.0 | | 9.0 | 9.0 | 6.5 | 9.0 | 9.0 |
| | .500 | 9.0 | | 1.0 | 9.0 | 9.0 | 9.0 | 8.5 | 7.0 | 9.0 | | 9.0 | 9.0 | 5.5 | 9.0 | 9.0 |
| | .250 | 9.0 | | 0.0 | 9.0 | 9.0 | 9.0 | 7.5 | 5.5 | 9.0 | | 9.0 | 8.5 | 4.0 | 9.0 | 9.0 |
| | .125 | 9.0 | | 0.0 | 9.0 | 9.0 | 7.5 | 7.0 | 2.5 | 5.5 | | 9.0 | 7.5 | 3.0 | 8.0 | 8.0 |
| | .063 | 9.0 | | 0.0 | 9.0 | 8.0 | 9.0 | 4.5 | 1.5 | 4.0 | | 9.0 | 6.0 | 2.0 | 7.5 | 8.5 |
| | .032 | 5.5 | | 0.0 | 8.0 | 6.5 | 7.0 | 3.5 | 0.0 | 3.5 | | 8.5 | 4.5 | 2.0 | 5.5 | 5.5 |
| 5-Isopropyl-5-methyl-2-(3-methyl-5-nitro-2-pyridyl)-2-imidazolin-4-one | 8.000 | 0.0 | 0.0 | 5.0 | 6.0 | 0.0 | 0.0 | 2.0 | 0.0 | 7.0 | | | | | | |
| Methyl 2-(5-isopropyl-5-methyl-4-oxo-2-imidazolin-2-yl)-5-propylnicotinate | 1.000 | 8.0 | | 0.0 | 7.0 | 9.0 | 9.0 | 7.0 | 3.0 | 9.0 | | 9.0 | 9.0 | 3.0 | 9.0 | 6.0 |
| | .500 | 7.0 | | 0.0 | 4.0 | 9.0 | 9.0 | 5.0 | 2.0 | 9.0 | | 8.0 | 8.0 | 2.0 | 7.0 | 3.0 |
| | .250 | 4.0 | | 0.0 | 4.0 | 2.0 | 9.0 | 4.0 | 1.0 | 3.0 | | 4.0 | 7.0 | 2.0 | 7.0 | 2.0 |
| | .125 | 3.0 | | 0.0 | 2.0 | 2.0 | 6.0 | 2.0 | | 3.0 | | 3.0 | 3.0 | 1.0 | 6.0 | 2.0 |
| | .063 | 1.0 | | 0.0 | 1.0 | 0.0 | 5.0 | 0.0 | 0.0 | 1.0 | | 2.0 | 1.0 | 1.0 | 4.0 | 2.0 |
| | .032 | 1.0 | | 0.0 | 1.0 | 0.0 | 4.0 | 0.0 | 0.0 | 0.0 | | 1.0 | 1.0 | 1.0 | 4.0 | 1.0 |
| Methyl 6-isopropyl-2-(5-isopropyl-5-methyl-4-oxo-2-imidazolin-2-yl)-nicotinate | 1.000 | 9.0 | | 7.0 | 9.0 | 8.0 | 8.0 | 9.0 | | 4.0 | | 9.0 | 9.0 | 8.0 | 7.0 | 6.0 |
| | .500 | 9.0 | | 7.0 | 9.0 | 8.0 | 7.0 | 9.0 | 0.0 | 3.0 | | 9.0 | 8.0 | 8.0 | 4.0 | 4.0 |
| | .250 | 9.0 | | 7.0 | 8.0 | 8.0 | 3.0 | 9.0 | 0.0 | 1.0 | | 9.0 | 6.0 | 7.0 | 4.0 | 4.0 |
| | .125 | 7.0 | | 4.0 | 5.0 | 3.0 | 1.0 | 6.0 | | 0.0 | | 9.0 | 4.0 | 5.0 | 0.0 | 3.0 |
| | .063 | 4.0 | | 0.0 | 2.0 | 0.0 | 0.0 | 3.0 | 0.0 | 0.0 | | 9.0 | 3.0 | 3.0 | 0.0 | 3.0 |
| | .032 | 2.0 | | 0.0 | 2.0 | 0.0 | 0.0 | 3.0 | 0.0 | 0.0 | | 9.0 | 2.0 | 3.0 | 0.0 | 1.0 |
| 6-(Dimethylamino)-2-(5-isopropyl-5- | 1.000 | 9.0 | | 6.0 | 9.0 | 8.0 | 9.0 | 8.0 | 8.0 | 9.0 | | 9.0 | 8.0 | 6.0 | 9.0 | 9.0 |
| | .500 | 7.0 | | 4.0 | 9.0 | 8.0 | 9.0 | 9.0 | 8.0 | 9.0 | | 9.0 | 8.0 | 6.0 | 7.0 | 9.0 |

TABLE XI-continued

| POST-EMERGENCE TESTS - RATES IN KG/HA | | | | | | | | | | | | | | | |
|---|---|---|---|---|---|---|---|---|---|---|---|---|---|---|---|
| methyl-4-oxo-2- | .250 | 7.0 | | 5.0 | 9.0 | 7.0 | 7.0 | 6.0 | 3.0 | 9.0 | 9.0 | 8.0 | 3.0 | 7.0 | 9.0 |
| imidazolin-2-yl)- | .125 | 7.0 | | 2.0 | 8.0 | 5.0 | 7.0 | 6.0 | 0.0 | 1.0 | 9.0 | 8.0 | 3.0 | 7.0 | 6.0 |
| nicotinic acid | .063 | 4.0 | | 2.0 | 9.0 | 0.0 | 2.0 | 3.0 | 0.0 | 9.0 | 9.0 | 8.0 | 2.0 | 7.0 | 9.0 |
| | .032 | 3.0 | | 1.0 | 4.0 | 0.0 | 3.0 | 2.0 | 0.0 | 0.0 | 9.0 | 7.0 | 1.0 | 6.0 | 3.0 |
| Methyl 5-isopropyl- | 1.000 | 8.0 | | 0.0 | 9.0 | 4.0 | 8.0 | 7.0 | 3.0 | 9.0 | 9.0 | 8.0 | 2.0 | 7.0 | 6.0 |
| 2-(5-isopropyl-5- | .500 | 7.0 | | 0.0 | 9.0 | 3.0 | 8.0 | 7.0 | 0.0 | 9.0 | 9.0 | 8.0 | 2.0 | 6.0 | 5.0 |
| methyl-4-oxo-2- | .250 | 5.0 | | 0.0 | 7.0 | 0.0 | 8.0 | 3.0 | 0.0 | 1.0 | 7.0 | 7.0 | 2.0 | 5.0 | 0.0 |
| imidazolin-2-yl)- | .125 | 5.0 | | 0.0 | 6.0 | 0.0 | 8.0 | 5.0 | 0.0 | 1.0 | 5.0 | 6.0 | 2.0 | 4.0 | 0.0 |
| nicotinate | .063 | 3.0 | | 0.0 | 0.0 | 0.0 | 3.0 | 1.0 | 0.0 | 0.0 | 2.0 | 0.0 | 1.0 | 0.0 | 0.0 |
| | .032 | 3.0 | | 0.0 | 0.0 | 0.0 | 3.0 | 0.0 | 0.0 | 0.0 | 2.0 | 0.0 | 0.0 | 0.0 | 0.0 |
| 6,7-Dihydro-2-(5- | 1.000 | 9.0 | | 9.0 | 9.0 | 9.0 | 9.0 | 9.0 | 9.0 | 9.0 | 9.0 | 9.0 | 6.0 | 9.0 | 9.0 |
| isopropyl-5-methyl- | .500 | 8.0 | | 8.0 | 9.0 | 9.0 | 9.0 | 9.0 | 9.0 | 9.0 | 9.0 | 9.0 | 6.0 | 9.0 | 9.0 |
| 4-oxo-2-imidazolin- | .250 | 8.0 | | 8.0 | 9.0 | 9.0 | 9.0 | 9.0 | 8.0 | 9.0 | 9.0 | 9.0 | 6.0 | 9.0 | 9.0 |
| 2-yl)-5H—1-pyrindine- | .125 | 7.0 | | 8.0 | 9.0 | 9.0 | 9.0 | 7.0 | 4.0 | 9.0 | 9.0 | 8.0 | 4.0 | 9.0 | 8.0 |
| 3-carboxylic acid | .063 | 5.0 | | 7.0 | 9.0 | 9.0 | 7.0 | 6.0 | 0.0 | 7.0 | 9.0 | 9.0 | 3.0 | 9.0 | 5.0 |
| 2-(5-Isopropyl-5- | 1.000 | 7.0 | | 9.0 | 9.0 | 9.0 | 9.0 | 9.0 | 9.0 | 9.0 | 9.0 | 9.0 | 7.0 | 9.0 | 9.0 |
| methyl-4-oxo-2- | .500 | 6.0 | | 7.0 | 9.0 | 9.0 | 9.0 | 8.0 | 9.0 | 9.0 | 9.0 | 7.0 | 7.0 | 9.0 | 9.0 |
| imidazolin-2-yl)-6- | .250 | 6.0 | | 7.0 | 9.0 | 9.0 | 9.0 | 9.0 | 8.0 | 9.0 | 9.0 | 7.0 | 6.0 | 9.0 | 9.0 |
| (trifluoromethyl)- | .125 | 3.0 | | 6.0 | 9.0 | 9.0 | 4.0 | 6.0 | 6.0 | 6.0 | 9.0 | 9.0 | 4.0 | 9.0 | 9.0 |
| nicotinic acid | .063 | 4.0 | | 6.0 | 9.0 | 7.0 | 5.0 | 9.0 | 4.0 | 9.0 | 9.0 | 7.0 | 3.0 | 9.0 | 9.0 |
| | .032 | 2.0 | | 3.0 | 9.0 | 0.0 | 2.0 | 6.0 | 0.0 | 0.0 | 9.0 | 6.0 | 3.0 | 9.0 | 7.0 |
| Isopropyl 5-ethyl-2- | 1.000 | 7.0 | | 1.0 | 0.0 | 0.0 | 8.0 | 2.0 | 0.0 | 6.0 | 1.0 | 3.0 | 2.0 | 6.0 | 0.0 |
| (5-isopropyl-5- | .500 | 7.0 | | 0.0 | 0.0 | 0.0 | 6.0 | 1.0 | 0.0 | 1.0 | 1.0 | 1.0 | 1.0 | 5.0 | 0.0 |
| methyl-4-oxo-2- | .250 | 7.0 | | 0.0 | 0.0 | 0.0 | 1.0 | 0.0 | 0.0 | 0.0 | 0.0 | 0.0 | 1.0 | 2.0 | 0.0 |
| imidazolin-2-yl)- | .125 | 5.0 | | 0.0 | 0.0 | 0.0 | 1.0 | 0.0 | 0.0 | 0.0 | 0.0 | 0.0 | 1.0 | 1.0 | 0.0 |
| nicotinate | .063 | 3.0 | | 0.0 | 0.0 | 0.0 | 1.0 | 0.0 | 0.0 | 0.0 | 0.0 | 0.0 | 1.0 | 1.0 | 0.0 |
| | .032 | 1.0 | | 0.0 | 0.0 | 0.0 | 0.0 | 0.0 | 0.0 | 0.0 | 0.0 | 0.0 | 1.0 | 1.0 | 0.0 |
| 2-Propynyl 5-ethyl- | 1.000 | 9.0 | | 8.0 | 9.0 | 8.0 | | 9.0 | 9.0 | 9.0 | 9.0 | 6.0 | 6.0 | 9.0 | 9.0 |
| 2-(5-isopropyl-5- | .500 | 9.0 | | 7.0 | 9.0 | 8.0 | 0.0 | 8.0 | 9.0 | 9.0 | 9.0 | 6.0 | 6.0 | 9.0 | 9.0 |
| methyl-4-oxo-2- | .250 | 9.0 | | 7.0 | 7.0 | 7.0 | 0.0 | 8.0 | 6.0 | 9.0 | 8.0 | 6.0 | 6.0 | 9.0 | 7.0 |
| imidazolin-2-yl)- | .125 | 8.0 | | 6.0 | 6.0 | 5.0 | 0.0 | 8.0 | 6.0 | 7.0 | 8.0 | 6.0 | 3.0 | 9.0 | 6.0 |
| nicotinate | .063 | 5.0 | | 4.0 | 2.0 | 4.0 | | 7.0 | 1.0 | 6.0 | 4.0 | 3.0 | 3.0 | 8.0 | 4.0 |
| | .032 | 2.0 | | 1.0 | 1.0 | 2.0 | | 3.0 | 0.0 | 2.0 | 1.0 | 2.0 | 2.0 | 7.0 | 2.0 |
| Calcium 5-ethyl-2- | 1.000 | 9.0 | | 6.0 | 9.0 | 8.0 | 9.0 | 9.0 | 9.0 | 9.0 | 9.0 | 9.0 | 8.0 | 9.0 | 9.0 |
| (5-isopropyl-5- | .500 | 9.0 | | 7.0 | 9.0 | 7.0 | 9.0 | 9.0 | 8.0 | 9.0 | 9.0 | 9.0 | 7.0 | 9.0 | 9.0 |
| methyl-4-oxo-2- | .250 | 9.0 | | 9.0 | 9.0 | 7.0 | | 9.0 | 8.0 | 9.0 | 9.0 | 7.0 | 7.0 | 9.0 | 9.0 |
| imidazolin-2-yl)- | .125 | 9.0 | | 7.0 | 9.0 | 6.0 | 9.0 | 8.0 | 8.0 | 9.0 | 9.0 | 7.0 | 6.0 | 9.0 | 8.0 |
| nicotinate | .063 | 6.0 | | 6.0 | 7.0 | 4.0 | 9.0 | 8.0 | 4.0 | 8.0 | 9.0 | 7.0 | 4.0 | 8.0 | 8.0 |
| | .032 | 7.0 | | 3.0 | 3.0 | 2.0 | 8.0 | 8.0 | 2.0 | 8.0 | 3.0 | 6.0 | 4.0 | 8.0 | 8.0 |
| Sodium 5-ethyl-2- | 1.000 | 9.0 | | 8.0 | 9.0 | 9.0 | 9.0 | 9.0 | 9.0 | 9.0 | 9.0 | 9.0 | 7.0 | 9.0 | 9.0 |
| (5-isopropyl-5- | .500 | 9.0 | | 8.0 | 9.0 | 9.0 | 9.0 | 9.0 | 9.0 | 9.0 | 9.0 | 8.0 | 7.0 | 9.0 | 9.0 |
| methyl-4-oxo-2- | .250 | 9.0 | | 6.0 | 9.0 | 9.0 | | 9.0 | 9.0 | 9.0 | 9.0 | 8.0 | 7.0 | 9.0 | 9.0 |
| imidazolin-2-yl)- | .125 | 9.0 | | 6.0 | 9.0 | 8.0 | | 7.0 | 6.0 | 9.0 | 9.0 | 7.0 | 5.0 | 9.0 | 9.0 |
| nicotinate | .063 | 9.0 | | 6.0 | 7.0 | 8.0 | 8.0 | 7.0 | 3.0 | 8.0 | 9.0 | 6.0 | 3.0 | 9.0 | 8.0 |
| | .032 | 8.0 | | 3.0 | 6.0 | 3.0 | 8.0 | 7.0 | 1.0 | 8.0 | 9.0 | 5.0 | 3.0 | 9.0 | 6.0 |
| Benzyl 5-ethyl-2- | 1.000 | 9.0 | | 6.0 | 9.0 | 5.0 | 8.0 | 7.0 | 7.0 | 9.0 | 7.0 | 7.0 | 3.0 | 9.0 | 6.0 |
| (5-isopropyl-5- | .500 | 9.0 | | 2.0 | 7.0 | 5.0 | 8.0 | 7.0 | 4.0 | 9.0 | 7.0 | 4.0 | 3.0 | 9.0 | 5.0 |
| methyl-4-oxo-2- | .250 | 3.0 | | 2.0 | 3.0 | 3.0 | 6.0 | 6.0 | 3.0 | 8.0 | 1.0 | 4.0 | 1.0 | 7.0 | 3.0 |
| imidazolin-2-yl)- | .125 | 1.0 | | 0.0 | 1.0 | 2.0 | 2.0 | 6.0 | 1.0 | 7.0 | 1.0 | 3.0 | 0.0 | 6.0 | 0.0 |
| nicotinate | .063 | 1.0 | | 0.0 | 0.0 | 2.0 | 2.0 | 4.0 | 0.0 | 4.0 | 1.0 | 2.0 | 0.0 | 6.0 | 0.0 |
| | .032 | 0.0 | | 0.0 | 0.0 | 1.0 | | 1.0 | 0.0 | 2.0 | 0.0 | 2.0 | 0.0 | 4.0 | 0.0 |
| Isopropylammonium | .050 | 9.0 | 9.0 | 8.8 | 9.0 | 9.0 | 9.0 | 9.0 | 8.8 | 9.0 | | | | | |

TABLE XI-continued

POST-EMERGENCE TESTS - RATES IN KG/HA

| Compound | RATE | BARNY ARDGR | GREEN FOX | P NUT SEDGE | WILD OATS | QUACK GRASS | FLD BINDWD | MRNGL RY SP | RAGWEED | VELVE TLEAF | S BARLY LA | CORN FIELD | RICE, NATO | SOYBEAN AD | SUNFLR XXX |
|---|---|---|---|---|---|---|---|---|---|---|---|---|---|---|---|
| 2-(5-isopropyl-5-methyl-4-oxo-2-imidazolin-2-yl)-nicotinate | .045 | 9.0 | 8.8 | 8.8 | 9.0 | 9.0 | 9.0 | 9.0 | 8.4 | 9.0 | | | | | |
| | .040 | 9.0 | 9.0 | 8.8 | 9.0 | 9.0 | 9.0 | 9.0 | 8.2 | 9.0 | | | | | |
| | .035 | 8.6 | 8.8 | 9.0 | 9.0 | 9.0 | 9.0 | 9.0 | 7.8 | 9.0 | | | | | |
| | .030 | 9.0 | 9.0 | 8.2 | 9.0 | 9.0 | 9.0 | 9.0 | 7.2 | 9.0 | | | | | |
| Ethyl 5-ethyl-2-(5-isopropyl-5-methyl-4-oxo-2-imidazolin-2-yl)-nicotinate | 1.000 | 8.0 | | 6.0 | 6.0 | 7.0 | | 8.0 | 0.0 | 9.0 | 5.0 | 6.0 | 3.0 | 8.0 | 8.0 |
| | .500 | 8.0 | | 2.0 | 3.0 | 3.0 | 7.0 | 5.0 | 0.0 | 7.0 | 2.0 | 3.0 | 2.0 | 8.0 | 4.0 |
| | .250 | 7.0 | | 1.0 | 1.0 | 1.0 | | 5.0 | 0.0 | 6.0 | 1.0 | 2.0 | 2.0 | 7.0 | 2.0 |
| | .125 | 5.0 | | 0.0 | 0.0 | 0.0 | 7.0 | 3.0 | 0.0 | 4.0 | 1.0 | 2.0 | 2.0 | 6.0 | 1.0 |
| | .063 | 2.0 | | 0.0 | 0.0 | 0.0 | 3.0 | 2.0 | 0.0 | 2.0 | 1.0 | 1.0 | 2.0 | 6.0 | 0.0 |
| | .032 | 1.0 | | 0.0 | 0.0 | 0.0 | | 0.0 | 0.0 | 1.0 | 1.0 | 1.0 | 2.0 | 3.0 | 0.0 |
| Furfuryl 5-ethyl-2-(5-isopropyl-5-methyl-4-oxo-2-imidazolin-2-yl)-nicotinate | 1.000 | 9.0 | | 7.0 | 9.0 | 8.0 | 9.0 | 9.0 | 9.0 | 9.0 | 9.0 | 8.0 | 6.0 | 9.0 | 9.0 |
| | .500 | 9.0 | | 5.0 | 9.0 | 7.0 | 9.0 | 9.0 | 8.0 | 9.0 | 9.0 | 6.0 | 5.0 | 9.0 | 8.0 |
| | .250 | 9.0 | | 5.0 | 8.0 | 6.0 | 9.0 | 9.0 | 8.0 | 9.0 | 9.0 | 6.0 | 5.0 | 9.0 | 9.0 |
| | .125 | 9.0 | | 4.0 | 7.0 | 6.0 | 8.0 | 8.0 | 8.0 | 9.0 | 8.0 | 6.0 | 5.0 | 9.0 | 7.0 |
| | .063 | 5.0 | | 3.0 | | 2.0 | 8.0 | 7.0 | 2.0 | 7.0 | 6.0 | 4.0 | 3.0 | 9.0 | 3.0 |
| | .032 | 1.0 | | 1.0 | 2.0 | 1.0 | 7.0 | 7.0 | 0.0 | 5.0 | 4.0 | 3.0 | 3.0 | 9.0 | 2.0 |
| Isopropylammonium 5-ethyl-2-(5-isopropyl-5-methyl-4-oxo-2-imidazolin-2-yl)-nicotinate | 1.000 | 9.0 | | 7.0 | 9.0 | 8.0 | 9.0 | 9.0 | 9.0 | 9.0 | | 9.0 | 8.0 | 9.0 | 9.0 |
| | .500 | 9.0 | | 5.0 | 9.0 | 8.0 | 9.0 | 9.0 | 8.0 | 9.0 | | 9.0 | 8.0 | 7.0 | 9.0 |
| | .250 | 9.0 | | 5.0 | 9.0 | 8.0 | 9.0 | 9.0 | 7.0 | 9.0 | | 9.0 | 7.0 | 6.0 | 9.0 |
| | .125 | 9.0 | | 5.0 | 9.0 | 7.0 | 9.0 | 9.0 | 7.0 | 9.0 | | 9.0 | 7.0 | 5.0 | 9.0 |
| | .063 | 9.0 | | 3.0 | 9.0 | 6.0 | 8.0 | 7.0 | 6.0 | 9.0 | | 6.0 | 6.0 | 4.0 | 9.0 |
| | .032 | 8.0 | | 1.0 | 4.0 | 2.0 | 7.0 | 7.0 | 2.0 | 6.0 | | 5.0 | 5.0 | 3.0 | 9.0 |
| Benzyltrimethylammonium 5-ethyl-2-(5-isopropyl-5-methyl-4-oxo-2-imidazolin-2-yl)nicotinate | 1.000 | 9.0 | | 6.0 | 9.0 | 9.0 | 9.0 | 9.0 | 9.0 | 9.0 | | 9.0 | 8.0 | 8.0 | 9.0 |
| | .500 | 9.0 | | 5.0 | 9.0 | 8.0 | 9.0 | 9.0 | 9.0 | 9.0 | | 9.0 | 7.0 | 7.0 | 9.0 |
| | .250 | 9.0 | | 4.0 | 8.0 | 7.0 | 9.0 | 8.0 | 8.0 | 9.0 | | 8.0 | 6.0 | 6.0 | 9.0 |
| | .125 | 8.0 | | 4.0 | 7.0 | 7.0 | 9.0 | 7.0 | 8.0 | 9.0 | | 8.0 | 6.0 | 5.0 | 9.0 |
| | .063 | 6.0 | | 4.0 | 7.0 | 6.0 | 9.0 | 7.0 | 2.0 | 9.0 | | 7.0 | 5.0 | 3.0 | 9.0 |
| | .032 | 3.0 | | 2.0 | 4.0 | 3.0 | 8.0 | 7.0 | 2.0 | 7.0 | | 6.0 | 0.0 | | 9.0 |
| 7-Ethyl-2-isopropyl-2-methyl-5H—imidazo-[1',2':1,2]pyrrolo-[3,4-b]pyridine-3-(2H),5-dione | 1.000 | 9.0 | | 9.0 | 9.0 | 9.0 | | 9.0 | 9.0 | 9.0 | 9.0 | 8.0 | 7.0 | 9.0 | 8.0 |
| | .500 | 9.0 | | 7.0 | 9.0 | 9.0 | 9.0 | 9.0 | 9.0 | 9.0 | 9.0 | 8.0 | 6.0 | 9.0 | 8.0 |
| | .250 | 9.0 | | 7.0 | 9.0 | 9.0 | | 9.0 | 7.0 | 9.0 | 9.0 | 7.0 | 6.0 | 9.0 | 8.0 |
| | .125 | 9.0 | | 7.0 | 9.0 | 8.0 | 8.0 | 8.0 | 4.0 | 9.0 | 9.0 | 7.0 | 5.0 | 9.0 | 8.0 |
| | .063 | 7.0 | | 7.0 | 9.0 | 6.0 | 7.0 | 8.0 | 4.0 | 9.0 | 9.0 | 7.0 | 4.0 | 9.0 | 7.0 |
| | .032 | 7.0 | | 4.0 | 4.0 | 2.0 | 7.0 | | 2.0 | 3.0 | 9.0 | 3.0 | 3.0 | 9.0 | 7.0 |
| 2-(5-Isopropyl-5-methyl-4-thiono-2-imidazolin-2-yl)-nicotinic acid | 1.000 | 9.0 | | 9.0 | 9.0 | 9.0 | 9.0 | 9.0 | 9.0 | 9.0 | | 9.0 | 9.0 | 9.0 | 9.0 |
| | .500 | 9.0 | | 9.0 | 9.0 | 9.0 | 9.0 | 9.0 | 9.0 | 9.0 | | 9.0 | 9.0 | 9.0 | 9.0 |
| | .250 | 9.0 | | 9.0 | 9.0 | 9.0 | 9.0 | 9.0 | 9.0 | 9.0 | | 9.0 | 9.0 | 9.0 | 9.0 |
| | .125 | 8.0 | | 8.0 | 9.0 | 9.0 | 9.0 | 9.0 | 7.0 | 9.0 | | 9.0 | 9.0 | 9.0 | 9.0 |
| | .063 | 7.0 | | 8.0 | 9.0 | 9.0 | 9.0 | 8.0 | 2.0 | 9.0 | | 9.0 | 9.0 | 9.0 | 9.0 |
| | .032 | 7.0 | | 7.0 | 9.0 | 9.0 | 9.0 | 4.0 | 0.0 | 9.0 | | 9.0 | 9.0 | 9.0 | 9.0 |

| Compound | RATE | BARNY ARDGR | GREEN FOX | P NUTSEDGE | WILD OATS | QUACK GRASS | FLD BINDWD | MRNGLRY SP | RAGWEED | VELVE TLEAF | CORN FIELD | RICE, NATO | SOYBEAN AD | SUNFLR XXX | S WHEAT ER |
|---|---|---|---|---|---|---|---|---|---|---|---|---|---|---|---|
| Sodium 2-(5-iso-propyl-5-methyl-4-oxo-2-imidazolin-2-yl)-3-quinoline-carboxylate | 4.000 | 9.0 | 9.0 | 9.0 | 9.0 | 9.0 | 9.0 | 8.0 | 8.0 | 9.0 | 9.0 | 9.0 | 5.0 | 9.0 | 9.0 |
| | 1.320 | 9.0 | | 9.0 | 9.0 | 9.0 | 9.0 | 9.0 | | 9.0 | 9.0 | 9.0 | 5.0 | 9.0 | 9.0 |
| | 1.000 | 9.0 | 9.0 | 8.0 | 9.0 | 9.0 | 9.0 | 7.5 | 8.5 | 8.5 | 9.0 | 9.0 | 5.0 | 9.0 | 9.0 |
| | .660 | 9.0 | | 7.0 | 9.0 | 9.0 | 9.0 | 8.0 | | 9.0 | 9.0 | 9.0 | 3.0 | 9.0 | 9.0 |
| | .500 | 9.0 | | 7.0 | 9.0 | 9.0 | 9.0 | 9.0 | 9.0 | 8.0 | 9.0 | 9.0 | 5.0 | 9.0 | 9.0 |
| | .330 | 9.0 | | 7.0 | 9.0 | 9.0 | 5.0 | 6.0 | | 9.0 | 9.0 | 8.0 | 2.0 | 9.0 | 9.0 |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| | .250 | 8.0 | | 7.0 | 9.0 | 9.0 | 9.0 | 7.0 | 9.0 | 5.0 | 9.0 | 9.0 | 5.0 | 9.0 | 9.0 |
| 2-(5-Isopropyl-5-methyl-4-oxo-2-imidazolin-2-yl)-3-quinoline-carboxaldehyde | 4.000 | 9.0 | 7.0 | 8.0 | 9.0 | 9.0 | 9.0 | 7.0 | 8.0 | 8.0 | 9.0 | 7.0 | 4.0 | 9.0 | 9.0 |
| | 1.000 | 6.0 | 6.0 | 8.0 | 9.0 | 9.0 | 7.0 | 5.0 | 5.0 | 6.0 | 9.0 | 6.0 | 3.0 | 9.0 | 7.0 |
| 2-[3-(Hydroxy-methyl)-2-quinolyl]-5-isopropyl-5-methyl-2-imidazolin-4-one | 1.000 | 9.0 | | 7.0 | 9.0 | 7.0 | 5.0 | 7.0 | 9.0 | 6.0 | 9.0 | 6.0 | 4.0 | 9.0 | 8.0 |
| | .500 | 9.0 | | 6.0 | 9.0 | 6.0 | 4.0 | 7.0 | | 3.0 | 9.0 | 6.0 | 3.0 | 9.0 | 7.0 |
| | .250 | 9.0 | | 5.0 | 6.0 | 6.0 | 3.0 | 7.0 | 7.0 | 2.0 | 8.0 | 4.0 | 2.0 | 9.0 | 4.0 |
| | .125 | 3.0 | | 4.0 | 3.0 | 2.0 | 1.0 | 6.0 | 7.0 | 0.0 | 8.0 | 3.0 | 1.0 | 7.0 | 2.0 |
| | .063 | 1.0 | | 1.0 | 1.0 | 2.0 | 1.0 | 6.0 | 1.0 | 0.0 | 7.0 | 2.0 | 1.0 | 7.0 | 1.0 |
| | .032 | 0.0 | | 0.0 | 0.0 | 0.0 | 0.0 | 2.0 | | 0.0 | 7.0 | 2.0 | 0.0 | 4.0 | 1.0 |
| Ammonium 2-(5-iso-propyl-5-methyl-4-oxo-2-imidazolin-2-yl)-3-quinoline-carboxylate | 4.000 | 9.0 | 9.0 | 9.0 | 9.0 | 9.0 | 9.0 | 9.0 | 8.0 | 9.0 | 9.0 | 9.0 | 6.0 | 9.0 | 9.0 |
| | 1.230 | 9.0 | | 7.0 | 9.0 | 8.0 | 9.0 | 9.0 | | 9.0 | 9.0 | 9.0 | 4.0 | 9.0 | 9.0 |
| | 1.000 | 9.0 | 9.0 | 8.5 | 9.0 | 9.0 | 9.0 | 8.0 | 8.0 | 8.0 | 9.0 | 9.0 | 5.0 | 9.0 | 9.0 |
| | .615 | 9.0 | | 5.0 | 9.0 | 9.0 | 9.0 | 8.0 | | 9.0 | 9.0 | 9.0 | 3.0 | 9.0 | 9.0 |
| | .500 | 9.0 | | 9.0 | 9.0 | 9.0 | 9.0 | 9.0 | 8.0 | 8.0 | 9.0 | 8.0 | 6.0 | 9.0 | 9.0 |
| | .308 | 9.0 | | 7.0 | 9.0 | 7.0 | 9.0 | 9.0 | | 9.0 | 9.0 | 9.0 | 3.0 | 9.0 | 9.0 |
| | .250 | 7.0 | | 8.0 | 9.0 | 9.0 | 9.0 | 9.0 | 9.0 | 6.0 | 9.0 | 7.0 | 5.0 | 9.0 | 9.0 |
| | .154 | 9.0 | | 6.0 | 9.0 | 7.0 | 5.0 | 9.0 | | 8.0 | 9.0 | 9.0 | 2.0 | 9.0 | 9.0 |
| 2-Isopropyl-2-methyl-5H—imidazo-[1',2':1,2]pyrrolo-[3,4-b]quinoline-3-(2H), 5-dione | 4.000 | 9.0 | 9.0 | 9.0 | 9.0 | 9.0 | 9.0 | 7.0 | 8.0 | 9.0 | 9.0 | 9.0 | 4.0 | 9.0 | 9.0 |
| | 1.000 | 9.0 | 9.0 | 9.0 | 9.0 | 9.0 | 9.0 | 7.0 | 8.0 | 9.0 | 9.0 | 9.0 | 4.0 | 9.0 | 9.0 |
| Ethyl 2-(5-isopropyl-5-methyl-4-oxo-2-imidazolin-2-yl)-3-quinolinecarboxylate | 4.000 | 9.0 | 8.0 | 7.0 | 9.0 | 6.0 | 6.0 | 7.0 | 7.0 | 7.0 | 9.0 | 4.0 | 5.0 | 7.0 | 6.0 |
| | 1.000 | 7.0 | 5.0 | 3.0 | 8.0 | 4.0 | 4.0 | 3.0 | 7.0 | 3.0 | 9.0 | 3.0 | 5.0 | 7.0 | 7.0 |
| | .500 | 2.0 | 5.0 | 3.0 | 8.0 | | 4.0 | 3.0 | 0.0 | 3.0 | 4.0 | 3.0 | 3.0 | 6.0 | 3.0 |
| | .250 | | 5.0 | 1.0 | 8.0 | 1.0 | 1.0 | 1.0 | 0.0 | 1.0 | 3.0 | 3.0 | 3.0 | 6.0 | 3.0 |
| 7-Chloro-2-(5-iso-propyl-5-methyl-4-oxo-2-imidazolin-2-yl)-3-quinolinecarbo-xylic acid | 4.000 | 9.0 | 9.0 | 4.0 | 9.0 | 9.0 | 9.0 | 8.0 | 7.0 | 8.0 | 9.0 | 9.0 | 5.0 | 9.0 | 7.0 |
| | 1.000 | 9.0 | 8.0 | 4.0 | 9.0 | 2.0 | 4.0 | 6.0 | 1.0 | 3.0 | 9.0 | 8.0 | 4.0 | 9.0 | 5.0 |
| | .500 | 9.0 | 7.0 | 1.0 | 9.0 | 1.0 | 3.0 | 1.0 | 0.0 | 1.0 | 9.0 | 7.0 | 3.0 | 9.0 | 4.0 |
| | .250 | 3.0 | 6.0 | 1.0 | 7.0 | 0.0 | 0.0 | 0.0 | 0.0 | 0.0 | 9.0 | 6.0 | 3.0 | 7.0 | 3.0 |
| | .125 | 0.0 | 3.0 | 0.0 | 1.0 | 0.0 | 0.0 | 0.0 | 0.0 | 0.0 | 8.0 | 3.0 | 2.0 | 5.0 | 2.0 |
| Methyl 2-[(1-car-bamoyl-1,2-dimethyl-propyl)-carbamoyl]-3-quinolinecarbo-xylate | 4.000 | 9.0 | 7.0 | 0.0 | 4.0 | 0.0 | 0.0 | 1.0 | 8.0 | 2.0 | 9.0 | 3.0 | 2.0 | 7.0 | 5.0 |
| | 1.000 | 2.0 | 5.0 | 0.0 | 0.0 | 0.0 | 0.0 | 0.0 | 1.0 | 0.0 | 3.0 | 1.0 | 1.0 | 2.0 | 3.0 |
| | .500 | 1.0 | 2.0 | 0.0 | 0.0 | 0.0 | 0.0 | 0.0 | 0.0 | 0.0 | 1.0 | 0.0 | 0.0 | 1.0 | 3.0 |
| Butyl 2-(5-iso-propyl-5-methyl-4-oxo-2-imidazolin-2-yl)-3-quinoline-carboxylate | 4.000 | 8.0 | 9.0 | 7.0 | 9.0 | 8.0 | 9.0 | 4.0 | 2.0 | 9.0 | 4.0 | 6.0 | 9.0 | 7.0 | 1.0 |
| | 1.000 | 3.0 | 6.0 | 2.0 | 3.0 | 2.0 | 7.0 | 3.0 | 0.0 | 9.0 | 2.0 | 0.0 | 5.0 | 7.0 | 0.0 |
| | .500 | 0.0 | 6.0 | 2.0 | 0.0 | 2.0 | 2.0 | 2.0 | 0.0 | 2.0 | 3.0 | 0.0 | 0.0 | 7.0 | 0.0 |
| 2-(5-Isopropyl-5-methyl-4-oxo-2-imidazolin-2-yl)-3-quinolinecarbo-xylic acid hydro-chloride | 4.000 | 9.0 | 8.0 | 8.0 | 9.0 | 9.0 | 9.0 | 9.0 | 9.0 | 9.0 | 9.0 | 9.0 | 5.0 | 9.0 | 9.0 |
| | 1.000 | 9.0 | 8.0 | 9.0 | 9.0 | 9.0 | 9.0 | 9.0 | 9.0 | 9.0 | 9.0 | 9.0 | 4.0 | 9.0 | 9.0 |
| | .500 | 9.0 | 9.0 | 7.0 | 9.0 | 9.0 | 9.0 | 7.0 | 9.0 | 7.0 | 9.0 | 9.0 | 4.0 | 9.0 | 9.0 |
| | .250 | 9.0 | 9.0 | 7.0 | 9.0 | 9.0 | 9.0 | 6.0 | 8.0 | 5.0 | 9.0 | 9.0 | 3.0 | 9.0 | 9.0 |
| | .125 | 9.0 | 8.0 | 5.0 | 9.0 | 8.0 | 7.0 | 5.0 | 5.0 | 5.0 | 9.0 | 9.0 | 3.0 | 9.0 | 9.0 |
| 5-Chloro-2-(5-iso-propyl-5-methyl-4- | 4.000 | 9.0 | 9.0 | 8.0 | 9.0 | 9.0 | 8.0 | 9.0 | 8.0 | 8.0 | 9.0 | 7.0 | 4.0 | 7.0 | 9.0 |
| | 1.000 | 9.0 | 7.0 | 1.0 | 9.0 | 3.0 | 0.0 | 4.0 | 5.0 | 3.0 | 9.0 | 7.0 | 4.0 | 7.0 | 9.0 |

TABLE XI-continued

| | POST-EMERGENCE TESTS - RATES IN KG/HA | | | | | | | | | | | | | | |
|---|---|---|---|---|---|---|---|---|---|---|---|---|---|---|---|
| oxo-2-imidazolin- | .500 | 9.0 | 7.0 | 0.0 | 9.0 | 2.0 | 0.0 | 4.0 | 5.0 | 2.0 | 9.0 | 7.0 | 3.0 | 7.0 | 9.0 |
| 2-yl)-3-quinoline- | .250 | 9.0 | 5.0 | 0.0 | 9.0 | 0.0 | 0.0 | 3.0 | 3.0 | 1.0 | 9.0 | 7.0 | 3.0 | 7.0 | 9.0 |
| carboxylic acid | .125 | 4.0 | 4.0 | 0.0 | 9.0 | 0.0 | 0.0 | 2.0 | 3.0 | 0.0 | 9.0 | 5.0 | 2.0 | 7.0 | 7.0 |
| 2-(5-Isopropyl-5- | 1.000 | 9.0 | | 7.0 | 9.0 | 6.0 | 9.0 | 8.0 | 9.0 | 5.0 | 8.0 | 5.0 | 3.0 | 8.0 | 9.0 |
| methyl-4-oxo-2- | .500 | 9.0 | | 6.0 | 9.0 | 4.0 | 9.0 | 8.0 | 9.0 | 2.0 | 8.0 | 4.0 | 1.0 | 7.0 | 7.0 |
| imidazolin-2-yl)- | .250 | 9.0 | | 1.0 | 4.0 | 3.0 | 9.0 | 7.0 | 8.0 | 1.0 | 6.0 | 1.0 | 1.0 | 6.0 | 3.0 |
| 6-nitro-3-quino- | .125 | 4.0 | | 0.0 | 2.0 | 1.0 | 7.0 | | | 0.0 | 7.0 | 1.0 | 1.0 | 5.0 | 2.0 |
| linecarboxylic acid | .063 | 1.0 | | 0.0 | 0.0 | 1.0 | 5.0 | 1.0 | 0.0 | 0.0 | 1.0 | 1.0 | 1.0 | 5.0 | 0.0 |
| 8-Chloro-1,3- | 8.000 | 8.0 | 0.0 | 5.0 | 8.0 | 2.0 | 0.0 | 2.0 | 2.0 | 0.0 | | | | | |
| dihydro-α-isopropyl- | | | | | | | | | | | | | | | |
| α-methyl-1,3-dioxo- | | | | | | | | | | | | | | | |
| 2H—pyrrolo[3,4-b]- | | | | | | | | | | | | | | | |
| quinoline-2-acetamide | | | | | | | | | | | | | | | |
| 2-(5-Isopropyl-5- | 8.000 | 9.0 | 6.0 | 8.0 | 9.0 | 9.0 | 9.0 | 6.0 | 7.0 | 5.0 | | | | | |
| methyl-4-oxo-2- | 1.000 | 0.0 | | 0.0 | 3.0 | 4.0 | 0.0 | 0.0 | 0.0 | 0.0 | 4.0 | 2.0 | 3.0 | 2.0 | 3.0 |
| imidazolin-2-yl)- | .500 | 0.0 | | 0.0 | 0.0 | 2.0 | 0.0 | 0.0 | 0.0 | 0.0 | 1.0 | 0.0 | 0.0 | 2.0 | 1.0 |
| 3-quinolinecarbox- | | | | | | | | | | | | | | | |
| aldehyde, oxime | | | | | | | | | | | | | | | |
| 2-(5-Isopropyl- | 1.000 | 0.0 | | 0.0 | 0.0 | 0.0 | 7.0 | 2.0 | 9.0 | 2.0 | 0.0 | 3.0 | 1.0 | 7.0 | 0.0 |
| 5-methyl-4-oxo- | .500 | 0.0 | | 0.0 | 0.0 | 0.0 | 4.0 | 1.0 | 9.0 | 0.0 | 0.0 | 2.0 | 0.0 | 5.0 | 0.0 |
| 2-imidazolin-2- | .250 | 0.0 | | 0.0 | 0.0 | 0.0 | 1.0 | 0.0 | 3.0 | 0.0 | 0.0 | 0.0 | 0.0 | 3.0 | 0.0 |
| yl)-6,8-dimethyl- | | | | | | | | | | | | | | | |
| 3-quinolinecarbo- | | | | | | | | | | | | | | | |
| xylic acid | | | | | | | | | | | | | | | |
| 2-(5-Isopropyl-5- | .500 | 8.0 | | 1.0 | 9.0 | 8.0 | 9.0 | 3.0 | 7.0 | 6.0 | 9.0 | 9.0 | 3.0 | 9.0 | 8.0 |
| methyl-4-oxo-2- | .250 | 8.0 | | 1.0 | 4.0 | 9.0 | 9.0 | 2.0 | 7.0 | 4.0 | 9.0 | 9.0 | 4.0 | 9.0 | 4.0 |
| imidazolin-2-yl)- | .125 | 7.0 | | 0.0 | 0.0 | 7.0 | 9.0 | 0.0 | 0.0 | 0.0 | 6.0 | 8.0 | 3.0 | 9.0 | 3.0 |
| 6-methyl-3-quino- | .063 | 4.0 | | 0.0 | 0.0 | 4.0 | 3.0 | 0.0 | 0.0 | 0.0 | 6.0 | 6.0 | 3.0 | 9.0 | 1.0 |
| linecarboxylic acid | .032 | 2.0 | | 0.0 | 0.0 | 0.0 | 2.0 | 0.0 | 0.0 | 0.0 | 4.0 | 4.0 | 3.0 | 5.0 | 0.0 |
| Methyl 2-(5-iso- | 1.000 | 9.0 | | 0.0 | 0.0 | 0.0 | 0.0 | 3.0 | 0.0 | 2.0 | 7.0 | 3.0 | 2.0 | 4.0 | 0.0 |
| propyl-5-methyl-4- | .500 | 9.0 | | 0.0 | 0.0 | 0.0 | 0.0 | 1.0 | 0.0 | 0.0 | 7.0 | 1.0 | 1.0 | 0.0 | 0.0 |
| oxo-2-imidazolin- | .250 | 7.0 | | 0.0 | 0.0 | 0.0 | 0.0 | 1.0 | 0.0 | 0.0 | 7.0 | 0.0 | 1.0 | 0.0 | 0.0 |
| 2-yl)-3-quinoline- | .125 | 5.0 | | 0.0 | 0.0 | 0.0 | 0.0 | 0.0 | 0.0 | 0.0 | 2.0 | 0.0 | 0.0 | 0.0 | 0.0 |
| carboxylate | .063 | 1.0 | | 0.0 | 0.0 | 0.0 | 0.0 | 0.0 | 0.0 | 0.0 | 0.0 | 0.0 | 0.0 | 0.0 | 0.0 |
| | .032 | 0.0 | | 0.0 | 0.0 | 0.0 | 0.0 | 0.0 | 0.0 | 0.0 | 0.0 | 0.0 | 0.0 | 0.0 | 0.0 |
| 6-Bromo-2-(5-iso- | 1.000 | 4.0 | | 0.0 | 9.0 | 2.0 | 0.0 | 2.0 | 8.0 | 2.0 | 9.0 | 9.0 | 0.0 | 9.0 | 9.0 |
| propyl-5-methyl-4- | .500 | 2.0 | | 0.0 | 8.0 | 1.0 | 0.0 | 2.0 | 2.0 | 0.0 | 9.0 | 7.0 | 0.0 | 9.0 | 6.0 |
| oxo-2-imidazolin-2- | .250 | 2.0 | | 0.0 | 8.0 | 0.0 | 0.0 | 0.0 | 2.0 | 0.0 | 8.0 | 5.0 | 0.0 | 9.0 | 5.0 |
| yl)-3-quinoline- | .125 | 0.0 | | 0.0 | 6.0 | 0.0 | 0.0 | 0.0 | 0.0 | 0.0 | 4.0 | 5.0 | 0.0 | 9.0 | 4.0 |
| carboxylic acid | .063 | 0.0 | | 0.0 | 3.0 | 0.0 | 0.0 | 0.0 | 0.0 | 0.0 | 3.0 | 3.0 | 0.0 | 9.0 | 4.0 |
| | .032 | 0.0 | | 0.0 | 3.0 | 0.0 | 0.0 | 0.0 | 0.0 | 0.0 | 2.0 | 2.0 | 0.0 | 9.0 | 4.0 |
| 5-Bromo-2-(5-iso- | 1.000 | 9.0 | | 1.0 | 9.0 | 8.0 | 4.0 | 4.0 | 2.0 | 2.0 | 9.0 | 8.0 | 2.0 | 2.0 | 6.0 |
| propyl-5-methyl-4- | .500 | 6.0 | | 0.0 | 9.0 | 7.0 | 4.0 | 3.0 | | 1.0 | 9.0 | 6.0 | 0.0 | 2.0 | 5.0 |
| oxo-2-imidazolin- | .250 | 3.0 | | 0.0 | 8.0 | 3.0 | | 1.0 | 0.0 | 0.0 | 9.0 | 6.0 | 0.0 | 1.0 | 5.0 |
| 2-yl)-3-quinoline- | .125 | 2.0 | | 0.0 | 7.0 | 1.0 | 0.0 | 1.0 | 0.0 | 0.0 | 9.0 | 6.0 | 0.0 | 1.0 | 5.0 |
| carboxylic acid | .063 | 0.0 | | 0.0 | 5.0 | 0.0 | 0.0 | 0.0 | 0.0 | 0.0 | 9.0 | 2.0 | 0.0 | 1.0 | 4.0 |
| | .032 | 0.0 | | 0.0 | 5.0 | 0.0 | 0.0 | 0.0 | 0.0 | 0.0 | 9.0 | 2.0 | 0.0 | 0.0 | 4.0 |
| 2-(5-Isopropyl-5- | 8.000 | 9.0 | 9.0 | 7.0 | 9.0 | 1.0 | 0.0 | 9.0 | 9.0 | 7.0 | | | | | |
| methyl-4-oxo-2- | 1.000 | 9.0 | | 7.0 | 7.0 | 9.0 | 9.0 | 6.0 | 9.0 | 2.0 | 9.0 | 7.0 | 0.0 | 9.0 | 9.0 |
| imidazolin-2-yl)- | .500 | 9.0 | | 3.0 | 9.0 | 8.0 | 7.0 | 4.0 | 3.0 | 1.0 | 9.0 | 7.0 | 0.0 | 9.0 | 7.0 |
| 3-quinolinecarbo- | .250 | 3.0 | | 3.0 | 7.0 | 6.0 | 4.0 | 2.0 | 2.0 | 0.0 | 9.0 | 5.0 | 0.0 | 9.0 | 6.0 |
| hydroxamic acid | .125 | 2.0 | | 1.0 | 6.0 | 5.0 | 2.0 | 1.0 | 0.0 | 0.0 | 9.0 | 4.0 | 0.0 | 8.0 | 5.0 |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| | .063 | 1.0 | | 0.0 | 5.0 | 0.0 | 0.0 | 1.0 | 0.0 | 0.0 | 9.0 | 4.0 | 0.0 | 3.0 | 5.0 |
| | .032 | 0.0 | | 0.0 | 3.0 | 0.0 | 0.0 | 1.0 | 0.0 | 0.0 | 8.0 | 3.0 | 0.0 | 2.0 | 4.0 |
| 2-(5-Isopropyl-5-methyl-4-oxo-2-imidazolin-2-yl)-4-methoxy-3-quinolinecarboxylic acid | 8.000 | 9.0 | 9.0 | 7.0 | 7.0 | 5.0 | 0.0 | 5.0 | 8.0 | 7.0 | | | | | |
| | 1.000 | 1.0 | | 4.0 | 4.0 | 7.0 | 9.0 | 9.0 | 9.0 | 3.0 | 9.0 | 2.0 | 3.0 | 9.0 | 4.0 |
| | .500 | 0.0 | | 1.0 | 4.0 | 7.0 | 9.0 | 7.0 | 7.0 | 0.0 | 9.0 | 2.0 | 2.0 | 9.0 | 3.0 |
| | .250 | 0.0 | | 0.0 | 2.0 | 7.0 | 5.0 | 6.0 | 6.0 | 0.0 | 5.0 | 2.0 | 2.0 | 9.0 | 3.0 |
| | .125 | 0.0 | | 0.0 | 1.0 | 3.0 | 3.0 | 5.0 | 3.0 | 0.0 | 2.0 | 1.0 | 0.0 | 9.0 | 2.0 |
| | .063 | 0.0 | | 0.0 | 0.0 | 0.0 | 0.0 | 2.0 | 0.0 | 0.0 | 1.0 | 0.0 | 0.0 | 9.0 | 2.0 |
| | .032 | 0.0 | | 0.0 | 0.0 | 0.0 | 0.0 | 1.0 | 0.0 | 0.0 | 1.0 | 0.0 | 0.0 | 2.0 | 2.0 |
| 4-Hydroxy-2-(5-isopropyl-5-methyl-4-oxo-2-imidazolin-2-yl)-3-quinolinecarboxylic acid hydrochloride | 8.000 | 9.0 | 7.0 | 1.0 | 8.0 | 5.0 | 0.0 | 7.0 | 9.0 | 5.0 | | | | | |
| | 1.000 | 0.0 | | 0.0 | 2.0 | 0.0 | 2.0 | 0.0 | 7.0 | 0.0 | 4.0 | 2.0 | 1.0 | 9.0 | 7.0 |
| | .500 | 0.0 | | 0.0 | 2.0 | 0.0 | | 0.0 | 7.0 | 0.0 | 2.0 | 1.0 | 1.0 | 9.0 | 3.0 |
| | .250 | 0.0 | | 0.0 | 2.0 | 0.0 | 0.0 | 0.0 | 7.0 | 0.0 | 2.0 | 1.0 | 0.0 | 6.0 | 3.0 |
| 2-(5-Isopropyl-5-methyl-4-oxo-2-imidazolin-2-yl)-6-methoxy-3-quinolinecarboxylic acid | 8.000 | 9.0 | 9.0 | 6.0 | 9.0 | 2.0 | 0.0 | 6.0 | 9.0 | 9.0 | | | | | |
| | 1.000 | 9.0 | | 2.0 | 9.0 | 8.0 | 9.0 | 6.0 | 7.0 | 3.0 | 9.0 | 9.0 | 6.0 | 9.0 | 6.0 |
| | .500 | 9.0 | | 1.0 | 9.0 | 7.0 | 6.0 | 2.0 | 7.0 | 3.0 | 9.0 | 7.0 | 5.0 | 9.0 | 4.0 |
| | .250 | 6.0 | | 1.0 | 9.0 | 5.0 | | 0.0 | 3.0 | | 9.0 | 9.0 | 5.0 | 9.0 | 4.0 |
| | .125 | 2.0 | | 0.0 | 7.0 | 3.0 | 6.0 | 0.0 | 1.0 | 1.0 | 9.0 | 5.0 | 3.0 | 8.0 | 3.0 |
| | .063 | 1.0 | | 0.0 | 6.0 | 1.0 | 0.0 | 0.0 | 0.0 | 0.0 | 4.0 | 4.0 | 1.0 | 5.0 | 3.0 |
| 2-(5-Isopropyl-5-methyl-4-oxo-2-imidazolin-2-yl)-8-methoxy-7-nitro-3-quinolinecarboxylic acid | 1.000 | 0.0 | | 0.0 | 0.0 | 0.0 | 0.0 | 0.0 | 0.0 | 0.0 | 9.0 | 0.0 | 0.0 | 4.0 | 0.0 |
| | .500 | 0.0 | | 0.0 | 0.0 | 0.0 | 0.0 | 0.0 | 0.0 | 0.0 | 9.0 | 0.0 | 0.0 | 2.0 | 0.0 |
| Benzyl 2-(5-isopropyl-5-methyl-4-oxo-2-imidazolin-2-yl)-3-quinolinecarboxylate | 1.000 | 9.0 | | 0.0 | 9.0 | 6.0 | 6.0 | 9.0 | 9.0 | 3.0 | 9.0 | 7.0 | 3.0 | 9.0 | 4.0 |
| | .500 | 9.0 | | 0.0 | 8.0 | 5.0 | 4.0 | 6.0 | 8.0 | 2.0 | 9.0 | 7.0 | 3.0 | 8.0 | 4.0 |
| | .250 | 9.0 | | 0.0 | 8.0 | 5.0 | 4.0 | 3.0 | 2.0 | 0.0 | 9.0 | 5.0 | 2.0 | 8.0 | 3.0 |
| | .125 | 9.0 | | 0.0 | 8.0 | 2.0 | 3.0 | 3.0 | 2.0 | 0.0 | 9.0 | 4.0 | 2.0 | 6.0 | 1.0 |
| | .063 | 6.0 | | 0.0 | 3.0 | 2.0 | 1.0 | 2.0 | 0.0 | 0.0 | 9.0 | 2.0 | 1.0 | 4.0 | 1.0 |
| 2-(5-Isopropyl-5-methyl-4-oxo-2-imidazolin-2-yl)-5-methyl-3-quinolinecarboxylic acid | 1.000 | | | 0.0 | 9.0 | 9.0 | 9.0 | 3.0 | 7.0 | 9.0 | 9.0 | 9.0 | 4.0 | 7.0 | 9.0 |
| | .500 | 9.0 | | 0.0 | 9.0 | 9.0 | 9.0 | 2.0 | 6.0 | 3.0 | 9.0 | 8.0 | 4.0 | 7.0 | 9.0 |
| | .250 | 9.0 | | 0.0 | 9.0 | 4.0 | 4.0 | | 5.0 | 1.0 | 9.0 | 7.0 | 4.0 | 6.0 | 3.0 |
| | .125 | 5.0 | | 0.0 | 7.0 | 2.0 | 2.0 | 2.0 | 1.0 | 1.0 | 9.0 | 4.0 | 2.0 | 6.0 | 3.0 |
| | .063 | 4.0 | | 0.0 | 6.0 | 1.0 | 0.0 | 1.0 | 1.0 | 1.0 | 9.0 | 4.0 | 2.0 | 2.0 | 2.0 |
| 2-(5-Ethyl-5-methyl-4-oxo-2-imidazolin-2-yl)-3-quinolinecarboxylic acid | 1.000 | 9.0 | | 9.0 | 9.0 | 9.0 | 9.0 | 7.0 | 8.0 | 8.0 | 9.0 | 9.0 | 4.0 | 9.0 | 7.0 |
| | .500 | 9.0 | | 9.0 | 9.0 | 9.0 | 6.0 | 7.0 | 7.0 | 5.0 | 9.0 | 6.0 | 3.0 | 9.0 | 7.0 |
| | .250 | 7.0 | | 9.0 | 9.0 | 7.0 | 4.0 | 4.0 | 6.0 | 3.0 | 9.0 | 5.0 | 3.0 | 9.0 | 4.0 |
| | .125 | 4.0 | | 7.0 | 8.0 | 7.0 | 4.0 | 4.0 | 3.0 | 1.0 | 9.0 | 5.0 | 2.0 | 9.0 | 3.0 |
| | .063 | 2.0 | | 5.0 | 4.0 | 3.0 | 4.0 | 2.0 | 2.0 | 0.0 | 9.0 | 5.0 | 0.0 | 9.0 | 3.0 |
| | .032 | 0.0 | | 3.0 | 1.0 | 2.0 | 2.0 | 1.0 | 2.0 | 0.0 | 6.0 | 3.0 | 0.0 | 4.0 | 2.0 |
| 2-(4-Oxo-1,3-diazaspiro[4.5]dec-2-en-2-yl)-3-quinolinecarboxylic acid | 1.000 | 8.0 | | 7.0 | 8.0 | 7.0 | 7.0 | 7.0 | 6.0 | 1.0 | 9.0 | 5.0 | 3.0 | 9.0 | 5.0 |
| | .500 | 4.0 | | 2.0 | 6.0 | 5.0 | 2.0 | 4.0 | 0.0 | 1.0 | 9.0 | 4.0 | 0.0 | 9.0 | 4.0 |
| | .250 | 2.0 | | 0.0 | 3.0 | 3.0 | 0.0 | 2.0 | 0.0 | 1.0 | 9.0 | 4.0 | 2.0 | 9.0 | 3.0 |
| | .125 | 2.0 | | 0.0 | 2.0 | 0.0 | 0.0 | 1.0 | 0.0 | 0.0 | 9.0 | 3.0 | 0.0 | 6.0 | 1.0 |
| | .063 | 0.0 | | 0.0 | 2.0 | 0.0 | 0.0 | 0.0 | 0.0 | 0.0 | 9.0 | 2.0 | 0.0 | 2.0 | 1.0 |
| | .032 | 0.0 | | 0.0 | 0.0 | 0.0 | 0.0 | 0.0 | 0.0 | 0.0 | 7.0 | 0.0 | 0.0 | 1.0 | 0.0 |
| Methyl 2-(5-isopropyl-5-methyl-4- | 8.000 | 9.0 | 5.0 | 0.0 | 9.0 | 0.0 | 5.0 | 0.0 | 0.0 | 0.0 | | | | | |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| oxo-2-imidazolin- | | | | | | | | | | | | | | | |
| 2-yl)-8-nitro-3- | | | | | | | | | | | | | | | |
| quinolinecarboxylate | | | | | | | | | | | | | | | |
| 2-(5-Isopropyl-5- | 1.000 | 3.0 | | 3.0 | 0.0 | 1.0 | 9.0 | 9.0 | 0.0 | 9.0 | 6.0 | 3.0 | 2.0 | 9.0 | 0.0 |
| methyl-4-oxo-2- | .500 | 1.0 | | 1.0 | 0.0 | 0.0 | 4.0 | 8.0 | 0.0 | 3.0 | 3.0 | 3.0 | 1.0 | 7.0 | 0.0 |
| imidazolin-2-yl)-4- | .250 | 1.0 | | 0.0 | 0.0 | 0.0 | | 6.0 | 0.0 | 1.0 | 3.0 | 2.0 | 0.0 | 5.0 | 0.0 |
| methyl-3-quinoline- | .125 | 0.0 | | 0.0 | 0.0 | 0.0 | 0.0 | 6.0 | 0.0 | 1.0 | 3.0 | 1.0 | 0.0 | 4.0 | 0.0 |
| carboxylic acid | .063 | 0.0 | | 0.0 | 0.0 | 0.0 | 0.0 | 2.0 | 0.0 | 0.0 | 3.0 | 1.0 | 0.0 | 4.0 | 0.0 |
| Diisopropylammonium | 4.000 | 9.0 | 9.0 | 9.0 | 9.0 | 9.0 | 9.0 | 9.0 | 9.0 | 9.0 | 9.0 | 9.0 | | 9.0 | |
| 2-(5-isopropyl-5- | 1.500 | 9.0 | | 7.0 | 9.0 | 9.0 | 9.0 | 6.0 | . | 9.0 | 9.0 | 9.0 | | 9.0 | |
| 1,3-Dihydro-α-iso- | 8.000 | 6.0 | 0.0 | 0.0 | 6.0 | 0.0 | 0.0 | 7.0 | 0.0 | 0.0 | | | | | |
| propyl-α,8-dimethyl- | | | | | | | | | | | | | | | |
| 1,3-dioxo-2H—pyrrolo- | | | | | | | | | | | | | | | |
| [3,4-b]quinoline-2- | | | | | | | | | | | | | | | |
| acetamide | | | | | | | | | | | | | | | |
| 8-Chloro-2-(5-iso- | 1.000 | 8.0 | | 3.0 | 6.0 | 7.0 | 4.0 | 5.0 | 9.0 | 7.0 | 9.0 | 7.0 | 3.0 | 9.0 | 4.0 |
| propyl-5-methyl-4- | .500 | 2.0 | | 1.0 | 3.0 | 5.0 | 3.0 | 3.0 | 8.0 | 5.0 | 9.0 | 4.0 | 2.0 | 9.0 | 1.0 |
| oxo-2-imidazolin- | .250 | 0.0 | | 0.0 | 1.0 | 2.0 | 0.0 | 1.0 | 8.0 | 4.0 | 7.0 | 3.0 | 2.0 | 9.0 | 0.0 |
| 2-yl)-3-quinoline- | .125 | 0.0 | | 0.0 | 0.0 | 1.0 | 0.0 | 0.0 | 3.0 | 4.0 | 7.0 | 3.0 | 0.0 | 8.0 | 0.0 |
| carboxylic acid | .063 | 0.0 | | 0.0 | 0.0 | 0.0 | 0.0 | 0.0 | 2.0 | 2.0 | 6.0 | 2.0 | 0.0 | 8.0 | 0.0 |
| | .032 | 0.0 | | 0.0 | 0.0 | 0.0 | 0.0 | 0.0 | 0.0 | 0.0 | 6.0 | 2.0 | 0.0 | 8.0 | 0.0 |
| 6-Fluoro-2-(5-iso- | 1.000 | 9.0 | | 7.0 | 9.0 | 9.0 | 8.0 | 8.0 | 9.0 | 9.0 | 9.0 | 6.0 | 5.0 | 9.0 | 9.0 |
| propyl-5-methyl-4- | .500 | 9.0 | | 6.0 | 9.0 | 8.0 | 8.0 | 7.0 | 8.0 | 9.0 | 9.0 | 6.0 | 4.0 | 9.0 | 9.0 |
| oxo-2-imidazolin-2- | .250 | 8.0 | | 6.0 | 9.0 | 8.0 | 8.0 | 6.0 | 8.0 | 9.0 | 9.0 | 5.0 | 3.0 | 9.0 | 9.0 |
| yl)-3-quinoline- | .125 | 8.0 | | 3.0 | 9.0 | 7.0 | 6.0 | 3.0 | 6.0 | 8.0 | 9.0 | 5.0 | 2.0 | 9.0 | 9.0 |
| carboxylic acid | .063 | 8.0 | | 2.0 | 8.0 | 6.0 | 5.0 | 2.0 | 6.0 | 6.0 | 9.0 | 4.0 | 1.0 | 9.0 | 8.0 |
| | .032 | 5.0 | | 1.0 | 0.0 | 4.0 | 2.0 | 1.0 | 2.0 | 5.0 | 8.0 | 3.0 | 1.0 | 9.0 | 5.0 |
| 2-(5-Isopropyl-5- | 1.000 | 9.0 | | 7.0 | 9.0 | 6.0 | 2.0 | 3.0 | 8.0 | 9.0 | 9.0 | 6.0 | 6.0 | 9.0 | 9.0 |
| methyl-4-oxo-2- | .500 | 7.0 | | 4.0 | 9.0 | 5.0 | 1.0 | 1.0 | 8.0 | 9.0 | 9.0 | 5.0 | 5.0 | 9.0 | 9.0 |
| imidazolin-2-yl)- | .250 | 5.0 | | 2.0 | 9.0 | 4.0 | 1.0 | 1.0 | 7.0 | 9.0 | 9.0 | 5.0 | 5.0 | 9.0 | 9.0 |
| 8-methoxy-3-quino- | .125 | 1.0 | | 0.0 | 8.0 | 3.0 | 1.0 | 0.0 | 6.0 | 9.0 | 9.0 | 4.0 | 4.0 | 9.0 | 5.0 |
| linecarboxylic acid | .063 | 0.0 | | 0.0 | 8.0 | 1.0 | 0.0 | 0.0 | 1.0 | 0.0 | 9.0 | 3.0 | 3.0 | 9.0 | 3.0 |
| | .032 | 0.0 | | 0.0 | 7.0 | 0.0 | 0.0 | 0.0 | 0.0 | 0.0 | 9.0 | 2.0 | 3.0 | 8.0 | 3.0 |
| Ethylammonium 2-(5- | 1.290 | 9.0 | | 8.0 | 9.0 | 9.0 | 9.0 | 9.0 | | 9.0 | 9.0 | 9.0 | 3.0 | 9.0 | 9.0 |
| isopropyl-5-methyl- | .645 | 9.0 | | 6.0 | 9.0 | 9.0 | 9.0 | 9.0 | | 9.0 | 9.0 | 9.0 | 3.0 | 9.0 | 9.0 |
| 4-oxo-2-imidazolin- | .323 | 9.0 | | 7.0 | 9.0 | 8.0 | 7.0 | 6.0 | | 9.0 | 9.0 | 9.0 | 3.0 | 9.0 | 9.0 |
| 2-yl)-3-quinoline- | .161 | 9.0 | | 5.0 | 9.0 | 7.0 | 9.0 | 6.0 | | 3.0 | 9.0 | 9.0 | 2.0 | 9.0 | 6.0 |
| carboxylate | .081 | 9.0 | | 5.0 | 9.0 | 6.0 | 4.0 | 6.0 | | 2.0 | 9.0 | 9.0 | 1.0 | 9.0 | 4.0 |
| | .040 | 3.0 | | 4.0 | 5.0 | 5.0 | | 4.0 | | 1.0 | 9.0 | 9.0 | 1.0 | 8.0 | 2.0 |
| Methylammonium 2-(5- | 1.220 | 9.0 | | 7.0 | 9.0 | 9.0 | 9.0 | 9.0 | | 9.0 | 9.0 | 9.0 | 5.0 | 9.0 | 9.0 |
| isopropyl-5-methyl- | .610 | 9.0 | | 7.0 | 9.0 | 8.0 | 9.0 | 7.0 | | 9.0 | 9.0 | 9.0 | 4.0 | 9.0 | 6.0 |
| 4-oxo-2-imidazolin- | .305 | 9.0 | | 7.0 | 9.0 | 8.0 | 9.0 | 6.0 | | 9.0 | 9.0 | 9.0 | 3.0 | 9.0 | 9.0 |
| 2-yl)-3-quinoline- | .153 | 9.0 | | 7.0 | 9.0 | 7.0 | 6.0 | 6.0 | | 5.0 | 9.0 | 9.0 | 2.0 | 9.0 | 7.0 |
| carboxylate | .076 | 9.0 | | 5.0 | 9.0 | 7.0 | 5.0 | 6.0 | | 2.0 | 9.0 | 9.0 | 1.0 | 9.0 | 4.0 |
| | .038 | 9.0 | | 3.0 | 9.0 | 4.0 | 2.0 | 2.0 | | 1.0 | 9.0 | 9.0 | 0.0 | 9.0 | 4.0 |
| Dimethylammonium 2- | 1.300 | 9.0 | | 7.0 | 9.0 | 9.0 | 9.0 | 9.0 | | 9.0 | 9.0 | 9.0 | 7.0 | 9.0 | 9.0 |
| (5-isopropyl-5-methyl- | .650 | 9.0 | | 8.0 | 9.0 | 9.0 | 9.0 | 6.0 | | 9.0 | 9.0 | 9.0 | 4.0 | 9.0 | 9.0 |
| 4-oxo-2-imidazolin- | .325 | 9.0 | | 7.0 | 9.0 | 7.0 | 9.0 | 9.0 | | 9.0 | 9.0 | 9.0 | 2.0 | 9.0 | 9.0 |
| 2-yl)-3-quinoline- | .163 | 9.0 | | 7.0 | 9.0 | 7.0 | 5.0 | 4.0 | | 4.0 | 9.0 | 9.0 | 3.0 | 9.0 | 8.0 |
| carboxylate | .081 | 8.0 | | 5.0 | 8.0 | 6.0 | 5.0 | 4.0 | | 3.0 | 9.0 | 9.0 | 1.0 | 9.0 | 8.0 |
| | .041 | 8.0 | | 5.0 | 7.0 | 5.0 | 5.0 | 6.0 | | 2.0 | 9.0 | 8.0 | 1.0 | 9.0 | 2.0 |
| Octylammonium 2-(5- | 1.570 | 9.0 | | 7.0 | 9.0 | 8.0 | 8.0 | 7.0 | | 9.0 | 9.0 | 9.0 | 3.0 | 9.0 | 8.0 |

TABLE XI-continued

POST-EMERGENCE TESTS - RATES IN KG/HA

| | | | | | | | | | | | | | | | |
|---|---|---|---|---|---|---|---|---|---|---|---|---|---|---|---|
| isopropyl-5-methyl- | .785 | 9.0 | | 9.0 | 9.0 | 8.0 | 8.0 | 8.0 | | 9.0 | 9.0 | 9.0 | 2.0 | 9.0 | 9.0 |
| 4-oxo-2-imidazolin- | .393 | 9.0 | | 7.0 | 9.0 | 8.0 | 7.0 | 6.0 | | 5.0 | 9.0 | 9.0 | 1.0 | 9.0 | 9.0 |
| 2-yl)-3-quinoline- | .196 | 8.0 | | 7.0 | 8.0 | 6.0 | 5.0 | 6.0 | | 4.0 | 9.0 | 7.0 | 0.0 | 9.0 | 6.0 |
| carboxylate | .098 | 8.0 | | 5.0 | 8.0 | 3.0 | 8.0 | 3.0 | | 2.0 | 9.0 | 7.0 | 1.0 | 9.0 | 4.0 |
| | .049 | 2.0 | | 5.0 | 7.0 | 7.0 | | 6.0 | | 1.0 | 9.0 | 6.0 | 1.0 | 8.0 | 2.0 |
| 2-(5-Isopropyl-5- | 1.000 | 7.0 | | 0.0 | 8.0 | 0.0 | 0.0 | 2.0 | 0.0 | 0.0 | 9.0 | 3.0 | 0.0 | 5.0 | 2.0 |
| methyl-4-oxo-2- | .500 | 2.0 | | 0.0 | 2.0 | 0.0 | 0.0 | 1.0 | 0.0 | 0.0 | 7.0 | 2.0 | 0.0 | 2.0 | 0.0 |
| imidazolin-2-yl)- | .250 | 0.0 | | 0.0 | 0.0 | 0.0 | 0.0 | 1.0 | 0.0 | 0.0 | 6.0 | 0.0 | 0.0 | 2.0 | 0.0 |
| 8-nitro-3-quino- | .125 | 0.0 | | 0.0 | 0.0 | 0.0 | 0.0 | 0.0 | 0.0 | 0.0 | 5.0 | 0.0 | 0.0 | 2.0 | 0.0 |
| line carboxylic | .063 | 0.0 | | 0.0 | 0.0 | 0.0 | 0.0 | 0.0 | 0.0 | 0.0 | 5.0 | 0.0 | 0.0 | 0.0 | 0.0 |
| acid | .032 | 0.0 | | 0.0 | 0.0 | 0.0 | 0.0 | 0.0 | 0.0 | 0.0 | 4.0 | 0.0 | 0.0 | 0.0 | 0.0 |
| (−)-2-(5-Isopropyl- | 1.000 | 8.8 | 9.0 | 7.0 | | 8.8 | 8.3 | 6.8 | 8.0 | 8.8 | | | | | |
| 5-methyl-4-oxo-2- | .800 | 8.8 | 9.0 | 5.8 | | 8.3 | 8.8 | 6.3 | 8.0 | 8.8 | | | | | |
| imidazolin-2-yl)- | .500 | 8.5 | 8.8 | 5.8 | | 7.5 | 8.0 | 5.5 | 7.8 | 7.5 | | | | | |
| 3-quinolinecarbo- | .400 | 8.5 | 8.5 | 5.5 | | 7.3 | 7.8 | 5.3 | 7.8 | 7.8 | | | | | |
| xylic acid | .300 | 7.8 | 8.5 | 4.5 | | 7.3 | 7.5 | 4.8 | 7.5 | 7.8 | | | | | |
| (+)-2-(5-Isopropyl- | 1.000 | 9.0 | 9.0 | 7.0 | | 8.8 | 8.8 | 8.0 | 9.0 | 8.8 | | | | | |
| 5-methyl-4-oxo-2- | .800 | 9.0 | 9.0 | 7.3 | | 9.0 | 9.0 | 7.8 | 9.0 | 9.0 | | | | | |
| imidazolin-2-yl)-3- | .500 | 9.0 | 9.0 | 6.8 | | 8.8 | 9.0 | 7.0 | 8.8 | 8.8 | | | | | |
| quinolinecarboxylic | .400 | 8.8 | 9.0 | 6.8 | | 8.3 | 9.0 | 7.0 | 7.8 | 8.0 | | | | | |
| acid | .300 | 8.8 | 8.8 | 6.8 | | 7.8 | 8.7 | 6.3 | 8.0 | 7.3 | | | | | |
| | .200 | 8.8 | 9.0 | 6.8 | | 8.3 | 8.3 | 6.0 | 7.5 | 7.3 | | | | | |
| | .150 | 9.0 | 8.8 | 5.8 | 8.3 | 8.3 | 5.0 | 7.8 | 7.0 | | | | | | |
| 2-(5-Isopropyl-5- | 1.000 | 8.0 | | 0.0 | 9.0 | 6.0 | 2.0 | 2.0 | 9.0 | 3.0 | 8.0 | 5.0 | 1.0 | 9.0 | 9.0 |
| methyl-4-oxo-2- | .500 | 6.0 | | 0.0 | 8.0 | 4.0 | 1.0 | 1.0 | 8.0 | 1.0 | 7.0 | 5.0 | 1.0 | 9.0 | 6.0 |
| imidazolin-2-yl)-6- | .250 | 2.0 | | 0.0 | 7.0 | 1.0 | 0.0 | 1.0 | | 0.0 | 7.0 | 2.0 | 0.0 | 9.0 | 5.0 |
| (trifluoromethyl)- | .125 | 1.0 | | 0.0 | 3.0 | 0.0 | 0.0 | 0.0 | | 0.0 | 7.0 | 1.0 | 0.0 | 9.0 | 2.0 |
| 3-quinolinecarbo- | .063 | 0.0 | | 0.0 | 0.0 | 0.0 | 0.0 | 0.0 | 0.0 | 0.0 | 1.0 | 0.0 | 0.0 | 2.0 | 0.0 |
| xylic acid | | | | | | | | | | | | | | | |
| Tallowammonium 2- | 2.080 | 9.0 | | 7.0 | 9.0 | 9.0 | 9.0 | 7.0 | | 9.0 | 9.0 | 9.0 | 4.0 | 9.0 | 9.0 |
| (5-isopropyl-5- | 1.040 | 9.0 | | 7.0 | 9.0 | 9.0 | 9.0 | 9.0 | | 9.0 | 9.0 | 9.0 | 3.0 | 9.0 | 9.0 |
| methyl-4-oxo-2- | .520 | 9.0 | | 7.0 | 9.0 | 7.0 | 9.0 | 9.0 | | 6.0 | 9.0 | 9.0 | 2.0 | 9.0 | 9.0 |
| imidazolin-2-yl)- | .260 | 9.0 | | 6.0 | 9.0 | 6.0 | 7.0 | 8.0 | | 3.0 | 9.0 | 8.0 | 1.0 | 9.0 | 6.0 |
| 3-quinolinecarbo- | .130 | 9.0 | | 5.0 | 8.0 | 5.0 | 6.0 | 0.0 | | 2.0 | 9.0 | 9.0 | 0.0 | 9.0 | 4.0 |
| xylate | .065 | 9.0 | | 4.0 | 3.0 | 4.0 | 2.0 | 0.0 | | 1.0 | 9.0 | 7.0 | 0.0 | 9.0 | 2.0 |
| Isopropylammonium | 1.320 | 9.0 | | 7.0 | 9.0 | 9.0 | 9.0 | 9.0 | | 9.0 | 9.0 | 9.0 | 6.0 | 9.0 | 9.0 |
| 2-(5-isopropyl-5- | .660 | 9.0 | | 7.0 | 9.0 | 9.0 | 9.0 | 8.0 | | 9.0 | 9.0 | 9.0 | 3.0 | 9.0 | 9.0 |
| methyl-4-oxo-2- | .330 | 9.0 | | 7.0 | 9.0 | 8.0 | 9.0 | 6.0 | | 7.0 | 9.0 | 9.0 | 3.0 | 9.0 | 9.0 |
| imidazolin-2-yl)- | .165 | 9.0 | | 7.0 | 9.0 | 6.0 | 9.0 | 6.0 | | 5.0 | 9.0 | 9.0 | 2.0 | 9.0 | 6.0 |
| 3-quinolinecarbo- | .083 | 9.0 | | 5.0 | 8.0 | 6.0 | 7.0 | 4.0 | | 3.0 | 9.0 | 9.0 | 1.0 | 9.0 | 4.0 |
| xylate | .041 | 5.0 | | 3.0 | 8.0 | 5.0 | 6.0 | 6.0 | | 2.0 | 9.0 | 8.0 | 0.0 | 9.0 | 2.0 |

| Compound | RATE | BARNY ARDGR | GREEN FOX | P NUTSEDGE | WILD OATS | QUACK GRASS | FLD BINDWD | MRNGLRY SP | RAGWEED | VELVE TLEAF | CORN FIELD | RICE, NATO | SOYBEAN WI | SUNFLR XXX |
|---|---|---|---|---|---|---|---|---|---|---|---|---|---|---|
| Diisopropylammonium | 4.000 | 9.0 | 9.0 | 9.0 | 9.0 | 9.0 | 9.0 | 9.0 | 9.0 | 9.0 | 9.0 | 9.0 | | 9.0 |
| 2-(5-isopropyl-5- | 1.500 | 9.0 | | 7.0 | 9.0 | 9.0 | 9.0 | 6.0 | | 9.0 | 9.0 | 9.0 | | 9.0 |
| methyl-4-oxo-2- | 1.000 | 9.0 | 8.0 | 7.5 | 9.0 | 9.0 | 9.0 | 8.5 | 8.5 | 8.0 | 9.0 | 8.5 | | 9.0 |
| imidazolin-2-yl)-3- | .750 | 9.0 | | 7.0 | 9.0 | 9.0 | 9.0 | 8.0 | | 9.0 | 9.0 | 9.0 | | 9.0 |
| quinolinecarboxylate | .500 | 9.0 | | 7.0 | 9.0 | 9.0 | 9.0 | 8.0 | 9.0 | 8.0 | 9.0 | 9.0 | | 9.0 |
| | .375 | 9.0 | | 7.0 | 9.0 | 9.0 | 9.0 | 6.0 | | 8.0 | 9.0 | 8.0 | | 9.0 |
| Calcium 2-(5-iso- | 4.000 | 9.0 | 9.0 | 9.0 | 9.0 | 9.0 | 9.0 | 8.0 | 9.0 | 9.0 | 9.0 | 9.0 | | 9.0 |
| propyl-5-methyl-4- | 1.000 | 9.0 | 8.0 | 9.0 | 9.0 | 9.0 | 8.5 | 8.0 | 9.0 | 8.0 | 9.0 | 9.0 | | 9.0 |

TABLE XI-continued

| POST-EMERGENCE TESTS - RATES IN KG/HA | | | | | | | | | | | | | | |
|---|---|---|---|---|---|---|---|---|---|---|---|---|---|---|
| oxo-2-imidazolin- | .500 | 9.0 | | 8.0 | 9.0 | 9.0 | 9.0 | 9.0 | 8.0 | 9.0 | 9.0 | 9.0 | | 9.0 |
| 2-yl)-3-quinoline- | .250 | 8.0 | | 7.0 | 9.0 | 9.0 | 9.0 | 9.0 | 8.0 | 6.0 | 9.0 | 7.0 | | 9.0 |
| carboxylate | .125 | 8.0 | | 7.0 | 9.0 | 9.0 | 4.0 | 2.0 | 6.0 | 4.0 | 9.0 | 7.0 | | 9.0 |
| | .063 | 8.0 | | 7.0 | 7.0 | 8.0 | 4.0 | 1.0 | 4.0 | 2.0 | 9.0 | 6.0 | | 9.0 |
| | .032 | 8.0 | | 2.0 | 7.0 | 7.0 | 3.0 | 1.0 | 4.0 | 2.0 | 9.0 | 5.0 | | 9.0 |
| 6-Chloro-2-(5-iso- | 1.000 | 9.0 | | 4.0 | 8.5 | 6.0 | 5.0 | 7.0 | 9.0 | 3.0 | 7.5 | 5.5 | 2.5 | 9.0 |
| propyl-5-methyl-4- | .500 | 9.0 | | 1.5 | 8.5 | 6.0 | 4.5 | 6.0 | 9.0 | 2.0 | 6.0 | 4.5 | 2.0 | 8.5 |
| oxo-2-imidazolin-2- | .250 | 8.5 | | 0.5 | 8.5 | 5.5 | 1.0 | 4.5 | 7.0 | 1.0 | 2.5 | 3.0 | 2.0 | 7.5 |
| yl)-3-quinoline- | .125 | 6.5 | | 0.0 | 7.5 | 2.5 | 0.0 | 3.0 | 6.5 | 0.0 | 0.5 | 3.0 | 1.0 | 8.0 |
| carboxylic acid | .063 | 2.5 | | 0.0 | 6.0 | 1.5 | 0.0 | 0.5 | 6.0 | 0.0 | 0.5 | 2.5 | 0.5 | 6.0 |
| | .032 | 1.0 | | 0.0 | 4.5 | 1.0 | 0.0 | 0.0 | 2.5 | 0.0 | 0.5 | 2.0 | 0.0 | 3.0 |
| 2-(5-Isopropyl-5- | 1.000 | 9.0 | | 9.0 | 9.0 | 9.0 | 9.0 | 9.0 | 9.0 | 9.0 | 9.0 | 9.0 | 9.0 | 9.0 |
| methyl-4-oxo-2- | .500 | 9.0 | | 9.0 | 9.0 | 9.0 | 9.0 | 9.0 | 9.0 | 9.0 | 9.0 | 9.0 | 9.0 | 9.0 |
| imidazolin-2-yl)- | .250 | 9.0 | | 9.0 | 9.0 | 9.0 | 9.0 | 9.0 | 9.0 | 9.0 | 9.0 | 9.0 | 9.0 | 9.0 |
| 5-methoxynicotinic | .125 | 9.0 | | 8.0 | 9.0 | 9.0 | 9.0 | 9.0 | 9.0 | 9.0 | 9.0 | 9.0 | 8.0 | 9.0 |
| acid | .063 | 9.0 | | 7.0 | 9.0 | 9.0 | 9.0 | 7.0 | 9.0 | 9.0 | 9.0 | 9.0 | 8.0 | 9.0 |
| | .032 | 9.0 | | 7.0 | 9.0 | 9.0 | 9.0 | 4.0 | 7.0 | 9.0 | 9.0 | 9.0 | 7.0 | 9.0 |
| 2-Ammonium-2,3-di- | 1.000 | 9.0 | | 7.0 | 9.0 | 9.0 | | 8.0 | 9.0 | 7.0 | 9.0 | 9.0 | 6.0 | 9.0 |
| methylbutyramide 2- | .500 | 9.0 | | 7.0 | 9.0 | 9.0 | | | | 7.0 | 9.0 | 9.0 | 5.0 | 9.0 |
| (5-isopropyl-5- | .250 | 9.0 | | 6.0 | 9.0 | 7.0 | | 7.0 | 9.0 | 7.0 | 9.0 | 7.0 | 5.0 | 9.0 |
| methyl-4-oxo-2-imida- | .125 | 8.0 | | 6.0 | 9.0 | 6.0 | 3.0 | 9.0 | 8.0 | 5.0 | 9.0 | 7.0 | 5.0 | 9.0 |
| zolin-2-yl)-3- | .063 | 7.0 | | 6.0 | 9.0 | 6.0 | 2.0 | 6.0 | 3.0 | 3.0 | 9.0 | 6.0 | 5.0 | 9.0 |
| quinolinecarboxylate | .032 | 3.0 | | 2.0 | 7.0 | 3.0 | 0.0 | | 0.0 | 2.0 | 9.0 | 6.0 | 4.0 | 6.0 |
| Tallowammonium 2- | 2.080 | 9.0 | | 7.0 | 9.0 | 9.0 | 9.0 | 7.0 | | 9.0 | 9.0 | 9.0 | | 9.0 |
| (5-isopropyl-5- | 1.040 | 9.0 | | 7.0 | 9.0 | 9.0 | 9.0 | 9.0 | | 9.0 | 9.0 | 9.0 | | 9.0 |
| methyl-4-oxo-2- | .520 | 9.0 | | 7.0 | 9.0 | 7.0 | 9.0 | 9.0 | | 6.0 | 9.0 | 9.0 | | 9.0 |
| imidazolin-2-yl)- | .260 | 9.0 | | 6.0 | 9.0 | 6.0 | 7.0 | 8.0 | | 3.0 | 9.0 | 8.0 | | 9.0 |
| 3-quinolinecar- | .130 | 9.0 | | 5.0 | 8.0 | 5.0 | 6.0 | 0.0 | | 2.0 | 9.0 | 9.0 | | 9.0 |
| boxylate | .065 | 9.0 | | 4.0 | 3.0 | 4.0 | 2.0 | 0.0 | | 1.0 | 9.0 | 7.0 | | 9.0 |
| 2-Isopropyl-2- | 1.000 | 9.0 | | 7.0 | 8.0 | 9.0 | 9.0 | 9.0 | 6.0 | 9.0 | 9.0 | 9.0 | | 9.0 |
| methyl-8-propyl-5H— | .500 | 6.0 | | 7.0 | 6.0 | 9.0 | 9.0 | 9.0 | 5.0 | 8.0 | 9.0 | 9.0 | | 9.0 |
| imidazo[1',2':1,2]- | .250 | 3.0 | | 7.0 | 4.0 | 8.0 | 7.0 | 7.0 | 3.0 | 3.0 | 9.0 | 8.0 | | 9.0 |
| pyrrolo[3,4-b]- | .125 | 3.0 | | 1.0 | 1.0 | 6.0 | 5.0 | 4.0 | 1.0 | 1.0 | 9.0 | 6.0 | | 5.0 |
| pyridine-3(2H), | .063 | 2.0 | | 0.0 | 1.0 | 2.0 | 4.0 | 2.0 | 0.0 | 0.0 | 5.0 | 4.0 | | 2.0 |
| 5-dione | .032 | 2.0 | | 0.0 | 1.0 | 0.0 | 2.0 | 1.0 | 0.0 | 0.0 | 3.0 | 2.0 | | 1.0 |
| 2,8-Diisopropyl-<br>2-methyl-5H—imidazo-<br>[1',2':1,2]pyrrolo-<br>[3,4-b]pyridine-3-<br>(2H), 5-dione | 8.000 | 9.0 | 9.0 | 9.0 | 9.0 | 9.0 | 9.0 | 9.0 | 9.0 | 9.0 | | | | |
| Isopropyl 2-(5- | 5.000 | 9.0 | 7.0 | 0.0 | 9.0 | 9.0 | 9.0 | 6.0 | 9.0 | 7.0 | | | | |
| isopropyl-5-methyl-<br>4-oxo-2-imidazolin-<br>2-yl)-6-propyl-<br>nicotinate | 1.000 | 0.0 | | 0.0 | 0.0 | 0.0 | 0.0 | 3.0 | 0.0 | 0.0 | 0.0 | 0.0 | | 0.0 |
| 5,6,7,8-Tetrahydro- | 1.000 | 9.0 | | 8.0 | 9.0 | 9.0 | 9.0 | 9.0 | 3.0 | 9.0 | 9.0 | 9.0 | | 9.0 |
| 2-(5-isopropyl-5- | .500 | 9.0 | | 6.0 | 9.0 | 9.0 | 9.0 | 9.0 | 2.0 | 9.0 | 9.0 | 9.0 | | 9.0 |
| methyl-4-oxo-2- | .250 | 6.0 | | 7.0 | 9.0 | 9.0 | 9.0 | 7.0 | 0.0 | 3.0 | 9.0 | 9.0 | | 9.0 |
| imidazolin-2-yl)- | .125 | 5.0 | | 2.0 | 7.0 | 9.0 | 9.0 | 5.0 | 0.0 | 1.0 | 9.0 | 8.0 | | 9.0 |
| 3-quinolinecarbo- | .063 | 3.0 | | 2.0 | 6.0 | 8.0 | 9.0 | 2.0 | 0.0 | 0.0 | 9.0 | 7.0 | | 9.0 |
| xylic acid | .032 | | | 1.0 | 4.0 | 7.0 | 0.0 | 2.0 | 0.0 | 0.0 | 9.0 | 4.0 | | 3.0 |
| 6-Butoxy-2-(5- | 8.000 | 9.0 | 9.0 | 9.0 | 9.0 | 9.0 | 9.0 | 9.0 | 7.0 | 7.0 | | | | |

TABLE XI-continued

| POST-EMERGENCE TESTS - RATES IN KG/HA | | | | | | | | | | | | | |
|---|---|---|---|---|---|---|---|---|---|---|---|---|---|
| isopropyl-5-methyl- | | | | | | | | | | | | | |
| 4-oxo-2-imidazolin- | | | | | | | | | | | | | |
| 2-yl)nicotinic acid | | | | | | | | | | | | | |
| 2-(5-Isopropyl-5- | 1.000 | 9.0 | 7.0 | 9.0 | 7.0 | 7.0 | 9.0 | 8.0 | 9.0 | 9.0 | 9.0 | 8.0 | 9.0 |
| methyl-4-oxo-2- | .500 | 9.0 | 7.0 | 9.0 | 6.0 | | 9.0 | 7.0 | 7.0 | 8.0 | 7.0 | 7.0 | 9.0 |
| imidazolin-2-yl)- | .250 | 9.0 | 6.0 | 7.0 | 6.0 | 4.0 | 9.0 | 3.0 | 6.0 | 8.0 | 7.0 | 7.0 | 9.0 |
| 6-(2-propynyloxy)- | .125 | 8.0 | 6.0 | 7.0 | 6.0 | 3.0 | 7.0 | 2.0 | 3.0 | 7.0 | 7.0 | 6.0 | 9.0 |
| nicotinic acid | | | | | | | | | | | | | |
| 2-(5-Isopropyl-5- | 1.000 | 0.0 | 0.0 | 7.0 | 0.0 | | | 0.0 | 0.0 | 8.0 | 6.0 | 3.0 | 5.0 |
| methyl-4-oxo-2- | .500 | 0.0 | 0.0 | 7.0 | 0.0 | | 0.0 | 0.0 | 0.0 | 8.0 | 6.0 | 2.0 | 5.0 |
| imidazolin-2-yl)- | | | | | | | | | | | | | |
| 6-p-tolylnicotinic | | | | | | | | | | | | | |
| acid | | | | | | | | | | | | | |
| 6-(Isopropylamino)- | 1.000 | 9.0 | 8.0 | 9.0 | 9.0 | 9.0 | 9.0 | 9.0 | 9.0 | 9.0 | 9.0 | 9.0 | 9.0 |
| 2-(5-isopropyl-5- | .500 | 9.0 | 7.0 | 9.0 | 9.0 | 9.0 | 9.0 | 8.0 | 9.0 | 9.0 | 9.0 | 8.0 | 9.0 |
| methyl-4-oxo-2- | .250 | 9.0 | 6.0 | 9.0 | 9.0 | 7.0 | 9.0 | 7.0 | 9.0 | 9.0 | 9.0 | 7.0 | 9.0 |
| imidazolin-2-yl)- | .125 | 9.0 | 6.0 | 9.0 | 9.0 | 7.0 | 9.0 | 7.0 | 7.0 | 9.0 | 8.0 | 6.0 | 9.0 |
| nicotinic acid | | | | | | | | | | | | | |
| 7-Ethyl-2-isopropyl- | 1.000 | 9.0 | 9.0 | 9.0 | 9.0 | | 9.0 | 9.0 | 9.0 | 9.0 | 8.0 | | 9.0 |
| 2-methyl-5H—imidazo- | .500 | 9.0 | 7.0 | 9.0 | 9.0 | 9.0 | 9.0 | 6.0 | 9.0 | 9.0 | 8.0 | | 9.0 |
| [1',2':1,2]pyrrolo- | .250 | 9.0 | 7.0 | 9.0 | 9.0 | | 9.0 | 7.0 | 9.0 | 9.0 | 7.0 | | 9.0 |
| [3,4-b]pyridine-3- | .125 | 9.0 | 7.0 | 9.0 | 8.0 | 8.0 | 8.0 | 4.0 | 9.0 | 9.0 | 7.0 | | 9.0 |
| (2H), 5-dione | .063 | 7.0 | 7.0 | 9.0 | 6.0 | 7.0 | 8.0 | 4.0 | 9.0 | 9.0 | 7.0 | | 9.0 |
| | .032 | 7.0 | 4.0 | 4.0 | 2.0 | 7.0 | | 2.0 | 3.0 | 9.0 | 3.0 | | 9.0 |

EXAMPLE 99

Preemergence Herbicidal Evaluation of Test Compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From 4 to 5 weeks after treatment, the tests are terminated and each cup is examined and rated according to the rating system set forth above. The herbicidal proficiency of the active ingredients of the present invention is evident from the test results which are recorded in Table XII below. When more than one test is involved for a given compound, the data are averaged.

TABLE XII

PRE-EMERGENCE TESTS - RATES IN KG/HA

| COMPOUNDS | RATE | BARN-YARDGR | GREEN FOX | P NUT SED-GE | WILD OATS | QUACK GRASS | FLD B INDWD | COCK-LEBUR | XXX MRNGLY | RAG-WEED | VELVET-LEAF | S BARLY LA | CORN FIELD | RICE, NATO | SOY-BEAN AD | SUN-FLA XXX | S WHEAT ER |
|---|---|---|---|---|---|---|---|---|---|---|---|---|---|---|---|---|---|
| Triethylammonium 2-(5-isopropyl-5-methyl-4-oxo 2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .125 | 7.0 | 9.0 | 9.0 | 9.0 | 9.0 | 9.0 | 9.0 | 9.0 | 8.0 | 9.0 | 9.0 | 9.0 | 9.0 | 8.0 | 9.0 | 9.0 |
| | .063 | 6.0 | 9.0 | 9.0 | 9.0 | 9.0 | 9.0 | 8.0 | 9.0 | 6.0 | 9.0 | 9.0 | 9.0 | 8.0 | 8.0 | 9.0 | 8.0 |
| | .032 | 3.0 | 8.0 | 8.0 | 8.0 | 8.0 | 9.0 | 8.0 | 9.0 | 1.0 | 9.0 | 8.0 | 7.0 | 7.0 | 7.0 | 8.0 | 8.0 |
| | .016 | 1.0 | 6.0 | 7.0 | 6.0 | 7.0 | 9.0 | 8.0 | 9.0 | 1.0 | 9.0 | 8.0 | 8.0 | 6.0 | | 8.0 | 8.0 |
| Sodium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 9.0 | 5.0 | 9.0 | 9.0 | 9.0 | 9.0 | 9.0 | 9.0 | 9.0 |
| | .032 | 6.0 | 8.0 | 9.0 | 8.0 | 9.0 | 9.0 | 9.0 | 9.0 | 2.0 | 9.0 | 9.0 | 9.0 | 9.0 | 9.0 | 9.0 | 8.0 |
| | .016 | 2.0 | 6.0 | 8.0 | 8.0 | 7.0 | 9.0 | 8.0 | 8.0 | 1.0 | 9.0 | 9.0 | 7.0 | 8.0 | 8.0 | 8.0 | 8.0 |
| Methyl 2-(5-isopropyl-5-methyl-4-oxo-2-imidazolin-2-yl)nicotinate | 10.000 | 9.0 | 9.0 | 9.0 | 9.0 | | | | 8.0 | 8.0 | 8.0 | | | | | | |
| | 2.000 | 9.0 | 9.0 | 9.0 | 9.0 | | 9.0 | 9.0 | 8.5 | 9.0 | 9.0 | 98. | 9.0 | | | | |
| | 1.000 | 9.0 | 9.0 | 9.0 | 9.0 | | 9.0 | 9.0 | 8.8 | 9.0 | 9.0 | | 9.0 | 9.0 | 9.0 | | |
| | .500 | 9.0 | 9.0 | 9.0 | 9.0 | 9.0 | 9.0 | 9.0 | 8.9 | 8.8 | 9.0 | 9.0 | 9.0 | 9.0 | 9.0 | 9.0 | 9.0 |
| | .250 | 8.7 | 8.9 | 9.0 | 9.0 | 9.0 | 9.0 | 9.0 | 8.6 | 8.0 | 9.0 | 9.0 | 9.0 | 9.0 | 8.8 | 9.0 | 9.0 |
| | .125 | 7.9 | 8.9 | 8.0 | 9.0 | 8.0 | 9.0 | 9.0 | 8.4 | 7.1 | 9.0 | 8.7 | 8.7 | 9.0 | 8.8 | 9.0 | 8.8 |
| | .063 | 6.7 | 7.9 | 8.5 | 8.8 | 0.0 | 9.0 | 8.7 | 8.0 | 4.6 | 8.8 | 8.7 | 8.3 | 7.9 | 7.6 | 8.1 | 8.8 |
| | .032 | 4.0 | 6.9 | 6.7 | 8.8 | 5.3 | 9.0 | 6.6 | 8.1 | 1.0 | 8.7 | 7.7 | 6.0 | 7.0 | 6.5 | 6.7 | 8.2 |
| | .016 | 2.4 | 5.6 | 4.8 | 6.3 | 4.3 | 9.0 | 4.4 | 6.6 | 0.2 | 7.8 | 6.8 | 2.2 | 5.8 | 4.7 | 3.3 | 7.2 |
| Methyl 2-(5-ethyl-5-methyl-4-oxo-2-imidazolin-2-yl)nicotinate | 10.000 | 8.0 | 9.0 | 9.0 | 8.0 | | | | 0.0 | 0.0 | 0.0 | | | | | | |
| | 1.000 | 9.0 | 0.0 | 9.0 | 9.0 | | | 8.0 | 0.0 | 9.0 | | 9.0 | 9.0 | 8.0 | | | |
| | .500 | 8.0 | 6.0 | 9.0 | 9.0 | | | 5.0 | 8.0 | 0.0 | 8.0 | | 8.0 | 9.0 | 8.0 | | |
| | .250 | 5.0 | 5.0 | 6.0 | 1.0 | | | 3.0 | 8.0 | 0.0 | 8.0 | | 5.0 | 5.0 | 7.0 | | |
| | .125 | 0.0 | 0.0 | 0.0 | 0.0 | | | 0.0 | 0.0 | 0.0 | 0.0 | | 3.0 | 3.0 | 5.0 | | |
| | .063 | 0.0 | 0.0 | 0.0 | 0.0 | | | 0.0 | 5.0 | 0.0 | 7.0 | | 0.0 | 0.0 | 1.0 | | |
| | .032 | 0.0 | 0.0 | 0.0 | 0.0 | | | 0.0 | 3.0 | 0.0 | 3.0 | | 0.0 | 0.0 | 0.0 | | |
| 2-Propynyl 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 7.0 | 9.0 | 8.0 | 9.0 | 9.0 | 9.0 | 9.0 | 9.0 | 7.0 | 9.0 | 9.0 | 8.0 | 9.0 | 8.0 | 9.0 | 9.0 |
| | .032 | 3.0 | 8.0 | 8.0 | 8.0 | 9.0 | 9.0 | 8.0 | 8.0 | 2.0 | 9.0 | 9.0 | 3.0 | 8.0 | 6.0 | 8.0 | 8.0 |
| | .016 | 2.0 | 7.0 | 8.0 | 8.0 | 9.0 | 9.0 | 8.0 | 8.0 | 1.0 | 9.0 | 8.0 | 2.0 | 7.0 | 5.0 | 0.0 | 7.0 |
| Calcium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .125 | 8.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .063 | 7.0 | 9.0 | 9.0 | 9.0 | 8.0 | 9.0 | 9.0 | 9.0 | 4.0 | 9.0 | 9.0 | 9.0 | 9.0 | 9.0 | 9.0 | 9.0 |
| | .032 | 5.0 | 7.0 | 8.0 | 8.0 | 9.0 | 9.0 | 9.0 | 9.0 | 3.0 | 9.0 | 9.0 | 8.0 | 9.0 | 9.0 | 8.0 | 8.0 |
| | .016 | 3.0 | 5.0 | 8.0 | 7.0 | 8.0 | 9.0 | 7.0 | 7.0 | 1.0 | 9.0 | 0.0 | 3.0 | 8.0 | 9.0 | 7.0 | 8.0 |
| Benzyl 2-(5-ethyl-5-methyl-4-oxo-2-imidazolin-2-yl)nicotinate | .500 | 7.0 | 9.0 | 9.0 | 4.0 | | 9.0 | 5.0 | 9.0 | 0.0 | 9.0 | 4.0 | 5.0 | 9.0 | 1.0 | 1.0 | 5.0 |
| | .250 | 6.0 | 8.0 | 5.0 | 2.0 | | 9.0 | 0.0 | 8.0 | 0.0 | 9.0 | 0.0 | 2.0 | 8.0 | 0.0 | 0.0 | 2.0 |
| | .125 | 1.0 | 6.0 | 2.0 | 0.0 | | 9.0 | 0.0 | 7.0 | 0.0 | 8.0 | 0.0 | 0.0 | 6.0 | | 0.0 | 0.0 |
| | .063 | 0.0 | 3.0 | 0.0 | 0.0 | | 9.0 | 0.0 | 1.0 | 0.0 | 5.0 | 0.0 | 0.0 | 2.0 | 0.0 | 0.0 | 0.0 |
| | .032 | 0.0 | 0.0 | 0.0 | 0.0 | | 9.0 | 0.0 | | 0.0 | 0.0 | 0.0 | 0.0 | 1.0 | 0.0 | 0.0 | 0.0 |
| | .016 | 0.0 | 0.0 | 0.0 | 0.0 | | 0.0 | 0.0 | 0.0 | 0.0 | 0.0 | 0.0 | 0.0 | 0.0 | 0.0 | 0.0 | 0.0 |
| Diisopropylammonium 2-(5-isopropyl-5- | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |

TABLE XII-continued

| | | PRE-EMERGENCE TESTS - RATES IN KG/HA | | | | | | | | | | | | | | | |
|---|---|---|---|---|---|---|---|---|---|---|---|---|---|---|---|---|---|
| methyl-4-oxo-2-imi-dazolin-2-yl)nico-tinate | .125 | 8.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 9.0 | 3.0 | 9.0 | 9.0 | 9.0 | 9.0 | 8.0 | 9.0 | 9.0 |
| | .032 | 3.0 | 7.0 | 8.0 | 8.0 | 9.0 | 9.0 | 8.0 | 9.0 | 2.0 | 9.0 | 8.0 | 3.0 | 9.0 | 8.0 | 8.0 | 8.0 |
| Dodecyl 2-(5-isopro-pyl-5-methyl-4-oxo-2-imidazolin-2-yl)-nicotinate | .500 | 9.0 | 9.0 | 9.0 | 9.0 | | 9.0 | 9.0 | 9.0 | 8.0 | 9.0 | 9.0 | 9.0 | 9.0 | 9.0 | 9.0 | 9.0 |
| | .250 | 8.0 | 9.0 | 9.0 | 9.0 | | 9.0 | 9.0 | 8.0 | 1.0 | 9.0 | 9.0 | 9.0 | 9.0 | 7.0 | 9.0 | 9.0 |
| | .125 | 7.0 | 8.0 | 9.0 | 0.0 | | 9.0 | 0.0 | 9.0 | 0.0 | 8.0 | 8.0 | 9.0 | 8.0 | 6.0 | 6.0 | 8.0 |
| | .063 | 8.0 | 7.0 | 9.0 | 8.0 | | 9.0 | 5.0 | 7.0 | 0.0 | 7.0 | 5.0 | 3.0 | 8.0 | 3.0 | 1.0 | 7.0 |
| | .032 | 0.0 | 5.0 | 7.0 | 3.0 | | 9.0 | 0.0 | 6.0 | 0.0 | 6.0 | 5.0 | 3.0 | 7.0 | | 0.0 | 6.0 |
| | .016 | 0.0 | 4.0 | 2.0 | 0.0 | | 7.0 | 0.0 | 0.0 | 0.0 | 1.0 | 2.0 | 2.0 | 5.0 | 1.0 | 0.0 | 1.0 |
| Ethyl 2-(5-isopropyl-5-methyl-4-oxo-2-imidazolin-2-yl)nic-otinate | .500 | 9.0 | 9.0 | 9.0 | 9.0 | | 9.0 | 8.8 | 9.0 | 9.0 | 9.0 | 9.0 | 9.0 | 9.0 | 9.0 | 9.0 | 9.0 |
| | .250 | 0.0 | 9.0 | 9.0 | 9.0 | | 9.0 | 8.0 | 9.0 | 9.0 | 9.0 | 9.0 | 9.0 | 9.0 | 9.0 | 9.0 | 9.0 |
| | .125 | 8.0 | 9.0 | 9.0 | 9.0 | | 9.0 | 8.0 | 9.0 | 7.0 | 9.0 | 9.0 | 9.0 | 9.0 | | 8.0 | 8.0 |
| | .065 | 5.0 | 7.0 | 8.0 | 9.0 | | 9.0 | 6.0 | 8.0 | 6.0 | 0.0 | 9.0 | 6.0 | 8.0 | 3.0 | 6.0 | 7.0 |
| | .032 | 2.0 | 6.0 | 5.0 | 6.0 | | 9.0 | 2.0 | 5.0 | 3.0 | 7.0 | 6.0 | 3.0 | 5.0 | | 0.0 | 3.0 |
| | .016 | 0.0 | 6.0 | 2.0 | 1.0 | | 9.0 | 0.0 | 3.0 | 0.0 | 4.0 | 4.0 | 1.0 | 4.0 | | 0.0 | 3.0 |
| 2-(Benzyloxy)ethyl 2-(5-isopropyl-5-methyl-4-oxo-2-imidazolin-2-yl)nicotinate | .500 | 7.0 | 9.0 | 9.0 | 9.0 | 9.0 | 9.0 | 9.0 | 9.0 | 8.8 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 9.0 | 7.0 | 9.0 | 9.0 | 9.0 | 9.0 | 6.0 | 9.0 | 9.0 |
| | .125 | 5.0 | 9.0 | 9.0 | 9.0 | 8.0 | 9.0 | 8.0 | 9.0 | 4.0 | 9.0 | 9.0 | 0.0 | 9.0 | 7.0 | 7.0 | 9.0 |
| | .063 | 4.0 | 9.0 | 8.0 | 8.0 | 9.0 | 9.0 | 3.0 | 9.0 | 0.0 | 9.0 | 7.0 | 7.0 | 8.0 | 7.0 | 7.0 | 8.0 |
| | .032 | 2.0 | 2.0 | 8.0 | 4.0 | 9.0 | 9.0 | 2.0 | 3.0 | 0.0 | 8.0 | 4.0 | 2.0 | 3.0 | 3.0 | 1.0 | 7.0 |
| | .016 | 0.0 | 1.0 | 7.0 | 3.0 | 9.0 | 1.0 | 1.0 | 1.0 | 0.0 | 7.0 | 3.0 | 1.0 | 2.0 | 3.0 | 0.0 | 4.0 |
| 2-(5-Isopropyl-5-methyl-4-oxo-2-imidazolin-2-yl)nicotinic acid | 10.000 | 0.0 | 9.0 | 9.0 | 8.0 | | | | 0.0 | 0.0 | 0.0 | | | | | | |
| | 2.000 | 9.0 | 9.0 | 9.0 | 9.0 | | | 9.0 | 8.0 | 9.0 | 9.0 | | 9.0 | 9.0 | 8.8 | | |
| | 1.000 | 9.0 | 9.0 | 9.0 | 9.0 | | | 9.0 | 8.0 | 9.0 | 9.0 | | 9.0 | 9.0 | 8.0 | | |
| | .500 | 9.0 | 9.0 | 9.0 | 9.0 | 9.0 | 9.0 | 9.0 | 8.5 | 8.5 | 0.5 | 9.0 | 9.0 | 9.0 | 8.5 | 9.0 | 9.0 |
| | .250 | 9.0 | 9.0 | 9.0 | 9.0 | 9.0 | 9.0 | 8.5 | 8.5 | 8.5 | 8.5 | 9.0 | 9.0 | 9.0 | 0.5 | 9.0 | 9.0 |
| | .125 | 8.0 | 9.0 | 9.0 | 9.0 | 9.0 | 9.0 | 8.5 | 9.0 | 0.5 | 0.5 | 9.0 | 9.0 | 9.0 | 8.5 | 9.0 | 9.0 |
| | .063 | 7.5 | 9.0 | 9.0 | 9.0 | 9.0 | 9.0 | 0.5 | 0.5 | 7.5 | 0.5 | 9.0 | 9.0 | 9.0 | 8.0 | 9.0 | 9.1 |
| | .032 | 7.0 | 0.0 | 9.0 | 8.0 | 9.0 | 9.0 | 8.5 | 8.0 | 3.5 | 8.5 | 9.0 | 0.5 | 9.0 | 7.0 | 9.0 | 9.1 |
| | .016 | 3.0 | 6.0 | 8.5 | 8.0 | 8.0 | 9.0 | 8.0 | 5.5 | 0.5 | 0.0 | 0.0 | 4.5 | 8.5 | 6.0 | 9.0 | 8.1 |
| 2-Propynyl 2-(5-ethyl-5-methyl-4-oxo-2-imi-dazolin-2-yl)nicotinate | .500 | 0.0 | 9.0 | 8.0 | 0.0 | 9.0 | 9.0 | 8.0 | 9.0 | 2.0 | 9.0 | 9.0 | 7.0 | 9.0 | 9.0 | 9.0 | 9.0 |
| | .250 | 4.0 | 9.0 | 9.0 | 6.0 | 7.0 | 9.0 | 7.0 | 8.0 | 1.0 | 9.0 | 8.0 | 6.0 | 8.0 | 9.0 | 7.0 | 8.0 |
| | .125 | 2.0 | 4.0 | 1.0 | 1.0 | 2.0 | 9.0 | 3.0 | 4.0 | 1.0 | 8.0 | 7.0 | 1.0 | 8.0 | 2.0 | 2.0 | 7.0 |
| | .063 | 1.0 | 2.0 | 0.0 | 0.0 | 1.0 | 9.0 | 1.0 | 3.0 | 0.0 | 7.0 | 3.0 | 0.0 | 4.0 | 1.0 | 1.0 | 2.0 |
| | .032 | 0.0 | 0.0 | 0.0 | 0.0 | 0.0 | 1.0 | 1.0 | 0.0 | 0.0 | 3.0 | 1.0 | 0.0 | 2.0 | | 0.0 | 1.0 |
| | .016 | 0.0 | 0.0 | 0.0 | 0.0 | 0.0 | 1.0 | 0.0 | 0.0 | 0.0 | 1.0 | 0.0 | 0.0 | 1.0 | 1.0 | 0.0 | 0.0 |
| 2-(5-ethyl-5-methyl-4-oxo-2-imidazolin-2-yl)-nicotinic acid | .500 | 8.0 | 9.0 | 9.0 | 9.0 | | 9.0 | 6.0 | 6.0 | 3.0 | 9.0 | 8.0 | 9.0 | 9.0 | | 9.0 | 9.0 |
| | .250 | 3.0 | 9.0 | 7.0 | 8.0 | | 9.0 | 1.0 | 8.0 | 0.0 | 9.0 | 7.0 | 6.0 | 9.0 | | 0.0 | 0.0 |
| | .125 | 3.0 | 8.0 | 9.0 | 6.0 | | 9.0 | 0.0 | 7.0 | 0.0 | 9.0 | 4.0 | 5.0 | 8.0 | | 0.0 | 7.0 |
| | .063 | 2.0 | 5.0 | 3.0 | 1.0 | | 9.0 | 0.0 | 6.0 | 0.0 | 8.0 | 2.0 | 0.0 | 8.0 | 1.0 | 0.0 | 3.0 |
| | .032 | 0.0 | 4.0 | 0.0 | 0.0 | | 9.0 | 0.0 | 0.0 | 0.0 | 7.0 | 0.0 | 0.0 | 5.0 | | 0.0 | 0.0 |
| | .016 | 8.0 | 0.0 | 0.0 | 0.0 | | 8.0 | 0.0 | 0.0 | 0.0 | 5.0 | 0.0 | 0.0 | 3.0 | | 0.0 | 0.0 |
| Methyl 2-(5-isopropyl-5-methyl-4-oxo-2-imi-dazolin-2-yl)nicotinate hydrochloride | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .063 | 6.0 | 9.0 | 9.0 | 9.0 | 9.0 | 9.0 | 9.0 | 9.0 | 6.0 | 9.0 | 9.0 | 9.0 | 9.0 | 9.0 | 9.0 | 9.0 |
| | .032 | 6.0 | 9.0 | 7.0 | 9.0 | 9.0 | 9.0 | 9.0 | 9.0 | 1.0 | 9.0 | 9.0 | 9.0 | 9.0 | 8.0 | 8.0 | 9.0 |
| | .016 | 2.0 | 7.0 | 7.0 | 7.0 | 9.0 | 9.0 | 4.0 | 9.0 | 0.0 | 9.0 | 9.0 | 7.0 | 8.0 | 8.0 | 7.0 | 9.0 |
| 1-Methyl-2-Propynyl 2-(5-isopropyl-5-methyl-4-oxo-2-imidazolin-2-yl)nicoti-nate | .500 | 9.0 | 9.0 | 9.0 | 9.0 | 9.0 | 9.0 | 9.0 | 9.0 | 9.0 | 9.0 | 9.0 | 9.0 | 9.0 | | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | |
| | .063 | 9.0 | 9.0 | 9.0 | 9.0 | 9.0 | 9.0 | 9.0 | 9.0 | 7.0 | 9.0 | 9.0 | 8.0 | 9.0 | 9.0 | 9.0 | |

TABLE XII-continued

PRE-EMERGENCE TESTS - RATES IN KG/HA

| | | | | | | | | | | | | | | | | | |
|---|---|---|---|---|---|---|---|---|---|---|---|---|---|---|---|---|---|
| | .032 | 7.0 | 9.0 | 9.0 | 9.0 | 8.0 | 9.0 | 9.0 | 9.0 | 2.0 | 9.0 | 9.0 | 7.0 | 9.0 | 9.0 | 9.0 | |
| | .016 | 3.0 | 9.0 | 8.0 | 9.0 | 2.0 | 9.0 | 9.0 | 9.0 | 1.0 | 9.0 | 8.0 | 3.0 | 7.0 | 6.0 | 8.0 | |
| Tert-butyl 2-(5-isopropyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | |
| 5-methyl-4-oxo-2- | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | |
| imidazolin-2-yl)nicotinate | .125 | 4.0 | 9.0 | 9.0 | 9.0 | 9.0 | 9.0 | 9.0 | 9.0 | 7.0 | 9.0 | 9.0 | 9.0 | 9.0 | 7.0 | 9.0 | |
| | .063 | 4.0 | 8.0 | 9.0 | 9.0 | 6.0 | 9.0 | 9.0 | 8.0 | 2.0 | 9.0 | 9.0 | 3.0 | 7.0 | 2.0 | 9.0 | |
| | .032 | 1.0 | 6.0 | 6.0 | 7.0 | 9.0 | 9.0 | 2.0 | 2.0 | 1.0 | 8.0 | 8.0 | 1.0 | 4.0 | 1.0 | 8.0 | |
| | .016 | 0.0 | 2.0 | 2.0 | 3.0 | 2.0 | 9.0 | | 1.0 | 0.0 | 2.0 | 8.0 | 1.0 | 2.0 | 0.0 | 4.0 | |
| Cyclohexyl 2-(5-isopropyl- | .500 | 9.0 | 9.0 | 8.0 | 9.0 | 8.0 | 9.0 | 9.0 | 9.0 | 2.0 | 9.0 | 9.0 | 9.0 | 9.0 | 7.0 | 9.0 | |
| 5-methyl-4-oxo-2-imidazo- | .250 | 6.0 | 9.0 | 8.0 | 9.0 | 8.0 | 9.0 | 9.0 | 9.0 | 2.0 | 9.0 | 8.0 | 7.0 | 7.0 | 6.0 | 8.0 | |
| lin-2-yl)nicotinate | .125 | 3.0 | 7.0 | 7.0 | 3.0 | 4.0 | 9.0 | 8.0 | 6.0 | 1.0 | 7.0 | 7.0 | 1.0 | 7.0 | 1.0 | 7.0 | |
| | .063 | 1.0 | 0.0 | 0.0 | 2.0 | 3.0 | 9.0 | 8.0 | 3.0 | 0.0 | 4.0 | 7.0 | 0.0 | 4.0 | 0.0 | 6.0 | |
| | .032 | 0.0 | 0.0 | 0.0 | 1.0 | 2.0 | 9.0 | 8.0 | 2.0 | 0.0 | 2.0 | 4.0 | 0.0 | 2.0 | 0.0 | 5.0 | |
| | .016 | 0.0 | 0.0 | 0.0 | 0.0 | 0.0 | 8.0 | 1.0 | 1.0 | 0.0 | 0.0 | 3.0 | 0.0 | 2.0 | 0.0 | 3.0 | |
| Octadecyl 2-(5-isopropyl- | .500 | 8.0 | 9.0 | 8.0 | 9.0 | 9.0 | 9.0 | 9.0 | 9.0 | 3.0 | 9.0 | 9.0 | 7.0 | 9.0 | 8.0 | 9.0 | |
| 5-methyl-4-oxo-2-imidazo- | .250 | 1.0 | 6.0 | 1.0 | 7.0 | 8.0 | 9.0 | 4.0 | 2.0 | 1.0 | 7.0 | 9.0 | 6.0 | 6.0 | 3.0 | 8.0 | |
| lin-2-yl)nicotinate | .125 | 0.0 | 4.0 | 1.0 | 7.0 | 3.0 | 9.0 | 2.0 | 1.0 | 0.0 | 6.0 | 7.0 | 1.0 | 4.0 | 2.0 | 8.0 | |
| | .063 | 0.0 | 0.0 | 0.0 | 2.0 | 0.0 | 9.0 | 1.0 | 1.0 | 0.0 | 1.0 | 7.0 | 0.0 | 0.0 | 0.0 | 4.0 | |
| | .032 | 0.0 | 0.0 | 0.0 | 1.0 | 0.0 | 3.0 | 0.0 | 0.0 | 0.0 | 0.0 | 2.0 | 0.0 | 0.0 | 0.0 | 2.0 | |
| | .016 | 0.0 | 0.0 | 0.0 | 0.0 | 0.0 | 3.0 | 0.0 | 0.0 | 0.0 | 0.0 | 1.0 | 0.0 | 0.0 | 0.0 | 2.0 | |
| Furfuryl 2-(5-isopropyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| 5-methyl-4-oxo-2-imidazo- | .250 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| lin-2-yl)nicotinate | .125 | 9.0 | 9.0 | 9.0 | 9.0 | 9.0 | 9.0 | 9.0 | 9.0 | 8.0 | 9.0 | 9.0 | 9.0 | 9.0 | 9.0 | 9.0 | 9.0 |
| | .063 | 8.0 | 9.0 | 9.0 | 9.0 | 9.0 | 9.0 | 9.0 | 9.0 | 2.0 | 9.0 | 9.0 | 9.0 | 9.0 | 9.0 | 9.0 | 9.0 |
| | .032 | 7.0 | 9.0 | 9.0 | 9.0 | 9.0 | 9.0 | 9.0 | 9.0 | 1.0 | 9.0 | 8.0 | 9.0 | 9.0 | 9.0 | 9.0 | 9.0 |
| | .016 | 3.0 | 9.0 | 8.0 | 9.0 | 9.0 | 9.0 | 4.0 | 8.0 | 0.0 | 8.0 | 8.0 | 7.0 | 8.0 | 6.0 | 9.0 | 9.0 |
| Isopropyl 2-(5-isopropyl- | .500 | 9.0 | 9.0 | 9.0 | 9.0 | 9.0 | 9.0 | 9.0 | 9.0 | 7.0 | 9.0 | 9.0 | 9.0 | 9.0 | 8.0 | 9.0 | 8.0 |
| 5-methyl-4-oxo-2-imidazo- | .250 | 8.0 | 9.0 | 8.0 | 9.0 | 9.0 | 9.0 | 7.0 | 9.0 | 6.0 | 9.0 | 9.0 | 9.0 | 9.0 | 8.0 | 9.0 | 8.0 |
| lin-2-yl)nicotinate | .125 | 1.0 | 8.0 | 7.0 | 8.0 | 9.0 | 9.0 | 9.0 | 9.0 | 1.0 | 9.0 | 8.0 | 7.0 | 9.0 | 7.0 | 6.0 | 8.0 |
| | .063 | 0.0 | 7.0 | 4.0 | 7.0 | 8.0 | 9.0 | 3.0 | 9.0 | 0.0 | 9.0 | 6.0 | 4.0 | 7.0 | 6.0 | 3.0 | 7.0 |
| | .032 | 0.0 | 3.0 | 0.0 | 2.0 | 8.0 | 9.0 | | 8.0 | 0.0 | 7.0 | 6.0 | 2.0 | 1.0 | 3.0 | 0.0 | 4.0 |
| | .016 | 0.0 | 1.0 | 0.0 | 0.0 | 9.0 | 6.0 | 2.0 | 4.0 | 0.0 | 7.0 | 8.0 | 1.0 | 1.0 | | 0.0 | 3.0 |
| Benzyl 2-(5-isopropyl-5- | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| methyl-4-oxo-2-imidazo- | .250 | 8.0 | 9.0 | 9.0 | 9.0 | 9.0 | 9.0 | 9.0 | 9.0 | 9.0 | 9.0 | 9.0 | 9.0 | 8.0 | 9.0 | 9.0 | |
| lin-2-yl)nicotinate | .125 | 8.0 | 9.0 | 9.0 | 9.0 | 9.0 | 9.0 | 9.0 | 9.0 | 5.0 | 9.0 | 9.0 | 9.0 | 9.0 | 8.0 | 8.0 | 9.0 |
| | .063 | 4.0 | 8.0 | 9.0 | 9.0 | 9.0 | 9.0 | 7.0 | 9.0 | 0.0 | 9.0 | 8.0 | 9.0 | 8.0 | 8.0 | 7.0 | 9.0 |
| | .032 | 1.0 | 8.0 | 6.0 | 2.0 | 9.0 | 9.0 | 2.0 | 9.0 | 0.0 | 9.0 | 3.0 | 3.0 | 2.0 | 6.0 | 3.0 | 7.0 |
| | .016 | 0.0 | 1.0 | 1.0 | 0.0 | 9.0 | 1.0 | | 0.0 | 0.0 | 0.0 | 0.0 | 0.0 | 1.0 | | 0.0 | 0.0 |
| 2-Decynyl 2-(5-isopropyl- | .500 | 9.0 | 9.0 | 9.0 | 9.0 | 9.0 | 9.0 | 9.0 | 9.0 | 9.0 | 9.0 | 9.0 | 9.0 | 9.0 | | 9.0 | 9.0 |
| 5-methyl-4-oxo-2-imidazo- | .250 | 9.0 | 9.0 | 9.0 | 9.0 | 9.0 | 9.0 | 9.0 | 9.0 | 9.0 | 9.0 | 9.0 | 7.0 | 9.0 | | 9.0 | 9.0 |
| lin-2-yl)nicotinate | .125 | 9.0 | 9.0 | 9.0 | 9.0 | 9.0 | 9.0 | 9.0 | 9.0 | 7.0 | 9.0 | 9.0 | 9.0 | 9.0 | | 9.0 | 9.0 |
| | .063 | 7.0 | 9.0 | 8.0 | 9.0 | 9.0 | 9.0 | 9.0 | 9.0 | 2.0 | 9.0 | 9.0 | 5.0 | 9.0 | | 6.0 | 9.0 |
| | .032 | 4.0 | 8.0 | 6.0 | 9.0 | 7.0 | 9.0 | 9.0 | 9.0 | 2.0 | 9.0 | 7.0 | 5.0 | 8.0 | | 6.0 | 9.0 |
| | .016 | 1.0 | 6.0 | 6.0 | 7.0 | 1.0 | 9.0 | 6.0 | 7.0 | 0.0 | 8.0 | 7.0 | 1.0 | 3.0 | | 1.0 | 8.0 |
| 2-Methoxymethyl 2-(5- | .500 | 9.0 | 9.0 | 9.0 | 9.0 | 9.0 | 9.0 | 9.0 | 9.0 | 9.0 | 9.0 | 9.0 | 9.0 | 9.0 | | 9.0 | 9.0 |
| isopropyl-5-methyl-4-oxo- | .250 | 9.0 | 9.0 | 9.0 | 9.0 | 9.0 | 9.0 | 9.0 | 9.0 | 9.0 | 9.0 | 9.0 | 9.0 | 9.0 | | 9.0 | 9.0 |
| 2-imidazolin-2-yl)nico- | .125 | 9.0 | 9.0 | 9.0 | 9.0 | 9.0 | 9.0 | 9.0 | 9.0 | 7.0 | 9.0 | 9.0 | 9.0 | 9.0 | | 9.0 | 9.0 |
| tinate | .063 | 7.0 | 9.0 | 9.0 | 9.0 | 9.0 | 9.0 | 9.0 | 9.0 | 6.0 | 9.0 | 9.0 | 9.0 | 9.0 | | 7.0 | 9.0 |
| | .032 | 6.0 | 8.0 | 8.0 | 9.0 | 7.0 | 9.0 | 9.0 | 8.0 | 1.0 | 9.0 | 8.0 | 8.0 | 9.0 | | 6.0 | 8.0 |
| | .016 | 1.0 | 7.0 | 7.0 | 4.0 | 3.0 | 9.0 | 9.0 | 7.0 | 0.0 | 9.0 | 8.0 | 1.0 | 8.0 | | 1.0 | 8.0 |
| Allyl 2-(5-isopropyl-5- | .500 | 9.0 | 9.0 | 9.0 | 9.0 | 9.0 | 9.0 | 9.0 | 9.0 | 9.0 | 9.0 | 9.0 | 9.0 | 9.0 | | 9.0 | 9.0 |
| methyl-4-oxo-2-imidazolin- | .250 | 9.0 | 9.0 | 9.0 | 9.0 | 9.0 | 9.0 | 9.0 | 9.0 | 9.0 | 9.0 | 9.0 | 9.0 | 9.0 | | 9.0 | 9.0 |

TABLE XII-continued

PRE-EMERGENCE TESTS - RATES IN KG/HA

| | | | | | | | | | | | | | | | | | |
|---|---|---|---|---|---|---|---|---|---|---|---|---|---|---|---|---|---|
| 2-yl)nicotinate | .125 | 9.0 | 9.0 | 9.0 | 9.0 | 9.0 | 9.0 | 9.0 | 9.0 | 7.0 | 9.0 | 9.0 | 9.0 | 9.0 | | 9.0 | 9.0 |
| | .063 | 8.0 | 9.0 | 8.0 | 9.0 | 8.0 | 9.0 | 9.0 | 9.0 | 7.0 | 9.0 | 9.0 | 8.0 | 9.0 | | 9.0 | 9.0 |
| | .032 | 7.0 | 9.0 | 8.0 | 9.0 | 3.0 | 9.0 | 9.0 | 8.0 | 6.0 | 9.0 | 9.0 | 7.0 | 9.0 | | 6.0 | 9.0 |
| | .016 | 3.0 | 8.0 | 6.0 | 8.0 | 3.0 | 9.0 | 6.0 | 8.0 | 1.0 | 8.0 | 8.0 | 2.0 | 3.0 | | 2.0 | 8.0 |
| 1-Methylallyl 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | | 9.0 | 9.0 |
| | .250 | 9.0 | 9.0 | 9.0 | 9.0 | 9.0 | 9.0 | 9.0 | 9.0 | 7.0 | 9.0 | 9.0 | 9.0 | 9.0 | | 9.0 | 9.0 |
| | .125 | 7.0 | 9.0 | 9.0 | 9.0 | 6.0 | 9.0 | 9.0 | 9.0 | 7.0 | 9.0 | 9.0 | 9.0 | 9.0 | | 8.0 | 9.0 |
| | .063 | 4.0 | 7.0 | 9.0 | 9.0 | | 9.0 | 8.0 | 8.0 | 1.0 | 9.0 | 9.0 | 3.0 | 0.0 | | 5.0 | 9.0 |
| | .032 | 3.0 | 6.0 | 8.0 | 9.0 | 2.0 | 9.0 | 8.0 | 8.0 | 0.0 | 9.0 | 9.0 | 1.0 | 7.0 | | 8.0 | 9.0 |
| | .016 | 1.0 | 3.0 | 7.0 | 3.0 | 0.0 | 9.0 | 2.0 | 8.0 | 0.0 | 9.0 | 7.0 | 0.0 | 4.0 | | 2.0 | 8.0 |
| 3-isopropyl-3-methyl-[3-H]-imidazol[1',2':1,2]pyrrolo[3,4,6-]pyridine-2(3-H),5-dione | .500 | 0.0 | 8.0 | 9.0 | 8.0 | 9.0 | 9.0 | 1.0 | 7.0 | 0.0 | 9.0 | 0.0 | 1.0 | 7.0 | 2.0 | 3.0 | 7.0 |
| | .250 | 0.0 | 3.0 | 4.0 | 1.0 | 0.0 | 9.0 | 1.0 | 1.0 | 0.0 | 7.0 | 7.0 | 0.0 | 7.0 | 2.0 | 0.0 | 7.0 |
| | .125 | 0.0 | 0.0 | 1.0 | 0.0 | 2.0 | 9.0 | 0.0 | 0.0 | 0.0 | 7.0 | 1.0 | 0.0 | 0.0 | | 0.0 | 1.0 |
| | .063 | 0.0 | 0.0 | 0.0 | 0.0 | | 4.0 | 0.0 | 0.0 | 0.0 | 0.0 | 0.0 | 0.0 | 0.0 | 1.0 | 0.0 | 0.0 |
| | .032 | 0.0 | 0.0 | 0.0 | 0.0 | | 4.0 | | 0.0 | 0.0 | | | 0.0 | 0.0 | | 0.0 | |
| | .016 | 0.0 | 0.0 | 0.0 | 0.0 | 0.0 | 1.0 | | 0.0 | 0.0 | | | 0.0 | 0.0 | | 0.0 | |

| COMPOUND | RATE | BARN-YARDGR | GREEN FOX | P NUT SEDGE | WILD OATS | QUACK GRASS | FLD B INDWD | MRNGLY SP | RAG-WEED | VELVET-LEAF | S BARLY LA | CORN FIELD | COTTON | RICE, NATO | SOYBEAN AD |
|---|---|---|---|---|---|---|---|---|---|---|---|---|---|---|---|
| 2-Methylallyl 2-(5-isopropyl-5-methyl-4-oxo-2-imidazolin-2-yl)nicotinate | .500 | 9.0 | 9.0 | 9.0 | 9.0 | 7.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 7.0 | 9.0 | 9.0 | 9.0 | 9.0 | 9.0 | 9.0 | 9.0 | 9.0 | 9.0 |
| | .125 | 7.0 | 9.0 | 9.0 | 9.0 | 7.0 | 9.0 | 9.0 | 8.0 | 9.0 | 9.0 | 8.0 | 9.0 | 9.0 | 9.0 |
| | .063 | 3.0 | 9.0 | 8.0 | 9.0 | 6.0 | 9.0 | 8.0 | 4.0 | 9.0 | 8.0 | 3.0 | 9.0 | 8.0 | 9.0 |
| | .032 | 1.0 | 7.0 | 7.0 | 8.0 | 3.0 | 9.0 | 7.0 | 0.0 | 9.0 | 8.0 | 2.0 | 6.0 | 7.0 | 6.0 |
| | .016 | 0.0 | 1.0 | 5.0 | 2.0 | 2.0 | 9.0 | 5.0 | 0.0 | 7.0 | 7.0 | 1.0 | 3.0 | 6.0 | 2.0 |
| 2-Butenyl 2-(5-isopropyl-5-methyl-4-oxo-2-imidazolin-2-yl)nicotinate | .500 | 9.0 | 9.0 | 9.0 | 9.0 | 8.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 7.0 | 9.0 | 9.0 | 9.0 | 9.0 | 9.0 | 9.0 | 9.0 | 9.0 | 9.0 |
| | .125 | 6.0 | 9.0 | 8.0 | 9.0 | 7.0 | 9.0 | 9.0 | 6.0 | 9.0 | 9.0 | 9.0 | 9.0 | 9.0 | 8.0 |
| | .063 | 4.0 | 9.0 | 8.0 | 9.0 | 5.0 | 9.0 | 9.0 | 3.0 | 9.0 | 9.0 | 9.0 | 9.0 | 9.0 | 9.0 |
| | .032 | 1.0 | 7.0 | 8.0 | 8.0 | 4.0 | 9.0 | 9.0 | 3.0 | 8.0 | 8.0 | 1.0 | 9.0 | 7.0 | 9.0 |
| | .016 | 1.0 | 2.0 | 6.0 | 5.0 | 2.0 | 7.0 | 1.0 | 0.0 | 6.0 | 8.0 | | 6.0 | 5.0 | 6.0 |
| Octadecyl 2-(5-isopropyl-5-methyl-4-oxo-2-imidazolin-2-yl)nicotinate | 8.000 | 8.0 | 8.0 | 8.0 | 8.0 | 9.0 | 9.0 | 7.0 | 9.0 | 8.0 | | | | | |
| | .500 | 8.0 | 9.0 | 8.0 | 9.0 | 9.0 | 9.0 | 9.0 | 3.0 | 9.0 | 9.0 | 7.0 | 8.0 | 9.0 | 7.0 |
| | .250 | 1.0 | 6.0 | 1.0 | 7.0 | 8.0 | 9.0 | 2.0 | 1.0 | 7.0 | 9.0 | 6.0 | 8.0 | 6.0 | 7.0 |
| | .125 | 0.0 | 4.0 | 1.0 | 7.0 | 3.0 | 9.0 | 1.0 | 0.0 | 6.0 | 7.0 | 1.0 | 0.0 | 4.0 | 1.0 |
| | .063 | 0.0 | 0.0 | 0.0 | 2.0 | 0.0 | 9.0 | 1.0 | 0.0 | 1.0 | 7.0 | 0.0 | 0.0 | 0.0 | 0.0 |
| Propyl 2-(5-isopropyl-5-methyl-4-imidazolin-2-yl)nicotinate | 8.000 | 9.0 | 9.0 | 9.0 | 9.0 | 9.0 | 9.0 | 8.0 | 8.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 7.0 | 9.0 | 9.0 | 9.0 | 8.0 | 9.0 | 9.0 | 8.0 | 9.0 | 9.0 | 7.0 | 9.0 | 9.0 | 9.0 |
| | .125 | 6.0 | 9.0 | 7.0 | 9.0 | 7.0 | 9.0 | 8.0 | 3.0 | 9.0 | 9.0 | 7.0 | 9.0 | 9.0 | 8.0 |
| | .063 | 2.0 | 8.0 | 7.0 | 7.0 | 6.0 | 9.0 | 4.0 | 1.0 | 8.0 | 9.0 | 4.0 | 7.0 | 6.0 | 7.0 |
| Butyl 2-(5-isopropyl-5-methyl-4-oxo-2-imidazolin-2-yl)-nicotinate | 8.000 | 9.0 | 9.0 | 9.0 | 9.0 | 9.0 | 9.0 | 8.0 | 9.0 | 9.0 | | | | | |
| | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .250 | 7.0 | 9.0 | 9.0 | 9.0 | 9.0 | 9.0 | 9.0 | 6.0 | 9.0 | 9.0 | 8.0 | 9.0 | 9.0 | 9.0 |
| | .125 | 3.0 | 9.0 | 8.0 | 9.0 | 8.0 | 9.0 | 9.0 | 1.0 | 9.0 | 8.0 | 8.0 | 9.0 | 7.0 | 7.0 |
| | .063 | 1.0 | 8.0 | 7.0 | 6.0 | 7.0 | 8.0 | 7.0 | 0.0 | 8.0 | 8.0 | 6.0 | 6.0 | 5.0 | 6.0 |
| Methyl 2-(5-isopropyl-5-methyl-4-oxo-2-imidazolin-2-yl)-6-methoxynicotinate | 8.000 | 9.0 | 9.0 | 9.0 | 9.0 | 9.0 | 9.0 | 8.0 | 8.0 | 9.0 | | | | | |
| | .500 | 9.0 | 9.0 | 9.0 | 9.0 | 9.0 | 9.0 | 9.0 | 3.0 | 8.0 | 9.0 | 9.0 | 9.0 | 9.0 | 9.0 |
| | .250 | 9.0 | 9.0 | 8.0 | 9.0 | 9.0 | 8.0 9.0 | 1.0 | 7.0 | 9.0 | 9.0 | 9.0 | 9.0 | 9.0 | |
| | .125 | 9.0 | 9.0 | 8.0 | 9.0 | 6.0 | 9.0 | 9.0 | 0.0 | 6.0 | 8.0 | 9.0 | 9.0 | 8.0 | 9.0 |
| | .063 | 8.0 | 9.0 | 7.0 | 8.0 | 5.0 | 8.0 | 7.0 | 0.0 | 2.0 | 7.0 | 2.0 | 3.0 | 7.0 | 8.0 |
| | .032 | 6.0 | 7.0 | 7.0 | 8.0 | 1.0 | 0.0 | | 0.0 | 2.0 | 6.0 | 1.0 | 1.0 | 3.0 | 2.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| | .016 | 1.0 | 6.0 | 6.0 | 7.0 | 0.0 | 0.0 | 0.0 | 0.0 | 0.0 | 4.0 | 1.0 | 0.0 | 0.0 | 1.0 |
| 2-Decenyl 2-(5-isopropyl-5-methyl-4-oxo-2-imidazolin-2-yl)nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 8.0 | 9.0 | 8.0 | 9.0 | 9.0 | 7.0 | 9.0 | 9.0 | 9.0 | 9.0 | 9.0 | 9.0 |
| | .125 | 7.0 | 9.0 | 8.0 | 9.0 | 8.0 | 9.0 | 9.0 | 2.0 | 9.0 | 9.0 | 7.0 | 9.0 | 9.0 | 7.0 |
| | .063 | 2.0 | 9.0 | 8.0 | 8.0 | 9.0 | 9.0 | 9.0 | 0.0 | 8.0 | 8.0 | 6.0 | 6.0 | 8.0 | 4.0 |
| N,N—diethyl 2-(5-isopropyl-5-methyl-4-oxo-2-imidazolin-2-yl)nicotinamide | 8.000 | 7.0 | 7.0 | 8.0 | 9.0 | 9.0 | 9.0 | 8.0 | 5.0 | 8.0 | | | | | |
| 3-Isopropyl-8-methoxy-3-methyl-5H—imidazo-[1',2':1,2]pyrrolo-[3,4-b]pyridine-2-(3H),5-dione | 8.000 | 9.0 | 9.0 | 9.0 | 9.0 | 9.0 | 9.0 | | 8.0 | 9.0 | | | | | |
| | .500 | 3.0 | 8.0 | 9.0 | 6.0 | 4.0 | 9.0 | 9.0 | 0.0 | 3.0 | 6.0 | 1.0 | 4.0 | 7.0 | 0.0 |
| | .250 | 1.0 | 8.0 | 9.0 | 2.0 | 3.0 | 9.0 | 1.0 | 0.0 | 0.0 | 6.0 | 0.0 | 4.0 | 4.0 | 0.0 |
| | .125 | 0.0 | 6.0 | 3.0 | 0.0 | 0.0 | 8.0 | 0.0 | 0.0 | 0.0 | 2.0 | 0.0 | 0.0 | 3.0 | |
| | .063 | 0.0 | 0.0 | 1.0 | 0.0 | 0.0 | 8.0 | 0.0 | 0.0 | 0.0 | 0.0 | 0.0 | 0.0 | 2.0 | 0.0 |
| | .032 | 0.0 | 0.0 | 0.0 | 0.0 | | 8.0 | 0.0 | 0.0 | 0.0 | 0.0 | 0.0 | 0.0 | 2.0 | |
| | .016 | 0.0 | 0.0 | 0.0 | 0.0 | 0.0 | 2.0 | 0.0 | 0.0 | 0.0 | 0.0 | 0.0 | 0.0 | 1.0 | 0.0 |
| 2-Chloroallyl 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 8.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 6.0 | 9.0 | 9.0 | 9.0 | 9.0 | 9.0 | 9.0 | 3.0 | 9.0 | 9.0 | 9.0 | 9.0 | 9.0 | 8.0 |
| | .032 | 4.0 | 9.0 | 9.0 | 9.0 | 9.0 | 9.0 | 8.0 | 3.0 | 9.0 | 9.0 | 7.0 | 7.0 | 9.0 | 7.0 |
| | .016 | 2.0 | 8.0 | 9.0 | 3.0 | 9.0 | 9.0 | 6.0 | 0.0 | 7.0 | 9.0 | 4.0 | 4.0 | 7.0 | 4.0 |
| Methyl 2-(1-acetyl-4-isopropyl-4-methyl-5-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .063 | 6.0 | 9.0 | 9.0 | 9.0 | 9.0 | 9.0 | 9.0 | 2.0 | 9.0 | 9.0 | 8.0 | 8.0 | 9.0 | 8.0 |
| | .032 | 3.0 | 9.0 | 4.0 | 7.0 | 9.0 | 9.0 | 8.0 | 1.0 | 8.0 | 9.0 | 6.0 | 6.0 | 8.0 | 6.0 |
| | .016 | 2.0 | 9.0 | 3.0 | 1.0 | 3.0 | 9.0 | 8.0 | 0.0 | 7.0 | 8.0 | 2.0 | 3.0 | 6.0 | 3.0 |
| Methyl 2-(5-cyclopropyl-5-methyl-4-oxo-2-imidazolin-2-yl)-nicotinate | .500 | 7.0 | 9.0 | 8.0 | 9.0 | 9.0 | 9.0 | 9.0 | 6.0 | 9.0 | 8.0 | 6.0 | 9.0 | 9.0 | 9.0 |
| | .250 | 3.0 | 9.0 | 8.0 | 7.0 | 9.0 | 9.0 | 9.0 | 1.0 | 9.0 | 8.0 | 3.0 | 7.0 | 9.0 | 9.0 |
| Hexyl 2-(5-isopropyl-5-methyl-4-oxo-2-imidazolin-2-yl)-nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 6.0 | 9.0 | 9.0 | 9.0 | 9.0 | 9.0 | 8.0 |
| | .125 | 7.0 | 9.0 | 8.0 | 9.0 | 8.0 | 9.0 | 9.0 | 3.0 | 8.0 | 9.0 | 8.0 | 8.0 | 9.0 | 8.0 |
| | .063 | 2.0 | 9.0 | 7.0 | 6.0 | 9.0 | 9.0 | 6.0 | 2.0 | 7.0 | 9.0 | 3.0 | 7.0 | 7.0 | 4.0 |
| | .032 | 2.0 | 7.0 | 6.0 | 2.0 | 9.0 | 9.0 | 4.0 | 1.0 | 7.0 | 6.0 | 3.0 | 4.0 | 7.0 | 4.0 |
| | .016 | 1.0 | 2.0 | 2.0 | 0.0 | 9.0 | 2.0 | 4.0 | 0.0 | 3.0 | 4.0 | 2.0 | 2.0 | 7.0 | 2.0 |
| 1-Methyl-2-butenyl 2-(5-isopropyl-5-methyl-4-oxo-2-imidazolin-2-yl)nicotinate | 8.000 | 8.0 | 9.0 | 9.0 | 9.0 | 9.0 | 9.0 | 9.0 | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 4.0 | 9.0 | 9.0 | 9.0 | 9.0 | 9.0 | 8.0 |
| | .063 | 4.0 | 9.0 | 9.0 | 9.0 | 9.0 | 9.0 | 9.0 | 3.0 | 9.0 | 9.0 | 8.0 | 9.0 | 9.0 | 6.0 |
| | .032 | 5.0 | 9.0 | 7.0 | 7.0 | 9.0 | 9.0 | 7.0 | 2.0 | 9.0 | 9.0 | 7.0 | 9.0 | 8.0 | 6.0 |
| | .016 | 1.0 | 8.0 | 3.0 | 4.0 | 6.0 | 9.0 | 7.0 | 1.0 | 8.0 | 8.0 | 2.0 | 4.0 | 4.0 | 4.0 |
| Methyl 2-(4-isopropyl-1,4-dimethyl-5-oxo-2-imidazolin-2-yl)-nicotinate | 5.000 | 9.0 | 9.0 | 9.0 | 9.0 | 9.0 | 9.0 | 9.0 | 9.0 | 8.0 | | | | | |
| | .500 | 6.0 | 9.0 | 7.0 | 9.0 | 4.0 | 9.0 | 9.0 | 0.0 | 9.0 | 8.0 | 2.0 | 4.0 | 9.0 | 8.0 |
| | .250 | 1.0 | 7.0 | 4.0 | 2.0 | 0.0 | 9.0 | 7.0 | 0.0 | 4.0 | 7.0 | 1.0 | 2.0 | 7.0 | 5.0 |
| | .125 | 1.0 | 4.0 | 3.0 | 0.0 | 0.0 | 9.0 | 0.0 | 0.0 | 3.0 | 7.0 | 0.0 | 1.0 | 7.0 | 4.0 |
| | .063 | 0.0 | 1.0 | 1.0 | 0.0 | 0.0 | 8.0 | | 0.0 | 2.0 | 7.0 | 0.0 | 1.0 | 7.0 | 1.0 |

TABLE XII-continued

| PRE-EMERGENCE TESTS - RATES IN KG/HA | | | | | | | | | | | | | | | |
|---|---|---|---|---|---|---|---|---|---|---|---|---|---|---|---|
| | .032 | 0.0 | 1.0 | 0.0 | 0.0 | 0.0 | 7.0 | 0.0 | 0.0 | | 6.0 | 0.0 | 1.0 | 6.0 | 1.0 |
| | .016 | 0.0 | 0.0 | 0.0 | 0.0 | 0.0 | 2.0 | 0.0 | 0.0 | 2.0 | | 0.0 | 0.0 | 3.0 | 1.0 |
| Methyl 2-(4-isopropyl- | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| 4-methyl-5-oxo-1- | .250 | 8.0 | 9.0 | 8.0 | 9.0 | 9.0 | 9.0 | 9.0 | 6.0 | 9.0 | 9.0 | 9.0 | 9.0 | 9.0 | 9.0 |
| pivaloyl-2-imidazolin- | .125 | 8.0 | 9.0 | 8.0 | 9.0 | 8.0 | 9.0 | 9.0 | 6.0 | 9.0 | 9.0 | 9.0 | 9.0 | 9.0 | 9.0 |
| 2-yl)nicotinate | .063 | 6.0 | 9.0 | 8.0 | 9.0 | 8.0 | 9.0 | 9.0 | 1.0 | 9.0 | 9.0 | 3.0 | 7.0 | 9.0 | 9.0 |
| | .032 | 2.0 | 8.0 | 6.0 | 8.0 | 8.0 | 7.0 | 9.0 | 1.0 | 8.0 | 8.0 | 1.0 | 4.0 | 9.0 | 7.0 |
| | .016 | 1.0 | 2.0 | 4.0 | 1.0 | 7.0 | 9.0 | 3.0 | 1.0 | 7.0 | 7.0 | 1.0 | 1.0 | 3.0 | 2.0 |
| Methyl 2-(4-oxo-1,3- | 8.000 | 9.0 | 9.0 | 9.0 | 9.0 | 9.0 | 9.0 | 7.0 | 8.0 | 9.0 | | | | | |
| diazaspiro[4.5]dec-2- | .500 | 8.0 | 9.0 | 7.0 | 6.0 | 6.0 | 9.0 | 3.0 | 0.0 | 9.0 | 9.0 | 2.0 | 4.0 | 6.0 | 9.0 |
| en-2-yl)nicotinate | .250 | 4.0 | 7.0 | 6.0 | 2.0 | 2.0 | 9.0 | 2.0 | 0.0 | 7.0 | 7.0 | 2.0 | 2.0 | 3.0 | 2.0 |
| | .125 | 2.0 | 4.0 | 1.0 | 0.0 | 1.0 | 6.0 | 1.0 | 0.0 | 3.0 | 3.0 | 1.0 | 1.0 | 3.0 | 0.0 |
| | .063 | 0.0 | 1.0 | 0.0 | 0.0 | 0.0 | 2.0 | 0.0 | 0.0 | 1.0 | 1.0 | 1.0 | 1.0 | 2.0 | 0.0 |
| | .032 | 0.0 | 0.0 | 0.0 | 0.0 | | 2.0 | | 0.0 | 1.0 | 0.0 | 0.0 | 1.0 | 2.0 | 0.0 |
| | .016 | 0.0 | 0.0 | 0.0 | 0.0 | | 1.0 | 0.0 | 0.0 | 0.0 | 0.0 | 0.0 | 0.0 | 2.0 | 0.0 |
| 3-Methyl-2-butenyl 2- | 8.000 | 9.0 | 9.0 | 9.0 | 9.0 | 9.0 | 9.0 | 8.0 | 9.0 | 9.0 | | | | | |
| (5-isopropyl-5-methyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin-2- | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| yl)nicotinate | .125 | 8.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 3.0 | 9.0 | 9.0 | 9.0 | 9.0 | 9.0 | 9.0 | 3.0 | 9.0 | 9.0 | 8.0 | 8.0 | 9.0 | 7.0 |
| | .032 | 1.0 | 9.0 | 9.0 | 8.0 | 7.0 | 9.0 | 3.0 | 0.0 | 8.0 | 8.0 6.0 | 6.0 | 9.0 | 7.0 | |
| | .016 | 0.0 | 9.0 | 4.0 | 6.0 | 7.0 | 7.0 | 1.0 | 0.0 | 8.0 | 8.0 | 4.0 | 3.0 | 4.0 | 4.0 |
| Benzyl 2-(4-oxo-1,3- | 8.000 | 9.0 | 9.0 | 9.0 | 9.0 | 9.0 | 9.0 | 8.0 | 9.0 | 9.0 | | | | | |
| diazaspiro[4.5]dec-<br>2-en-2-yl)nicotinate | .500 | 0.0 | 0.0 | 6.0 | 0.0 | 8.0 | 9.0 | 3.0 | 0.0 | 3.0 | 0.0 | 0.0 | 0.0 | 1.0 | 0.0 |
| 2-(5-Isopropyl-5- | 8.000 | 9.0 | 9.0 | 9.0 | 9.0 | 9.0 | 9.0 | 8.0 | 9.0 | 9.0 | | | | | |
| methyl-4-oxo-2- | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| imidazolin-2-yl)- | .250 | 7.0 | 9.0 | 9.0 | 9.0 | 9.0 | 9.0 | 9.0 | 8.0 | 9.0 | 9.0 | 9.0 | 9.0 | 9.0 | 8.0 |
| nicotinohydroxamic | .125 | 7.0 | 9.0 | 9.0 | 9.0 | 9.0 | 9.0 | 9.0 | | 9.0 | 9.0 | 7.0 | 9.0 | 9.0 | 8.0 |
| acid | .063 | 2.0 | 9.0 | 9.0 | 7.0 | 8.0 | 9.0 | 7.0 | | 8.0 | 8.0 | 7.0 | 6.0 | 9.0 | 4.0 |
| Benzyl 2-(5-isopropyl- | 8.000 | 9.0 | 9.0 | 9.0 | 9.0 | 9.0 | 9.0 | 8.0 | 9.0 | 9.0 | | | | | |
| 5-methyl-4-oxo-2- | .500 | 3.0 | 9.0 | 7.0 | 9.0 | 7.0 | 9.0 | 8.0 | 0.0 | 9.0 | 9.0 | 8.0 | 6.0 | 8.0 | 7.0 |
| imidazolin-2-yl)<br>nicotinate | .250 | 1.0 | 4.0 | 6.0 | 7.0 | 4.0 | 9.0 | 7.0 | 0.0 | 8.0 | 8.0 | 3.0 | 4.0 | 6.0 | 5.0 |
| 6-methoxy-2-(5- | 5.000 | 9.0 | 9.0 | 9.0 | 9.0 | 9.0 | 9.0 | 9.0 | 9.0 | 9.0 | | | | | |
| isopropyl-5-methyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin- | .250 | 8.0 | 9.0 | 9.0 | 9.0 | 9.0 | 9.0 | 9.0 | 7.0 | 9.0 | 9.0 | 9.0 | 9.0 | 9.0 | 9.0 |
| 2-yl)nicotinic acid | .125 | 7.0 | 9.0 | 9.0 | 9.0 | 9.0 | 9.0 | 9.0 | 7.0 | 8.0 | 9.0 | 9.0 | 8.0 | 9.0 | 9.0 |
| | .063 | 3.0 | 9.0 | 9.0 | 9.0 | 8.0 | 9.0 | 9.0 | 1.0 | 4.0 | 7.0 | 3.0 | 7.0 | 9.0 | 3.0 |
| 2-(4-oxo-1,3- | .500 | 6.0 | 8.0 | 8.0 | 6.0 | 7.0 | 9.0 | 8.0 | 7.0 | 9.0 | 8.5 | 4.5 | 8.5 | 9.0 | 1.0 |
| diazaspiro[4.5]-<br>dec-2-en-2-yl)<br>nicotinic acid | .250 | 1.0 | 7.0 | 2.0 | 3.0 | 1.0 | 9.0 | 3.0 | 3.0 | 9.0 | 5.0 | 1.5 | 7.5 | 8.0 | 0.0 |
| α-Methylbenzylammonium | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-(5-isopropyl-5-methyl- | .250 | 9.0 | 9.0 | 9.0 | 9.0 | 9.0 | 9.0 | 9.0 | 6.0 | 9.0 | 9.0 | 9.0 | 9.0 | 9.0 | 9.0 |
| 4-oxo-2-imidazolin-2- | .125 | 8.0 | 9.0 | 9.0 | 9.0 | 9.0 | 9.0 | 9.0 | 6.0 | 9.0 | 9.0 | 9.0 | 9.0 | 9.0 | 7.0 |
| yl)nicotinate | .063 | 7.0 | 9.0 | 8.0 | 9.0 | 9.0 | 9.0 | 9.0 | 0.0 | 9.0 | 9.0 | 9.0 | 9.0 | 9.0 | 6.0 |
| | .032 | 3.0 | 9.0 | 7.0 | 8.0 | 9.0 | 9.0 | 7.0 | 0.0 | 9.0 | 9.0 | 9.0 | 9.0 | 8.0 | 6.0 |
| | .016 | 2.0 | 4.0 | 4.0 | 4.0 | 9.0 | 9.0 | 6.0 | 0.0 | 8.0 | 7.0 | 5.0 | 6.0 | 5.0 | 3.0 |
| α-Cyclopropyl-5,7- | .500 | 9.0 | 9.0 | 9.0 | 9.0 | 8.0 | 9.0 | 9.0 | 9.0 | 9.0 | 9.0 | 9.0 | 9.0 | 9.0 | 9.0 |
| dihydro-α-methyl-5,7- | .250 | 6.0 | 9.0 | 9.0 | 9.0 | 8.0 | 9.0 | 9.0 | 6.0 | 9.0 | 9.0 | 9.0 | 9.0 | 9.0 | 9.0 |
| dioxo-6H—pyrrolo[3,4-b]- | .125 | 3.0 | 6.0 | 6.0 | 7.0 | 9.0 | 8.0 | 8.0 | 2.0 | 9.0 | 9.0 | 9.0 | 7.0 | 9.0 | 7.0 |

TABLE XII-continued

| | | PRE-EMERGENCE TESTS - RATES IN KG/HA | | | | | | | | | | | | | |
|---|---|---|---|---|---|---|---|---|---|---|---|---|---|---|---|
| pyridine-6-acetamide | .063 | 1.0 | 3.0 | 6.0 | 3.0 | 0.0 | 9.0 | 4.0 | 0.0 | 7.0 | 7.0 | 4.0 | 4.0 | 3.0 | |
| 2-(5-Cyclopropyl-5-methyl-4-oxo-2-imidazolin-2-yl)-nicotinic acid | 5.000 | 9.0 | 9.0 | 9.0 | 9.0 | 9.0 | 9.0 | 8.0 | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 7.0 | 9.0 | 9.0 | 9.0 | 9.0 | 9.0 | 9.0 | 7.0 | 9.0 | 9.0 | 9.0 | 9.0 | 9.0 | 9.0 |
| | .063 | 3.0 | 9.0 | 9.0 | 9.0 | 8.0 | 9.0 | 9.0 | 3.0 | 9.0 | 9.0 | 9.0 | 9.0 | 8.0 | 9.0 |
| | .032 | 1.0 | 9.0 | 7.0 | 8.0 | 6.0 | 9.0 | 6.0 | 2.0 | 9.0 | 9.0 | 7.0 | 6.0 | 8.0 | 9.0 |
| | .016 | 1.0 | 6.0 | 3.0 | 6.0 | 3.0 | 9.0 | 2.0 | 1.0 | 8.0 | 7.0 | 2.0 | 2.0 | 3.0 | 4.0 |
| 1,1-Dimethyl-2-propynyl 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 8.0 |
| | .250 | 9.0 | 9.0 | 9.0 | 9.0 | 7.0 | 9.0 | 9.0 | 8.0 | 9.0 | 9.0 | 9.0 | 9.0 | 9.0 | 8.0 |
| | .125 | 7.0 | 9.0 | 7.0 | 9.0 | 7.0 | 9.0 | 9.0 | 8.0 | 9.0 | 9.0 | 9.0 | 9.0 | 9.0 | 8.0 |
| | .063 | 5.0 | 9.0 | 6.0 | 9.0 | 6.0 | 9.0 | 9.0 | 3.0 | 9.0 | 8.0 | 7.0 | 9.0 | 9.0 | 9.0 |
| | .032 | 1.0 | 9.0 | 4.0 | 7.0 | 6.0 | 9.0 | 7.0 | 0.0 | 8.0 | 8.0 | 3.0 | 8.0 | 7.0 | 5.0 |
| | .016 | 0.0 | 7.0 | 1.0 | 1.0 | 1.0 | 9.0 | 7.0 | 0.0 | 7.0 | 7.0 | 2.0 | 5.0 | 3.0 | 1.0 |
| 2-trimethylammoniumethyl 2-(5-isopropyl-5-methyl-4-oxo-2-imidazolin-2-yl)-nicotinate iodide | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 7.0 | 9.0 | 9.0 | 9.0 | 9.0 | 9.0 | 8.0 |
| | .125 | 8.0 | 9.0 | 9.0 | 9.0 | 9.0 | 9.0 | 9.0 | 6.0 | 9.0 | 9.0 | 9.0 | 9.0 | 9.0 | 8.0 |
| | .063 | 7.0 | 9.0 | 9.0 | 9.0 | 8.0 | 9.0 | 9.0 | 1.0 | 9.0 | 9.0 | 9.0 | 8.0 | 9.0 | 8.0 |
| N—(2-Hydroxyethyl)-2-(5-isopropyl-5-methyl-4-oxo-2-imidazolin-2-yl)nicotinamide | 8.000 | 8.0 | 9.0 | 9.0 | 9.0 | 9.0 | 9.0 | 8.0 | 8.0 | 8.0 | | | | | |
| | .500 | 4.0 | 7.0 | 9.0 | 9.0 | 9.0 | 9.0 | 8.0 | 0.0 | 7.0 | 9.0 | 7.0 | 6.0 | 8.0 | 6.0 |
| | .250 | 1.0 | 3.0 | 4.0 | 7.0 | 9.0 | 8.0 | 6.0 | 0.0 | 3.0 | 4.0 | 5.0 | 1.0 | 6.0 | 3.0 |
| | .125 | 0.0 | 2.0 | 3.0 | 3.0 | 9.0 | 7.0 | 5.0 | 0.0 | 3.0 | 3.0 | 2.0 | 1.0 | 6.0 | 3.0 |
| | .063 | 0.0 | 0.0 | 1.0 | 0.0 | 4.0 | 2.0 | 0.0 | 0.0 | 2.0 | 1.0 | 1.0 | 0.0 | 4.0 | 1.0 |
| | .032 | 0.0 | 0.0 | 0.0 | 0.0 | 0.0 | 0.0 | 0.0 | 0.0 | 1.0 | 1.0 | 1.0 | 0.0 | 3.0 | 1.0 |
| | .016 | 0.0 | 0.0 | 0.0 | 0.0 | 0.0 | 0.0 | 0.0 | 0.0 | 0.0 | 1.0 | 0.0 | 0.0 | 3.0 | 1.0 |
| Ammonium 2-(5-Isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 8.0 |
| | .063 | 9.0 | 9.0 | 9.0 | 9.0 | 9.0 | 9.0 | 9.0 | 2.0 | 9.0 | 9.0 | 9.0 | 8.0 | 9.0 | 8.0 |
| | .032 | 4.0 | 9.0 | 7.0 | 8.0 | 9.0 | 9.0 | 7.0 | 0.0 | 8.0 | 9.0 | 9.0 | 7.0 | 9.0 | 8.0 |
| | .016 | 0.0 | 9.0 | 2.0 | 7.0 | 9.0 | 9.0 | 0.0 | 0.0 | 8.0 | 8.0 | 7.0 | 4.0 | 6.0 | 3.0 |
| Methyl 2-(4-isopropyl-1-lauroyl-4-methyl-5-oxo-2-imidazolin-2-yl)-nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 8.0 | 9.0 | 7.0 | 9.0 | 9.0 | 8.0 | 9.0 | 9.0 | 9.0 | 9.0 | 8.0 | 9.0 |
| | .125 | 8.0 | 9.0 | 6.0 | 9.0 | 7.0 | 9.0 | 9.0 | 3.0 | 9.0 | 9.0 | 9.0 | 9.0 | 8.0 | 9.0 |
| | .063 | 3.0 | 9.0 | 4.0 | 9.0 | 3.0 | 7.0 | 2.0 | 0.0 | 9.0 | 8.0 | 6.0 | 7.0 | 8.0 | 9.0 |
| | .032 | 0.0 | 4.0 | 0.0 | 6.0 | 1.0 | 7.0 | 0.0 | 0.0 | 7.0 | 7.0 | 3.0 | 1.0 | 6.0 | 3.0 |
| 1,1-Dimethylallyl 2-(5-isopropyl-5-methyl-4-oxo-2-imidazolin-2-yl)-nicotinate | 8.000 | 9.0 | 9.0 | 9.0 | 9.0 | 9.0 | 9.0 | 8.0 | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 2.0 | 9.0 | 9.0 | 9.0 | 9.0 | 9.0 | 9.0 | 3.0 | 9.0 | 9.0 | 9.0 | 9.0 | 9.0 | 9.0 |
| | .032 | 2.0 | 7.0 | 8.0 | 8.0 | 3.0 | 9.0 | 8.0 | 1.0 | 8.0 | 8.0 | 9.0 | 7.0 | 7.0 | 6.0 |
| | .016 | 0.0 | 1.0 | 3.0 | 4.0 | 2.0 | 9.0 | 2.0 | | 3.0 | 8.0 | 8.0 | 6.0 | 7.0 | 3.0 |
| 2-Propynyl 2-(5-cyclopropyl-5-methyl-4-oxo-2-imidazolin-2-yl)nicotinate | .250 | 6.0 | 9.0 | 7.0 | 7.0 | 9.0 | 9.0 | 9.0 | 1.0 | 8.0 | 9.0 | 6.0 | 8.0 | 9.0 | 9.0 |
| | .125 | 4.0 | 3.0 | 8.0 | 4.0 | 9.0 | 9.0 | 7.0 | 1.0 | 8.0 | 6.0 | 4.0 | 7.0 | 4.0 | 9.0 |
| | .063 | 0.0 | 1.0 | 0.0 | 1.0 | 3.0 | 9.0 | | 0.0 | 4.0 | 4.0 | 2.0 | 3.0 | 2.0 | |
| | .032 | 0.0 | 0.0 | 0.0 | 1.0 | 0.0 | 9.0 | 0.0 | 0.0 | 3.0 | 3.0 | 1.0 | 0.0 | 2.0 | |
| | .016 | 0.0 | 0.0 | 0.0 | 1.0 | 0.0 | 7.0 | 0.0 | 0.0 | 0.0 | 2.0 | 1.0 | 0.0 | 1.0 | |
| 2-Propynyl 2-(4-oxo-1,3-diazaspiro[4.5]-dec-2-en-2-yl)nicotinate | 5.000 | 8.0 | 9.0 | 8.0 | 8.0 | 9.0 | 9.0 | 8.0 | 8.0 | 8.0 | | | | | |
| | .500 | 9.0 | 4.0 | 8.0 | 7.0 | 8.0 | 9.0 | 8.0 | 0.0 | 7.0 | 7.0 | 1.0 | 6.0 | 6.0 | 9.0 |
| | .250 | 1.0 | 2.0 | 3.0 | 7.0 | 2.0 | 9.0 | 9.0 | 0.0 | 6.0 | 2.0 | 0.0 | 1.0 | 8.0 | 0.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| N—(2-Chloroethyl)-2-(5-isopropyl-5-methyl-4-oxo-2-imidazolin-2-yl)nicotinamide | .500 | 9.0 | 9.0 | 9.0 | 9.0 | 9.0 | 9.0 | 9.0 | 9.0 | 9.0 | 9.0 | 9.0 | 9.0 | 9.0 | 8.0 |
| | .250 | 6.0 | 9.0 | 9.0 | 9.0 | 9.0 | 9.0 | 9.0 | 7.0 | 9.0 | 9.0 | 9.0 | 9.0 | 9.0 | 7.0 |
| | .125 | 4.0 | 7.0 | 9.0 | 9.0 | 7.0 | 9.0 | 9.0 | | 9.0 | 9.0 | 9.0 | 9.0 | 7.0 | 6.0 |
| | .063 | 2.0 | 4.0 | 7.0 | 9.0 | 7.0 | 9.0 | 7.0 | 6.0 | 8.0 | 9.0 | 8.0 | 8.0 | 9.0 | 5.0 |
| | .032 | 1.0 | 3.0 | 4.0 | 8.0 | 6.0 | 9.0 | 5.0 | | 7.0 | 9.0 | 7.0 | 7.0 | 6.0 | 5.0 |
| | .016 | 0.0 | 2.0 | 1.0 | 7.0 | 4.0 | 3.0 | 4.0 | 2.0 | 2.0 | 9.0 | 6.0 | 6.0 | 5.0 | 1.0 |
| p-Methoxybenzyl 2-(5-isopropyl-5-methyl-4-oxo-2-imidazolin-2-yl)nicotinate | 8.000 | 9.0 | 9.0 | 9.0 | 8.0 | 9.0 | 9.0 | 8.0 | 8.0 | 7.0 | | | | | |
| | .500 | 9.0 | 9.0 | 9.0 | 9.0 | 8.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 8.0 | 9.0 | 9.0 | 7.0 | 9.0 | 9.0 | 9.0 | 9.0 | 9.0 | 8.0 |
| | .125 | 9.0 | 9.0 | 9.0 | 9.0 | 7.0 | 9.0 | 8.0 | 2.0 | 9.0 | 9.0 | 9.0 | 8.0 | 9.0 | 7.0 |
| | .063 | 3.0 | 7.0 | 6.0 | 8.0 | 7.0 | 9.0 | 8.0 | 2.0 | 9.0 | 9.0 | 6.0 | 6.0 | 9.0 | 6.0 |
| | .032 | 0.0 | 4.0 | 4.0 | 3.0 | 3.0 | 9.0 | 8.0 | 0.0 | 8.0 | 7.0 | 2.0 | 6.0 | 6.0 | 1.0 |
| | .016 | 0.0 | 2.0 | 1.0 | 1.0 | 0.0 | 9.0 | 0.0 | 0.0 | 6.0 | 8.0 | 2.0 | 2.0 | 3.0 | |
| Barium 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 8.0 | 9.0 | 8.0 | 9.0 | 9.0 | 9.0 | 9.0 | 8.0 | 9.0 | 9.0 | 9.0 | 9.0 | 9.0 | 8.0 |
| | .063 | 8.0 | 9.0 | 9.0 | 9.0 | 9.0 | 9.0 | 9.0 | 3.0 | 9.0 | 9.0 | 9.0 | 9.0 | 9.0 | 7.0 |
| | .032 | 1.0 | 9.0 | 8.0 | 9.0 | 9.0 | 9.0 | 9.0 | 0.0 | 8.0 | 9.0 | 9.0 | 9.0 | 9.0 | 7.0 |
| | .016 | 0.0 | 6.0 | 7.0 | 7.0 | 9.0 | 9.0 | 9.0 | 0.0 | 8.0 | 8.0 | 7.0 | 4.0 | 5.0 | |
| Cupric 2-(5-isopropyl-5-methyl-4-oxo-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 4.0 | 9.0 | 9.0 | 9.0 | 9.0 | 9.0 | 8.0 | 4.0 | 9.0 | 9.0 | 9.0 | 9.0 | 9.0 | 9.0 |
| | .032 | 2.0 | 9.0 | 8.0 | 9.0 | 9.0 | 9.0 | 8.0 | 0.0 | 9.0 | 9.0 | 9.0 | 9.0 | 9.0 | 7.0 |
| | .016 | 1.0 | 6.0 | 6.0 | 5.0 | 9.0 | 9.0 | 3.0 | 0.0 | 9.0 | 8.0 | 6.0 | 3.0 | 5.0 | 4.0 |
| Potassium 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 6.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 6.0 | 9.0 | 9.0 | 9.0 | 9.0 | 9.0 | 9.0 | 3.0 | 9.0 | 9.0 | 9.0 | 8.0 | 9.0 | 9.0 |
| | .032 | 2.0 | 9.0 | 9.0 | 9.0 | 9.0 | 9.0 | 9.0 | 0.0 | 9.0 | 9.0 | 9.0 | 9.0 | 9.0 | 9.0 |
| | .016 | 1.0 | 9.0 | 6.0 | 6.0 | 8.0 | 8.0 | 3.0 | 0.0 | 8.0 | 9.0 | 9.0 | 5.0 | 9.0 | 4.0 |
| Lithium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 6.0 | 9.0 | 9.0 | 9.0 | 9.0 | 9.0 | 9.0 |
| Magnesium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 8.0 | 9.0 | 9.0 | 9.0 | 8.0 | 9.0 | 9.0 | 9.0 | 8.0 | 9.0 | 8.0 |
| | .063 | 9.0 | 9.0 | 9.0 | 9.0 | 9.0 | 9.0 | 9.0 | 1.0 | 9.0 | 9.0 | 9.0 | 8.0 | 9.0 | 7.0 |
| | .032 | 2.0 | 9.0 | 9.0 | 9.0 | 9.0 | 9.0 | 9.0 | 0.0 | 9.0 | 9.0 | 9.0 | 8.0 | 7.0 | 4.0 |
| | .016 | 0.0 | 9.0 | 3.0 | 6.0 | 8.0 | 9.0 | 4.0 | 0.0 | 7.0 | 7.0 | 7.0 | 5.0 | 6.0 | 4.0 |
| Piperidinium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .125 | 7.0 | 9.0 | 9.0 | 9.0 | 9.0 | 9.0 | 9.0 | 7.0 | 9.0 | 9.0 | 9.0 | 9.0 | 9.0 | 9.0 |
| | .063 | 1.0 | 9.0 | 9.0 | 9.0 | 9.0 | 9.0 | 9.0 | 0.0 | 9.0 | 9.0 | 9.0 | 8.0 | 9.0 | 7.0 |
| | .032 | 1.0 | 9.0 | 9.0 | 8.0 | 9.0 | 9.0 | 8.0 | 0.0 | 9.0 | 9.0 | 9.0 | 9.0 | 9.0 | 7.0 |
| | .016 | 0.0 | 7.0 | 2.0 | 3.0 | 9.0 | 9.0 | 4.0 | 0.0 | 9.0 | 9.0 | 9.0 | 2.0 | 4.0 | 7.0 |
| p-Chlorobenzyl 2-(5-isopropyl-5-methyl-4-oxo-2-imidazolin-2-yl)nicotinate | 8.000 | 9.0 | 9.0 | 9.0 | 8.0 | 9.0 | 9.0 | 9.0 | 8.0 | 9.0 | | | | | |
| | .500 | 9.0 | 9.0 | 9.0 | 9.0 | 8.0 | 9.0 | 9.0 | 7.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 7.0 | 9.0 | 9.0 | 9.0 | 8.0 | 9.0 | 9.0 |
| | .125 | 9.0 | 8.0 | 9.0 | 8.0 | 8.0 | 9.0 | 7.0 | 4.0 | 9.0 | 8.0 | 4.0 | 6.0 | 9.0 | 6.0 |
| | .063 | 1.0 | 6.0 | 7.0 | 7.0 | 7.0 | 9.0 | 4.0 | 0.0 | 8.0 | 7.0 | 4.0 | 4.0 | 7.0 | |
| | .032 | 1.0 | 4.0 | 8.0 | 4.0 | 7.0 | 9.0 | 7.0 | 0.0 | 4.0 | 4.0 | 1.0 | 1.0 | 6.0 | |

TABLE XII-continued

| | PRE-EMERGENCE TESTS - RATES IN KG/HA | | | | | | | | | | | | | | |
|---|---|---|---|---|---|---|---|---|---|---|---|---|---|---|---|
| | .016 | 0.0 | 1.0 | 0.0 | 1.0 | 2.0 | 9.0 | 0.0 | 0.0 | 4.0 | 6.0 | 1.0 | 0.0 | 4.0 | |
| p-Nitrobenzyl 2-(5-isopropyl-5-methyl-4-oxo-2-imidazolin-2-yl)nicotinate | 8.000 | 9.0 | 9.0 | 9.0 | 8.0 | 9.0 | 9.0 | 8.0 | 8.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 6.0 | 9.0 | 9.0 | 9.0 | 8.0 | 9.0 | 9.0 |
| | .063 | 3.0 | 7.0 | 7.0 | 8.0 | 9.0 | 9.0 | 7.0 | 1.0 | 9.0 | 9.0 | 3.0 | 7.0 | 9.0 | 8.0 |
| | .032 | 1.0 | 6.0 | 8.0 | 6.0 | 7.0 | 9.0 | 7.0 | 0.0 | 4.0 | 8.0 | 2.0 | 6.0 | 8.0 | 3.0 |
| | .016 | 0.0 | 3.0 | 0.0 | 4.0 | 3.0 | 9.0 | 3.0 | 0.0 | 4.0 | 8.0 | 2.0 | 1.0 | 6.0 | 2.0 |
| Benzyltrimethylammonium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 7.0 | 8.0 | 8.0 | 9.0 | 9.0 | 9.0 | 9.0 | 6.0 | 9.0 | 9.0 | 9.0 | 9.0 | 9.0 | 8.0 |
| | .063 | 9.0 | 7.0 | 9.0 | 8.0 | 9.0 | 9.0 | 9.0 | | 8.0 | 9.0 | 9.0 | 8.0 | 7.0 | 6.0 |
| | .032 | 0.0 | 3.0 | 5.0 | 5.0 | 9.0 | 9.0 | 8.0 | 0.0 | 7.0 | 8.0 | 7.0 | 6.0 | 6.0 | 6.0 |
| | .016 | 0.0 | 1.0 | 4.0 | 4.0 | 7.0 | 9.0 | 4.0 | 0.0 | 6.0 | 8.0 | 4.0 | 2.0 | 6.0 | 4.0 |
| Omega-Aminohexylammonium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 5.0 | 9.0 | 9.0 | 9.0 | 9.0 | 9.0 | 9.0 | 5.0 | 9.0 | 9.0 | 9.0 | 9.0 | 9.0 | 9.0 |
| | .063 | 3.0 | 9.0 | 8.0 | 9.0 | 9.0 | 9.0 | 9.0 | 0.0 | 9.0 | 9.0 | 7.0 | 9.0 | 9.0 | 7.0 |
| Tallowammonium 2-(5-isopropyl-5-methyl-4-oxo-2-imidazolin-2-yl)nicotinate | 8.000 | 9.0 | 9.0 | 9.0 | 9.0 | 9.0 | 9.0 | | 9.0 | 9.0 | | | | | |
| | .500 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 7.0 | 8.0 | 9.0 | 9.0 | 9.0 | 9.0 | 9.0 | 9.0 | 9.0 | 9.0 | 9.0 | 9.0 | 8.0 | 9.0 |
| | .063 | 9.0 | 9.0 | 9.0 | 9.0 | 9.0 | 9.0 | 9.0 | 9.0 | 9.0 | 9.0 | 9.0 | 9.0 | 9.0 | 8.0 |
| | .032 | 2.0 | 6.0 | 7.0 | 7.0 | 8.0 | 9.0 | 9.0 | 0.0 | 9.0 | 9.0 | 9.0 | 9.0 | 7.0 | 7.0 |
| | .016 | 0.0 | 2.0 | 0.0 | 6.0 | 6.0 | 9.0 | 6.0 | | 5.0 | 7.0 | 9.0 | 3.0 | 5.0 | 2.0 |
| Carbomethoxymethyl 2-(5-isopropyl-5-methyl-4-oxo-2-imidazolin-2-yl)-nicotinate | 8.000 | 9.0 | 9.0 | 8.0 | 8.0 | 9.0 | 9.0 | 9.0 | 8.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 6.0 | 9.0 | 9.0 | 9.0 | 9.0 | 9.0 | 8.0 |
| | .063 | 6.0 | 9.0 | 7.0 | 9.0 | 8.0 | 9.0 | 9.0 | 3.0 | 7.0 | 9.0 | 9.0 | 9.0 | 9.0 | 6.0 |
| | .032 | 1.0 | 3.0 | 8.0 | 6.0 | 7.0 | 9.0 | 8.0 | 0.0 | 7.0 | 7.0 | 3.0 | 4.0 | 7.0 | 4.0 |
| | .016 | 1.0 | 3.0 | 1.0 | 2.0 | 4.0 | 9.0 | 2.0 | 0.0 | 3.0 | 7.0 | 2.0 | 3.0 | 7.0 | 2.0 |
| Dodecylammonium 2-(5-isopropyl-5-methyl-4-oxo-2-imidazolin-2-yl)nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 4.0 | 7.0 | 9.0 | 9.0 | 9.0 | 9.0 | 9.0 | 9.0 | 9.0 | 9.0 | 9.0 | 8.0 | 9.0 | 9.0 |
| | .063 | 4.0 | 7.0 | 6.0 | 9.0 | 9.0 | 9.0 | 9.0 | | 9.0 | 9.0 | 9.0 | 8.0 | 9.0 | 8.0 |
| | .032 | 1.0 | 7.0 | 1.0 | 7.0 | 8.0 | 9.0 | 8.0 | | 9.0 | 9.0 | 7.0 | 8.0 | 7.0 | 6.0 |
| | .016 | 0.0 | 0.0 | 0.0 | 2.0 | 8.0 | 9.0 | 2.0 | | 9.0 | 7.0 | 3.0 | 3.0 | 4.0 | 3.0 |
| 1,1,3,3-Tetramethylbutylammonium 2-(5-isopropyl-5-methyl-4-oxo-2-imidazolin-2-yl)nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 1.0 | 8.0 | 9.0 | 9.0 | 9.0 | 9.0 | 9.0 | 9.0 | 9.0 | 9.0 | 9.0 | 9.0 | 8.0 | 9.0 |
| | .063 | 1.0 | 7.0 | 9.0 | 9.0 | 9.0 | 9.0 | 9.0 | | 9.0 | 9.0 | 9.0 | 8.0 | 8.0 | 7.0 |
| | .032 | 1.0 | 4.0 | 7.0 | 8.0 | 8.0 | 9.0 | 9.0 | | 9.0 | 9.0 | 9.0 | 8.0 | 8.0 | |
| | .016 | 0.0 | 2.0 | 2.0 | 6.0 | 7.0 | 9.0 | 7.0 | | 5.0 | 9.0 | 7.0 | 4.0 | 6.0 | 3.0 |
| Dibutylammonium 2-(5-isopropyl-5-methyl-4-oxo-2-imidazolin-2-yl)nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 7.0 | 9.0 | 9.0 | 9.0 | 9.0 | 9.0 | 9.0 | 9.0 | 9.0 | 9.0 | 9.0 | 9.0 | 7.0 |
| | .063 | 4.0 | 8.0 | 8.0 | 9.0 | 9.0 | 9.0 | 9.0 | | 9.0 | 9.0 | 9.0 | 8.0 | 9.0 | 7.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| | .032 | 0.0 | 3.0 | 7.0 | 6.0 | 9.0 | 9.0 | 8.0 | | 9.0 | 9.0 | 9.0 | 3.0 | 7.0 | |
| | .016 | 0.0 | 1.0 | 1.0 | 4.0 | 4.0 | 9.0 | 4.0 | | 4.0 | 7.0 | 6.0 | 1.0 | 4.0 | 1.0 |
| 2-(Methylamino)ethyl 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| 1-Methylpyrrolidinium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 2.0 | 9.0 | 9.0 | 9.0 | 8.0 | 9.0 | 7.0 |
| | .032 | 3.0 | 8.0 | 9.0 | 9.0 | 9.0 | 9.0 | 9.0 | 2.0 | 9.0 | 9.0 | 9.0 | 8.0 | 9.0 | 9.0 |
| | .016 | 0.0 | 6.0 | 8.0 | 7.0 | 9.0 | 9.0 | 8.0 | 0.0 | 4.0 | 9.0 | 7.0 | | 8.0 | 3.0 |
| Octylammonium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .063 | 4.0 | 9.0 | 9.0 | 9.0 | 9.0 | 9.0 | 9.0 | 2.0 | 9.0 | 9.0 | 9.0 | 8.0 | 9.0 | 9.0 |
| | .032 | 2.0 | 8.0 | 8.0 | 9.0 | 9.0 | 9.0 | 9.0 | | 9.0 | 9.0 | 9.0 | 8.0 | 9.0 | 9.0 |
| | .016 | 0.0 | 6.0 | 9.0 | 8.0 | 9.0 | 9.0 | 6.0 | | 8.0 | 9.0 | 6.0 | 4.0 | 8.0 | 9.0 |
| Benzylammonium 2-(5-isopropyl-5-methyl-4-oxo-2-imidazolin-2-yl)nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 7.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 7.0 | 9.0 | 9.0 | 9.0 | 9.0 | 9.0 | 9.0 | | 9.0 | 9.0 | 9.0 | 8.0 | 9.0 | 7.0 |
| | .032 | 2.0 | 4.0 | 6.0 | 9.0 | 7.0 | 9.0 | 4.0 | | 7.0 | 7.0 | 9.0 | 5.0 | 8.0 | 5.0 |
| | .016 | 0.0 | 3.0 | 3.0 | 5.0 | 7.0 | 9.0 | 2.0 | | 3.0 | 7.0 | 4.0 | 2.0 | 5.0 | 3.0 |
| Cyclohexlammonium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 4.0 | 8.0 | 9.0 | 9.0 | 9.0 | 9.0 | 9.0 | 1.0 | 9.0 | 9.0 | 9.0 | 9.0 | 9.0 | 9.0 |
| Morpholinium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .063 | 8.0 | 9.0 | 9.0 | 9.0 | 9.0 | 9.0 | 9.0 | 6.0 | 9.0 | 9.0 | 9.0 | 9.0 | 9.0 | 9.0 |
| | .032 | 4.0 | 9.0 | 9.0 | 8.0 | 9.0 | 9.0 | 9.0 | 2.0 | 9.0 | 9.0 | 9.0 | 8.0 | 9.0 | 9.0 |
| 4-Phenylbutylammonium 2-(5-isopropyl-methyl-4-oxo-2-imidazolin-2-yl)nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 9.0 | 9.0 | 9.0 | 9.0 | 9.0 | 9.0 | 8.0 |
| | .125 | 7.0 | 8.0 | 9.0 | 9.0 | 9.0 | 9.0 | 9.0 | 4.0 | 9.0 | 9.0 | 9.0 | 9.0 | 9.0 | 8.0 |
| | .063 | 4.0 | 8.0 | 9.0 | 9.0 | 9.0 | 9.0 | 9.0 | 3.0 | 9.0 | 9.0 | 9.0 | 9.0 | 9.0 | 8.0 |
| | .032 | 1.0 | 4.0 | 7.0 | 7.0 | 7.0 | 9.0 | 9.0 | 0.0 | 9.0 | 8.0 | 9.0 | 6.0 | 7.0 | 6.0 |
| | 0.16 | 0.0 | 2.0 | 4.0 | 2.0 | 3.0 | 9.0 | 4.0 | 0.0 | 4.0 | 8.0 | 4.0 | 2.0 | 3.0 | 3.0 |
| Phenethylammonium 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 6.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 6.0 | 9.0 | 9.0 | 8.0 | 9.0 | 9.0 | 9.0 |
| | .032 | 3.0 | 9.0 | 8.0 | 9.0 | 7.0 | 9.0 | 9.0 | 4.0 | 9.0 | 9.0 | 9.0 | 8.0 | 9.0 | 9.0 |
| | .016 | 1.0 | 7.0 | 6.0 | 3.0 | 9.0 | 9.0 | 3.0 | 4.0 | 6.0 | 7.0 | 6.0 | 3.0 | 7.0 | 9.0 |
| Dimethoxymethyl-ammonium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 5.0 | 9.0 | 9.0 | 9.0 | 8.0 | 9.0 | 9.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| 2,2'-Diethoxydiethyl-ammonium 2-(5-isopropyl-5-methyl-4-oxo-2-imidazolin-2-yl)-nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 8.0 | 9.0 | 9.0 | 9.0 | 9.0 | 9.0 | 9.0 |
| | .032 | 4.0 | 9.0 | 9.0 | 9.0 | 9.0 | 9.0 | 9.0 | 1.0 | 9.0 | 9.0 | 9.0 | 8.0 | 9.0 | 9.0 |
| | .016 | 1.0 | 7.0 | 8.0 | 7.0 | 9.0 | 9.0 | 8.0 | 1.0 | 7.0 | 8.0 | 7.0 | 3.0 | 8.0 | 9.0 |
| 3-Methoxypropylammonium 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 6.0 | 9.0 | 9.0 | 9.0 | 9.0 | 9.0 | 9.0 | 3.0 | 9.0 | 9.0 | 7.0 | 8.0 | 9.0 | 9.0 |
| | .032 | 5.0 | 9.0 | 5.0 | 8.0 | 9.0 | 9.0 | 8.0 | | 9.0 | 9.0 | 4.0 | 8.0 | 9.0 | 7.0 |
| | .016 | 0.0 | 7.0 | 2.0 | 6.0 | 9.0 | 9.0 | 2.0 | 3.0 | | 7.0 | 1.0 | 4.0 | 7.0 | 5.0 |
| 3-Carboethoxypropyl 2-(5-isopropyl-5-methyl-4-oxo-2-imidazolin-2-yl)nicotinate | 8.000 | 9.0 | 9.0 | 9.0 | 8.0 | 9.0 | 9.0 | 8.0 | 8.0 | 8.0 | | | | | |
| | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 6.0 | 8.0 | 9.0 | 7.0 | 9.0 | 9.0 | 9.0 | 1.0 | 9.0 | 8.0 | 6.0 | 7.0 | 8.0 | 7.0 |
| | .063 | 2.0 | 2.0 | 4.0 | 9.0 | 8.0 | 9.0 | 7.0 | 1.0 | 8.0 | 9.0 | 8.0 | 7.0 | 9.0 | |
| | .032 | 1.0 | 2.0 | 3.0 | 3.0 | 8.0 | 9.0 | 4.0 | 0.0 | 8.0 | 8.0 | 3.0 | 6.0 | 7.0 | 3.0 |
| | .016 | 0.0 | 1.0 | 0.0 | 1.0 | 4.0 | 9.0 | 0.0 | 0.0 | 8.0 | 9.0 | 1.0 | 2.0 | 6.0 | 2.0 |
| 1-Carbomethoxyethyl 2-(5-isopropyl-5-methyl-4-oxo-2-imidazolin-2-yl)nicotinate | 8.000 | 9.0 | 9.0 | 9.0 | 8.0 | 9.0 | 9.0 | 8.0 | 8.0 | 8.0 | | | | | |
| | .500 | 8.0 | 9.0 | 9.0 | 9.0 | 9.0 | 9.0 | 9.0 | 7.0 | 9.0 | 9.0 | 9.0 | 9.0 | 9.0 | 9.0 |
| | .250 | 7.0 | 9.0 | 9.0 | 9.0 | 9.0 | 9.0 | 9.0 | 6.0 | 8.0 | 9.0 | 9.0 | 9.0 | 9.0 | 8.0 |
| | .125 | 3.0 | 4.0 | 9.0 | 7.0 | 8.0 | 9.0 | 6.0 | 1.0 | 8.0 | 8.0 | 9.0 | 6.0 | 9.0 | 3.0 |
| | .063 | 1.0 | 1.0 | 3.0 | 7.0 | 7.0 | 9.0 | 4.0 | 0.0 | 3.0 | 8.0 | 3.0 | 6.0 | 6.0 | |
| | .032 | 1.0 | 0.0 | 8.0 | 1.0 | 8.0 | 9.0 | 0.0 | 0.0 | 4.0 | 7.0 | 2.0 | 1.0 | 7.0 | |
| Methyl 5-bromo-2-(5-isopropyl-5-methyl-4-oxo-2-imidazolin-2-yl)nicotinate | 8.000 | 9.0 | 9.0 | 9.0 | 8.0 | 9.0 | 9.0 | 8.0 | 9.0 | 8.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 7.0 |
| | .250 | 9.0 | 7.0 | 9.0 | 9.0 | 7.0 | 9.0 | 9.0 | 9.0 | 9.0 | 9.0 | 9.0 | 9.0 | 9.0 | 4.0 |
| | .125 | 7.0 | 6.0 | 9.0 | 9.0 | 8.0 | 9.0 | 9.0 | 8.0 | 8.0 | 7.0 | 7.0 | 6.0 | 9.0 | 3.0 |
| | .063 | 2.0 | 1.0 | 6.0 | 3.0 | 4.0 | 9.0 | 7.0 | 7.0 | 3.0 | 7.0 | 4.0 | 2.0 | 7.0 | 1.0 |
| | .032 | 1.0 | 1.0 | 4.0 | 2.0 | 3.0 | 9.0 | 4.0 | 2.0 | 4.0 | 6.0 | 2.0 | 1.0 | 6.0 | |
| | .016 | 0.0 | 0.0 | 1.0 | 0.0 | 0.0 | 9.0 | 0.0 | 0.0 | 0.0 | 5.0 | 1.0 | 0.0 | 5.0 | 0.0 |
| 3-Carboethoxy-2-propenyl 2-(5-isopropyl-5-methyl-4-oxo-2-imidazolin-2-yl)nicotinate | 8.000 | 9.0 | 9.0 | 9.0 | 8.0 | 9.0 | 9.0 | 8.0 | 8.0 | 8.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .125 | 6.0 | 9.0 | 9.0 | 9.0 | 9.0 | 9.0 | 6.0 | 5.0 | 9.0 | 9.0 | 9.0 | 9.0 | 9.0 | 9.0 |
| | .063 | 5.0 | 7.0 | 9.0 | 9.0 | 8.0 | 9.0 | 7.0 | 3.0 | 8.0 | 8.0 | 9.0 | 8.0 | 9.0 | 7.0 |
| | .032 | 4.0 | 6.0 | 9.0 | 6.0 | 7.0 | 9.0 | 7.0 | 1.0 | 8.0 | 8.0 | 4.0 | 7.0 | 7.0 | 4.0 |
| | .016 | 2.0 | 2.0 | 3.0 | 3.0 | 4.0 | 9.0 | 0.0 | 1.0 | 3.0 | 7.0 | 3.0 | 2.0 | 6.0 | |
| 3-Butenyl 2-(5-isopropyl-5-methyl-4-oxo-2-imidazolin-2-yl)nicotinate | 8.000 | 9.0 | 9.0 | 9.0 | 8.0 | 9.0 | 9.0 | 9.0 | 9.0 | 8.0 | | | | | |
| | .500 | 9.0 | 9.0 | 9.0 | 9.0 | 9.0 | 9.0 | 9.0 | 8.0 | 9.0 | 9.0 | 9.0 | 9.0 | 9.0 | |
| | .250 | 9.0 | 9.0 | 9.0 | 9.0 | 9.0 | 9.0 | 9.0 | 4.0 | 9.0 | 9.0 | 9.0 | 9.0 | 9.0 | |
| | .125 | 6.0 | 9.0 | 9.0 | 9.0 | 9.0 | 9.0 | 9.0 | 2.0 | 9.0 | 9.0 | 9.0 | 8.0 | 9.0 | |
| | .063 | 3.0 | 9.0 | 7.0 | 9.0 | 9.0 | 9.0 | 9.0 | 1.0 | 8.0 | 9.0 | 9.0 | 7.0 | 7.0 | |
| | .032 | 1.0 | 0.0 | 3.0 | 7.0 | 6.0 | 6.0 | 7.0 | 0.0 | 4.0 | 8.0 | 5.0 | 3.0 | 4.0 | |
| | .016 | 0.0 | 0.0 | 1.0 | 4.0 | 3.0 | | 0.0 | 0.0 | 2.0 | 7.0 | 2.0 | 1.0 | 2.0 | |
| 4-Carbomethoxybutyl 2-(5-isopropyl-5-methyl-4-oxo-2-imidazolin-2-yl)-nicotinate | 8.000 | 9.0 | 9.0 | 9.0 | 8.0 | 9.0 | 9.0 | 8.0 | 8.0 | 8.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 7.0 | 9.0 | 9.0 | 9.0 | 9.0 | 9.0 | 9.0 |
| | .125 | 9.0 | 6.0 | 9.0 | 9.0 | 9.0 | 9.0 | 9.0 | 6.0 | 9.0 | 9.0 | 9.0 | 8.0 | 7.0 | 9.0 |
| | .063 | 8.0 | 4.0 | 9.0 | 9.0 | 8.0 | 9.0 | 9.0 | 5.0 | 7.0 | 8.0 | 7.0 | 8.0 | 7.0 | 8.0 |

TABLE XII-continued

| PRE-EMERGENCE TESTS - RATES IN KG/HA | | | | | | | | | | | | | | | |
|---|---|---|---|---|---|---|---|---|---|---|---|---|---|---|---|
| | .032 | 4.0 | 4.0 | 9.0 | 6.0 | 7.0 | 9.0 | 9.0 | 0.0 | 8.0 | 8.0 | 3.0 | 3.0 | 6.0 | 4.0 |
| | .016 | 1.0 | 1.0 | 4.0 | 4.0 | 4.0 | 9.0 | 3.0 | 0.0 | 3.0 | 8.0 | 2.0 | 1.0 | 5.0 | 1.0 |
| Ferrous 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 9.0 | 8.0 | 9.0 | 9.0 | 9.0 | 9.0 | 9.0 | 0.0 | 9.0 | 9.0 | 9.0 | 9.0 | 9.0 | 7.0 |
| | .032 | 9.0 | 7.0 | 9.0 | 9.0 | 9.0 | 9.0 | 8.0 | | 9.0 | 9.0 | 9.0 | 8.0 | 8.0 | 7.0 |
| | .016 | 9.0 | 6.0 | 3.0 | 8.0 | 8.0 | 9.0 | 9.0 | | 8.0 | 7.0 | 9.0 | 7.0 | 9.0 | 5.0 |
| Ferric 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 7.0 | 8.0 | 9.0 | 9.0 | 9.0 | 9.0 | 9.0 | 3.0 | 9.0 | 9.0 | 9.0 | 8.0 | 9.0 | 9.0 |
| | .032 | 6.0 | 8.0 | 9.0 | 9.0 | 9.0 | 9.0 | 9.0 | | 9.0 | 9.0 | 9.0 | 8.0 | 9.0 | 8.0 |
| | .016 | 3.0 | 9.0 | 9.0 | 9.0 | 9.0 | 9.0 | 6.0 | | 9.0 | 9.0 | 9.0 | 8.0 | 9.0 | 7.0 |
| Diethanolammonium 2-(5-isopropyl-5-methyl-4-oxo-2-imidazolin-2-yl)nicotinate | 8.000 | 9.0 | 9.0 | 9.0 | 9.0 | 9.0 | 9.0 | | 9.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 4.0 | 9.0 | 8.0 | 9.0 | 9.0 | 9.0 | 9.0 | | 9.0 | 9.0 | 9.0 | 8.0 | 9.0 | 9.0 |
| | .032 | 2.0 | 6.0 | 8.0 | 7.0 | 8.0 | 9.0 | 7.0 | | 9.0 | 9.0 | 9.0 | 8.0 | 7.0 | 7.0 |
| | .016 | 1.0 | 3.0 | 0.0 | 6.0 | 4.0 | 9.0 | 9.0 | 0.0 | 6.0 | 9.0 | 7.0 | 3.0 | 7.0 | 5.0 |
| p-tert-Butylbenzyl 2-(5-isopropyl-5-methyl-4-oxo-2-imidazolin-2-yl)-nicotinate | 8.000 | 9.0 | 9.0 | 8.0 | 8.0 | 9.0 | 9.0 | 8.0 | 8.0 | 8.0 | | | | | |
| | .500 | 9.0 | 9.0 | 9.0 | 9.0 | 9.0 | 9.0 | 9.0 | 7.0 | 9.0 | 9.0 | 9.0 | 9.0 | 9.0 | 7.0 |
| | .250 | 8.0 | 8.0 | 9.0 | 9.0 | 9.0 | 9.0 | 9.0 | 7.0 | 9.0 | 9.0 | 9.0 | 7.0 | 9.0 | 7.0 |
| | .125 | 4.0 | 7.0 | 9.0 | 7.0 | 9.0 | 9.0 | 7.0 | 4.0 | 9.0 | 7.0 | 7.0 | 6.0 | 7.0 | 6.0 |
| | .063 | 1.0 | 1.0 | 3.0 | 4.0 | 7.0 | 9.0 | 7.0 | 2.0 | 3.0 | 7.0 | 6.0 | 3.0 | 7.0 | 4.0 |
| Phenethyl 2-(5-isopropyl-5-methyl-4-oxo-2-imidazolin-2-yl)nicotinate | 8.000 | 9.0 | 9.0 | 9.0 | 8.0 | 9.0 | 9.0 | 8.0 | 8.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 4.0 | 9.0 | 9.0 | 9.0 | 9.0 | 9.0 | 9.0 |
| | .125 | 4.0 | 9.0 | 7.0 | 9.0 | 8.0 | 9.0 | 6.0 | 2.0 | 8.0 | 9.0 | 9.0 | 9.0 | 8.0 | 8.0 |
| | .063 | 2.0 | 6.0 | 7.0 | 9.0 | 8.0 | 9.0 | 7.0 | 1.0 | 8.0 | 9.0 | 9.0 | 6.0 | 8.0 | |
| Cinnamyl 2-(5-isopropyl-5-methyl-4-oxo-2-imidazolin-2-yl)nicotinate | 8.000 | 9.0 | 9.0 | 9.0 | 9.0 | 9.0 | 9.0 | 8.0 | 8.0 | 9.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 6.0 | 9.0 | 9.0 | 9.0 | 9.0 | 9.0 | 8.0 |
| | .125 | 6.0 | 8.0 | 9.0 | 9.0 | 9.0 | 9.0 | 9.0 | | 9.0 | 9.0 | 9.0 | 8.0 | 8.0 | 7.0 |
| | .063 | 3.0 | 7.0 | 7.0 | 8.0 | 9.0 | 9.0 | 8.0 | 0.0 | 8.0 | 9.0 | 9.0 | 7.0 | 7.0 | 6.0 |
| | .032 | 1.0 | 7.0 | 7.0 | 6.0 | 7.0 | 9.0 | 8.0 | | 8.0 | 9.0 | 7.0 | 7.0 | 6.0 | 5.0 |
| | .016 | 1.0 | 4.0 | 2.0 | 6.0 | 4.0 | 9.0 | 6.0 | | 3.0 | 8.0 | 3.0 | 2.0 | 4.0 | 3.0 |
| 5-α-Hydroxy-3α-isopropyl-3-methyl-5H-imidazo[1',2':1,2]-pyrrolo[3,4-b]pyridin-2-(3H)dione | 8.000 | 9.0 | 9.0 | 9.0 | 9.0 | 9.0 | 9.0 | 9.0 | 9.0 | 9.0 | | | | | |
| | .500 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 8.0 | 9.0 | 9.0 | 9.0 | 9.0 | 9.0 | 9.0 | 9.0 | 9.0 | 9.0 | 9.0 | 9.0 |
| | .125 | 8.0 | 9.0 | 7.0 | 9.0 | 7.0 | 9.0 | 9.0 | 9.0 | 9.0 | 9.0 | 5.0 | 8.0 | 7.0 | 7.0 |
| | .063 | 1.0 | 9.0 | 3.0 | 7.0 | 4.0 | 9.0 | 9.0 | 9.0 | 9.0 | 8.0 | 4.0 | 7.0 | 6.0 | 3.0 |
| | .032 | 0.0 | 9.0 | 0.0 | 4.0 | 3.0 | 9.0 | 8.0 | 7.0 | 7.0 | 7.0 | 1.0 | 2.0 | 4.0 | 1.0 |
| | .016 | 0.0 | 7.0 | 0.0 | 2.0 | 2.0 | 9.0 | 8.0 | 5.0 | 4.0 | 6.0 | 1.0 | 1.0 | 4.0 | 0.0 |
| 5-Isopropyl-5-methyl-2-(3-methyl-2-pyridyl)-2-imidazolin-4-one | 8.000 | 7.0 | 9.0 | 9.0 | 9.0 | 9.0 | 9.0 | 8.0 | 8.0 | 8.0 | | | | | |
| | .500 | 0.0 | 4.0 | 0.0 | 9.0 | 2.0 | 9.0 | 3.0 | 6.0 | 4.0 | 9.0 | 1.0 | 1.0 | 2.0 | 1.0 |
| 3,7-Dimethyl-2,6-octadienyl 2-(5-isopropyl-5-methyl-4-oxo-2-imidazolin- | 8.000 | 9.0 | 9.0 | 9.0 | 9.0 | 9.0 | 9.0 | 8.0 | 9.0 | 9.0 | | | | | |
| | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 8.0 |
| | .125 | 3.0 | 9.0 | 9.0 | 9.0 | 9.0 | 9.0 | 8.0 | 3.0 | 9.0 | 9.0 | 9.0 | 9.0 | 9.0 | 6.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| 2-yl)nicotinate | | | | | | | | | | | | | | | |
| 2,3-Dihydroxypropyl | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-(5-isopropyl-5- | .250 | 9.0 | 9.0 | 9.0 | 9.0 | 9.0 | 9.0 | 9.0 | 7.0 | 9.0 | 9.0 | 9.0 | 9.0 | 9.0 | 9.0 |
| methyl-4-oxo-2- | .125 | 9.0 | 9.0 | 9.0 | 9.0 | 9.0 | 9.0 | 9.0 | 6.0 | 9.0 | 9.0 | 9.0 | 9.0 | 9.0 | 9.0 |
| imidazolin-2-yl)- | .063 | 2.0 | 7.0 | 8.0 | 9.0 | 9.0 | 9.0 | 9.0 | 0.0 | 9.0 | 9.0 | 9.0 | 8.0 | 9.0 | 6.0 |
| nicotinate | .032 | 1.0 | 7.0 | 8.0 | 7.0 | 9.0 | 9.0 | 9.0 | 0.0 | 3.0 | 2.0 | 9.0 | 6.0 | 9.0 | 3.0 |
| | .016 | 0.0 | 2.0 | 1.0 | 4.0 | 1.0 | 9.0 | 6.0 | 0.0 | 1.0 | 3.0 | 7.0 | | 4.0 | 2.0 |
| 4-Pentynyl 2-(5- | .500 | 8.0 | 9.0 | 9.0 | 9.0 | 9.0 | 9.0 | 9.0 | 9.0 | 9.0 | 9.0 | 9.0 | 9.0 | 9.0 | 8.0 |
| isopropyl-5-methyl- | .250 | 7.0 | 9.0 | 9.0 | 9.0 | 9.0 | 9.0 | 9.0 | 7.0 | 9.0 | 9.0 | 9.0 | 8.0 | 9.0 | 8.0 |
| 4-oxo-2-imidazolin- | .125 | 6.0 | 9.0 | 8.0 | 9.0 | 9.0 | 9.0 | 9.0 | 5.0 | 9.0 | 9.0 | 9.0 | 8.0 | 8.0 | 8.0 |
| 2-yl)nicotinate | .063 | 3.0 | 7.0 | 8.0 | 9.0 | 9.0 | 9.0 | 7.0 | 2.0 | 9.0 | 9.0 | 9.0 | 8.0 | 8.0 | 7.0 |
| | .032 | 2.0 | 4.0 | 8.0 | 9.0 | 8.0 | 8.0 | 7.0 | 0.0 | 8.0 | 9.0 | 7.0 | 7.0 | 6.0 | 4.0 |
| | .016 | 0.0 | 2.0 | 4.0 | 4.0 | 2.0 | 4.0 | 3.0 | 0.0 | 4.0 | 9.0 | 5.0 | 2.0 | 5.0 | 2.0 |
| 2-(5-Isopropyl-5- | 8.000 | 9.0 | 9.0 | 9.0 | 9.0 | 9.0 | 9.0 | 8.0 | 9.0 | 8.0 | | | | | |
| methyl-4-oxo-2- | 1.000 | 9.0 | 9.0 | 9.0 | 9.0 | 9.0 | 9.0 | | 9.0 | 9.0 | 9.0 | 9.0 | 9.0 | | 9.0 |
| imidazolin-2-yl)-3- | .500 | 8.5 | 9.0 | 9.0 | 9.0 | 9.0 | 9.0 | 8.0 | 9.0 | 8.5 | 9.0 | 9.0 | 9.0 | 9.0 | 5.5 |
| quinolinecarboxylic | .250 | 9.0 | 9.0 | 9.0 | 9.0 | 9.0 | 9.0 | 7.0 | 8.5 | 8.0 | 9.0 | 9.0 | 9.0 | 9.0 | 3.0 |
| acid | .125 | 9.0 | 8.5 | 9.0 | 9.0 | 9.0 | 9.0 | 7.0 | 8.0 | 7.5 | 9.0 | 9.0 | 9.0 | 9.0 | 3.0 |
| | .063 | 6.0 | 7.0 | 7.5 | 8.5 | 8.5 | 9.0 | 3.0 | 6.5 | 5.5 | 8.5 | 9.0 | 8.0 | 3.0 | 1.5 |
| | .032 | 2.0 | 5.0 | 7.5 | 7.5 | 7.0 | 9.0 | 1.0 | 3.5 | 4.5 | 8.5 | 9.0 | 7.0 | | 1.0 |
| 6,6-Dimethyl-2- | .500 | 9.0 | 9.0 | 9.0 | 9.0 | 9.0 | 9.0 | 9.0 | 3.0 | 9.0 | 9.0 | 9.0 | 8.0 | 9.0 | 8.0 |
| norpinene-2-ethyl | .250 | 7.0 | 9.0 | 9.0 | 9.0 | 9.0 | 9.0 | 9.0 | 1.0 | 9.0 | 9.0 | 9.0 | 8.0 | 9.0 | 8.0 |
| 2-(5-isopropyl-5- | .125 | 3.0 | 9.0 | 7.0 | 9.0 | 9.0 | 9.0 | 8.0 | 0.0 | 8.0 | 9.0 | 9.0 | 7.0 | 9.0 | 7.0 |
| methyl-4-oxo-2-yl)- | .063 | 1.0 | 6.0 | 8.0 | 9.0 | 7.0 | 8.0 | 4.0 | 0.0 | 8.0 | 9.0 | 7.0 | 4.0 | 7.0 | 4.0 |
| nicotinate | .032 | 1.0 | 4.0 | 4.0 | 8.0 | 7.0 | 9.0 | 4.0 | 0.0 | 4.0 | 9.0 | 5.0 | 4.0 | 6.0 | 3.0 |
| | .016 | 1.0 | 4.0 | 2.0 | 7.0 | 7.0 | 9.0 | 0.0 | 0.0 | 4.0 | 9.0 | 5.0 | 3.0 | 6.0 | 1.0 |
| α-Carbomethoxy- | 8.000 | 9.0 | 9.0 | 9.0 | 8.0 | 9.0 | 9.0 | 8.0 | 8.0 | 9.0 | | | | | |
| benzyl 2-(5-isopropyl- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 5-methyl-4-oxo- | .250 | 7.0 | 9.0 | 9.0 | 9.0 | 9.0 | 9.0 | 9.0 | 7.0 | 9.0 | 9.0 | 9.0 | 9.0 | 9.0 | 9.0 |
| 2-imidazolin-2-yl)- | .125 | 4.0 | 9.0 | 9.0 | 9.0 | 9.0 | 9.0 | 7.0 | 3.0 | 9.0 | 9.0 | 9.0 | 9.0 | 9.0 | 7.0 |
| nicotinate | .063 | 3.0 | 9.0 | 8.0 | 9.0 | 9.0 | 9.0 | 7.0 | 0.0 | 9.0 | 9.0 | 9.0 | 7.0 | 9.0 | |
| | .032 | 1.0 | 7.0 | 0.0 | 4.0 | 4.0 | 9.0 | 6.0 | 0.0 | 6.0 | 8.0 | 9.0 | 5.0 | 6.0 | 6.0 |
| Methyl 2-(1-acetyl- | .500 | 0.0 | 7.0 | 7.0 | 8.0 | 8.0 | 9.0 | 9.0 | 0.0 | 9.0 | 9.0 | 7.0 | 7.0 | 7.0 | 7.0 |
| 4-isopropyl-4-methyl- | .250 | 0.0 | 7.0 | 1.0 | 7.0 | 7.0 | 9.0 | 8.0 | 0.0 | 9.0 | 7.0 | 7.0 | 7.0 | 7.0 | |
| 5-oxo-2-imidazolin-2- | .125 | 0.0 | 6.0 | 3.0 | 4.0 | 6.0 | 9.0 | 7.0 | 0.0 | 8.0 | 4.0 | 3.0 | 6.0 | 4.0 | 6.0 |
| yl)nicotinate-1-oxide | .063 | 0.0 | 3.0 | 0.0 | 2.0 | 3.0 | 8.0 | 4.0 | 0.0 | 6.0 | 2.0 | 3.0 | 3.0 | 3.0 | 5.0 |
| | .032 | 0.0 | 3.0 | 0.0 | 0.0 | 0.0 | 9.0 | 1.0 | 0.0 | 3.0 | 0.0 | 0.0 | 1.0 | 2.0 | 3.0 |
| | .016 | 0.0 | 2.0 | 0.0 | 0.0 | 0.0 | 0.0 | 1.0 | 0.0 | 1.0 | 0.0 | 0.0 | 0.0 | 0.0 | |
| 3-Methyl-3-butenyl | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| 2-(5-isopropyl-5- | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| methyl-4-oxo-2- | .125 | 7.0 | 9.0 | 7.0 | 9.0 | 9.0 | 9.0 | 8.0 | 3.0 | 9.0 | 9.0 | 7.0 | 8.0 | 9.0 | 7.0 |
| imidazolin-2-yl)- | .063 | 6.0 | 7.0 | 8.0 | 9.0 | 9.0 | 9.0 | 6.0 | 0.0 | 9.0 | 9.0 | 7.0 | 8.0 | 9.0 | 7.0 |
| nicotinate | .032 | 2.0 | 6.0 | 6.0 | 9.0 | 9.0 | 9.0 | 4.0 | 0.0 | 8.0 | 9.0 | 7.0 | 7.0 | 9.0 | 4.0 |
| | .016 | 2.0 | 5.0 | 4.0 | 5.0 | 7.0 | 7.0 | 1.0 | 0.0 | 8.0 | 9.0 | 7.0 | 5.0 | 8.0 | |
| 10-Undecenyl 2- | .500 | 9.0 | 9.0 | 9.0 | 9.0 | 9.0 | 9.0 | 9.0 | 9.0 | 9.0 | 9.0 | 9.0 | 9.0 | 9.0 | 8.0 |
| (5-isopropyl-5- | .250 | 9.0 | 9.0 | 9.0 | 9.0 | 9.0 | 9.0 | 9.0 | 8.0 | 9.0 | 9.0 | 9.0 | 8.0 | 9.0 | 8.0 |
| methyl-4-oxo-2- | .125 | 7.0 | 9.0 | 7.0 | 9.0 | 9.0 | 9.0 | 9.0 | 3.0 | 9.0 | 9.0 | 9.0 | | 8.0 | 7.0 |
| imidazolin-2-yl)- | .063 | 3.0 | 8.0 | 7.0 | 9.0 | 8.0 | 9.0 | 8.0 | 1.0 | 8.0 | 9.0 | 9.0 | 7.0 | 8.0 | 4.0 |
| nicotinate | .032 | 2.0 | 3.0 | 7.0 | 7.0 | 7.0 | 9.0 | 7.0 | 0.0 | 8.0 | 7.0 | 7.0 | 6.0 | 7.0 | 3.0 |
| | .016 | 1.0 | 0.0 | 7.0 | 3.0 | 5.0 | 3.0 | 1.0 | 0.0 | 6.0 | 7.0 | 7.0 | 1.0 | 4.0 | 1.0 |
| 5-Bromo-2-(5- | 8.000 | 9.0 | 9.0 | 9.0 | 8.0 | 9.0 | 9.0 | 8.0 | 8.0 | 9.0 | | | | | |
| isopropyl-5-methyl- | .500 | 8.0 | 9.0 | 9.0 | 9.0 | 9.0 | 9.0 | 9.0 | 9.0 | 9.0 | 9.0 | 9.0 | 9.0 | 9.0 | 7.0 |

TABLE XII-continued

| PRE-EMERGENCE TESTS - RATES IN KG/HA | | | | | | | | | | | | | | | |
|---|---|---|---|---|---|---|---|---|---|---|---|---|---|---|---|
| 4-oxo-2-imidazolin-2-yl)nicotinic acid | .250 | 8.0 | 9.0 | 7.0 | 6.0 | 9.0 | 6.0 | 9.0 | 8.0 | 7.0 | 8.0 | 8.0 | 9.0 | 9.0 | 5.0 |
| | .125 | 3.0 | 8.0 | 9.0 | 6.0 | 8.0 | 9.0 | 8.0 | 8.0 | 7.0 | 8.0 | 9.0 | 8.0 | 9.0 | 4.0 |
| | .063 | 1.0 | 6.0 | 8.0 | 3.0 | 3.0 | 6.0 | 2.0 | 2.0 | 3.0 | 3.0 | 3.0 | 4.0 | 9.0 | 3.0 |
| | .032 | 0.0 | 6.0 | 2.0 | 2.0 | 1.0 | 9.0 | 1.0 | 1.0 | 2.0 | 3.0 | 3.0 | 3.0 | 9.0 | 2.0 |
| | .016 | 0.0 | 4.0 | 0.0 | 0.0 | 0.0 | 0.0 | 1.0 | 0.0 | 1.0 | 2.0 | 2.0 | 2.0 | 9.0 | 1.0 |
| α-methylbenzyl 2-(5-isopropyl-5-methyl-4-oxo-2-imidazolin-2-yl)-nicotinate | 8.000 | 9.0 | 9.0 | 9.0 | 9.0 | 9.0 | 9.0 | 8.0 | 9.0 | 9.0 | | | | | |
| | .500 | 9.0 | 9.0 | 9.0 | 9.0 | 9.0 | 9.0 | 9.0 | 8.0 | 9.0 | 9.0 | 9.0 | 8.0 | 9.0 | 7.0 |
| | .250 | 9.0 | 9.0 | 9.0 | 9.0 | 8.0 | 9.0 | 9.0 | 4.0 | 9.0 | 9.0 | 9.0 | 8.0 | 9.0 | 6.0 |
| | .125 | 3.0 | 8.0 | 3.0 | 8.0 | 6.0 | 7.0 | 6.0 | 1.0 | 7.0 | 8.0 | 7.0 | 5.0 | 6.0 | 6.0 |
| | .063 | 1.0 | 8.0 | 3.0 | 6.0 | 7.0 | 7.0 | 5.0 | 1.0 | 4.0 | 6.0 | 6.0 | 1.0 | 5.0 | 3.0 |
| | .032 | 0.0 | 7.0 | 1.0 | 3.0 | 3.0 | 2.0 | 4.0 | 0.0 | 2.0 | 4.0 | 3.0 | 0.0 | 3.0 | 1.0 |
| Methyl 2-(5-isopropyl-5-methyl-4-oxo-2-imidazolin-2-yl)-nicotinate-1-oxide | 8.000 | 8.0 | 9.0 | 8.0 | 8.0 | 9.0 | 9.0 | 8.0 | 9.0 | 8.0 | | | | | |
| | .500 | 2.0 | 8.0 | 7.0 | 9.0 | 8.0 | 9.0 | 9.0 | 7.0 | 9.0 | 8.0 | 8.0 | 7.0 | 9.0 | |
| | .250 | 1.0 | 9.0 | 8.0 | 9.0 | 8.0 | 9.0 | 9.0 | 3.0 | 9.0 | 7.0 | 7.0 | 6.0 | 8.0 | |
| | .125 | 0.0 | 3.0 | 3.0 | 9.0 | 7.0 | 9.0 | 7.0 | 0.0 | 8.0 | 7.0 | 7.0 | 6.0 | 7.0 | 6.0 |
| | .063 | 0.0 | 3.0 | 2.0 | 7.0 | 7.0 | 9.0 | 6.0 | 0.0 | 8.0 | 4.0 | 3.0 | 5.0 | 4.0 | 2.0 |
| | .032 | 0.0 | 2.0 | 1.0 | 7.0 | 4.0 | 9.0 | 6.0 | 0.0 | 7.0 | 4.0 | 3.0 | 4.0 | 3.0 | 2.0 |
| | .016 | 0.0 | 2.0 | 0.0 | 6.0 | 2.0 | 9.0 | 2.0 | 0.0 | 3.0 | 3.0 | 2.0 | 3.0 | 1.0 | 1.0 |
| Methyl 6-chloro-2-(5-isopropyl-5-methyl-4-oxo-2-imidazolin-2-yl)-nicotinate | 8.000 | 9.0 | 9.0 | 9.0 | 9.0 | 8.0 | 9.0 | 9.0 | 9.0 | 9.0 | | | | | |
| | .500 | 8.0 | 9.0 | 9.0 | 9.0 | 9.0 | 9.0 | 9.0 | 9.0 | 7.0 | 9.0 | 9.0 | 8.0 | 9.0 | 7.0 |
| | .250 | 7.0 | 9.0 | 9.0 | 9.0 | 7.0 | 9.0 | 7.0 | 8.0 | 4.0 | 9.0 | 7.0 | 8.0 | 9.0 | 6.0 |
| | .125 | 3.0 | 7.0 | 6.0 | 9.0 | 9.0 | 7.0 | 7.0 | 8.0 | 3.0 | 8.0 | 4.0 | 7.0 | 8.0 | |
| | .063 | 2.0 | 5.0 | 3.0 | 9.0 | 9.0 | 3.0 | 7.0 | 4.0 | 3.0 | 7.0 | 4.0 | 5.0 | 6.0 | 4.0 |
| | .032 | 1.0 | 3.0 | 2.0 | 9.0 | 1.0 | 2.0 | 5.0 | 0.0 | 0.0 | 6.0 | 4.0 | 3.0 | 5.0 | 2.0 |
| | .016 | 0.0 | 1.0 | 0.0 | 7.0 | 0.0 | 1.0 | 4.0 | 0.0 | 0.0 | 3.0 | 1.0 | 1.0 | 1.0 | 0.0 |
| 2-Isopropyl-2-methyl-5-H—imidazo[1',2':1,2]-pyrrolo[3,4-b]pyridine-3(2H),5-dione | 8.000 | 9.0 | 9.0 | 9.0 | 8.0 | 9.0 | 9.0 | 8.0 | 8.0 | 8.0 | | | | | |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 8.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 9.0 | 9.0 | 9.0 | 9.0 | 9.0 | 9.0 | 9.0 | 6.0 | 9.0 | 9.0 | 9.0 | 9.0 | 9.0 | 9.0 |
| | .032 | 1.0 | 9.0 | 3.0 | 9.0 | 9.0 | 9.0 | 8.0 | 0.0 | 9.0 | 9.0 | 9.0 | 8.0 | 9.0 | 5.0 |
| | .016 | 1.0 | 9.0 | 0.0 | 9.0 | 3.0 | 9.0 | 2.0 | 0.0 | 7.0 | 8.0 | 9.0 | 7.0 | 9.0 | 3.0 |
| 2-[3-(Hydroxymethyl)-2-pyridyl]-5-isopropyl-5-methyl-2-imidazo-4-one | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 8.0 | 9.0 | 7.0 |
| | .063 | 8.0 | 9.0 | 9.0 | 9.0 | 9.0 | 9.0 | 9.0 | 4.0 | 9.0 | 9.0 | 9.0 | 8.0 | 9.0 | 7.0 |
| | .032 | 8.0 | 9.0 | 9.0 | 9.0 | 9.0 | 9.0 | 8.0 | 2.0 | 9.0 | 9.0 | 9.0 | 8.0 | 9.0 | 7.0 |
| | .016 | 4.0 | 8.0 | 7.0 | 8.0 | 9.0 | 9.0 | 6.0 | 0.0 | 9.0 | 9.0 | 8.0 | 7.0 | 8.0 | 7.0 |
| Carboethoxymethyl 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 5.0 | 9.0 | 9.0 | 9.0 | 9.0 | 9.0 | 8.0 |
| | .125 | 9.0 | 9.0 | 9.0 | 9.0 | 9.0 | 9.0 | 9.0 | 6.0 | 9.0 | 9.0 | 9.0 | 9.0 | 9.0 | 8.0 |
| | .063 | 8.0 | 9.0 | 9.0 | 9.0 | 9.0 | 9.0 | 9.0 | 1.0 | 8.0 | 9.0 | 9.0 | 8.0 | 9.0 | 7.0 |
| | .032 | 5.0 | 7.0 | 7.0 | 9.0 | 9.0 | 9.0 | 7.0 | 0.0 | 8.0 | 9.0 | 9.0 | 7.0 | 9.0 | 7.0 |
| | .016 | 4.0 | 7.0 | 8.0 | 8.0 | 8.0 | 9.0 | | 0.0 | 8.0 | 9.0 | 7.0 | 6.0 | 9.0 | 7.0 |
| Carbobenzyloxymethyl 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 7.0 | 9.0 | 9.0 | 9.0 | 9.0 | 9.0 | 8.0 |
| | .125 | 7.0 | 9.0 | 9.0 | 9.0 | 9.0 | 9.0 | 9.0 | 4.0 | 9.0 | 9.0 | 9.0 | 8.0 | 9.0 | 7.0 |
| | .063 | 7.0 | 7.0 | 9.0 | 9.0 | 9.0 | 9.0 | 9.0 | 2.0 | 9.0 | 9.0 | 9.0 | 8.0 | 9.0 | 5.0 |
| | .032 | 2.0 | 7.0 | 3.0 | 8.0 | 9.0 | 9.0 | 3.0 | 0.0 | 8.0 | 9.0 | 8.0 | 6.0 | 8.0 | 5.0 |
| | .016 | 1.0 | 4.0 | 1.0 | 4.0 | 7.0 | 9.0 | 3.0 | 0.0 | 8.0 | 9.0 | 3.0 | 3.0 | 4.0 | 4.0 |
| Carboxymethyl 2-(5-isopropyl-5-methyl- | .500 | 9.0 | 9.0 | 9.0 | 9.0 | 9.0 | 9.0 | 9.0 | 9.0 | 9.0 | 9.0 | 9.0 | 9.0 | 9.0 | 8.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 8.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| 4-oxo-2-imidazolin- | .125 | 9.0 | 9.0 | 9.0 | 9.0 | 9.0 | 9.0 | 9.0 | 8.0 | 9.0 | 9.0 | 9.0 | 9.0 | 9.0 | 8.0 |
| 2-yl)nicotinate | .063 | 5.0 | 8.0 | 9.0 | 9.0 | 9.0 | 9.0 | 8.0 | 2.0 | 9.0 | 9.0 | 9.0 | 8.0 | 9.0 | 7.0 |
| | .032 | 3.0 | 7.0 | 2.0 | 9.0 | 9.0 | 9.0 | 7.0 | 0.0 | 8.0 | 9.0 | 9.0 | 8.0 | 9.0 | |
| | .016 | 0.0 | 4.0 | 0.0 | 2.0 | 5.0 | 3.0 | 6.0 | 0.0 | 7.0 | 8.0 | 3.0 | 4.0 | 6.0 | 3.0 |
| Cyanomethyl 2-(5- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| isopropyl-5-methyl- | .250 | 8.0 | 9.0 | 9.0 | 9.0 | 9.0 | 9.0 | 9.0 | 9.0 | 9.0 | 9.0 | 9.0 | 9.0 | 9.0 | 8.0 |
| 4-oxo-2-imidazolin- | .125 | 6.0 | 9.0 | 9.0 | 9.0 | 9.0 | 9.0 | 9.0 | 7.0 | 9.0 | 9.0 | 9.0 | 9.0 | 9.0 | 8.0 |
| 2-yl)nicotinate | .063 | 6.0 | 9.0 | 9.0 | 9.0 | 9.0 | 9.0 | 9.0 | 6.0 | 9.0 | 9.0 | 9.0 | 8.0 | 9.0 | 7.0 |
| | .032 | 3.0 | 8.0 | 8.0 | 8.0 | 8.0 | 9.0 | 7.0 | 0.0 | 9.0 | 7.0 | 7.0 | 7.0 | 9.0 | 5.0 |
| | .016 | 2.0 | 5.0 | 3.0 | 1.0 | 6.0 | 9.0 | 4.0 | 0.0 | 8.0 | 9.0 | 7.0 | 2.0 | 4.0 | 4.0 |
| Methyl (−)-2-(5- | .500 | 9.0 | 9.0 | 9.0 | 9.0 | 9.0 | 9.0 | 9.0 | 7.0 | 9.0 | 9.0 | 9.0 | 9.0 | 9.0 | 7.0 |
| isopropyl-5-methyl- | .250 | 4.0 | 7.0 | 8.0 | 9.0 | 9.0 | 9.0 | 9.0 | 7.0 | 9.0 | 9.0 | 9.0 | 8.0 | 7.0 | 5.0 |
| 4-oxo-2-imidazolin- | .125 | 3.0 | 7.0 | 9.0 | 8.0 | 9.0 | 9.0 | 9.0 | 6.0 | 9.0 | 8.0 | 5.0 | 8.0 | 7.0 | 5.0 |
| 2-yl)nicotinate | .063 | 1.0 | 2.0 | 4.0 | 1.0 | 5.0 | 9.0 | 8.0 | 0.0 | 8.0 | 6.0 | 3.0 | 3.0 | 4.0 | 4.0 |
| | .032 | 0.0 | 1.0 | 3.0 | 0.0 | 8.0 | 7.0 | 7.0 | 0.0 | 8.0 | 5.0 | 2.0 | 2.0 | 3.0 | 2.0 |
| Methyl (+)-2-(5- | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| isopropyl-5-methyl- | .063 | 7.0 | 9.0 | 9.0 | 9.0 | 9.0 | 9.0 | 9.0 | 7.0 | 9.0 | 9.0 | 9.0 | 9.0 | 9.0 | 9.0 |
| 4-oxo-2-imidazolin- | .032 | 7.0 | 8.0 | 9.0 | 9.0 | 9.0 | 9.0 | 9.0 | 4.0 | 9.0 | 9.0 | 9.0 | 9.0 | 9.0 | 9.0 |
| 2-yl)nicotinate | .016 | 4.0 | 4.0 | 9.0 | 8.0 | 9.0 | 9.0 | 9.0 | 0.0 | 9.0 | 9.0 | 8.0 | 9.0 | 6.0 | 8.0 |
| Benzyl (+)-2-(5- | .500 | 8.0 | 9.0 | 9.0 | 9.0 | 9.0 | 9.0 | 9.0 | 9.0 | 9.0 | 9.0 | 8.0 | 8.0 | 9.0 | 7.0 |
| isopropyl-5-methyl- | .250 | 4.0 | 7.0 | 8.0 | 6.0 | 9.0 | 9.0 | 8.0 | 2.0 | 9.0 | 9.0 | 6.0 | 8.0 | 8.0 | 3.0 |
| 4-oxo-2-imidazolin- | .125 | 3.0 | 5.0 | 7.0 | 1.0 | 6.0 | 9.0 | 8.0 | 1.0 | 9.0 | 4.0 | 5.0 | 7.0 | 4.0 | 3.0 |
| 2-yl)nicotinate | .063 | 1.0 | 1.0 | 1.0 | 0.0 | 2.0 | 9.0 | 1.0 | 0.0 | 4.0 | 4.0 | 3.0 | 4.0 | 3.0 | 2.0 |
| | .032 | 1.0 | 1.0 | 1.0 | 0.0 | 2.0 | 2.0 | 1.0 | 0.0 | 4.0 | 3.0 | 3.0 | 0.0 | 2.0 | 1.0 |
| | .016 | 0.0 | 1.0 | 0.0 | 0.0 | 2.0 | 1.0 | 0.0 | 0.0 | 3.0 | 3.0 | 2.0 | 0.0 | 2.0 | 1.0 |
| Benzyl (−)-2-(5- | .500 | 9.0 | | 9.0 | 9.0 | 9.0 | 9.0 | 9.0 | 9.0 | 9.0 | 9.0 | 9.0 | 9.0 | 9.0 | 9.0 |
| isopropyl-5-methyl- | .250 | 9.0 | | 9.0 | 9.0 | 9.0 | 9.0 | 9.0 | 9.0 | 9.0 | 9.0 | 9.0 | 9.0 | 9.0 | 9.0 |
| 4-oxo-2-imidazolin- | .125 | 8.0 | | 7.0 | 9.0 | 9.0 | 9.0 | 9.0 | 6.0 | 9.0 | 9.0 | 9.0 | 9.0 | 9.0 | 6.0 |
| 2-yl)nicotinate | .063 | 7.0 | | 7.0 | 9.0 | 9.0 | 9.0 | 9.0 | 1.0 | 9.0 | 9.0 | 9.0 | 9.0 | 9.0 | 6.0 |
| | .032 | 3.0 | | 6.0 | 6.0 | 8.0 | 7.0 | 7.0 | 1.0 | 9.0 | 9.0 | 7.0 | 8.0 | 6.0 | 4.0 |
| | .016 | 1.0 | | 2.0 | 2.0 | 8.0 | 7.0 | 3.0 | 0.0 | 4.0 | 8.0 | 4.0 | 6.0 | 5.0 | 2.0 |
| (−)-2-(5-Isopropyl- | .500 | 9.0 | | 9.0 | 9.0 | 9.0 | 9.0 | 9.0 | 9.0 | 9.0 | 9.0 | 9.0 | 9.0 | 9.0 | 9.0 |
| 5-methyl-4-oxo-2- | .250 | 9.0 | | 9.0 | 9.0 | 9.0 | 9.0 | 9.0 | 7.0 | 9.0 | 9.0 | 9.0 | 9.0 | 9.0 | 7.0 |
| imidazolin-2-yl)- | .125 | 7.0 | | 9.0 | 9.0 | 9.0 | 9.0 | 9.0 | 7.0 | 9.0 | 9.0 | 9.0 | 9.0 | 9.0 | 5.0 |
| nicotinic acid | .063 | 1.0 | | 8.0 | 3.0 | 9.0 | 9.0 | 9.0 | 1.0 | 9.0 | 9.0 | 7.0 | 8.0 | 9.0 | 4.0 |
| | .032 | 0.0 | | 5.0 | 1.0 | 9.0 | 9.0 | 8.0 | 0.0 | 9.0 | 9.0 | 5.0 | 7.0 | 9.0 | 3.0 |
| | .016 | 0.0 | | 1.0 | 0.0 | 7.0 | 9.0 | 8.0 | 0.0 | 9.0 | 7.0 | 4.0 | 5.0 | 7.0 | 2.0 |
| (+)-2-(5-Isopropyl- | .500 | 9.0 | | 9.0 | 9.0 | 9.0 | 9.0 | 9.0 | 9.0 | 9.0 | 9.0 | 9.0 | 9.0 | 9.0 | 9.0 |
| 5-methyl-4-oxo-2- | .250 | 9.0 | | 9.0 | 9.0 | 9.0 | 9.0 | 9.0 | 9.0 | 9.0 | 9.0 | 9.0 | 9.0 | 9.0 | 9.0 |
| imidazolin-2-yl)- | .125 | 9.0 | | 9.0 | 9.0 | 9.0 | 9.0 | 9.0 | 9.0 | 9.0 | 9.0 | 9.0 | 9.0 | 9.0 | 9.0 |
| nicotinic acid | .063 | 9.0 | | 9.0 | 9.0 | 9.0 | 9.0 | 9.0 | 8.0 | 9.0 | 9.0 | 9.0 | 9.0 | 9.0 | 9.0 |
| | .032 | 8.0 | | 9.0 | 9.0 | 9.0 | 9.0 | 9.0 | 3.0 | 9.0 | 9.0 | 9.0 | 9.0 | 9.0 | 9.0 |
| | .016 | 8.0 | | 9.0 | 9.0 | 9.0 | 9.0 | 9.0 | 1.0 | 9.0 | 9.0 | 9.0 | 8.0 | 9.0 | 8.0 |
| 2-(5-Isopropyl-5- | 8.000 | 9.0 | 9.0 | 9.0 | 9.0 | 9.0 | 9.0 | | 9.0 | 9.0 | | | | | |
| methyl-4-oxo-2- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| imidazolin-2-yl)- | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| nicotinic acid | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| hydrochloride | .063 | 8.0 | 9.0 | 9.0 | 9.0 | 9.0 | 9.0 | 9.0 | 6.0 | 9.0 | 9.0 | 9.0 | 9.0 | 9.0 | 9.0 |
| | .032 | 8.0 | 9.0 | 9.0 | 8.0 | 9.0 | 9.0 | 9.0 | 3.0 | 9.0 | 9.0 | 9.0 | 9.0 | 7.0 | 7.0 |
| Methyl 2-(1-benzoyl- | 8.000 | 9.0 | 9.0 | 9.0 | 9.0 | 9.0 | 9.0 | | 9.0 | 9.0 | | | | | |
| 4-isopropyl-4- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| methyl-5-oxo-2- | .250 | 9.0 | 9.0 | 9.0 | 9.0 | 9.0 | 9.0 | 9.0 | 8.0 | 9.0 | 9.0 | 9.0 | 9.0 | 9.0 | 9.0 |

TABLE XII-continued

| | PRE-EMERGENCE TESTS - RATES IN KG/HA | | | | | | | | | | | | | | |
|---|---|---|---|---|---|---|---|---|---|---|---|---|---|---|---|
| imidazolin-2-yl)- | .125 | 9.0 | 9.0 | 9.0 | 9.0 | 9.0 | 9.0 | 9.0 | 7.0 | 9.0 | 9.0 | 9.0 | 9.0 | 7.0 | 9.0 |
| nicotinate | .063 | 7.0 | 9.0 | 9.0 | 9.0 | 9.0 | 9.0 | 9.0 | 4.0 | 9.0 | 9.0 | 9.0 | 9.0 | 7.0 | 8.0 |
| | .032 | 4.0 | 7.0 | 6.0 | 7.0 | 8.0 | 9.0 | 6.0 | 2.0 | 9.0 | 9.0 | 9.0 | 8.0 | 7.0 | 7.0 |
| | .016 | 2.0 | 1.0 | 3.0 | 5.0 | 6.0 | 9.0 | 4.0 | 1.0 | 7.0 | 9.0 | 8.0 | 7.0 | 7.0 | 6.0 |
| Methyl 6-dimethyl- | .500 | 9.0 | 9.0 | 0.0 | 7.0 | 7.0 | 6.0 | 0.0 | 0.0 | 9.0 | 9.0 | 7.0 | 2.0 | 8.0 | 6.0 |
| amino-2-(5-isopropyl- | .250 | 8.0 | 9.0 | 0.0 | 5.0 | 2.0 | 1.0 | 0.0 | 0.0 | 2.0 | 8.0 | 3.0 | 2.0 | 8.0 | |
| 5-methyl-4-oxo-2- | .125 | 3.0 | 6.0 | 0.0 | 1.0 | 1.0 | 0.0 | 0.0 | 0.0 | 0.0 | 6.0 | 3.0 | 1.0 | 5.0 | 4.0 |
| imidazolin-2-yl)- | .063 | 0.0 | 3.0 | 0.0 | 0.0 | 0.0 | 0.0 | 0.0 | 0.0 | 0.0 | 9.0 | 3.0 | 0.0 | 2.0 | 4.0 |
| nicotinate | | | | | | | | | | | | | | | |
| Methyl 2-(1-Chloro- | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| acetyl-4-isopropyl- | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| 4-methyl-5-oxo-2- | .125 | 7.0 | 9.0 | 9.0 | 9.0 | 9.0 | 9.0 | 9.0 | 8.0 | 9.0 | 9.0 | 9.0 | 9.0 | 9.0 | 9.0 |
| imidazolin-2-yl)- | .063 | 6.0 | 9.0 | 8.0 | 9.0 | 9.0 | 9.0 | 9.0 | 1.0 | 9.0 | 9.0 | 9.0 | 8.0 | 9.0 | 8.0 |
| nicotinate | .032 | 3.0 | 9.0 | 8.0 | 9.0 | 9.0 | 9.0 | 9.0 | 1.0 | 9.0 | 9.0 | 7.0 | 7.0 | 9.0 | 8.0 |
| | .016 | 2.0 | 8.0 | 7.0 | 7.0 | 7.0 | 9.0 | 9.0 | 0.0 | 8.0 | 8.0 | 6.0 | | 7.0 | 7.0 |
| Methyl 2-(4-isopropyl- | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| 4-methyl-5-oxo-1- | .250 | 8.0 | 9.0 | 9.0 | 9.0 | 9.0 | 9.0 | 9.0 | 8.0 | 9.0 | 9.0 | 9.0 | 9.0 | 9.0 | 8.0 |
| propionyl-2-imidazolin- | .125 | 8.0 | 9.0 | 9.0 | 9.0 | 9.0 | 9.0 | 9.0 | 5.0 | 9.0 | 9.0 | 9.0 | 9.0 | 9.0 | 8.0 |
| 2-yl)nicotinate | .063 | 3.0 | 9.0 | 9.0 | 9.0 | 9.0 | 9.0 | 9.0 | 1.0 | 9.0 | 9.0 | 9.0 | 8.0 | 7.0 | 8.0 |
| | .032 | 3.0 | 9.0 | 8.0 | 8.0 | 8.0 | 9.0 | 7.0 | 1.0 | 9.0 | 9.0 | 9.0 | 7.0 | 7.0 | 7.0 |
| | .016 | 2.0 | 7.0 | 6.0 | 7.0 | 6.0 | 9.0 | 6.0 | 1.0 | 9.0 | 9.0 | 9.0 | 7.0 | 7.0 | 7.0 |
| O—[2-(5-Isopropyl-5- | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| methyl-4-oxo-2- | .250 | 8.0 | 9.0 | 9.0 | 9.0 | 9.0 | 9.0 | 9.0 | 7.0 | 9.0 | 9.0 | 9.0 | 9.0 | 9.0 | 9.0 |
| imidazolin-2-yl)- | .125 | 8.0 | 9.0 | 9.0 | 9.0 | 9.0 | 9.0 | 9.0 | 6.0 | 9.0 | 9.0 | 9.0 | 9.0 | 9.0 | 8.0 |
| nicotinoyl]acetone | .063 | 6.0 | 9.0 | 9.0 | 9.0 | 9.0 | 9.0 | 9.0 | 6.0 | 9.0 | 9.0 | 9.0 | 9.0 | 9.0 | 8.0 |
| oxime | .032 | 4.0 | 9.0 | 9.0 | 9.0 | 9.0 | 9.0 | 8.0 | 1.0 | 9.0 | 8.0 | 9.0 | 8.0 | 9.0 | 7.0 |
| | .016 | 0.0 | 6.0 | 7.0 | 1.0 | 9.0 | 3.0 | 3.0 | 0.0 | 6.0 | 7.0 | 5.0 | 4.0 | 8.0 | 4.0 |
| 2-(3-Acetyl-2-pyridyl)- | .500 | 7.0 | 7.0 | 8.0 | 9.0 | 9.0 | 9.0 | 8.0 | 0.0 | 9.0 | 9.0 | 9.0 | 7.0 | 7.0 | 7.0 |
| 5-isopropyl-5-methyl- | .250 | 1.0 | 7.0 | 1.0 | 7.0 | 6.0 | 9.0 | 7.0 | 0.0 | 7.0 | 8.0 | 7.0 | 5.0 | 7.0 | 6.0 |
| 2-imidazolin-4-one | .125 | 0.0 | 1.0 | 0.0 | 0.0 | 4.0 | 1.0 | 9.0 | 0.0 | 3.0 | 6.0 | 5.0 | 2.0 | 3.0 | 4.0 |
| | .063 | 0.0 | 0.0 | 0.0 | 0.0 | 0.0 | | 1.0 | 0.0 | 2.0 | 6.0 | 4.0 | 1.0 | 3.0 | 3.0 |
| Benzyl 2-(4-isopropyl- | .500 | 9.0 | 9.0 | 9.0 | 9.0 | 9.0 | 9.0 | 9.0 | 8.0 | 9.0 | 9.0 | 9.0 | 9.0 | 9.0 | 9.0 |
| 4-methyl-5-oxo-1- | .250 | 9.0 | 9.0 | 9.0 | 9.0 | 9.0 | 9.0 | 9.0 | 2.0 | 9.0 | 9.0 | 9.0 | 9.0 | 9.0 | 8.0 |
| propionyl-2-imidazolin- | .125 | 7.0 | 9.0 | 9.0 | 8.0 | 9.0 | 9.0 | 9.0 | 2.0 | 9.0 | 9.0 | 9.0 | 9.0 | 9.0 | 7.0 |
| 2-yl)nicotinate | .063 | 3.0 | 9.0 | 7.0 | 2.0 | 8.0 | 9.0 | 9.0 | 1.0 | 9.0 | 9.0 | 7.0 | 3.0 | 8.0 | 5.0 |
| | .032 | 4.0 | 8.0 | 7.0 | 6.0 | 3.0 | 9.0 | 9.0 | 1.0 | 7.0 | 8.0 | 5.0 | 6.0 | 8.0 | 5.0 |
| | .016 | 0.0 | 3.0 | 2.0 | 1.0 | 2.0 | 4.0 | 0.0 | 0.0 | 7.0 | 7.0 | 4.0 | 4.0 | 6.0 | 4.0 |
| Benzyl 2-(4-isopropyl- | .500 | 9.0 | 9.0 | 9.0 | 9.0 | 9.0 | 9.0 | 9.0 | 7.0 | 9.0 | 9.0 | 9.0 | 9.0 | 9.0 | 8.0 |
| 4-methyl-5-oxo-1- | .250 | 8.0 | 9.0 | 9.0 | 9.0 | 9.0 | 9.0 | 9.0 | 5.0 | 9.0 | 9.0 | 9.0 | 9.0 | 9.0 | 7.0 |
| pivaloyl-2-imidazolin- | .125 | 7.0 | 9.0 | 8.0 | 8.0 | 8.0 | 9.0 | 9.0 | 2.0 | 9.0 | 9.0 | 9.0 | 8.0 | 9.0 | 7.0 |
| 2-yl)nicotinate | .063 | 3.0 | 9.0 | 9.0 | 7.0 | 9.0 | 9.0 | 5.0 | 1.0 | 9.0 | 9.0 | 7.0 | 8.0 | 7.0 | 6.0 |
| | .032 | 2.0 | 6.0 | 6.0 | 5.0 | 3.0 | 9.0 | 5.0 | 0.0 | 9.0 | 7.0 | 4.0 | 7.0 | 7.0 | 5.0 |
| | .016 | 0.0 | 1.0 | 2.0 | 1.0 | 2.0 | 2.0 | | 0.0 | 1.0 | 5.0 | 4.0 | 4.0 | 6.0 | 4.0 |
| Trimethyl 2-(5- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| isopropyl-5-methyl- | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| 4-oxo-2-imidazolin- | .125 | 9.0 | 9.0 | 9.0 | 9.0 | 9.0 | 9.0 | 9.0 | 6.0 | 9.0 | 9.0 | 9.0 | 9.0 | 9.0 | 9.0 |
| 2-yl)-β-oxo-α-phosphino- | .063 | 4.0 | 9.0 | 9.0 | 9.0 | 9.0 | 9.0 | 7.0 | 1.0 | 9.0 | 9.0 | 9.0 | 9.0 | 9.0 | 7.0 |
| 3-pyridinepropionic | .032 | 0.0 | 7.0 | 9.0 | 7.0 | 9.0 | 9.0 | 5.0 | 0.0 | 8.0 | 9.0 | 9.0 | 7.0 | 9.0 | 7.0 |
| acid | .016 | 0.0 | 7.0 | 7.0 | 1.0 | 7.0 | 9.0 | 2.0 | 0.0 | 6.0 | 8.0 | 7.0 | 3.0 | 9.0 | 3.0 |
| Methyl 2-[4-isopropyl- | .500 | 2.0 | 4.0 | 8.0 | 7.0 | 7.0 | 9.0 | 6.0 | 0.0 | 4.0 | 7.0 | 7.0 | 6.0 | 6.0 | 9.0 |
| 4-methyl-1-(methyl- | .250 | 1.0 | 2.0 | 2.0 | 3.0 | 1.0 | 7.0 | 3.0 | 0.0 | 2.0 | 6.0 | 5.0 | 4.0 | 4.0 | 9.0 |
| sulfonyl)-5-oxo-2- | .125 | 0.0 | 0.0 | 2.0 | 1.0 | 1.0 | 2.0 | 0.0 | 0.0 | 1.0 | 2.0 | 3.0 | | 2.0 | 3.0 |

TABLE XII-continued

| PRE-EMERGENCE TESTS - RATES IN KG/HA | | | | | | | | | | | | | | | |
|---|---|---|---|---|---|---|---|---|---|---|---|---|---|---|---|
| imidazolin-2-yl)-nicotinate | | | | | | | | | | | | | | | |
| 2-Propynyl 2-(1-Acetyl-4-isopropyl-4-methyl-5-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 8.0 | 9.0 | 9.0 | 9.0 | 9.0 | 9.0 | 9.0 | 8.0 | 9.0 | 9.0 | 9.0 | 9.0 | 9.0 | 8.0 |
| | .063 | 9.0 | 9.0 | 9.0 | 9.0 | 9.0 | 9.0 | 8.0 | 5.0 | 9.0 | 9.0 | 9.0 | 9.0 | 9.0 | 9.0 |
| | .032 | 6.0 | 9.0 | 7.0 | 8.0 | 9.0 | 9.0 | 7.0 | 4.0 | 9.0 | 9.0 | 8.0 | 6.0 | 9.0 | 6.0 |
| | .016 | 2.0 | 6.0 | 8.0 | 6.0 | 9.0 | 9.0 | 5.0 | 2.0 | 7.0 | 9.0 | 9.0 | 4.0 | 9.0 | 4.0 |
| 2-Ethanolammonium 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 6.0 | 9.0 | 9.0 | 9.0 | 9.0 | 9.0 | 9.0 |
| | .032 | 6.0 | 9.0 | 9.0 | 9.0 | 9.0 | 9.0 | 9.0 | 7.0 | 9.0 | 9.0 | 9.0 | 9.0 | 9.0 | 9.0 |
| | .016 | 0.0 | 9.0 | 9.0 | 8.0 | 9.0 | 9.0 | 8.0 | 5.0 | 9.0 | 8.0 | 7.0 | 7.0 | 9.0 | 9.0 |
| Pyrrolidinium 2-(5-isopropyl-5-methyl-4-oxo-2-imidazolin-2-yl)-nicotinate | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .063 | 8.0 | 9.0 | 9.0 | 9.0 | 9.0 | 9.0 | 8.0 | 6.0 | 9.0 | 9.0 | 9.0 | 8.0 | 9.0 | 8.0 |
| | .032 | 5.0 | 9.0 | 9.0 | 9.0 | 9.0 | 9.0 | 8.0 | 4.0 | 9.0 | 9.0 | 9.0 | 8.0 | 9.0 | 7.0 |
| | .016 | 0.0 | 7.0 | 9.0 | 6.0 | 9.0 | 9.0 | 5.0 | 0.0 | 9.0 | 9.0 | 7.0 | 4.0 | 9.0 | 6.0 |
| Diethylammonium 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 2.0 | 9.0 | 9.0 | 9.0 | 9.0 | 9.0 | 9.0 |
| | .032 | 2.0 | 9.0 | 9.0 | 9.0 | 9.0 | 9.0 | 8.0 | 1.0 | 9.0 | 9.0 | 9.0 | 8.0 | 9.0 | 9.0 |
| | .016 | 0.0 | 8.0 | 9.0 | 7.0 | 9.0 | 9.0 | 7.0 | 0.0 | 9.0 | 9.0 | 9.0 | 7.0 | 9.0 | 7.0 |
| Isopropylammonium 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 8.0 | 9.0 | 9.0 | 9.0 | 9.0 | 9.0 | 9.0 | 9.0 | 9.0 | 9.0 | 9.0 | 9.0 |
| | .063 | 7.0 | 9.0 | 9.0 | 9.0 | 9.0 | 9.0 | 9.0 | 7.0 | 9.0 | 9.0 | 9.0 | 9.0 | 9.0 | 9.0 |
| | .032 | 3.0 | 9.0 | 7.0 | 9.0 | 9.0 | 9.0 | 8.0 | 8.0 | 9.0 | 9.0 | 9.0 | 8.0 | 9.0 | 8.0 |
| | .016 | 0.0 | 9.0 | 6.0 | 7.0 | 9.0 | 9.0 | 7.0 | 2.0 | 9.0 | 9.0 | 9.0 | 7.0 | 9.0 | |
| 2-Methylallyl-ammonium 2-(5-isopropyl-5-methyl-4-oxo-2-imidazolin-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .032 | 6.0 | 9.0 | 9.0 | 9.0 | 9.0 | 9.0 | 9.0 | 3.0 | 9.0 | 8.0 | 9.0 | 8.0 | 9.0 | 9.0 |
| | .016 | 0.0 | 7.0 | 9.0 | 8.0 | 9.0 | 9.0 | 9.0 | 0.0 | 8.0 | 9.0 | 9.0 | 8.0 | 9.0 | 9.0 |
| Isobutylammonium 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 6.0 | 9.0 | 9.0 | 9.0 | 9.0 | 9.0 | 9.0 |
| | .063 | 9.0 | 9.0 | 9.0 | 9.0 | 9.0 | 9.0 | 9.0 | 6.0 | 9.0 | 9.0 | 9.0 | 9.0 | 9.0 | 9.0 |
| | .032 | 6.0 | 9.0 | 9.0 | 9.0 | 9.0 | 9.0 | 9.0 | 5.0 | 9.0 | 9.0 | 9.0 | 9.0 | 9.0 | 9.0 |
| | .016 | 0.0 | 7.0 | 9.0 | 8.0 | 9.0 | 9.0 | 9.0 | 4.0 | 9.0 | 8.0 | 9.0 | 7.0 | 8.0 | 9.0 |
| 2-Methoxy-1-methyl-ethylammonium 2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .063 | 9.0 | 9.0 | 3.0 | 9.0 | 9.0 | 9.0 | 9.0 | 3.0 | 9.0 | 9.0 | 9.0 | 9.0 | 9.0 | 9.0 |
| | .032 | 7.0 | 9.0 | 7.0 | 7.0 | 9.0 | 9.0 | 9.0 | 3.0 | 9.0 | 9.0 | 9.0 | 9.0 | 9.0 | 9.0 |
| | .016 | 0.0 | 7.0 | 9.0 | 9.0 | 9.0 | 9.0 | 9.0 | 0.0 | 9.0 | 9.0 | 9.0 | 8.0 | 9.0 | 9.0 |
| tert-Butylammonium 2-(5-isopropyl-5-methyl-4-oxo-2- | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 8.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 6.0 | 9.0 | 9.0 | 9.0 | 9.0 | 9.0 | 9.0 |

TABLE XII-continued

PRE-EMERGENCE TESTS - RATES IN KG/HA

| Compound | RATE | BARN-YARDGR | GREEN FOX | P NUT SED-GE | WILD OATS | QUACK GRASS | FLD B INDWD | MRNGLRY SP | RAG-WEED | VELVET-LEAF | S BARLY LA | CORN FIELD | RICE, NATO | SOY-BEAN AD | SUN-FLR XXX | S WHEAT ER |
|---|---|---|---|---|---|---|---|---|---|---|---|---|---|---|---|---|
| imidazolin-2-yl)-nicotinate | .063 | 7.0 | 9.0 | 9.0 | 9.0 | 9.0 | 9.0 | 9.0 | 6.0 | 9.0 | 9.0 | 9.0 | | 9.0 | 9.0 | 9.0 |
| | .032 | 4.0 | 9.0 | 8.0 | 9.0 | 9.0 | 9.0 | 9.0 | 1.0 | 9.0 | 9.0 | 9.0 | | 8.0 | 7.0 | 6.0 |
| | .016 | 0.0 | 6.0 | 8.0 | 7.0 | 9.0 | 9.0 | 8.0 | 0.0 | 8.0 | 9.0 | 9.0 | | 7.0 | 9.0 | 4.0 |
| 2,2,2-Trichloroethyl 2-(5-isopropyl-5-methyl-4-oxo-2-imidazolin-2-yl)-nicotinate | .500 | 9.0 | 9.0 | 9.0 | 9.0 | 9.0 | 9.0 | 9.0 | 9.0 | 9.0 | 9.0 | 9.0 | | 9.0 | 9.0 | 9.0 |
| | .250 | 8.0 | 9.0 | 9.0 | 9.0 | 9.0 | 9.0 | 9.0 | 9.0 | 9.0 | 9.0 | 9.0 | | 9.0 | 9.0 | 9.0 |
| | .125 | 7.0 | 9.0 | 9.0 | 9.0 | 9.0 | 9.0 | 9.0 | 7.0 | 9.0 | 9.0 | 9.0 | | 9.0 | 9.0 | 9.0 |
| | .063 | 6.0 | 9.0 | 9.0 | 9.0 | 9.0 | 9.0 | 8.0 | 3.0 | 9.0 | 9.0 | 9.0 | | 9.0 | 8.0 | 9.0 |
| | .032 | 1.0 | 9.0 | 9.0 | 9.0 | 9.0 | 9.0 | 8.0 | 1.0 | 9.0 | 9.0 | 9.0 | | 8.0 | 8.0 | 6.0 |
| | .016 | 0.0 | 6.0 | 2.0 | 1.0 | 7.0 | 9.0 | 0.0 | 0.0 | 4.0 | 6.0 | 9.0 | | 2.0 | 7.0 | 3.0 |
| 6-Chloro-2-(5-isopropyl-5-methyl-4-oxo-2-imidazolin-2-yl)nicotinic acid | .500 | 9.0 | 9.0 | 9.0 | 9.0 | 9.0 | 9.0 | 9.0 | 9.0 | 9.0 | 9.0 | 9.0 | | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | | 9.0 | 9.0 | 9.0 |
| | .125 | 8.0 | 9.0 | 9.0 | 9.0 | 9.0 | 9.0 | 9.0 | 9.0 | 9.0 | 9.0 | 9.0 | | 9.0 | 9.0 | 9.0 |
| | .063 | 7.0 | 9.0 | 9.0 | 9.0 | 9.0 | 9.0 | 9.0 | 9.0 | 9.0 | 9.0 | 9.0 | | 9.0 | 8.0 | 9.0 |
| | .032 | 6.0 | 9.0 | 9.0 | 9.0 | 9.0 | 9.0 | 9.0 | 9.0 | 8.0 | 9.0 | 9.0 | | 9.0 | 8.0 | 7.0 |
| | .016 | 3.0 | 7.0 | 9.0 | 9.0 | 9.0 | 9.0 | 6.0 | 3.0 | 7.0 | 9.0 | 7.0 | | 7.0 | 7.0 | |
| 1-Ethylmethyl 2-(1-carboxy-4-isopropyl-4-methyl-5-oxo-2-imidazolin-2-yl)-nicotinate | .500 | 8.0 | 9.0 | 9.0 | 9.0 | 9.0 | 9.0 | 9.0 | 6.0 | 9.0 | 9.0 | 9.0 | | 9.0 | 9.0 | 9.0 |
| | .250 | 8.0 | 9.0 | 9.0 | 9.0 | 9.0 | 9.0 | 9.0 | 3.0 | 9.0 | 9.0 | 9.0 | | 9.0 | 9.0 | 9.0 |
| | .125 | 6.0 | 9.0 | 8.0 | 9.0 | 8.0 | 9.0 | 8.0 | 1.0 | 9.0 | 9.0 | 9.0 | | 8.0 | 7.0 | 7.0 |
| | .063 | 4.0 | 8.0 | 7.0 | 9.0 | 7.0 | 9.0 | 7.0 | 1.0 | 9.0 | 7.0 | 9.0 | | 8.0 | 7.0 | 7.0 |
| | .032 | 3.0 | 7.0 | 4.0 | 4.0 | 4.0 | 9.0 | 6.0 | 0.0 | 9.0 | 6.0 | 5.0 | | 3.0 | 6.0 | |
| | .016 | 1.0 | 4.0 | 2.0 | 2.0 | 2.0 | 8.0 | 4.0 | 0.0 | 9.0 | 5.0 | 3.0 | | 3.0 | 5.0 | |
| Methyl 2-[4-isopropyl-4-methyl-5-oxo-1-(p-tolysulfonyl)-2-imidazolin-2-yl)-nicotinic acid | .500 | 2.0 | 9.0 | 8.0 | 7.0 | 8.0 | 8.0 | 8.0 | 0.0 | 9.0 | 8.0 | 6.0 | | 4.0 | 7.0 | 9.0 |
| | .250 | 0.0 | 7.0 | 6.0 | 6.0 | 7.0 | 9.0 | 1.0 | 0.0 | 9.0 | 7.0 | 6.0 | | 2.0 | 6.0 | 9.0 |
| | .125 | 0.0 | 5.0 | 5.0 | 4.0 | 4.0 | 9.0 | 0.0 | 0.0 | 9.0 | 4.0 | 3.0 | | | 3.0 | 2.0 |
| | .063 | 0.0 | 2.0 | 3.0 | 0.0 | 1.0 | 9.0 | 0.0 | 0.0 | 2.0 | 1.0 | 3.0 | | | 2.0 | 2.0 |
| | .032 | 0.0 | 0.0 | 3.0 | 0.0 | 0.0 | 9.0 | 0.0 | 0.0 | 0.0 | 1.0 | 2.0 | | 1.0 | | 1.0 |
| | .016 | 0.0 | 0.0 | 1.0 | 0.0 | 0.0 | 9.0 | 0.0 | 0.0 | 0.0 | 0.0 | 2.0 | | | 2.0 | |
| 5-Butyl-2-(5-isopropyl-5-methyl-4-oxo-2-imidazolin-2-yl)nicotinic acid | .500 | 9.0 | 9.0 | 0.0 | 7.0 | 9.0 | 9.0 | 7.0 | 7.0 | 8.0 | 9.0 | 9.0 | | 4.0 | 9.0 | 3.0 |
| | .250 | 6.0 | 7.0 | 0.0 | 4.0 | 9.0 | 9.0 | 4.0 | 6.0 | 7.0 | 8.0 | 7.0 | | 2.0 | 9.0 | 1.0 |
| | .125 | 2.0 | 2.0 | 0.0 | 1.0 | 8.0 | 9.0 | 3.0 | 3.0 | 3.0 | 3.0 | 6.0 | | 1.0 | 9.0 | 1.0 |
| | .063 | 1.0 | 1.0 | 0.0 | 0.0 | 4.0 | 8.0 | 2.0 | 1.0 | 1.0 | 3.0 | 4.0 | | 1.0 | 9.0 | 0.0 |
| | .032 | 0.0 | 0.0 | 0.0 | 0.0 | 4.0 | 2.0 | 1.0 | 0.0 | 0.0 | 7.0 | 1.0 | | 0.0 | 8.0 | 0.0 |
| | .016 | 0.0 | 0.0 | 0.0 | 0.0 | 1.0 | 0.0 | 0.0 | 0.0 | 0.0 | 3.0 | 0.0 | | 0.0 | 0.0 | 0.0 |
| 2-Isopropyl-2-methyl-8-propyl-5H—imidazo-[1',2':1,2]pyrrolo-[3,4-b]pyridine-3-(2H), 5-dione | .500 | 6.0 | | 9.0 | 4.0 | 9.0 | 9.0 | 7.0 | 5.0 | 6.0 | 9.0 | 9.0 | | | 2.0 | 7.0 |
| | .250 | 6.0 | | 9.0 | 4.0 | 8.0 | 9.0 | 7.0 | 5.0 | 6.0 | 6.0 | 7.0 | | | 0.0 | 4.0 |
| | .125 | 1.0 | | 3.0 | 2.0 | 5.0 | 6.0 | 5.0 | 5.0 | 3.0 | 4.0 | 7.0 | | | 0.0 | 2.0 |
| | .063 | 0.0 | | 2.0 | 0.0 | 3.0 | 3.0 | 3.0 | | 2.0 | 2.0 | 4.0 | | | 0.0 | 2.0 |
| | .032 | 0.0 | | 1.0 | 0.0 | 3.0 | 2.0 | 2.0 | | 1.0 | 2.0 | 4.0 | | | 0.0 | 2.0 |
| | .016 | 0.0 | | 1.0 | 0.0 | 0.0 | 0.0 | 1.0 | 0.0 | 0.0 | 2.0 | 2.0 | | | 0.0 | 2.0 |
| 2,8-Diisopropyl-2-methyl-5H—imidazo-[1',2':1,2]pyrrolo-[3,4-b]pyridine-3-(2H), 5-dione | 8.000 | 9.0 | 9.0 | 9.0 | 8.0 | 9.0 | 9.0 | 8.0 | 8.0 | 8.0 | | | | | | |
| 2-(5-Isopropyl-5-methyl-4-oxo-2-imidazolin-2-yl)-6-phenoxynicotinic acid | .500 | 9.0 | 9.0 | 7.0 | 6.0 | 9.0 | 6.0 | 7.0 | 2.0 | 6.0 | 8.0 | 9.0 | 9.0 | 4.0 | 9.0 | |
| | .250 | 7.0 | 8.0 | 1.0 | 3.0 | 9.0 | | 3.0 | 1.0 | 5.0 | 7.0 | 2.0 | 9.0 | 3.0 | 3.0 | |
| | .125 | 3.0 | 7.0 | 0.0 | 0.0 | 2.0 | 3.0 | 1.0 | 1.0 | 3.0 | 2.0 | 1.0 | 9.0 | 0.0 | 2.0 | |
| | .063 | 0.0 | 3.0 | 0.0 | 0.0 | 1.0 | 0.0 | 0.0 | 0.0 | 1.0 | 1.0 | 1.0 | 2.0 | 0.0 | 2.0 | |

TABLE XII-continued

| | PRE-EMERGENCE TESTS - RATES IN KG/HA | | | | | | | | | | | | | | | |
|---|---|---|---|---|---|---|---|---|---|---|---|---|---|---|---|---|
| | .032 | 0.0 | 0.0 | 0.0 | 0.0 | 0.0 | 0.0 | 0.0 | 0.0 | 0.0 | 0.0 | 1.0 | 0.0 | 0.0 | 2.0 | |
| | .016 | 0.0 | 0.0 | 0.0 | 0.0 | 0.0 | 0.0 | 0.0 | 0.0 | 0.0 | 0.0 | 1.0 | 0.0 | 0.0 | 2.0 | |
| Methyl 2-[1-(p-chloro- | .500 | 9.0 | 9.0 | 9.0 | 9.0 | 9.0 | 9.0 | 9.0 | 9.0 | 9.0 | 9.0 | 9.0 | 9.0 | 9.0 | 9.0 | |
| benzoyl)-4-isopropyl- | .250 | 9.0 | 9.0 | 9.0 | 9.0 | 9.0 | 9.0 | 9.0 | 8.0 | 9.0 | 9.0 | 9.0 | 9.0 | 9.0 | 9.0 | |
| 4-methyl-5-oxo-2- | .125 | 9.0 | 9.0 | 9.0 | 9.0 | 9.0 | 9.0 | 9.0 | 7.0 | 9.0 | 9.0 | 9.0 | 9.0 | 9.0 | 9.0 | |
| imidazolin-2-yl]- | .063 | 4.0 | 9.0 | 9.0 | 9.0 | 9.0 | 9.0 | 8.0 | 3.0 | 9.0 | 9.0 | 9.0 | 7.0 | 7.0 | 9.0 | |
| nicotinoate | .032 | 3.0 | 9.0 | 8.0 | 7.0 | 9.0 | 9.0 | 6.0 | 1.0 | 9.0 | 9.0 | 9.0 | 6.0 | | 5.0 | |
| | .016 | 1.0 | 3.0 | 6.0 | 4.0 | 8.0 | 3.0 | 4.0 | 0.0 | 9.0 | 8.0 | 4.0 | 6.0 | | 4.0 | |
| Methyl 2-(1-p-anisoyl-4- | .500 | 9.0 | 9.0 | 9.0 | 9.0 | 9.0 | 9.0 | 9.0 | 9.0 | 9.0 | 9.0 | 9.0 | 9.0 | 9.0 | 9.0 | |
| isopropyl-4-methyl-5-oxo- | .250 | 7.0 | 9.0 | 9.0 | 9.0 | 9.0 | 9.0 | 9.0 | 8.0 | 9.0 | 9.0 | 9.0 | 9.0 | 9.0 | 9.0 | |
| 2-imidazolin-2-yl)- | .125 | 7.0 | 9.0 | 8.0 | 9.0 | 9.0 | 9.0 | 9.0 | 5.0 | 9.0 | 9.0 | 9.0 | 9.0 | 9.0 | 9.0 | |
| nicotinate | .063 | 5.0 | 9.0 | 8.0 | 9.0 | 9.0 | 9.0 | 8.0 | 4.0 | 9.0 | 9.0 | 9.0 | 8.0 | 9.0 | 7.0 | |
| | .032 | 4.0 | 7.0 | 8.0 | 8.0 | 9.0 | 8.0 | 5.0 | 1.0 | 9.0 | 9.0 | 6.0 | 7.0 | 6.0 | 4.0 | |
| | .016 | 2.0 | 3.0 | 2.0 | 6.0 | 7.0 | 3.0 | 2.0 | 0.0 | 7.0 | 8.0 | 4.0 | 7.0 | | 3.0 | |
| Methyl 2-[4-isopropyl-4- | 8.000 | 9.0 | 9.0 | 9.0 | 8.0 | 9.0 | 9.0 | 7.0 | 9.0 | 8.0 | | | | | | |
| methyl-1-p-nitrobenzoyl)- | .500 | 9.0 | 9.0 | 9.0 | 9.0 | 9.0 | 9.0 | 9.0 | 8.0 | 9.0 | 9.0 | 9.0 | 9.0 | 9.0 | 9.0 | |
| 5-oxo-2-imidazolin-2-yl)- | .250 | 9.0 | 9.0 | 9.0 | 9.0 | 9.0 | 9.0 | 9.0 | 6.0 | 9.0 | 9.0 | 9.0 | 9.0 | 9.0 | 9.0 | |
| nicotinate | .125 | 8.0 | 9.0 | 8.0 | 9.0 | 9.0 | 9.0 | 9.0 | 2.0 | 9.0 | 9.0 | 9.0 | 9.0 | 9.0 | 9.0 | |
| | .063 | 5.0 | 7.0 | 7.0 | 8.0 | 8.0 | 9.0 | 8.0 | 1.0 | 9.0 | 9.0 | 8.0 | 7.0 | 6.0 | 5.0 | |
| | .032 | 3.0 | 4.0 | 7.0 | 7.0 | 9.0 | 9.0 | 4.0 | 0.0 | 8.0 | 6.0 | 6.0 | 6.0 | 4.0 | 3.0 | |
| 6-Ethoxy-2-(5-iso- | .500 | 9.0 | 9.0 | 9.0 | 9.0 | 9.0 | 9.0 | 9.0 | 5.0 | 9.0 | 9.0 | 9.0 | 9.0 | 9.0 | 9.0 | 8.0 |
| propyl-5-methyl-4- | .250 | 8.0 | 8.0 | 9.0 | 7.0 | 9.0 | 9.0 | 9.0 | 3.0 | 7.0 | 8.0 | 9.0 | 9.0 | 8.0 | 9.0 | 7.0 |
| oxo-2-imidazolin-2- | .125 | 3.0 | 3.0 | 9.0 | 6.0 | 9.0 | 9.0 | 9.0 | 2.0 | 7.0 | 7.0 | 9.0 | 7.0 | | 9.0 | 6.0 |
| yl)nicotinic acid | .063 | 0.0 | 1.0 | 9.0 | 4.0 | 4.0 | 9.0 | 7.0 | 1.0 | 4.0 | 3.0 | 4.0 | 6.0 | 6.0 | 4.0 | 2.0 |
| | .032 | 0.0 | 0.0 | 7.0 | 1.0 | 4.0 | 6.0 | 1.0 | 0.0 | 4.0 | 1.0 | 3.0 | 2.0 | 3.0 | 3.0 | 0.0 |
| | .016 | 0.0 | 0.0 | 7.0 | 0.0 | 1.0 | 1.0 | 0.0 | 0.0 | 1.0 | 1.0 | 2.0 | 1.0 | | 2.0 | 0.0 |
| 2-(5-Isopropyl-5- | .500 | 9.0 | 9.0 | 9.0 | 9.0 | 9.0 | 9.0 | 9.0 | 7.0 | 8.0 | 9.0 | 9.0 | 9.0 | 7.0 | 9.0 | 8.0 |
| methyl-4-oxo-2- | .250 | 8.0 | 9.0 | 9.0 | 6.0 | 7.0 | 9.0 | 8.0 | 3.0 | 6.0 | 7.0 | 8.0 | 9.0 | | 7.0 | 6.0 |
| imidazolin-2-yl)- | .125 | 2.0 | 1.0 | 9.0 | 4.0 | 7.0 | 6.0 | 7.0 | 3.0 | 5.0 | 4.0 | 7.0 | 3.0 | 3.0 | 7.0 | 4.0 |
| 6-(methylthio)- | .063 | 1.0 | 0.0 | 6.0 | 0.0 | 3.0 | 2.0 | 3.0 | 3.0 | 2.0 | 1.0 | 3.0 | 2.0 | | 5.0 | 0.0 |
| nicotinic acid | | | | | | | | | | | | | | | | |
| 2-(5-Isopropyl-5- | 4.000 | 9.0 | 9.0 | 9.0 | 9.0 | 9.0 | 9.0 | 9.0 | 9.0 | 9.0 | | 9.0 | 9.0 | 9.0 | 9.0 | 9.0 |
| methyl-4-oxo-2- | 1.000 | 9.0 | 9.0 | 9.0 | 9.0 | 9.0 | 9.0 | 9.0 | 9.0 | 9.0 | | 9.0 | 9.0 | 9.0 | 9.0 | 9.0 |
| imidazolin-2-yl)- | | | | | | | | | | | | | | | | |
| 5-methylnicotinic | | | | | | | | | | | | | | | | |
| acid | | | | | | | | | | | | | | | | |
| Methyl 2-(5-isopropyl | 4.000 | 9.0 | 9.0 | 9.0 | 9.0 | 9.0 | 9.0 | 9.0 | 9.0 | 9.0 | | 9.0 | 9.0 | 9.0 | 9.0 | 9.0 |
| 5-methyl-4-oxo-2- | 1.000 | 9.0 | 9.0 | 9.0 | 9.0 | 9.0 | 9.0 | 9.0 | 9.0 | 9.0 | | 9.0 | 9.0 | 9.0 | 9.0 | 9.0 |
| imidazolin-2-yl)-5- | | | | | | | | | | | | | | | | |
| methylnicotinate | | | | | | | | | | | | | | | | |
| Methyl 5-(hydroxy- | 4.000 | 3.0 | 4.0 | 8.0 | 4.0 | 9.0 | 8.0 | 8.0 | 2.0 | 6.0 | | 9.0 | 9.0 | 4.0 | 7.0 | |
| methyl)-2-(5-iso- | 1.000 | 1.0 | 4.0 | 9.0 | 2.0 | 9.0 | 7.0 | 7.0 | 1.0 | 5.0 | | 7.0 | 7.0 | 2.0 | 7.0 | |
| propyl-5-methyl-4- | | | | | | | | | | | | | | | | |
| oxo-2-imidazolin- | | | | | | | | | | | | | | | | |
| 2-yl)nicotinate | | | | | | | | | | | | | | | | |
| Methyl 5-butyl-2- | .500 | 0.0 | 6.0 | 0.0 | 0.0 | 9.0 | 9.0 | 3.0 | 3.0 | 3.0 | 3.0 | 0.0 | 9.0 | | 3.0 | |
| (5-isopropyl-5- | .250 | 0.0 | 2.0 | 0.0 | 0.0 | 7.0 | 9.0 | 2.0 | 1.0 | 1.0 | 3.0 | 0.0 | 8.0 | 3.0 | 2.0 | |
| methyl-4-oxo-2- | .125 | 0.0 | 0.0 | 0.0 | 0.0 | 3.0 | 6.0 | 2.0 | 1.0 | 0.0 | 1.0 | 0.0 | 8.0 | 0.0 | 0.0 | |
| imidazolin-2-yl)- | .063 | 0.0 | 0.0 | 0.0 | 0.0 | 1.0 | 5.0 | 1.0 | 0.0 | 0.0 | 0.0 | 0.0 | 4.0 | 0.0 | 0.0 | |
| nicotinate | .032 | 0.0 | 0.0 | 0.0 | 0.0 | 0.0 | | 0.0 | 0.0 | 0.0 | 0.0 | 0.0 | 3.0 | 0.0 | 0.0 | |
| 2-(5-Isopropyl-5- | 4.000 | 3.0 | 8.0 | 1.0 | 4.0 | 9.0 | 9.0 | 2.0 | 1.0 | 3.0 | | 9.0 | 9.0 | 4.0 | 5.0 | |
| methyl-4-oxo-2- | 1.000 | 1.0 | 8.0 | 0.0 | 2.0 | 9.0 | 6.0 | 1.0 | 0.0 | 3.0 | | 3.0 | 9.0 | 1.0 | 2.0 | |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| imidazolin-2-yl)-5-phenylnicotinic acid | .500 | 0.0 | 2.0 | 0.0 | 1.0 | 0.0 | 2.0 | 0.0 | 0.0 | 0.0 | 3.0 | 6.0 | 1.0 | 2.0 | |
| | .250 | 0.0 | 0.0 | 0.0 | 1.0 | 0.0 | 0.0 | 0.0 | 0.0 | 0.0 | 1.0 | 5.0 | 0.0 | 2.0 | |
| 2-(5-Isopropyl-5-methyl-4-oxo-2-imidazolin-2-yl)-6-phenylnicotinic acid | 4.000 | 3.0 | 4.0 | 9.0 | 3.0 | 9.0 | 9.0 | 4.0 | 4.0 | 7.0 | 9.0 | 7.0 | 6.0 | 9.0 | |
| | 1.000 | 2.0 | 4.0 | 9.0 | 9.0 | 9.0 | 9.0 | 4.0 | 6.0 | 6.0 | 9.0 | 5.0 | 4.0 | 9.0 | |
| | .500 | 2.0 | 4.0 | 9.0 | | 9.0 | 9.0 | | | 5.0 | | | | 9.0 | |
| 2-(5-Isopropyl-5-methyl-4-oxo-2-imidazolin-2-yl)-6-methylnicotinic acid | 4.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 9.0 | 9.0 | 9.0 |
| Methyl 2-(5-isopropyl-5-methyl-4-oxo-2-imidazolin-2-yl)-6-phenylnicotinate | .500 | 9.0 | | 7.0 | 4.0 | 9.0 | 1.0 | 4.0 | 2.0 | 0.0 | 7.0 | 3.0 | 1.0 | 2.0 | 2.0 |
| | .250 | 4.0 | | 2.0 | 1.0 | 6.0 | 1.0 | 2.0 | 0.0 | 0.0 | 4.0 | 0.0 | 1.0 | 1.0 | 2.0 |
| | .125 | 3.0 | | 2.0 | 1.0 | 4.0 | 0.0 | 1.0 | 0.0 | 0.0 | 2.0 | 0.0 | 0.0 | 0.0 | 1.0 |
| 5-Isopropyl-5-methyl-2-[3-(2-oxazolin-2-yl)-2-pyridyl]-2-imidazolin-4-one | .500 | 7.0 | 9.0 | 9.0 | 9.0 | 9.0 | 9.0 | 9.0 | 9.0 | 9.0 | 9.0 | 9.0 | | 9.0 | 9.0 |
| | .250 | 6.0 | 9.0 | 7.0 | 9.0 | 9.0 | 8.0 | 9.0 | 5.0 | 8.0 | 9.0 | 9.0 | | 8.0 | 9.0 |
| | .125 | 5.0 | 6.0 | 7.0 | 9.0 | 9.0 | 7.0 | 7.0 | 4.0 | 8.0 | 9.0 | 9.0 | | 7.0 | 9.0 |
| | .063 | 1.0 | 4.0 | 1.0 | 6.0 | 7.0 | 9.0 | 4.0 | 0.0 | 4.0 | 7.0 | 9.0 | | 4.0 | 9.0 |
| | .032 | 0.0 | 0.0 | 1.0 | 4.0 | 4.0 | 0.0 | 1.0 | 0.0 | 3.0 | 4.0 | 6.0 | | 1.0 | 8.0 |
| | .016 | 0.0 | 0.0 | 0.0 | 2.0 | 0.0 | 0.0 | 0.0 | 0.0 | 1.0 | 4.0 | 3.0 | | 1.0 | 6.0 |
| 5-Ethyl-2-(5-isopropyl-5-methyl-4-oxo-2-imidazolin-2-yl)nicotinic acid | 4.000 | 9.0 | 9.0 | 9.0 | 9.0 | 9.0 | 9.0 | 9.0 | 9.0 | 9.0 | 9.0 | 9.0 | 8.0 | 9.0 | 9.0 |
| | 1.000 | 9.0 | 9.0 | 9.0 | 9.0 | 9.0 | 9.0 | 9.0 | 9.0 | 9.0 | 9.0 | 9.0 | 6.0 | 9.0 | 9.0 |
| | .500 | 9.0 | 9.0 | 9.0 | 8.7 | 9.0 | 9.0 | 9.0 | 9.0 | 9.0 | 9.0 | 9.0 | 5.7 | 9.0 | 9.0 |
| | .250 | 9.0 | | 9.0 | 9.0 | 9.0 | 9.0 | 9.0 | 9.0 | 9.0 | 9.0 | 9.0 | 5.0 | 9.0 | 9.0 |
| | .125 | 9.0 | | 9.0 | 8.5 | 9.0 | 9.0 | 8.0 | 7.5 | 9.0 | 9.0 | 9.0 | 3.5 | 9.0 | 7.5 |
| | .063 | 6.0 | | 9.0 | 7.5 | 9.0 | 9.0 | 7.0 | 4.0 | 8.5 | 8.0 | 9.0 | 2.5 | 9.0 | 3.0 |
| | .032 | 2.0 | | 8.5 | 3.5 | 9.0 | 9.0 | 4.5 | 0.0 | 7.5 | 5.5 | 9.0 | 1.0 | 8.5 | 1.5 |
| Methyl 5-ethyl-2-(5-isopropyl-5-methyl-4-oxo-2-imidazolin-2-yl)nicotinate | 1.000 | | | | | | | | | | 9.0 | | | | |
| | .500 | 9.0 | 9.0 | 9.0 | 9.0 | 9.0 | 9.0 | 7.0 | 8.0 | 9.0 | 5.4 | 9.0 | | 9.0 | 9.0 |
| | .250 | 9.0 | 7.0 | 9.0 | 8.0 | 9.0 | 9.0 | 8.0 | 7.0 | 6.0 | 4.4 | 9.0 | | 9.0 | 9.0 |
| | .125 | 7.0 | 7.0 | 8.0 | 7.0 | 9.0 | 9.0 | 6.0 | 2.0 | 5.0 | 1.9 | 9.0 | | 6.0 | 9.0 |
| | .063 | 2.0 | 1.0 | 7.0 | 4.0 | 9.0 | 5.0 | 4.0 | 1.0 | 4.0 | 3.7 | 9.0 | | 6.0 | 7.0 |
| | .032 | 1.0 | 0.0 | 4.0 | 2.0 | 7.0 | 4.0 | 2.0 | 0.0 | 4.0 | 0.0 | 8.0 | | 6.0 | 7.0 |
| 6-Ethyl-2-(5-isopropyl-5-methyl-4-oxo-2-imidazolin-2-yl)nicotinic acid | .500 | 9.0 | | 9.0 | 8.0 | 9.0 | 9.0 | 9.0 | 9.0 | 9.0 | 9.0 | 9.0 | 6.0 | 9.0 | 9.0 |
| | .250 | 9.0 | | 9.0 | 7.0 | 9.0 | 9.0 | 9.0 | 9.0 | 8.0 | 9.0 | 9.0 | 5.0 | 9.0 | 7.0 |
| | .125 | 6.0 | | 9.0 | 7.0 | 9.0 | 9.0 | 9.0 | 9.0 | 7.0 | 9.0 | 8.0 | 3.0 | 8.0 | 7.0 |
| | .063 | 4.0 | | 9.0 | 6.0 | 4.0 | 9.0 | 6.0 | 9.0 | 5.0 | 4.0 | 8.0 | 2.0 | 4.0 | 5.0 |
| | .032 | 0.0 | | 9.0 | 3.0 | 2.0 | 3.0 | 3.0 | 9.0 | 3.0 | | 8.0 | 1.0 | 4.0 | 4.0 |
| | .016 | 0.0 | | 5.0 | 0.0 | 1.0 | 1.0 | 0.0 | 4.0 | 2.0 | 4.0 | 3.0 | 1.0 | 1.0 | 4.0 |
| Ethyl 2-(5-isopropyl-5-methyl-4-oxo-2-imidazolin-2-yl)-6-propylnicotinate | .500 | 8.0 | | 0.0 | 7.0 | 0.0 | 7.0 | 7.0 | 9.0 | 7.0 | 2.0 | 4.0 | 0.0 | 0.0 | 4.0 |
| | .250 | 3.0 | | 0.0 | 7.0 | 0.0 | 2.0 | 5.0 | 9.0 | 4.0 | 2.0 | 2.0 | 0.0 | 0.0 | 3.0 |
| | .125 | 1.0 | | 0.0 | 4.0 | 0.0 | 2.0 | 3.0 | 6.0 | 4.0 | 2.0 | 1.0 | 0.0 | 0.0 | 3.0 |
| | .063 | 0.0 | | 0.0 | 3.0 | 0.0 | 0.0 | 2.0 | 4.0 | 1.0 | 2.0 | 1.0 | 0.0 | 0.0 | 2.0 |
| 2-(5-Isopropyl-5-methyl-4-oxo-2-imidazolin-2-yl)-6-propylnicotinic acid | .500 | 8.0 | | 9.0 | 7.0 | 9.0 | 9.0 | 9.0 | 6.0 | 8.0 | 9.0 | 9.0 | 3.0 | 7.0 | 7.0 |
| | .250 | 4.0 | | 8.0 | 5.0 | 8.0 | 9.0 | 7.0 | 6.0 | 7.0 | 6.0 | 9.0 | | 6.0 | 4.0 |
| | .125 | 4.0 | | 8.0 | 5.0 | 4.0 | 8.0 | 5.0 | | 4.0 | 6.0 | 9.0 | 2.0 | 3.0 | 4.0 |
| | .063 | 0.0 | | 3.0 | 3.0 | 4.0 | 5.0 | 3.0 | | 0.0 | 6.0 | 4.0 | 0.0 | 2.0 | 3.0 |
| Methyl 2-(5-isopropyl-5-methyl-4-oxo-2-imidazolin- | .500 | 9.0 | | 7.0 | 7.0 | 9.0 | 9.0 | 7.0 | 0.0 | 4.0 | 9.0 | 7.0 | 0.0 | 0.0 | 6.0 |
| | .250 | 9.0 | | 4.0 | 6.0 | 9.0 | 7.0 | 7.0 | 0.0 | 2.0 | 4.0 | 4.0 | 0.0 | 0.0 | 5.0 |
| | .125 | 7.0 | | 0.0 | 2.0 | 5.0 | 4.0 | 2.0 | | 0.0 | 3.0 | 3.0 | 0.0 | 0.0 | 3.0 |

TABLE XII-continued

| PRE-EMERGENCE TESTS - RATES IN KG/HA | | | | | | | | | | | | | | | |
|---|---|---|---|---|---|---|---|---|---|---|---|---|---|---|---|
| 2-yl)-6-propyl- | .063 | 5.0 | | 0.0 | 2.0 | 2.0 | 1.0 | 2.0 | | 0.0 | 3.0 | 3.0 | 0.0 | 0.0 | 2.0 |
| nicotinate | | | | | | | | | | | | | | | |
| Ethyl 6-ethyl-2- | .500 | 8.0 | | 8.0 | 9.0 | 9.0 | 9.0 | 7.0 | 7.0 | 7.0 | 6.0 | 7.0 | 4.0 | 6.0 | 5.0 |
| (5-isopropyl-5- | .250 | 7.0 | | 8.0 | 7.0 | 4.0 | 9.0 | 7.0 | | 7.0 | 1.0 | 5.0 | 2.0 | 4.0 | 4.0 |
| methyl-4-oxo-2- | .125 | 3.0 | | 6.0 | 5.0 | 0.0 | 7.0 | 4.0 | 0.0 | 6.0 | 0.0 | 5.0 | 0.0 | 2.0 | 3.0 |
| imidazolin-2-yl)- | .063 | 1.0 | | 3.0 | 4.0 | 0.0 | 4.0 | 4.0 | 0.0 | 5.0 | 0.0 | 4.0 | 0.0 | 1.0 | 3.0 |
| nicotinate | | | | | | | | | | | | | | | |
| Isopropyl 6-ethyl- | .500 | 6.0 | | 3.0 | 4.0 | 5.0 | 7.0 | 7.0 | 4.0 | 6.0 | 4.0 | 5.0 | 0.0 | 3.0 | 5.0 |
| 2-(5-isopropyl-5- | .250 | 3.0 | | 1.0 | 4.0 | 5.0 | 3.0 | 6.0 | 2.0 | 6.0 | 3.0 | 4.0 | 0.0 | 1.0 | 3.0 |
| methyl-4-oxo-2- | .125 | 1.0 | | 0.0 | 2.0 | 4.0 | 2.0 | 4.0 | 2.0 | 4.0 | 3.0 | 2.0 | 0.0 | 1.0 | 3.0 |
| imidazolin-2-yl)- | | | | | | | | | | | | | | | |
| nicotinate | | | | | | | | | | | | | | | |
| 6-Isopropyl-2-(5- | .500 | 6.0 | | 9.0 | 5.0 | 9.0 | 9.0 | 7.0 | 3.0 | 7.0 | 7.0 | 6.0 | 5.0 | 5.0 | 4.0 |
| isopropyl-5-methyl- | .250 | 3.0 | | 8.0 | 4.0 | 4.0 | 9.0 | 6.0 | 3.0 | 5.0 | 5.0 | 5.0 | 3.0 | 4.0 | 4.0 |
| 4-oxo-2-imidazolin- | .125 | 1.0 | | 2.0 | 3.0 | 1.0 | 5.0 | 3.0 | 2.0 | 5.0 | | 4.0 | 3.0 | 3.0 | 2.0 |
| 2-yl)nicotinic acid | .063 | 1.0 | | 2.0 | 3.0 | 1.0 | 5.0 | 2.0 | 1.0 | 4.0 | 2.0 | 2.0 | 1.0 | 2.0 | 2.0 |
| Methyl 6-isopropyl- | 8.000 | 9.0 | 9.0 | 9.0 | 8.0 | 9.0 | 9.0 | 8.0 | 8.0 | 8.0 | | | | | |
| 2-(5-isopropyl-5- | .500 | 9.0 | | 8.0 | 7.0 | 9.0 | 9.0 | 7.0 | 0.0 | 7.0 | 7.0 | 6.0 | 5.0 | 6.0 | 7.0 |
| methyl-4-oxo-2- | .250 | 8.0 | | 6.0 | 7.0 | 9.0 | 9.0 | 6.0 | 0.0 | 6.0 | 7.0 | 6.0 | 3.0 | 2.0 | 5.0 |
| imidazolin-2-yl)- | .125 | 7.0 | | 7.0 | 5.0 | 9.0 | 8.0 | 4.0 | 0.0 | 3.0 | 7.0 | 5.0 | 2.0 | 2.0 | 4.0 |
| nicotinate | .063 | 6.0 | | 2.0 | 4.0 | 4.0 | 3.0 | 4.0 | 0.0 | 1.0 | 3.0 | 4.0 | 2.0 | 1.0 | 3.0 |
| | .032 | 4.0 | | 1.0 | 3.0 | 3.0 | 3.0 | 0.0 | 0.0 | 1.0 | 3.0 | 3.0 | 2.0 | 0.0 | 2.0 |
| Methyl 6-ethyl-2-(5- | 5.000 | 9.0 | 9.0 | 9.0 | 8.0 | 9.0 | 9.0 | 8.0 | 8.0 | 8.0 | | | | | |
| isopropyl-5-methyl- | .500 | 9.0 | | 9.0 | 9.0 | 9.0 | 9.0 | 9.0 | 3.0 | 8.0 | 9.0 | 9.0 | 4.0 | 8.0 | 7.0 |
| 4-oxo-2-imidazolin- | .250 | 9.0 | | 9.0 | 9.0 | 9.0 | 9.0 | 7.0 | | 7.0 | 8.0 | 8.0 | 3.0 | 8.0 | 4.0 |
| 2-yl)nicotinate | .125 | 9.0 | | 7.0 | 7.0 | 9.0 | 9.0 | 7.0 | 3.0 | 4.0 | 3.0 | 7.0 | 1.0 | 5.0 | 4.0 |
| | .063 | 7.0 | | 5.0 | 5.0 | 7.0 | 4.0 | 6.0 | 3.0 | 3.0 | 3.0 | 7.0 | 0.0 | 1.0 | 4.0 |
| | .032 | 5.0 | | 3.0 | 5.0 | 2.0 | 4.0 | 4.0 | | 1.0 | 3.0 | 4.0 | 0.0 | 1.0 | 3.0 |
| Ethyl 6-isopropyl-2- | 8.000 | 9.0 | 9.0 | 9.0 | 8.0 | 9.0 | 9.0 | 8.0 | 9.0 | 8.0 | | | | | |
| (5-isopropyl-5-methyl- | .500 | 6.0 | | 2.0 | 7.0 | 7.0 | 9.0 | 4.0 | 0.0 | 3.0 | 0.0 | 3.0 | 0.0 | 0.0 | 0.0 |
| 4-oxo-2-imidazolin-2- | .250 | 1.0 | | 0.0 | 2.0 | 1.0 | 9.0 | 1.0 | 0.0 | 1.0 | 0.0 | 0.0 | 0.0 | 0.0 | 0.0 |
| yl)nicotinate | .125 | 0.0 | | 0.0 | 1.0 | 0.0 | 3.0 | 0.0 | 0.0 | 0.0 | 0.0 | 0.0 | 0.0 | 0.0 | 0.0 |
| Isopropyl 6-isopropyl- | 5.000 | 8.0 | 7.0 | 6.0 | 5.0 | 0.0 | 9.0 | 8.0 | 7.0 | 7.0 | | | | | |
| 2-(5-isopropyl-5- | | | | | | | | | | | | | | | |
| methyl-4-oxo-2-imida- | | | | | | | | | | | | | | | |
| zolin-2-yl)nicotinate | | | | | | | | | | | | | | | |
| 2-(5-Isopropyl-5- | .500 | 9.0 | | 8.0 | 9.0 | 9.0 | 9.0 | 8.0 | 7.0 | 9.0 | 9.0 | 9.0 | 3.0 | 9.0 | 9.0 |
| methyl-4-oxo-2- | .250 | 8.0 | | 4.0 | 7.0 | 8.0 | 9.0 | 7.0 | 7.0 | 7.0 | 9.0 | 8.0 | 1.0 | 7.0 | 7.0 |
| imidazolin-2-yl)- | .125 | 7.0 | | 2.0 | 6.0 | 9.0 | 9.0 | 5.0 | 6.0 | 7.0 | 7.0 | 9.0 | 1.0 | 7.0 | 5.0 |
| 5-propylnicotinic | .063 | 3.0 | | 1.0 | 4.0 | 7.0 | 9.0 | 3.0 | 5.0 | 6.0 | 3.0 | 7.0 | 1.0 | 5.0 | 4.0 |
| acid | .032 | 2.0 | | 1.0 | 4.0 | 6.0 | 9.0 | 0.0 | 5.0 | 4.0 | 3.0 | 6.0 | 1.0 | 3.0 | 2.0 |
| | .016 | 1.0 | | 0.0 | 2.0 | 3.0 | 7.0 | 0.0 | 4.0 | 2.0 | 3.0 | 2.0 | 1.0 | 3.0 | 2.0 |
| 2-(5-Isopropyl-5- | .500 | 8.0 | | 9.0 | 9.0 | 9.0 | 9.0 | 9.0 | 9.0 | 9.0 | 9.0 | 9.0 | 8.0 | 9.0 | 9.0 |
| methyl-4-oxo-2- | .250 | 9.0 | | 9.0 | 8.0 | 9.0 | 9.0 | 9.0 | 6.0 | 9.0 | 9.0 | 9.0 | 5.0 | 8.0 | 9.0 |
| imidazolin-2-yl)- | .125 | 4.0 | | 9.0 | 8.0 | 9.0 | 9.0 | 9.0 | 5.0 | 8.0 | 9.0 | 8.0 | 4.0 | 8.0 | 8.0 |
| 5,6-dimethyl- | .063 | 3.0 | | 8.0 | 7.0 | 9.0 | 9.0 | 6.0 | 4.0 | 6.0 | 9.0 | 9.0 | 4.0 | 6.0 | 7.0 |
| nicotinic acid | .032 | 1.0 | | 8.0 | 7.0 | 9.0 | 9.0 | 4.0 | 4.0 | 4.0 | 9.0 | 9.0 | 4.0 | 6.0 | 7.0 |
| 6-Isopropyl-2-(5- | .500 | 6.0 | | 9.0 | 6.0 | 9.0 | 9.0 | 8.0 | 0.0 | 7.0 | 9.0 | 6.0 | 8.0 | 7.0 | 6.0 |
| isopropyl-5-methyl- | .250 | 2.0 | | 8.0 | 6.0 | 6.0 | 9.0 | 4.0 | 0.0 | 5.0 | 9.0 | 6.0 | 6.0 | 6.0 | 6.0 |
| 4-oxo-2-imidazolin- | .125 | 1.0 | | 8.0 | 5.0 | 6.0 | 9.0 | 2.0 | 0.0 | 4.0 | 7.0 | 5.0 | 5.0 | 5.0 | 4.0 |
| 2-yl)nicotinic acid | .063 | 0.0 | | 3.0 | 4.0 | 2.0 | 5.0 | 1.0 | 0.0 | 2.0 | 4.0 | 4.0 | 3.0 | 3.0 | 3.0 |
| | .032 | 0.0 | | 0.0 | 0.0 | 2.0 | 0.0 | 0.0 | 0.0 | 1.0 | 3.0 | 3.0 | 3.0 | 2.0 | 2.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| Methyl 2-(5-isopropyl-5-methyl-4-oxo-2-imidazolin-2-yl)nicotinate | .500 | 8.0 | | 9.0 | 9.0 | 9.0 | 9.0 | 8.0 | 9.0 | 7.0 | 9.0 | 8.0 | 7.0 | 9.0 | 9.0 |
| | .250 | 7.0 | | 7.0 | 9.0 | 9.0 | 9.0 | 7.0 | 7.0 | 6.0 | 9.0 | 7.0 | 6.0 | 9.0 | 9.0 |
| | .125 | 7.0 | | 8.0 | 9.0 | 9.0 | 9.0 | 7.0 | 6.0 | 5.0 | 8.0 | 6.0 | 5.0 | 7.0 | 9.0 |
| | .063 | 4.0 | | 5.0 | 8.0 | 9.0 | 9.0 | 5.0 | 5.0 | 3.0 | 8.0 | 5.0 | 3.0 | 7.0 | 9.0 |
| | .032 | 2.0 | | 4.0 | 7.0 | 7.0 | 7.0 | 3.0 | 4.0 | 2.0 | 6.0 | 4.0 | 2.0 | 4.0 | 7.0 |
| 5-Isopropyl-2-(5-isopropyl-5-methyl-4-oxo-2-imidazolin-2-yl)nicotinic acid | .500 | 9.0 | | 8.0 | 9.0 | 9.0 | 9.0 | 9.0 | 7.0 | 8.0 | 9.0 | 9.0 | 4.0 | 8.0 | 9.0 |
| | .250 | 9.0 | | 3.0 | 8.0 | 9.0 | 9.0 | 7.0 | 6.0 | 7.0 | 9.0 | 9.0 | 3.0 | 7.0 | 8.0 |
| | .125 | 7.0 | | 3.0 | 8.0 | 9.0 | 9.0 | 7.0 | 6.0 | 4.0 | 9.0 | 9.0 | 2.0 | 7.0 | 7.0 |
| | .063 | 5.0 | | 1.0 | 7.0 | 7.0 | 9.0 | 4.0 | 2.0 | 4.0 | 8.0 | 7.0 | 2.0 | 7.0 | 5.0 |
| | .032 | 3.0 | | 0.0 | 5.0 | 5.0 | 6.0 | 1.0 | 2.0 | 1.0 | 6.0 | 6.0 | 0.0 | 4.0 | 4.0 |
| 4-Isopropyl-1,4-dimethyl-2-(3-methyl-2-pyridyl)-2-imidazolin-5-one | 5.000 | 0.0 | 2.0 | 0.0 | 6.0 | 0.0 | 9.0 | 0.0 | 0.0 | 0.0 | | | | | |
| Methyl 2-(5-isopropyl-5-methyl-4-oxo-2-imidazolin-2-yl)-5-propylnicotinate | .500 | 8.0 | | 3.0 | 8.0 | 9.0 | 9.0 | 4.0 | 7.0 | 9.0 | 9.0 | 9.0 | 1.0 | 9.0 | 8.0 |
| | .250 | 6.0 | | 1.0 | 7.0 | 9.0 | 9.0 | 4.0 | 3.0 | 8.0 | 8.0 | 9.0 | 1.0 | 7.0 | 7.0 |
| | .125 | 6.0 | | 0.0 | 5.0 | 9.0 | 9.0 | 1.0 | 3.0 | 7.0 | 9.0 | 5.0 | 0.0 | 6.0 | 6.0 |
| | .063 | 3.0 | | 0.0 | 3.0 | 4.0 | 4.0 | 1.0 | | 3.0 | 3.0 | 3.0 | 0.0 | 3.0 | 3.0 |
| Methyl 6-isopropyl-2-(5-isopropyl-5-methyl-4-oxo-2-imidazolin-2-yl)nicotinate | .500 | 9.0 | | 7.0 | 9.0 | 9.0 | 8.0 | 9.0 | 0.0 | 6.0 | 9.0 | 8.0 | 8.0 | 6.0 | 7.0 |
| | .250 | 9.0 | | 7.0 | 8.0 | 9.0 | 8.0 | 8.0 | 0.0 | 3.0 | 9.0 | 7.0 | 7.0 | 3.0 | 7.0 |
| | .125 | 8.0 | | 4.0 | 5.0 | 9.0 | 4.0 | 7.0 | 0.0 | 1.0 | 9.0 | 6.0 | 5.0 | 0.0 | 4.0 |
| | .063 | 6.0 | | 1.0 | 3.0 | 4.0 | 2.0 | 4.0 | 0.0 | 1.0 | 6.0 | 3.0 | 2.0 | 0.0 | 3.0 |
| 6-(Dimethylamino)-2-(5-isopropyl-5-methyl-4-oxo-2-imidazolin-2-yl)-nicotinic acid | .500 | 9.0 | | 9.0 | 9.0 | 9.0 | 9.0 | 9.0 | 3.0 | 9.0 | 9.0 | 9.0 | 7.0 | 8.0 | 9.0 |
| | .250 | 6.0 | | 9.0 | 9.0 | 9.0 | 9.0 | 9.0 | 3.0 | 9.0 | 9.0 | 9.0 | 6.0 | 8.0 | 8.0 |
| | .125 | 3.0 | | 9.0 | 9.0 | 9.0 | 9.0 | 9.0 | 0.0 | 8.0 | 5.0 | 9.0 | 3.0 | 7.0 | 6.0 |
| | .063 | 1.0 | | 7.0 | 3.0 | 9.0 | 9.0 | 4.0 | 0.0 | 6.0 | 1.0 | 2.0 | 3.0 | 2.0 | 3.0 |
| | .032 | 0.0 | | 0.0 | 1.0 | 9.0 | 8.0 | 4.0 | 0.0 | 6.0 | 0.0 | 1.0 | 2.0 | 1.0 | 0.0 |
| Methyl 5-isopropyl-2-(5-isopropyl-5-methyl-4-oxo-2-imidazolin-2-yl)-nicotinate | .500 | 9.0 | | 6.0 | 9.0 | 9.0 | 9.0 | 7.0 | 3.0 | 9.0 | 9.0 | 9.0 | 0.0 | 8.0 | 8.0 |
| | .250 | 9.0 | | 1.0 | 9.0 | 9.0 | 9.0 | 9.0 | 0.0 | 7.0 | 8.0 | 9.0 | 0.0 | 6.0 | 7.0 |
| | .125 | 4.0 | | 0.0 | 9.0 | 7.0 | 9.0 | 7.0 | 0.0 | 6.0 | 7.0 | 9.0 | 0.0 | 6.0 | 3.0 |
| | .063 | 1.0 | | 0.0 | 2.0 | 4.0 | 9.0 | 7.0 | 0.0 | 3.0 | 2.0 | 8.0 | 0.0 | 1.0 | 0.0 |
| | .032 | 0.0 | | 0.0 | 1.0 | 1.0 | 9.0 | 7.0 | 0.0 | 1.0 | 1.0 | 6.0 | 0.0 | 0.0 | 0.0 |
| 6,7-Dihydro-2-(5-isopropyl-5-methyl-4-oxo-2-imidazolin-2-yl)-5H—1-pyrindine-3-carboxylic acid | .500 | 9.0 | | 9.0 | 8.0 | 9.0 | 9.0 | 9.0 | 9.0 | 8.0 | 9.0 | 9.0 | 7.0 | 9.0 | 9.0 |
| | .250 | 9.0 | | 9.0 | 9.0 | 9.0 | 9.0 | 9.0 | 8.0 | 9.0 | 9.0 | 9.0 | 7.0 | 9.0 | 9.0 |
| | .125 | 9.0 | | 9.0 | 8.0 | 9.0 | 9.0 | 8.0 | 8.0 | 6.0 | 9.0 | 9.0 | 5.0 | 9.0 | 7.0 |
| | .063 | 9.0 | | 9.0 | 3.0 | 9.0 | 9.0 | 9.0 | 3.0 | 6.0 | 8.0 | 9.0 | 3.0 | 8.0 | 1.0 |
| | .032 | 2.0 | | 8.0 | 3.0 | 9.0 | 9.0 | 6.0 | 0.0 | 3.0 | 3.0 | 9.0 | 3.0 | 8.0 | 1.0 |
| 2-(5-Isopropyl-5-methyl-4-oxo-2-imidazolin-2-yl)-6-(trifluoromethyl)-nicotinic acid | .500 | 1.0 | | 9.0 | 9.0 | 9.0 | 9.0 | 8.0 | 9.0 | 7.0 | 9.0 | 9.0 | 8.0 | 9.0 | 9.0 |
| | .250 | 1.0 | | 9.0 | 9.0 | 9.0 | 9.0 | 9.0 | 1.0 | 7.0 | 9.0 | 9.0 | 7.0 | 9.0 | 9.0 |
| | .125 | 0.0 | | 4.0 | 7.0 | 9.0 | 9.0 | 0.0 | 0.0 | 6.0 | 9.0 | 6.0 | 5.0 | 9.0 | 8.0 |
| | .063 | 0.0 | | 4.0 | 1.0 | 9.0 | 9.0 | 0.0 | 0.0 | 2.0 | 9.0 | 5.0 | 3.0 | 7.0 | 5.0 |
| | .032 | 0.0 | | 2.0 | 0.0 | 9.0 | 9.0 | 0.0 | 0.0 | 2.0 | 2.0 | 0.0 | 1.0 | 2.0 | 2.0 |
| Isopropyl 5-ethyl-2-(5-isopropyl-5-methyl-4-oxo-2-imidazolin-2-yl)-nicotinate | .500 | 9.0 | | 9.0 | 7.0 | 9.0 | 9.0 | 4.0 | 2.0 | 8.0 | 5.0 | 9.0 | 4.0 | 7.0 | 3.0 |
| | .250 | 9.0 | | 9.0 | 6.0 | 9.0 | 9.0 | 2.0 | 1.0 | 7.0 | 4.0 | 9.0 | 3.0 | 7.0 | 3.0 |
| | .125 | 9.0 | | 1.0 | 2.0 | 9.0 | 7.0 | 0.0 | 0.0 | 7.0 | 2.0 | 5.0 | 1.0 | 7.0 | 0.0 |
| | .063 | 8.0 | | 0.0 | 1.0 | 9.0 | 6.0 | 0.0 | 0.0 | 4.0 | 2.0 | 4.0 | 0.0 | 3.0 | 0.0 |
| 2-Propynyl 5-ethyl-2-(5-isopropyl-5-methyl-4-oxo-2- | .500 | 9.0 | | 9.0 | 9.0 | 9.0 | 9.0 | 9.0 | 9.0 | 9.0 | 9.0 | 9.0 | 4.0 | 9.0 | 9.0 |
| | .250 | 9.0 | | 9.0 | 9.0 | 9.0 | 9.0 | 9.0 | 9.0 | 9.0 | 8.0 | 9.0 | 4.0 | 9.0 | 8.0 |
| | .125 | 9.0 | | 9.0 | 9.0 | 9.0 | 9.0 | 9.0 | 9.0 | 9.0 | 7.0 | 9.0 | 3.0 | 9.0 | 6.0 |

TABLE XII-continued

PRE-EMERGENCE TESTS - RATES IN KG/HA

| | | | | | | | | | | | | | | | | |
|---|---|---|---|---|---|---|---|---|---|---|---|---|---|---|---|---|
| imidazolin-2-yl)- | .063 | 8.0 | | 7.0 | 7.0 | 9.0 | 9.0 | 8.0 | 7.0 | 9.0 | | 7.0 | 9.0 | 3.0 | 8.0 | 6.0 |
| nicotinate | .032 | 8.0 | | 8.0 | 4.0 | 9.0 | 9.0 | 7.0 | 7.0 | 7.0 | | 5.0 | 6.0 | 2.0 | 8.0 | 5.0 |
| Calcium 5-ethyl-2- | .500 | 9.0 | | 9.0 | 9.0 | 9.0 | 9.0 | 9.0 | 9.0 | 9.0 | | 9.0 | 9.0 | 5.0 | 9.0 | 9.0 |
| (5-isopropyl-5- | .250 | 9.0 | | 9.0 | 9.0 | 9.0 | 9.0 | 9.0 | 9.0 | 9.0 | | 9.0 | 9.0 | 4.0 | 9.0 | 9.0 |
| methyl-4-oxo-2- | .125 | 9.0 | | 9.0 | 8.0 | 9.0 | 9.0 | 8.0 | 9.0 | 9.0 | | 8.0 | 9.0 | 3.0 | 9.0 | 7.0 |
| imidazolin-2-yl)- | .063 | 9.0 | | 9.0 | 3.0 | 9.0 | 9.0 | 7.0 | 7.0 | 9.0 | | 6.0 | 9.0 | 3.0 | 9.0 | 7.0 |
| nicotinate | .032 | 6.0 | | 9.0 | 4.0 | 9.0 | 9.0 | 5.0 | 4.0 | 7.0 | | 6.0 | 9.0 | 2.0 | 9.0 | 4.0 |
| Sodium 5-ethyl-2- | .500 | 9.0 | | 9.0 | 9.0 | 9.0 | 9.0 | 9.0 | 9.0 | 9.0 | | 9.0 | 9.0 | 6.0 | 9.0 | 9.0 |
| (5-isopropyl-5- | .250 | 8.0 | | 9.0 | 9.0 | 9.0 | 9.0 | 9.0 | 9.0 | 9.0 | | 9.0 | 9.0 | 5.0 | 9.0 | 8.0 |
| methyl-4-oxo-2- | .125 | 8.0 | | 9.0 | 7.0 | 9.0 | 9.0 | 9.0 | 9.0 | 9.0 | | 8.0 | 9.0 | 5.0 | 9.0 | 8.0 |
| imidazolin-2-yl)- | .063 | 7.0 | | 9.0 | 7.0 | 9.0 | 9.0 | 7.0 | 3.0 | 9.0 | | 4.0 | 9.0 | 3.0 | 8.0 | 3.0 |
| nicotinate | .032 | 5.0 | | 9.0 | 7.0 | 9.0 | 9.0 | 4.0 | 2.0 | 7.0 | | 3.0 | 9.0 | 3.0 | 7.0 | 1.0 |
| Benzyl 5-ethyl-2- | .500 | 9.0 | | 9.0 | 9.0 | 9.0 | 9.0 | 8.0 | 9.0 | 9.0 | | 8.0 | 9.0 | 4.0 | 9.0 | 7.0 |
| (5-isopropyl-5- | .250 | 9.0 | | 9.0 | 9.0 | 9.0 | 9.0 | 6.0 | 7.0 | 8.0 | | 6.0 | 9.0 | 3.0 | 9.0 | 4.0 |
| methyl-4-oxo-2- | .125 | 9.0 | | 9.0 | 6.0 | 7.0 | 9.0 | 2.0 | 7.0 | 8.0 | | 6.0 | 9.0 | 3.0 | 7.0 | 3.0 |
| imidazolin-2-yl)- | .063 | 3.0 | | 6.0 | 1.0 | 6.0 | 4.0 | 0.0 | 1.0 | 7.0 | | 3.0 | 5.0 | 2.0 | 6.0 | 1.0 |
| nicotinate | .032 | 1.0 | | | 0.0 | 3.0 | 4.0 | 0.0 | 0.0 | 4.0 | | 1.0 | 3.0 | 1.0 | 4.0 | 0.0 |
| Methyl 6-ethoxy-2- | .500 | 9.0 | 9.0 | 9.0 | 9.0 | 9.0 | 9.0 | 8.0 | 2.0 | 7.0 | 9.0 | 9.0 | 6.0 | | 5.0 | 8.0 |
| (5-isopropyl-5- | .250 | 9.0 | 9.0 | 7.0 | 5.0 | 6.0 | 8.0 | 7.0 | 0.0 | 4.0 | 7.0 | 9.0 | 5.0 | | 3.0 | 7.0 |
| methyl-4-oxo-2- | .125 | 7.0 | 7.0 | 7.0 | 3.0 | 2.0 | 4.0 | 5.0 | 0.0 | 1.0 | 4.0 | 7.0 | 5.0 | 4.0 | 2.0 | 3.0 |
| imidazolin-2-yl)- | .063 | 5.0 | 5.0 | 1.0 | 0.0 | 0.0 | 0.0 | 1.0 | 0.0 | 0.0 | 0.0 | 6.0 | 2.0 | | 2.0 | 1.0 |
| nicotinate | .032 | 2.0 | 2.0 | 0.0 | 0.0 | 0.0 | 0.0 | 0.0 | 0.0 | 0.0 | 0.0 | 4.0 | 0.0 | 1.0 | 0.0 | 0.0 |
| Ethyl 5-ethyl-2- | .500 | 9.0 | | 9.0 | 9.0 | 9.0 | 9.0 | 9.0 | 9.0 | 9.0 | | 9.0 | 9.0 | 2.0 | 9.0 | 9.0 |
| (5-isopropyl-5- | .250 | 9.0 | | 9.0 | 9.0 | 9.0 | 9.0 | 6.0 | 8.0 | 8.0 | | 8.0 | 9.0 | 2.0 | 9.0 | 8.0 |
| methyl-4-oxo-2- | .125 | 8.0 | | 7.0 | 6.0 | 9.0 | 9.0 | 5.0 | 4.0 | 7.0 | | 7.0 | 9.0 | 2.0 | 7.0 | 6.0 |
| imidazolin-2-yl)- | .063 | 7.0 | | 5.0 | 3.0 | 9.0 | 9.0 | 2.0 | 0.0 | 7.0 | | 3.0 | 9.0 | 1.0 | 7.0 | 2.0 |
| nicotinate | .032 | 7.0 | | 3.0 | 1.0 | 9.0 | 9.0 | 0.0 | 0.0 | 5.0 | | 3.0 | 3.0 | 1.0 | 7.0 | 1.0 |
| Furfuryl 5-ethyl-2- | .500 | 9.0 | | 9.0 | 9.0 | 9.0 | 9.0 | 9.0 | 9.0 | 9.0 | | 9.0 | 9.0 | 4.0 | 9.0 | 9.0 |
| (5-isopropyl-5- | .250 | 9.0 | | 9.0 | 9.0 | 9.0 | 9.0 | 9.0 | 9.0 | 9.0 | | 8.0 | 9.0 | 4.0 | 9.0 | 9.0 |
| methyl-4-oxo-2- | .125 | 8.0 | | 9.0 | 8.0 | 9.0 | 9.0 | 6.0 | 7.0 | 9.0 | | 8.0 | 9.0 | 4.0 | 9.0 | 6.0 |
| imidazolin-2-yl)- | .063 | 7.0 | | 9.0 | 6.0 | 9.0 | 9.0 | 3.0 | 4.0 | 8.0 | | 7.0 | 9.0 | 3.0 | 7.0 | 3.0 |
| nicotinate | .032 | 4.0 | | 9.0 | 2.0 | 9.0 | 9.0 | 2.0 | 2.0 | 6.0 | | 6.0 | 9.0 | 2.0 | 7.0 | 1.0 |
| Isopropylammonium 5- | .500 | 9.0 | | 9.0 | 9.0 | 9.0 | 9.0 | 9.0 | 9.0 | 9.0 | | 9.0 | 9.0 | 7.0 | 9.0 | 9.0 |
| ethyl-2-(5-isopropyl- | .250 | 9.0 | | 9.0 | 9.0 | 9.0 | 9.0 | 9.0 | 9.0 | 9.0 | | 9.0 | 9.0 | 6.0 | 9.0 | 8.0 |
| 5-methyl-4-oxo-2- | .125 | 9.0 | | 9.0 | 9.0 | 9.0 | 9.0 | 7.0 | 9.0 | 9.0 | | 7.0 | 9.0 | 5.0 | 9.0 | 7.0 |
| imidazolin-2-yl)- | .063 | 7.0 | | 9.0 | 8.0 | 9.0 | 9.0 | 6.0 | 6.0 | 8.0 | | 7.0 | 9.0 | 4.0 | 9.0 | 5.0 |
| nicotinate | .032 | 2.0 | | 9.0 | 6.0 | 9.0 | 9.0 | 2.0 | 2.0 | 7.0 | | 5.0 | 9.0 | 2.0 | 7.0 | 2.0 |
| Benzyltrimethylammonium | .500 | 9.0 | | 9.0 | 9.0 | 9.0 | 9.0 | 9.0 | 9.0 | 9.0 | | 9.0 | 9.0 | 6.0 | 9.0 | 9.0 |
| 5-ethyl-2-(5-isopropyl- | .250 | 9.0 | | 9.0 | 9.0 | 9.0 | 9.0 | 9.0 | 8.0 | 9.0 | | 9.0 | 9.0 | 5.0 | 9.0 | 8.0 |
| 5-methyl-4-oxo-2-imida- | .125 | 7.0 | | 9.0 | 8.0 | 9.0 | 9.0 | 6.0 | 7.0 | 9.0 | | 8.0 | 9.0 | 4.0 | 9.0 | 6.0 |
| zolin-2-yl)nicotinate | .063 | 3.0 | | 9.0 | 7.0 | 9.0 | 9.0 | 4.0 | 3.0 | 9.0 | | 7.0 | 9.0 | 3.0 | 8.0 | 3.0 |
| 7-Ethyl-2-isopropyl-2- | .500 | 9.0 | | 9.0 | 9.0 | 9.0 | 9.0 | 9.0 | 9.0 | 9.0 | 9.0 | 9.0 | | 4.0 | 9.0 | 9.0 |
| methyl-5H—imidazo- | .250 | 9.0 | | 9.0 | 9.0 | 9.0 | 9.0 | 9.0 | 8.0 | 9.0 | 9.0 | 9.0 | | 4.0 | 9.0 | 8.0 |
| [1',2':1,2]pyrrolo- | .125 | 9.0 | | 9.0 | 8.0 | 9.0 | 9.0 | 7.0 | 8.0 | 9.0 | 7.0 | 9.0 | | 3.0 | 9.0 | 7.0 |
| [3,4-b]pyridine-3- | .063 | 9.0 | | 9.0 | 7.0 | 9.0 | 9.0 | 4.0 | 5.0 | 9.0 | 4.0 | 9.0 | | 2.0 | 9.0 | 5.0 |
| (2H),5-dione | .032 | 1.0 | | 8.0 | 5.0 | 9.0 | 9.0 | 0.0 | 0.0 | 8.0 | 3.0 | 9.0 | | 2.0 | 7.0 | 2.0 |
| Methyl 2-(5-iso- | 4.000 | 9.0 | 9.0 | 9.0 | 9.0 | 9.0 | 9.0 | 9.0 | 9.0 | 9.0 | | 9.0 | 9.0 | 9.0 | 9.0 | 9.0 |
| propyl-5-methyl- | 1.000 | 9.0 | 9.0 | 9.0 | 9.0 | 9.0 | 9.0 | 9.0 | 9.0 | 9.0 | | 9.0 | 9.0 | 9.0 | 9.0 | 9.0 |
| 4-oxo-2-imidazolin- | .500 | 9.0 | 9.0 | 9.0 | 9.0 | 9.0 | 9.0 | 9.0 | 9.0 | 9.0 | | 9.0 | 9.0 | 6.0 | 9.0 | 9.0 |
| 2-yl)-6-methyl- | | | | | | | | | | | | | | | | |
| nicotinate | | | | | | | | | | | | | | | | |
| Methyl 5-(1-hydroxy- | 4.000 | 7.0 | 9.0 | 9.0 | 9.0 | 9.0 | 9.0 | 9.0 | 0.0 | 8.0 | | 8.0 | 9.0 | 4.0 | 7.0 | 9.0 |

TABLE XII-continued

PRE-EMERGENCE TESTS - RATES IN KG/HA

| | | | | | | | | | | | | | | |
|---|---|---|---|---|---|---|---|---|---|---|---|---|---|---|
| 1-methylethyl)-2-(5-isopropyl-5-methyl-4-oxo-2-imidazolin-2-yl)-nicotinate | 1.000 | 3.0 | 2.0 | 3.0 | 4.0 | 7.0 | 9.0 | 3.0 | 0.0 | 6.0 | 7.0 | 9.0 | 2.0 | 7.0 | 8.0 |
| | .500 | 1.0 | 0.0 | 0.0 | 1.0 | 5.0 | 6.0 | 0.0 | 0.0 | 5.0 | 4.0 | 7.0 | 1.0 | 2.0 | 5.0 |
| 5-(1-Hydroxy-1-methylethyl)-2-(5-isopropyl-5-methyl-4-oxo-2-imidazolin-2-yl)-nicotinic acid | 4.000 | 8.0 | 9.0 | 9.0 | 9.0 | 9.0 | 9.0 | 9.0 | 6.0 | 9.0 | 9.0 | 9.0 | 2.0 | 9.0 | 9.0 |
| | 1.000 | 5.0 | 9.0 | 6.0 | 8.0 | 9.0 | 9.0 | 9.0 | 0.0 | 7.0 | 7.0 | 9.0 | 1.0 | 4.0 | 8.0 |
| | .500 | 2.0 | 3.0 | 1.0 | 2.0 | 6.0 | 9.0 | 6.0 | 0.0 | 6.0 | 6.0 | 9.0 | 1.0 | 2.0 | 7.0 |
| Isopropyl 2-(5-isopropyl-5-methyl-4-oxo-2-imidazolin-2-yl)-6-propyl-nicotinate | 5.000 | 8.0 | 8.0 | 7.0 | 7.0 | 9.0 | 9.0 | 8.0 | 9.0 | 8.0 | | | | | |
| 6-(Isopropylamino)-2-(5-isopropyl-5-methyl-4-oxo-2-imidazolin-2-yl)-nicotinic acid | .500 | 8.0 | | 9.0 | 9.0 | 9.0 | 9.0 | 9.0 | 9.0 | 8.0 | 9.0 | 9.0 | 7.0 | 9.0 | 9.0 |
| | .250 | 7.0 | | 8.0 | 9.0 | 9.0 | 9.0 | 8.0 | 8.0 | 8.0 | 9.0 | 9.0 | 7.0 | 9.0 | 9.0 |
| | .125 | 3.0 | | 8.0 | 9.0 | 9.0 | 9.0 | 8.0 | 6.0 | 6.0 | 7.0 | 8.0 | 6.0 | 9.0 | 8.0 |
| | .063 | 2.0 | | 2.0 | 9.0 | 9.0 | 4.0 | 4.0 | 5.0 | 5.0 | 5.0 | 7.0 | 5.0 | 7.0 | 7.0 |
| | .032 | 1.0 | | 1.0 | 3.0 | 3.0 | 1.0 | 1.0 | 0.0 | 4.0 | 3.0 | 4.0 | 3.0 | 2.0 | 3.0 |

| Compound | RATE | BARNYARDGR | GREEN FOX | P NUT SEDGE | WILD OATS | QUACK GRASS | FLD B INDWD | MRNGLRY SP | RAGWEED | VELVETLEAF | CORN FIELD | RICE, NATO | SUNFLR XXX | S WHEAT ER |
|---|---|---|---|---|---|---|---|---|---|---|---|---|---|---|
| 2-(5-Isopropyl-5-methyl-4-thiono-2-imidazolin-2-yl)-nicotinic acid | .500 | 9.0 | 9.0 | 9.0 | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | 9.0 | 9.0 | 9.0 | 7.0 | 9.0 | 9.0 | 9.0 | 9.0 | 9.0 |
| | .125 | 7.0 | 9.0 | 9.0 | 9.0 | 9.0 | 9.0 | 9.0 | 4.0 | 9.0 | 9.0 | 9.0 | 9.0 | 9.0 |
| | .063 | 5.0 | 9.0 | 7.0 | 9.0 | 9.0 | 9.0 | 4.0 | 4.0 | 9.0 | 9.0 | 9.0 | 5.0 | 9.0 |
| | .032 | 1.0 | 4.0 | 7.0 | 7.0 | 7.0 | 8.0 | 1.0 | 0.0 | 3.0 | 9.0 | 6.0 | 5.0 | 9.0 |
| Sodium 2-(5-iso-propyl-5-methyl-4-oxo-2-imidazolin-2-yl)-3-quinoline-carboxylate | 4.000 | 9.0 | 9.0 | 9.0 | 9.0 | 9.0 | 9.0 | 9.0 | 9.0 | 9.0 | 9.0 | 9.0 | 9.0 | 9.0 |
| | 1.000 | 9.0 | 9.0 | 9.0 | 9.0 | 9.0 | 9.0 | 9.0 | 9.0 | 9.0 | 9.0 | 9.0 | 9.0 | 9.0 |
| | .660 | 9.0 | | 9.0 | 9.0 | 9.0 | 9.0 | 9.0 | 9.0 | 9.0 | 9.0 | 9.0 | 9.0 | 9.0 |
| | .500 | 9.0 | | 9.0 | 9.0 | 9.0 | 9.0 | 9.0 | 9.0 | 9.0 | 9.0 | 9.0 | 9.0 | 9.0 |
| | .330 | 9.0 | | 9.0 | 9.0 | 9.0 | 9.0 | 9.0 | 9.0 | 8.0 | 9.0 | 9.0 | 9.0 | 9.0 |
| 2-(5-Isopropyl-5-methyl-4-oxo-2-imidazolin-2-yl)-3-quinolinecarbox-aldehyde | 4.000 | 9.0 | 9.0 | 9.0 | 9.0 | 9.0 | 9.0 | 9.0 | 9.0 | 9.0 | 9.0 | 9.0 | 9.0 | 9.0 |
| | 1.000 | 9.0 | 9.0 | 9.0 | 9.0 | 9.0 | 9.0 | 8.0 | 9.0 | 9.0 | 9.0 | 9.0 | 9.0 | 9.0 |
| 2-[3-(Hydroxymethyl)-2-quinolyl]-5-iso-propyl-5-methyl-2-imidazolin-4-one | 4.000 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | | 9.0 | 9.0 | 9.0 | 9.0 | 9.0 | 9.0 | 8.0 | 9.0 | 9.0 | 9.0 | 8.0 |
| | .250 | 8.0 | | 9.0 | 9.0 | 9.0 | 9.0 | 9.0 | 9.0 | 7.0 | 9.0 | 9.0 | 9.0 | 7.0 |
| | .125 | 7.0 | | 9.0 | 8.0 | 9.0 | 9.0 | 9.0 | 9.0 | 7.0 | 9.0 | 9.0 | 7.0 | 7.0 |
| | .063 | 5.0 | | 9.0 | 7.0 | 9.0 | 9.0 | 8.0 | | 6.0 | 9.0 | 6.0 | 7.0 | 6.0 |

| COMPOUND | RATE | BARN-YARDGR | GREEN FOX | P NUT SEDGE | WILD OATS | QUACK GRASS | FLD B INDWD | MRNGLRY SP | RAG-WEED | VELVET-LEAF | CORN FIELD | RICE, NATO | SOYBEAN AD | SUNFLR XXX | S WHEAT ER |
|---|---|---|---|---|---|---|---|---|---|---|---|---|---|---|---|
| Ammonium 2-(5-iso-propyl-5-methyl-4-oxo-2-imidazolin-2-yl)-3-quinoline-carboxylate | 4.000 | 9.0 | 9.0 | 9.0 | 9.0 | 9.0 | 9.0 | 9.0 | 9.0 | 9.0 | 9.0 | 9.0 | 5.0 | 9.0 | 9.0 |
| | 1.000 | 9.0 | 9.0 | 9.0 | 9.0 | 9.0 | 9.0 | 9.0 | 9.0 | 9.0 | 9.0 | 9.0 | 4.0 | 9.0 | 9.0 |
| | .615 | 9.0 | | 9.0 | 9.0 | 9.0 | 9.0 | 8.0 | 9.0 | 9.0 | 9.0 | 9.0 | 3.0 | 9.0 | 9.0 |
| | .500 | 9.0 | | 9.0 | 9.0 | 9.0 | 9.0 | 9.0 | 9.0 | 9.0 | 9.0 | 9.0 | 5.0 | 9.0 | 9.0 |
| | .308 | 9.0 | | 9.0 | 9.0 | 9.0 | 9.0 | 8.0 | 9.0 | 8.0 | 9.0 | 9.0 | 5.0 | 9.0 | 9.0 |

TABLE XII-continued

| PRE-EMERGENCE TESTS - RATES IN KG/HA | | | | | | | | | | | | | | | |
|---|---|---|---|---|---|---|---|---|---|---|---|---|---|---|---|
| 2-Isopropyl-2- | 4.000 | 9.0 | 9.0 | 9.0 | 9.0 | 9.0 | 9.0 | 9.0 | 9.0 | 9.0 | 9.0 | 9.0 | 8.0 | 9.0 | 9.0 |
| methyl-5H—imidazo- | 1.000 | 9.0 | 9.0 | 9.0 | 9.0 | 9.0 | 9.0 | 8.0 | 9.0 | 9.0 | 9.0 | 9.0 | 5.0 | 9.0 | 9.0 |
| [1',2':1,2]pyrrolo- | | | | | | | | | | | | | | | |
| [3,4-b]quinoline-3- | | | | | | | | | | | | | | | |
| (2H), 5-dione | | | | | | | | | | | | | | | |
| Ethyl 2-(5-isopropyl- | 4.000 | 9.0 | 9.0 | 9.0 | 9.0 | 9.0 | 9.0 | 8.0 | 9.0 | 9.0 | 9.0 | 9.0 | 4.0 | 9.0 | 9.0 |
| 5-methyl-4-oxo-2- | 1.000 | 9.0 | 9.0 | 7.0 | 9.0 | 9.0 | 9.0 | 6.0 | 7.0 | 8.0 | 9.0 | 7.0 | 3.0 | 8.0 | 8.0 |
| imidazolin-2-yl)-3- | .500 | 8.0 | 4.0 | 5.0 | 2.0 | 9.0 | 8.0 | 3.0 | 4.0 | 7.0 | 4.0 | 3.0 | | 4.0 | 4.0 |
| quinolinecarboxylate | | | | | | | | | | | | | | | |
| 7-Chloro-2-(5-iso- | 4.000 | 9.0 | 9.0 | 9.0 | 9.0 | 9.0 | 9.0 | 9.0 | 8.0 | 8.0 | 9.0 | 9.0 | | 9.0 | 7.0 |
| propyl-5-methyl-4- | 1.000 | 4.0 | 9.0 | 7.0 | 9.0 | 8.0 | 9.0 | 8.0 | 7.0 | 7.0 | 9.0 | 9.0 | | 7.0 | 5.0 |
| oxo-2-imidazolin-2- | .500 | 2.0 | 6.0 | 7.0 | 9.0 | 9.0 | 9.0 | 6.0 | 2.0 | 3.0 | 9.0 | 9.0 | | 7.0 | 3.0 |
| yl)-3-quinoline- | .250 | 1.0 | 3.0 | 2.0 | 7.0 | 8.0 | 6.0 | 2.0 | 0.0 | 1.0 | 9.0 | 3.0 | | 5.0 | 2.0 |
| carboxylic acid | | | | | | | | | | | | | | | |
| Methyl 2-[(1-car- | 4.000 | 0.0 | 0.0 | 0.0 | 0.0 | 6.0 | 3.0 | 0.0 | 0.0 | 0.0 | 0.0 | 0.0 | | 0.0 | 0.0 |
| bamoyl-1,2-dimethyl- | | | | | | | | | | | | | | | |
| propyl)carbamoyl]-3- | | | | | | | | | | | | | | | |
| quinolinecarboxylate | | | | | | | | | | | | | | | |
| Butyl 2-(5-isopropyl- | 4.000 | 9.0 | 9.0 | 8.0 | 9.0 | 9.0 | 9.0 | 8.0 | 9.0 | 9.0 | 9.0 | 9.0 | 9.0 | 9.0 | 9.0 |
| 5-methyl-4-oxo-2- | 1.000 | 7.0 | 9.0 | 8.0 | 4.0 | 9.0 | 9.0 | 3.0 | 6.0 | 8.0 | 8.0 | 2.0 | 3.0 | 7.0 | 3.0 |
| imidazolin-2-yl)-3- | .500 | 2.0 | 4.0 | 7.0 | 2.0 | 3.0 | 8.0 | 1.0 | 0.0 | 4.0 | 3.0 | 1.0 | 2.0 | 3.0 | 3.0 |
| quinolinecarboxylate | .250 | 1.0 | 1.0 | 1.0 | 1.0 | 9.0 | 9.0 | 0.0 | 0.0 | 3.0 | 2.0 | 0.0 | 1.0 | 2.0 | 0.0 |
| 2-(5-Isopropyl-5- | 4.000 | 1.0 | 1.0 | 9.0 | 6.0 | 2.0 | 9.0 | 2.0 | 0.0 | 1.0 | 9.0 | 2.0 | | 3.0 | 4.0 |
| methyl-4-oxo-2- | 1.000 | 0.0 | 0.0 | 0.0 | 0.0 | 0.0 | 0.0 | 0.0 | 0.0 | 0.0 | 0.0 | 0.0 | | 0.0 | 0.0 |
| 3-quinolinecarbox- | .250 | 0.0 | 0.0 | 0.0 | 0.0 | 0.0 | 0.0 | 0.0 | 0.0 | 0.0 | 0.0 | 0.0 | | 0.0 | 0.0 |
| amide | .125 | 0.0 | 0.0 | 0.0 | 0.0 | 0.0 | 0.0 | 0.0 | 0.0 | 0.0 | 0.0 | 0.0 | | 0.0 | 0.0 |
| | .063 | 0.0 | 0.0 | 0.0 | 0.0 | 0.0 | 0.0 | 0.0 | 0.0 | 0.0 | 0.0 | 0.0 | | 0.0 | 0.0 |
| 5-Dimethylamino-2,5- | 4.000 | 9.0 | 9.0 | 9.0 | 9.0 | 9.0 | 9.0 | 9.0 | 9.0 | 9.0 | 9.0 | 9.0 | | 9.0 | 9.0 |
| dihydro-2-isopropyl- | 1.000 | 9.0 | 9.0 | 9.0 | 9.0 | 9.0 | 9.0 | 9.0 | 9.0 | 9.0 | 9.0 | 9.0 | | 9.0 | 9.0 |
| 2-methyl-3H—imidazo- | .500 | 9.0 | 9.0 | 9.0 | 9.0 | 9.0 | 9.0 | 9.0 | 9.0 | 8.0 | 9.0 | 9.0 | | 9.0 | 9.0 |
| [1',2':1,2]pyrrolo- | .250 | 8.0 | 9.0 | 9.0 | 9.0 | 9.0 | 9.0 | 7.0 | 9.0 | 7.0 | 9.0 | 9.0 | | 9.0 | 9.0 |
| [3,4-b]quinolin-3- | .125 | 6.0 | 8.0 | 9.0 | 7.0 | 8.0 | 9.0 | 9.0 | 6.0 | 6.0 | 9.0 | 7.0 | | 9.0 | 8.0 |
| one | .063 | 2.0 | 7.0 | 8.0 | 7.0 | 7.0 | 9.0 | 4.0 | 4.0 | 4.0 | 9.0 | 7.0 | | 6.0 | 5.0 |
| 2-[3-(α-Hydroxy-α- | 4.000 | 0.0 | 0.0 | 9.0 | 0.0 | 9.0 | 7.0 | 4.0 | 0.0 | 0.0 | 8.0 | 7.0 | | 8.0 | 3.0 |
| methylbenzyl)-2- | 1.000 | 0.0 | 0.0 | 0.0 | 0.0 | 7.0 | 1.0 | 1.0 | 0.0 | 0.0 | 9.0 | 7.0 | | 6.0 | 0.0 |
| quinolyl]-5-iso- | .500 | 0.0 | 0.0 | 0.0 | 0.0 | 2.0 | 0.0 | 0.0 | 0.0 | 0.0 | 3.0 | 3.0 | | 2.0 | 0.0 |
| propyl-5-methyl- | | | | | | | | | | | | | | | |
| 2-imidazolin-4-one | | | | | | | | | | | | | | | |
| 2-(5-Isopropyl-5- | 4.000 | 9.0 | 9.0 | 9.0 | 9.0 | 9.0 | 9.0 | 9.0 | 9.0 | 9.0 | 9.0 | 9.0 | | 9.0 | 9.0 |
| methyl-4-oxo-2- | 1.000 | 8.0 | 9.0 | 9.0 | 9.0 | 9.0 | 9.0 | 9.0 | 9.0 | 7.0 | 9.0 | 9.0 | | 8.0 | 9.0 |
| imidazolin-2-yl)- | .500 | 9.0 | 9.0 | 9.0 | 9.0 | 9.0 | 9.0 | 9.0 | 9.0 | 7.0 | 9.0 | 9.0 | | 8.0 | 9.0 |
| 3-quinolinecarbo- | .250 | 5.0 | 6.0 | 7.0 | 9.0 | 9.0 | 9.0 | 7.0 | 7.0 | 5.0 | 9.0 | 9.0 | | 9.0 | 9.0 |
| xylic acid hydro- | .125 | 4.0 | 3.0 | 7.0 | 9.0 | 9.0 | 9.0 | 5.0 | 7.0 | 3.0 | 9.0 | 8.0 | | 8.0 | 7.0 |
| chloride | .063 | 1.0 | 2.0 | 4.0 | 7.0 | 8.0 | 8.0 | 2.0 | 0.0 | 1.0 | 9.0 | 9.0 | | 7.0 | 5.0 |
| 6-Chloro-2-(5-iso- | 4.000 | 9.0 | 9.0 | 8.0 | 9.0 | 9.0 | 9.0 | 9.0 | 9.0 | 8.0 | 9.0 | 9.0 | 6.0 | 9.0 | 9.0 |
| propyl-5-methyl-4- | 1.000 | 9.0 | 9.0 | 8.0 | 9.0 | 9.0 | 8.0 | 9.0 | 9.0 | 8.0 | 9.0 | 9.0 | 5.0 | 9.0 | 9.0 |
| oxo-2-imidazolin- | .500 | 9.0 | 9.0 | 8.0 | 9.0 | 9.0 | 9.0 | 9.0 | 9.0 | 8.0 | 8.5 | 9.0 | 5.0 | 9.0 | 9.0 |
| 2-yl)-3-quinoline- | .250 | 9.0 | | 8.0 | 9.0 | 9.0 | 9.0 | 8.0 | 9.0 | 7.0 | 9.0 | 9.0 | 3.0 | 9.0 | 9.0 |
| carboxylic acid | .125 | 9.0 | | 9.0 | 8.0 | 9.0 | 9.0 | 7.0 | 8.0 | 7.0 | 3.0 | 9.0 | 2.0 | 9.0 | 8.0 |
| | .063 | 6.0 | | 8.0 | 8.0 | 9.0 | 9.0 | 4.0 | 8.0 | 5.0 | 0.0 | 9.0 | 0.0 | 8.0 | 6.0 |
| 5-Chloro-2-(5-iso- | 4.000 | 9.0 | 9.0 | 9.0 | 9.0 | 9.0 | 9.0 | 9.0 | 9.0 | 9.0 | 9.0 | 9.0 | | 8.0 | 9.0 |
| propyl-5-methyl-4- | 1.000 | 9.0 | 9.0 | 9.0 | 9.0 | 9.0 | 9.0 | 9.0 | 9.0 | 7.0 | 9.0 | 9.0 | | 8.0 | 9.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| oxo-2-imidazolin-2-yl)-3-quinoline-carboxylic acid | .500 | 9.0 | 8.0 | 9.0 | 9.0 | 9.0 | 9.0 | 9.0 | 9.0 | 7.0 | 9.0 | 9.0 | | 7.0 | 9.0 |
| | .250 | 9.0 | 7.0 | 9.0 | 9.0 | 9.0 | 9.0 | 9.0 | 9.0 | 5.0 | 9.0 | 9.0 | | 6.0 | 8.0 |
| | .125 | 8.0 | 3.0 | 7.0 | 9.0 | 8.0 | 9.0 | 7.0 | 6.0 | 3.0 | 9.0 | 7.0 | | 3.0 | 6.0 |
| | .063 | 3.0 | 0.0 | 2.0 | 7.0 | 6.0 | 9.0 | 2.0 | 0.0 | 0.0 | 9.0 | 5.0 | | 3.0 | 5.0 |
| 2-(5-Isopropyl-5-methyl-4-oxo-2-imidazolin-2-yl)-6-nitro-3-quinoline-carboxylic acid | 4.000 | 9.0 | 9.0 | 8.0 | 9.0 | 9.0 | 9.0 | 9.0 | 8.0 | 9.0 | 9.0 | 9.0 | 3.0 | 9.0 | 9.0 |
| | 1.000 | 9.0 | 9.0 | 9.0 | 9.0 | 9.0 | 9.0 | 9.0 | 8.0 | 7.0 | 9.0 | 9.0 | 3.0 | 8.0 | 9.0 |
| | .500 | 8.5 | 8.0 | 7.0 | 7.0 | 9.0 | 9.0 | 8.5 | 7.5 | 6.0 | 8.5 | 9.0 | 3.0 | 8.0 | 8.5 |
| | .250 | 9.0 | | 3.0 | 8.0 | 9.0 | 9.0 | 8.0 | 9.0 | 4.0 | 9.0 | 9.0 | | 8.0 | 7.0 |
| | .125 | 6.0 | | 3.0 | 3.0 | 9.0 | 8.0 | 5.0 | 2.0 | 4.0 | 9.0 | 9.0 | 2.0 | 7.0 | 5.0 |
| | .063 | 2.0 | | 1.0 | 1.0 | 9.0 | | 5.0 | | 2.0 | 7.0 | 7.0 | 1.0 | 5.0 | 3.0 |
| 8-Chloro-1,3-dihydro-α-isopropyl-α-methyl-1,3-dioxo-2H—pyrrolo[3,4-b]-quinoline-2-acetamide | 8.000 | 8.0 | 7.0 | 1.0 | 8.0 | 6.0 | 9.0 | 3.0 | 8.0 | 0.0 | | | | | |
| 2-(5-Isopropyl-5-methyl-4-oxo-2-imidazolin-2-yl)-7-methyl-3-quinoline-carboxylic acid | 4.000 | 9.0 | 9.0 | 8.0 | 9.0 | 9.0 | 9.0 | 9.0 | 9.0 | 9.0 | 9.0 | 9.0 | 9.0 | 9.0 | 9.0 |
| | 1.000 | 9.0 | 9.0 | 8.0 | 9.0 | 9.0 | 9.0 | 9.0 | 9.0 | 8.0 | 9.0 | 9.0 | 7.0 | 9.0 | 9.0 |
| | .500 | 9.0 | 9.0 | 9.0 | 5.0 | 9.0 | 9.0 | 9.0 | 7.0 | 8.0 | 9.0 | 9.0 | 7.0 | 8.0 | 8.0 |
| 2-(5-Isopropyl-5-methyl-4-oxo-2-imidazolin-2-yl)-3-quinoline-carbonitrile | 8.000 | 0.0 | 0.0 | 2.0 | 6.0 | 6.0 | 7.0 | 6.0 | 0.0 | 3.0 | | | | | |
| N—2-(Hydroxyethyl)-2-(5-isopropyl-5-methyl-4-oxo-2-imidazolin-2-yl)-3-quinolinecarbox-amide | 4.000 | 9.0 | 9.0 | 9.0 | 9.0 | 9.0 | 6.0 | 9.0 | 9.0 | 7.0 | 9.0 | 7.0 | 6.0 | 9.0 | 9.0 |
| | 1.000 | 9.0 | 8.0 | 7.0 | 9.0 | 9.0 | 6.0 | 9.0 | 8.0 | 7.0 | 9.0 | 4.0 | 4.0 | 7.0 | 7.0 |
| | .500 | 5.0 | 7.0 | 7.0 | 7.0 | 9.0 | 6.0 | 8.0 | 6.0 | 5.0 | 8.0 | 3.0 | 4.0 | 7.0 | 7.0 |
| Furfuryl 2-(5-iso-propyl-5-methyl-4-oxo-2-imidazolin-2-yl)-3-quinoline-carboxylate | 4.000 | 9.0 | 9.0 | 9.0 | 9.0 | 9.0 | 9.0 | 9.0 | 9.0 | 9.0 | 9.0 | 9.0 | 6.0 | 9.0 | 9.0 |
| | 1.000 | 9.0 | 9.0 | 9.0 | 9.0 | 9.0 | 9.0 | 9.0 | 9.0 | 9.0 | 9.0 | 9.0 | 5.0 | 9.0 | 9.0 |
| | .500 | 9.0 | 9.0 | 9.0 | 9.0 | 9.0 | 9.0 | 9.0 | 9.0 | 8.0 | 9.0 | 9.0 | 5.0 | 9.0 | 9.0 |
| 5-Isopropyl-5-methyl-2-[3-(2-oxazolin-2-yl)-2-quinolyl]-2-imidazolin-4-one | 4.000 | 9.0 | 9.0 | 9.0 | 9.0 | 9.0 | 9.0 | 9.0 | 9.0 | 9.0 | 9.0 | 9.0 | 6.0 | 9.0 | 9.0 |
| | 1.000 | 9.0 | 9.0 | 9.0 | 9.0 | 9.0 | 9.0 | 8.0 | 9.0 | 8.0 | 9.0 | 9.0 | 4.0 | 9.0 | 9.0 |
| | .500 | 9.0 | 9.0 | 9.0 | 8.0 | 9.0 | 9.0 | 8.0 | 9.0 | 7.0 | 9.0 | 9.0 | 4.0 | 8.0 | 8.0 |
| 4-Chloro-2-(5-iso-propyl-5-methyl-4-oxo-2-imidazolin-2-yl)-3-quinoline-carboxylic acid | 4.000 | 2.0 | 0.0 | 9.0 | 1.0 | 9.0 | 9.0 | 9.0 | 0.0 | 9.0 | 3.0 | 6.0 | 3.0 | 8.0 | 3.0 |
| | 1.000 | 0.0 | 0.0 | 3.0 | 0.0 | 9.0 | 9.0 | 7.0 | 0.0 | 3.0 | 1.0 | 3.0 | 0.0 | 2.0 | 1.0 |
| | .500 | 0.0 | 0.0 | 0.0 | 0.0 | 2.0 | 9.0 | 2.0 | 0.0 | 1.0 | 0.0 | 2.0 | 0.0 | 0.0 | 0.0 |
| 2-(5-Isopropyl-5-methyl-4-oxo-2-imidazolin-2-yl)-3-quinolinecarbox-aldehyde, oxime | 8.000 | 8.0 | 7.0 | 9.0 | 8.0 | 9.0 | 9.0 | 2.0 | 0.0 | 7.0 | | | | | |
| | 4.000 | 7.0 | 8.0 | | 6.0 | | | | | | 7.0 | 7.0 | 2.0 | 7.0 | 6.0 |
| | 1.000 | 7.0 | 8.0 | | 6.0 | | | | | | 7.0 | 7.0 | 2.0 | 6.0 | 6.0 |
| | .500 | 2.0 | 3.0 | 7.0 | 4.0 | 9.0 | 2.0 | 3.0 | 8.0 | 2.0 | 9.0 | 4.0 | | 6.0 | |
| | .250 | 1.0 | 1.0 | 7.0 | 1.0 | 3.0 | 1.0 | 2.0 | 8.0 | 1.0 | 7.0 | 4.0 | | 5.0 | |
| | .125 | 1.0 | 0.0 | 3.0 | 0.0 | 0.0 | 0.0 | 1.0 | 6.0 | 0.0 | 5.0 | 3.0 | 3.0 | | |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| 2-(5-Isopropyl-5-methyl-4-oxo-2-imidazolin-2-yl)-6-methyl-3-quinolinecarboxylic acid | .500 | 6.0 | 2.0 | 3.0 | 6.0 | 9.0 | 8.0 | 7.0 | 8.0 | 7.0 | 9.0 | 9.0 | | 7.0 | 9.0 |
| | .250 | 3.0 | 1.0 | 3.0 | 6.0 | 8.0 | 4.0 | 6.0 | 8.0 | 4.0 | 9.0 | 8.0 | | 7.0 | 9.0 |
| | .125 | 2.0 | 0.0 | 1.0 | 3.0 | 7.0 | 2.0 | 3.0 | 6.0 | 2.0 | 7.0 | 6.0 | | 7.0 | 6.0 |
| | .063 | 1.0 | 0.0 | 1.0 | 2.0 | 5.0 | 0.0 | 2.0 | 5.0 | 2.0 | 4.0 | 4.0 | | 4.0 | |
| Methyl 2-(5-isopropyl-5-methyl-4-oxo-2-imidazolin-2-yl)-3-quinolinecarboxylate | .500 | 9.0 | | 2.0 | 0.0 | 4.0 | 9.0 | 2.0 | 9.0 | 3.0 | 3.0 | 0.0 | 2.0 | 2.0 | 0.0 |
| | .250 | 9.0 | | 0.0 | 0.0 | 1.0 | 2.0 | 0.0 | 8.0 | 1.0 | 1.0 | 0.0 | 1.0 | 0.0 | 0.0 |
| | .125 | 8.0 | | 0.0 | 0.0 | 0.0 | 1.0 | | | 0.0 | 0.0 | 0.0 | 1.0 | 0.0 | 0.0 |
| 6-Bromo-2-(5-isopropyl-5-methyl-4-oxo-2-imidazolin-2-yl)-3-quinolinecarboxylic acid | .500 | 8.0 | | 2.0 | 7.0 | 9.0 | 7.0 | 7.0 | 8.0 | 5.0 | 7.0 | 7.0 | 3.0 | 9.0 | 8.0 |
| | .250 | 6.0 | | 1.0 | 7.0 | 9.0 | | 6.0 | 8.0 | 4.0 | 4.0 | 4.0 | 2.0 | 7.0 | 8.0 |
| | .125 | 6.0 | | 0.0 | 7.0 | 7.0 | 0.0 | 4.0 | 7.0 | 0.0 | 4.0 | 4.0 | 2.0 | 7.0 | 6.0 |
| | .063 | 3.0 | | 0.0 | 5.0 | 7.0 | 0.0 | 3.0 | 6.0 | 0.0 | 3.0 | 3.0 | 1.0 | 6.0 | 5.0 |
| | .032 | 1.0 | | 0.0 | 5.0 | | 0.0 | 3.0 | 6.0 | 0.0 | 2.0 | 2.0 | 1.0 | 4.0 | 4.0 |
| 5-Bromo-2-(5-isopropyl-5-methyl-4-oxo-2-imidazolin-2-yl)-3-quinolinecarboxylic acid | .500 | 8.0 | | 6.0 | 9.0 | 9.0 | 9.0 | 9.0 | 8.0 | 6.0 | 9.0 | 9.0 | 3.0 | 5.0 | 9.0 |
| | .250 | 4.0 | | 6.0 | 8.0 | 9.0 | 9.0 | 7.0 | 8.0 | 3.0 | 9.0 | 7.0 | 2.0 | 4.0 | 7.0 |
| | .125 | 4.0 | | 2.0 | 8.0 | 4.0 | 2.0 | 8.0 | 6.0 | 4.0 | 9.0 | 8.0 | 2.0 | 4.0 | 7.0 |
| | .063 | 2.0 | | 1.0 | 8.0 | 4.0 | | 3.0 | | 2.0 | 9.0 | 5.0 | 1.0 | 3.0 | 5.0 |
| | .032 | 1.0 | | 0.0 | 8.0 | 4.0 | | 2.0 | 4.0 | 2.0 | 4.0 | 5.0 | 1.0 | 2.0 | 5.0 |
| | .016 | 0.0 | | 0.0 | 5.0 | 1.0 | 2.0 | 2.0 | 2.0 | 0.0 | 4.0 | 3.0 | 0.0 | 2.0 | 4.0 |
| 2-(5-Isopropyl-5-methyl-4-oxo-2-imidazolin-2-yl)-3-quinolinecarbohydroxamic acid | 8.000 | 9.0 | 9.0 | 9.0 | 8.0 | 9.0 | 9.0 | 8.0 | 9.0 | 8.0 | | | | | |
| | .500 | 7.0 | | 5.0 | 9.0 | 9.0 | 9.0 | 9.0 | 9.0 | 8.0 | 9.0 | 9.0 | 5.0 | 9.0 | 6.0 |
| | .250 | 7.0 | | 9.0 | 7.0 | 9.0 | 9.0 | 7.0 | 9.0 | 6.0 | 9.0 | 8.0 | 4.0 | 9.0 | 5.0 |
| | .125 | 2.0 | | 8.0 | 7.0 | 9.0 | 6.0 | 6.0 | 6.0 | 4.0 | 9.0 | 7.0 | 3.0 | 8.0 | 3.0 |
| | .063 | 1.0 | | 2.0 | 4.0 | 6.0 | 3.0 | 5.0 | 6.0 | 3.0 | 5.0 | 5.0 | 2.0 | 7.0 | 3.0 |
| | .032 | 0.0 | | 1.0 | 4.0 | 6.0 | 1.0 | 5.0 | | 2.0 | 7.0 | 3.0 | 2.0 | 4.0 | 3.0 |
| | .016 | 0.0 | | 0.0 | 3.0 | | 1.0 | 0.0 | | 2.0 | 5.0 | 2.0 | 2.0 | 3.0 | 2.0 |
| 2-(5-Isopropyl-5-methyl-4-oxo-2-imidazolin-2-yl)-4-methoxy-3-quinolinecarboxylic acid | 8.000 | 8.0 | 9.0 | 9.0 | 7.0 | 9.0 | 9.0 | 8.0 | 9.0 | 9.0 | | | | | |
| | .500 | 0.0 | | 7.0 | 4.0 | 8.0 | 9.0 | 9.0 | 6.0 | 6.0 | 6.0 | 4.0 | 4.0 | 9.0 | 4.0 |
| | .250 | 0.0 | | 4.0 | 3.0 | 7.0 | 6.0 | 3.0 | 5.0 | 6.0 | 3.0 | 3.0 | 2.0 | 9.0 | 3.0 |
| | .125 | 0.0 | | 1.0 | 3.0 | 6.0 | 6.0 | 2.0 | 3.0 | 3.0 | 3.0 | 3.0 | 2.0 | 6.0 | 2.0 |
| | .063 | 0.0 | | 0.0 | 1.0 | 4.0 | 4.0 | 2.0 | | 2.0 | 2.0 | 2.0 | 1.0 | 3.0 | 1.0 |
| | .032 | 0.0 | | 0.0 | 1.0 | 3.0 | | 2.0 | | 1.0 | 2.0 | 1.0 | 1.0 | 2.0 | 1.0 |
| 4-Hydroxy-2-(5-isopropyl-5-methyl-4-oxo-2-imidazolin-2-yl)-3-quinolinecarboxylic acid hydrochloride | 8.000 | 9.0 | 7.0 | 6.0 | 5.0 | 9.0 | 9.0 | 9.0 | 9.0 | 8.0 | | | | | |
| 2-(5-Isopropyl-5-methyl-4-oxo-2-imidazolin-2-yl)-6-methoxy-3-quinolinecarboxylic acid | 8.000 | 9.0 | 9.0 | 9.0 | 9.0 | 9.0 | 9.0 | 8.0 | 9.0 | 8.0 | | | | | |
| | .500 | 9.0 | | 9.0 | 8.0 | 9.0 | 9.0 | 8.0 | 9.0 | 8.0 | 9.0 | 9.0 | 4.0 | 9.0 | 6.0 |
| | .250 | 7.0 | | 7.0 | 7.0 | 9.0 | 9.0 | 6.0 | 7.0 | 7.0 | 7.0 | 9.0 | 3.0 | 9.0 | 6.0 |
| | .125 | 5.0 | | 4.0 | 6.0 | 9.0 | 9.0 | 6.0 | 5.0 | 6.0 | 7.0 | 9.0 | 3.0 | 9.0 | 4.0 |
| | .063 | 4.0 | | 3.0 | 4.0 | 7.0 | 3.0 | 3.0 | 4.0 | 6.0 | 6.0 | 8.0 | 2.0 | 4.0 | 4.0 |
| 2-(5-Isopropyl-5-methyl-4-oxo-2-imidazolin-2-yl)-8-methoxy-7-nitro-3-quinolinecar- | .500 | 2.0 | | 0.0 | 0.0 | 9.0 | 0.0 | 0.0 | 0.0 | 0.0 | 9.0 | 0.0 | 2.0 | 2.0 | 1.0 |
| | .250 | 1.0 | | 0.0 | 0.0 | 7.0 | 0.0 | 0.0 | 0.0 | 0.0 | 3.0 | 0.0 | 1.0 | 1.0 | 0.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| boxylic acid | | | | | | | | | | | | | | | |
| Benzyl 2-(5-iso- | .500 | 8.0 | | 8.0 | 6.0 | 7.0 | 8.0 | 3.0 | 2.0 | 4.0 | 8.0 | 4.0 | 2.0 | 6.0 | 2.0 |
| propyl-5-methyl-4- | .250 | 3.0 | | 2.0 | 2.0 | 3.0 | 4.0 | 2.0 | 0.0 | 2.0 | 6.0 | 2.0 | 1.0 | 5.0 | 1.0 |
| oxo-2-imidazolin- | .125 | 1.0 | | 0.0 | 1.0 | 1.0 | 1.0 | 2.0 | | 0.0 | 5.0 | 0.0 | 1.0 | 4.0 | 0.0 |
| 2-yl)-3-quinoline- | | | | | | | | | | | | | | | |
| carboxylic acid | | | | | | | | | | | | | | | |
| 2-(5-Isopropyl-5- | .500 | 9.0 | | 3.0 | 8.0 | 9.0 | 9.0 | 7.0 | 9.0 | 6.0 | 9.0 | 9.0 | 6.0 | 5.0 | 7.0 |
| methyl-4-oxo-2- | .250 | 7.0 | | 2.0 | 9.0 | 9.0 | 9.0 | 7.0 | 8.0 | 5.0 | 9.0 | 9.0 | 5.0 | 5.0 | 6.0 |
| imidazolin-2-yl)- | .125 | 7.0 | | 1.0 | 7.0 | 6.0 | 9.0 | 6.0 | 6.0 | 3.0 | 9.0 | 9.0 | 4.0 | 5.0 | 5.0 |
| 5-methyl-3-quin- | .063 | 5.0 | | 1.0 | 5.0 | 4.0 | 4.0 | 3.0 | 4.0 | 1.0 | 8.0 | 8.0 | 4.0 | 4.0 | 3.0 |
| olinecarboxylic | .032 | 4.0 | | 0.0 | 4.0 | 4.0 | 0.0 | 2.0 | 4.0 | 1.0 | 6.0 | 6.0 | 3.0 | 3.0 | 2.0 |
| acid | | | | | | | | | | | | | | | |
| 2-(5-Ethyl-5-methyl- | .500 | 6.0 | | 9.0 | 7.0 | 7.0 | 9.0 | 7.0 | 4.0 | 6.0 | 9.0 | 9.0 | 4.0 | 8.0 | 5.0 |
| 4-oxo-2-imidazolin- | .250 | 3.0 | | 8.0 | 6.0 | 6.0 | 3.0 | 6.0 | 3.0 | 5.0 | 9.0 | 8.0 | 3.0 | 5.0 | 3.0 |
| 2-yl)-3-quinoline- | .125 | | | 8.0 | 4.0 | 4.0 | 1.0 | 4.0 | 0.0 | 3.0 | 9.0 | 8.0 | 0.0 | 5.0 | 2.0 |
| carboxylic acid | .063 | 0.0 | | 2.0 | 4.0 | 2.0 | 1.0 | 2.0 | 0.0 | 1.0 | 6.0 | 6.0 | 2.0 | 4.0 | 2.0 |
| 2-(4-Oxo-1,3-diaza- | .500 | 3.0 | | 3.0 | 6.0 | 7.0 | 4.0 | 4.0 | 4.0 | 7.0 | 9.0 | 9.0 | 1.0 | 6.0 | 3.0 |
| spiro[4.5]dec-2-en- | .250 | 3.0 | | 0.0 | 4.0 | 5.0 | 2.0 | 2.0 | 3.0 | 2.0 | 4.0 | 8.0 | 1.0 | 4.0 | 2.0 |
| 2-yl)-3-quinoline- | .125 | 3.0 | | 0.0 | 2.0 | 3.0 | 0.0 | 1.0 | 0.0 | 0.0 | 4.0 | 2.0 | 1.0 | 3.0 | 2.0 |
| carboxylic acid | .063 | 2.0 | | 0.0 | 2.0 | 1.0 | 0.0 | 0.0 | 0.0 | 0.0 | 4.0 | 0.0 | 1.0 | 2.0 | 1.0 |
| Methyl 2-(5-iso- | 8.000 | 6.0 | 8.0 | 0.0 | 7.0 | 3.0 | 7.0 | 0.0 | 0.0 | 2.0 | | | | | |
| propyl-5-methyl-4- | | | | | | | | | | | | | | | |
| oxo-2-imidazolin- | | | | | | | | | | | | | | | |
| 2-yl)-8-nitro-3- | | | | | | | | | | | | | | | |
| quinolinecarboxylate | | | | | | | | | | | | | | | |
| 2-(5-Isopropyl-5- | .500 | 2.0 | | 8.0 | 0.0 | 2.0 | 9.0 | 3.0 | 3.0 | 5.0 | 7.0 | 9.0 | 0.0 | 6.0 | 0.0 |
| methyl-4-oxo-2- | .250 | 0.0 | | 0.0 | 0.0 | 0.0 | 9.0 | 2.0 | 0.0 | 5.0 | 5.0 | 2.0 | 0.0 | 1.0 | 0.0 |
| imidazolin-2-yl)-4- | .125 | 0.0 | | 0.0 | 0.0 | 0.0 | 3.0 | 1.0 | 0.0 | 4.0 | 0.0 | 0.0 | 0.0 | 0.0 | 0.0 |
| methyl-3-quinoline- | .063 | 0.0 | | 0.0 | 0.0 | 0.0 | 3.0 | 1.0 | 0.0 | 2.0 | 0.0 | 0.0 | 0.0 | 0.0 | 0.0 |
| carboxylic acid | | | | | | | | | | | | | | | |
| 1,3-Dihydro-α-iso- | 8.000 | 6.0 | 0.0 | 0.0 | 8.0 | 6.0 | 8.0 | 3.0 | 6.0 | 0.0 | | | | | |
| propyl-α,8-dimethyl- | | | | | | | | | | | | | | | |
| 1,3-dioxo-2H—pyrrolo- | | | | | | | | | | | | | | | |
| [3,4-b]quinoline-2- | | | | | | | | | | | | | | | |
| acetamide | | | | | | | | | | | | | | | |
| 8-Chloro-2-(5-iso- | .500 | 3.0 | | 4.0 | 6.0 | 9.0 | 9.0 | 7.0 | 9.0 | 6.0 | 9.0 | 9.0 | 1.0 | 9.0 | 2.0 |
| propyl-5-methyl-4- | .250 | 1.0 | | 3.0 | 4.0 | 7.0 | 9.0 | 5.0 | 9.0 | 5.0 | 8.0 | 9.0 | 1.0 | 9.0 | 2.0 |
| oxo-2-imidazolin- | .125 | 1.0 | | 0.0 | 3.0 | 4.0 | 6.0 | 3.0 | 6.0 | 3.0 | 8.0 | 7.0 | 1.0 | 7.0 | 1.0 |
| 2-yl)-3-quinoline- | .063 | 0.0 | | 0.0 | 1.0 | 0.0 | | 2.0 | 0.0 | 1.0 | 3.0 | 7.0 | 1.0 | 5.0 | 0.0 |
| carboxylic acid | .032 | 0.0 | | 0.0 | 1.0 | | 1.0 | 0.0 | 0.0 | 1.0 | 1.0 | 4.0 | 0.0 | 5.0 | 0.0 |
| 6-Fluoro-2-(5-iso- | .500 | 9.0 | | 9.0 | 9.0 | 9.0 | 9.0 | 9.0 | 9.0 | 9.0 | 9.0 | 9.0 | 4.0 | 9.0 | 9.0 |
| propyl-5-methyl-4- | .250 | 9.0 | | 8.0 | 9.0 | 9.0 | 9.0 | 9.0 | 9.0 | 8.0 | 9.0 | 9.0 | 4.0 | 9.0 | 9.0 |
| oxo-2-imidazolin-2- | .125 | 3.0 | | 9.0 | 9.0 | 9.0 | 9.0 | 7.0 | 9.0 | 7.0 | 9.0 | 9.0 | 2.0 | 8.0 | 8.0 |
| yl)-3-quinoline- | .063 | 2.0 | | 9.0 | 9.0 | 9.0 | 9.0 | 7.0 | 8.0 | 6.0 | 8.0 | 9.0 | 2.0 | 7.0 | 8.0 |
| carboxylic acid | .032 | 1.0 | | 7.0 | 9.0 | 8.0 | 7.0 | 6.0 | 2.0 | 2.0 | 2.0 | 6.0 | 1.0 | 6.0 | 5.0 |
| 2-(5-Isopropyl-5- | .500 | 7.0 | | 9.0 | 9.0 | 9.0 | 9.0 | 7.0 | 7.0 | 7.0 | 9.0 | 9.0 | 6.0 | 9.0 | 8.0 |
| methyl-4-oxo-2- | .250 | 7.0 | | 8.0 | 9.0 | 9.0 | 9.0 | 6.0 | 7.0 | 6.0 | 9.0 | 9.0 | 6.0 | 9.0 | 7.0 |
| imidazolin-2-yl)- | .125 | 3.0 | | 7.0 | 9.0 | 9.0 | 6.0 | 3.0 | 1.0 | 2.0 | 9.0 | 8.0 | 4.0 | 9.0 | 7.0 |
| 8-methoxy-3-quino- | .063 | 2.0 | | 7.0 | 3.0 | 9.0 | 4.0 | 1.0 | 0.0 | 2.0 | 9.0 | 8.0 | 2.0 | 8.0 | 3.0 |
| linecarboxylic acid | .032 | 0.0 | | 2.0 | 0.0 | 9.0 | 0.0 | 0.0 | 0.0 | 0.0 | 9.0 | 7.0 | 1.0 | 7.0 | 1.0 |
| Methyl 2-(1-acetyl- | .500 | 9.0 | | 8.0 | 8.0 | 8.0 | 9.0 | 3.0 | 7.0 | 6.0 | 9.0 | 9.0 | 6.0 | 9.0 | 8.0 |
| 4-isopropyl-4- | .250 | 8.0 | | 8.0 | 8.0 | 9.0 | 9.0 | 3.0 | 8.0 | 3.0 | 9.0 | 7.0 | 3.0 | 9.0 | 7.0 |

TABLE XII-continued

| PRE-EMERGENCE TESTS - RATES IN KG/HA | | | | | | | | | | | | | | |
|---|---|---|---|---|---|---|---|---|---|---|---|---|---|---|
| methyl-5-oxo-2-imidazolin-2-yl)-3-quinolinecarboxylate | .125 | 7.0 | 8.0 | 7.0 | 9.0 | 9.0 | 0.0 | 3.0 | 1.0 | 6.0 | 7.0 | 1.0 | 7.0 | 7.0 |
| | .063 | 3.0 | 8.0 | 4.0 | 7.0 | 7.0 | 0.0 | 1.0 | 0.0 | 1.0 | 4.0 | 0.0 | 7.0 | 7.0 |
| | .032 | 1.0 | 8.0 | 1.0 | 3.0 | 9.0 | 0.0 | 1.0 | 0.0 | 0.0 | 0.0 | 0.0 | 1.0 | 2.0 |
| 2-(5-Isopropyl-5-methyl-4-oxo-2-imidazolin-2-yl)-6-(trifluoromethyl)-3-quinolinecarboxylic acid | .500 | 7.0 | 0.0 | 9.0 | 9.0 | 9.0 | 8.0 | 9.0 | 5.0 | 8.0 | 9.0 | 6.0 | 9.0 | 8.0 |
| | .250 | 5.0 | 0.0 | 8.0 | 4.0 | 9.0 | 1.0 | 8.0 | 2.0 | 2.0 | 7.0 | 2.0 | 9.0 | 7.0 |
| | .125 | 1.0 | 0.0 | 8.0 | 1.0 | 0.0 | | 4.0 | 2.0 | 2.0 | 5.0 | 2.0 | 8.0 | 5.0 |
| | .063 | 0.0 | 0.0 | 3.0 | 0.0 | 0.0 | 0.0 | | 0.0 | 1.0 | 2.0 | 1.0 | 7.0 | 2.0 |
| | .032 | 0.0 | 0.0 | 2.0 | 0.0 | 0.0 | 0.0 | 0.0 | 0.0 | 1.0 | 0.0 | 1.0 | 7.0 | 1.0 |
| Methyl 2-(5-Isopropyl-5-methyl-4-oxo-2-imidazolin-2-yl)-6-nitro-3-quinolinecarboxylate | .500 | 0.0 | 0.0 | 0.0 | 0.0 | 8.0 | 0.0 | 0.0 | 0.0 | 0.0 | 0.0 | 0.0 | 0.0 | 0.0 |
| 6,7-Dichloro-2-(5-isopropyl-5-methyl-4-oxo-2-imidazolin-2-yl)-3-quinolinecarboxylic acid | .500 | 8.0 | 9.0 | 8.0 | 9.0 | 9.0 | 8.0 | 9.0 | 4.0 | 5.0 | 8.0 | 4.0 | 8.0 | 7.0 |
| | .250 | 0.0 | 2.0 | 8.0 | 7.0 | 3.0 | 6.0 | 9.0 | 2.0 | 3.0 | 7.0 | 1.0 | 8.0 | 6.0 |
| | .125 | 0.0 | | 5.0 | 7.0 | 3.0 | 8.0 | 2.0 | 2.0 | 3.0 | 2.0 | 1.0 | 7.0 | 4.0 |
| | .063 | 0.0 | 2.0 | 0.0 | 2.0 | 0.0 | 0.0 | 1.0 | 1.0 | 0.0 | 0.0 | 0.0 | 7.0 | 3.0 |
| | .032 | 0.0 | | 0.0 | | | 0.0 | 0.0 | 1.0 | 0.0 | 0.0 | 0.0 | 3.0 | 2.0 |
| Ethylammonium 2-(5-isopropyl-5-methyl-4-oxo-2-imidazolin-2-yl)-3-quinolinecarboxylate | .645 | 9.0 | 9.0 | 9.0 | 9.0 | 9.0 | 7.0 | 9.0 | 9.0 | 9.0 | 9.0 | 5.0 | 9.0 | 9.0 |
| | .323 | 9.0 | 9.0 | 8.0 | 9.0 | 9.0 | 8.0 | 9.0 | 9.0 | 9.0 | 9.0 | 4.0 | 9.0 | 9.0 |
| | .161 | 6.0 | 9.0 | 8.0 | 9.0 | 9.0 | 8.0 | 9.0 | 8.0 | 9.0 | 9.0 | 4.0 | 9.0 | 9.0 |
| | .081 | 7.0 | 9.0 | 8.0 | 9.0 | 9.0 | 8.0 | 8.0 | 8.0 | 9.0 | 9.0 | 2.0 | 7.0 | 6.0 |
| | .040 | 3.0 | 8.0 | 7.0 | 6.0 | 9.0 | 7.0 | 8.0 | 7.0 | 9.0 | 9.0 | 2.0 | 7.0 | 3.0 |
| Methylammonium 2-(5-isopropyl-5-methyl-4-oxo-2-imidazolin-2-yl)-3-quinolinecarboxylate | .610 | 9.0 | 9.0 | 9.0 | 9.0 | 9.0 | 8.0 | 9.0 | 9.0 | 9.0 | 9.0 | 7.0 | 9.0 | 9.0 |
| | .305 | 9.0 | 9.0 | 9.0 | 9.0 | 9.0 | 7.0 | 9.0 | 9.0 | 9.0 | 9.0 | 5.0 | 9.0 | 9.0 |
| | .153 | 9.0 | 9.0 | 8.0 | 9.0 | 9.0 | 7.0 | 9.0 | 9.0 | 9.0 | 9.0 | 4.0 | 7.0 | 7.0 |
| | .076 | 8.0 | 9.0 | 8.0 | 9.0 | 9.0 | 8.0 | 9.0 | 8.0 | 9.0 | 9.0 | 3.0 | 7.0 | 5.0 |
| Dimethylammonium 2-(5-isopropyl-5-methyl-4-oxo-2-imidazolin-2-yl)-3-quinolinecarboxylate | .650 | 9.0 | 9.0 | 9.0 | 9.0 | 9.0 | 8.0 | 9.0 | 9.0 | 9.0 | 9.0 | 3.0 | 9.0 | 9.0 |
| | .325 | 9.0 | 9.0 | 9.0 | 9.0 | 9.0 | 8.0 | 9.0 | 8.0 | 9.0 | 9.0 | 4.0 | 9.0 | 9.0 |
| | .163 | 4.0 | 9.0 | 8.0 | 9.0 | 9.0 | 6.0 | 9.0 | 9.0 | 9.0 | 9.0 | 4.0 | 8.0 | 9.0 |
| | .081 | | 9.0 | 8.0 | 9.0 | 9.0 | 8.0 | 9.0 | 9.0 | 9.0 | 9.0 | 2.0 | 8.0 | 7.0 |
| 2-Ammonium-2,3-dimethylbutyramide 2-(5-isopropyl-5-methyl-4-oxo-2-imidazolin-2-yl)-3-quinolinecarboxylate | .500 | 9.0 | 9.0 | 9.0 | 9.0 | 9.0 | 9.0 | 9.0 | 9.0 | 9.0 | 9.0 | 6.0 | 9.0 | 9.0 |
| | .250 | 9.0 | 9.0 | 9.0 | 9.0 | 9.0 | 9.0 | 9.0 | 9.0 | 9.0 | 9.0 | 5.0 | 9.0 | 9.0 |
| | .125 | 9.0 | 9.0 | 9.0 | 9.0 | 9.0 | 9.0 | 9.0 | 9.0 | 9.0 | 9.0 | 5.0 | 9.0 | 8.0 |
| | .063 | 7.0 | 9.0 | 9.0 | 9.0 | 9.0 | 9.0 | 9.0 | 7.0 | 9.0 | 9.0 | 3.0 | 9.0 | 8.0 |
| 6-Acetamido-2-(5-isopropyl-5-methyl-4-oxo-2-imidazolin-2-yl)-3-quinolinecarboxylic acid | .500 | 6.0 | 9.0 | 2.0 | 4.0 | 9.0 | 3.0 | 3.0 | 4.0 | 8.0 | 9.0 | 2.0 | 6.0 | 1.0 |
| | .250 | 0.0 | 9.0 | 1.0 | 4.0 | 9.0 | 1.0 | 0.0 | 2.0 | 7.0 | 4.0 | 1.0 | 3.0 | 1.0 |
| | .125 | 0.0 | 9.0 | 0.0 | 2.0 | 1.0 | 0.0 | 0.0 | 1.0 | 7.0 | 1.0 | 0.0 | 1.0 | 0.0 |
| | .063 | 0.0 | 3.0 | 0.0 | 0.0 | | 0.0 | 0.0 | 0.0 | 1.0 | 0.0 | 0.0 | 1.0 | 0.0 |
| Methyl 6-(dimethylamino)-2-(5-isopropyl-5-methyl-4-oxo-2-imidazolin-2-yl)-3-quinolinecarboxylate | .250 | 0.0 | 8.0 | 0.0 | 0.0 | 0.0 | 0.0 | 0.0 | 0.0 | 0.0 | 0.0 | 0.0 | 0.0 | 0.0 |
| | .125 | 0.0 | | 0.0 | 0.0 | 0.0 | 0.0 | 0.0 | 0.0 | 0.0 | 0.0 | 0.0 | 0.0 | 0.0 |
| | .063 | 0.0 | 8.0 | 0.0 | 0.0 | 0.0 | 0.0 | 0.0 | 0.0 | 0.0 | 0.0 | 0.0 | 0.0 | 0.0 |
| | .032 | 0.0 | 8.0 | 0.0 | 0.0 | 0.0 | 0.0 | 0.0 | 0.0 | 0.0 | 0.0 | 0.0 | 0.0 | 0.0 |

TABLE XII-continued

PRE-EMERGENCE TESTS - RATES IN KG/HA

| COMPOUND | RATE | BARN-YARDGR | GREEN FOX | P NUT SEDGE | WILD OATS | QUACK GRASS | FLD B INDWD | MRNGLRY SP | RAG-WEED | VELVET-LEAF | S BARLY LA | CORN FIELD | RICE, NATO | SOY-BEAN AD | SUNFLR XXX | S WHEAT ER |
|---|---|---|---|---|---|---|---|---|---|---|---|---|---|---|---|---|
| Isopropylammonium | .660 | 9.0 | | | 9.0 | 9.0 | 9.0 | 9.0 | 7.0 | 9.0 | 9.0 | 9.0 | 9.0 | 6.0 | 9.0 | 9.0 |
| 2-(5-isopropyl-5- | .330 | 8.0 | | | 9.0 | 9.0 | 9.0 | 9.0 | 8.0 | 9.0 | 9.0 | 9.0 | 9.0 | 6.0 | 9.0 | 9.0 |
| methyl-4-oxo-2- | .165 | 8.0 | | | 9.0 | 8.0 | 9.0 | 8.0 | 7.0 | 9.0 | 9.0 | 9.0 | 9.0 | 1.0 | 8.0 | 8.0 |
| imidazolin-2-yl)- | .083 | 3.0 | | | 9.0 | 8.0 | 9.0 | 9.0 | 8.0 | 9.0 | 8.0 | 9.0 | 9.0 | 4.0 | 7.0 | 6.0 |
| 3-quinolinecarbo- | .041 | | | | 9.0 | 5.0 | 9.0 | 9.0 | 6.0 | 9.0 | 7.0 | 9.0 | 9.0 | 3.0 | 7.0 | 6.0 |
| xylate | | | | | | | | | | | | | | | | |
| Octylammonium 2-(5- | .785 | 9.0 | | | 9.0 | 9.0 | 9.0 | 9.0 | 8.0 | 9.0 | 9.0 | 9.0 | 9.0 | 2.0 | 9.0 | 9.0 |
| isopropyl-5-methyl- | .393 | 9.0 | | | 9.0 | 9.0 | 9.0 | 9.0 | 8.0 | 9.0 | 9.0 | 9.0 | 9.0 | 3.0 | 9.0 | 9.0 |
| 4-oxo-2-imidazolin- | .196 | 9.0 | | | 9.0 | 9.0 | 9.0 | 9.0 | 7.0 | 9.0 | 9.0 | 9.0 | 9.0 | 2.0 | 9.0 | 9.0 |
| 2-yl)-3-quinoline- | .098 | 8.0 | | | 9.0 | 8.0 | 9.0 | 9.0 | 7.0 | 9.0 | 9.0 | 9.0 | 9.0 | 4.0 | 8.0 | 6.0 |
| carboxylate | .049 | 2.0 | | | 8.0 | 7.0 | 9.0 | 9.0 | 7.0 | 9.0 | 9.0 | 9.0 | 9.0 | 0.0 | 8.0 | 5.0 |
| Methyl 2-(5-iso- | .500 | 9.0 | 9.0 | 0.0 | 7.0 | 9.0 | 9.0 | 7.0 | 7.0 | 8.0 | 9.0 | 9.0 | 9.0 | 3.0 | 4.0 | 9.0 |
| propyl-5-methyl-4- | .250 | 6.0 | 7.0 | 0.0 | 4.0 | 9.0 | 9.0 | 4.0 | 6.0 | 7.0 | 8.0 | 7.0 | 9.0 | 1.0 | 4.0 | 6.0 |
| oxo-2-imidazolin- | .125 | 2.0 | 2.0 | 0.0 | 1.0 | 8.0 | 9.0 | 3.0 | 3.0 | 3.0 | 3.0 | 6.0 | 9.0 | 1.0 | 2.0 | 4.0 |
| 2-yl)-6-phenoxy- | .063 | 1.0 | 1.0 | 0.0 | 0.0 | 4.0 | 8.0 | 2.0 | 1.0 | 1.0 | 3.0 | 4.0 | 9.0 | 0.0 | 0.0 | 4.0 |
| nicotinate | .032 | 0.0 | 0.0 | 0.0 | 0.0 | 4.0 | 2.0 | 1.0 | 0.0 | 0.0 | 7.0 | 1.0 | 8.0 | 0.0 | | 2.0 |
| 8-Bromo-1,3-dihydro-α-isopropyl-α-methyl-1,3-dioxo-2H—pyrrolo-[3,4-b]quinoline-2-acetamide | 8.000 | 5.0 | 0.0 | 0.0 | 8.5 | 5.5 | 1.0 | 1.5 | 7.0 | 0.5 | | | | | | |
| α-Cyclopropyl-1,3-dihydro-α-methyl-1,3-dioxo-2H—pyrrolo-[3,4-b]quinoline-2-acetonitrile | 8.000 | 0.0 | 0.0 | 0.0 | 0.0 | 9.0 | 9.0 | 0.0 | 9.0 | 0.0 | | | | | | |
| Methyl 2-(5-iso- | .500 | 3.0 | | 2.0 | 8.0 | 9.0 | 7.0 | 8.0 | 9.0 | 5.0 | | 3.0 | 6.0 | 2.0 | 2.0 | 4.0 |
| propyl-5-methyl-4- | .250 | 1.0 | | 1.0 | 7.0 | 3.0 | 4.0 | 8.0 | 0.0 | 2.0 | | 3.0 | 5.0 | 1.0 | 2.0 | 3.0 |
| oxo-2-imidazolin- | .125 | 0.0 | | 1.0 | 2.0 | 1.0 | 0.0 | | 0.0 | 0.0 | | 1.0 | 2.0 | 1.0 | 1.0 | 1.0 |
| 2-yl)-6-(methylamino)-nicotinate | .063 | 0.0 | | 0.0 | 1.0 | 0.0 | 0.0 | 2.0 | 0.0 | 0.0 | | 0.0 | 1.0 | 0.0 | 0.0 | 0.0 |

| COMPOUND | RATE | BARN-YARDGR | GREEN FOX | P NUT SEDGE | WILD OATS | QUACK GRASS | FLD B INDWD | MRNGLRY SP | RAG-WEED | VELVET-LEAF | CORN FIELD | RICE, NATO | SOYBEAN WI | SUNFLR XXX | S WHEAT ER |
|---|---|---|---|---|---|---|---|---|---|---|---|---|---|---|---|
| Diisopropylammonium | 4.000 | 9.0 | 9.0 | 9.0 | 9.0 | 9.0 | 9.0 | 9.0 | 9.0 | 9.0 | 9.0 | 9.0 | | 9.0 | |
| 2-(5-isopropyl-5- | 1.000 | 9.0 | 9.0 | 9.0 | 9.0 | 9.0 | 9.0 | 9.0 | 9.0 | 9.0 | 9.0 | 9.0 | | 9.0 | |
| methyl-4-oxo-2- | .750 | 9.0 | | 9.0 | 9.0 | 9.0 | 9.0 | 8.0 | 9.0 | 9.0 | 9.0 | 9.0 | | 9.0 | |
| imidazolin-2-yl)-3- | .500 | 9.0 | | 9.0 | 9.0 | 9.0 | 9.0 | 9.0 | 9.0 | 9.0 | 9.0 | 9.0 | | 9.0 | |
| quinolinecarboxylate | .375 | 9.0 | | 9.0 | 9.0 | 9.0 | 9.0 | 8.0 | 9.0 | 9.0 | 9.0 | 9.0 | | 9.0 | |
| | .250 | 9.0 | | 9.0 | 9.0 | 9.0 | 9.0 | 9.0 | 9.0 | 9.0 | 9.0 | 9.0 | | 9.0 | |
| Calcium 2-(5-iso- | 4.000 | 9.0 | 9.0 | 9.0 | 9.0 | 9.0 | 9.0 | 9.0 | 9.0 | 9.0 | 9.0 | 9.0 | | 9.0 | |
| propyl-5-methyl-4- | 1.000 | 9.0 | 9.0 | 9.0 | 9.0 | 9.0 | 9.0 | 9.0 | 9.0 | 9.0 | 9.0 | 9.0 | | 9.0 | |
| oxo-2-imidazolin- | .500 | 9.0 | | 9.0 | 9.0 | 9.0 | 9.0 | 9.0 | 9.0 | 9.0 | 9.0 | 9.0 | | 9.0 | |
| 2-yl)-3-quinoline- | .250 | 9.0 | | 9.0 | 9.0 | 9.0 | 9.0 | 9.0 | 9.0 | 9.0 | 9.0 | 9.0 | | 9.0 | |
| carboxylate | .125 | 9.0 | | 9.0 | 9.0 | 9.0 | 9.0 | 9.0 | 9.0 | 9.0 | 9.0 | 9.0 | | 9.0 | |
| 6-Chloro-2-(5-iso- | 4.000 | 9.0 | 9.0 | 8.0 | 9.0 | 9.0 | 9.0 | 9.0 | 9.0 | 8.0 | 9.0 | 9.0 | | 9.0 | |
| propyl-5-methyl-4- | 2.000 | | | 9.0 | | | | | | | 9.0 | | 5.0 | | |
| oxo-2-imidazolin-2- | 1.000 | 9.0 | 9.0 | 8.0 | 9.0 | 9.0 | 8.0 | 9.0 | 9.0 | 8.0 | 8.5 | 9.0 | 2.0 | 9.0 | |

TABLE XII-continued

| PRE-EMERGENCE TESTS - RATES IN KG/HA | | | | | | | | | | | | | | |
|---|---|---|---|---|---|---|---|---|---|---|---|---|---|---|
| yl)-3-quinoline-carboxylic acid | .500 | 9.0 | 9.0 | 7.8 | 9.0 | 9.0 | 9.0 | 9.0 | 9.0 | 8.0 | 8.0 | 9.0 | 2.0 | 9.0 |
| | .250 | 8.5 | | 7.0 | 9.0 | 9.0 | 8.5 | 8.0 | 9.0 | 7.0 | 5.7 | 9.0 | 1.0 | 9.0 |
| | .125 | 8.0 | | 6.3 | 8.5 | 9.0 | 7.5 | 7.5 | 8.5 | 7.0 | 3.7 | 8.5 | 0.5 | 8.5 |
| Methyl 2-(5-iso-propyl-5-methyl-4-oxo-2-imidazolin-2-yl)-6-methyl-nicotinate | 4.000 | 9.0 | 9.0 | 9.0 | 9.0 | 9.0 | 9.0 | 9.0 | 9.0 | 9.0 | 9.0 | 9.0 | | 9.0 |
| | 1.000 | 9.0 | 9.0 | 9.0 | 9.0 | 9.0 | 9.0 | 9.0 | 9.0 | 9.0 | 9.0 | 9.0 | | 9.0 |
| | .500 | 9.0 | 9.0 | 9.0 | 9.0 | 9.0 | 9.0 | 9.0 | 9.0 | 9.0 | 9.0 | 9.0 | | 9.0 |
| 2-(5-Isopropyl-5-methyl-4-oxo-2-imidazolin-2-yl)-7-methyl-3-quino-linecarboxylic acid | 4.000 | 9.0 | 9.0 | 8.0 | 9.0 | 9.0 | 9.0 | 9.0 | 9.0 | 9.0 | 9.0 | 9.0 | | 9.0 |
| | 1.000 | 9.0 | 9.0 | 8.0 | 9.0 | 9.0 | 9.0 | 9.0 | 9.0 | 8.0 | 9.0 | 9.0 | | 9.0 |
| | .500 | 9.0 | 9.0 | 9.0 | 5.0 | 9.0 | 9.0 | 9.0 | 7.0 | 8.0 | 9.0 | 9.0 | | 8.0 |
| 5-Isopropyl-5-methyl-2-[3-(2-oxazolin-2-yl)-2-yl)-2-quinolyl]-2-imidazolin-4-one | 4.000 | 9.0 | 9.0 | 9.0 | 9.0 | 9.0 | 9.0 | 9.0 | 9.0 | 9.0 | 9.0 | 9.0 | | 9.0 |
| | 1.000 | 9.0 | 9.0 | 9.0 | 9.0 | 9.0 | 9.0 | 8.0 | 9.0 | 8.0 | 9.0 | 9.0 | | 9.0 |
| | .500 | 9.0 | 9.0 | 9.0 | 8.0 | 9.0 | 9.0 | 8.0 | 9.0 | 7.0 | 9.0 | 9.0 | | 8.0 |
| 2-Isopropyl-2-methyl-8-propyl-5H—imidazo[1',2':1,2]-pyrrolo[3,4-b]-pyridine-3(2H), 5-dione | .500 | 6.0 | | 9.0 | 4.0 | 9.0 | 9.0 | 7.0 | 5.0 | 6.0 | 9.0 | 9.0 | | 7.0 |
| | .250 | 6.0 | | 9.0 | 4.0 | 8.0 | 9.0 | 7.0 | 5.0 | 6.0 | 6.0 | 7.0 | | 4.0 |
| | .125 | 1.0 | | 3.0 | 2.0 | 5.0 | 6.0 | 5.0 | 5.0 | 3.0 | 4.0 | 7.0 | | 2.0 |
| | .063 | 0.0 | | 2.0 | 0.0 | 3.0 | 3.0 | 3.0 | | 2.0 | 2.0 | 4.0 | | 2.0 |
| 2,8-Diisopropyl-2-methyl-5H—imidazo-[1',2':1,2]pyrrolo-[3,4-b]pyridine-3-(2H), 5-dione | 8.000 | 9.0 | 9.0 | 9.0 | 8.0 | 9.0 | 9.0 | 8.0 | 8.0 | 8.0 | | | | |
| Isopropyl 2-(5-isopropyl-5-methyl-4-oxo-2-imidazolin-2-yl)-6-propyl-nicotinate | 5.000 | 8.0 | 8.0 | 7.0 | 7.0 | 9.0 | 9.0 | 8.0 | 9.0 | 8.0 | | | | |
| 5,6,7,8-Tetrahydro-2-(5-isopropyl-5-methyl-4-oxo-2-imidazolin-2-yl)-3-quinolinecarbo-xylic acid | .500 | 9.0 | | 9.0 | 9.0 | 9.0 | 9.0 | 9.0 | 9.0 | 9.0 | 9.0 | 9.0 | | 9.0 |
| | .250 | 6.0 | | 8.0 | 7.0 | 9.0 | 9.0 | 8.0 | 7.0 | 8.0 | 8.0 | 9.0 | | 6.5 |
| | .125 | 7.0 | | 7.0 | 8.0 | 9.0 | 9.0 | 9.0 | 9.0 | 9.0 | 9.0 | 9.0 | | 7.0 |
| | .063 | 5.5 | | 3.0 | 6.0 | 7.5 | 9.0 | 6.5 | 6.0 | 6.0 | 6.5 | 7.0 | | 5.5 |
| 6-Butoxy-2-(5-isopropyl-5-methyl-4-oxo-2-imidazolin-2-yl)nicotinic acid | 8.000 | 9.0 | 9.0 | 9.0 | 9.0 | 9.0 | 9.0 | 6.0 | 8.0 | 9.0 | | | | |
| 2-(5-Isopropyl-5-methyl-4-oxo-2-imidazolin-2-yl)-6-(2-propynyloxy)-nicotinic acid | .500 | 7.0 | | 9.0 | 9.0 | 9.0 | 9.0 | 9.0 | 9.0 | 7.0 | 9.0 | 9.0 | | 9.0 |
| | .250 | 5.0 | | 9.0 | 9.0 | 9.0 | 9.0 | 9.0 | 9.0 | 7.0 | 9.0 | 9.0 | | 8.0 |
| | .125 | 2.0 | | 8.0 | 3.0 | 9.0 | 6.0 | 4.0 | 4.0 | 5.0 | 6.0 | 8.0 | | 7.0 |
| 2-(5-Isopropyl-5- | .500 | 8.0 | | 6.0 | 4.0 | 9.0 | 4.0 | 8.0 | 0.0 | 6.0 | 7.0 | 5.0 | 6.0 | 7.0 |

TABLE XII-continued

PRE-EMERGENCE TESTS - RATES IN KG/HA

| | | | | | | | | | | | | | | | |
|---|---|---|---|---|---|---|---|---|---|---|---|---|---|---|---|
| methyl-4-oxo-2-imidazolin-2-yl)-6-p-tolylnicotinic acid | .250 | 2.0 | | 3.0 | 1.0 | 4.0 | 3.0 | 3.0 | 0.0 | 3.0 | 2.0 | 3.0 | 5.0 | 6.0 | |
| | .125 | 0.0 | | 1.0 | 0.0 | 2.0 | 1.0 | 1.0 | 0.0 | 2.0 | 2.0 | 1.0 | 4.0 | 3.0 | |
| 6-(Isopropylamino)-2-(5-isopropyl-5-methyl-4-oxo-2-imidazolin-2-yl)-nicotinic acid | .500 | 8.0 | | 9.0 | 9.0 | 9.0 | 9.0 | 9.0 | 9.0 | 8.0 | 9.0 | 9.0 | | 9.0 | |
| | .250 | 7.0 | | 8.0 | 9.0 | 9.0 | 9.0 | 8.0 | 8.0 | 8.0 | 9.0 | 9.0 | | 9.0 | |
| | .125 | 3.0 | | 8.0 | 9.0 | 9.0 | 9.0 | 8.0 | 6.0 | 6.0 | 7.0 | 8.0 | | 9.0 | |
| | .063 | 2.0 | | 2.0 | 9.0 | 9.0 | 4.0 | 4.0 | 5.0 | 5.0 | 5.0 | 7.0 | | 7.0 | |
| | .032 | 1.0 | | 1.0 | 3.0 | 3.0 | 1.0 | 1.0 | 0.0 | 4.0 | 3.0 | 4.0 | | 2.0 | |
| | .016 | 0.0 | | 0.0 | 0.0 | 0.0 | 0.0 | 0.0 | 0.0 | 2.0 | 2.0 | 2.0 | 1.0 | | |
| 7-Ethyl-2-isopropyl-2-methyl-5H—imidazo-[1',2':1,2]pyrrolo-[3,4-b]pyridine-3-(2H), 5-dione | .500 | 9.0 | | 9.0 | 9.0 | 9.0 | 9.0 | 9.0 | 9.0 | 9.0 | 9.0 | 9.0 | | 9.0 | |
| | .250 | 9.0 | | 9.0 | 9.0 | 9.0 | 9.0 | 9.0 | 8.0 | 9.0 | 9.0 | 9.0 | | 9.0 | |
| | .125 | 9.0 | | 9.0 | 8.0 | 9.0 | 9.0 | 7.0 | 8.0 | 9.0 | 7.0 | 9.0 | | 9.0 | |
| | .063 | 9.0 | | 9.0 | 7.0 | 9.0 | 9.0 | 4.0 | 5.0 | 9.0 | 4.0 | 9.0 | | 9.0 | |
| | .032 | 1.0 | | 8.0 | 5.0 | 9.0 | 9.0 | 0.0 | 0.0 | 8.0 | 3.0 | 9.0 | | 7.0 | |
| | .016 | 0.0 | | 4.0 | 3.0 | 9.0 | 9.0 | | 0.0 | 6.0 | 5.0 | 9.0 | | 7.0 | |
| Methyl 6,7,8,9-tetrahydro-2-(5-isopropyl-5-methyl-4-oxo-2-imidazolin-2-yl)-5H—cyclohepta-[b]pyridine-3-carboxylate | .500 | 0.0 | | 7.0 | 6.0 | 4.0 | 9.0 | 0.0 | 0.0 | 0.0 | 7.0 | 3.0 | | 4.0 | |
| | .250 | 0.0 | | 9.0 | 1.0 | 4.0 | 7.0 | 0.0 | 0.0 | 0.0 | 0.0 | 1.0 | | 0.0 | |
| | .125 | 0.0 | | 8.0 | 0.0 | 4.0 | 5.0 | 0.0 | 0.0 | 0.0 | 0.0 | 0.0 | | 0.0 | |
| | .063 | 0.0 | | 8.0 | 0.0 | 2.0 | | 0.0 | 0.0 | 0.0 | 0.0 | 0.0 | | 0.0 | |
| | .032 | 0.0 | | 8.0 | 0.0 | 1.0 | 5.0 | 0.0 | 0.0 | 0.0 | 0.0 | 0.0 | | 0.0 | |
| | .016 | 0.0 | | 8.0 | 0.0 | 0.0 | 5.0 | 0.0 | 0.0 | 0.0 | 0.0 | 0.0 | | 0.0 | |
| 2-Ammonium-2,3-dimethylbutyramide 2-(5-isopropyl-5-methyl-4-oxo-2-imidazolin-2-yl)-3-quinolinecarboxylate | .500 | 9.0 | | 9.0 | 9.0 | 9.0 | 9.0 | 9.0 | 9.0 | 9.0 | 9.0 | 9.0 | | 9.0 | |
| | .250 | 9.0 | | 9.0 | 9.0 | 9.0 | 9.0 | 9.0 | 9.0 | 9.0 | 9.0 | 9.0 | | 9.0 | |
| | .125 | 9.0 | | 9.0 | 9.0 | 9.0 | 9.0 | 9.0 | 9.0 | 9.0 | 9.0 | 9.0 | | 9.0 | |
| | .063 | 7.0 | | 9.0 | 9.0 | 9.0 | 9.0 | 9.0 | 9.0 | 7.0 | 9.0 | 9.0 | | 9.0 | |
| | .032 | 7.0 | | 9.0 | 9.0 | 9.0 | 9.0 | 8.0 | 8.0 | 6.0 | 9.0 | 9.0 | | 9.0 | |
| | .016 | 2.0 | | 9.0 | 5.0 | 8.0 | 9.0 | 8.0 | | 6.0 | 9.0 | 9.0 | | 9.0 | |
| Tallowammonium 2-(5-isopropyl-5-methyl-4-oxo-2-imidazolin-2-yl)-3-quinolinecarboxylate | 1.040 | 9.0 | | 9.0 | 9.0 | 9.0 | 9.0 | 8.0 | 9.0 | 9.0 | 9.0 | 9.0 | | 8.0 | |
| | .520 | 9.0 | | 9.0 | 9.0 | 9.0 | 9.0 | 8.0 | 9.0 | 9.0 | 9.0 | 9.0 | | 8.0 | |
| | .260 | 9.0 | | 9.0 | 8.0 | 9.0 | 9.0 | 8.0 | 9.0 | 8.0 | 9.0 | 9.0 | | 8.0 | |
| | .130 | 9.0 | | 9.0 | 8.0 | 9.0 | 9.0 | 7.0 | 9.0 | 6.0 | 9.0 | 9.0 | | 8.0 | |
| | .065 | 2.0 | | 9.0 | 3.0 | 7.0 | 9.0 | 8.0 | 7.0 | 9.0 | 9.0 | 9.0 | | 8.0 | |
| 2-(5-Isopropyl-5-methyl-4-oxo-2-imidazolin-2-yl)-5-methyoxynicotonic acid | .500 | 9.0 | | 9.0 | 9.0 | 9.0 | 9.0 | 9.0 | 9.0 | 9.0 | 9.0 | 9.0 | 9.0 | 9.0 | |
| | .250 | 9.0 | | 9.0 | 9.0 | 9.0 | 9.0 | 9.0 | 9.0 | 9.0 | 9.0 | 9.0 | 9.0 | 9.0 | |
| | .125 | 9.0 | | 9.0 | 9.0 | 9.0 | 9.0 | 9.0 | 9.0 | 9.0 | 9.0 | 9.0 | 8.0 | 8.0 | |
| | .063 | 9.0 | | 9.0 | 9.0 | 9.0 | 9.0 | 9.0 | 9.0 | 9.0 | 9.0 | 9.0 | 6.0 | 7.0 | |
| | .032 | 7.0 | | 3.0 | 8.0 | 8.0 | 9.0 | 4.0 | 9.0 | 8.0 | 9.0 | 9.0 | 6.0 | 7.0 | |
| | .016 | 7.0 | | | 6.0 | 7.0 | 9.0 | 7.0 | 8.0 | 7.0 | 9.0 | 8.0 | 5.0 | 7.0 | |
| 2-(5-Isopropyl-5-methyl-4-oxo-2-imidazolin-2-yl)-6,7-dimethyl-3-quinolinecarboxylic acid | .500 | 7.0 | 7.0 | 8.0 | 8.0 | 9.0 | 8.0 | 7.0 | 7.0 | 3.0 | 9.0 | 4.0 | 7.0 | | |
| | .250 | 3.0 | 5.0 | 6.0 | 6.0 | 7.0 | 3.0 | 3.0 | 5.0 | 2.0 | 8.0 | 3.0 | 5.0 | | |
| | .125 | 1.0 | 2.0 | 4.0 | 4.0 | 7.0 | 3.0 | 3.0 | 5.0 | 6.0 | 7.0 | 3.0 | 5.0 | | |
| Tallowammonium 2-(5-isopropyl-5-methyl-4-oxo-2-imidazolin-2-yl)-3-quinolinecarboxylate | 1.040 | 9.0 | | 9.0 | 9.0 | 9.0 | 9.0 | 8.0 | 9.0 | 9.0 | 9.0 | 9.0 | 2.0 | 8.0 | 9.0 |
| | .520 | 9.0 | | 9.0 | 9.0 | 9.0 | 9.0 | 8.0 | 9.0 | 9.0 | 9.0 | 9.0 | 4.0 | 8.0 | 9.0 |
| | .260 | 9.0 | | 9.0 | 8.0 | 9.0 | 9.0 | 8.0 | 9.0 | 8.0 | 9.0 | 9.0 | 1.0 | 8.0 | 8.0 |
| | .130 | 9.0 | | 9.0 | 8.0 | 9.0 | 9.0 | 7.0 | 9.0 | 6.0 | 9.0 | 9.0 | 1.0 | 8.0 | 6.0 |
| | .065 | 2.0 | | 9.0 | 3.0 | 7.0 | 9.0 | 8.0 | 7.0 | 9.0 | 9.0 | 9.0 | 1.0 | 8.0 | 4.0 |

EXAMPLE 100

Evaluation of the defoliation effect of the compounds of the invention on cotton In the following tests, the appropriate compounds are dissolved or dispersed in acetone-water (1:1) mixtures at the final concentration corresponding to the kg/ha rates indicated in Table XIII below. The solutions also contain 0.1% to 0.25% v/v colloidal BIOFILM ® (a product of Colloidal Products Corp.) which is a mixture of alkyl aryl polyoxyethanol, free and combined fatty acids, glycol ethers, dialkylbenzene carboxylate and 2-propanol.

The plant species used in these tests is cotton (*Gossypium hirsutum,* var. Stoneville 213).

The solution or dispersion of the compound under test is sprayed at the rate of 40 ml per pot (one plant per pot) applied to the foliage. The plants are well established seedlings of 4th leaf stage at the time of test.

The pots are watered immediately before treatment. Following treatment, the plants are placed in a random arrangement on greenhouse benches. Normal watering and fertilizing practices are followed (pesticides are applied to plants as needed). Minimum day and night temperatures of 18.3° C. are maintained during cooler periods of the year. Normal daily fluctuations occur during the summer season. Plants are sprayed to provide the kg/ha rates indicated in Table XIII below. Each treatment is replicated six times and the controls 12 times.

The plants are harvested 15 days after the postemergence application of the test solutions and the number of defoliated, dessicated or senescent leaves counted on each plant. Said plants are also examined for bud growth. Data obtained are reported in Table XIII below, as averages for each treatment.

TABLE XIII

Evaluation of the defoliation, dessication and/or senescent effect of test compounds on cotton plants

| Compound | Rate kg/ha | No. of leaves defoliated, dessicated or senescent | Young bud regrowth |
|---|---|---|---|
| Control | — | 0.5 | 5.5 |
| Methyl 2-(5-isopropyl | 2.0 | 3.7 | 2.0 |
| 5-methyl-4-oxo-2- | 1.0 | 1.8 | 0.5 |
| imidazolin-2-yl)nico- | 0.5 | 3.3 | 0.83 |
| tinate | | | |
| 2-(5-isopropyl-5-methyl- | 2.0 | 3.53 | 0 |
| 4-oxo-2-imidazolin- | 1.0 | 4.63 | 0 |
| 2-yl)nicotinic acid | 0.5 | 2.13 | 0 |
| Methyl 2-(5-ethyl-5-methyl- | 2.0 | 5.33 | 2.6 |
| 4-oxo-2-imidazolin-2-yl | 1.0 | 5.33 | 3.0 |
| nicotinate | 0.5 | 3.79 | 4.3 |
| 2-(5-ethyl-5-methyl-4- | 2.0 | 1.0 | 5.0 |
| oxo-2-imidazolin-2- | 1.0 | 3.3 | 3.5 |
| yl)nicotinic acid | 0.5 | 2.5 | 4.8 |
| 2-propynyl 2-(5-isopropyl- | 2.0 | 5.2 | 0 |
| 5-methyl-4-oxo-2-imida- | 1.0 | 3.3 | 0.33 |
| zolin-2-yl)nicotinate | 0.5 | 2.5 | 0 |
| 2-(5,5-dimethyl-4-oxo-2- | 2.0 | 5.36 | 5.5 |
| imidazolin-2-yl)nicotinic | 1.0 | 6.5 | 7.0 |
| acid | 0.5 | 6.5 | 7.8 |
| Calcium 2-(5-isopropyl- | 4.0 | 5.0 | 0 |
| 5-methyl-4-oxo-2-imidazo- | 2.0 | 4.0 | 0 |
| lin-2-yl)nicotinate | 1.0 | 3.1 | 1.2 |
| Furfuryl 2-(5-isopropyl- | 4.0 | 4.0 | 0 |
| 5-methyl-4-oxo-2-imidaz- | 2.0 | 4.5 | 0 |
| olin-2-yl)nicotinate | 1.0 | 2.83 | 0 |
| Triethylammonium 2-(5- | 4.0 | 4.3 | 0 |
| isopropyl-5-methyl-4- | 2.0 | 5.0 | 0 |
| oxo-2-imidazolin-2-yl)- | 1.0 | 3.2 | 0.5 |
| nicotinate | | | |

EXAMPLE 101

Evaluation of test compounds as aquatic herbicides using the water hyacinth *Eichhornia crassipes* as the plant species In these test paddies having established water hyacinth populations and seeded with 5 tilapia, eleven months prior to compound evaluations, are sprayed with 333 liters/ha of test solution containing 0.5% by weight of a surfactant and sufficient test compound to provide from 0.125 to 1.0 kg/ha of said test compound.

At 44 days after the post-emergence treatment, the test paddies are examined and the results recorded and reported in the table below.

TABLE XIV

Evaluation of test compounds as aquatic herbicides using the water hyacinth *Eichhornia crassipes*

| Compound | Rate kg/ha | Phytotoxicity rating | % Regrowth |
|---|---|---|---|
| 2-(5-Isopropyl-5-methyl- | 0.125 | 3 | 0 |
| 4-oxo-2-imidazolin-2-yl)- | 0.25 | 6 | 0 |
| nicotinic acid | 0.50 | 7 | 0 |
| | 1.0 | 9 | 0 |
| Calcium 2-(5-isopropyl-5- | 0.125 | 4 | 0 |
| methyl-4-oxo-2-imidazolin- | 0.25 | 6 | 0 |
| 2-yl)nicotinate | 0.50 | 8 | 0 |
| | 1.0 | 9 | 0 |
| Furfuryl 2-(5-isopropyl-5- | 0.125 | 3 | 0 |
| methyl-4-oxo-2-imidazolin- | 0.25 | 5 | 0 |
| 2-yl)nicotinate | 0.50 | 7 | 0 |
| | 1.0 | 9 | 0 |
| Antreated check | — | — | 100* |

Phytotoxicity rating: (0:9)-0 = no effect; 9 = weed completely dead
*Continuously producing new plantlets

I claim:

1. A compound having the structure:

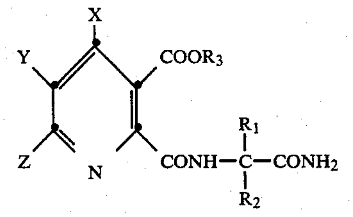

wherein $R_1$ is $C_1$–$C_4$ alkyl;

$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;

$R_3$ is hydrogen,

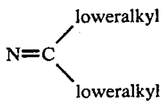

$C_1$–$C_{12}$ alkyl optionally substituted with one of of the following groups: $C_1$–$C_3$ alkoxy, halogen, hydroxyl, $C_3$–$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium halide;

$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;

$C_3$–$C_6$ cycloalkyl optionally substituted with one or two $C_1$–$C_3$ alkyl groups;

$C_3$–$C_{16}$ alkynyl; or,

A cation;

X is hydrogen, halogen, hydroxyl or methyl, with the proviso that when Y and Z are taken together to form a ring and YZ is represented by the structure: $—(CH_2)_n—$, where n is 3 or 4, X is hydrogen;

Y and Z are each hydrogen, halogen, $C_1$–$C_6$ alkyl, hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino or $C_1$–$C_4$ alkylsulfonyl group, or phenyl optionally substituted with one $C_1$–$C_4$ alkyl, $C_1$–$C_4$ alkoxy or halogen; and, when taken together, Y and Z may form a ring in which YZ are represented by the structure: $—(CH_2)_n—$, where n is an integer of 3 or 4, provided that X is hydrogen; or

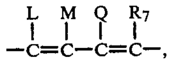, where L, M, Q and $R_7$ are each hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, $NO_2$, CN, phenyl, phenoxy, amino, $C_1$–$C_4$ alkylamino, diloweralkylamino, chlorophenyl, methylphenyl, or phenoxy substituted with one Cl, $CF_3$, $NO_2$ or $CH_3$ group, with the proviso that only one of L, M, Q or $R_7$ may represent a substituent other than hydrogen, halogen, $C_1$–$C_4$ alkyl or $C_1$–$C_4$ alkoxy;

and the N-oxides thereof provided that in the N-oxidase Y and Z cannot be aklkylamino, dialkylamino or alkylthio; and when $R_1$ and $R_2$ represent different substituents, the optical isomers thereof.

2. A compound according to claim 1, methyl 2-[(carbamoyl-1,2-dimethylpropyl)carbamoyl]quinoline-3-carboxylate.

3. A compound according to claim 1, methyl 2-[(1-carbamoyl-1,2-dimethylpropyl)carbamoyl]nicotinate.

4. A compound according to claim 1, benzyl 2-[(1-carbamoyl-1-methylpropyl)carbamoyl]nicotinate.

5. A compound according to claim 1, dodecyl 2-[(1-carbamoyl-1,2-dimethylpropyl)carbamoyl]nicotinate.

6. A compound according to claim 1 2-[(1-carbamoyl-1,2-dimethylpropyl)carbamoyl]-3-quinolinecarboxylic acid.

7. A compound according to claim 1 2-[(1-carbamoyl-1,2-dimethylpropyl)carbamoyl]nicotinic acid.

8. A compound according to claim 1 wherein $R_3$ is a cation of alkali metals, alkaline earth metals, manganese, copper, iron, zinc, cobalt, lead, silver, nickel, ammonium or organic ammonium comprised of a positively charged nitrogen atom joined to form one to four aliphatic groups, each containing from 1 to 20 carbon atoms.

* * * * *